United States Patent
Watanabe et al.

(10) Patent No.: US 10,647,675 B2
(45) Date of Patent: May 12, 2020

(54) BIARYL DERIVATIVE AND MEDICINE CONTAINING SAME

(71) Applicant: KAKEN PHARMACEUTICAL CO., LTD., Tokyo (JP)

(72) Inventors: Atsushi Watanabe, Kyoto (JP); Yuuki Sato, Kyoto (JP); Keiji Ogura, Kyoto (JP); Yoshiyuki Tatsumi, Kyoto (JP)

(73) Assignee: KAKEN PHARMACEUTICAL CO., LTD., Tokyo (JP)

( * ) Notice: Subject to any disclaimer, the term of this patent is extended or adjusted under 35 U.S.C. 154(b) by 0 days.

(21) Appl. No.: 15/759,125

(22) PCT Filed: Sep. 14, 2016

(86) PCT No.: PCT/JP2016/077029
§ 371 (c)(1),
(2) Date: Mar. 9, 2018

(87) PCT Pub. No.: WO2017/047602
PCT Pub. Date: Mar. 23, 2017

(65) Prior Publication Data
US 2019/0055199 A1    Feb. 21, 2019

(30) Foreign Application Priority Data
Sep. 18, 2015 (JP) .................. 2015-185966

(51) Int. Cl.
*C07D 213/643* (2006.01)
*C07D 401/14* (2006.01)
(Continued)

(52) U.S. Cl.
CPC ........ *C07D 213/643* (2013.01); *A61K 31/444* (2013.01); *A61K 31/4425* (2013.01); *A61K 31/4709* (2013.01); *A61K 31/4725* (2013.01); *A61K 31/498* (2013.01); *A61K 31/4985* (2013.01); *A61K 31/506* (2013.01); *A61K 31/535* (2013.01); *A61K 31/5355* (2013.01); *A61P 31/10* (2018.01); *C07D 213/64* (2013.01); *C07D 213/65* (2013.01); *C07D 213/68* (2013.01); *C07D 213/76* (2013.01); *C07D 239/34* (2013.01); *C07D 241/18* (2013.01); *C07D 401/04* (2013.01); *C07D 401/12* (2013.01); *C07D 401/14* (2013.01); *C07D 405/14* (2013.01); *C07D 413/14* (2013.01); *C07D 417/14* (2013.01); *C07D 471/04* (2013.01); *C07D 487/04* (2013.01); *C07D 498/04* (2013.01); *C07F 7/0812* (2013.01)

(58) Field of Classification Search
None
See application file for complete search history.

(56) References Cited

U.S. PATENT DOCUMENTS 7,432,375 B2 * 10/2008 Graczyk .............. C07D 471/04
546/113
2006/0264460 A1    11/2006 Green et al.
(Continued)

FOREIGN PATENT DOCUMENTS

JP        H11-503114 A    3/1999
JP        H11-505546 A    5/1999
(Continued)

OTHER PUBLICATIONS

European Patent Office, Extended European Search Report in European Patent Application No. 16846473.3 (dated Feb. 4, 2019).
(Continued)

*Primary Examiner* — Heidi Reese
(74) *Attorney, Agent, or Firm* — Leydig, Voit & Mayer, Ltd.

(57) ABSTRACT

Provided is a compound showing excellent Antifungal activity against *Trichophyton* fungus, which is a major causative microorganism of superficial mycosis, and high effectiveness on diseases caused by *Trichophyton* fungi. A biaryl derivative represented by the formula (I) or a salt thereof:

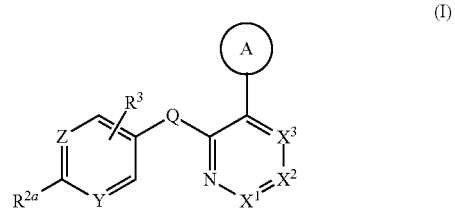

(I)

wherein ring A is an optionally substituted phenyl, or an optionally substituted 5- or 6-membered ring heteroaryl (ring A may be further condensed to form an optionally substituted fused ring); Q is $CH_2$, $C=O$, NH, O, S or the like; $X^1$, $X^2$ and $X^3$ are $CR^1$ or N; Y is CH or N; Z is $CR^{2b}$ or N; $R^{2a}$ and $R^{2b}$ are each a hydrogen atom, a halogen atom, an optionally substituted $C_1$-$C_6$ alkyl group, a $C_1$-$C_6$ haloalkyl group or the like; $R^{2a}$ and $R^{2b}$ may form, together with carbon atoms bonded thereto, an optionally substituted carbocycle, or an optionally substituted heterocycle.

22 Claims, No Drawings

(51) Int. Cl.

| | | |
|---|---|---|
| C07D 405/14 | (2006.01) | |
| C07D 413/14 | (2006.01) | |
| C07D 401/12 | (2006.01) | |
| C07D 239/34 | (2006.01) | |
| C07D 417/14 | (2006.01) | |
| C07D 471/04 | (2006.01) | |
| C07D 498/04 | (2006.01) | |
| C07D 213/65 | (2006.01) | |
| A61K 31/535 | (2006.01) | |
| A61K 31/444 | (2006.01) | |
| A61K 31/5355 | (2006.01) | |
| A61K 31/4709 | (2006.01) | |
| C07D 241/18 | (2006.01) | |
| C07D 213/64 | (2006.01) | |
| A61K 31/4425 | (2006.01) | |
| A61K 31/4725 | (2006.01) | |
| A61K 31/4985 | (2006.01) | |
| A61K 31/506 | (2006.01) | |
| A61K 31/498 | (2006.01) | |
| A61P 31/10 | (2006.01) | |
| C07D 213/68 | (2006.01) | |
| C07D 213/76 | (2006.01) | |
| C07D 401/04 | (2006.01) | |
| C07D 487/04 | (2006.01) | |
| C07F 7/08 | (2006.01) | |

(56) References Cited

U.S. PATENT DOCUMENTS

| | | |
|---|---|---|
| 2007/0105904 A1 | 5/2007 | Tanaka et al. |
| 2010/0273764 A1 | 10/2010 | Andrews et al. |
| 2014/0235616 A1 | 8/2014 | Benazet et al. |

FOREIGN PATENT DOCUMENTS

| | | | |
|---|---|---|---|
| JP | 2008-540656 A | 11/2008 | |
| JP | 2012-525395 A | 10/2012 | |
| JP | 2014-526545 A | 10/2014 | |
| RU | 2380365 C1 | 1/2010 | |
| WO | WO 1996/029301 A1 | 9/1996 | |
| WO | WO 1996/036633 A1 | 11/1996 | |
| WO | WO 2001/097613 A2 | 12/2001 | |
| WO | WO 2002/012236 A1 | 2/2002 | |
| WO | WO 2004/035564 A1 | 4/2004 | |
| WO | WO-2004035564 A1 * | 4/2004 | ........... C07D 401/04 |
| WO | WO 2004/052280 A2 | 6/2004 | |
| WO | WO 2004/078756 A2 | 9/2004 | |
| WO | WO 2004/078757 A2 | 9/2004 | |
| WO | WO 2004/080972 A1 | 9/2004 | |
| WO | WO 2005/113494 A2 | 12/2005 | |
| WO | WO 2006/078621 A2 | 7/2006 | |
| WO | WO 2007/087276 A1 | 8/2007 | |
| WO | WO 2007/100646 A1 | 9/2007 | |
| WO | WO 2008/040651 A1 | 4/2008 | |
| WO | WO 2008/057280 A2 | 5/2008 | |
| WO | WO 2008/135824 A1 | 11/2008 | |
| WO | WO 2009/103652 A1 | 8/2009 | |
| WO | WO 2010/057126 A1 | 5/2010 | |
| WO | WO 2010/077992 A1 | 7/2010 | |
| WO | WO 2011/022440 A2 | 2/2011 | |
| WO | WO 2011/099764 A2 | 8/2011 | |
| WO | WO 2011/161201 A1 | 12/2011 | |
| WO | WO 2012/019093 A1 | 2/2012 | |
| WO | WO 2012/052540 A1 | 4/2012 | |
| WO | WO 2012/080729 A2 | 6/2012 | |
| WO | WO 2012/146125 A1 | 11/2012 | |
| WO | WO 2012/170976 A2 | 12/2012 | |
| WO | WO 2013/058256 A1 | 4/2013 | |
| WO | WO 2013/086397 A1 | 6/2013 | |
| WO | WO 2013/171729 A2 | 11/2013 | |
| WO | WO 2014/008458 A2 | 1/2014 | |
| WO | WO 2014/151393 A2 | 9/2014 | |
| WO | WO 2016/007534 A1 | 1/2016 | |
| WO | WO 2016/098793 A1 | 6/2016 | |
| WO | WO 2017/021879 A1 | 2/2017 | |

OTHER PUBLICATIONS

Abramovitch et al., "Intramolecular Cyclization of Aryloxenium Ions. C—O—C and C—C Bond Formation. A Novel Ortho Effect," *J. Org. Chem.*, 47(24): 4817-4818 (1982).

Atkinson et al., "2. Triazaphenanthrenes. Part IV. Some 9-aryl-3-methyl-1 : 2 : 10-triazaphenanthrenes," *J. Chem. Soc.*, 0: 6-9 (1959).

Chong et al., "2-Pyridonate Titanium Complexes for Chemoselectivity. Accessing Intramolecular Hydroaminoalkylation over Hydroamination," *Org. Lett.*, 15(23): 6002-6005 (2013).

Koley et al., "Regioselective Synthesis of 2,3-Substituted Pyridines by Orthogonal Cross-Coupling Strategies," *Eur. J. Chem.*, 2011(10): 1972-1979 (2011).

Lipshutz et al., "Copper-in-Charcoal (Cu/C) Promoted Diaryl Ether Formation," *Org. Lett.*, 9(6): 1089-1092 (2007).

McNamara et al., "Synthesis and serotonin transporter activity of 1,3-bis(aryl)-2-nitro-1-propenes as a new class of anticancer agents," *Bioorg. Med. Chem.*, 19(3): 1328-1348 (2011).

Moraski et al., "Structure-activity relationship of new anti-tuberculosis agents derived from oxazoline and oxazole benzyl esters," *Eur. J. Med. Chem.*, 45(5): 1703-1716 (2010).

Ran et al., "Studies on pyridine derivatives (VIII): Synthesis and bioactivity of 2-alkylamino-5-(2-aryloypyrid-3-yl)-1,3,4-thiodiazoles," *Chinese Journal of Pesticide Science*, 12(3): 269-273 (2010).

Röver et al., "6-Alkoxy-5-aryl-3-pyridinecarboxamides, a New Series of Bioavailable Cannabinoid Receptor Type 1 (CB1) Antagonists Including Peripherally Selective Compounds," *J. Med. Chem.*, 56(24): 9874-9896 (2013).

Tolstaya et al., "Nucleophilic substitution in O-phenyldibenzofuranium and 10-phenylxanthonium cations," *Russian Chemical Bulletin*, 46(4): 789-797 (1997).

Zhang et al., "Synthesis and Research of Biological Activity of Triazole Thiones," *Agrochemicals*, 51(4): 243-245 (2012).

Japanese Patent Office, International Search Report in International Application No. PCT/JP2016/077029 (dated Dec. 20, 2016).

Japanese Patent Office, Written Opinion of the International Searching Authority in International Application No. PCT/JP2016/077029 (dated Dec. 20, 2016).

Das et al., "Design, synthesis and pharmacological evaluation of novel polycyclic heteroarene ethers as PDE10A inhibitors: Part II," *Bioorg. Med. Chem. Lett.*, 24(15): 3238-3242 (2014).

Smith et al., "Structure-Based Design of a Novel Series of Potent, Selective Inhibitors of the Class I Phosphatidylinositol 3-Kinases," *J. Med. Chem.*, 55(11): 5188-5219 (2012).

* cited by examiner

BIARYL DERIVATIVE AND MEDICINE CONTAINING SAME

CROSS-REFERENCE TO RELATED APPLICATIONS

This patent application is the U.S. national phase of International Patent Application No. PCT/JP2016/077029, filed Sep. 14, 2016, which claims the benefit of Japanese Patent Application No. 2015-185966, filed on Sep. 18, 2015, which are incorporated by reference in their entireties herein.

TECHNICAL FIELD

The present invention relates to a novel biaryl derivative, and a medicament and an antifungal agent each containing same as an active ingredient.

BACKGROUND ART

Mycosis includes superficial mycosis represented by various trichophytoses, cutaneous candidiasis, tinea versicolor and the like, and deep mycosis represented by fungal meningitis, fungal respiratory infection, fungemia, mycosis of urinary tract and the like.

Superficial mycosis is a mycosis wherein epidermis, hair, nail and the like are infected with fungi, and trichophytosis caused by fungi of the genus *Trichophyton* as the major causative microorganism accounts for about 90% of the whole, and candidiasis and tinea versicolor account for the remaining 10%. The number of domestic patients with trichophytosis is estimated to be 21 million for tinea pedis and 12 million for tinea unguium.

Tinea unguium is a refractory disease, and oral antifungal agents such as terbinafine, itraconazole and the like are generally used for the treatment. Since the treatment requires oral administration of the medicament for at least 3 months, medication adherence of the patients is low. In addition, insufficient eradication effect against fungi at the site of infection also poses problems of recurrence and relapse after the treatment. Furthermore, drug-drug interaction, and side effects such as hepatopathy, gastrointestinal disorder and the like also pose problems, and the treatment is sometimes restricted in elderly people and patients with complication or pre-existing disease.

Therefore, an antifungal agent highly effective against tinea unguium by topical application free from systemic side effects and drug interaction is demanded. To exhibit effects by topical administration, the medicament is required to sufficiently penetrate into the thick horny layers of the nail plate and show an antifungal activity against *Trichophyton* fungi in the nail and nail bed.

As an external preparation for the treatment of tinea unguium, a nail lacquer preparation of amorolfine has already been applied clinically overseas. While amorolfine shows a superior anti-*Trichophyton* activity, it shows low penetrability into the nail, and its clinical effect is not sufficient.

As a biaryl derivative, the following compound is known. Patent Document 1 describes a compound represented by the formula:

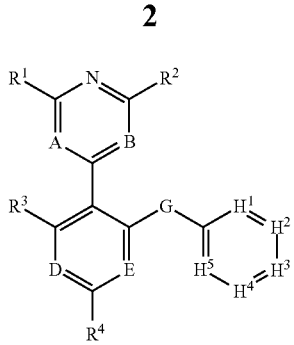

wherein each symbol is as defined is Patent Document 1 as a compound having an inhibitory activity against kinases such as Tie-2 and the like.

Patent Document 2 describes a compound represented by the formula:

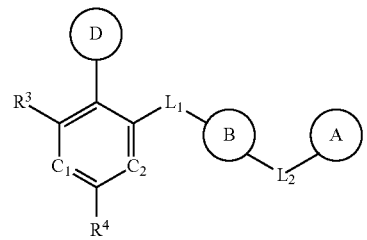

wherein each symbol is as defined in Patent Document 2, as a compound having an inhibitory activity against protein kinases such as Tie-2 and the like.

Patent Document 3 describes a compound represented by the formula:

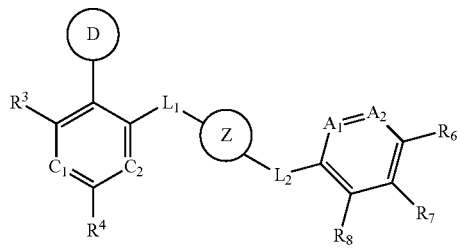

wherein each symbol is as defined in Patent Document 3, as a compound having an Aurora kinase inhibitory activity.

Patent Document 4 describes a compound represented by the formula:

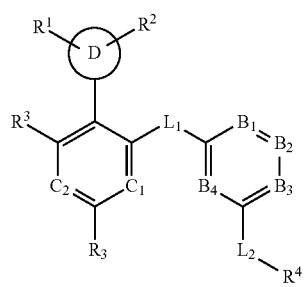

wherein each symbol is as defined in Patent Document 4, as a compound having an inhibitory activity against protein kinases such as Tie-2 and the like.

It is disclosed that the above-mentioned compounds are useful for the treatment of angiogenesis and cancer by inhibiting various kinases.

On the other hand, Patent Document 5 describes a compound represented by the formula:

[Chemical structure]

wherein each symbol is as defined in Patent Document 5, as a compound having a phosphodiesterase 10 inhibitory activity.

Patent Document 6 describes a compound represented by the formula:

[Chemical structure]

wherein each symbol is as defined in Patent Document 6, as a compound having a phosphodiesterase 10 inhibitory activity.

It is disclosed that these above-mentioned compounds are useful for the treatment of obesity, non-insulin-dependent diabetes mellitus, schizophrenia, bipolar disorder, obsessive-compulsive disorder and the like by inhibiting phosphodiesterase 10.

However, these prior art documents do not specifically disclose the compound of the formula (I) of the present invention, and do not describe or suggest that the compound has an anti-*Trichophyton* activity, and is useful for the treatment of diseases caused by *Trichophyton* fungi.

DOCUMENT LIST

Patent Documents

Patent Document 1: WO 05/113494
Patent Document 2: WO 07/100646
Patent Document 3: WO 07/087276
Patent Document 4: WO 08/057280
Patent Document 5: WO 10/057126
Patent Document 6: WO 10/077992

SUMMARY OF THE INVENTION

Problems to be Solved by the Invention

An object of the present invention is to provide a novel compound or a salt thereof which shows high effectiveness for diseases caused by *Trichophyton* fungi since it has an excellent antifungal activity against *Trichophyton* fungi which is a major causative microorganism of superficial mycosis. Furthermore, the present invention aims to provide a novel compound or a salt thereof, which is useful as a topical therapeutic agent for tinea unguium due to its superior nail permeability.

Means of Solving the Problems

The present inventors have conducted intensive studies in an attempt to solve the aforementioned problems and found that a biaryl derivative represented by the following formula (I) has an excellent antifungal activity against *Trichophyton* fungi and completed the present invention.

Accordingly, the present invention provides the following.

(1) A biaryl derivative represented by the formula (I) or a salt thereof:

(I)

[Chemical structure]

wherein,
ring A is an optionally substituted phenyl, or an optionally substituted 5- or 6-membered ring heteroaryl (said ring A is optionally further condensed to form an optionally substituted fused ring),
Q is $CH_2$, $CF_2$, S=O, $SO_2$, C=O, NH, O or S,
$X^1$, $X^2$ and $X^3$ are each independently CH, $CR^1$ or N,
Y is CH or N,
Z is $CR^{2b}$ or N,
$R^1$ is a hydrogen atom, a halogen atom, a $C_1$-$C_6$ alkyl group, a $C_1$-$C_6$ haloalkyl group, a $C_1$-$C_6$ alkoxy group or a $C_1$-$C_6$ haloalkoxy group,
$R^{2a}$ and $R^{2b}$ are each independently a hydrogen atom, a halogen atom, a hydroxyl group, a cyano group, a formyl group, an optionally substituted $C_1$-$C_6$ alkyl group, an optionally substituted $C_1$-$C_6$ haloalkyl group, an optionally substituted $C_1$-$C_6$ alkoxy group, an optionally substituted $C_1$-$C_6$ haloalkoxy group, an optionally substituted $C_1$-$C_4$ alkoxy-$C_1$-$C_4$ alkyl group, an optionally substituted $C_1$-$C_4$ alkoxy-$C_1$-$C_4$ haloalkyl group, an optionally substituted $C_1$-$C_6$ alkylcarbonyl group, an optionally substituted $C_1$-$C_6$ alkoxycarbonyl group, an optionally substituted $C_1$-$C_6$ alkylcarbonyloxy group, an optionally substituted $C_3$-$C_7$ cycloalkyl group, an optionally substituted heterocycloalkyl group, an optionally substituted heterocycloalkyloxy group, an optionally substituted $C_2$-$C_6$ alkenyl group, an optionally substituted $C_2$-$C_6$ alkenyloxy group, an optionally substituted $C_2$-$C_6$ alkenyl-$C_1$-$C_6$ alkyl group, an optionally substituted $C_2$-$C_6$ alkenyl-$C_1$-$C_6$ alkoxy group, an optionally substituted $C_2$-$C_6$ alkenyloxy-$C_1$-$C_4$ alkyl group, an optionally substituted $C_2$-$C_6$ alkenyloxy-$C_1$-$C_4$ alkoxy group, an optionally substituted $C_2$-$C_6$ alkenyloxy-$C_1$-$C_4$ haloalkyl group, an optionally substituted $C_2$-$C_6$ alkenyloxy-$C_1$-$C_4$ haloalkoxy group, an optionally substituted $C_2$-$C_6$ alkynyl group, an optionally substituted $C_2$-$C_6$ alkynyloxy group, an optionally substituted $C_2$-$C_6$ alkynyl-$C_1$-$C_6$ alkyl group, an optionally substituted $C_2$-$C_6$ alkynyl-$C_1$-$C_6$ alkoxy group, an optionally substituted $C_2$-$C_6$ alkynyloxy-$C_1$-$C_4$ alkyl group, an optionally substituted $C_2$-$C_6$ alkynyloxy-$C_1$-$C_4$ alkoxy group, an optionally substituted $C_2$-$C_6$ alkynyloxy-$C_1$-$C_4$ haloalkyl group, an optionally substituted $C_2$-$C_6$ alkynyloxy-$C_1$-$C_4$ haloalkoxy group, —NR$^a$R$^b$ {R$^a$ and R$^b$ are each independently a hydrogen atom or an optionally substituted $C_1$-$C_6$ group (provided that R$^a$ and R$^b$ are not hydrogen atoms at the same time)}, an optionally substituted $C_1$-$C_6$ haloalkylthio group, a pentafluorosulfanyl group, or a group represented by the formula (I-A)

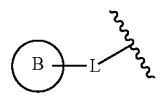
(I-A)

{wherein,
L is a single bond, —(CH$_2$)$_p$—, —O(CH$_2$)$_p$—, —(CH$_2$)$_2$O—, —(CH$_2$)$_p$O(CH$_2$)$_q$—, —NR$^c$(CH$_2$)$_p$—, —(CH$_2$)$_p$NR$^c$— or —(CH$_2$)$_p$NR$^c$(CH$_2$)$_q$—, wherein one or more hydrogen atoms of (CH$_2$)$_p$ and (CH$_2$)$_q$ are each optionally substituted by a halogen atom, a $C_1$-$C_4$ alkyl group or a $C_3$-$C_7$ cycloalkyl group,
p is 1, 2 or 3,
q is 1, 2 or 3,
R$^c$ is a hydrogen atom or a $C_1$-$C_6$ alkyl group, and
ring B is an optionally substituted carbocycle, or an optionally substituted heterocycle), or
when Z is CR$^{2a}$, R$^{2a}$ and R$^{2b}$ optionally form, together with carbon atoms bonded thereto, an optionally substituted carbocycle or an optionally substituted heterocycle, and
R$^3$ is a hydrogen atom, a halogen atom, an optionally substituted $C_1$-$C_6$ alkyl group, a $C_1$-$C_6$ haloalkyl group, an optionally substituted $C_1$-$C_6$ alkoxy group, a $C_1$-$C_6$ haloalkoxy group, an optionally substituted $C_3$-$C_7$ cycloalkyl group, an optionally substituted $C_2$-$C_6$ alkenyl group, an optionally substituted $C_2$-$C_6$ alkynyl group, or an optionally substituted aralkyl group.
(1-A) The biaryl derivative of (1) or a salt thereof, wherein, in the aforementioned formula (I), Q is CH$_2$, C=O, NH, O or S,
X$^1$, X$^2$ and X$^3$ are each independently CR$^1$ or N,
R$^{2a}$ and R$^{2b}$ are each independently a hydrogen atom, a halogen atom, a hydroxyl group, a cyano group, a formyl group, an optionally substituted $C_1$-$C_6$ alkyl group, a $C_1$-$C_6$ haloalkyl group, an optionally substituted $C_1$-$C_6$ alkoxy group, a $C_1$-$C_6$ haloalkoxy group, a $C_1$-$C_4$ alkoxy-$C_1$-$C_4$ alkyl group, a $C_1$-$C_4$ alkoxy-$C_1$-$C_4$ haloalkyl group, an optionally substituted $C_1$-$C_6$ alkylcarbonyl group, an optionally substituted $C_1$-$C_6$ alkoxycarbonyl group, an optionally substituted $C_1$-$C_6$ alkylcarbonyloxy group, an optionally substituted $C_3$-$C_7$ cycloalkyl group, an optionally substituted heterocycloalkyl group, an optionally substituted $C_2$-$C_6$ alkenyl group, an optionally substituted $C_2$-$C_6$ alkenyl-$C_1$-$C_6$ alkyl group, an optionally substituted $C_2$-$C_6$ alkenyl-$C_1$-$C_6$ alkoxy group, an optionally substituted $C_2$-$C_6$ alkynyl group, an optionally substituted $C_2$-$C_6$ alkynyl-$C_1$-$C_6$ alkyl group, an optionally substituted $C_2$-$C_6$ alkynyl-$C_1$-$C_6$ alkoxy group, —NR$^a$R$^b$ (R$^a$ and R$^b$ are each independently a hydrogen atom or an optionally substituted $C_1$-$C_6$ alkyl group (provided that R$^a$ and R$^b$ are not hydrogen atoms at the same time)}, an optionally substituted $C_1$-$C_6$ alkylthio group, a pentafluorosulfanyl group, or a group represented by the formula (I-A) {wherein L is —(CH$_2$)$_p$—, —O(CH$_2$)$_p$—, —(CH$_2$)$_p$O—, —(CH$_2$)$_p$O(CH$_2$)$_q$—, —NR$^c$(CH$_2$)$_p$—, —(CH$_2$)$_p$NR$^c$— or —(CH$_2$)$_p$NR$^c$(CH$_2$)$_q$—, wherein (CH$_2$)$_p$ and (CH$_2$)$_q$ are each optionally substituted by a halogen atom, a $C_1$-$C_4$ alkyl group or a $C_3$-$C_7$ cycloalkyl group, and p, q, R$^c$ and ring B are as defined in (1)}, and
when Z is CR$^{2a}$, R$^{2a}$ and R$^{2b}$ optionally form, together with carbon atoms bonded thereto, an optionally substituted carbocycle or an optionally substituted heterocycle.
(2) The biaryl derivative of (1) or a salt thereof, wherein, in the aforementioned formula (I), Q is NH, O or S.
(3) the biaryl derivative of (2) or a salt thereof, wherein, in the aforementioned formula (I), Q is O.
(4) The biaryl derivative of any one of (1)-(3) or a salt thereof, wherein, in the aforementioned formula (I), X$^1$ and X$^3$ are CH, X$^2$ is CR$^1$ or N, and R$^1$ is a hydrogen atom or a halogen atom.
(4-A) the biaryl derivative of any one of (1)-(3) or a salt thereof, wherein, in the aforementioned formula (I), X$^1$ and X$^3$ are CR$^1$, X$^2$ is CR$^1$ or N, and R$^1$ is a hydrogen atom or a halogen atom.
(5) The biaryl derivative of (4) or a salt thereof, wherein, in the aforementioned formula (I), X$^1$ and X$^3$ are CH, and X$^2$ is CH or N.
(6) The biaryl derivative of any one of (1)-(5) or a salt thereof, wherein, in the aforementioned formula (I), ring A is an optionally substituted phenyl, or an optionally substituted 6-membered ring heteroaryl (said ring A is optionally further condensed to form an optionally substituted fused ring).
(7) The biaryl derivative of any one of (1)-(6) or a salt thereof, wherein, in the aforementioned formula (I), ring A is a ring selected from the group consisting of the following formulas:

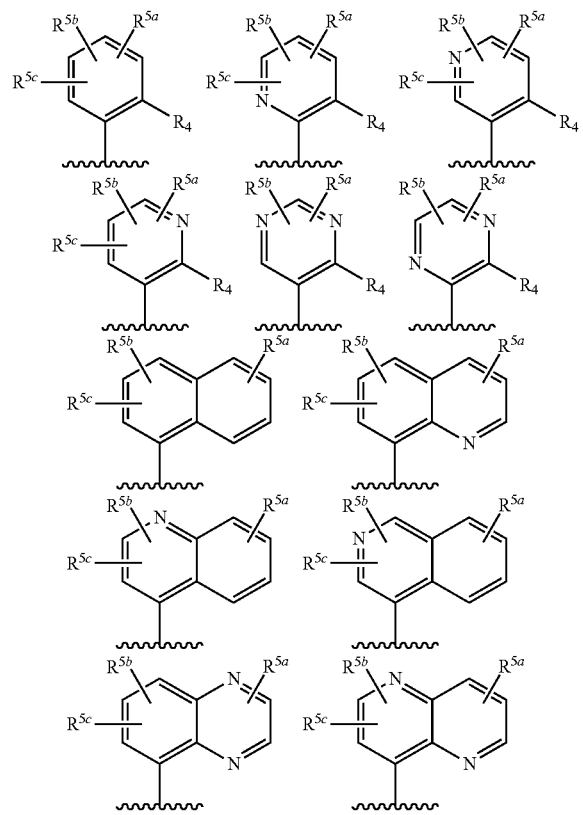

-continued

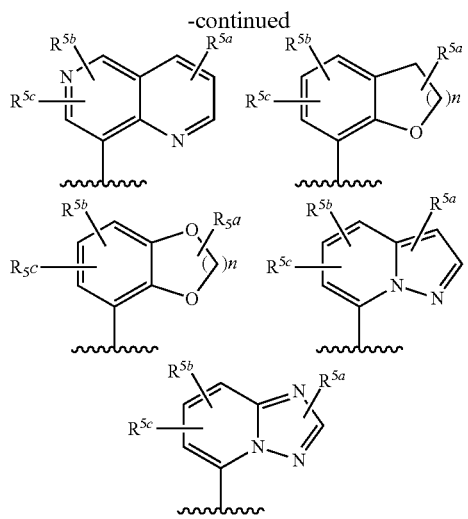

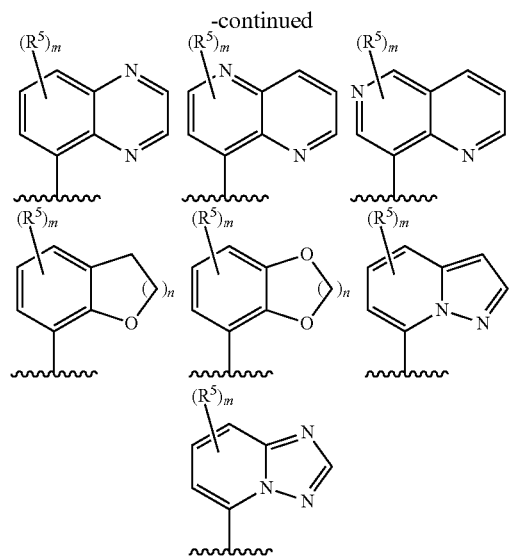

wherein n is 1 or 2,

R⁴ is a hydrogen atom, a halogen atom, a cyano group, a hydroxyl group, an optionally substituted $C_1$-$C_6$ alkyl group, a $C_1$-$C_6$ haloalkyl group, an optionally substituted $C_3$-$C_7$ cycloalkyl group, a heterocycloalkyl group, heterocycloalkyloxy group, a 5-membered ring heteroaryl group, an optionally substituted $C_1$-$C_6$ alkoxy group, a $C_1$-$C_6$ haloalkoxy group, a $C_2$-$C_6$ alkenyl group, a $C_2$-$C_6$ alkenyl-$C_1$-$C_6$ alkoxy group, a $C_2$-$C_6$ alkynyl group, a $C_2$-$C_6$ alkynyl-$C_1$-$C_6$ alkoxy group, a $C_1$-$C_6$ alkylthio group, —NR$^d$R$^e$ (R$^d$ and R$^e$ are each independently a hydrogen atom or a $C_1$-$C_6$ alkyl group), a nitro group, a formyl group, a $C_1$-$C_6$ alkylcarbonyl group, a $C_1$-$C_6$ alkoxycarbonyl group or a $C_1$-$C_6$ alkylcarbonyloxy group, and R$^{5a}$, R$^{5b}$ and R$^{5c}$ are each independently a hydrogen atom, a halogen atom, a cyano group, a $C_1$-$C_6$ alkyl group, a $C_1$-$C_6$ alkoxy group, a $C_1$-$C_6$ haloalkyl group, a $C_1$-$C_6$ haloalkoxy group, a $C_3$-$C_7$ cycloalkyl group, a $C_1$-$C_6$ alkylcarbonyl group or a $C_1$-$C_6$ alkoxycarbonyl group.

(7-A) The biaryl derivative of any one of (1)-(6) or a salt thereof, wherein, in the aforementioned formula (I), ring A is a ring selected from the group consisting of the following formulas:

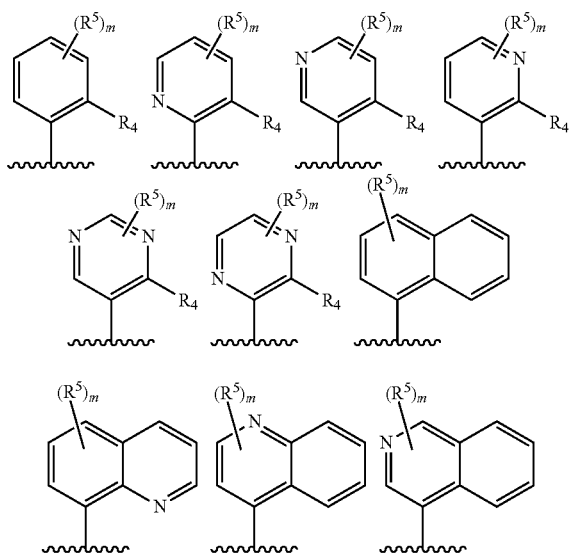

wherein m is 0, 1 or 2, n is 1 or 2,

R⁴ is a hydrogen atom, a halogen atom, a cyano group, a hydroxyl group, an optionally substituted $C_1$-$C_6$ alkyl group, a $C_1$-$C_6$ haloalkyl group, an optionally substituted $C_3$-$C_7$ cycloalkyl group, a heterocycloalkyl group, a 5-membered ring heteroaryl group, an optionally substituted $C_1$-$C_6$ alkoxy group, a $C_1$-$C_6$ haloalkoxy group, a $C_2$-$C_6$ alkenyl group, a $C_2$-$C_6$ alkynyl group, a $C_1$-$C_6$ alkylthio group, —NR$^d$R$^e$ (R$^d$ and R$^e$ are each independently a hydrogen atom or a $C_1$-$C_6$ alkyl group), a nitro group, a formyl group, a $C_1$-$C_6$ alkylcarbonyl group, a $C_1$-$C_6$ alkoxycarbonyl group or a $C_1$-$C_6$ alkylcarbonyloxy group, and each R⁵ is independently a hydrogen atom, a halogen atom, a cyano group, a $C_1$-$C_6$ alkyl group, a $C_1$-$C_6$ alkoxy group, a $C_1$-$C_6$ haloalkyl group, a $C_1$-$C_6$ haloalkoxy group, a $C_3$-$C_7$ cycloalkyl group, a $C_1$-$C_6$ alkylcarbonyl group or a $C_1$-$C_6$ alkoxycarbonyl group.

(8) The biaryl derivative of (7) or a salt thereof, wherein, in the aforementioned formula (I), ring A is a ring selected from the group consisting of the following formulas:

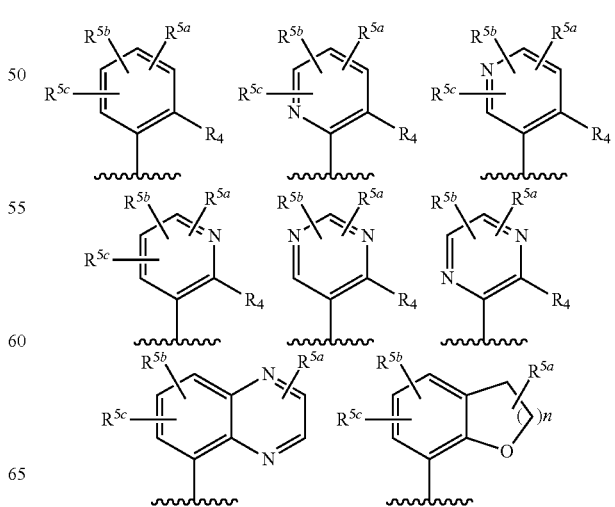

-continued

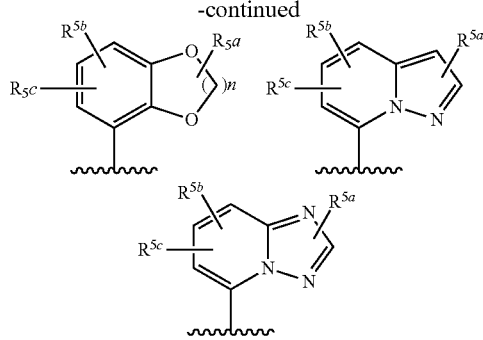

wherein n, $R^4$, $R^{5a}$, $R^{5b}$ and $R^{5c}$ are as defined in (7).

(8-A) the biaryl derivative of (7-A) or a salt thereof, wherein, in the aforementioned formula (I), ring A is a ring selected from the group consisting of the following formulas:

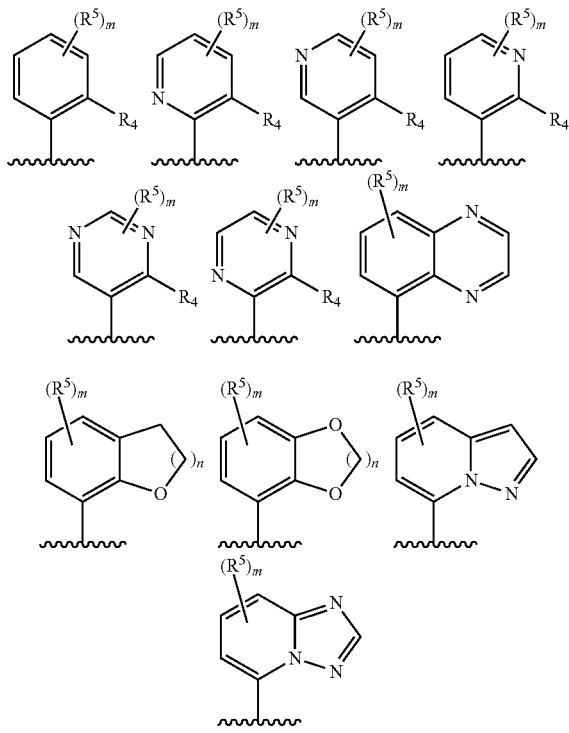

wherein, m, n, $R^4$ and $R^5$ are as defined in (7-A).

(9) The biaryl derivative of (7) or (8) or a salt therefor, wherein $R^4$ is a halogen atom, a cyano group, a $C_1$-$C_6$ alkyl group, a $C_1$-$C_6$ haloalkyl group, a $C_3$-$C_7$ cycloalkyl group, a $C_1$-$C_6$ alkoxy group, a $C_1$-$C_6$ haloalkoxy group, a vinyl group, an ethynyl group or a $C_1$-$C_6$ alkylthio group.

(10) The biaryl derivative of (9) or a salt thereof, wherein $R^4$ is a halogen atom, a $C_1$-$C_4$ alkyl group, a $C_1$-$C_4$ haloalkyl group, a cyclopropyl group, a $C_1$-$C_4$ alkoxy group or a $C_1$-$C_4$ haloalkoxy group.

(11) The biaryl derivative of (1) or a salt thereof, wherein, in the aforementioned formula (I),
Q is O,
ring A is a ring selected from the group consisting of the following formulas:

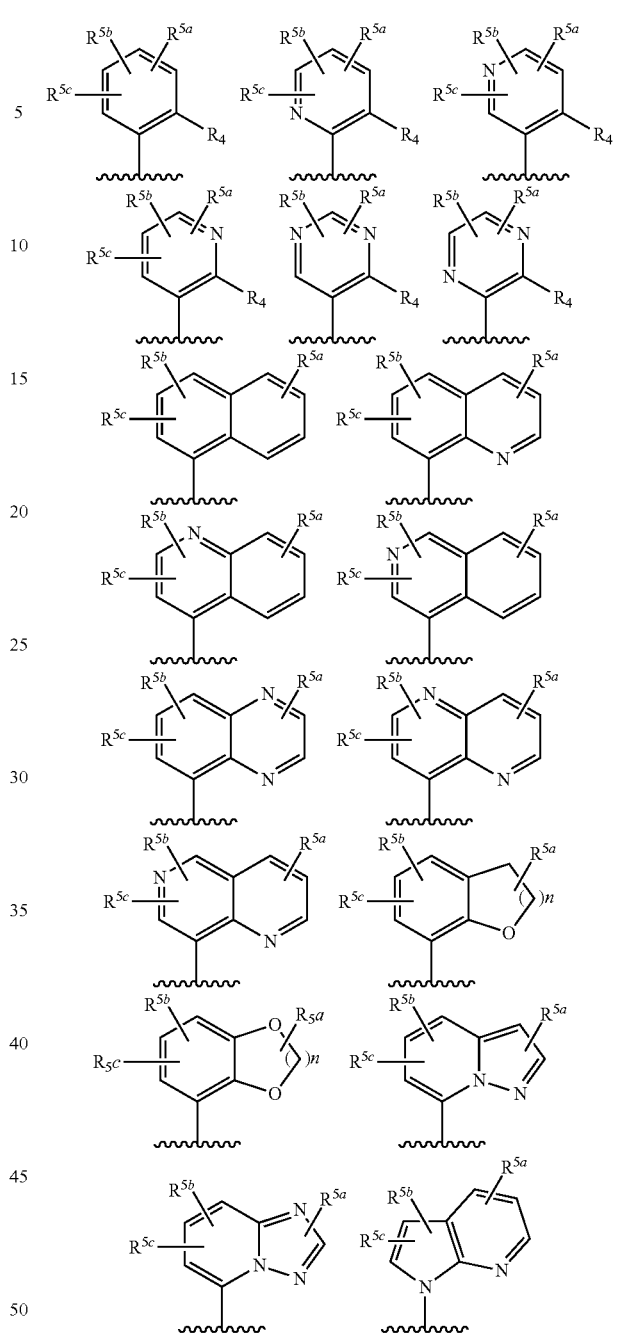

wherein n is 1 or 2,
$R^4$ is a halogen atom, a cyano group, a hydroxyl group, an optionally substituted $C_1$-$C_6$ alkyl group, a $C_1$-$C_6$ haloalkyl group, an optionally substituted $C_3$-$C_7$ cycloalkyl group, a heterocycloalkyl group, a 5-membered ring heteroaryl group, an optionally substituted $C_1$-$C_6$ alkoxy group, a $C_1$-$C_6$ haloalkoxy group, a $C_2$-$C_6$ alkenyl group, a $C_2$-$C_6$ alkynyl group, a $C_1$-$C_6$ alkylthio group, —$NR^dR^e$ ($R^d$ and $R^e$ are each independently a hydrogen atom or a $C_1$-$C_6$ alkyl group), a nitro group, a formyl group, a $C_1$-$C_6$ alkylcarbonyl group, a $C_1$-$C_6$ alkoxycarbonyl group or a $C_1$-$C_6$ alkylcarbonyloxy group, and $R^{5a}$, $R^{5b}$ and $R^{5c}$ are each independently a hydrogen atom, a halogen atom, a cyano group, a $C_1$-$C_6$ alkyl group, a $C_1$-$C_6$ alkoxy group, a $C_1$-$C_6$ haloalkyl group, a $C_1$-$C_6$ haloalkoxy group, a $C_3$-$C_7$ cycloalkyl group, a $C_1$-$C_6$ alkylcarbonyl group or a $C_1$-$C_6$ alkoxycarbonyl group.

(11-A) The biaryl derivative of (1) or a salt thereof, wherein, in the aforementioned formula (I),
Q is O,
ring A is a ring selected from the group consisting of the following formulas

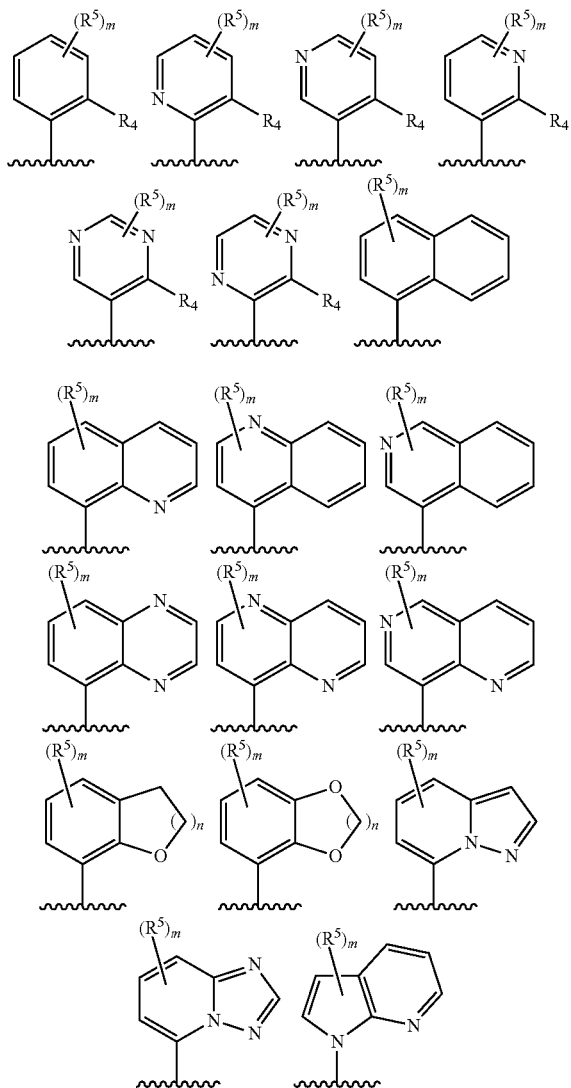

wherein m, is 0, 1 or 2,
n is 1 or 2,
$R^4$ is a halogen atom, a cyano group, a hydroxyl group, an optionally substituted $C_1$-$C_6$ alkyl group, a $C_1$-$C_6$ haloalkyl group, an optionally substituted $C_3$-$C_7$ cycloalkyl group, a heterocycloalkyl group, a 5-membered ring heteroaryl group, an optionally substituted $C_1$-$C_6$ alkoxy group, a $C_1$-$C_6$ haloalkoxy group, a $C_2$-$C_6$ alkenyl group, a $C_2$-$C_6$ alkynyl group, a $C_1$-$C_6$ alkylthio group, —$NR^dR^e$ ($R^d$ and $R^e$ are each independently a hydrogen atom or a $C_1$-$C_6$ alkyl group), a nitro group, a formyl group, a $C_1$-$C_6$ alkylcarbonyl group, a $C_1$-$C_6$ alkoxycarbonyl group or a $C_1$-$C_6$ alkylcarbonyloxy group, and
each $R^5$ is independently a hydrogen atom, a halogen atom, a cyano group, a $C_1$-$C_6$ alkyl group, a $C_1$-$C_6$ alkoxy group, a $C_1$-$C_6$ haloalkyl group, a $C_1$-$C_6$ haloalkoxy group, a $C_3$-$C_7$ cycloalkyl group, a $C_1$-$C_6$ alkylcarbonyl group or a $C_1$-$C_6$ alkoxycarbonyl group.

(12) The biaryl derivative of any one of (1)-(5) or a salt thereof, wherein, in the aforementioned formula (I), ring A is a 5-membered ring heteroaryl (said ring A is optionally further condensed to form an optionally substituted fused ring).

(13) The biaryl derivative of (12) or a salt thereof, wherein, in the aforementioned formula (I), ring A is a ring selected from the group consisting of the following formulas:

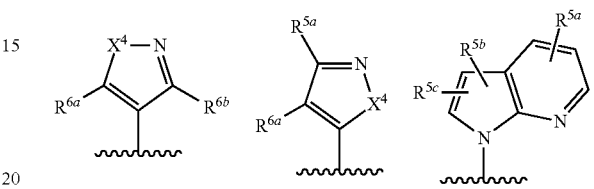

wherein $X^4$ is $NR^f$ ($R^f$ is a hydrogen atom or a $C_1$-$C_6$ alkyl group), O or S,
$R^{5a}$, $R^{5b}$ and $R^{5c}$ are each independently a hydrogen atom, a halogen atom, a cyano group, a $C_1$-$C_6$ alkyl group, a $C_1$-$C_6$ alkoxy group, a $C_1$-$C_6$ haloalkyl group, a $C_1$-$C_6$ haloalkoxy group, a $C_3$-$C_7$ cycloalkyl group, a $C_1$-$C_6$ alkylcarbonyl group or a $C_1$-$C_6$ alkoxycarbonyl group, and
$R^{6a}$ and $R^{6b}$ are each independently a hydrogen atom, a halogen atom, an optionally substituted $C_1$-$C_6$ alkyl group, a $C_1$-$C_6$ haloalkyl group, an optionally substituted $C_3$-$C_7$ cycloalkyl group, an optionally substituted $C_1$-$C_6$ alkoxy group, a $C_1$-$C_6$ haloalkoxy group, or an optionally substituted $C_1$-$C_6$ alkylthio group.

(13-A) The biaryl derivative of (12) or a salt thereof, wherein, in the aforementioned formula (I), ring A is a ring selected from the group consisting of the following formulas:

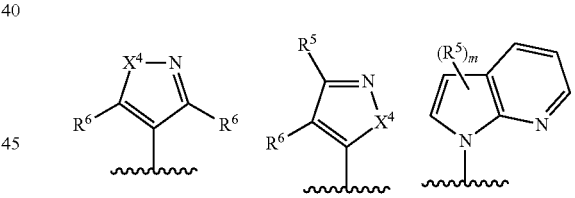

wherein $X^4$ is $NR^f$ ($R^f$ is a hydrogen atom or a $C_1$-$C_6$ alkyl group), O or S,
m is 0, 1 or 2,
each $R^5$ is independently a hydrogen atom, a halogen atom, a cyano group, a $C_1$-$C_6$ alkyl group, a $C_1$-$C_6$ alkoxy group, a $C_1$-$C_6$ haloalkyl group, a $C_1$-$C_6$ haloalkoxy group, a $C_3$-$C_7$ cycloalkyl group, a $C_1$-$C_6$ alkylcarbonyl group or a $C_1$-$C_6$ alkoxycarbonyl group, and
each $R^6$ is independently a hydrogen atom, a halogen atom, an optionally substituted $C_1$-$C_6$ alkyl group, a $C_1$-$C_6$ haloalkyl group, an optionally substituted $C_3$-$C_7$ cycloalkyl group, an optionally substituted $C_1$-$C_6$ alkoxy group, a $C_1$-$C_6$ haloalkoxy group, or an optionally substituted $C_1$-$C_6$ alkylthio group).

(14) the biaryl derivative of any one of (1)-(13) or a salt thereof, wherein, in the aforementioned formula (I), when Z is $CR^{2b}$, $R^{2a}$ and $R^{2b}$ are each independently a hydrogen atom, a halogen atom, a cyano group, an optionally substituted $C_1$-$C_6$ alkyl group, an optionally substituted $C_1$-$C_6$ haloalkyl group, an optionally substituted $C_1$-$C_6$ alkoxy group, an optionally substituted $C_1$-$C_6$ haloalkoxy group, an optionally substituted $C_1$-$C_6$ alkoxy-$C_1$-$C_4$ alkyl group, an optionally substituted $C_1$-$C_4$ alkoxy-$C_1$-$C_4$ haloalkyl group, an optionally substituted $C_1$-$C_6$ alkylcarbonyl group, an optionally substituted $C_1$-$C_6$ alkoxycarbonyl group, an optionally substituted $C_3$-$C_7$ cycloalkyl group, an optionally substituted heterocycloalkyl group, an optionally substituted $C_2$-$C_6$ alkenyl-$C_1$-$C_6$ alkoxy group, an optionally substituted $C_2$-$C_6$ alkynyl-$C_1$-$C_6$ alkoxy group, —$NR^aR^b$ {$R^a$ and $R^b$ are each independently a hydrogen atom or an optionally substituted $C_1$-$C_6$ alkyl group (provided that $R^a$ and $R^b$ are not hydrogen atoms at the same time)}, an optionally substituted $C_1$-$C_6$ alkylthio group, a pentafluorosulfanyl group, or a group represented by the formula (I-A)

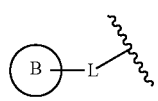

(I-A)

{wherein,

L is a single bond, —$(CH_2)_p$—, —$O(CH_2)_p$—, —$(CH_2)_pO$—, —$NR^c(CH_2)_p$— or —$(CH_2)_pNR^c$, wherein one or more hydrogen atoms of $(CH_2)_p$ are optionally substituted by a halogen atom, p is 1 or 2, $R^c$ is a hydrogen atom or a methyl group, and ring B is an optionally substituted phenyl, or an optionally substituted 5- or 6-membered ring heteroaryl} or $R^{2a}$ and $R^{2b}$ optionally form, together with carbon atoms bonded thereto, an optionally substituted carbocycle.

(14-A) The biaryl derivative of (14) or a salt thereof, wherein, in the aforementioned formula (I), when Z is $CR^{2b}$, $R^{2a}$ and $R^{2b}$ are each independently a hydrogen atom, a halogen atom, a cyano group, an optionally substituted $C_1$-$C_6$ alkyl group, a $C_1$-$C_6$ haloalkyl group, an optionally substituted $C_1$-$C_6$ alkoxy group, a $C_1$-$C_6$ haloalkoxy group, a $C_1$-$C_4$ alkoxy-$C_1$-$C_4$ alkyl group, a $C_1$-$C_4$ alkoxy-$C_1$-$C_4$ haloalkyl group, an optionally substituted $C_1$-$C_6$ alkylcarbonyl group, an optionally substituted $C_1$-$C_6$ alkoxycarbonyl group, an optionally substituted $C_3$-$C_7$ cycloalkyl group, an optionally substituted heterocycloalkyl group, an optionally substituted $C_2$-$C_6$ alkenyl-$C_1$-$C_6$ alkoxy group, an optionally substituted $C_2$-$C_6$ alkynyl-$C_1$-$C_6$ alkoxy group, —$NR^aR^b$ {$R^a$ and $R^b$ are each independently a hydrogen atom or an optionally substituted $C_1$-$C_6$ alkyl group (provided that $R^a$ and $R^b$ are not hydrogen atoms at the same time)}, an optionally substituted $C_1$-$C_6$ alkylthio group, a pentafluorosulfanyl group, or a group represented by the formula (I-A) {wherein L is —$(CH_2)_p$—, —$O(CH_2)_p$—, —$(CH_2)_pO$—, —$NR^c(CH_2)_p$— or —$(CH_2)_pNR^c$—, wherein $(CH_2)_p$ is optionally substituted by a halogen atom, and p, $R^c$ and ring B are as defined in (14)}, or $R^{2a}$ and $R^{2b}$ optionally form, together with carbon atoms bonded thereto, an optionally substituted carbocycle.

(15) The biaryl derivative of (14) or a salt thereof, wherein, in the aforementioned formula (I), when Z is $CR^{2b}$, $R^{2a}$ and $R^{2b}$ are each independently a hydrogen atom, a $C_1$-$C_4$ alkyl group, a $C_1$-$C_4$ haloalkyl group, a $C_1$-$C_4$ alkoxy group, a $C_1$-$C_4$ haloalkoxy group, a $C_1$-$C_4$ alkoxy-$C_1$-$C_4$ alkyl group, a $C_1$-$C_4$ alkoxy-$C_1$-$C_4$ haloalkyl group or a $C_3$-$C_7$ cycloalkyl group (provided that $R^{2a}$ and $R^{2b}$ are not hydrogen atoms at the same time).

(16) The biaryl derivative of any one of (1)-(15) or a salt thereof, wherein, in the aforementioned formula (I), when Z is $CR^{2b}$, $R^{2b}$ is a hydrogen atom or a $C_1$-$C_4$ alkyl group.

(17) The biaryl derivative of (1) or a salt thereof, wherein the compound represented by the aforementioned formula (I) is any of:

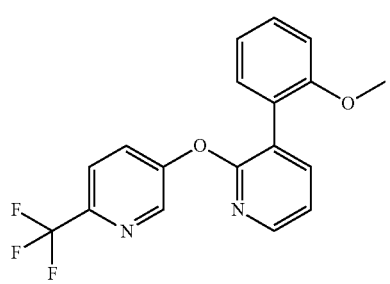

(I-1)

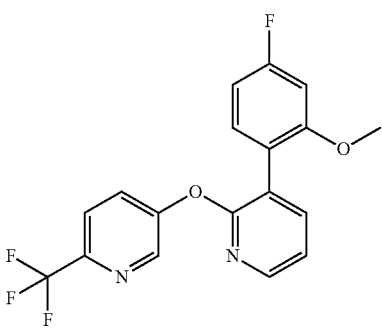

(I-12)

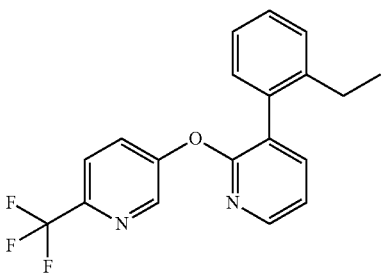

(I-16)

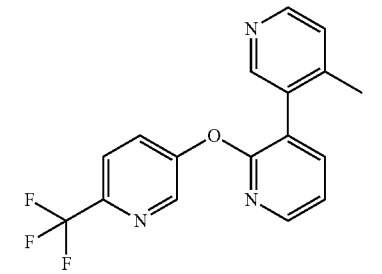

(I-25)

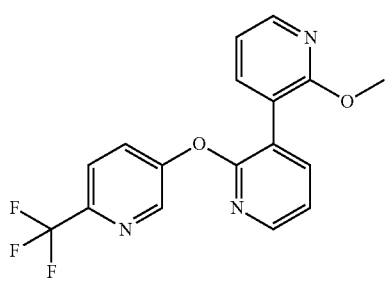
(I-26)
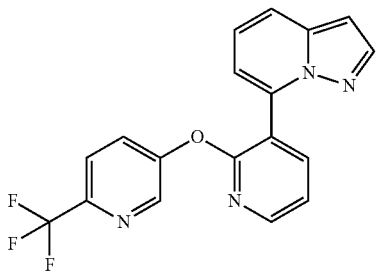
(I-44)
(I-28)
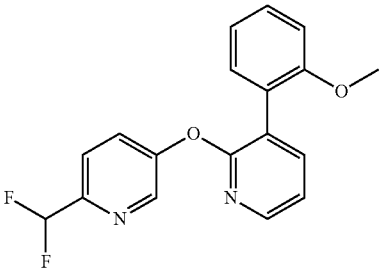
(I-72)
(I-31)
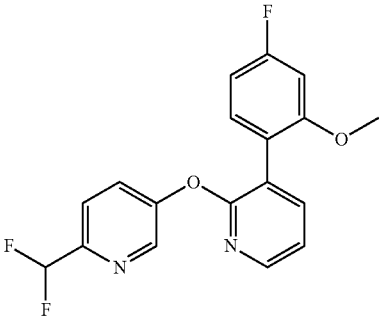
(I-73)
(I-35)
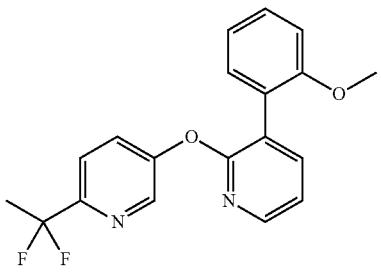
(I-81)
(I-37)
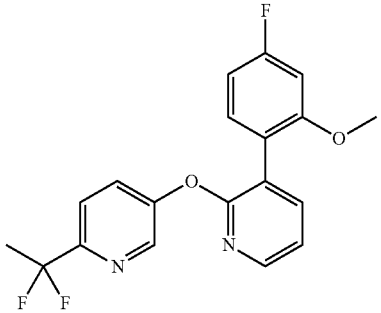
(I-82)

(I-83)
(I-84)
(I-88)
(I-90)
(I-96)
(I-100)
(I-110)
(I-115)
(I-117)
(I-119)

(I-120) 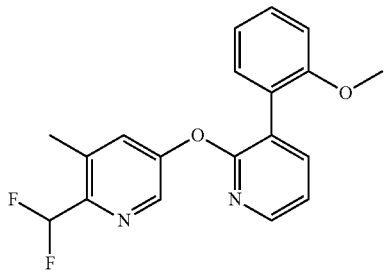
(I-121) 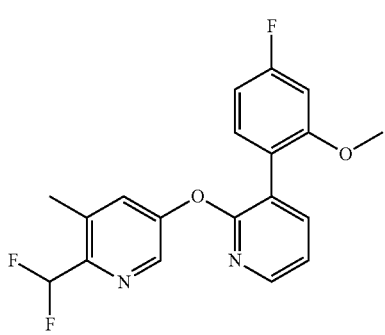
(I-125) 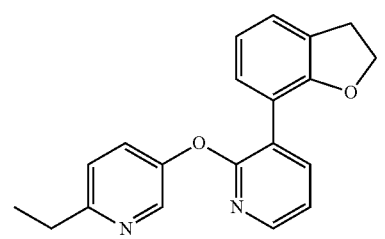
(I-134) 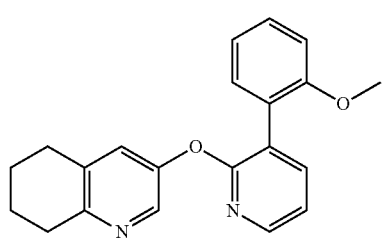
(I-145) 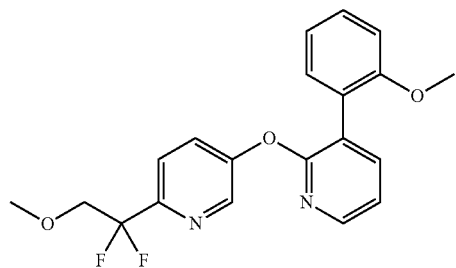
(I-161) 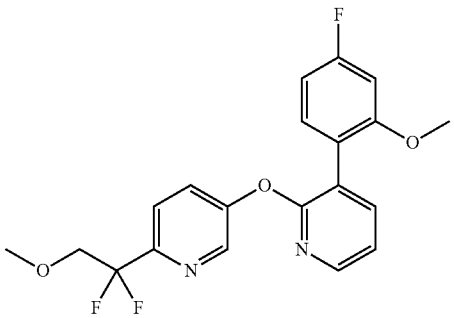
(I-162) 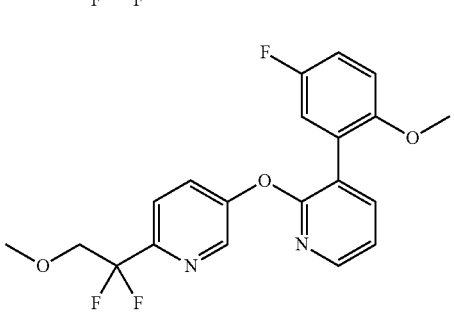
(I-179) 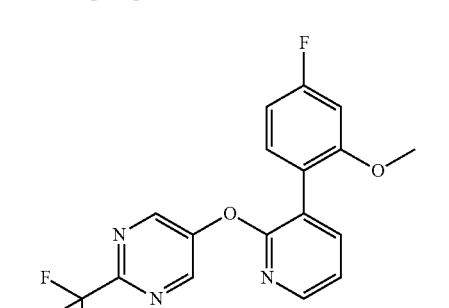
(I-185) 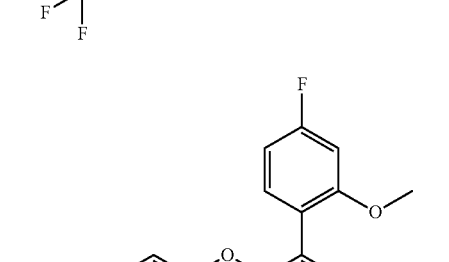
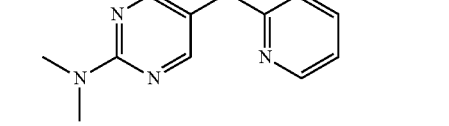
(I-192) 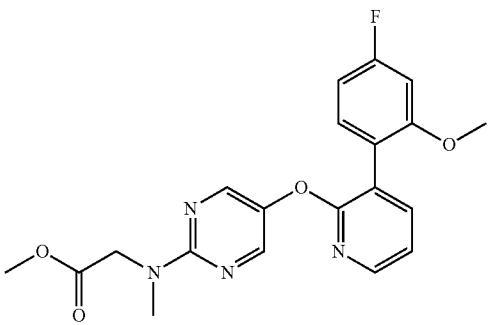

(I-201)
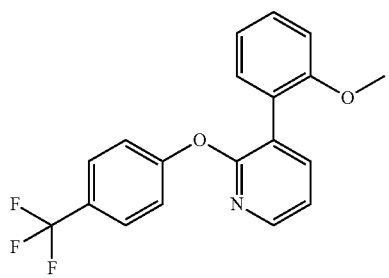
(I-206)
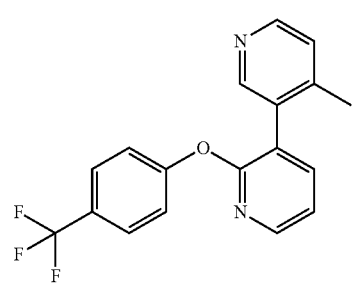
(I-210)
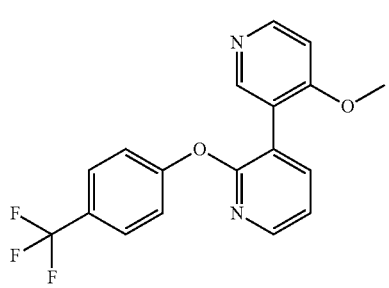
(I-212)
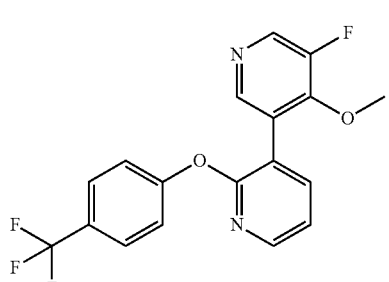
(I-216)
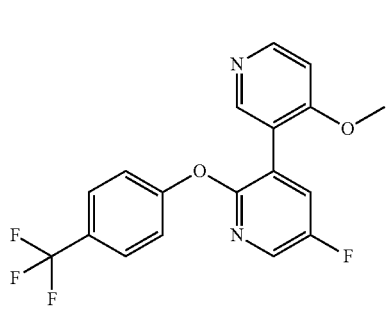
(I-218)
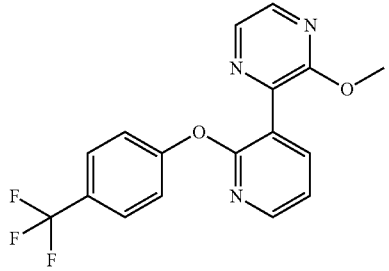
(I-219)
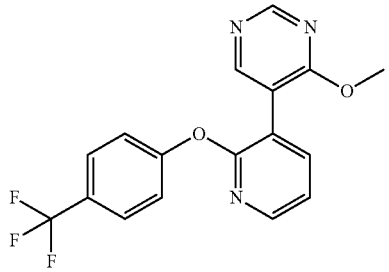
(I-226)
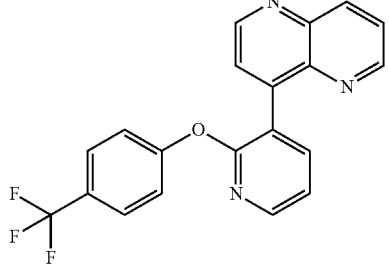
(I-227)
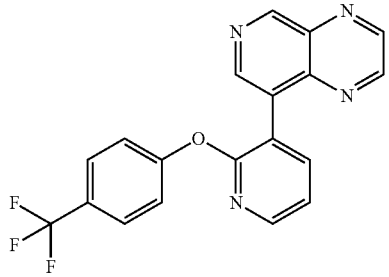
(I-228)
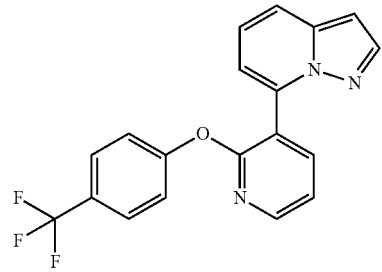
(I-235)
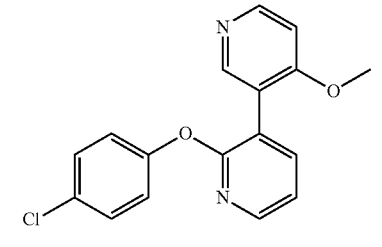

(I-237)
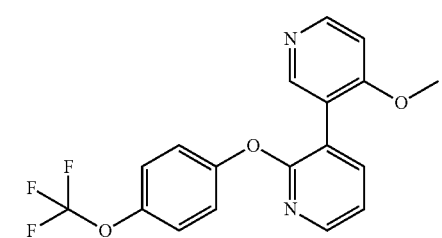
(I-245)
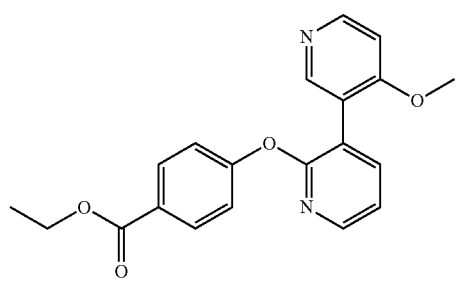
(I-252)
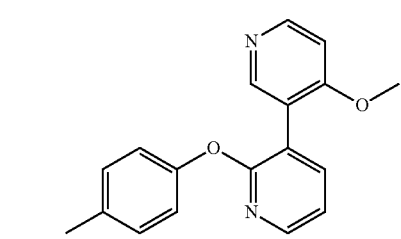
(I-253)
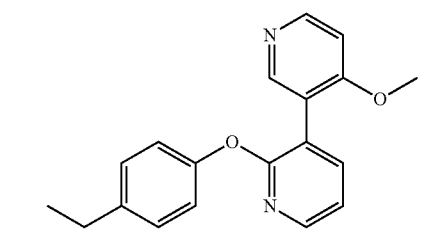
(I-261)
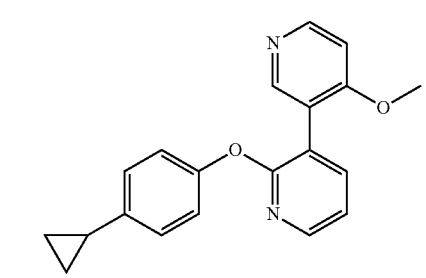
(I-269)
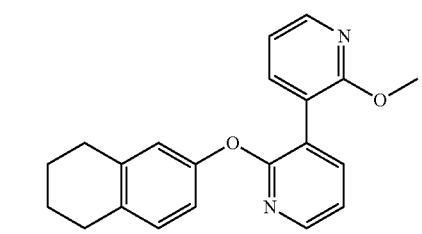
(I-282)
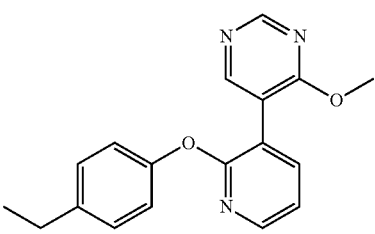
(I-294)
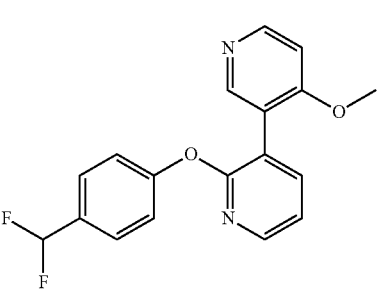
(I-295)
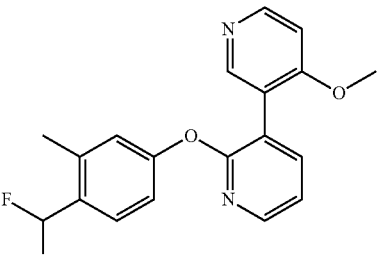
(I-297)
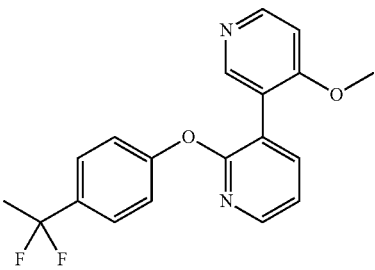
(I-298)
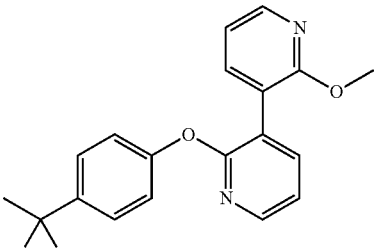
(I-303)
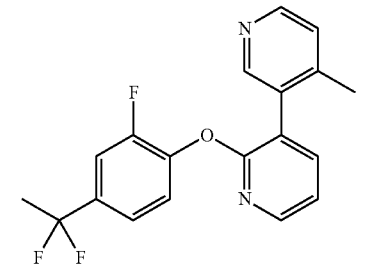

(I-304) 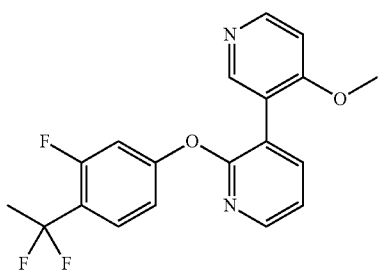
(I-310) 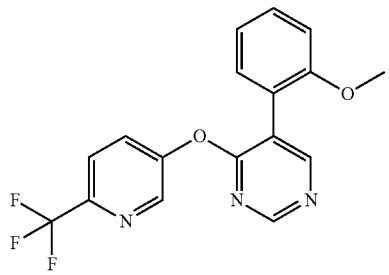
(I-312) 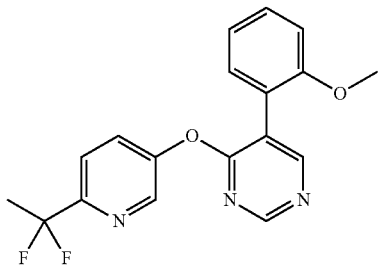
(I-317) 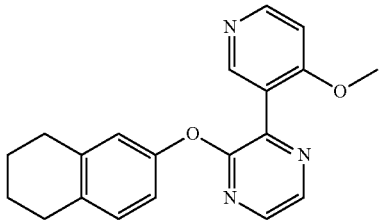
(I-324) 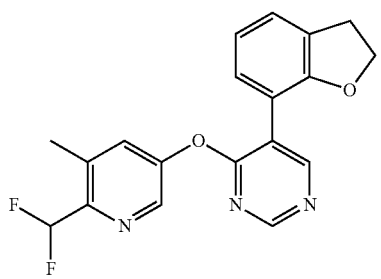
(I-330) 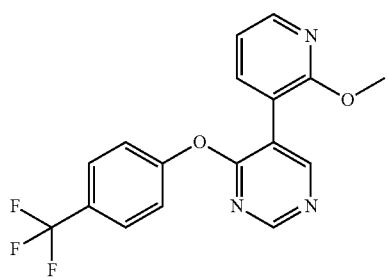
(I-335) 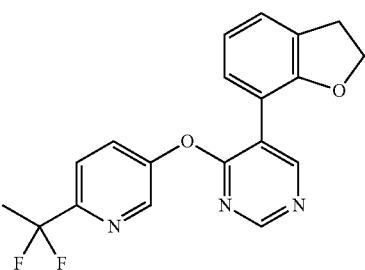
(I-343) 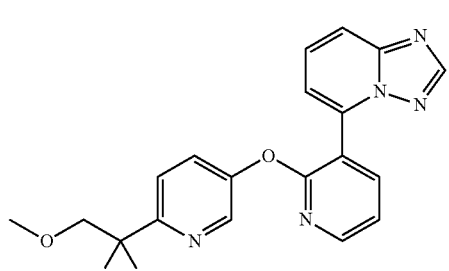
(I-350) 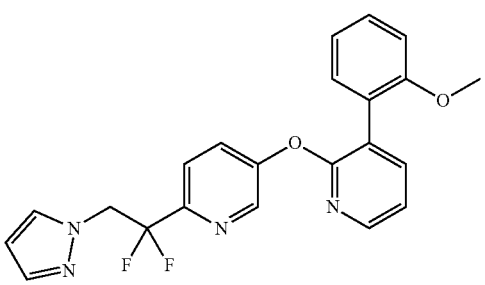
(I-354) 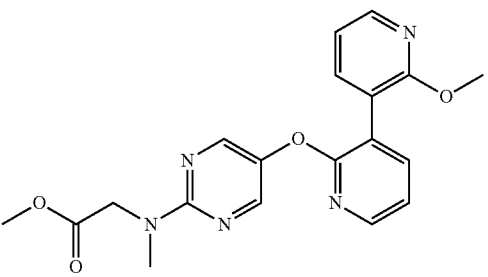
(I-355) 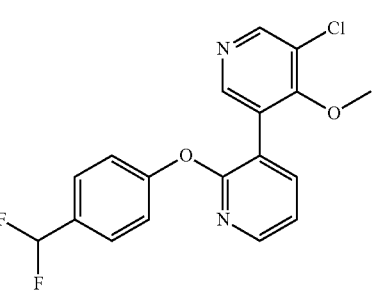

-continued (I-356)
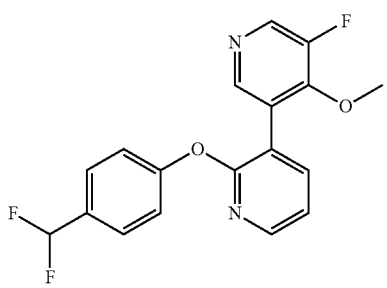

(I-358)
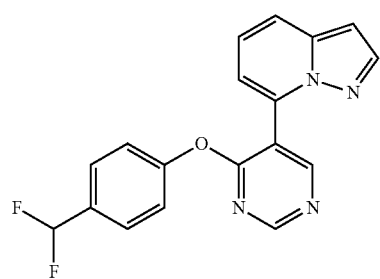

(I-359)
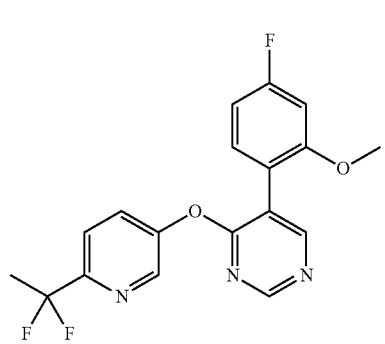

(I-360)
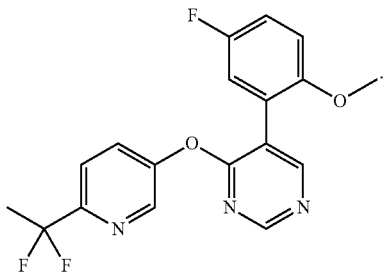

(18) A medicament comprising the biaryl derivative of any one of (1)-(17) or a salt thereof.
(19) an antifungal agent comprising the biaryl derivative of any one of (1)-(17) or a salt thereof as an active ingredient.
(20) A therapeutic agent for superficial mycosis, comprising the biaryl derivative of any one of (1)-(17) or a salt thereof as an active ingredient.
(21) A therapeutic agent for tinea unguium, comprising the biaryl derivative of any one of (1)-(17) or a salt thereof as an active ingredient.
(22) Use of the biaryl derivative of any one of (1)-(17) or a salt thereof in the production of an antifungal agent, a therapeutic agent for superficial mycosis or a therapeutic agent for tinea unguium.
(23) Use of the biaryl derivative of any one of (1)-(17) or a salt thereof for use in the prophylaxis or treatment of fungal infections, superficial mycosis or tinea unguium.
(24) A method for preventing or treating fungal infections, superficial mycosis or tinea unguium in a mammal, comprising administering an effective amount of the biaryl derivative of any one of (1)-(17) or a salt thereof to the mammal.

Effect of the Invention

The biaryl derivative or a salt thereof of the present invention has an excellent antifungal activity against *Trichophyton* fungi which is a major causative microorganism of superficial mycosis, and is useful as a prophylactic or therapeutic drug for infections caused by *Trichophyton* fungi in mammals including human. Moreover, since the biaryl derivative or a salt thereof of the present invention also has excellent nail permeability, it is particularly useful as a topical therapeutic agent for tinea unguium.

DESCRIPTION OF EMBODIMENTS

Each substituent in the aforementioned formula (I) is explained below.

Specific examples of the "halogen atom" include fluorine atom, chlorine atom, bromine atom or iodine atom.

The "$C_1$-$C_6$ alkyl group" means a straight chain or branched alkyl group having 1-6 carbon atoms, and specific examples thereof include methyl group, ethyl group, n-propyl group, isopropyl group, n-butyl group, isobutyl group, tert-butyl group, sec-butyl group, n-pentyl group, tert-pentyl group, 3-methylbutyl group (isopentyl group), neopentyl group, n-hexyl group and the like.

The "$C_1$-$C_4$ alkyl group" means a straight chain or branched alkyl group having 1-4 carbon atoms, and specific examples thereof include methyl group, ethyl group, n-propyl group, isopropyl group, n-butyl group, isobutyl group, tert-butyl group, sec-butyl group and the like.

The "$C_1$-$C_6$ haloalkyl group" means an alkyl group wherein one or more hydrogen atoms of the aforementioned "$C_1$-$C_6$ alkyl group" are substituted by a halogen atom, and specific examples thereof include trifluoromethyl group, difluoromethyl group, monofluoromethyl group, 1,1-difluoroethyl group, 2,2,2-trifluoroethyl group, 1,1,2-trifluoroethyl group, 1,1,2,2,2-pentafluoroethyl group, 2-bromo-1,1-difluoroethyl group and the like.

The "$C_1$-$C_4$ haloalkyl group" means an alkyl group wherein one or more hydrogen atoms of the aforementioned "$C_1$-$C_4$ alkyl group" are substituted by a halogen atom, and specific examples thereof include trifluoromethyl group, difluoromethyl group, monofluoromethyl group, 1,1-difluoroethyl group, 2,2,2-trifluoroethyl group, 1,1,2-trifluoroethyl group, 1,1,2,2,2-pentafluoroethyl group, 2-bromo-1,1-difluoroethyl group and the like.

The "$C_1$-$C_6$ alkoxy group" means an alkoxy group wherein the alkyl moiety is as defined in the aforementioned "$C_1$-$C_6$ alkyl group", and specific examples thereof include methoxy group, ethoxy group, n-propoxy group, isopropoxy group, n-butoxy group, isobutoxy group, tert-butoxy group, sec-butoxy group, n-pentyloxy group, tert-amyloxy group, 3-methylbutoxy group, neopentyloxy group, n-hexyloxy group and the like.

The "$C_1$-$C_4$ alkoxy group" means an alkoxy group wherein the alkyl moiety is as defined in the aforementioned "$C_1$-$C_4$ alkyl group", and specific examples thereof include methoxy group, ethoxy group, n-propoxy group, isopropoxy group, n-butoxy group, isobutoxy group, tert-butoxy group, sec-butoxy group and the like.

The "$C_1$-$C_6$ haloalkoxy group" means a haloalkoxy group wherein the haloalkyl moiety is as defined in the aforementioned "$C_1$-$C_6$ haloalkyl group", and specific examples thereof include trifluoromethoxy group, difluoromethoxy group, 2,2,2-trifluoroethoxy group and the like.

The "$C_1$-$C_4$ haloalkoxy group" means a haloalkoxy group wherein the haloalkyl moiety is as defined in the aforementioned "$C_1$-$C_4$ haloalkyl group", and specific examples thereof include trifluoromethoxy group, difluoromethoxy group, 2,2,2-trifluoroethoxy group and the like.

The "$C_1$-$C_4$ alkoxy-$C_1$-$C_4$ alkyl group" is the aforementioned "$C_1$-$C_4$ alkyl group" substituted by the aforementioned "$C_1$-$C_4$ alkoxy group", and these can be bonded at any substitutable positions. For example, methoxymethyl group, ethoxymethyl group, methoxyethyl group, ethoxyethyl group and the like can be mentioned.

The "$C_1$-$C_4$ alkoxy-$C_1$-$C_4$ haloalkyl group" is the aforementioned "$C_1$-$C_4$ haloalkyl group" substituted by the aforementioned "$C_1$-$C_4$ alkoxy group", and these can be bonded at any substitutable positions. For example, difluoro(methoxy)methyl group, difluoro(ethoxy)methyl group, 1,1-difluoro-2-methoxyethyl group, 1,1-difluoro-2-ethoxyethyl and the like can be mentioned.

The "$C_1$-$C_6$ alkylcarbonyl group" means an alkylcarbonyl group wherein the alkyl moiety is the aforementioned "$C_1$-$C_6$ alkyl group", and specific examples thereof include methylcarbonyl group, ethylcarbonyl group, n-propylcarbonyl group, isopropylcarbonyl group, n-butylcarbonyl group, isobutylcarbonyl group, tert-butylcarbonyl group, sec-butylcarbonyl group, n-pentylcarbonyl group, tert-amylcarbonyl group, 3-methylbutylcarbonyl group, neopentylcarbonyl group, n-hexylcarbonyl group and the like.

The "$C_1$-$C_6$ alkoxycarbonyl group" means an alkoxycarbonyl group wherein the alkoxy moiety is the aforementioned "$C_1$-$C_6$ alkoxy group", and specific examples thereof include methoxycarbonyl group, ethoxycarbonyl group, n-propoxycarbonyl group, isopropoxycarbonyl group, n-butoxycarbonyl group, isobutoxycarbonyl group, tert-butoxycarbonyl group, sec-butoxycarbonyl group, n-pentyloxycarbonyl group, tert-pentyloxycarbonyl group, 3-methylbutoxycarbonyl group, neopentyloxycarbonyl group, n-hexyloxycarbonyl group and the like.

The "$C_1$-$C_6$ alkylcarbonyloxy group" means an alkylcarbonyloxy group wherein the alkylcarbonyl moiety is the aforementioned "$C_1$-$C_6$ alkylcarbonyl group", and specific examples thereof include methylcarbonyloxy group, ethylcarbonyloxy group, n-propylcarbonyloxy group, isopropylcarbonyloxy group and the like.

The "$C_3$-$C_7$ cycloalkyl group" is a monocyclic saturated carbocyclic group having 3-7 carbon atoms. Specific examples thereof include cyclopropyl group, cyclobutyl group, cyclopentyl group, cyclohexyl group, cycloheptyl group and the like.

The "heterocycloalkyl group" is a monocyclic saturated heterocyclic group. Specific examples thereof include pyrrolidinyl group (e.g., 1-pyrrolidinyl group, 2-pyrrolidinyl group, 3-pyrrolidinyl group), piperidinyl group (e.g., 1-piperidinyl group, 4-piperidinyl group), homopiperidinyl group (e.g., 1-homopiperidinyl group, 4-homopiperidinyl group), tetrahydrofuranyl group (e.g., 2-tetrahydrofuranyl group, 3-tetrahydrofuranyl group), tetrahydropyranyl group (e.g., 4-tetrahydropyranyl group), piperazinyl group (e.g., 1-piperazinyl group), homopiperazinyl group (e.g., 1-homopiperazinyl group), morpholino group and the like. Suitable examples of the "heterocycloalkyl group" include a 5- to 7-membered monocyclic saturated heterocyclic group containing, besides carbon atom, one or more (e.g., 1-4) hetero atoms selected from a nitrogen atom, a sulfur atom and an oxygen atom.

The "heterocycloalkyloxy group" means a heterocycloalkyloxy group wherein the heterocycloalkyl moiety is the aforementioned "heterocycloalkyl group", and specific examples thereof include pyrrolidinyloxy group, and tetrahydropyranyloxy group.

The "$C_2$-$C_6$ alkenyl group" means a straight chain or branched alkenyl group having 2-6 carbon atoms and having one or more double bonds, and specific examples thereof include vinyl group, 1-propenyl group, isopropenyl group, allyl group, 2-methylallyl group, 1-butenyl group, 2-butenyl group, 3-butenyl group, isobutenyl group, 2-methyl-1-propenyl group, 1-methyl-1-propenyl group, 1-pentenyl group, 2-pentenyl group, 1-hexenyl group, 2-methylbut-3-en-1-yl group and the like.

The "$C_2$-$C_6$ alkenyloxy group" means an alkenyloxy group wherein the alkenyl moiety is the aforementioned "$C_2$-$C_6$ alkenyl group", and specific examples thereof include vinyloxy group, allyloxy group, 1-butenyloxy group, 2-butenyloxy group, 3-butenyloxy group and the like.

The "$C_2$-$C_6$ alkenyl-$C_1$-$C_6$ alkyl group" is the aforementioned "$C_1$-$C_6$ alkyl group" substituted by the aforementioned "$C_2$-$C_6$ alkenyl group", and these can be bonded at any substitutable positions. For example, allyl group, 2-methylallyl group, but-3-en-1-yl group, 2-methylbut-3-en-1-yl group and the like can be mentioned.

The "$C_2$-$C_6$ alkenyl-$C_1$-$C_6$ alkoxy group" is the aforementioned "$C_1$-$C_6$ alkoxy group" substituted by the aforementioned "$C_2$-$C_6$ alkenyl group", and these can be bonded at any substitutable positions. For example, allyloxy group, 2-methylallyloxy group, but-3-en-1-yloxy group, 2-methylbut-3-en-1-yloxy group and the like can be mentioned.

The "$C_2$-$C_6$ alkenyloxy-$C_1$-$C_4$ alkyl group" is the aforementioned "$C_1$-$C_4$ alkyl group" substituted by the aforementioned "$C_2$-$C_6$ alkenyloxy", and these can be bonded at any substitutable positions. For example, allyloxymethyl group and the like can be mentioned.

The "$C_2$-$C_6$ alkenyloxy-$C_1$-$C_4$ alkoxy group" is the aforementioned "$C_1$-$C_4$ alkoxy group" substituted by the aforementioned "$C_2$-$C_6$ alkenyloxy", and these can be bonded at any substitutable positions. For example, allyloxymethoxy group and the like can be mentioned.

The "$C_2$-$C_6$ alkenyloxy-$C_1$-$C_4$ haloalkyl group" is the aforementioned "$C_1$-$C_4$ haloalkyl group" substituted by the aforementioned "$C_2$-$C_6$ alkenyloxy", and these can be bonded at any substitutable positions.

The "$C_2$-$C_6$ alkenyloxy-$C_1$-$C_4$ haloalkoxy group" is the aforementioned "$C_1$-$C_4$ haloalkoxy group" substituted by the aforementioned "$C_2$-$C_6$ alkenyloxy", and these can be bonded at any substitutable positions.

The "$C_2$-$C_6$ alkynyl group" means a straight chain or branched alkynyl group having 2-6 carbon atoms and having one or more triple bonds, and specific examples thereof include ethynyl group, 1-propynyl group, 2-propynyl group, 1-butynyl group, 2-butynyl group, 3-butynyl group, 3-methyl-1-butynyl group, 1-pentynyl group, 2-pentynyl group, 3-methyl-1-pentynyl group, 4-methyl-2-pentynyl group, 1-hexynyl group and the like.

The "$C_2$-$C_6$ alkynyloxy group" means an alkynyloxy group wherein the alkynyl moiety is the aforementioned "$C_2$-$C_6$ alkynyl group", and specific examples thereof include 2-propynyloxy group, 2-butynyloxy group, 2-pentynyloxy group, 4-methyl-2-pentynyloxy group and the like.

The "$C_2$-$C_6$ alkynyl-$C_1$-$C_6$ alkyl group" is the aforementioned "$C_1$-$C_6$ alkyl group" substituted by the aforementioned "$C_2$-$C_6$ alkynyl group", and these can be bonded at any substitutable positions. For example, 2-propynyl group, 2-butynyl group, 2-pentynyl group, 4-methyl-2-pentynyl group and the like can be mentioned.

The "$C_2$-$C_6$ alkynyl-$C_1$-$C_6$ alkoxy group" is the aforementioned "$C_1$-$C_6$ alkoxy group" substituted by the aforementioned "$C_2$-$C_6$ alkynyl group", and these can be bonded at any substitutable positions. For example, 2-propynyloxy group, 2-butynyloxy group, 2-pentynyloxy group, 4-methyl-2-pentynyloxy group and the like can be mentioned.

The "$C_2$-$C_6$ alkynyloxy-$C_1$-$C_4$ alkyl group" is the aforementioned "$C_1$-$C_4$ alkyl group" substituted by the aforementioned "$C_2$-$C_6$ alkynyloxy", and these can be bonded at any substitutable positions.

The "$C_2$-$C_6$ alkynyloxy-$C_1$-$C_4$ alkoxy group" is the aforementioned "$C_1$-$C_4$ alkoxy group" substituted by the aforementioned "$C_2$-$C_6$ alkynyloxy", and these can be bonded at any substitutable positions.

The "$C_2$-$C_6$ alkynyloxy-$C_1$-$C_4$ haloalkyl group" is the aforementioned "$C_1$-$C_4$ haloalkyl group" substituted by the aforementioned "$C_2$-$C_6$ alkynyloxy", and these can be bonded at any substitutable positions. Specific examples thereof include 1,1-difluoro-2-(prop-2-yn-1-yloxy)ethyl group and the like.

The "$C_2$-$C_6$ alkynyloxy-$C_1$-$C_4$ haloalkoxy group" is the aforementioned "$C_1$-$C_4$ haloalkoxy group" substituted by the aforementioned "$C_2$-$C_6$ alkynyloxy", and these can be bonded at any substitutable positions.

The "$C_1$-$C_6$ alkylthio group" means an alkylthio group wherein the alkyl moiety is as defined in the aforementioned "$C_1$-$C_6$ alkyl group", and specific examples thereof include methylthio group, ethylthio group, n-propylthio group, isopropylthio group, n-butylthio group, isobutylthio group, tert-butylthio group, sec-butylthio group, n-pentylthio group, tert-pentylthio group, 3-methylbutylthio group, neopentylthio group, n-hexylthio group and the like.

The "$C_1$-$C_6$ haloalkylthio group" means an alkylthio group wherein one or more hydrogen atoms of the aforementioned "$C_1$-$C_6$ alkylthio group" are substituted by a halogen atom, and specific examples thereof include trifluoromethylthio group and the like.

The "carbocycle" means phenyl, or 5- to 7-membered monocyclic saturated or unsaturated carbocycle. The "heterocycle" means "5- or 6-membered ring heteroaryl" or a 5- to 7-membered monocyclic saturated or unsaturated heterocycle. The "5- or 6-membered ring heteroaryl" means the "5-membered ring heteroaryl" or the "6-membered ring heteroaryl".

The "5-membered ring heteroaryl" is a 5-membered monocyclic aromatic heterocycle containing, besides carbon atom, one or more (e.g., 1-4) hetero atoms selected from a nitrogen atom, a sulfur atom and an oxygen atom. For example, pyrrole, furan, thiophene, imidazole, pyrazole, oxazole, isoxazole, thiazole, isothiazole, thiadiazole, oxadiazole, triazole, tetrazole and the like can be mentioned.

Examples of the "5-membered ring heteroaryl" group include pyrrolyl group (e.g., 2-pyrrolyl group), furyl group (e.g., 3-furyl group), thienyl group (e.g., 2-thienyl group), imidazolyl group (e.g., 4-imidazolyl group), pyrazolyl group (e.g., 3-pyrazolyl group), oxazolyl group (e.g., 2-oxazolyl group), isoxazolyl group (e.g., 3-isoxazolyl group, 4-isoxazolyl group, 5-isoxazolyl group), thiazolyl group (e.g., 2-thiazolyl group, 5-thiazolyl group), isothiazolyl group (e.g., 3-isothiazolyl group, 4-isothiazolyl group), thiadiazolyl group, oxadiazolyl group, triazolyl group (e.g., 1,2,3-triazol-2-yl group), tetrazolyl group and the like.

The "6-membered ring heteroaryl" means a 6-membered monocyclic aromatic heterocycle containing besides carbon atom, one or more (e.g., 1-3) nitrogen atoms. For example, pyridine, pyridazine, pyrimidine, pyrazine, triazine and the like can be mentioned.

Examples of the "6-membered ring heteroaryl" group include pyridyl group (e.g., 2-pyridyl group, 3-pyridyl group, 4-pyridyl group), pyridazinyl group (e.g., 3-pyridazinyl group), pyrimidinyl group (e.g., 5-pyrimidinyl group), pyrazinyl group (e.g., 2-pyrazinyl group) and the like.

Ring A may be "further condensed to form an optionally substituted fused ring". Here, "further condensed" means that carbocyclo or heterocycle is further condensed at a position in ring A where condensation is possible. For example, when ring A is "phenyl", "fused ring wherein phenyl and carbocycle are condensed" or "fused ring wherein phenyl and heterocycle are condensed" is formed; when ring A "5-membered ring heteroaryl", "fused ring wherein 5-membered ring heteroaryl and carbocycle are condensed", or "fused ring wherein 5-membered ring heteroaryl and heterocycle are condensed" is formed; and when ring A is "6-membered ring heteroaryl", "fused ring wherein 6-membered ring heteroaryl and carbocycle are condensed" or "fused ring wherein 6-membered ring heteroaryl and heterocycle are condensed" is formed.

Examples of the aforementioned "fused ring wherein phenyl and carbocycle are condensed" include indane, indene, naphthalene, dihydronaphthalene, tetrahydronaphthalene and the like.

Examples of the group of "fused ring wherein phenyl and carbocycle are condensed" include indan-4-yl, indan-5-yl, 1H-inden-4-yl, 1H-inden-5-yl, naphthalene-1-yl, naphthalen-2-yl, 5,6-dihydronaphthalen-1-yl, 7,8-dihydronaphthalen-1-yl, 5,6-dihydronaphthalen-2-yl, 5,6,7,8-tetrahydronaphthalen-1-yl, 5,6,7,8-tetrahydronaphthalen-2-yl and the like.

Examples of the aforementioned "fused ring wherein phenyl and heterocycle are condensed" include quinoline, tetrahydroquinoline, isoquinoline, tetrahydroisoquinoline, quinoxaline, quinazoline, cinnoline, indole, indoline, isoindole, isoindoline, indazole, indazoline, benzofuran, dihydrobenzofuran, isobenzofuran, 1,3-benzodioxale, 1,4-benzodioxane, benzothiophene, benzimidazole, benzothiazole, benzoxazole, benzisoxazole, benzisothiazole, chromane, chromene and the like.

Examples of the group of "fused ring wherein phenyl and heterocycle are condensed" include quinolin-5-yl, quinolin-6-yl, quinolin-8-yl, isoquinolin-5-yl, isoquinolin-6-yl, quinoxalin-5-yl, quinoxalin-6-yl, quinazolin-5-yl, quinazolin-6-yl, indol-4-yl, indol-5-yl, benzofuran-4-yl, benzofuran-5-yl, dihydrobenzofuran-7-yl, benzo[d][1,3]dioxol-4-yl, 1,4-benzodioxan-5-yl, benzothiophen-4-yl, benzothiophen-5-yl, benzimidazol-4-yl, benzimidazol-5-yl, benzothiazol-4-yl, benzothiazol-5-yl, benzoxazol-4-yl, benzoxazol-5-yl, benzoxazol-7-yl, chroman-8-yl and the like.

Examples of the aforementioned "fused ring wherein 5-membered ring heteroaryl and carbocycle are condensed" include indole, benzofuran, benzothiophene, benzimidazole, benzothiazole, benzoxazole, indazole, benzisoxazole, benzisothiazole and the like.

Examples of the group of "fused ring wherein 5-membered ring heteroaryl and carbocycle are condensed" include indol-1-yl, indol-2-yl, indol-3-yl, benzofuran-2-yl, benzofuran-3-yl, benzothiophen-2-yl, benzothiophen-3-yl, benzimidazol-2-yl, benzoxazol-2-yl, benzothiazol-2-yl, indazol-3-yl, benzisoxazol-3-yl, benzisothiazol-3-yl and the like.

Examples of the aforementioned "fused ring wherein 5-membered ring heteroaryl and heterocycle are condensed" include pyrrolopyridine, pyrazolopyridine, pyrazolopyrimidine, imidazopyridine, triazolopyridine, dihydropyrazolooxazole and the like.

Examples of the group of "fused ring wherein 5-membered ring heteroaryl and heterocycle are condensed" include 1H-pyrrolo[2,3-b]pryidin-3-yl, 1H-pyrazolo[3,4-b]pyridin-3-yl, pyrazolo[1,5-a]pyridin-3-yl, 2,3-dihydropyrazolo[5,1-b]oxazol-7-yl, [5,6,7,8]tetrahydropyrazolo[5,1-b][1,3]oxazepin-3-yl and the like.

Examples of the aforementioned "fused ring wherein 6-membered ring heteroaryl and carbocycle are condensed" include quinoline, isoquinoline, quinazoline and the like.

Examples of the group of "fused ring wherein 6-membered ring heteroaryl and carbocycle are condensed" include quinolin-4-yl, isoquinolin-1-yl, isoquinolin-4-yl, quinazolin-4-yl and the like.

Examples of the aforementioned "fused ring wherein 6-membered ring heteroaryl and heterocycle are condensed" include pyrazolopyridine, pyrazolopyrimidine, imidazopyridine, imidazopyrimidine, imidazopyrazine, triazolopyridine, naphthyridine, pyridopyrazine, azaindazole and the like.

Examples of the group of "fused ring wherein 6-membered ring heteroaryl and heterocycle are condensed" include pyrazolo[1,5-a]pyridin-7-yl, pyrazolo[1,5-a]pyrimidin-7-yl, imidazo[1,5-a]pyridin-8-yl, imidazo[1,2-c]pyrimidin-8-yl, imidazo[1,2-a]pyridin-5-yl, [1,2,4]triazolo[1,5-a]pyridin-5-yl, 1,5-naphthyridin-4-yl, pyrido[3,4-b]pyrazin-8-yl, azaindazolyl and the like.

The "aralkyl group" is the aforementioned "$C_1$-$C_6$ alkyl group" substituted by a phenyl group, a 5-membered ring heteroaryl group, a 6-membered ring heteroaryl group or the like, and these can be bonded at any substitutable positions. For example, benzyl group, phenethyl group, 1-phenylethyl group, 1-phenylpropyl group, 3-phenylpropyl group and the like can be mentioned.

The term "substituted" in the present specification means, unless particularly indicated, that one or more hydrogen atoms are substituted by an atom other than a hydrogen atom or a functional group at any positions.

In the formula (I), the substituent of the "optionally substituted phenyl", and "optionally substituted 5- or 6-membered ring heteroaryl" for ring A is a substituent selected from the group consisting of a halogen atom, a cyano group, a hydroxyl group, an optionally substituted $C_1$-$C_6$ alkyl group (same as "optionally substituted $C_1$-$C_6$ alkyl group" for $R^4$), a $C_1$-$C_6$ haloalkyl group, an optionally substituted $C_3$-$C_7$ cycloalkyl group (same as "optionally substituted $C_3$-$C_7$ cycloalkyl group" for $R^4$), a heterocycloalkyl group, a heterocycloalkyloxy group, a 5-membered ring heteroaryl group, an optionally substituted $C_1$-$C_6$ alkoxy group (same as "optionally substituted $C_1$-$C_6$ alkoxy group" for $R^4$), a $C_1$-$C_6$ haloalkoxy group, a $C_2$-$C_6$ alkenyl group, a $C_2$-$C_6$ alkenyloxy group, a $C_2$-$C_6$ alkynyl group, a $C_2$-$C_6$ alkynyloxy group, a $C_1$-$C_6$ alkylthio group, —$NR^dR^e$ ($R^d$ and $R^e$ are each independently a hydrogen atom or a $C_1$-$C_6$ alkyl group), a nitro group, a formyl group, a $C_1$-$C_6$ alkylcarbonyl group, a $C_1$-$C_6$ alkoxycarbonyl group and a $C_1$-$C_6$ alkylcarbonyloxy group. One or more of these can be substituted at any substitutable positions.

In the formula (I), the substituent of the "optionally substituted fused ring", for ring A is a substituent selected from the group consisting of an oxo group, a halogen atom, a cyano group, a $C_1$-$C_6$ alkyl group, a $C_1$-$C_6$ alkoxy group, a $C_1$-$C_6$ haloalkyl group, a $C_1$-$C_6$ haloalkoxy group, a $C_3$-$C_7$ cycloalkyl group, a $C_1$-$C_6$ alkylcarbonyl group, a $C_1$-$C_6$ alkoxycarbonyl group and a $C_1$-$C_6$ alkylcarbonyloxy group. One or more of these can be substituted at any substitutable positions.

In the formula (I-A), the substituent of the "optionally substituted carbocycle", and "optionally substituted heterocycle" for ring B is a substituent selected from the group consisting of a halogen atom, a cyano group, a $C_1$-$C_6$ alkyl group, a $C_1$-$C_6$ haloalkyl group, a $C_1$-$C_6$ alkoxy group and a $C_1$-$C_6$ haloalkoxy group. One or more of these can be substituted at any substitutable positions.

In the formula (I), the substituent of the "optionally substituted $C_1$-$C_6$ alkyl group", "optionally substituted $C_1$-$C_6$ haloalkyl group", "optionally substituted $C_1$-$C_6$ alkoxy group", and "optionally substituted $C_1$-$C_6$ haloalkoxy group" for $R^{2a}$ and $R^{2b}$ is a substituent selected from the group consisting of a halogen atom, a cyano group, a hdyroxy group, —$OR^g$ ($R^g$ is a $C_1$-$C_6$ alkyl group, a $C_1$-$C_6$ haloalkyl group, a $C_1$-$C_4$ alkoxy-$C_1$-$C_4$ alkyl group, a $C_2$-$C_6$ alkenyl-$C_1$-$C_6$ alkyl group, a $C_2$-$C_6$ alkynyl-$C_1$-$C_6$ alkyl group, a cyanomethyl group, —$CONR^jR^k$ ($R^j$ and $R^k$ are each independently a hydrogen atom or a $C_1$-$C_6$ alkyl group), a $C_3$-$C_7$ cycloalkyl group, or a $C_1$-$C_6$ alkylcarbonyl group), a $C_1$-$C_6$ alkylcarbonyl group, a $C_1$-$C_6$ alkoxycarbonyl group, a $C_1$-$C_6$ alkylcarbonyloxy group, a heterocycloalkyl group, and —$NR^hR^i$ ($R^h$ is a $C_1$-$C_6$ alkyl group, $R^i$ is a hydrogen atom, a $C_1$-$C_6$ alkyl group, a $C_1$-$C_6$ alkoxy group, a cyanomethyl group, a $C_1$-$C_6$ alkylcarbonyl group or a $C_1$-$C_6$ alkoxycarbonyl group). One or more of these can be substituted at any substitutable positions.

In the formula (I), the substituent of the "optionally substituted $C_1$-$C_4$ alkoxy-$C_1$-$C_4$ alkyl group", "optionally substituted $C_1$-$C_4$ alkoxy-$C_1$-$C_4$ haloalkyl group", "optionally substituted $C_1$-$C_6$ alkylcarbonyl group", "optionally substituted $C_1$-$C_6$ alkoxycarbonyl group", "optionally substituted $C_1$-$C_6$ alkylcarbonyloxy group", "optionally substituted $C_3$-$C_7$ cycloalkyl group", "optionally substituted heterocycloalkyl group", "optionally substituted heterocycloalkyloxy group", "optionally substituted $C_2$-$C_6$ alkenyl group", "optionally substituted $C_2$-$C_6$ alkenyloxy group", "optionally substituted $C_2$-$C_6$ alkenyl-$C_1$-$C_6$ alkyl group", "optionally substituted $C_2$-$C_6$ alkenyl-$C_1$-$C_6$ alkoxy group", "optionally substituted $C_2$-$C_6$ alkenyloxy-$C_1$-$C_4$ alkyl group", "optionally substituted $C_2$-$C_6$ alkenyloxy-$C_1$-$C_4$ alkoxy group", "optionally substituted $C_2$-$C_6$ alkenyloxy-$C_1$-$C_4$ haloalkyl group", "optionally substituted $C_2$-$C_6$ alkenyloxy-$C_1$-$C_4$ haloalkoxy group", "optionally substituted $C_2$-$C_6$ alkynyl group", "optionally substituted $C_2$-$C_6$ alkynyloxy group", "optionally substituted $C_2$-$C_6$ alkynyl-$C_1$-$C_6$ alkyl group", "optionally substituted $C_2$-$C_6$ alkynyl-$C_1$-$C_6$ alkoxy group", "optionally substituted $C_2$-$C_6$ alkynyloxy-$C_1$-$C_4$ alkyl group", "optionally substituted $C_2$-$C_6$ alkynyloxy-$C_1$-$C_4$ alkoxy group", "optionally substituted $C_2$-$C_6$ alkynyloxy-$C_1$-$C_4$ haloalkyl group", "optionally substituted $C_2$-$C_6$ alkynyloxy-$C_1$-$C_4$ haloalkoxy group", "optionally substituted $C_1$-$C_6$ alkylthio group", and "optionally substituted $C_1$-$C_6$ haloalkylthio group" for $R^{2a}$ and $R^{2b}$ is a substituent selected from the group consisting of a halogen atom, a cyano group, a $C_1$-$C_6$ group, a $C_1$-$C_6$ haloalkyl group, a $C_1$-$C_6$ alkoxy group, a $C_1$-$C_6$ haloalkoxy group and a $C_1$-$C_4$ alkoxy-$C_1$-$C_4$ alkyl group. One or more of these can be substituted at any substitutable positions.

In the formula (I), the substituent of the "optionally substituted $C_1$-$C_6$ alkyl group" for $R^a$ and $R^b$ is a substituent selected from the group consisting of a halogen atom, a cyano group, a $C_1$-$C_6$ alkoxy group, a $C_1$-$C_6$ haloalkoxy group, a $C_1$-$C_6$ alkylcarbonyl group, a $C_1$-$C_6$ alkoxycarbonyl group, a $C_1$-$C_6$ alkylcarbonyloxy group, a $C_3$-$C_7$ cycloalkyl group, a heterocycloalkyl group, a heterocycloalkyloxy group, a $C_2$-$C_6$ alkenyl group, a $C_2$-$C_6$ alkenyloxy group, a $C_2$-$C_6$ alkynyl group and a $C_2$-$C_6$ alkynyloxy group. One or more of these can be substituted at any substitutable positions.

In the formula (I), when Z is $CR^{2b}$, the substituent of the "optionally substituted carbocycle", and "optionally substituted heterocycle" formed by $R^{2a}$ and $R^{2b}$, together with carbon atoms bonded thereto, is a substituent selected from the group consisting of an oxo group, a halogen atom, a cyano group, a hydroxyl group, a $C_1$-$C_6$ alkyl group, a $C_1$-$C_6$ haloalkyl group, a $C_1$-$C_6$ alkoxy group, a $C_1$-$C_6$ haloalkoxy group, a $C_1$-$C_6$ alkylcarbonyl group, a $C_1$-$C_6$ alkoxycarbonyl group, a $C_1$-$C_6$ alkylcarbonyloxy group and —$NR^jR^k$ ($R^j$ and $R^k$ are each independently a hydrogen atom or a $C_1$-$C_6$ alkyl group). One or more of these can be substituted at any substitutable positions.

In the formula (I), the substituent of the "optionally substituted $C_1$-$C_6$ alkyl group", "optionally substituted $C_1$-$C_6$ alkoxy group", "optionally substituted $C_3$-$C_7$ cycloalkyl group", "optionally substituted $C_2$-$C_6$ alkenyl group", "optionally substituted $C_2$-$C_6$ alkynyl group", and "optionally substituted aralkyl group" for $R^3$ is a substituent selected from the group consisting of a halogen atom, a cyano group, a $C_1$-$C_6$ alkyl group, a $C_1$-$C_6$ haloalkyl group, a $C_1$-$C_6$ alkoxy group, and a $C_1$-$C_6$ haloalkyoxy group. One or more of these can be substituted at any substitutable positions.

In the formula (I), the substituent of the "optionally substituted $C_1$-$C_6$ alkyl group", and "optionally substituted $C_1$-$C_6$ alkoxy group" for $R^4$ is a substituent selected from the group consisting of a halogen atom, a cyano group, a hydroxyl group, a $C_1$-$C_6$ alkoxy group, a $C_1$-$C_6$ haloalkyoxy group, a $C_2$-$C_6$ alkenyl group, a $C_2$-$C_6$ alkynyl group, a $C_3$-$C_7$ cycloalkyl group and a heterocycloalkyl group. One or more of these can be substituted at any substitutable positions.

The substituent of the "optionally substituted $C_3$-$C_7$ cycloalkyl group" for $R^4$ is a substituent selected from the group consisting of a halogen atom, a cyano group, a $C_1$-$C_6$ alkyl group, a $C_1$-$C_6$ haloalkyl group, a $C_1$-$C_6$ alkoxy group and a $C_1$-$C_6$ haloalkyoxy group. One or more of these can be substituted at any substitutable positions.

In the formula (I), the substituent of the "optionally substituted $C_1$-$C_6$ alkyl group", and "optionally substituted $C_1$-$C_6$ alkoxy group", "optionally substituted $C_3$-$C_7$ cycloalkyl group", and "optionally substituted $C_1$-$C_6$ alkylthio group" for $R^6$, $R^{6a}$ and $R^{6b}$ is a substituent selected from the group consisting of a halogen atom, a cyano group, a $C_1$-$C_6$ alkyl group, a $C_1$-$C_6$ haloalkyl group, a $C_1$-$C_6$ alkoxy group and a $C_1$-$C_6$ haloalkyoxy group. One or more of these can be substituted at any substitutable positions.

In the aforementioned definitions, the number of the substituents is preferably 1-5, more preferably 1-3.

A preferable atom or substituent for the compound of the formula (I) or a pharmacologically acceptable salt thereof of the present invention is explained below.

Q is preferably $CH_2$, CO, NH, O, or S, more preferably NH, O or S, further preferably NH or O, particularly preferably O.

$X^1$, $X^2$ and $X^3$ are each independently $CR^1$ or N, preferably, $X^1$ is $CR^1$, and $X^2$ and $X^3$ are each $CR^1$ or N, more preferably $X^1$ and $X^3$ are each $CR^1$, and $X^2$ is $CR^1$ or N.

In another embodiment of the present invention, $X^1$, $X^2$ and $X^3$ are each independently CH, $CR^1$ or N, preferably $X^1$ is CH and $X^2$ and $X^3$ are each independently $CR^1$ or N, more preferably, $X^1$ and $X^3$ are CH, and $X^2$ is $CR^1$ or N, further preferably, $X^1$ and $X^3$ are CH, and $X^2$ is CH or N.

Z is preferably $CR^{2b}$.

$R^1$ is preferably a hydrogen atom, a halogen atom, a methyl group or a methoxy group, more preferably, a hydrogen atom or a halogen atom, further preferably, a hydrogen atom.

Preferably, $R^{2a}$ and $R^{2b}$ are each independently a hydrogen atom, a halogen atom, a cyano group, an optionally substituted $C_1$-$C_6$ alkyl group, an optionally substituted $C_1$-$C_6$ haloalkyl group, an optionally substituted $C_1$-$C_6$ alkoxy group, an optionally substituted $C_1$-$C_6$ haloalkoxy group, an optionally substituted $C_1$-$C_4$ alkoxy-$C_1$-$C_4$ alkyl group, an optionally substituted $C_1$-$C_4$ alkoxy-$C_1$-$C_4$ haloalkyl group, an optionally substituted $C_1$-$C_6$ alkylcarbonyl group, an optionally substituted $C_1$-$C_6$ alkoxycarbonyl group, an optionally substituted $C_1$-$C_6$ alkylcarbonyloxy group, an optionally substituted $C_3$-$C_7$ cycloalkyl group, an optionally substituted heterocycloalkyl group, an optionally substituted $C_2$-$C_6$ alkenyl-$C_1$-$C_6$ alkoxy group, an optionally substituted $C_2$-$C_6$ alkynyl-$C_1$-$C_6$ alkoxy group, —$NR^aR^b$ {$R^a$ and $R^b$ are each independently a hydrogen atom or an optionally substituted $C_1$-$C_6$ alkyl group, (provided that $R^a$ and $R^b$ are not hydrogen atoms at the same time)}, an optionally substituted $C_1$-$C_6$ alkylthio group, a pentafluorosulfanyl group, or a group represented by the formula (I-A)

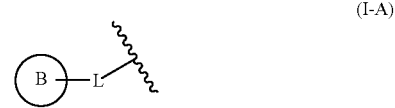

(I-A)

{wherein,
L is a single bond, —$(CH_2)_p$—, —$O(CH_2)_p$—, —$(CH_2)_pO$—, —$NR^c(CH_2)_p$— or —$(CH_2)_pNR^c$—, wherein one or more hydrogen atoms of $(CH_2)_p$ are optionally substituted by a halogen atom,
p is 1 or 2,
$R^c$ is a hydrogen atom or a methyl group, and
ring B is an optionally substituted phenyl, or an optionally substituted 5- or 6-membered ring heteroaryl}, or when Z is $CR^{2b}$, $R^{2a}$ and $R^{2b}$ optionally form, together with carbon atoms bonded thereto, an optionally substituted carbocycle, more preferably, $R^{2a}$ and $R^{2b}$ are each independently a hydrogen atom, a halogen atom, a cyano group, a $C_1$-$C_6$ alkyl group, a $C_1$-$C_6$ haloalkyl group, a $C_1$-$C_6$ alkoxy group, a $C_1$-$C_6$ haloalkoxy group, a $C_1$-$C_4$ alkoxy-$C_1$-$C_4$ alkyl group, $C_1$-$C_4$ alkoxy-$C_1$-$C_4$ haloalkyl group, a $C_1$-$C_6$ alkylcarbonyl group, a $C_1$-$C_6$ alkoxycarbonyl group, a $C_3$-$C_7$ cycloalkyl group, a $C_2$-$C_6$ alkenyl-$C_1$-$C_6$ alkoxy group, a $C_2$-$C_6$ alkynyl-$C_1$-$C_6$ alkoxy group, or a group represented by the formula (I-A)

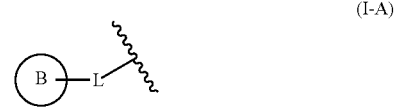

(I-A)

{wherein,
L is a single bond, —$(CH_2)_p$—, —$O(CH_2)_p$—, —$(CH_2)_pO$—,
p is 1 or 2, and ring B is a phenyl optionally substituted by a halogen atom, a $C_1$-$C_4$ alkyl group, a $C_1$-$C_4$ alkoxy group or a cyano group, or a 5- or 6-membered ring heteroaryl optionally substituted by a halogen atom, a $C_1$-$C_4$ alkyl group, a $C_1$-$C_4$ alkoxy group or a cyano group} ($R^{2a}$ and $R^{2b}$ are not hydrogen atoms at the same time), further preferably, $R^{2a}$ and $R^{2b}$ are each independently a hydrogen atom, a $C_1$-$C_4$ alkyl group, a $C_1$-$C_4$ haloalkyl group, a $C_1$-$C_4$ alkoxy group, a $C_1$-$C_4$ haloalkoxy group, a $C_1$-$C_4$ alkoxy-$C_1$-$C_4$ alkyl group, a $C_1$-$C_4$ alkoxy-$C_1$-$C_4$ haloalkyl group, or a $C_3$-$C_7$ cycloalkyl group ($R^{2a}$ and $R^{2b}$ are not hydrogen atoms at the same time), particularly preferably, $R^{2a}$ is a $C_1$-$C_4$ alkyl group, a $C_1$-$C_4$ haloalkyl group, a $C_1$-$C_4$ alkoxy group, a $C_1$-$C_4$ haloalkoxy group, a $C_1$-$C_4$ alkoxy-$C_1$-$C_4$ alkyl group, a $C_1$-$C_4$ alkoxy-$C_1$-$C_4$ haloalkyl group or a cyclopropyl group, and $R^{2b}$ is a hydrogen atom or a $C_1$-$C_4$ alkyl group.

In another embodiment of the present invention, $R^{2a}$ and $R^{2b}$ are preferably each independently a hydrogen atom, a halogen atom, a cyano group, a $C_1$-$C_6$ alkyl group, a $C_1$-$C_6$ alkyl group substituted by —$OR^g$ ($R^g$ is a $C_1$-$C_6$ alkyl group, a $C_1$-$C_6$ haloalkyl group, a $C_1$-$C_4$ alkoxy-$C_1$-$C_4$ alkyl group, a $C_2$-$C_6$ alkenyl-$C_1$-$C_6$ alkyl group, a $C_2$-$C_6$ alkynyl-$C_1$-$C_6$ alkyl group, a cyanomethyl group, —$CONR^jR^k$ ($R^j$ and $R^k$ are each independently a hydrogen atom or a $C_1$-$C_6$ alkyl group), a $C_3$-$C_7$ cycloalkyl group, or a $C_1$-$C_6$ alkylcarbonyl group, a $C_1$-$C_6$ alkyl group substituted by a $C_1$-$C_6$ alkoxycarbonyl group, a $C_1$-$C_6$ alkyl group substituted by a cyano group, a $C_1$-$C_6$ haloalkyl group, a $C_1$-$C_6$ haloalkyl group substituted by a heterocycloalkyl group, a $C_1$-$C_6$ haloalkyl group substituted by —$NR^hR^i$ ($R^h$ is a $C_1$-$C_6$ alkyl group, and $R^i$ is a hydrogen atom, a $C_1$-$C_6$ alkyl group, a $C_1$-$C_6$ alkoxy group, a cyanomethyl group, a $C_1$-$C_6$ alkylcarbonyl group or a $C_1$-$C_6$ alkoxycarbonyl group), a $C_1$-$C_6$ alkoxy group, a $C_1$-$C_6$ alkoxy group substituted by a $C_1$-$C_6$ alkoxycarbonyl group, a $C_1$-$C_6$ haloalkoxy group, a $C_1$-$C_4$ alkoxy-$C_1$-$C_4$ alkyl group, a $C_1$-$C_4$ alkoxy-$C_1$-$C_4$ haloalkyl group, a $C_1$-$C_4$ alkoxy-$C_1$-$C_4$ haloalkyl group substituted by $C_1$-$C_4$ alkoxy, a $C_1$-$C_6$ alkylcarbonyl group, a $C_1$-$C_6$ alkylcarbonyl group, a $C_1$-$C_6$ alkylcarbonyloxy group, a $C_3$-$C_7$ cycloalkyl group, a $C_3$-$C_7$ cycloalkyl group substituted by a $C_1$-$C_6$ alkyl group, a $C_3$-$C_7$ cycloalkyl group substituted by a $C_1$-$C_4$ alkoxy-$C_1$-$C_4$ alkyl group, a heterocycloalkyl group, a heterocycloalkyloxy group, a $C_2$-$C_6$ alkenyl group, a $C_2$-$C_6$ alkenyloxy group, a $C_2$-$C_6$ alkenyl-$C_1$-$C_6$ alkyl group, a $C_2$-$C_6$ alkenyl-$C_1$-$C_6$ alkoxy group, a $C_2$-$C_6$ alkenyloxy-$C_1$-$C_4$ alkyl group, a $C_2$-$C_6$ alkenyloxy-$C_1$-$C_4$ alkoxy group, a $C_2$-$C_6$ alkenyloxy-$C_1$-$C_4$ haloalkyl group, a $C_2$-$C_6$ alkenyloxy-$C_1$-$C_4$ haloalkoxy group, a $C_2$-$C_6$ alkynyl group, a $C_2$-$C_6$ alkynyloxy group, a $C_2$-$C_6$ alkynyl-$C_1$-$C_6$ alkyl group, a $C_2$-$C_6$ alkynyl-$C_1$-$C_6$ alkoxy group, a $C_2$-$C_6$ alkynyloxy-$C_1$-$C_4$ alkyl group, a $C_2$-$C_6$ alkynyloxy-$C_1$-$C_4$ alkoxy group, a $C_2$-$C_6$ alkynyloxy-$C_1$-$C_4$ haloalkyl group, a $C_2$-$C_6$ alkynyloxy-$C_1$-$C_4$ haloalkyl group, —$NR^aR^b$ {$R^a$ and $R^b$ are each independently a hydrogen atom, a $C_1$-$C_6$ alkyl group, a $C_1$-$C_6$ alkyl group substituted by a cyano group, a $C_1$-$C_6$ alkyl group substituted by a $C_1$-$C_4$ alkyl group, a $C_1$-$C_6$ alkyl group substituted by a $C_1$-$C_6$ alkoxycarbonyl group, a $C_1$-$C_6$ alkyl group substituted by a $C_3$-$C_7$ cycloalkyl group, or a $C_1$-$C_6$ alkyl group substituted by a $C_2$-$C_6$ alkenyl group (provided that $R^a$ and $R^b$ are not hydrogen atoms at the same time)}, a $C_1$-$C_6$ alkylthio group, a $C_1$-$C_6$ haloalkylthio group, a pentafluorosulfanyl group, or a group represented by the formula (I-A)

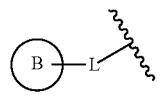

(I-A)

{wherein,

L is a single bond, —$(CH_2)_p$—, —$O(CH_2)_p$—, —$(CH_2)_pO$—, —$NR^c(CH_2)_p$— or —$(CH_2)_pNR^c$, wherein one or more hydrogen atom of $(CH_2)_p$ are optionally substituted by a halogen atom, p is 1 or 2, $R^c$ is a hydrogen atom or a methyl group, and ring B is a phenyl, pyrrolyl, furyl, thienyl, imidazolyl, triazolyl, pyrazolyl, oxazolyl, isoxazolyl, thiazolyl, isothiazolyl, thiadiazolyl, oxadiazolyl, pyridyl, pyridazinyl, pyrimidinyl, or pyrazinyl}, or when Z is $CR^{2b}$, $R^{2a}$ and $R^{2b}$ may be joined to form —$(CH_2)_r$— (r is 3, 4, 5 or 6) optionally substituted by a halogen atom, a hydroxyl group or an oxo group.

More preferably, $R^{2a}$ is a hydrogen atom, a halogen atom, a cyano group, a $C_1$-$C_6$ alkyl group, a $C_1$-$C_6$ alkyl group substituted by —$OR^g$ ($R^g$ is a $C_1$-$C_6$ alkyl group, a $C_1$-$C_6$ haloalkyl group, a $C_1$-$C_4$ alkoxy-$C_1$-$C_4$ alkyl group, a $C_2$-$C_6$ alkenyl-$C_1$-$C_6$ alkyl group, a $C_2$-$C_6$ alkynyl-$C_1$-$C_6$ alkyl group, a cyanomethyl group, —$CONR^jR^k$ ($R^j$ and $R^k$ are each independently a hydrogen atom or a $C_1$-$C_6$ alkyl group, a $C_3$-$C_7$ cycloalkyl group, or a $C_1$-$C_6$ alkylcarbonyl group, a $C_1$-$C_6$ alkyl group substituted by a $C_1$-$C_6$ alkoxycarbonyl group, a $C_1$-$C_6$ alkyl group substituted by a cyano group, a $C_1$-$C_6$ haloalkyl group, a $C_1$-$C_6$ haloalkyl group substituted by a heterocycloalkyl group, a $C_1$-$C_6$ haloalkyl group substituted —$NR^hR^i$ ($R^h$ is a $C_1$-$C_6$ alkyl group, and $R^i$ is a hydrogen atom, a $C_1$-$C_6$ alkyl group or a $C_1$-$C_6$ alkylcarbonyl group), a $C_1$-$C_6$ alkoxy group, a $C_1$-$C_6$ alkoxy group substituted by a $C_1$-$C_6$ alkoxycarbonyl group, a $C_1$-$C_6$ haloalkoxy group, a $C_1$-$C_4$ alkoxy-$C_1$-$C_4$ alkyl group, a $C_1$-$C_4$ alkoxy-$C_1$-$C_4$ haloalkyl group, a $C_1$-$C_4$ alkoxy-$C_1$-$C_4$ haloalkyl group substituted by a $C_1$-$C_4$ alkoxy group, a $C_1$-$C_6$ alkylcarbonyl group, a $C_1$-$C_6$ alkoxycarbonyl group, a $C_1$-$C_6$ alkylcarbonyloxy group, a $C_3$-$C_7$ cycloalkyl group, a $C_3$-$C_7$ cycloalkyl group substituted by a $C_1$-$C_6$ alkyl group, a $C_3$-$C_7$ cycloalkyl group substituted by a $C_1$-$C_4$ alkoxy-$C_1$-$C_4$ alkyl group, a heterocycloalkyl group, heterocycloalkyloxy group, a $C_2$-$C_6$ alkenyl group, a $C_2$-$C_6$ alkenyloxy group, a $C_1$-$C_6$ alkynyl group, a $C_2$-$C_6$ alkynyloxy group, a $C_2$-$C_6$ alkynyloxy-$C_1$-$C_4$ alkyl group, —$NR^aR^b$ {$R^a$ and $R^b$ are each independently a hydrogen atom, a $C_1$-$C_6$ alkyl group, a $C_1$-$C_6$ alkyl group substituted by a cyano group, a $C_1$-$C_6$ alkyl group substituted by a $C_1$-$C_4$ alkoxy group, a $C_1$-$C_6$ alkyl group substituted by a $C_1$-$C_6$ alkoxycarbonyl group, a $C_1$-$C_6$ alkyl group substituted by a $C_3$-$C_7$ cycloalkyl group, or a a $C_1$-$C_6$ alkyl group substituted by a $C_2$-$C_6$ alkenyl group (provided that $R^a$ and $R^b$ are not hydrogen atoms at the same time)}, a $C_1$-$C_6$ alkylthio group, a $C_1$-$C_6$ haloalkylthio group, a pentafluorosulfanyl group, or a group represented by the formula (I-A)

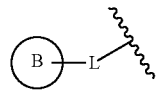

(I-A)

{wherein,

L is a single bond, —(CH$_2$)$_p$—, —O(CH$_2$)$_p$—, —(CH$_2$)$_p$O—, —NR$^c$(CH$_2$)$_p$— or —(CH$_2$)$_p$NR$^c$—, wherein one or more hydrogen atoms of (CH$_2$)$_p$ are optionally substituted by a halogen atom, p is 1 or 2, R$^c$ is a hydrogen atom or a methyl group, and ring B is a phenyl, imidazolyl, pyrazolyl, oxazolyl, thiazolyl, or oxadiazolyl}, and R$^{2b}$ is a hydrogen atom, a halogen atom, a cyano group, a C$_1$-C$_6$ alkyl group, a C$_1$-C$_6$ haloalkyl group, a C$_1$-C$_6$ alkoxy group, a C$_1$-C$_6$ haloalkoxy group, or a C$_3$-C$_7$ cycloalkyl group, or when Z is CR$^{2b}$, R$^{2a}$ and R$^{2b}$ may be joined to form —(CH$_2$)$_r$— (r is 3, 4, 5 or 6) optionally substituted by a halogen atom, a hydroxyl group or an oxo group.

Further preferably, R$^{2a}$ is a hydrogen atom, a halogen atom, a cyano group, a C$_1$-C$_6$ alkyl group, a C$_1$-C$_6$ haloalkyl group, a C$_1$-C$_6$ alkoxy group, a C$_1$-C$_6$ haloalkoxy group, a C$_1$-C$_4$ alkoxy-C$_1$-C$_4$ alkyl group, a C$_1$-C$_4$ alkoxy-C$_1$-C$_4$ haloalkyl group, a C$_1$-C$_6$ alkylcarbonyl group, a C$_1$-C$_6$ alkoxycarbonyl group, a C$_3$-C$_7$ cycloalkyl group, —NR$^a$R$^b$ {R$^a$ and R$^b$ are each independently a hydrogen atom, a C$_1$-C$_6$ alkyl group, a C$_1$-C$_6$ alkyl group substituted by a C$_1$-C$_4$ alkoxy group or a C$_1$-C$_6$ alkyl group substituted by a C$_1$-C$_6$ alkoxycarbonyl group (provided that R$^a$ and R$^b$ are not hydrogen atoms at the same time)} or a group represented by the formula (I-A)

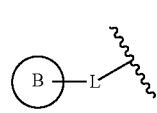

(I-A)

{wherein,

L is a single bond, —(CH$_2$)$_p$—, —O(CH$_2$)$_p$—, —(CH$_2$)$_p$O—, wherein one or more hydrogen atoms of (CH$_2$)$_p$ are optionally substituted by a halogen atom, p is 1 or 2, and ring B is a phenyl or pyrazolyl}, and R$^{2b}$ is a hydrogen atom, a halogen atom, or a methyl group, or when Z is CR$^{2b}$, R$^{2a}$ and R$^{2b}$ may be joined to form —(CH$_2$)$_r$— (r is 3 or 4).

R$^3$ is preferably a hydrogen atom, a fluorine atom or a methyl group, more preferably a hydrogen atom.

Ring A is an optionally substituted phenyl or an optionally substituted 5- or 6-membered ring heteroaryl (said ring A is optionally further condensed to form a fused ring), preferably, ring A is an optionally substituted ring selected from the group consisting of phenyl, naphthyl, pyridyl, pyrimidinyl, pyrazinyl, pyrazolyl, thiazolyl, isothiazolyl, oxazolyl, isoxazolyl, quinolyl, isoquinolyl, quinoxalinyl, naphthyridinyl, pyridopyrazinyl, indolyl, pyrazolopyridyl, pyrazolopyrazinyl, triazolopyridyl, dihydrobenzofuranyl, chromanyl, 1,3-benzodioxolyl, 1,4-benzodioxanyl, azaindazolyl, pyrazolopyrimidinyl, benzoxazolyl, imidazopyridyl and imidazopyrimidinyl.

More preferably, ring A is a ring selected from the group consisting of the following formulas:

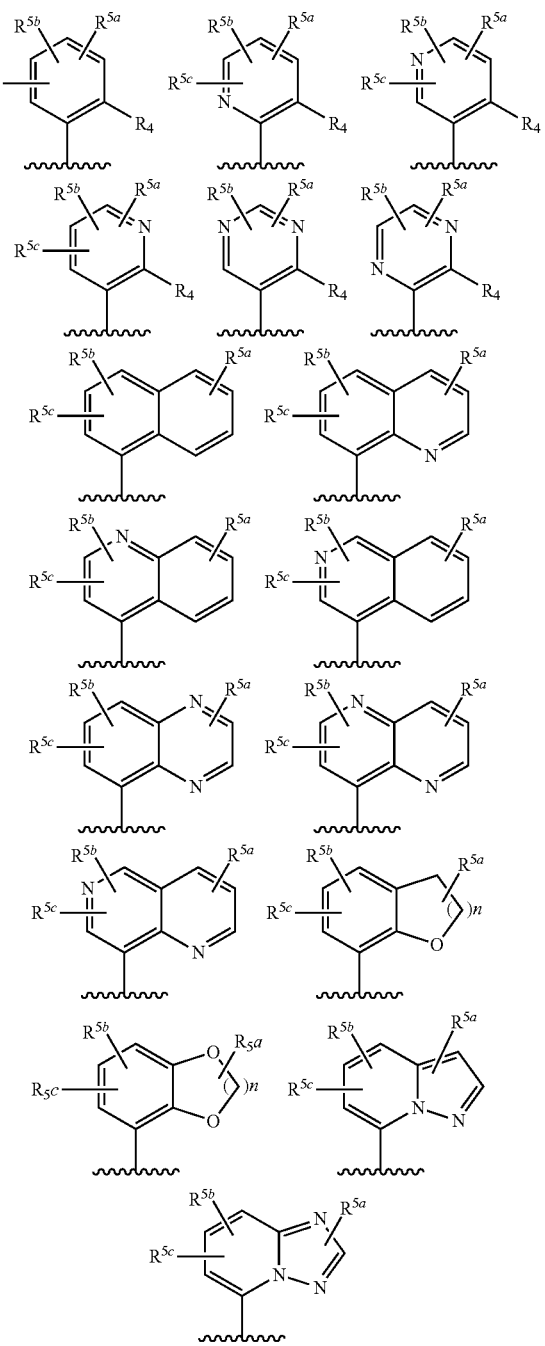

wherein R$^4$, R$^{5a}$, R$^{5b}$, R$^{5c}$ and n are as defined in the aforementioned embodiment (7), further preferably, ring A is a ring selected from the group consisting of the following formulas:

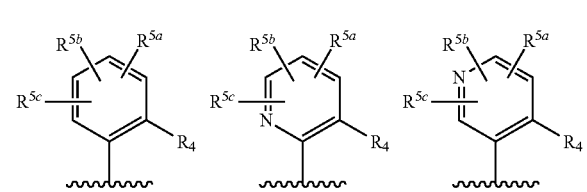

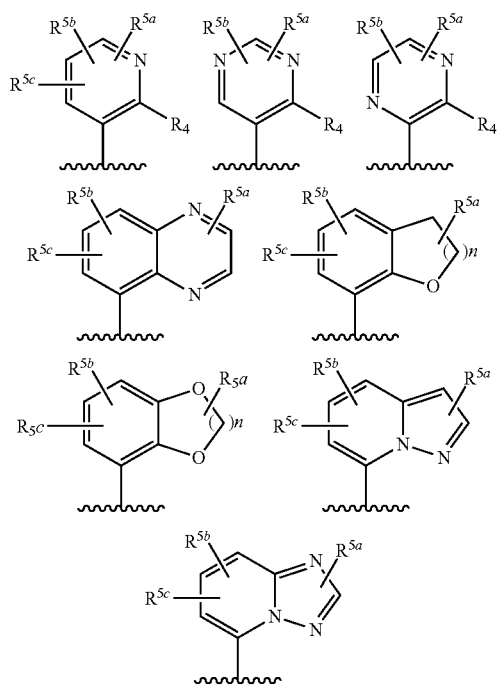

wherein $R^4$, $R^{5a}$, $R^{5b}$, $R^{5c}$ and n are as defined in the aforementioned embodiment (7), In another embodiment of the present invention, ring A is phenyl (said ring A is optionally further condensed to form a fused ring), preferably, ring A is a ring selected from the group consisting of the following formulas:

wherein $R^4$, $R^{5a}$, $R^{5b}$, $R^{5c}$ and n are as defined in the aforementioned embodiment (7), more preferably, ring A is a ring selected from the group consisting of the following formulas:

wherein $R^4$, $R^{5a}$, $R^{5b}$, $R^{5c}$ and n are as defined in the aforementioned embodiment (7).

In another embodiment of the present invention, ring A is 6-membered ring heteroaryl (said ring A is optionally further condensed to form a fused ring), preferably, ring A is a ring selected from the group consisting of the following formulas:

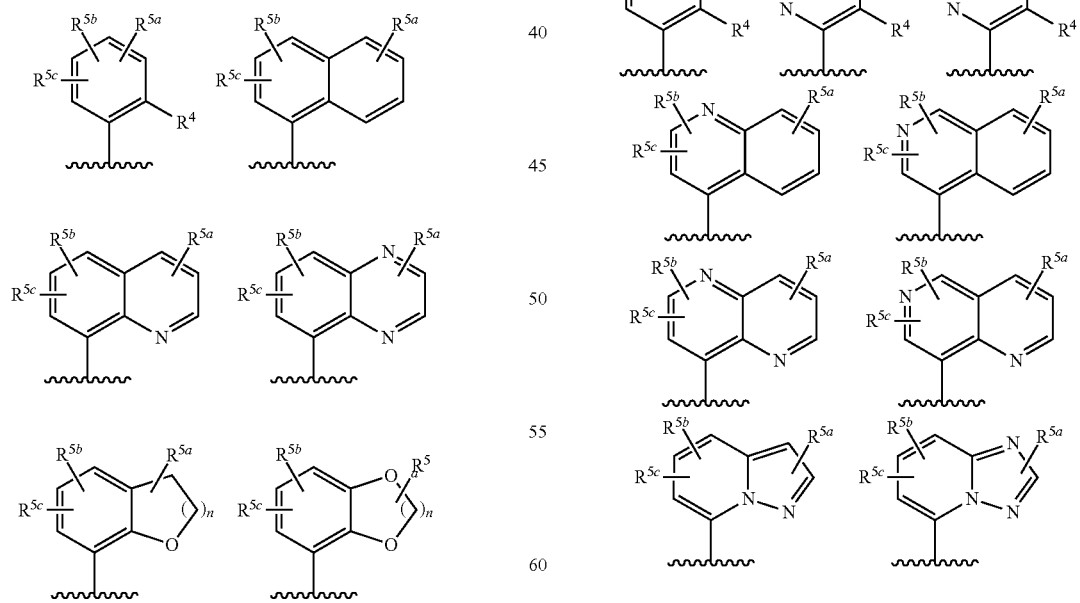

wherein $R^4$, $R^{5a}$, $R^{5b}$, and $R^{5c}$ are as defined in the aforementioned embodiment (7), more preferably, ring A is a ring selected from the group consisting of the following formulas:

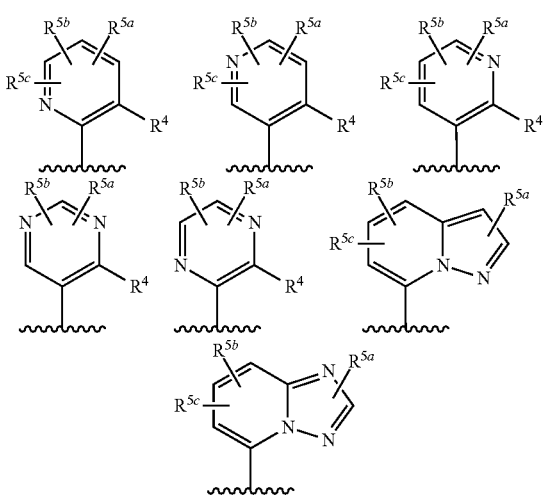

wherein $R^4$, $R^{5a}$, $R^{5b}$, and $R^{5c}$ are as defined in the aforementioned embodiment (7).

In another embodiment of the present invention, ring A is 5-membered ring heteroaryl (said ring A is optionally further condensed to form a fused ring), preferably, ring A is a ring selected from the group consisting of the following formulas:

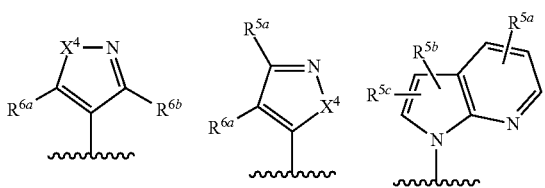

wherein $R^{5a}$, $R^{5b}$, $R^{5c}$, $R^{6a}$, $R^{6b}$ and $X^4$ are as defined in the aforementioned embodiment (13), more preferably, ring A is a ring represented by the following formula:

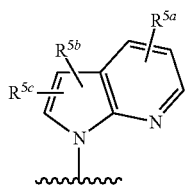

wherein $R^{5a}$, $R^{5b}$, and $R^{5c}$ are as defined in the aforementioned embodiment (13).

In another embodiment of the present invention, more preferably, ring A is a ring selected from the group consisting of the following formulas:

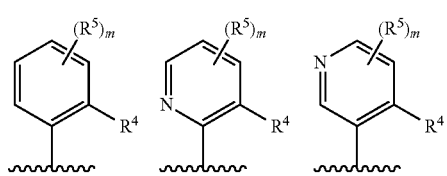

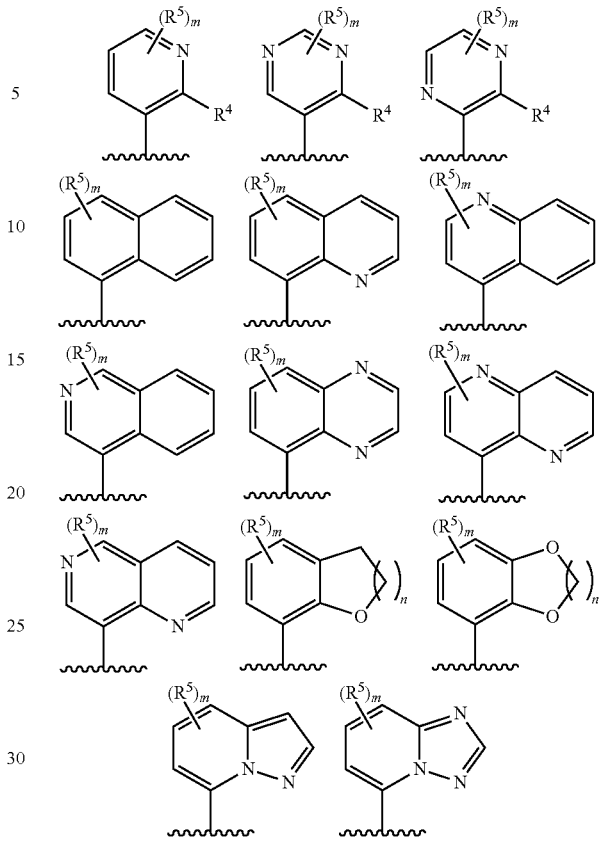

wherein $R^4$, $R^5$, m and n are as defined in the aforementioned embodiment (7A), further preferably, ring A is a ring selected from the group consisting of the following formulas:

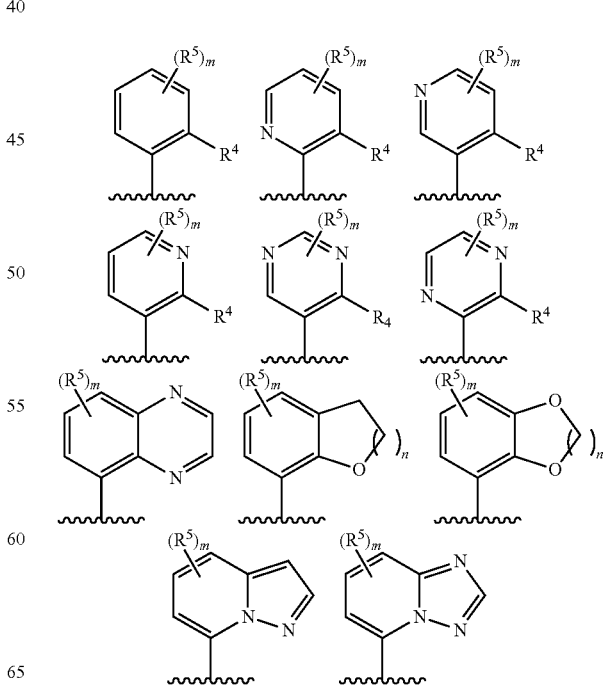

wherein, $R^4$, $R^5$, m and n are as defined in the aforementioned embodiment (7A).

In another embodiment of the present invention, ring A is phenyl (said ring A is optionally further condensed to form a fused ring), preferably, ring A is a ring selected from the group consisting of the following formulas:

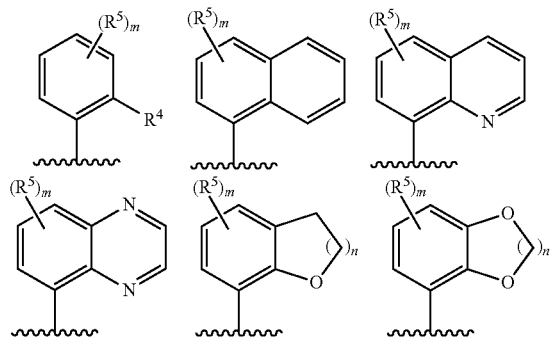

wherein $R^4$, $R^5$, m and n are as defined in the aforementioned embodiment (7A), more preferably, ring A is a ring selected from the group consisting of the following formulas:

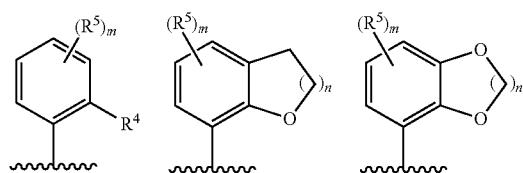

wherein $R^4$, $R^5$, m and n are as defined in the aforementioned embodiment (7A).

In another embodiment of the present invention, ring A is 6-membered ring heteroaryl (said ring A is optionally further condensed to form a fused ring), preferably, ring A is a ring selected from the group consisting of the following formulas:

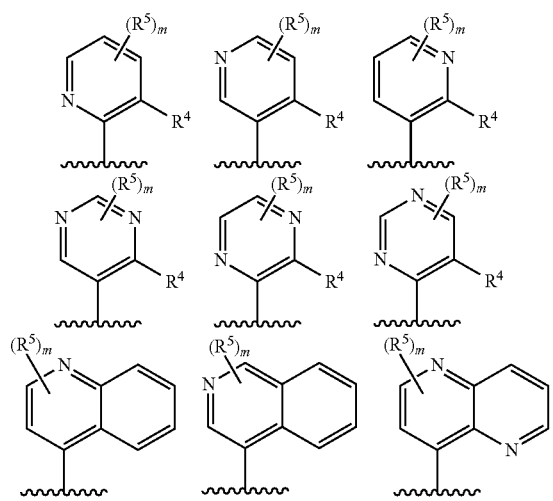

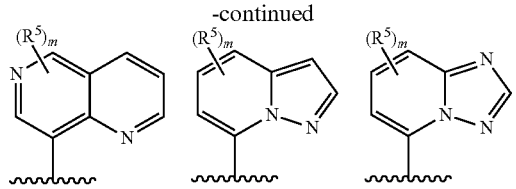

wherein $R^4$, $R^5$ and m are as defined in the aforementioned embodiment (7A), more preferably, ring A is a ring selected from the group consisting of the following formulas:

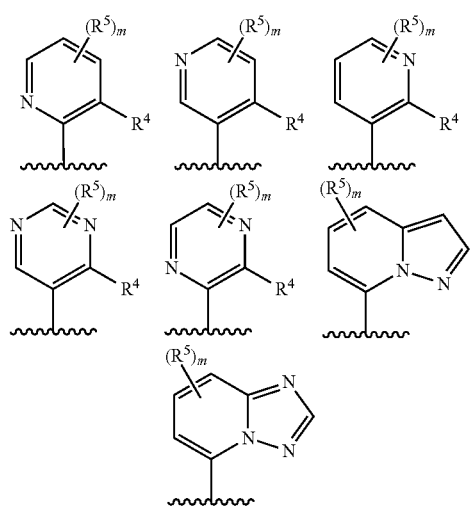

wherein $R^4$, $R^5$ and m are as defined in the aforementioned embodiment (7A).

In another embodiment of the present invention, ring A is 5-membered ring heteroaryl (said ring A is optionally further condensed to form a fused ring), preferably, ring A is a ring selected from the group consisting of the following formulas:

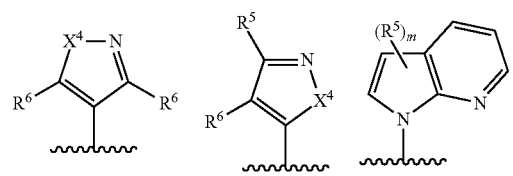

wherein $R^5$, $R^6$, $X^4$ and m are as defined in the aforementioned embodiment (13A), more preferably, ring A is a ring represented by the following formula:

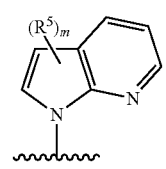

wherein $R^5$ and m are as defined in the aforementioned embodiment (13A).

$R^4$ is preferably a hydrogen atom, a halogen atom, a cyano group, a $C_1$-$C_6$ alkyl group, a $C_1$-$C_6$ haloalkyl group, a $C_3$-$C_7$ cycloalkyl group, a $C_1$-$C_6$ alkoxy group, a $C_1$-$C_6$ haloalkoxy group, a vinyl group, an ethynyl group, a $C_1$-$C_6$ alkylthio group, —NR$^d$R$^e$ (R$^d$ and R$^e$ are each independently a hydrogen atom or a $C_1$-$C_6$ alkyl group), a $C_1$-$C_6$ alkylcarbonyl group or a $C_1$-$C_6$ alkoxycarbonyl group, more preferably, a halogen atom, a cyano group, a $C_1$-$C_6$ alkyl group, a $C_1$-$C_6$ haloalkyl group, a $C_3$-$C_7$ cycloalkyl group, a $C_1$-$C_6$ alkoxy group, a $C_1$-$C_6$ haloalkoxy group, a vinyl group, an ethynyl group or a $C_1$-$C_6$ alkylthio group, further preferably, a halogen atom, a $C_1$-$C_4$ alkyl group, a $C_1$-$C_4$ haloalkyl group, a cyclopropyl group, a $C_1$-$C_4$ alkoxy group or a $C_1$-$C_4$ haloalkoxy group, particularly preferably, a halogen atom, a methyl group, an ethyl group or a methoxy group.

$R^5$, $R^{5a}$, $R^{5b}$ and $R^{5c}$ are each preferably a hydrogen atom, a halogen atom, a cyano group, a $C_1$-$C_4$ alkyl group, a $C_1$-$C_4$ haloalkyl group or a $C_3$-$C_7$ cycloalkyl group, more preferably, a hydrogen atom, a halogen atom, a $C_1$-$C_4$ alkyl group or a $C_1$-$C_4$ haloalkyl group.

$R^6$, $R^{6a}$ and $R^{6b}$ are each preferably a hydrogen atom, a halogen atom, a $C_1$-$C_6$ alkyl group, a $C_1$-$C_6$ haloalkyl group, a $C_1$-$C_6$ alkoxy group or a a $C_1$-$C_6$ haloalkoxy group, more preferably, a hydrogen atom, a halogen atom, a $C_1$-$C_4$ alkyl group or a $C_1$-$C_4$ haloalkyl group.

$X^4$ is preferably NR$^f$ (R$^f$ is a hydrogen atom or a $C_1$-$C_4$ alkyl group) or O, more preferably, NR$^f$ (R$^f$ is a hydrogen atom or a methyl group) or O.

In another embodiment of the present invention, ring A is preferably a ring selected from the group consisting of phenyl, pyrrolyl, furyl, thienyl, imidazolyl, pyrazolyl, oxazolyl, isoxazolyl, thiazolyl, isothiazolyl, thiadiazolyl, oxadiazolyl, pyridyl, pyridazinyl, pyrimidinyl, pyrazinyl, indanyl, indenyl, naphthyl, dihydronaphthyl, tetrahydronaphthyl, quinolyl, isoquinolyl, quinoxalinyl, quinazolinyl, indolyl, benzofuranyl, dihydrobenzofuranyl, 1,3-benzodioxolyl, 1,4-benzodioxanyl, benzothiophenyl, benzimidazolyl, benzothiazolyl, benzoxazolyl, chromanyl, indazolyl, benzisoxazolyl, benzisothiazolyl, pyrrolopyridyl, pyrazolopyridyl, dihydropyrazolooxazolyl, tetrahydropyrazolooxazepinyl, pyrazolopyrimidinyl, imidazopyridyl, imidazopyrimidinyl, imidazopyrazinyl, triazolopyridyl, naphthyridinyl, pyridopyrazinyl, and azaindazolyl, each of which is optionally substituted by one or more substituents selected from the group consisting of a halogen atom, a cyano group, a hydroxyl group, a $C_1$-$C_6$ alkyl group, a $C_1$-$C_6$ alkyl group substituted by a a $C_1$-$C_6$ alkoxy group, a $C_1$-$C_6$ haloalkyl group, a $C_3$-$C_7$ cycloalkyl group, a heterocycloalkyl group, a heterocycloalkyloxy group, a pyrrolyl group, a furyl group, a thienyl group, an imidazolyl group, a pyrazolyl group, an oxazolyl group, an isoxazolyl group, a thiazolyl group, an isothiazolyl group, a thiadiazolyl group, an oxadiazolyl group, a $C_1$-$C_6$ alkoxy group, a $C_1$-$C_6$ alkoxy group substituted by a $C_3$-$C_7$ cycloalkyl group, a $C_1$-$C_6$ haloalkoxy group, a $C_2$-$C_6$ alkenyl group, a $C_2$-$C_6$ alkenyloxy group, a $C_2$-$C_6$ alkynyl group, a $C_2$-$C_6$ alkynyloxy group, a $C_1$-$C_6$ alkylthio group, —NR$^d$R$^e$ (R$^d$ and R$^e$ are each independently a hydrogen atom or a $C_1$-$C_6$ alkyl group), a nitro group, a formyl group, a $C_1$-$C_6$ alkylcarbonyl group, a $C_1$-$C_6$ alkoxycarbonyl group and a $C_1$-$C_6$ alkylcarbonyloxy group.

More preferably, ring A is preferably a ring selected from the group consisting of phenyl, oxazolyl, isoxazolyl, thiazolyl, isothiazolyl, pyridyl, pyridazinyl, pyrimidinyl, pyrazinyl, quinolyl, isoquinolyl, quinoxalinyl, quinazolinyl, indolyl, dihydrobenzofuranyl, chromanyl, benzisoxazolyl, pyrrolopyridyl, pyrazolopyridyl, pyrazolopyrimidinyl, imidazopyrazinyl, triazolopyridyl, naphthyridinyl, and pyridopyrazinyl, each of which is optionally substituted by one or more substituents selected from the group consisting of a halogen atom, a cyano group, a hydroxyl group, a $C_1$-$C_6$ alkyl group, a $C_1$-$C_6$ alkyl group substituted by a $C_1$-$C_6$ alkoxy group, a $C_1$-$C_6$ haloalkyl group, a $C_3$-$C_7$ cycloalkyl group, a heterocycloalkyl group, a heterocycloalkyloxy group, an imidazolyl group, a pyrazolyl group, a $C_1$-$C_6$ alkoxy group, a $C_1$-$C_6$ alkoxy group substituted by a $C_3$-$C_7$ cycloalkyl group, a $C_1$-$C_6$ haloalkoxy group, a $C_2$-$C_6$ alkynyloxy group, a $C_1$-$C_6$ alkylthio group, —NR$^d$R$^e$ (R$^d$ and R$^e$ are each independently a hydrogen atom or a $C_1$-$C_6$ alkyl group), a nitro group, a formyl group, a $C_1$-$C_6$ alkylcarbonyl group, a $C_1$-$C_6$ alkoxycarbonyl group and a $C_1$-$C_6$ alkylcarbonyloxy group.

Further preferably, ring A is a ring selected from the group consisting of phenyl, pyridyl, pyrimidinyl, pyrazinyl, quinoxalinyl, dihydrobenzofuranyl, pyrazolopyridyl, triazolopyridyl, naphthyridinyl, and pyridopyrazinyl, each of which is optionally substituted by one or more substituents selected from the group consisting of a halogen atom, a $C_1$-$C_6$ alkyl group, a $C_1$-$C_6$ haloalkyl group and a $C_1$-$C_6$ alkoxy group.

A preferable embodiment of compound (I) or a pharmaceutically acceptable salt thereof of the present invention is a compound comprising a combination of preferable atoms and groups of the above-mentioned Q, ring A, $X^1$, $X^2$, $X^3$, $X^4$, Z, $R^1$, $R^{2a}$, $R^{2b}$, $R^3$, $R^4$, $R^5$ and $R^6$. For example, the following compounds are preferable.

(i) A compound wherein, in the formula (I), Q is O;

$X^1$ and $X^3$ are CR$^1$;

$X^2$ is CR$^1$ or N;

$R^1$ is a hydrogen atom or a halogen atom;

Z is CR$^{2b}$;

$R^{2a}$ and $R^{2b}$ are each independently selected from the group consisting of a hydrogen atom, a halogen atom, a cyano group, a $C_1$-$C_6$ alkyl group, a $C_1$-$C_6$ haloalkyl group, a $C_1$-$C_6$ alkoxy group, a $C_1$-$C_6$ haloalkoxy group, a $C_1$-$C_4$ alkoxy-$C_1$-$C_4$ alkyl group, a $C_1$-$C_4$ alkoxy-$C_1$-$C_4$ haloalkyl group, a $C_1$-$C_6$ alkylcarbonyl group, a $C_1$-$C_6$ alkoxycarbonyl group, a $C_3$-$C_7$ cycloalkyl group, a $C_2$-$C_6$ alkenyl-$C_1$-$C_6$ alkoxy group, a $C_2$-$C_6$ alkynyl-$C_1$-$C_6$ alkoxy group and a group represented by the formula (I-A)

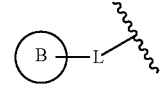

(I-A)

{wherein,

L is a single bond, —(CH$_2$)$_p$—, —O(CH$_2$)$_p$— or —(CH$_2$)$_p$O—, p is 1 or 2, and ring B is a phenyl optionally substituted by a halogen atom, a $C_1$-$C_4$ alkyl group, a $C_1$-$C_4$ alkoxy group or a cyano group, or a 5- or 6-membered ring heteroaryl optionally substituted by a halogen atom, a $C_1$-$C_4$ alkyl group, a $C_1$-$C_4$ alkoxy group or a cyano group} (provided that R$^{2a}$ and R$^{2b}$ are not hydrogen atoms at the same time);

$R^3$ is a hydrogen atom; and ring A is a ring selected from the group consisting of the following formulas:

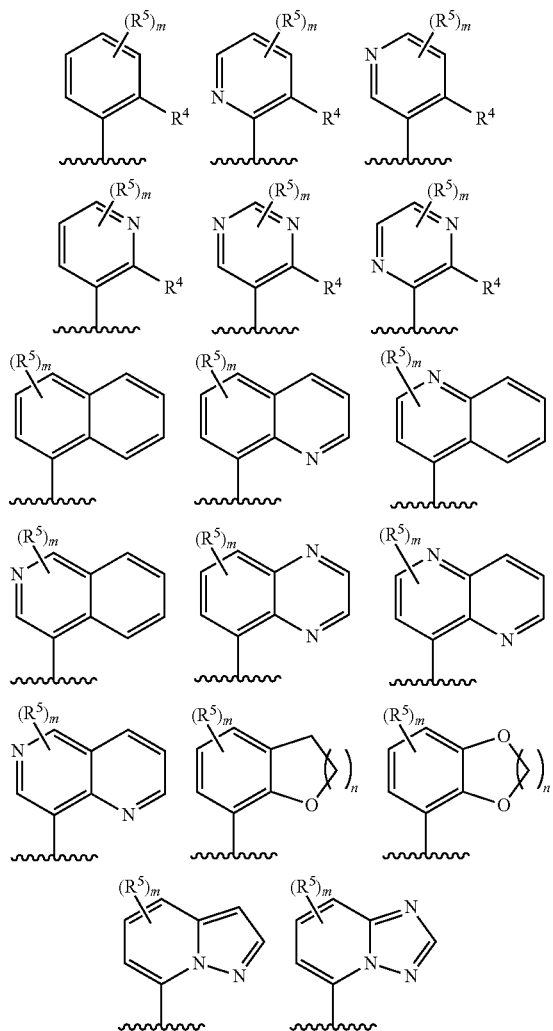

wherein m, is 0, 1 or 2, n is 1 or 2, $R^4$ is selected from the group consisting of a halogen atom, a cyano group, a $C_1$-$C_6$ alkyl group, a $C_1$-$C_6$ haloalkyl group, a $C_3$-$C_7$ cycloalkyl group, a $C_1$-$C_6$ alkoxy group, a $C_1$-$C_6$ haloalkoxy group, a vinyl group, an ethynyl group and a $C_1$-$C_6$ alkylthio group, and $R^5$ is selected from the group consisting of a hydrogen atom, a halogen atom, a $C_1$-$C_4$ alkyl group and a $C_1$-$C_4$ haloalkyl group.

(ii) A compound wherein, in the aforementioned compound (i), ring A is a ring selected from the group consisting of the following formulas:

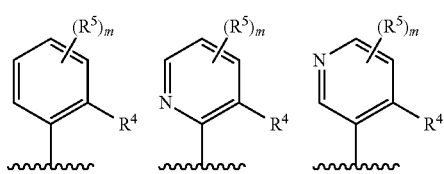

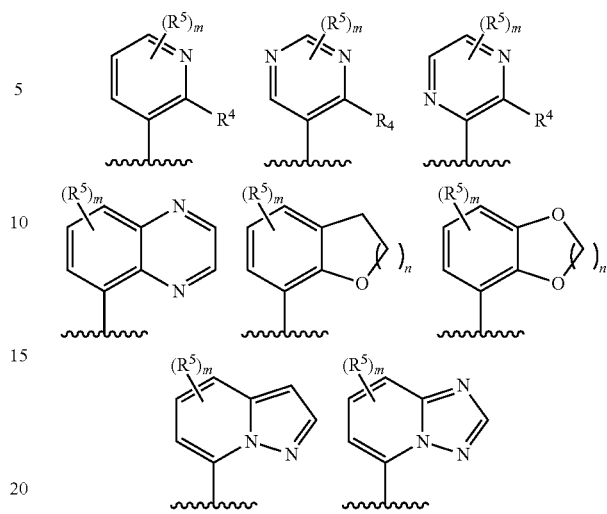

wherein m, n $R^4$ and $R^5$ are as defined in (i).

(iii) A compound wherein, in the aforementioned compound (i), $R^4$ is selected from the group consisting of a halogen atom, a $C_1$-$C_4$ alkyl group, a $C_1$-$C_4$ haloalkyl group, a cyclopropyl group, a $C_1$-$C_4$ alkoxy group and a $C_1$-$C_4$ haloalkoxy group.

(iv) A compound wherein, in the aforementioned compound (i), $R^{2a}$ and $R^{2b}$ are each independently selected from the group consisting of a hydrogen atom, a $C_1$-$C_4$ alkyl group, a $C_1$-$C_4$ haloalkyl group, a $C_1$-$C_4$ alkoxy group, a $C_1$-$C_4$ haloalkoxy group, a $C_1$-$C_4$ alkoxy-$C_1$-$C_4$ alkyl group, a $C_1$-$C_4$ alkoxy-$C_1$-$C_4$ haloalkyl group, and a $C_3$-$C_7$ cycloalkyl group (provided that $R^{2a}$ and $R^{2b}$ are not hydrogen atoms at the same time).

(v) Specifically, compounds selected from the following are more preferable.

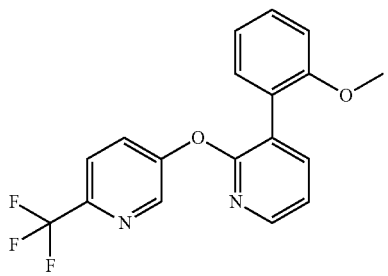

(I-1)

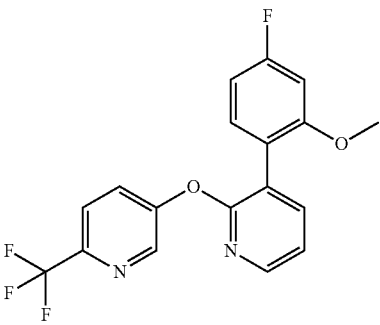

(I-12)

(I-16) 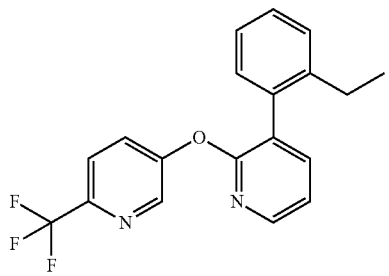
(I-25) 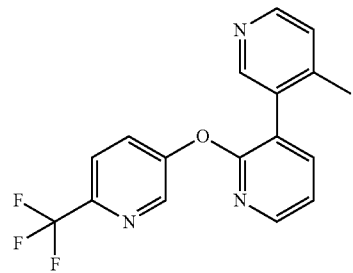
(I-26) 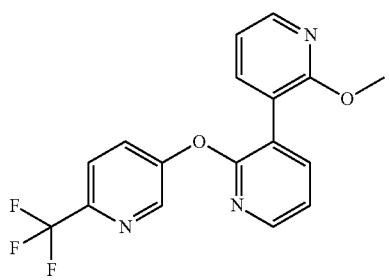
(I-28) 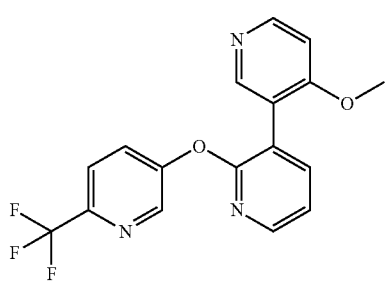
(I-31) 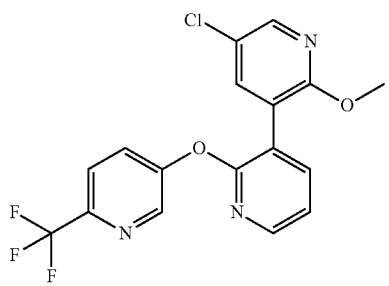
(I-35) 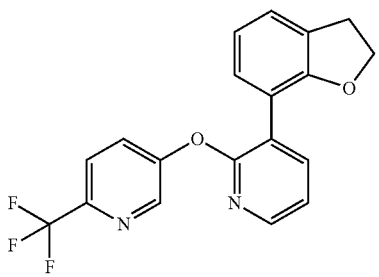 [SMILES: FC(F)(F)c1ccc(Oc2ncccc2-c2cccc3c2OCC3)cn1]
(I-37) 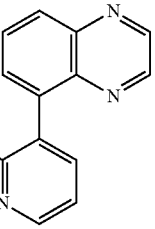
(I-44) 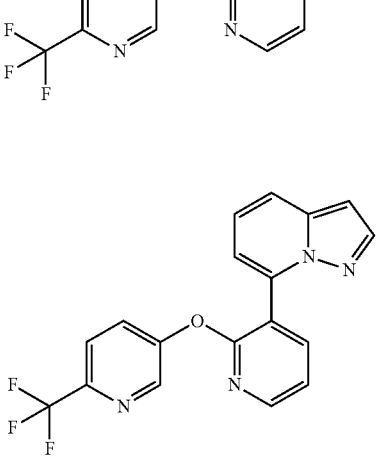
(I-72) 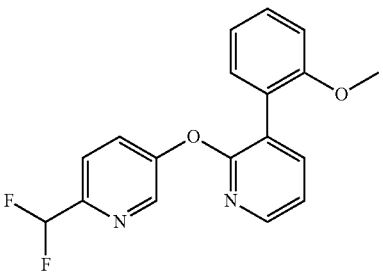
(I-73) 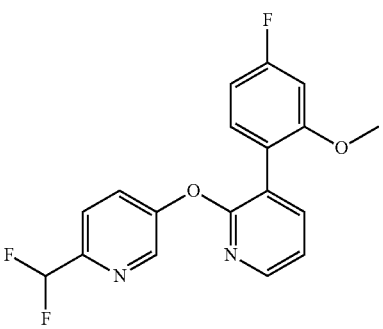

(I-81) 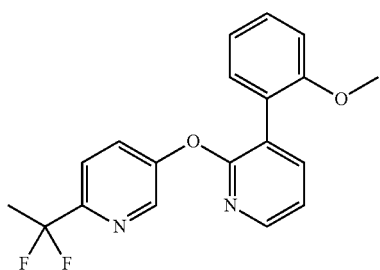
(I-82) 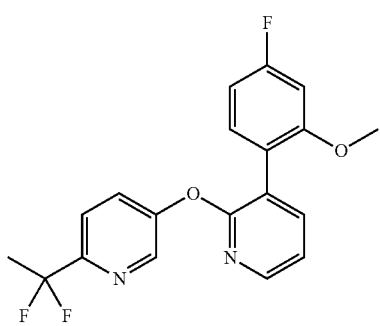
(I-83) 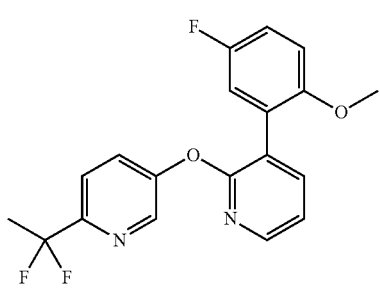
(I-84) 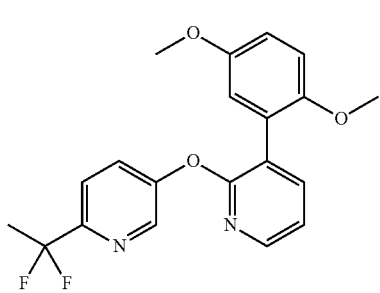
(I-88) 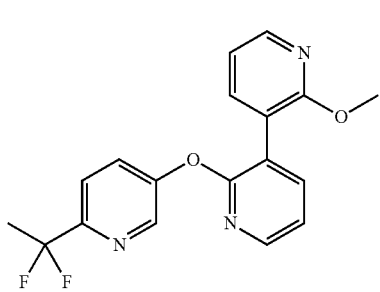 [SMILES: COc1ncccc1-c1cccnc1Oc1ccc(C(C)(F)F)nc1]
(I-90) 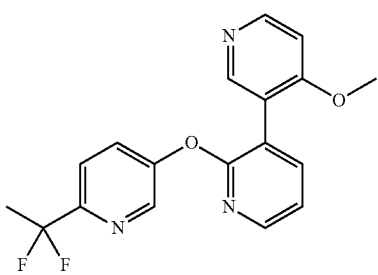 [SMILES: COc1ccncc1-c1cccnc1Oc1ccc(C(C)(F)F)nc1]
(I-96) 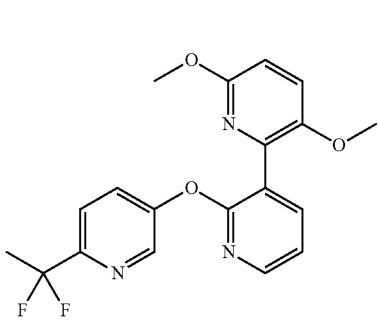 [SMILES: COc1ccc(OC)c(-c2cccnc2Oc2ccc(C(C)(F)F)nc2)n1]
(I-100) 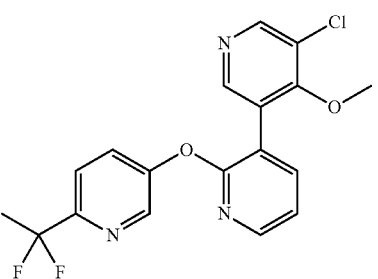 [SMILES: COc1c(Cl)cncc1-c1cccnc1Oc1ccc(C(C)(F)F)nc1]
(I-110)
(I-115) 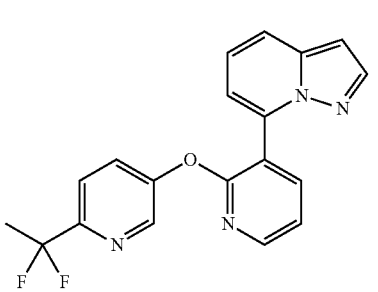

(I-117)
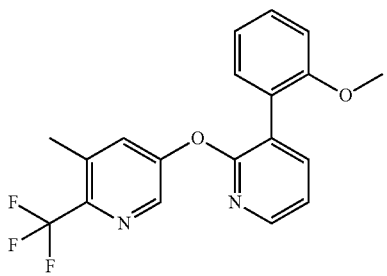
(I-119)
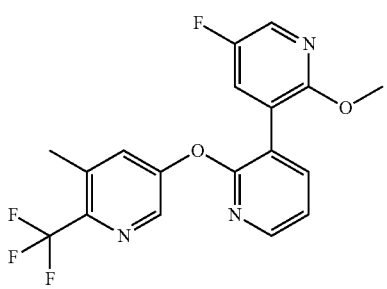
(I-120)
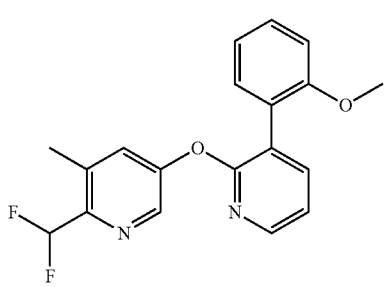
(I-121)
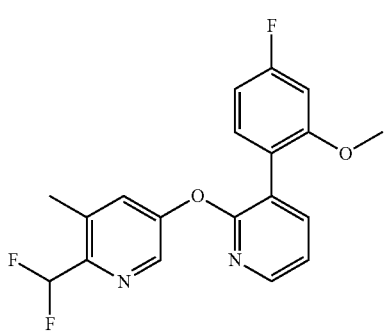
(I-125)
(I-134)
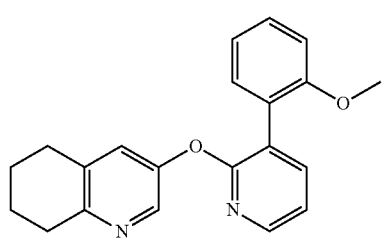
(I-145)
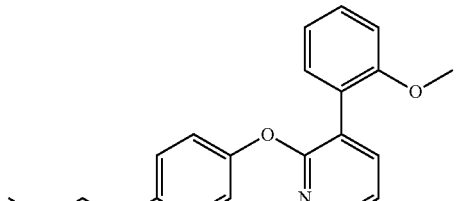
(I-161)
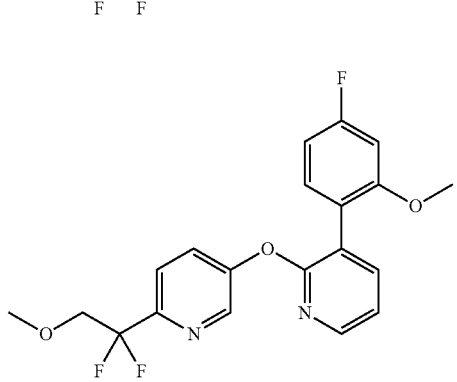
(I-162)
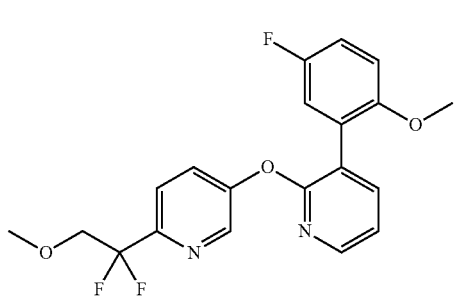
(I-179)
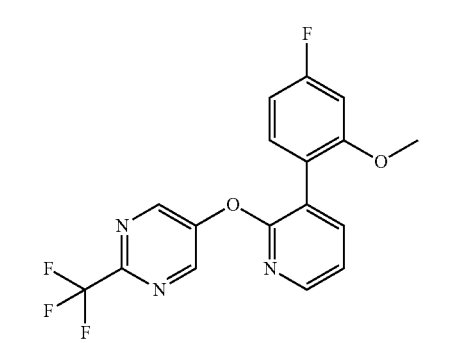
(I-185)
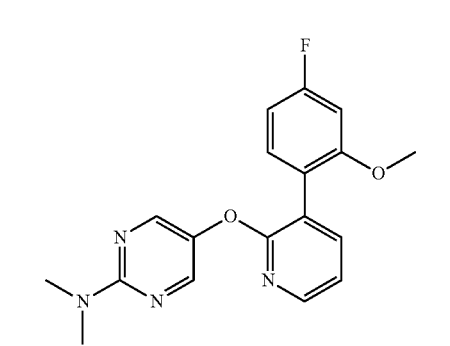

-continued
(I-192)
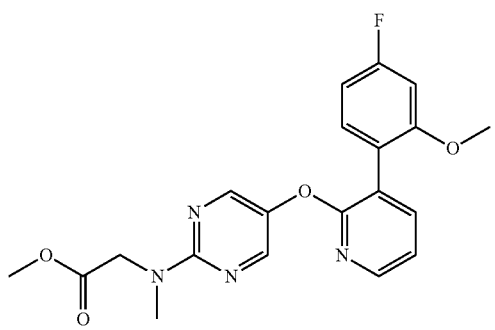
(I-201)
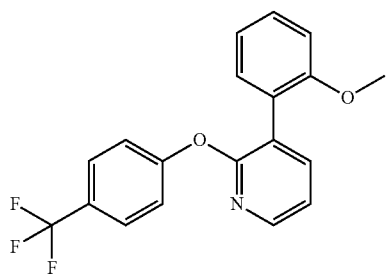
(I-206)
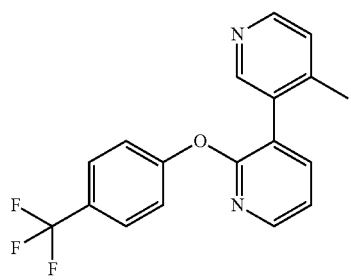
(I-210)
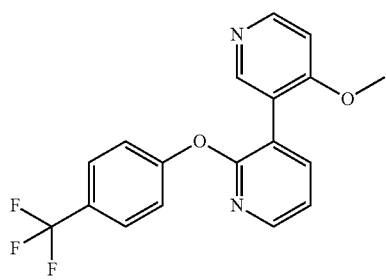
(I-212)
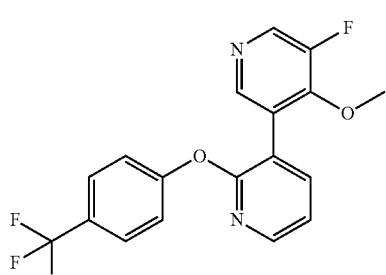
-continued
(I-216)
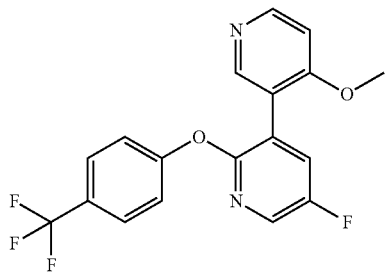
(I-218)
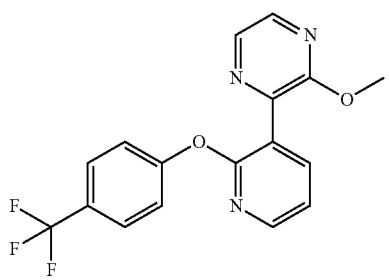
(I-219)
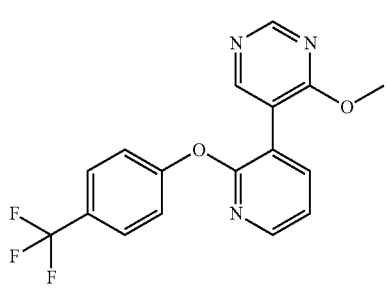
(I-226)
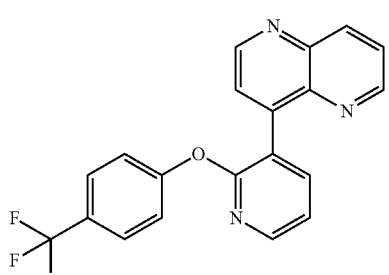
(I-227)
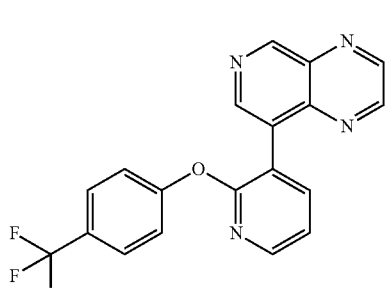

(I-228) 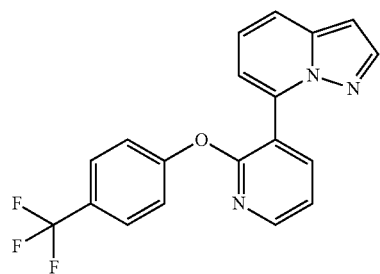
(I-235) 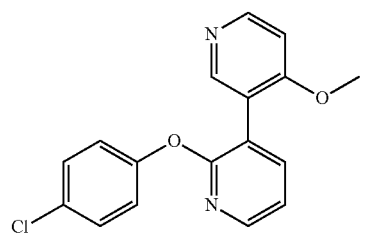
(I-237) 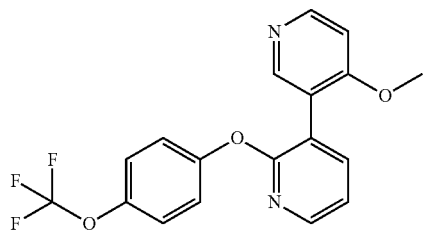
(I-245) 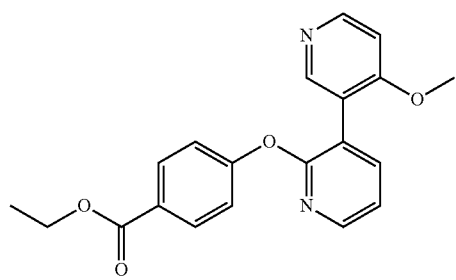
(I-252) 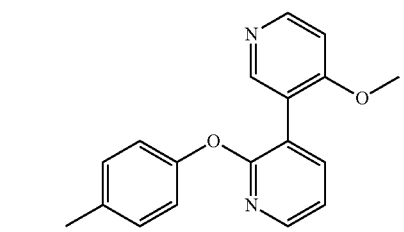
(I-253) 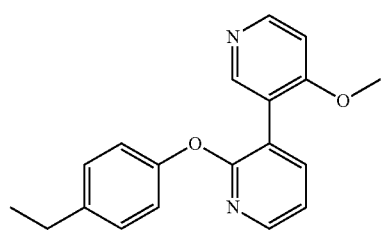
(I-261) 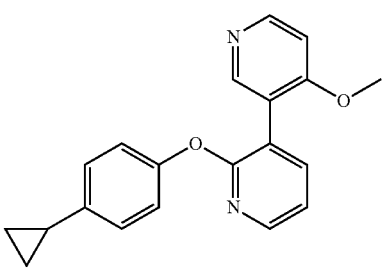
(I-269) 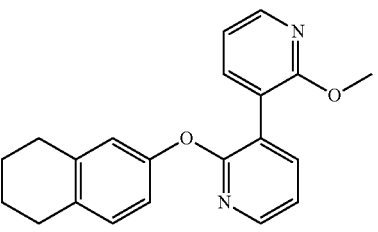
(I-282) 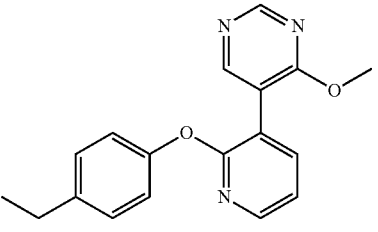
(I-294) 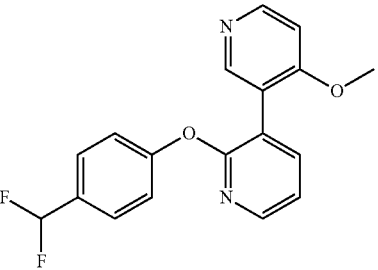
(I-295) 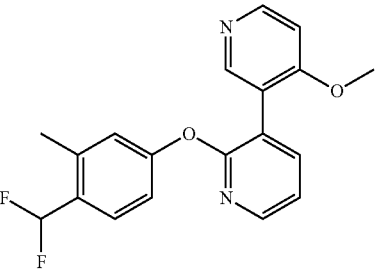
(I-297) 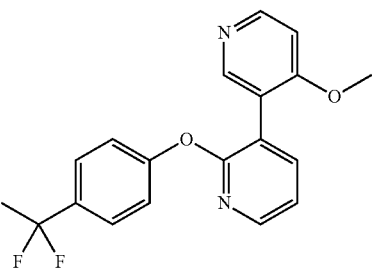

(I-298) 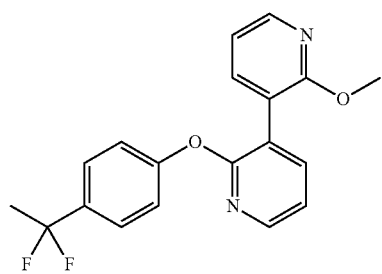
(I-303) 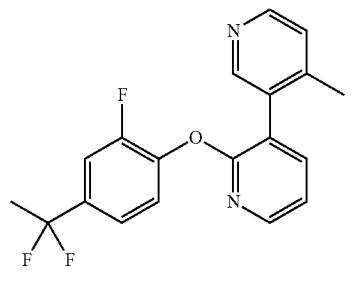
(I-304) 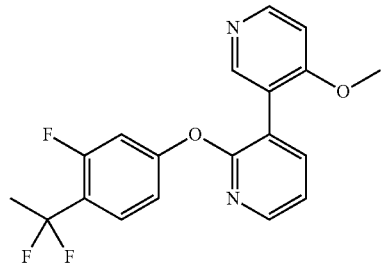
(I-310) 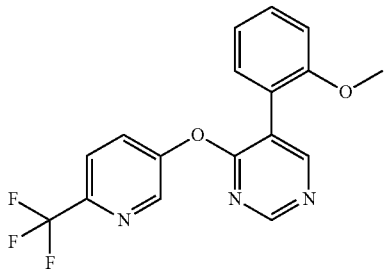
(I-312) 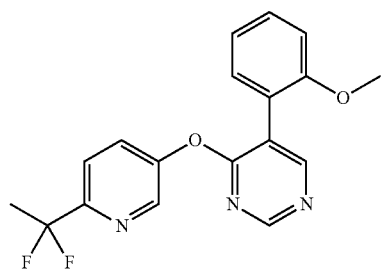
(I-317) 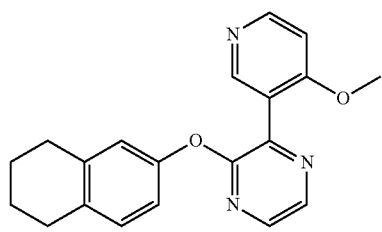
(I-324) 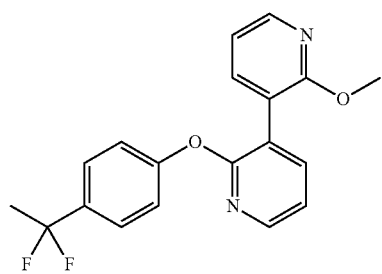
(I-330) 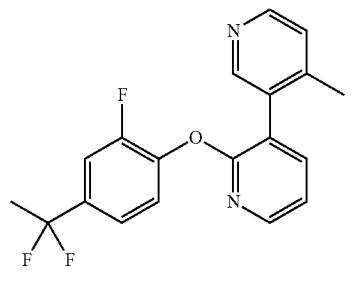
(I-335) 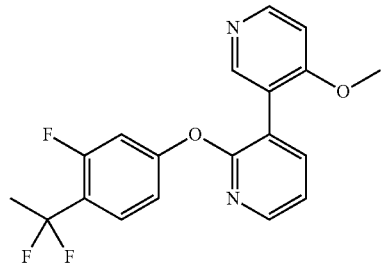
(I-343) 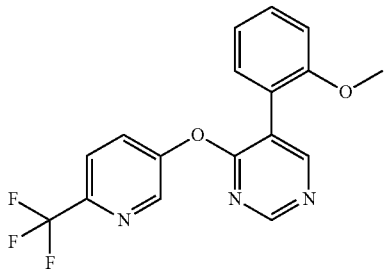
(I-350) 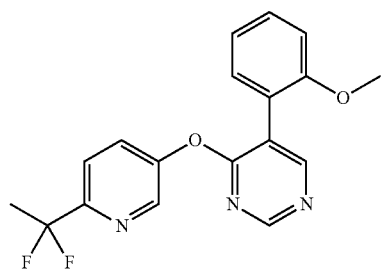

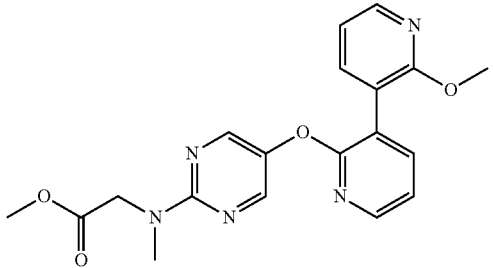
(I-354)

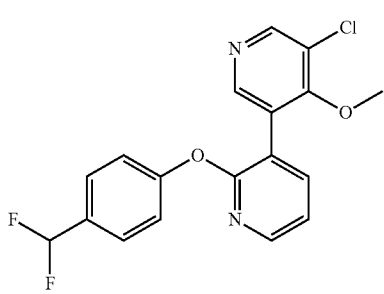
(I-355)

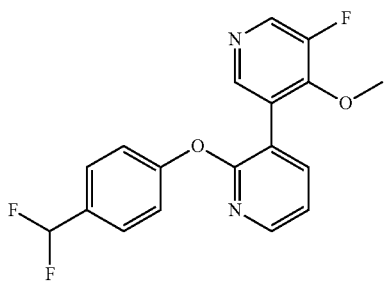
(I-356)

(I-358)

(I-359)

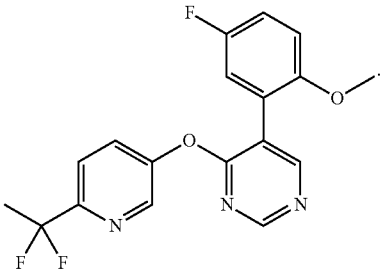
(I-360)

In another embodiment of the present invention, a preferable embodiment of compound (I) or a pharmaceutically acceptable salt thereof of the present invention is a compound comprising a combination of preferable atoms and groups of the above-mentioned Q, ring A, $X^1$, $X^2$, $X^3$, $X^4$, Z, $R^1$, $R^{2a}$, $R^{2b}$, $R^3$, $R^4$, $R^5$, $R^{5a}$, $R^{5b}$, $R^{5c}$, $R^6$, $R^{6a}$, and $R^{6b}$. For example, the following compounds are preferable.

(i) A compound wherein, in the formula (I), Q is O;
$X^1$ is CH;
$X^2$ and $X^3$ are each independently $CR^1$ or N;
$R^1$ is a hydrogen atom or a halogen atom;
Z is $CR^{2b}$;
$R^{2a}$ and $R^{2b}$ are each independently selected from the group consisting of a hydrogen atom, a halogen atom, a cyano group, a $C_1$-$C_6$ alkyl group, a $C_1$-$C_6$ haloalkyl group, a $C_1$-$C_6$ alkoxy group, a $C_1$-$C_6$ haloalkoxy group, a $C_1$-$C_4$ alkoxy-$C_1$-$C_4$ alkyl group, a $C_1$-$C_4$ alkoxy-$C_1$-$C_4$ haloalkyl group, a $C_1$-$C_6$ alkylcarbonyl group, a $C_1$-$C_6$ alkoxycarbonyl group, a $C_3$-$C_7$ cycloalkyl group a $C_2$-$C_6$ alkenyl-$C_1$-$C_6$ alkoxy group, a $C_1$-$C_6$ alkynyl-$C_1$-$C_6$ alkoxy group and a group represented by the formula (I-A)

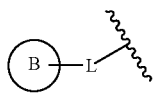
(I-A)

{wherein,
L is a single bond, —$(CH_2)_p$—, —$O(CH_2)_p$— or —$(CH_2)_pO$—,
p is 1 or 2, and
ring B is a phenyl optionally substituted by a halogen atom, a $C_1$-$C_4$ alkyl group, a $C_1$-$C_4$ alkoxy group or a cyano group, or a 5- or 6-membered ring heteroaryl optionally substituted by a halogen atom, a $C_1$-$C_4$ alkyl group, a $C_1$-$C_4$ alkoxy group or a cyano group} (provided that $R^{2a}$ and $R^{2b}$ are not hydrogen atoms at the same time);
$R^3$ is a hydrogen atom; and
ring A is a ring selected from the group consisting of the following formulas:

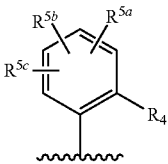

-continued

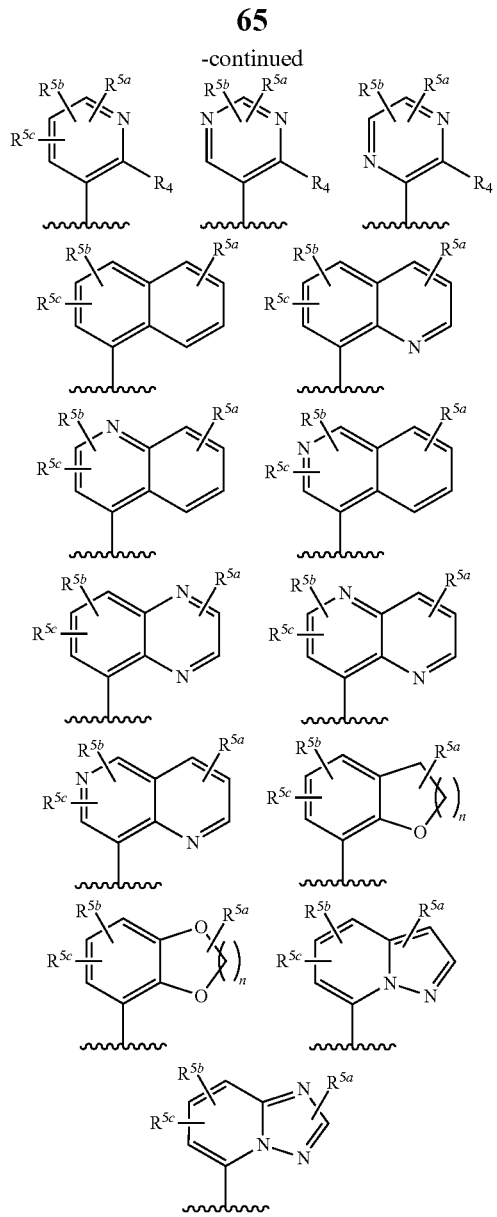

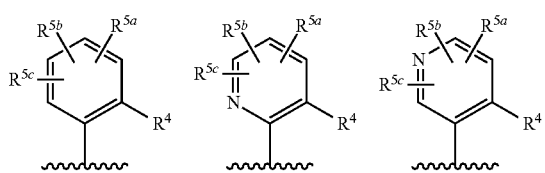

wherein n is 1 or 2, R⁴ is selected from the group consisting of a halogen atom, a cyano group, a $C_1$-$C_6$ alkyl group, a $C_1$-$C_6$ haloalkyl group, a $C_3$-$C_7$ cycloalkyl group, a $C_1$-$C_6$ alkoxy group, a $C_1$-$C_6$ haloalkoxy group, a vinyl group, an ethynyl group and a $C_1$-$C_6$ alkylthio group, and $R^{5a}$, $R^{5b}$ and $R^{5c}$ are each independently selected from the group consisting of a hydrogen atom, a halogen atom, a $C_1$-$C_4$ alkyl group and a $C_1$-$C_4$ haloalkyl group.

(ii) A compound wherein, in the aforementioned compound (i), ring A is a ring selected from the group consisting of the following formulas:

-continued

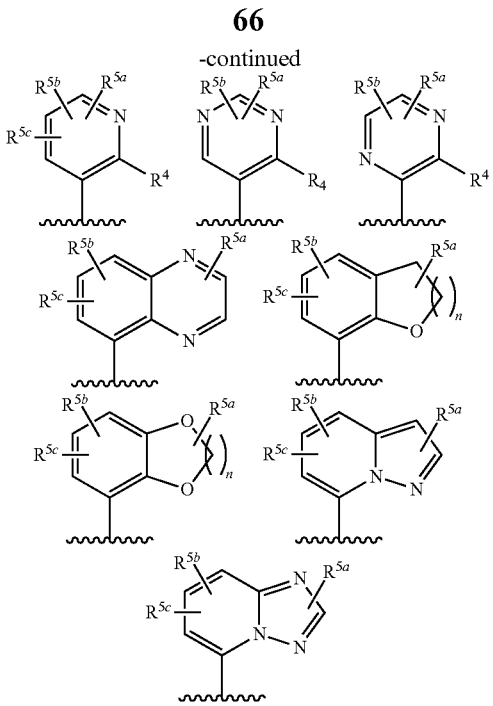

wherein n, $R^4$, $R^{5a}$, $R^{5b}$ and $R^{5c}$ are as defined in (i).

In another embodiment of the present invention, a preferable embodiment of compound (I) or a pharmaceutically acceptable salt thereof of the present invention is a compound comprising a combination of preferable atoms and groups of the above-mentioned Q, ring A, $X^1$, $X^2$, $X^3$, $X^4$, Z, $R^1$, $R^{2a}$, $R^{2b}$, $R^3$, $R^4R^5$, $R^{5a}$, $R^{5b}$, $R^{5c}$, $R^6$, $R^{6a}$ and $R^{6b}$. For example, the following compounds are preferable.

(i) A compound wherein, in the formula (I), Q is O;
$X^1$ is CH;
$X^2$ and $X^3$ are each independently $CR^1$ or N;
$R^1$ is a hydrogen atom or a halogen atom;
Z is $CR^{2b}$;
$R^{2a}$ is selected from the group consisting of a hydrogen atom, a halogen atom, a cyano group, a $C_1$-$C_6$ alkyl group, a $C_1$-$C_6$ haloalkyl group, a $C_1$-$C_6$ alkoxy group, a $C_1$-$C_6$ haloalkoxy group, a $C_1$-$C_4$ alkoxy-$C_1$-$C_4$ alkyl group, a $C_1$-$C_4$ alkoxy-$C_1$-$C_4$ haloalkyl group, a $C_1$-$C_6$ alkylcarbonyl group, a $C_1$-$C_6$ alkoxycarbonyl group, a $C_3$-$C_7$ cycloalkyl group, —$NR^aR^b$ {$R^a$ and $R^b$ are each independently a hydrogen atom, a $C_1$-$C_6$ alkyl group, a $C_1$-$C_6$ alkyl group substituted by a $C_1$-$C_4$ alkoxy group or a $C_1$-$C_6$ alkyl group substituted by a $C_1$-$C_6$ alkoxycarbonyl group (provided that $R^a$ and $R^b$ are not hydrogen atoms at the same time)}, and a group represented by the formula (I-A)

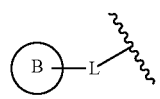

(I-A)

{wherein,
L is a single bond, —$(CH_2)_p$—, —$O(CH_2)_p$— or —$(CH_2)_pO$—, wherein one or more hydrogen atoms of $(CH_2)_p$ are optionally substituted by a halogen atom,
p is 1 or 2, and
ring B is phenyl or pyrazolyl};
$R^{2b}$ is selected from the group consisting of a hydrogen atom, a halogen atom and a $C_1$-$C_6$ alkyl group;

R³ is a hydrogen atom or a halogen atom; and ring A is a ring selected from the group consisting of phenyl, pyridyl, pyrimidinyl, pyrazinyl, quinoxalinyl, dihydrobenzofuranyl, pyrazolopyridyl, triazolopyridyl, naphthyridinyl and pyridopyrazinyl, each of which is optionally substituted by one or more substituents selected from the group consisting of a halogen atom, a $C_1$-$C_6$ alkyl group, a $C_1$-$C_6$ haloalkyl group and a $C_1$-$C_6$ alkoxy group.

(ii) A compound wherein, in the formula (I), Q is O;

$X^1$ and $X^3$ are CH;

$X^2$ is $CR^1$ or N;

$R^1$ is a hydrogen atom or a halogen atom;

Z is $CR^{2b}$;

$R^{2a}$ is selected from the group consisting of a hydrogen atom, a halogen atom, a $C_1$-$C_6$ alkyl group, a $C_1$-$C_6$ haloalkyl group, a $C_1$-$C_6$ alkoxy group, a $C_1$-$C_6$ haloalkoxy group, a $C_1$-$C_4$ alkoxy-$C_1$-$C_4$ alkyl group, a $C_1$-$C_4$ alkoxy-$C_1$-$C_4$ haloalkyl group, a $C_1$-$C_6$ alkylcarbonyl group, a $C_1$-$C_6$ alkoxycarbonyl group, a $C_3$-$C_7$ cycloalkyl group and —$NR^aR^b$ {$R^a$ and $R^b$ are each independently a hydrogen atom, a $C_1$-$C_6$ alkyl group, a $C_1$-$C_6$ alkyl group substituted by a $C_1$-$C_6$ alkoxy group or a $C_1$-$C_6$ alkyl group substituted by a $C_1$-$C_6$ alkoxycarbonyl group (provided that $R^a$ and $R^b$ are not hydrogen atoms at the same time)};

$R^{2b}$ is selected from the group consisting of a hydrogen atom, a halogen atom, and a methyl group; and ring A is a ring selected from the group consisting of phenyl, pyridyl, pyrimidinyl, pyrazinyl, quinoxalinyl, dihydrobenzofuranyl, pyrazolopyridyl, triazolopyridyl, naphthyridinyl, and pyridopyrazinyl, each of which is optionally substituted by one or more substituents selected from the group consisting of a halogen atom, a $C_1$-$C_6$ alkyl group, a $C_1$-$C_6$ haloalkyl group and a $C_1$-$C_6$ alkoxy group.

(iii) A compound wherein, in the formula (I), Q is O;

$X^1$ and $X^3$ are CH;

$X^2$ is CH or N;

Z is $CR^{2b}$;

$R^{2a}$ and $R^{2b}$ are joined to form —$(CH_2)_r$— (r is 3, 4, 5 or 6) optionally substituted by a halogen atom, a hydroxyl group or an oxo group, and ring A is a ring selected from the group consisting of phenyl, pyridyl, pyrimidinyl, pyrazinyl, quinoxalinyl, dihydrobenzofuranyl, pyrazolopyridyl, triazolopyridyl, naphthyridinyl and pyridopyrazinyl, each of which is optionally substituted by one or more substituents selected from the group consisting of a halogen atom, a $C_1$-$C_6$ alkyl group, a $C_1$-$C_6$ haloalkyl group and a $C_1$-$C_6$ alkoxy group.

The salt of compound (I) is preferably a pharmacologically acceptable salt. The "pharmacologically acceptable salt" of compound (I) is not particularly limited as long as it is a pharmacologically acceptable salt. Examples thereof include inorganic acid salts such as hydrochloride, hydrobromide, nitrate, sulfate, phosphate and the like, organic carboxylic acid salts such as acetate, oxalate, fumarate, maleate, malonate, citrate, succinate, lactate, tartrate, malate and the like, aromatic carboxylic acid salts such as salicylate, benzoate and the like, organic sulfonates such as methanesulfonate, benzenesulfonate and the like, alkali metal salts such as lithium salt, sodium salt, potassium salt and the like, alkaline earth metal salts such as calcium salt and the like, magnesium salt and the like.

When the compound represented by the formula (I) of the present invention contains an asymmetric carbon, a racemate, diastereoisomers and individual optically active forms thereof are all encompassed in the present invention. When geometric isomers are present, (E) form, (Z) form and a mixture thereof are all encompassed in the present invention.

When the compound represented by the formula (I) of the present invention contains solvates such as hydrate and the like, they are also encompassed in the present invention.

A compound represented by the formula (I), which is the biaryl derivative of the present invention, can be produced by various methods and can be produced, for example, by the method shown by scheme 1 or scheme 2.

A compound represented by the formula (I) can be produced by a method shown by the following scheme 1 (Step 1-1 to Step 1-4).

Scheme 1:

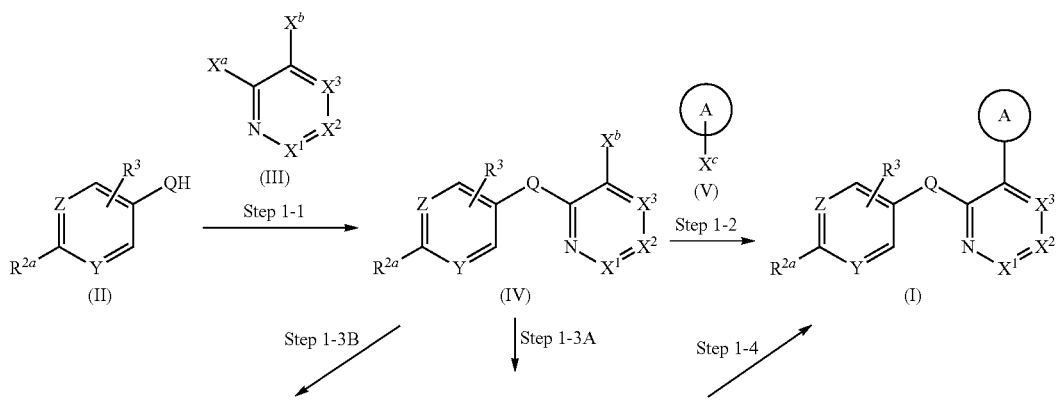

-continued

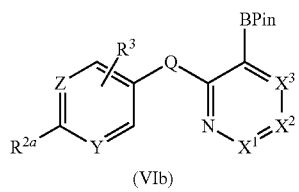 (VIb)

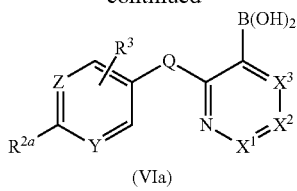 (VIa)

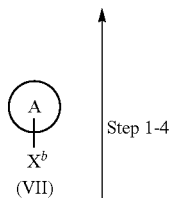 (VII)

Step 1-4 wherein A, $R^{2a}$, $R^3$, Q, $X^1$, $X^1$, $X^2$, $X^3$, Y and Z are as defined in the aforementioned formula (I); $X^a$ is a fluorine atom, a chlorine atom or a bromine atom, $X^b$ is a chlorine atom, a bromine atom or an iodine atom; and $X^c$ is —B(OH)$_2$ or —BPin (4,4,5,5-tetramethyl-1,3,2-dioxaborolan-2-yl).

A compound represented by the formula (I) can be obtained by $S_N$ aryl reaction of a compound represented by the formula (II) and a compound represented by the formula (III) to give aryl halide compound (IV), followed by Suzuki-Miyaura cross coupling with various boronic acids or boronic acid esters (V) having ring A. Also, compound (I) can be obtained by leading aryl halide compound (IV) to boronic acid compound (VIa) or boronic acid ester compound (VIb), and performing Suzuki-Miyaura cross coupling reaction with various aryl halides (VII) having ring A. Each step is explained in detail in the following.

<Step 1-1>

In Step 1-1, a compound represented by the formula (IV) is produced by reacting a compound represented by the formula (II) and a compound represented by the formula (III) in the presence of a base. As the base to be used, potassium carbonate, sodium carbonate, cesium carbonate, lithium carbonate, tripotassium phosphate, potassium hydroxide, sodium hydroxide, lithium hydroxide, potassium tert-butoxide, sodium tert-butoxide, potassium fluoride, potassium hexamethyldisilazane, sodium hydride or the like can be mentioned. To smoothly perform the reaction, an additive may be co-present, and potassium iodide, sodium iodide, tetrabutylammonium iodide, potassium bromide, sodium bromide, tetrabutylammonium bromide or the like can be added as an additive. The reaction solvent is not particularly limited as long as it does not markedly inhibit the reaction, and N,N-dimethylformamide, N,N-dimethylacetamide, dimethyl sulfoxide, N-methylpyrrolidone, acetone, acetonitrile, methanol, ethanol, tetrahydrofuran, 1,4-dioxane, 2-methoxyethanol, a mixed solvent thereof or the like are preferable. Water can also be added as a reaction solvent. The amount of water to be added is not particularly limited and is, for example, not more than 10% (v/v) of the whole solvent. The reaction temperature is not particularly limited, and the reaction is generally performed from room temperature to 150° C., and the reaction time is preferably 1-24 hr. In addition, microwave can also be used for this reaction.

In Step 1-1, when a compound represented by the formula (II) is an amine compound (Q=NH), a compound represented by the formula (IV) can be produced by reacting a compound represented by the formula (II) with a compound represented by the formula (III) in the presence of an acid.

<Step 1-2>

In Step 1-2, a compound represented by the formula (I) can be produced by reacting a mixture of a compound represented by the formula (IV) and a boronic acid or a boronic acid ester represented by the formula (V) with a palladium catalyst in the presence of a base. This reaction is preferably performed under an inert gas atmosphere such as argon and the like. As the base to be used, potassium carbonate, sodium carbonate, cesium carbonate, lithium carbonate, tripotassium phosphate, potassium hydroxide, sodium hydroxide, lithium hydroxide, potassium tert-butoxide, potassium hexamethyldisilazane, triethylamine, diisopropylethylamine, 1,8-diazabicyclo[5.4.0]undec-7-ene (DBU) or the like can be mentioned. To smoothly perform the reaction, an additive may be co-present. As the additive, trialkylphosphines such as trimethylphosphine, tri-tert-butylphosphine and the like; tricycloalkylphosphines such as tricyclohexylphosphine and the like; triarylphosphines such as triphenylphosphine, tritolylphosphine and the like; trialkyl phosphites such as trimethyl phosphite, triethyl phosphite, tributyl phosphite and the like; tricycloalkyl phosphites such as tricyclohexyl phosphite and the like; triaryl phosphites such as triphenyl phosphite and the like; imidazolium salts such as 1,3-bis(2,4,6-trimethylphenyl)imidazolium chloride and the like; diketones such as acetylacetone, octafluoroacetylacetone and the like; amines such as trimethylamine, triethylamine, tripropylamine, triisopropylamine, tributylamine and the like; 1,1'-bis(diphenylphosphino)ferrocene; 2,2'-bis(diphenylphosphino)-1,1'-binaphthyl; 2-dicyclohexylphosphino-2',6'-dimethoxybiphenyl; 2-dicyclohexylphosphino-2',4',6'-triisopropylbiphenyl 2-(di-tert-butylphosphino)-2',4',6'-triisopropylbiphenyl; 2-dicyclohexylphosphino-2'-(N,N-dimethylamino)biphenyl; 4,5-bis(diphenylphosphino)-9,9-dimethylxanthene; and 2-(di-tert-butylphosphino)biphenyl can be mentioned. These can also be used in combination. The reaction solvent is not particularly limited as long as it does not markedly inhibit the reaction, N,N-dimethylformamide, N,N-dimethylacetamide, dimethyl sulfoxide, N-methylpyrrolidone, acetonitrile, methanol, ethanol, 2-propanol, n-butyl alcohol, t-amyl alcohol, tetrahydrofuran, 1,4-dioxane, dimethoxyethane, toluene, cyclopentyl methyl ether (CPME), water or a mixed solvent thereof and the like can be mentioned. As the palladium catalyst, metal palladium such as palladium-carbon, palladium black and the like; organic palladium salts such as tetrakis(triphenylphosphine)palladium, dichlorobis (triphenylphosphine)palladium, palladium acetate, palladium chloride-1,1'-bis(diphenylphosphino)ferrocene, bis[di-tert-butyl(4-dimethylaminophenyl)phosphine] dichloropalladium and the like; polymer-supported organic palladium complexes such as polymer-bound bis(acetato) triphenylphosphinepalladium(II), polymer-bound di)acetato)dicyclohexylphenylphosphinepalladium(II) and the like, and the like can be mentioned. These may be used in combination. The amount of the palladium catalyst to be added is generally 1-50 mol %, preferably about 5-20 mol %, relative to a compound represented by the formula (IV). The reaction temperature is not particularly limited, and the reaction is generally performed from room temperature to 120° C., and the reaction time is preferably 1-24 hr. This reaction can also be performed under microwave irradiation at about 120° C. for a reaction time of 10 min-2 hr.
<Step 1-3A>

In Step 1-3A, a boronic acid compound represented by the formula (VIa) can be produced by halometal exchange by reacting a compound represented by the formula (IV) with a Grignard reagent, an organic lithium reagent or a zinc reagent, reacting same with a boronic acid ester, and performing hydrolysis thereof. This reaction is preferably performed under an inert gas atmosphere such as argon and the like. As the Grignard reagent, magnesium, isopropylmagnesium bromide, isopropylmagnesium chloride, isopropylmagnesium chloride-lithium chloride or the like can be mentioned; as the organic lithium reagent, normal butyllithium, sec-butyllithium, tert-butyllithium and the like can be mentioned; and as the zinc reagent, activated zinc, zinc bromide, zinc chloride or the like can be mentioned. The reaction solvent is not particularly limited as long as it does not markedly inhibit the reaction, tetrahydrofuran, diethyl ether, 1,4-dioxane, dimethoxyethane or the like is preferable. The reaction temperature is not particularly limited, and the reaction is generally performed from −78° C. to 100° C., and the reaction time is preferably 1-24 hr.
<Step 1-3B>

In Step 1-3B, a compound represented by the formula (VIb) can be produced by reacting a mixture of a compound represented by the formula (IV) and a boronic acid ester compound with a palladium catalyst in the presence of a base. This reaction is preferably performed under an inert gas atmosphere such as argon and the like. As the base to be used, potassium carbonate, sodium carbonate, cesium carbonate, lithium carbonate, tripotassium phosphate, potassium hydroxide, sodium hydroxide, lithium hydroxide, potassium tert-butoxide, potassium hexamethyldisilazane, triethylamine, diisopropylethylamine, DBU or the like can be mentioned. To smoothly perform the reaction, an additive may be co-present, and triphenylphosphine or the like can be added as an additive. The reaction solvent is not particularly limited as long as it does not markedly inhibit the reaction, and N,N-dimethylformamide, N,N-dimethylacetamide, dimethyl sulfoxide, N-methylpyrrolidone, acetonitrile, methanol, ethanol, 2-propanol, n-butyl alcohol, t-amyl alcohol, tetrahydrofuran, 1,4-dioxane, dimethoxyethane, toluene, CPME, water or a mixed solvent thereof and the like can be mentioned. As the palladium catalyst, tetrakis(triphenylphosphine)palladium, dichlorobis(triphenylphosphine) palladium, palladium acetate, palladium chloride-1,1'-bis (diphenylphosphino)ferrocene, bis[di-tert-butyl(4-dimethylaminophenyl)phosphine]dichloropalladium or the like can be mentioned. The amount of the palladium catalyst to be added is generally 1-50 mol %, preferably about 5-20 mol %, relative to a compound represented by the formula (IV). The reaction temperature is not particularly limited, and the reaction is generally performed from room temperature to 120° C., and the reaction time is preferably 1-24 hr. Similar to Step 1-2, this reaction can also be performed under microwave irradiation at about 120° C. for a reaction time of 10 min-2 hr.
<Step 1-4>

Step 1-4 can be similarly performed as in Step 1-2. That is, in Step 1-4, a compound represented by the formula (I) can be produced by reacting a mixture of a boronic acid compound represented by the formula (VIa) or a boronic acid ester compound represented by the formula (VIb) and an aryl halide compound represented by the formula (VII) with a palladium catalyst in the presence of a base.

The aforementioned compound (I) can also be produced by the method shown by the following scheme 2 (Step 2-1 to Step 2-2).

Scheme 2:

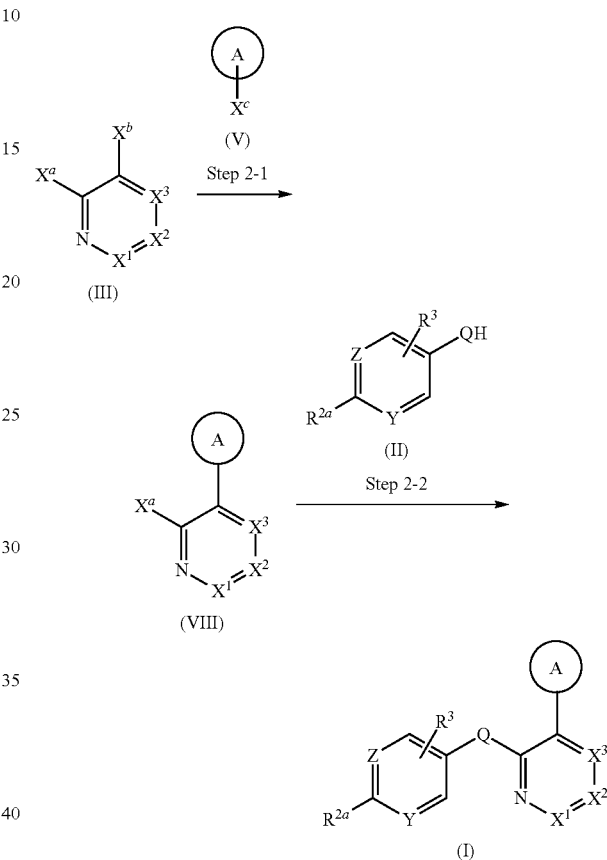

wherein A, $R^{2a}$, $R^3$, Q, $X^1$, $X^2$, $X^3$, Y and Z are as defined above; $X^a$ is a fluorine atom, a chlorine atom or a bromine atom, $X^b$ is a chlorine atom, a bromine atom or an iodine atom; and $X^c$ is —B(OH)$_2$ or —BPin.

A compound represented by the formula (I) can be obtained by Suzuki-Miyaura cross coupling reaction of a compound represented by the formula (III) and various boronic acids or boronoic acid esters (V) having ring A to give a compound represented by the formula (VIII), followed by $S_N$ aryl reaction of a compound represented by the formula (VIII) and a compound represented by the formula (II). Step 2-1 can also be performed by exchanging $X^b$ and $X^c$ under similar conditions.
<Step 2-1>

In Step 2-1, a compound represented by the formula (VIII) can be produced by reacting a mixture of a compound represented by the formula (III) and a boronic acid or a boronic acid ester represented by the formula (V) with a palladium catalyst in the presence of a base. This reaction is preferably performed under an inert gas atmosphere such as argon and the like. As the base to be used, potassium carbonate, sodium carbonate, cesium carbonate, lithium carbonate, tripotassium phosphate, potassium hydroxide, sodium hydroxide, lithium hydroxide, potassium tert-butoxide, potassium hexamethyldisilazane, triethylamine, diisopropylethylamine, DBU or the like can be mentioned. To smoothly perform the reaction, an additive may be co-present, and triphenylphosphine and the like can be added as an additive. The reaction solvent is not particularly limited as long as it does not markedly inhibit the reaction, N,N-dimethylformamide, N,N-dimethylacetamide, dimethyl sulfoxide, N-methylpyrrolidone, acetonitrile, methanol, ethanol, 2-propanol, n-butyl alcohol, t-amyl alcohol, tetrahydrofuran, 1,4-dioxane, dimethoxyethane, toluene, CPME, water or a mixed solvent thereof and the like can be mentioned. As the palladium catalyst, tetrakis(triphenylphosphine)palladium, dichlorobis(triphenylphosphine)palladium, palladium acetate, palladium chloride-1,1'-bis(diphenylphosphino)ferrocene, bis[di-tert-butyl(4-dimethylaminophenyl)phosphine]dichloropalladium or the like can be mentioned. The amount of the palladium catalyst to be added is generally 1-50 mol %, preferably 5-20 mol %, relative to a compound represented by the formula (III). The reaction temperature is not particularly limited, and the reaction is generally performed from room temperature to 120° C., and the reaction time is preferably 1-24 hr. This reaction can also be performed under microwave irradiation at about 120° C. for a reaction time of 10 min-2 hr.

<Step 2-2>

In Step 2-2, a compound represented by the formula (I) can be produced by reacting a compound represented by the formula (VIII) and a compound represented by the formula (II) in the presence of a base. As the base to be used, potassium carbonate, sodium carbonate, cesium carbonate, lithium carbonate, tripotassium phosphate, potassium hydroxide, sodium hydroxide, lithium hydroxide, potassium tert-butoxide, sodium tert-butoxide, potassium fluoride, potassium hexamethyldisilazane, sodium hydride or the like can be mentioned. To smoothly perform the reaction, an additive may be co-present and, as an additive, potassium iodide, sodium iodide, tetrabutylammonium iodide, potassium bromide, sodium bromide, tetrabutylammonium bromide or the like can be added. The reaction solvent is not particularly limited as long as it does not markedly inhibit the reaction, and N,N-dimethylformamide, N,N-dimethylacetamide, dimethyl sulfoxide, N-methylpyrrolidone, acetone, acetonitrile, methanol, ethanol, tetrahydrofuran, 1,4-dioxane, 2-methoxyethanol or a mixed solvent thereof and the like are preferable. Also, water can be added as a reaction solvent. The amount of water to be added is not particularly limited, and for example, not more than 10% (v/v) relative to the whole solvent is preferable. The reaction temperature is not particularly limited, and the reaction is generally performed from room temperature to 180° C., and the reaction time is preferably 1-24 hr. This reaction can also be performed by using a microwave.

In Step 2-2, when a compound represented by the formula (II) is an amine compound (Q=NH), a compound represented by the formula (I) can be produced by reacting a compound represented by the formula (II) with a compound represented by the formula (VIII) in the presence of an acid.

The thus-obtained compound of the formula (I) or a salt thereof can be induced to another compound of the formula (I) or a salt thereof by, for example, subjecting to a known reaction such as condensation reaction, addition reaction, oxidation reaction, reduction reaction, substitution reaction, halogenation, dehydration reaction, hydrolysis and the like, or an appropriately combination thereof.

The compound of the present invention produced by the aforementioned method is isolated and purified as a free compound, a salt thereof, various solvates such as a hydrate, ethanol solvate and the like thereof or a crystalline polymorphic substance. A pharmacologically acceptable salt of the compound of the present invention can be produced by a conventional salt formation reaction. Isolation and purification are performed by applying a chemical operation such as extraction partition, crystallization, various fractionation chromatographies and the like. In addition, an optical isomer can be obtained as a stereochemically pure isomer by selecting a suitable starting compound or by optical resolution of a racemic compound.

The biaryl derivative (I) or a salt thereof of the present invention shows an excellent antifungal activity against *Trichophyton* fungus (e.g., genus *Trichophyton*, genus *Microsporum* etc.) which is the major causative microorganism of superficial mycosis. Therefore, a medicament containing same as an active ingredient is useful as a prophylactic or therapeutic drug for infections caused by *Trichophyton* fungi in mammals including human. Examples of the infections caused by *Trichophyton* fungi include tinea pedis, tinea unguium, tinea corporis, tinea cruris, and tinea capitis. The compound of the present invention shows an excellent effect on tinea unguium since it has superior nail permeability.

A medicament containing the biaryl derivative (I) or a salt thereof of the present invention as an active ingredient is the compound alone or a mixture of the compound and a pharmacologically acceptable liquid or solid carrier, for example, excipient, binder, diluent, expander, disintegrant, stabilizer, preservative, buffer, emulsifier, aromatic, colorant, sweetening agent, thickening agent, corrigent, solubilizing agents, or other additives, which can be prepared by a conventional method in the art.

The medicament of the present invention can be administered orally or parenterally in the dosage form of, for example, tablets (including sugar-coated tablets, film-coated tablets), powders, granules, capsules, oral liquids, injections, suppositories, sustained-release preparations, lotions, liniments, ointments, patches, suspensions, emulsions, transdermal patches, cutaneous liquids, creams, aerosols and the like to a mammal (e.g., human, monkey, bovine, horse, pig, dog, cat, rabbit, guinea pig, rat, mouse and the like). Where necessary, other medicaments may also be blended.

When the compound of the present invention is topically administered, the dosage form is not particularly limited as long as it is used as a pharmaceutical composition for topical administration. For example, when it is administered to the skin or nail, a dosage form such as liquids, lotions, ointments, creams, gels, patches (e.g., tape, poultice), nail lacquers and the like can be formulated. For formulation of these, pharmaceutically acceptable ones such as a water-soluble base, an oily base, an emulsifying base and the like can be used without any particular limitation, and they can be formulated according to a conventional method in the art. In the above-mentioned preparation, the active ingredient may be in a suspended state.

When it is administered to the skin or nail as an external preparation, the content of the active ingredient is, for example, 0.01-20 wt %, preferably 0.5-15 wt %. The compound of the present invention as an active ingredient only needs to be administered as a general daily dose of about 1-about 100000 μg/cm$^2$, preferably about 10-about 10000 μg/cm$^2$, which can be administered in one or more portions.

When the compound of the present invention is orally administered, dosage forms such as tablets, orally disintegrating tablets, capsules, granules, powders, oral liquids, syrups, oral jellies, oral sprays and the like can be prepared. For formulation of these, each can be prepared by a conventional method in the art. For example, when it is orally administered to an adult patient, a general single dose of the compound of the present invention as an active ingredient is about 0.1-100 mg/kg, which can be administered in one or more portions.

EXAMPLES

The features of the present invention are more specifically explained in the following by referring to Examples and Experimental Examples. The materials, amounts of use, proportions, contents of treatment, treatment procedures and the like shown in the following Examples can be appropriately changed as long as they do not deviate from the gist of the present invention. Therefore, the scope of the present invention should not be interpreted limitatively by the specific examples shown below. For the reaction by microwave irradiation, a microwave synthesizer Initiator+ (manufactured by Biotage) was used.

$^1$H-NMR spectrum shown below was measured by JNM-ECA400 spectrometer (400 MHz, manufactured by JEOL Ltd.) or AVANCEIII HD400 (400 MHz, manufactured by Bruker Biospin K.K.), by using deuterated chloroform (CDCl$_3$) or deuterated dimethyl sulfoxide (DMSO-d$_6$) as a solvent, and tetramethylsilane (TMS) as an internal standard. In the measurement results of the chemical shift, ppm shows δ value and Hz shows J value of binding constant. In the abbreviations, s means singlet, d means doublet, t means triplet, q means quartet, quin means quintet, sext means sextet, sep means septet, m means multiplet, and br means broad. Mass spectrum (ESI-MS) was measured by Exactive (manufactured by Thermo Fisher Scientific K.K.) and according to the electrospray ionization method. The property values of compound (I-1)-compound (I-582) in respective Examples are shown in Tables 1 to 71.

Abbreviations in each Example mean the following.
BINAP: 2,2'-bis(diphenylphosphino)-1,1'-binaphthyl
Bn: benzyl
Boc: tert-butoxycarbonyl
t-Bu: tert-butyl
mCPBA: meta-chloroperbenzoic acid
c-Pr: cyclopropyl
DAST: N,N-diethylaminosulfur trifluoride
DCM: dichloromethane
dba: dibenzylideneacetone
dppf: 1,1'-bis(diphenylphosphino)ferrocene
DIAD: diisopropyl azodicarboxylate
DIBAL: diisobutylaluminum hydride
DIPEA: N,N-diisopropylethylamine
DMA: N,N-dimethylacetamide
DMAP: N,N-dimethyl-4-aminopyridine
DMF: N,N-dimethylformamide
DMP: Dess-Martin periodinane
DMSO: dimethyl sulfoxide
EDCI: 1-ethyl-3-(3-dimethylaminopropyl)carbodiimide
HATU: 1-[bis(dimethylamino)methylene]-1H-1,2,3-triazolo[4,5-b]pyridinium 3-oxide hexafluorophosphate
HOBt: 1-hydroxybenzotriazole
i: iso
IPA: isopropyl alcohol
LDA: lithium diisopropylamide
n: normal
NBS: N-bromosuccinimide
NCS: N-chlorosuccinimide
NIS: N-iodosuccinimide
NMP: N-methyl-2-pyrrolidone
p: para
Ph: phenyl
Pin: pinacol
Pr: propyl
TBAB: tetra-n-butylammonium bromide
TBAF: tetra-n-butylammonium fluoride
TBAT: tetra-n-butylammonium iodide
TBS: tert-butyldimethylsilyl
TEA: triethylamine
Tf: trifluoromethanesulfonyl
TMS: tetramethylsilane
THF: tetrahydrofuran
Ts: p-toluenesulfonyl
(A-$^{ta}$Phos)$_2$PdCl$_2$: bis(di-tert-butyl(4-dimethylaminophenyl)phosphine)dichloropalladium(II)

Example 1

Production of 3-(2-methoxyphenyl)-2-{[6-(trifluoromethyl)pyridin-3-yl]oxy}pyridine (I-1)

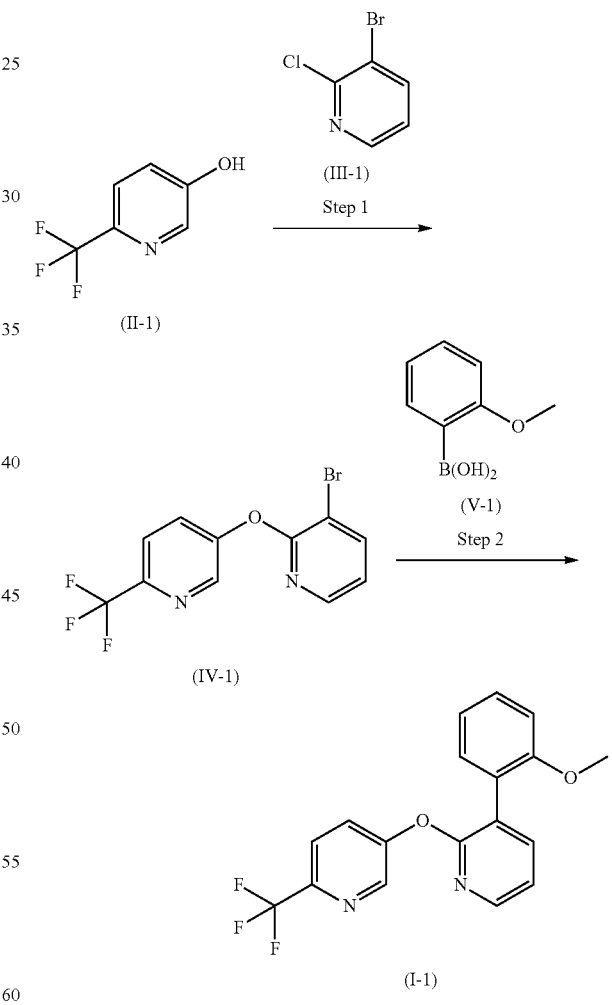

Step 1

Compound (III-1) (2.12 g, 11.0 mmol) and 6-(trifluoromethyl)pyridin-3-ol (II-1) (1.80 g, 11.0 mmol) were dissolved in DMSO (13 mL), cesium carbonate (4.31 g, 13.2 mmol) was added, and the mixture was stirred at 120° C. for 18 hr. The reaction mixture was cooled, water was added, and the mixture was extracted with ethyl acetate. The organic layer was washed successively with water and saturated brine, dried over anhydrous sodium sulfate, and filtered. The solvent was evaporated under reduced pressure, and the residue was purified by silica gel column chromatography (n-hexane:ethyl acetate=95:5→90:10) to give compound (IV-1) (yield 2.67 g, 76%) as a colorless oil.

$^1$H-NMR (400 MHz, CDCl$_3$) δ: 7.01 (1H, dd, J=4.6, 7.8 Hz), 7.71 (1H, dd, J=2.3, 8.7 Hz), 7.76 (1H, d J=8.2 Hz), 8.00 (1H, dd, J=1.8, 7.8 Hz), 8.07 (1H, dd, J=1.8, 5.0 Hz), 8.63 (1H, d, J=2.3 Hz).

ESI-MS m/z: 319, 321 [M+H]$^+$.

Step 2

Compound (IV-1) (40.0 mg, 0.125 mmol), 2-methoxyphenylboronic acid (V-1) (24.6 mg, 0.162 mmol), (A-$^{ta}$-Phos)$_2$PdCl$_2$ (4.4 mg, 0.0062 mmol) and cesium carbonate (81.0 mg, 0.249 mmol) were dissolved in 1,4-dioxane (1.0 mL) and water (0.2 mL), and the mixture was stirred under microwave irradiation at 120° C. for 30 min. The reaction mixture was allowed to cool, water was added, and the mixture was extracted with ethyl acetate. The organic layer was washed with saturated brine, dried over anhydrous sodium sulfate, and filtered. The solvent was evaporated under reduced pressure, and the residue was purified by silica gel column chromatography (n-hexane:ethyl acetate=95:5→80:20) to give compound (I-1) (yield 32.9 mg, 76%) as a white solid.

Example 2

Production of 3-(3-methoxyphenyl)-2-{[6-(trifluoromethyl)pyridin-3-yl]oxy}pyridine (I-2)

By a production method similar to that in compound (I-1), compound (I-2) (yield 40.5 mg, 93%) was obtained as a pale-yellow oil from compound (IV-1) (40.0 mg, 0.125 mmol) and 3-methoxyphenylboronic acid (V-2) (24.8 mg, 0.163 mmol).

Example 3

Production of 3-(2-fluorophenyl)-2-{[6-(trifluoromethyl)pyridin-3-yl]oxy}pyridine (I-3)

By a production method similar to that in compound (I-1), compound (I-3) (yield 39.2 mg, 94%) was obtained as a colorless oil from compound (IV-1) (40.0 mg, 0.125 mmol) and 2-fluorophenylboronic acid (V-3) (22.8 mg, 0.163 mmol).

Example 4

Production of 3-(2-chlorophenyl)-2-{[6-(trifluoromethyl)pyridin-3-yl]oxy}pyridine (I-4)

By a production method similar to that in compound (I-1), compound (I-4) (yield 41.4 mg, 94%) was obtained as a colorless oil from compound (IV-1) (40.0 mg, 0.125 mmol) and 2-chlorophenylboronic acid (V-4) (22.8 mg, 0.163 mmol).

Example 5

Production of 3-(2-bromophenyl)-2-{[6-(trifluoromethyl)pyridin-3-yl]oxy}pyridine (I-5)

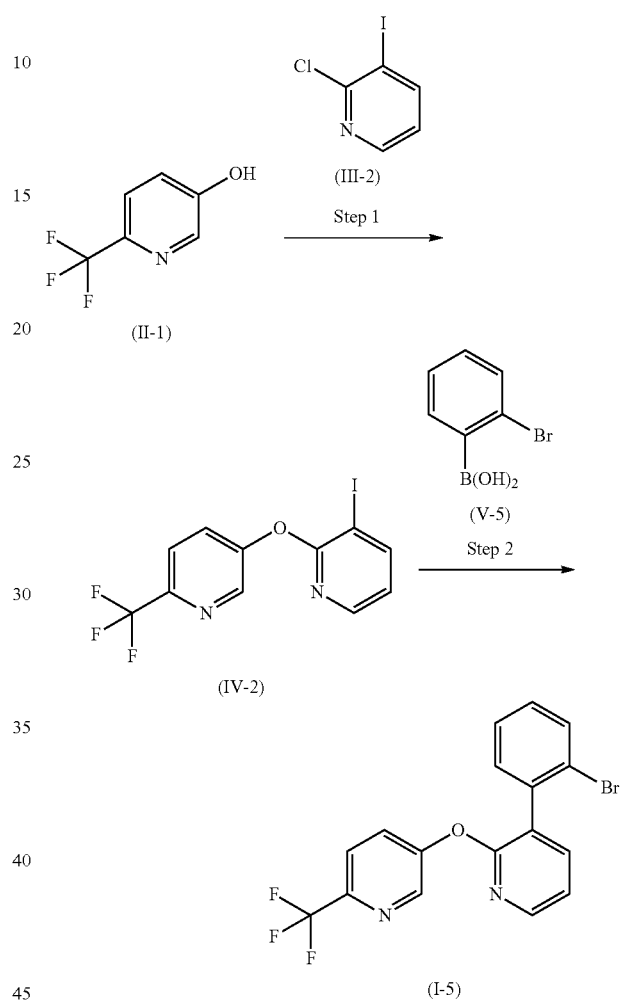

Step 1

2-chloro-3-iodopyridine (III-2) (1.00 g, 4.18 mmol) and compound (II-1) (819 mg, 5.20 mmol) were dissolved in DMSO (8.4 mL), cesium carbonate (1.91 g, 5.85 mmol) was added, and the mixture was stirred at 120° C. for 23 hr. The reaction mixture was cooled, water was added, and the mixture was extracted with ethyl acetate. The organic layer was washed successively with water and saturated brine, dried over anhydrous sodium sulfate, and filtered. The solvent was evaporated under reduced pressure, and the residue was purified by silica gel column chromatography (n-hexane:ethyl acetate) to give compound (IV-2) (yield 964 mg, 63%) as a colorless oil.

Step 2

By a production method similar to that in compound (I-1), compound (I-5) (yield 138 mg, 42%) was obtained as a colorless oil from compound (IV-2) (305 mg, 0.834 mmol) and 2-bromophenylboronic acid (V-5) (168 mg, 0.834 mmol).

Example 6

Production of 3-(2,6-difluorophenyl)-2-{[6-(trifluoromethyl)pyridin-3-yl]oxy}pyridine (I-6)

By a production method similar to that in compound (I-1), compound (I-6) (yield 4.5 mg, 14%) was obtained as a colorless oil from compound (IV-1) (30.0 mg, 0.0940 mmol) and 2,6-difluorophenylboronic acid (V-6) (22.3 mg, 0.141 mmol).

Example 7

Production of 3-(2,5-difluorophenyl)-2-{[6-(trifluoromethyl)pyridin-3-yl]oxy}pyridine (I-7)

By a production method similar to that in compound (I-1), compound (I-7) (yield 26.9 mg, 81%) was obtained as a colorless oil from compound (IV-1) (30.0 mg, 0.0940 mmol) and 2,5-difluorophenylboronic acid (V-7) (22.3 mg, 0.141 mmol).

Example 8

Production of 3-(2,4-difluorophenyl)-2-{[6-(trifluoromethyl)pyridin-3-yl]oxy}pyridine (I-8)

By a production method similar to that in compound (I-1), compound (I-8) (yield 30.6 mg, 92%) was obtained as a colorless oil from compound (IV-1) (30.0 mg, 0.0940 mmol) and 2,4-difluorophenylboronic acid (V-8) (22.3 mg, 0.141 mmol).

Example 9

Production of 3-(2,3-difluorophenyl)-2-{[6-(trifluoromethyl)pyridin-3-yl]oxy}pyridine (I-9)

By a production method similar to that in compound (I-1), compound (I-9) (yield 31.8 mg, 96%) was obtained as a colorless oil from compound (IV-1) (30.0 mg, 0.0940 mmol) and 2,3-difluorophenylboronic acid (V-9) (22.3 mg, 0.141 mmol).

Example 10

Production of 3-(2-fluoro-6-methoxyphenyl)-2-{[6-(trifluoromethyl)pyridin-3-yl]oxy}pyridine (I-10)

By a production method similar to that in compound (I-1), compound (I-10) (yield 28.0 mg, 82%) was obtained as a colorless oil from compound (IV-1) (30.0 mg, 0.0940 mmol) and 2-fluoro-6-methoxyphenylboronic acid (V-10) (23.4 mg, 0.141 mmol).

Example 11

Production of 3-(5-fluoro-2-methoxyphenyl)-2-{[6-(trifluoromethyl)pyridin-3-yl]oxy}pyridine (I-11)

By a production method similar to that in compound (I-1), compound (I-11) (yield 28.8 mg, 84%) was obtained as a colorless oil from compound (IV-1) (30.0 mg, 0.0940 mmol) and 5-fluoro-2-methoxyphenylboronic acid (V-11) (20.1 mg, 0.122 mmol).

Example 12

Production of 3-(4-fluoro-2-methoxyphenyl)-2-{[6-(trifluoromethyl)pyridin-3-yl]oxy}pyridine (I-12)

By a production method similar to that in compound (I-1), compound (I-12) (yield 33.4 mg, 98%) was obtained as a colorless oil from compound (IV-1) (30.0 mg, 0.0940 mmol) and 4-fluoro-2-methoxyphenylboronic acid (V-12) (23.4 mg, 0.141 mmol).

Example 13

Production of 3-(3-fluoro-2-methoxyphenyl)-2-{[6-(trifluoromethyl)pyridin-3-yl]oxy}pyridine (I-13)

By a production method similar to that in compound (I-1), compound (I-13) (yield 34.0 mg, 99%) was obtained as a colorless oil from compound (IV-1) (30.0 mg, 0.0940 mmol) and 3-fluoro-2-methoxyphenylboronic acid (V-13) (23.4 mg, 0.141 mmol).

Example 14

Production of 3-[2-(methylthio)phenyl)]-2-{[6-(trifluoromethyl)pyridin-3-yl]oxy}pyridine (I-14)

By a production method similar to that in compound (I-1), compound (I-14) (yield 26.5 mg, 73%) was obtained as a white solid from compound (IV-1) (30.0 mg, 0.0940 mmol) and 2-methylthiophenylboronic acid (V-14) (23.4 mg, 0.141 mmol).

Example 15

Production of 3-(2-nitrophenyl)-2-{[6-(trifluoromethyl)pyridin-3-yl]oxy}pyridine (I-15)

By a production method similar to that in compound (I-1), compound (I-15) (yield 470 mg, 83%) was obtained as a white solid from compound (IV-1) (500 mg, 1.57 mmol) and 2-nitrophenylboronic acid (V-15) (394 mg, 2.34 mmol).

Example 16

Production of 3-(2-ethylphenyl)-2-{[6-(trifluoromethyl)pyridin-3-yl]oxy}pyridine (I-16)

By a production method similar to that in compound (I-1), compound (I-16) (yield 29.8 mg, 92%) was obtained as a colorless oil from compound (IV-1) (30.0 mg, 0.0940 mmol) and 2-ethylphenylboronic acid (V-16) (21.1 mg, 0.141 mmol).

Example 17

Production of 3-(2-ethoxyphenyl)-2-{[6-(trifluoromethyl)pyridin-3-yl]oxy}pyridine (I-17)

By a production method similar to that in compound (I-1), compound (I-17) (yield 37.4 mg, quantitative) was obtained as a colorless oil from compound (IV-1) (30.0 mg, 0.0940 mmol) and 2-ethoxyphenylboronic acid (V-17) (23.4 mg, 0.141 mmol).

Example 18

Production of 2-(2-{[6-(trifluoromethyl)pyridin-3-yl]oxy}pyridin-3-yl)phenol (I-18)

By a production method similar to that in compound (I-1), compound (I-18) (yield 190 mg, 91%) was obtained as an orange solid from compound (IV-1) (200 mg, 0.627 mmol) and 2-hydroxyphenylboronic acid (V-18) (130 mg, 0.941 mmol).

Example 19

Production of 1-[2-(2-{[6-(trifluoromethyl)pyridin-3-yl]oxy}pyridin-3-yl)phenyl]ethanone (I-19)

By a production method similar to that in compound (I-1), compound (I-19) (yield 472 mg, 84%) was obtained as a yellow oil from compound (IV-1) (500 mg, 1.57 mmol) and 2-acetylphenylboronic acid (V-19) (284 mg, 1.73 mmol).

Example 20

Production of methyl 2-(2-{[6-(trifluoromethyl)pyridin-3-yl]oxy}pyridin-3-yl)benzoate (I-20)

By a production method similar to that in compound (I-1), compound (I-20) (yield 414 mg, 71%) was obtained as a colorless oil from compound (IV-1) (500 mg, 1.57 mmol) and 2-methoxycarbonylphenylboronic acid (V-20) (367 mg, 2.04 mmol).

Example 21

Production of 3-(2-trifluoromethoxyphenyl)-2-{[6-(trifluoromethyl)pyridin-3-yl]oxy}pyridine (I-21)

By a production method similar to that in compound (I-1), compound (I-21) (yield 34.1 mg, 91%) was obtained as a colorless oil from compound (IV-1) (30.0 mg, 0.0940 mmol) and 2-trifluoromethoxyphenylboronic acid (V-21) (29.0 mg, 0.141 mmol).

Example 22

Production of [2-(2-{[6-(trifluoromethyl)pyridin-3-yl]oxy}pyridin-3-yl)phenyl]methanol (I-22)

Compound (IV-1) (162 mg, 0.509 mmol), 2-hydroxymethylphenylboronic acid (V-22) (113 mg, 0.764 mmol), (A-$^{ta}$Phos)$_2$PdCl$_2$ (18.1 mg, 0.0255 mmol) and cesium carbonate (332 mg, 1.02 mmol) were dissolved in 1,4-dioxane (2.5 mL) and water (0.50 mL), and the mixture was stirred at room temperature for 20 hr. The reaction mixture was allowed to cool, water was added, and the mixture was extracted with ethyl acetate. The organic layer was washed with saturated brine, dried over anhydrous sodium sulfate, and filtered. The solvent was evaporated under reduced pressure, and the residue was purified by silica gel column chromatography (n-hexane:ethyl acetate) to give compound (I-22) (yield 146 mg, 83%) as a white solid.

Example 23

Production of 3-(5-chloro-2-methoxyphenyl)-2-{[6-(trifluoromethyl)pyridin-3-yl]oxy}pyridine (I-23)

By a production method similar to that in compound (I-1), compound (I-23) (yield 191 mg, 80%) was obtained as a pale-yellow solid from compound (IV-1) (200 mg, 0.627 mmol) and 5-chloro-2-methoxyphenylboronic acid (V-23) (175 mg, 0.940 mmol).

Example 24

Production of 2-methyl-2'-{[6-(trifluoromethyl)pyridin-3-yl]oxy}-3,3'-bipyridine (I-24)

By a production method similar to that in compound (I-1), compound (I-24) (yield 23.5 mg, 75%) was obtained as a white solid from compound (IV-1) (30.0 mg, 0.0944 mmol) and 2-methylpyridine-3-boronic acid (V-24) (18.3 mg, 0.141 mmol).

Example 25

Production of 3'-methyl-2-{[6-(trifluoromethyl)pyridin-3-yl]oxy}-3,3'-bipyridine (I-25)

By a production method similar to that in compound (I-1), compound (I-25) (yield 16.1 mg, 52%) was obtained as a colorless oil from compound (IV-1) (30.0 mg, 0.0943 mmol) and 4-methylpyridine-3-boronic acid (V-25) (17.3 mg, 0.113 mmol).

Example 26

Production of 2-methoxy-2'-{[6-(trifluoromethyl)pyridin-3-yl]oxy}-3,3'-bipyridine (I-26)

By a production method similar to that in compound (I-1), compound (I-26) (yield 43.0 mg, 99%) was obtained as a white solid from compound (IV-1) (40.0 mg, 0.125 mmol) and 2-methoxypyridine-3-boronic acid (V-26) (24.9 mg, 0.163 mmol).

Example 27

Production of 2'-methoxy-2-{[6-(trifluoromethyl)pyridin-3-yl]oxy}-3,4'-bipyridine (I-27)

By a production method similar to that in compound (I-1), compound (I-27) (yield 7.1 mg, 16%) was obtained as a colorless oil from compound (IV-1) (40.0 mg, 0.125 mmol) and 3-methoxypyridine-4-boronic acid (V-27) (24.9 mg, 0.163 mmol).

Example 28

Production of 4'-methoxy-2-{[6-(trifluoromethyl)pyridin-3-yl]oxy}-3,3'-bipyridine (I-28)

By a production method similar to that in compound (I-1), compound (I-28) (yield 15.4 mg, 35%) was obtained as a white solid from compound (IV-1) (40.0 mg, 0.125 mmol) and 4-methoxypyridine-3-boronic acid (V-28a) (24.9 mg, 0.163 mmol).

Example 29

Production of 2-methoxy-6-methyl-2'-{[6-(trifluoromethyl)pyridin-3-yl]oxy}-3,3'-bipyridine (I-29)

By a production method similar to that in compound (I-1), compound (I-29) (yield 25.4 mg, 75%) was obtained as a colorless oil from compound (IV-1) (30.0 mg, 0.0940 mmol) and 2-methoxy-6-methylpyridine-3-boronic acid (V-29) (20.4 mg, 0.122 mmol).

Example 30

Production of 2-methoxy-5-methyl-2'-{[6-(trifluoromethyl)pyridin-3-yl]oxy}-3,3'-bipyridine (I-30)

By a production method similar to that in compound (I-1), compound (I-30) (yield 22.4 mg, 66%) was obtained as a pale-yellow oil from compound (IV-1) (30.0 mg, 0.0940 mmol) and 2-methoxy-5-methylpyridine-3-boronic acid (V-30) (20.4 mg, 0.122 mmol).

Example 31

Production of 5-chloro-2-methoxy-2'-{[6-(trifluoromethyl)pyridin-3-yl]oxy}-3,3'-bipyridine (I-31)

By a production method similar to that in compound (I-1), compound (I-31) (yield 24.2 mg, 67%) was obtained as a colorless oil from compound (IV-1) (30.0 mg, 0.0940 mmol) and 5-chloro-2-methoxypyridine-3-boronic acid (V-31) (19.4 mg, 0.103 mmol).

Example 32

Production of 5-fluoro-2-methoxy-2'-{[6-(trifluoromethyl)pyridin-3-yl]oxy}-3,3'-bipyridine (I-32)

Compound (IV-1) (32.0 mg, 0.100 mmol), 5-fluoro-2-methoxypyridine-3-boronic acid (V-32) (22.3 mg, 0.130 mmol), (A-$^{ta}$Phos)$_2$PdCl$_2$ (3.6 mg, 0.0050 mmol) and cesium carbonate (65.4 mg, 0.201 mmol) were dissolved in 1,4-dioxane (0.8 mL)/water (0.16 mL) mixed solution, and the mixture was stirred at 100° C. for 4 hr. The reaction mixture was allowed to cool, water was added, and the mixture was extracted with ethyl acetate. The organic layer was washed with saturated brine, dried over anhydrous sodium sulfate, and filtered. The solvent was evaporated under reduced pressure, and the residue was purified by silica gel column chromatography (NH silica gel, n-hexane:ethyl acetate=95:5→85:15) to give compound (I-32) (yield 22.7 mg, 62%) as a colorless oil.

Example 33

Production of 5-(2-{[6-(trifluoromethyl)pyridin-3-yl]oxy}pyridin-3-yl)isoquinoline (I-33)

Compound (IV-1) (307 mg, 0.961 mmol), 5-isoquinolineboronic acid (V-33) (258 mg, 1.44 mmol), (A-$^{ta}$Phos)$_2$PdCl$_2$ (34.1 mg, 0.0481 mmol) and cesium carbonate (626 mg, 1.92 mmol) were dissolved in 1,4-dioxane (4.0 mL) and water (0.80 mL), and the mixture was stirred at 110° C. for 14 hr. The reaction mixture was allowed to cool, water was added to the reaction mixture, and the mixture was extracted with ethyl acetate. The organic layer was washed successively with water and saturated brine, dried over anhydrous sodium sulfate, and filtered. The solvent was evaporated under reduced pressure, and the residue was purified by silica gel column chromatography (n-hexane:ethyl acetate) to give compound (I-33) (yield 222 mg, 63%) as a white solid.

Example 34

Production of 8-(2-{[6-(trifluoromethyl)pyridin-3-yl]oxy}pyridin-3-yl)quinoline (I-34)

By a production method similar to that in compound (I-33), compound (I-34) (yield 182 mg, 79%) was obtained as a white solid from compound (IV-1) (200 mg, 0.627 mmol) and 8-quinolineboronic acid (V-34) (163 mg, 0.941 mmol).

Example 35

Production of 3-(2,3-dihydrobenzofuran-7-yl)-2-{[6-(trifluoromethyl)pyridin-3-yl]oxy}pyridine (I-35)

By a production method similar to that in compound (I-1), compound (I-35) (yield 37.2 mg, 83%) was obtained as a white solid from compound (IV-1) (40.0 mg, 0.125 mmol) and 2,3-dihydrobenzofuran-7-boronic acid pinacol ester (V-35a) (40.0 mg, 0.163 mmol).

Example 36

Production of 5-(2-{[6-(trifluoromethyl)pyridin-3-yl]oxy}pyridin-3-yl)quinoline (I-36)

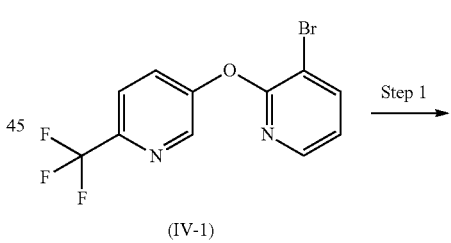

(IV-1)

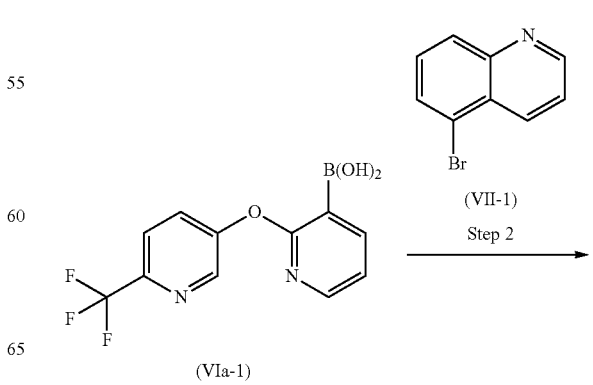

(VIa-1)

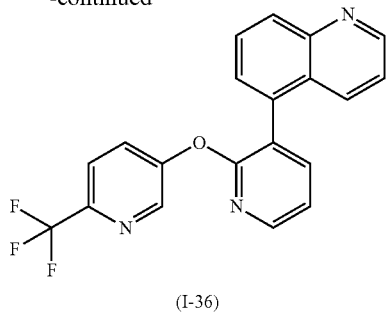

(I-36)

Step 1

To a solution of magnesium (1.52 g, 62.5 mmol) and lithium chloride (1.33 g, 31.3 mmol) in THF (25 mL) was slowly added dropwise 0.99 ml/L DIBAL toluene solution (253 μL, 0.250 mmol), and the mixture was stirred for 5 min. To the reaction mixture was added a solution of compound (IV-1) (7.98 g, 25.0 mmol) in THF (10 mL) and the mixture was stirred at room temperature for 30 min. Under ice-cooling, triisopropyl borate (11.5 mL, 50.0 mmol) was added and the mixture was stirred under ice-cooling for 1 hr. To the reaction mixture was added 0.1 mol/L hydrochloric acid, and the mixture was extracted with ethyl acetate. The organic layer was dried over anhydrous sodium sulfate, and filtered. The solvent was evaporated under reduced pressure, and the residue was purified by silica gel column chromatography (n-hexane:ethyl acetate=90:10→0:100, then ethyl acetate:methanol=90:10) to give compound (VIa-1) (yield 3.94 g, 56%) as a pale-brown solid.

Step 2

5-bromoquinoline (VII-1) (200 mg, 0.961 mmol), compound (VIa-1) (380 mg, 1.44 mmol), (A-$^{ta}$Phos)$_2$PdCl$_2$ (34.1 mg, 0.0481 mmol) and cesium carbonate (626 mg, 1.92 mmol) were dissolved in 1,4-dioxane (4.0 mL) and water (0.8 mL), and the mixture was stirred at 100° C. for 14 hr. The reaction mixture was allowed to cool, water was added, and the mixture was extracted with ethyl acetate. The organic layer was washed with saturated brine, dried over anhydrous sodium sulfate, and filtered. The solvent was evaporated under reduced pressure, and the residue was purified by silica gel column chromatography (n-hexane:ethyl acetate=100:0→70:30) to give compound (I-36) (yield 312 mg, 90%) as a white solid.

Example 37

Production of 5-(2-{[6-(trifluoromethyl)pyridin-3-yl]oxy}pyridin-3-yl)quinoxaline (I-37)

By a production method similar to that in compound (I-36), compound (I-37) (yield 18.4 mg, 47%) was obtained as a colorless oil from 5-bromoquinoxaline (VII-2) (29.7 mg, 0.137 mmol) and compound (VIa-1) (30.0 mg, 0.108 mmol).

Example 38

Production of 3-(chroman-8-yl)-2-{[6-(trifluoromethyl)pyridin-3-yl]oxy}pyridine (I-38)

By a production method similar to that in compound (I-36), compound (I-38) (yield 6.2 mg, 16%) was obtained as a colorless oil from 8-bromochromane (VII-3) (27.0 mg, 0.127 mmol) and compound (VIa-1) (30.0 mg, 0.106 mmol).

8-Bromochromane can be synthesize according to a known method. For example, the method is described in Tetrahedron Lett. 1998; 39: 2219-222.

Example 39

Production of 3-(2,2-difluorobenzo[1,3]dioxol-4-yl)-2-{[6-(trifluoromethyl)pyridin-3-yl]oxy}pyridine (I-39)

By a production method similar to that in compound (I-36), compound (I-39) (yield 12.2 mg, 29%) was obtained as a colorless oil from 4-bromo-2,2-difluorobenzo[1,3]dioxole (VII-4) (30.0 mg, 0.127 mmol) and compound (VIa-1) (30.0 mg, 0.106 mmol).

Example 40

Production of 7-(2-{[6-(trifluoromethyl)pyridin-3-yl]oxy}pyridin-3-yl)-2,3-dihydro-1H-inden-1-one (I-40)

By a production method similar to that in compound (I-36), compound (I-40) (yield 185 mg, 53%) was obtained as a yellow solid from 7-bromo-1-indanone (VII-5) (324 mg, 1.14 mmol) and compound (VIa-1) (200 mg, 0.948 mmol).

Example 41

Production of 3-(5-fluoro-2,3-dihydrobenzofuran-7-yl)-2-{[6-(trifluoromethyl)pyridin-3-yl]oxy}pyridine (I-41)

By a production method similar to that in compound (I-36), compound (I-41) (yield 24.6 mg, 47%) was obtained as a white solid from compound (VIa-1) (39.3 mg, 0.138 mmol) and 7-bromo-5-fluoro-2,3-dihydrobenzofuran (VII-6) (30.0 mg, 0.138 mmol).

7-Bromo-5-fluoro-2,3-dihydrobenzofuran can be synthesized according to a known method. For example, it is described in U.S. Pat. No. 5,817,690A.

Example 42

Production of 7-(2-{[6-(trifluoromethyl)pyridin-3-yl]oxy}pyridin-3-yl)-1H-indole (I-42)

By a production method similar to that in compound (I-36), compound (I-42) (yield 20.8 mg, 38%) was obtained as a colorless oil from 7-bromoindole (VII-7) (30.0 mg, 0.153 mmol) and compound (VIa-1) (65.0 mg, 0.230 mmol).

Example 43

Production of 8-(2-{[6-(trifluoromethyl)pyridin-3-yl]oxy}pyridin-3-yl)-isoquinoline (I-43)

By a production method similar to that in compound (I-33), compound (I-43) (yield 118 mg, quantitative) was obtained as a white solid from compound (IV-1) (100 mg, 0.313 mmol) and 8-isoquinolineboronic acid (V-36) (81.3 mg, 0.470 mmol).

Example 44

Production of 7-(2-{[6-(trifluoromethyl)pyridin-3-yl]oxy}pyridin-3-yl)-pyrazolo[1,5-a]pryidine (I-44)

By a production method similar to that in compound (I-36), compound (I-44) (yield 39.6 mg, 79%) was obtained as a white solid from 7-bromopyrazolo[1,5-a]pyridine (VII-8) (30.5 mg, 0.155 mmol) and compound (VIa-1) (40.0 mg, 0.141 mmol).

Example 45

Production of 5-(2-{[6-(trifluoromethyl)pyridin-3-yl]oxy}pyridin-3-yl)-[1,2,4]triazolo[1,5-a]pryidine (I-45)

By a production method similar to that in compound (I-36), compound (I-45) (yield 7.1 mg, 19%) was obtained as a white solid from 5-bromo-[1,2,4]triazolo[1,5-a]pyridine (VII-9) (27.2 mg, 0.137 mmol) and compound (VIa-1) (30.0 mg, 0.108 mmol).

Example 46

Production of 3-(2-{[6-(trifluoromethyl)pyridin-3-yl]oxy}pyridin-3-yl)-1H-pyrazolo[3,4-b]pryidine (I-46)

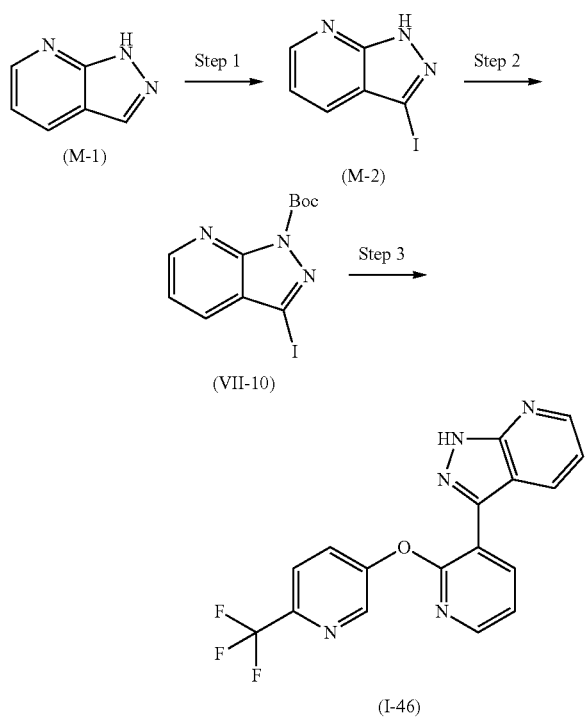

Step 1

Compound (M-1) (100 mg, 0.839 mmol) was dissolved in acetonitrile (2.8 mL), NIS (208 mg, 0.923 mmol) was added and the mixture was stirred at 75° C. for 17 hr. The reaction mixture was allowed to cool, ethyl acetate was added, and the mixture was successively washed with water and saturated brine, dried over anhydrous sodium sulfate, and filtered. The solvent was evaporated under reduced pressure to give compound (M-2).

Step 2

Compound (M-2) was dissolved in THF (8.4 mL), TEA (234 μL, 1.68 mmol), (Boc)$_2$O (289 μL, 1.26 mmol) and DMAP (10.3 mg, 0.0839 mmol) were successively added, and the mixture was stirred at room temperature for 1 hr. Water was added to the reaction mixture, and the mixture was extracted with ethyl acetate. The organic layer was washed successively with water and saturated brine, dried over anhydrous sodium sulfate, and filtered. The solvent was evaporated under reduced pressure, and the residue was purified by silica gel column chromatography (n-hexane: ethyl acetate) to give compound (VII-10) (yield 151 mg, 52%) as a white solid.

Step 3

By a production method similar to that in compound (I-36), compound (I-46) (yield 63.7 mg, 62%) was obtained as a colorless oil from compound (VII-10) (100 mg, 0.290 mmol) and compound (VIa-1) (99.6 mg, 0.377 mmol).

Example 47

Production of 1-methyl-3-(2-{[6-(trifluoromethyl)pyridin-3-yl]oxy}pyridin-3-yl)-1H-pyrazolo[3,4-b]pryidine (I-47)

Compound (I-46) (29.6 mg, 0.0828 mmol) was dissolved in DMF (1.0 mL), sodium hydride (4.8 mg, 0.099 mmol) was added at 0° C., and the mixture was stirred at 0° C. for 15 min. Thereafter, methyl iodide (6.2 μL, 0.099 mmol) was added at 0° C., and the mixture was warmed to room temperature and stirred for 13 hr. Water was added to the reaction mixture, and the mixture was extracted with ethyl acetate. The organic layer was washed successively with water and saturated brine, dried over anhydrous sodium sulfate, and filtered. The solvent was evaporated under reduced pressure, and the residue was purified by silica gel column chromatography (n-hexane:ethyl acetate) to give compound (I-47) (yield 17.2 mg, 56%) as a colorless oil.

Example 48

Production of 5-methyl-7-(2-{[6-(trifluoromethyl)pyridin-3-yl]oxy}pyridin-3-yl)-pyrazolo[1,5-a]pyrimidine (I-48)

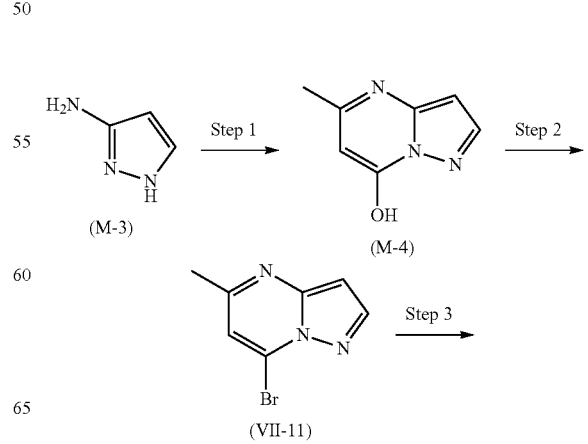

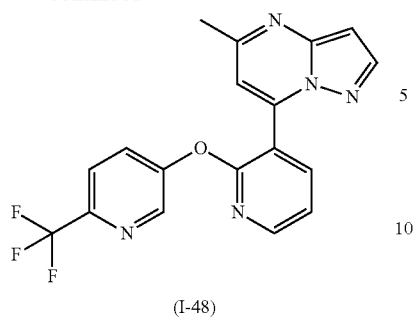

(I-48)

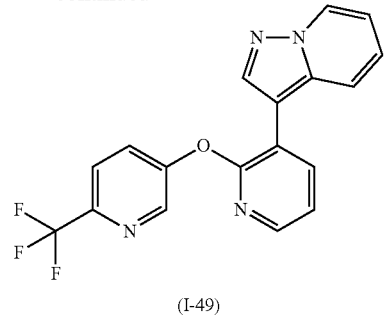

(I-49)

Step 1

3-Aminopyrazole (M-3) (1.00 g, 12.0 mmol) was dissolved in acetic acid (6.0 mL), methyl acetoacetate (1.30 mL, 12.0 mmol) was added and the mixture was stirred with heating under reflux for 1 hr. The reaction mixture was allowed to cool to room temperature, and the precipitated solid was collected by filtration, and washed successively with water and ethanol to give compound (M-4) (yield 910 mg, 51%) as a white solid.

Step 2

Compound (M-4) (800 mg, 5.36 mmol) was dissolved in acetonitrile (50 mL), potassium carbonate (2.23 g, 16.1 mmol) and phosphorus oxybromide (4.62 g, 16.1 mmol) were added, and the mixture was stirred with heating under reflux for 4 hr. The mixture was allowed to cool to room temperature, and the solvent was evaporated under reduced pressure. Chloroform was added, and the organic layer was washed with saturated sodium hydrogen carbonate, and dried over anhydrous sodium sulfate. After filtration, and the solvent was evaporated under reduced pressure. The residue was purified by silica gel column chromatography (n-hexane:ethyl acetate) to give compound (VII-11) yield (833 mg, 73%) as a pale-yellow solid.

Step 3

By a production method similar to that in compound (I-36), compound (I-48) (yield 63.3 mg, 36%) was obtained as a white solid from compound (VII-11) (100 mg, 0.472 mmol) and compound (VIa-1) (201 mg, 0.707 mmol).

Example 49

Production of 3-(2-{[6-(trifluoromethyl)pyridin-3-yl]oxy}pyridin-3-yl)-pyrazolo[1,5-a]pryidine (I-49)

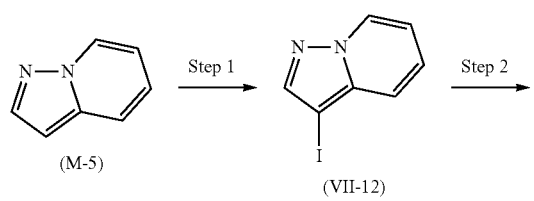

Step 1

Pyrazolo[1,5-a]pyridine (M-5) (300 mg, 2.54 mmol) was dissolved in acetonitrile (5.0 mL), NIS (628 mg, 2.79 mmol) was added and the mixture was stirred at room temperature for 1 hr. After filtration, and the solvent was evaporated under reduced pressure. The residue was purified by silica gel column chromatography (n-hexane:ethyl acetate) to give compound (VII-12) (yield 556 mg, 90%) as a pale-yellow solid.

Step 2

By a production method similar to that in compound (I-36), compound (I-49) (yield 2.9 mg, 8%) was obtained as a colorless oil from compound (VII-12) (33.7 mg, 0.138 mmol) and compound (VIa-1) (30.0 mg, 0.106 mmol).

Example 50

Production of 1-(2-{[6-(trifluoromethyl)pyridin-3-yl]oxy}pyridin-3-yl)-1H-pyrrolo[2,3-b]pryidine (I-50)

Compound (IV-1) (100 mg, 0.313 mmol), 7-azaindole (48.1 mg, 0.407 mmol), cesium carbonate (204 mg, 0.627 mmol) and 1,10-phenanthroline (11.3 mg, 0.0627 mmol) were dissolved in 1,4-dioxane (1.0 mL), copper(I) iodide (6.0 mg, 0.031 mmol) was added, and the mixture was stirred under an argon atmosphere at 120° C. for 48 hr. The mixture was allowed to cool, diluted with ethyl acetate, and filtered through Celite (registered trademark). The solvent was evaporated under reduced pressure. The residue was purified by silica gel column chromatography (n-hexane: ethyl acetate=70:30→40:60) to give compound (I-50) (yield 16.6 mg, 15%) as a colorless oil.

Example 51

Production of 3-chloro-7-(2-{[6-(trifluoromethyl)pyridin-3-yl]oxy}pyridin-3-yl)-pyrazolo[1,5-a]pyridine (I-51)

Compound (I-44) (40.0 mg, 0.112 mmol) was dissolved in DMF (0.55 mL), NCS (16.5 mg, 0.123 mmol) was added, and the mixture was stirred at room temperature for 22 hr. NCS (6.0 mg, 0.045 mmol) was added, and the mixture was further stirred for 16 hr. Thereafter, water was added, and the mixture was extracted with ethyl acetate, and the organic layer was washed successively with water and saturated brine, dried over anhydrous sodium sulfate, and filtered, and the solvent was evaporated under reduced pressure. The residue was purified by silica gel column chromatography (n-hexane:ethyl acetate=95:5→70:30) to give compound (I-51) (yield 27.6 mg, 63%) as a white solid.

Example 52

Production of 3-bromo-7-(2-{[6-(trifluoromethyl) pyridin-3-yl]oxy}pyridin-3-yl)-pyrazolo[1,5-a]pyridine (I-52)

Compound (I-44) (100 mg, 0.281 mmol) was dissolved in DMF (1.4 mL), NBS (54.9 mg, 0.309 mmol) was added, and the mixture was stirred at room temperature for 17 hr. Water was added, and the mixture was extracted with ethyl acetate. The organic layer was washed successively with water and saturated brine, dried over anhydrous sodium sulfate, and filtered, and the solvent was evaporated under reduced pressure. The residue was purified by silica gel column chromatography (n-hexane:ethyl acetate=95:5→70:30) to give compound (I-52) (yield 116 mg, 95%) as a pale-green solid.

Example 53

Production of 3-methyl-7-(2-{[6-(trifluoromethyl) pyridin-3-yl]oxy}pyridin-3-yl)-pyrazolo[1,5-a]pyridine (I-53)

Compound (I-52) (50.0 mg, 0.115 mmol), methylboronic acid (21.0 mg, 0.351 mmol), potassium carbonate (47.6 mg, 0.345 mmol) and Pd(PPh$_3$)$_4$ (6.6 mg, 5.7 µmol) were dissolved in 1,4-dioxane (0.50 mL) and water (0.10 mL), and the mixture was stirred under microwave irradiation at 120° C. for 30 min. Methylboronic acid (34.0 mg, 0.568 mmol) was added, and the mixture was further stirred under microwave irradiation at 120° C. for 30 min. The mixture was allowed to cool, water was added, and the mixture was extracted with ethyl acetate. The organic layer was washed with saturated brine, dried over anhydrous sodium sulfate, and filtered, and the solvent was evaporated under reduced pressure. The residue was purified by silica gel column chromatography (n-hexane:ethyl acetate=95:5→80:20) to give compound (I-53) (yield 9.2 mg, 21%) as a colorless oil.

Example 54

Production of 7-(2-{[6-(trifluoromethyl)pyridin-3-yl]oxy}pyridin-3-yl)-pyrazolo[1,5-a]pyridine-3-carbonitrile (I-54)

Compound (I-52) (100 mg, 0.230 mmol) was dissolved in NMP (1.0 mL), copper cyanide (45.3 mg, 0.506 mmol) was added, and the mixture was stirred under microwave irradiation at 180° C. for 2 hr. The mixture was allowed to cool, diluted with ethyl acetate, and filtered through Celite. The filtrate was washed with water and saturated brine, dried over anhydrous sodium sulfate, and filtered, and the solvent was evaporated under reduced pressure. The residue was purified by silica gel column chromatography (n-hexane: ethyl acetate=70:30→50:50) to give compound (I-54) (yield 52.8 mg, 60%) as a pale-yellow solid.

Example 55

Production of 3-[2-(cyclobutylmethoxy)phenyl]-2-{[6-(trifluoromethyl)pyridin-3-yl]oxy}pyridine (I-55)

Compound (I-18) (30.0 mg, 0.0903 mmol) was dissolved in DMF (0.5 mL), 50-72% sodium hydride (6.5 mg, 0.14 mmol) and bromomethylcyclobutane (15.2 µL, 0.135 mmol) were successively added, and the mixture was stirred at room temperature for 4.5 hr. Water was added, and the mixture was extracted with ethyl acetate. The organic layer was washed successively with water and saturated brine, dried over anhydrous sodium sulfate, and filtered. The solvent was evaporated under reduced pressure, and the residue was purified by silica gel column chromatography (n-hexane:ethyl acetate) to give compound (I-55) (yield 16.7 mg, 46%) as a colorless oil.

Example 56

Production of 3-[2-(2-propyn-1-yloxy)phenyl]-2-{[6-(trifluoromethyl)pyridin-3-yl]oxy}pryidine (I-56)

By a production method similar to that in compound (I-55), compound (I-56) (yield 27.4 mg, 82%) was obtained as a colorless oil from compound (I-18) (30.0 mg, 0.0903 mmol) and propargylbromide (10.2 µL, 0.135 mmol).

Example 57

Production of 3-[2-(cyclopropylmethoxy)phenyl]-2-{[6-(trifluoromethyl)pyridin-3-yl]oxy}pryidine (I-57)

By a production method similar to that in compound (I-55), compound (I-57) (yield 22.0 mg, 63%) was obtained as a colorless oil from compound (I-18) (30.0 mg, 0.0903 mmol) and bromomethylcyclopropane (13.1 µL, 0.135 mmol).

Example 58

Production of 3-{2-[(tetrahydro-2H-pyran-4-yl)oxy] phenyl}-2-{[6-(trifluoromethyl)pyridin-3-yl] oxy}pyridine (I-58)

Compound (I-18) (30.0 mg, 0.0903 mmol), triphenylphosphine (28.3 mg, 0.108 mmol), DIAD (27.0 µL, 0.135 mmol) and 4-hydroxytetrahydropyran (113 mg, 0.764 mmol) were dissolved in THF (0.5 mL), and the mixture was stirred at room temperature for 23 hr. The solvent was evaporated under reduced pressure, and the residue was purified by silica gel column chromatography (n-hexane: ethyl acetate) to give compound (I-58) (yield 11.7 mg, 31%) as a white solid.

Example 59

Production of 3-(2-cyclopropylphenyl)-2-{[6-(trifluoromethyl)pyridin-3-yl]oxy}pryidine (I-59)

By a production method similar to that in compound (I-53), compound (I-59) (yield 7.6 mg, 21%) was obtained as a colorless oil from compound (I-5) (40.0 mg, 0.101 mmol) and cyclopropylboronic acid (15.8 mg, 0.152 mmol).

Example 60

Production of 3-[2-methoxymethyl)phenyl]-2-{[6-(trifluoromethyl)pyridin-3-yl]oxy}pryidine (I-60)

Compound (I-22) (40.0 mg, 0.116 mmol) was dissolved in DCM (0.40 mL) and, under ice-cooling, TEA (50.0 µL, 0.358 mmol) and methanesulfonyl chloride (10.0 µL, 0.129 mmol) were successively added, and the mixture was stirred at room temperature for 30 min. Methanol (1.0 mL) and sodium methoxide (25.0 mg, 0.463 mmol) were added, and the mixture was stirred at room temperature for 12 hr. Water was added to the reaction mixture, and the mixture was extracted with ethyl acetate. The organic layer was washed successively with water and saturated brine, dried over anhydrous sodium sulfate, and filtered. The solvent was evaporated under reduced pressure and the residue was purified by silica gel column chromatography (n-hexane: ethyl acetate) to give compound (I-60) (yield 13.4 mg, 32%) as a colorless oil.

Example 61

Production of 2-(2-{[6-(trifluoromethyl)pyridin-3-yl]oxy}pyridin-3-yl)-aniline (I-61)

Compound (I-15) (250 mg, 0.692 mmol) was dissolved in methanol (4.0 mL) and ethyl acetate (2.0 mL), palladium carbon (25.0 mg, 10 w/w %) was added, and the mixture was stirred under a hydrogen atmosphere at room temperature for 5 hr. The reaction mixture was filtered. The solvent was evaporated under reduced pressure, and the residue was purified by silica gel column chromatography (n-hexane: ethyl acetate) to give compound (I-61) (yield 173 mg, 76%) as a white solid.

Example 62

Production of N,N-dimethyl-2-(2-{[6-(trifluoromethyl)pyridin-3-yl]oxy}pyridin-3-yl)-aniline (I-62)

Compound (I-61) (30.0 mg, 0.0906 mmol) was dissolved in DMF (0.30 mL), 50% sodium hydride (17.4 mg, 0.362 mmol) and methyl iodide (26 μL, 0.0362 mmol) were added, and the mixture was stirred at room temperature for 14.5 hr. Water was added to the reaction mixture, and the mixture was extracted with ethyl acetate. The organic layer was washed successively with water and saturated brine, dried over anhydrous sodium sulfate, and filtered. The solvent was evaporated under reduced pressure, and the residue was purified by silica gel column chromatography (n-hexane: ethyl acetate) to give compound (I-62) (yield 20.1 mg, 62%) as a colorless oil.

Example 63

Production of 2-(2-{[6-(trifluoromethyl)pyridin-3-yl]oxy}pyridin-3-yl)-benzaldehyde (I-63)

By a production method similar to that in compound (I-1), compound (I-63) (yield 260 mg, 80%) was obtained as a white solid compound (IV-1) (300 mg, 0.940 mmol) and compound 2-formylphenylboronic acid (V-37) (367 mg, 2.04 mmol).

Example 64

Production of 3-(2-ethynylphenyl)-2-{[6-(trifluoromethyl)pyridin-3-yl]oxy}pyridine (I-64)

Compound (I-63) (30.0 mg, 0.0870 mmol) and potassium carbonate (24.1 mg, 0.174 mmol) were dissolved in methanol (0.87 mL), dimethyl (1-diazo-2-oxopropyl)phosphonate (Ohira-Bestmann reagent) (15.7 μL, 0.105 mmol) was added, after which the mixture was stirred at room temperature for 16 hr. Water was added to the reaction mixture, and the mixture was extracted with ethyl acetate. The organic layer was washed successively with water and saturated brine, dried over anhydrous sodium sulfate, and filtered. The solvent was evaporated under reduced pressure, and the residue was purified by silica gel column chromatography (n-hexane:ethyl acetate) to give compound (I-64) (yield 18.4 mg, 63%) as a colorless oil.

Example 65

Production of 3-(2-methoxyphenyl)-4-methyl-2-{[6-(trifluoromethyl)pyridin-3-yl]oxy}pyridine (I-65)

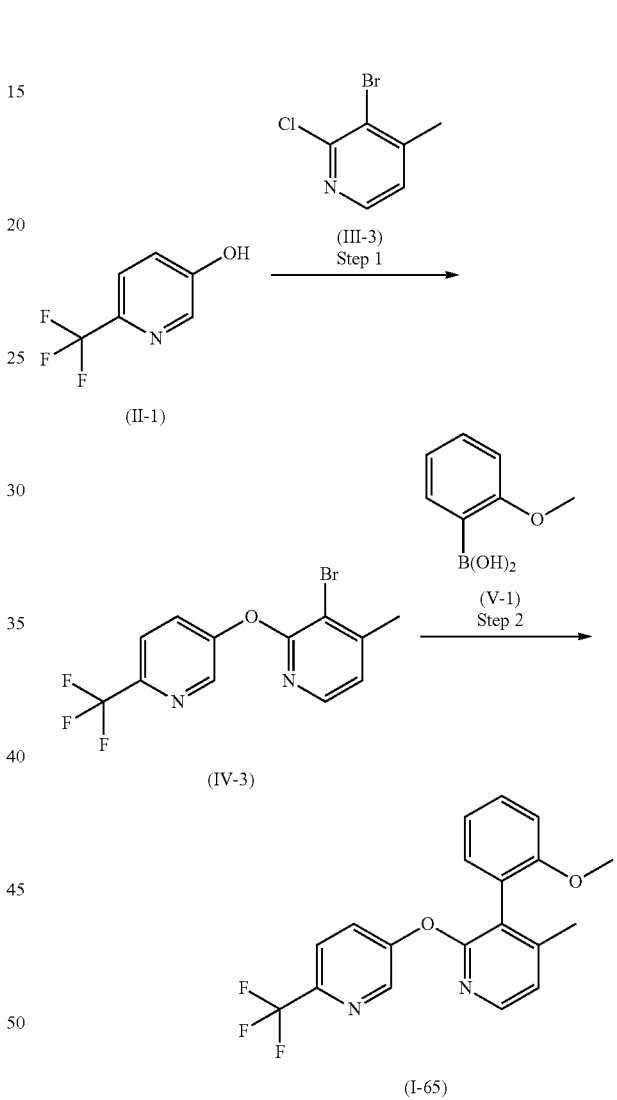

Step 1

Compound (III-3) (200 mg, 0.969 mmol) and compound (II-1) (158 mg, 0.969 mmol) were dissolved in DMSO (3.0 mL), cesium carbonate (411 mg, 1.26 mmol) was added and the mixture was stirred at 120° C. for 16 hr. The reaction mixture was cooled water was added, and the mixture was extracted with ethyl acetate. The organic layer was washed successively with water and saturated brine, dried over anhydrous sodium sulfate, and filtered. The solvent was evaporated under reduced pressure, and the residue was purified by silica gel column chromatography (n-hexane: ethyl acetate) to give compound (IV-3) (yield 79.4 mg, 25%) as a white solid.

Step 2

Compound (IV-3) (35.6 mg, 0.107 mmol), 2-methoxyphenylboronic acid (V-1) (24.5 mg, 0.161 mmol), (A-$^{ta}$-Phos)$_2$PdCl$_2$ (11.4 mg, 0.0161 mmol) and cesium carbonate (105 mg, 0.322 mmol) were dissolved in 1,4-dioxane (1.0 mL) and water (0.2 mL), and the mixture was stirred under microwave irradiation at 120° C. for 30 min. The reaction mixture was allowed to cool, water was added, and the mixture was extracted with ethyl acetate. The organic layer was washed with saturated brine, dried over anhydrous sodium sulfate, and filtered. The solvent was evaporated under reduced pressure, and the residue was purified by silica gel column chromatography (n-hexane:ethyl acetate) to give compound (I-65) (yield 33.2 mg, 86%) as a white solid.

Example 66

Production of 3-(2-methoxyphenyl)-5-methyl-2-{[6-(trifluoromethyl)pyridin-3-yl]oxy}pyridine (I-66)

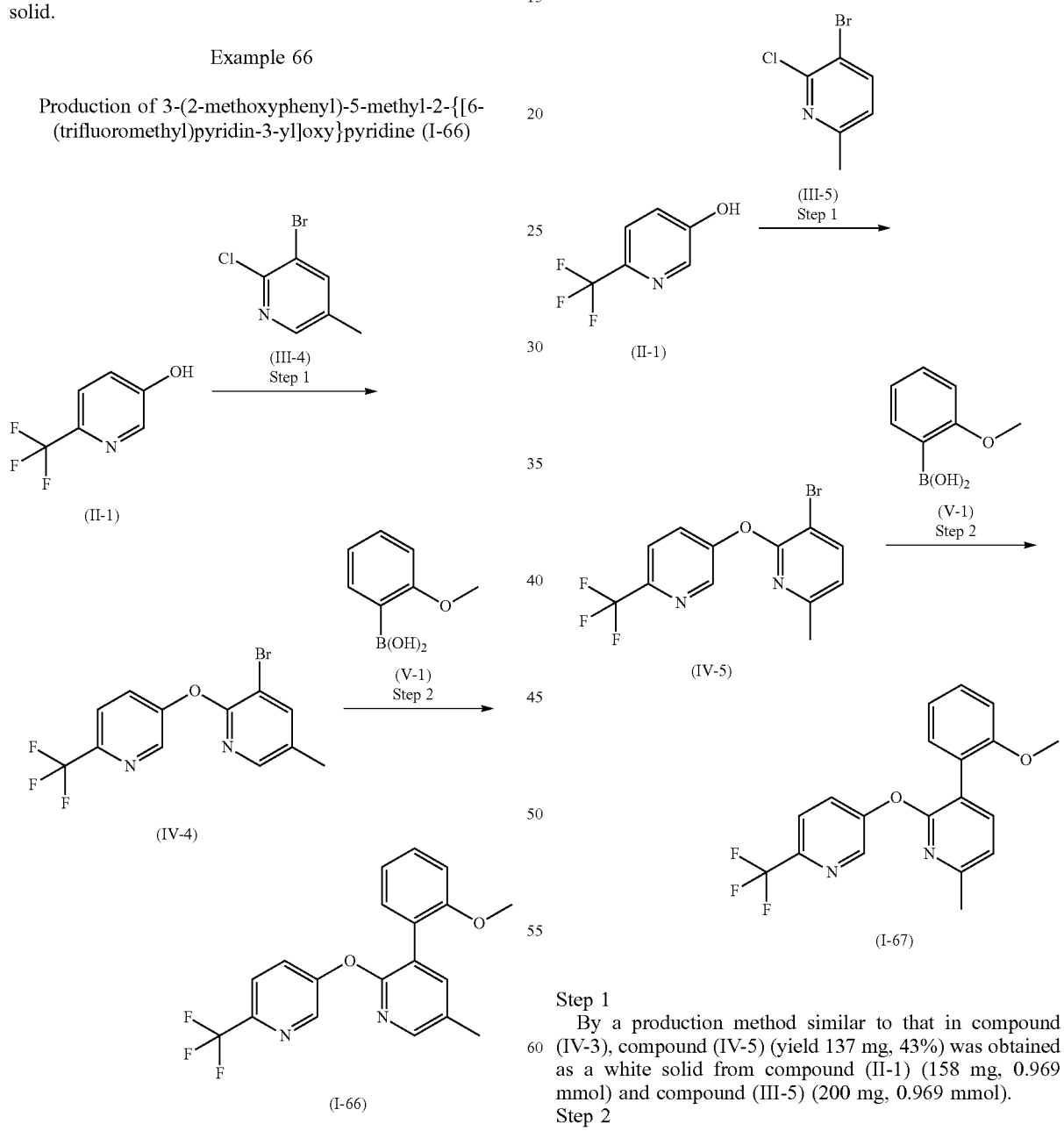

Step 1

By a production method similar to that in compound (IV-3), compound (IV-4) (yield 33.3 mg, 10%) was obtained as a colorless oil from compound (II-1) (158 mg, 0.969 mmol) and compound (III-4) (200 mg, 0.969 mmol).

Step 2

By a production method similar to that in compound (IV-65), compound (IV-66) (yield 32.9 mg, 91%) was obtained as a colorless oil from compound (IV-4) (33.3 mg, 0.100 mmol) and compound (V-1) (22.8 mg, 0.150 mmol).

Example 67

Production of 3-(2-methoxyphenyl-6-methyl-2-{[6-(trifluoromethyl)pyridin-3-yl]oxy}pyridine (I-67)

Step 1

By a production method similar to that in compound (IV-3), compound (IV-5) (yield 137 mg, 43%) was obtained as a white solid from compound (II-1) (158 mg, 0.969 mmol) and compound (III-5) (200 mg, 0.969 mmol).

Step 2

By a production method similar to that in compound (I-65), compound (I-67) (yield 30.2 mg, 75%) was obtained as a colorless oil from compound (IV-5) (37.2 mg, 0.112 mmol) and compound (V-1) (25.5 mg, 0.168 mmol).

Example 68

Production of 3-(2-methoxyphenyl)-2-{[6-(methylpyridin-3-yl]oxy}pyridine (I-68)

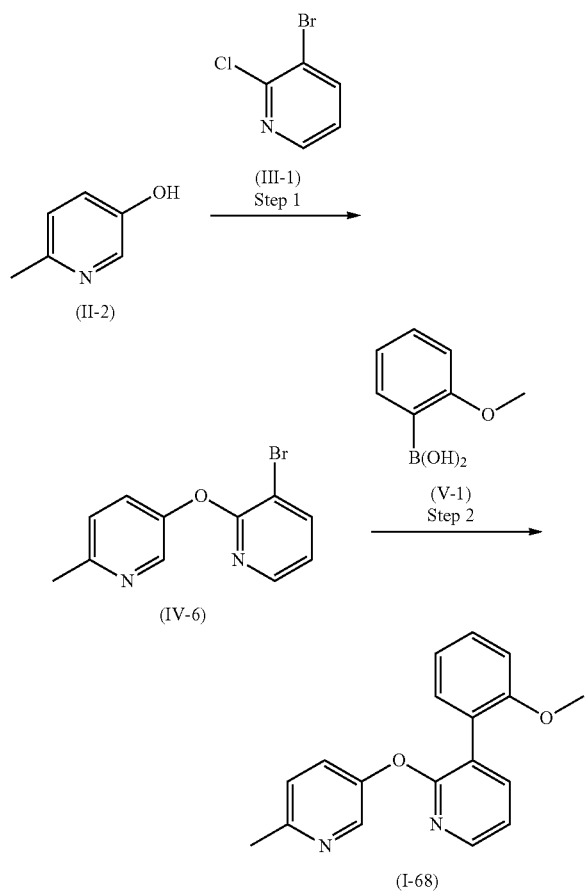

Step 1

Compound (III-1) (5.46 mg, 28.4 mmol) and compound (II-2) (3.25 g, 29.8 mmol) were dissolved in DMSO (20 mL), cesium carbonate (13.9 g, 42.5 mmol) was added and the mixture was stirred at 130° C. for 17 hr. The reaction mixture was cooled, water was added, and the mixture was extracted with ethyl acetate. The organic layer was washed successively with water and saturated brine, dried over anhydrous sodium sulfate, and filtered. The solvent was evaporated under reduced pressure, and the residue was purified by silica gel column chromatography (n-hexane:ethyl acetate=90:10→40:60) to give compound (IV-6) (yield 7.30 g, 97%) as a yellow oil.

Step 2

Compound (IV-6) (7.29 g, 27.5 mmol), 2-methoxyphenylboronic acid (V-1) (4.39 g, 28.9 mmol), (A-$^{ta}$Phos)$_2$PdCl$_2$ (195 mg, 0.275 mmol) and cesium carbonate (26.9 g, 82.5 mmol) were dissolved in 1,4-dioxane (50 mL) and water (5 mL), and the mixture was stirred at 120° C. for 20 hr. The reaction mixture was allowed to cool, water was added, and the mixture was extracted with ethyl acetate. The organic layer was washed with saturated brine, dried over anhydrous sodium sulfate, and filtered. The solvent was evaporated under reduced pressure, and the residue was purified by silica gel column chromatography (n-hexane:ethyl acetate=95:5→60:40) to give compound (I-68) (yield 7.86 g, 98%) as an orange oil.

Example 69

Production of (5-{[3-(2-methoxyphenyl)-pyridin-2-yl]oxy}pyridin-2-yl)methyl acetate (I-69)

To a solution of compound (I-68) (7.86 g, 26.9 mmol) in DCM (30 mL) was added mCPBA (8.07 g, 32.3 mmol) at 0° C., and the mixture was stirred at room temperature for 2.5 hr. To the reaction mixture was added saturated aqueous sodium hydrogen carbonate solution, and the mixture was extracted with chloroform. The organic layer was washed with saturated brine, dried over anhydrous sodium sulfate, and filtered. The solvent was evaporated under reduced pressure.

The residue was dissolved in acetic anhydride (25 mL), and the mixture was stirred at 60° C. for 14 hr. The solvent was evaporated under reduced pressure, and the residue was diluted with ethyl acetate, and washed successively with saturated aqueous sodium hydrogen carbonate solution and saturated brine. The organic layer was dried over anhydrous sodium sulfate, and filtered. The solvent was evaporated under reduced pressure, and the residue was purified by silica gel column chromatography (NH silica gel, n-hexane:ethyl acetate=98:2→0:100) to give compound (I-69) (yield 6.59 g, 70%) as a white solid.

Example 70

Production of (5-{[3-(2-methoxyphenyl)pyridin-2-yl]oxy}pyridin-2-yl)methanol (I-70)

To a solution of compound (I-69) (6.59 g, 18.8 mmol) in methanol (50 ml) was added potassium carbonate (0.520 g, 3.76 mmol) as 0° C., and the mixture was stirred at room temperature for 67 hr. Water was added to the reaction mixture, and the mixture was extracted with chloroform. The organic layer was washed with saturated brine, dried over anhydrous sodium sulfate, and filtered. The solvent was evaporated under reduced pressure, and the residue was purified by silica gel column chromatography (NH silica gel, n-hexane:ethyl acetate=98:2→0:100) to give compound (I-70) (yield 5.80 g, quantitative) as a colorless oil.

Example 71

Production of 5-{[3-(2-methoxyphenyl)pyridin-2-yl]oxy}picolinaldehyde (I-71)

To a solution of compound (I-70) (500 mg, 1.62 mmol) in DCM (8.0 mL) was added DMP (825 mg, 1.95 mmol), and the mixture was stirred at room temperature for 7 hr. The reaction mixture was diluted with chloroform, and aqueous sodium sulfite solution and saturated aqueous sodium hydrogen carbonate solution were added. The organic layer was separated, washed with saturated brine, dried over anhydrous sodium sulfate, and filtered. The solvent was evaporated under reduced pressure, and the residue was purified by silica gel column chromatography (n-hexane:ethyl acetate=40:60→0:100) to give compound (I-71) (yield 492 mg, 99%) as a white solid.

Example 72

Production of 2-{[6-(difluoromethyl)pyridin-3-yl]oxy}(2-methoxyphenyl)pyridine (I-72)

To a solution of compound (I-71) (50.0 mg, 0.163 mmol) in DCM (1.0 mL) was added DAST (72.0 μL, 0.490 mmol), and the mixture was stirred at room temperature for 12 hr. Water was added to the reaction mixture, and the mixture was extracted with chloroform. The organic layer was washed with saturated brine, dried over anhydrous sodium sulfate, and filtered. The solvent was evaporated under reduced pressure, and the residue was purified by silica gel column chromatography (n-hexane:ethyl acetate=90:10→70:30) to give compound (I-72) (yield 48.3 mg, 90%) as a colorless oil.

Example 73

Production of 2-{[6-(difluoromethyl)pyridin-3-yl]oxy}-3-(4-fluoro-2-methoxyphenyl)pyridine (I-73)

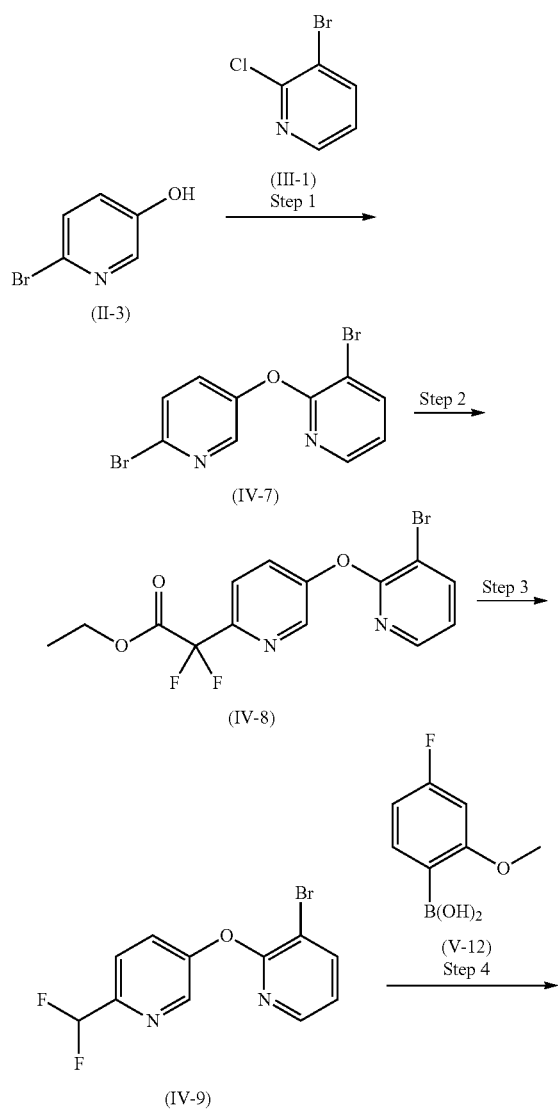

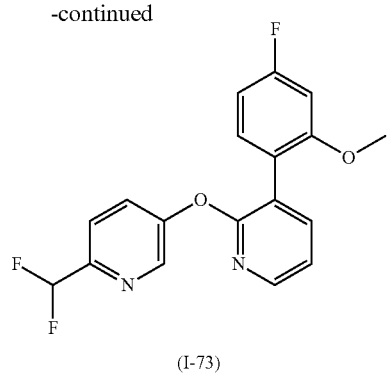

(I-73)

Step 1
To a solution of compound (III-1) (400 mg, 2.30 mmol) and compound (II-3) (487 mg, 2.53 mmol) in DMSO (4.6 mL) was added cesium carbonate (1.50 g, 4.60 mmol) and the mixture was stirred at 120° C. for 19 hr. The reaction mixture was cooled, water was added, and the mixture was extracted with ethyl acetate. The organic layer was washed successively with water and saturated brine, and the solvent was evaporated under reduced pressure. The residue was purified by silica gel column chromatography (n-hexane:ethyl acetate) to give compound (IV-7) (yield 372 g, 49%) as a white solid.

Step 2
To a solution of compound (IV-7) (372 mg, 1.13 mmol) in ethyl 2-bromo-2,2-difluoroacetate (145 μL, 1.13 mmol) in DMSO (3.8 mL) was added copper (165 mg, 2.59 mmol) and the mixture was stirred at 80° C. for 16 hr. The reaction mixture was cooled, diluted with isopropyl acetate, saturated potassium dihydrogen phosphate solution was added, and the mixture was stirred for 10 min. The reaction mixture was extracted with ethyl acetate, the organic layer was washed successively with water and saturated brine, and the solvent was evaporated under reduced pressure. The residue was purified by silica gel column chromatography (n-hexane:ethyl acetate) to give compound (IV-8) (yield 172 mg, 40%) as a colorless oil.

Step 3
To a solution of compound (IV-8) (2.00 g, 5.36 mmol) in NMP (10.0 mL) was added magnesium chloride hexahydrate (1.09 g, 5.36 mmol), and the mixture was stirred under microwave irradiation at 180° C. for 15 min. The reaction mixture was allowed to cool, water was added, and the mixture was extracted with ethyl acetate. The organic layer was washed successively with water and saturated brine, dried over anhydrous sodium sulfate, and filtered. The solvent was evaporated under reduced pressure, and the residue was purified by silica gel column chromatography (n-hexane:ethyl acetate=100:0→80:20) to give compound (IV-9) (yield 946 mg, 59%) as a white solid.

Step 4
By a production method similar to that in compound (I-1), compound (I-73) (yield 27.9 mg, 81%) was obtained as a white solid from compound (IV-9) (30.0 mg, 0.100 mmol) and 4-fluoro-2-methoxyphenylboronic acid (V-12) (22.0 mg, 0.130 mmol).

Example 74

Production of 2-{[6-(difluoromethyl)pyridin-3-yl]oxy}-3-(2-fluoro-5-methoxyphenyl)pyridine (I-74)

By a production method similar to that in compound (I-1), compound (I-74) (yield 33.7 mg, 98%) was obtained as a white solid from compound (IV-9) (30.0 mg, 0.100 mmol) and 2-fluoro-5-methoxyphenylboronic acid (V-38) (22.0 mg, 0.130 mmol).

Example 75

Production of 2-{[6-(difluoromethyl)pyridin-3-yl]oxy}-3-(4-fluoro-3-methoxyphenyl)pyridine (I-75)

By a production method similar to that in compound (I-1), compound (I-75) (yield 30.5 mg, 88%) was obtained as a white solid from compound (IV-9) (30.0 mg, 0.100 mmol) and 4-fluoro-3-methoxyphenylboronic acid (V-39) (22.0 mg, 0.130 mmol).

Example 76

Production of 3-(4,5-difluoro-2-methoxyphenyl)-2-{[6-(difluoromethyl)pyridin-3-yl]oxy}pyridine (I-76)

By a production method similar to that in compound (I-1), compound (I-76) (yield 43.5 mg, 90%) was obtained as a colorless oil from compound (IV-9) (40.0 mg, 0.133 mmol) and 4,5-difluoro-2-methoxyphenylboronic acid (V-40) (32.5 mg, 0.173 mmol).

Example 77

Production of 3-(2,4-difluoro-5-methoxyphenyl)-2-{[6-(difluoromethyl)pyridin-3-yl]oxy}pyridine (I-77)

By a production method similar to that in compound (I-1), compound (I-77) (yield 24.0 mg, 66%) was obtained as a white solid from compound (IV-9) (30.0 mg, 0.100 mmol) and 2,4-difluoro-5-methoxyphenylboronic acid (V-41) (24.3 mg, 0.130 mmol).

Example 78

Production of 2'-{[6-(difluoromethyl)pyridin-3-yl]oxy}-2,6-dimethoxy-3,3'-bipyridine (I-78)

By a production method similar to that in compound (I-1), compound (I-78) (yield 29.7 mg, 83%) was obtained as a colorless oil from compound (IV-9) (30.0 mg, 0.100 mmol) and 2,6-dimethoxypyridine-3-boronic acid (V-42) (23.7 mg, 0.130 mmol).

Example 79

Production of 2,2-difluoro-2-(5-{[3-(2-methoxyphenyl)pyridin-2-yl]oxy}pyridin-2-yl)ethanol (I-79)

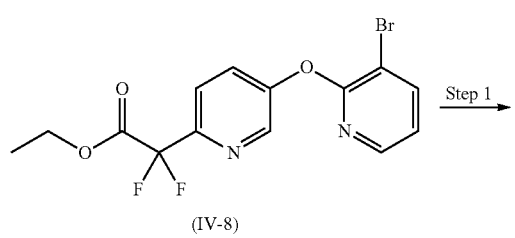

(IV-8)

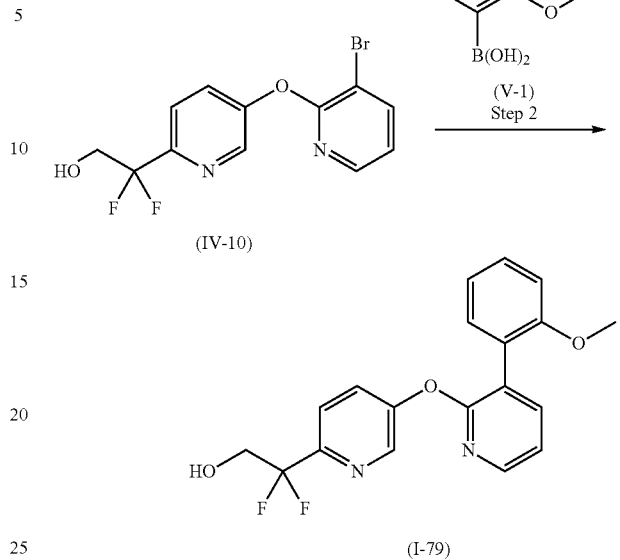

Step 1
Compound (IV-8) (372 mg, 1.00 mmol) was dissolved in methanol (2.5 mL) and THF (2.5 mL) mixed solution and, under ice-cooling, sodium borohydride (56.6 mg, 1.50 mmol) was added, and the mixture was stirred at room temperature for 15 hr. The solvent was evaporated under reduced pressure, and the residue was purified by silica gel column chromatography (n-hexane:ethyl acetate) to give compound (IV-10) (yield 273 mg, 83%) as a colorless oil.

By a production method similar to that in compound (I-1), compound (I-79) (yield 24.4 mg, 74%) was obtained as a colorless oil from compound (IV-10) (142 mg, 0.448 mmol) and 2-methoxyphenylboronic acid (V-1) (102 mg, 0.672 mmol).

Reference Example 80

Production of 2,2-difluoro-2-(5-{[3-(2-methoxyphenyl)pyridin-2-yl]oxy}pyridin-2-yl)ethyl trifluoromethanesulfonate (I-80)

To a solution of compound (I-79) (244 mg, 0.681 mmol) in DCM (3.4 mL) were successively added, under ice-cooling pyridine (83.0 μL, 1.02 mmol) and trifluoromethanesulfonic anhydride (127 μL, 0.749 mmol), and the mixture was stirred at room temperature for 5 hr. Water was added to the reaction mixture, and the mixture was extracted with ethyl acetate. The organic layer was washed successively with water and saturated brine, dried over anhydrous sodium sulfate, and filtered. The solvent was evaporated under reduced pressure, and the residue was purified by silica gel column chromatography (n-hexane:ethyl acetate) to give compound (I-80) (yield 220 mg, 66%) as a pale-yellow oil.

Example 81

Production of 2-{[6-(1,1-difluoroethyl)pyridin-3-yl]oxy}-3-(2-methoxyphenyl)pyridine (I-81)

To a solution of compound (I-80) (50.0 mg, 0.102 mmol) in THF (0.50 mL) was added, under ice-cooling sodium borohydride (38.6 mg, 1.02 mmol), and the mixture was stirred at 70° C. for 16 hr. Water was added to the reaction mixture, and the mixture was extracted with chloroform, and the organic layer was purified by silica gel column chromatography (n-hexane:ethyl acetate) to give compound (I-81) (yield 6.2 mg, 18%) as a colorless oil.

Example 82

Production of 2-{[5-(1,1-difluoroethyl)pyridin-3-yl]oxy}-3-(4-fluoro-2-methoxyphenyl)pyridine (I-82)

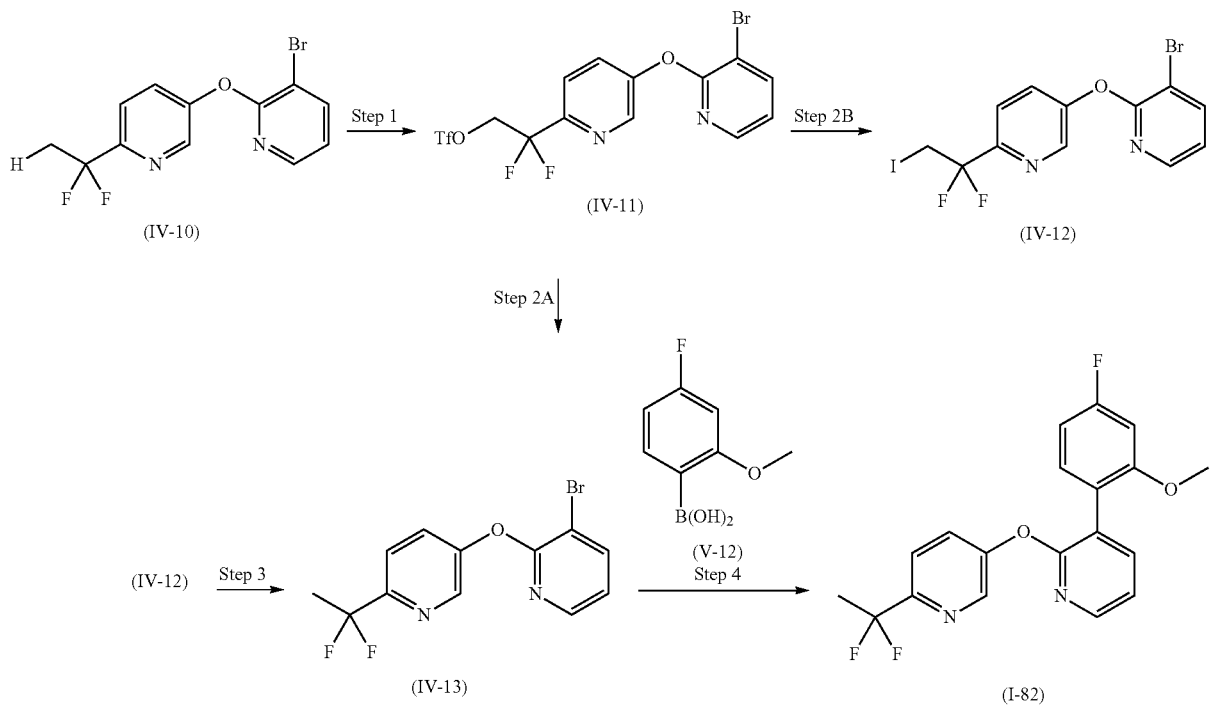

Step 1

By a production method similar to that in compound (I-80), compound (IV-11) (yield 3.18 mg, 91%) was obtained as a pale-yellow oil from compound (IV-10) (2.60 g, 7.55 mmol) and 2,4-trifluoromethanesulfonic anhydride (1.91 mL, 11.3 mmol).

Step 2A

To a solution of compound (IV-11) (500 mg, 1.08 mmol) in THF (3.6 mL) was added, under ice-cooling 1 mol/L THF solution of lithium aluminum hydride (5.40 mL, 5.40 mmol) and the mixture was stirred at 60° C. for 4.5 hr. To the reaction mixture was added a saturated aqueous solution of Rochelle salt and the mixture was stirred overnight. Water was added to the reaction mixture, and the mixture was extracted with ethyl acetate. The organic layer was washed successively with water and saturated brine, dried over anhydrous sodium sulfate, and filtered. The solvent was evaporated under reduced pressure, and the residue was purified by silica gel column chromatography (n-hexane:ethyl acetate) to give compound (I-13) (yield 61.0 mg, 18%) as a colorless oil.

Step 2B

Compound (IV-11) (28.0 g, 60.4 mmol) was dissolved in acetone (121 mL), sodium iodide (45.3 g, 302 mmol) was added, and the mixture was stirred at room temperature for 14 hr. Water was added to the reaction mixture, and the mixture was extracted with ethyl acetate. The organic layer was washed successively with water and saturated brine, dried over anhydrous sodium sulfate, and filtered. The solvent was evaporated under reduced pressure to give compound (IV-12) (yield 26.6 g, quantitative) as a white solid.

Step 3

Compound (IV-12) was dissolved in THF (121 mL), tributyltin hydride (48.4 mL, 181 mmol) was added, and the mixture was stirred at 60° C. for 2 hr. Water was added to the reaction mixture, and the mixture was extracted with ethyl acetate. The organic layer was washed successively with water and saturated brine, dried over anhydrous sodium sulfate, and filtered. The solvent was evaporated under reduced pressure, and the residue was purified by silica gel column chromatography (n-hexane:ethyl acetate) to give compound (IV-13) [yield 14.1 g, 74% (2 steps)].

By a production method similar to that in compound (I-1), compound (I-82) (yield 28.8 mg, 88%) was obtained as a colorless oil from compound (IV-13) (30.0 mg, 0.0952 mmol) and 4-fluoro-2-methoxyphenylboronic acid (V-12) (24.3 mg, 0.143 mmol).

Example 83

Production of 2-{[6-(1,1-difluoroethyl)pyridin-3-yl]oxy}-3-(5-fluoro-2-methoxyphenyl)pyridine (I-83)

By a production method similar to that in compound (I-1), compound (I-83) (yield 32.5 mg, 95%) was obtained as a white solid from compound (IV-13) (30.0 mg, 0.0952 mmol) and 5-fluoro-2-methoxyphenylboronic acid (V-11) (19.4 mg, 0.114 mmol).

Example 84

Production of 2-{[6-(1,1-difluoroethyl)pyridin-3-yl]oxy}-3-(2,5-dimethoxyphenyl)pyridine (I-84)

By a production method similar to that in compound (I-1), compound (I-84) (yield 39.5 mg, 84%) was obtained as a colorless oil from compound (IV-13) (40.0 mg, 0.127 mmol) and 2,5-dimethoxyphenylboronic acid (V-43) (30.0 mg, 0.165 mmol).

Example 85

Production of 3-(2,4-difluoro-5-methoxyphenyl)-2-{[6-(1,1-(difluoroethyl)pyridin-3-yl]oxy}pyridine (I-85)

By a production method similar to that in compound (I-1), compound (I-85) (yield 22.3 mg, 62%) was obtained as a colorless oil from compound (IV-13) (30.0 mg, 0.0952 mmol) and 2,4-difluoro-5-methoxyphenylboronic acid (V-41) (21.5 mg, 0.114 mmol).

Example 86

Production of 2-{[6-(1,1-difluoroethyl)pyridin-3-yl]oxy}-3-[2-(difluoromethyl)phenyl]pyridine (I-86)

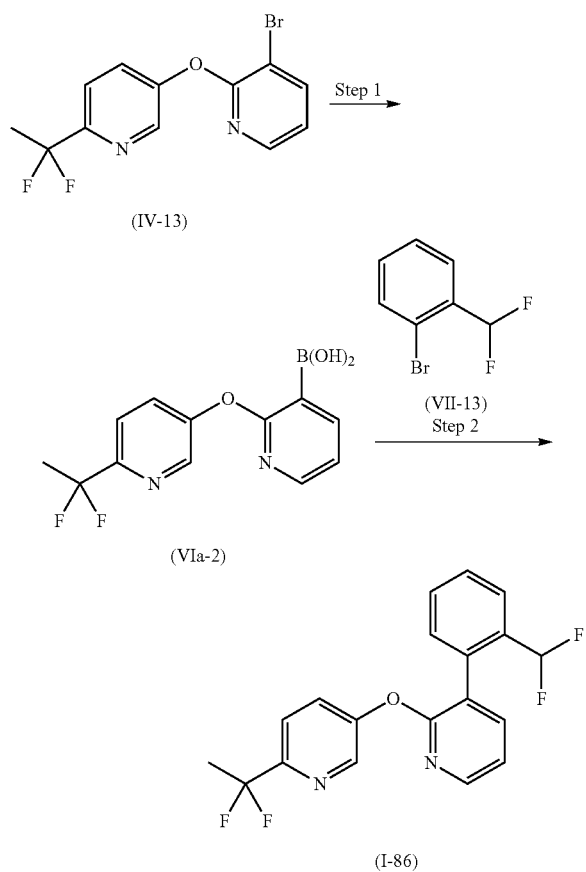

Step 1

To a solution of compound (I-13) (1.50 g, 4.76 mmol) in THF (9.5 mL) was added 1.3 mol/L THF solution of iPrMgBr.LiCl (7.3 mL, 9.5 mmol) and the mixture was stirred for 30 min. Thereafter, under ice-cooling, triisopropyl borate (3.3 mL, 14 mmol) was added and the mixture was stirred for 1 hr. Then, 1 mol/L hydrochloric acid (20 mL) was added and the mixture was stirred for 30 min. Water was added to the reaction mixture, and the mixture was extracted with ethyl acetate. The organic layer was washed successively with water and saturated brine, dried over anhydrous sodium sulfate, and filtered. The solvent was evaporated under reduced pressure to give compound (VIa-2) (yield 1.20 g, 90%) as a pale-yellow solid.

Step 2

By a production method similar to that in compound (I-36), compound (I-86) (yield 24.1 mg, 55%) was obtained as a colorless oil from compound (VIa-2) (33.8 mg, 0.121 mmol) and 2-difluoromethylbromobenzene (VII-13) (30.0 mg, 0.145 mmol).

Example 87

Production of 2-(2-{[6-(1,1-difluoroethyl)pyridin-3-yl]oxy}pyridin-3-yl)-6-fluorobenzonitrile (I-87)

Compound (VIa-2) (40.0 mg, 0.143 mmol), 2-bromo-6-fluorobenzonitrile (VII-14) (19.1 mg, 0.0955 mmol), (A-$^{ta}$-Phos)$_2$PdCl$_2$ (3.4 mg, 0.0048 mmol) and cesium carbonate (62.1 mg, 0.191 mmol) were dissolved in n-butanol (0.50 mL), and the mixture was stirred under microwave irradiation at 120° C. for 30 min. Water was added to the reaction mixture, and the mixture was extracted with ethyl acetate. The organic layer was washed successively with water and saturated brine, dried over anhydrous sodium sulfate, and filtered. The solvent was evaporated under reduced pressure, and the residue was purified by silica gel column chromatography (n-hexane:ethyl acetate=100:0→50:50) to give compound (I-87) (yield 19.4 mg, 57%) as a colorless oil.

Example 88

Production of 2-{[6-(1,1-difluoroethyl)pyridin-3-yl]oxy}-2'-methoxy-3,3'-bipyridine (I-88)

By a production method similar to that in compound (I-1), compound (I-88) (yield 16.4 mg, 50%) was obtained as a colorless oil from compound (IV-13) (30.0 mg, 0.0952 mmol) and 2-methoxypyridine-3-boronic acid (V-26) (21.8 mg, 0.143 mmol).

Example 89

Production of 2-{[6-(1,1-difluoroethyl)pyridin-3-yl]oxy}-3'-methoxy-3,4'-bipyridine (I-89)

By a production method similar to that in compound (I-1), compound (I-89) (yield 9.3 mg, 17%) was obtained as a white solid from compound (IV-13) (50.5 mg, 0.159 mmol) and 3-methoxypyridine-4-boronic acid pinacol ester (V-27a) (29.1 mg, 0.124 mmol).

Example 90

Production of 2-{[6-(1,1-difluoroethyl)pyridin-3-yl]oxy}-4'-methoxy-3,3'-bipyridine (I-90)

By a production method similar to that in compound (I-1), compound (I-90) (yield 22.3 mg, 68%) was obtained as a white solid from compound (IV-13) (30.0 mg, 0.0952 mmol) and 4-methoxypyridine-3-boronic acid monohydrate (V-28) (17.5 mg, 0.102 mmol).

Example 91

Production of 2-{[6-(1,1-difluoroethyl)pyridin-3-yl]oxy}-4'-methyl-3,3'-bipyridine (I-91)

By a production method similar to that in compound (I-1), compound (I-91) (yield 15.4 mg, 44%) was obtained as a white solid from compound (IV-13) (30.0 mg, 0.0952 mmol) and 4-methylpyridine-3-boronic acid (V-25) (17.5 mg, 0.129 mmol).

Example 92

Production of 2-{[6-(1,1-difluoroethyl)pyridin-3-yl]oxy}-3'-fluoro-3,4'-bipyridine (I-92)

By a production method similar to that in compound (I-1), compound (I-92) (yield 15.2 mg, 48%) was obtained as a colorless oil from compound (IV-13) (30.0 mg, 0.0952 mmol) and 3-fluoropyridine-4-boronic acid (V-44) (20.1 mg, 0.143 mmol).

Example 93

Production of 2-{[6-(1,1-difluoroethyl)pyridin-3-yl]oxy}-5'-methyl-3,3'-bipyridine (I-93)

By a production method similar to that in compound (I-1), compound (I-93) (yield 46.7 mg, 75%) was obtained as a white colorless oil from compound (IV-13) (60.0 mg, 0.190 mmol) and 5-methylpyridine-3-boronic acid (V-45) (20.1 mg, 0.143 mmol).

Example 94

Production of 2'-{[6-(1,1-difluoroethyl)pyridin-3-yl]oxy}-2,6-dimethoxy-3,3'-bipyridine (I-94)

By a production method similar to that in compound (I-1), compound (I-94) (yield 29.6 mg, 83%) was obtained as a colorless oil from compound (IV-13) (30.0 mg, 0.0952 mmol) and 2,6-dimethoxypyridine-3-boronic acid (V-42) (20.8 mg, 0.114 mmol).

Example 95

Production of 2'-{[6-(1,1-difluoroethyl)pyridin-3-yl]oxy}-6-methoxy-2,3'-bipyridine (I-95)

By a production method similar to that in compound (I-1), compound (I-95) (yield 21.3 mg, 49%) was obtained as a colorless oil from compound (IV-13) (40.0 mg, 0.127 mmol) and 6-methoxypyridine-2-boronic acid pinacol ester (V-46a) (38.8 mg, 0.165 mmol).

Example 96

Production of 2'-{[6-(1,1-difluoroethyl)pyridin-3-yl]oxy}-3,6-dimethoxy-2,3'-bipyridine (I-96)

By a production method similar to that in compound (I-36), compound (I-96) (yield 36.8 mg, 69%) was obtained as a colorless oil from compound (VIa-2) (40.0 mg, 0.143 mmol) and 2-bromo-3,6-dimethoxypyridine (VII-15) (40.5 mg, 0.186 mmol).

Example 97

Production of 4'-chloro-2-{[6-(1,1-difluoroethyl)pyridin-3-yl]oxy}-5'-fluoro-3,3'-bipyridine (I-97)

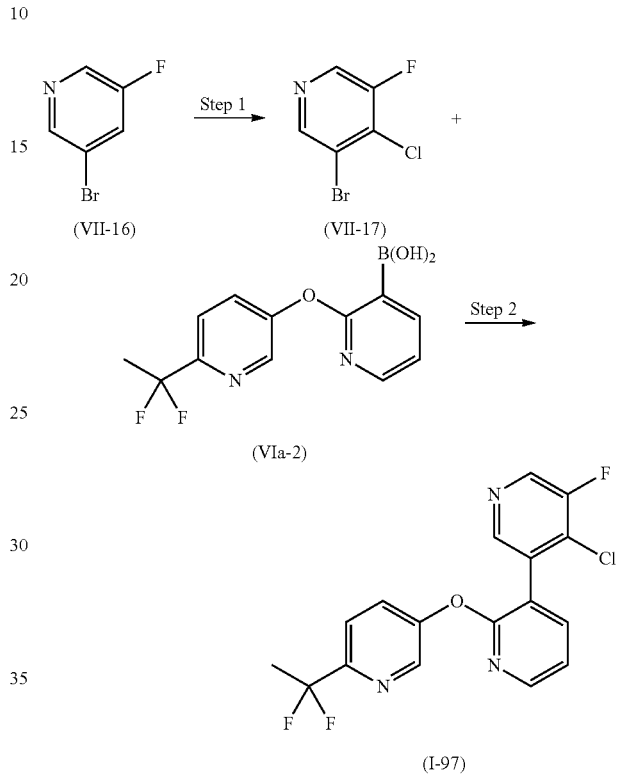

Step 1

To a solution of LDA (2.0 mol/L THF solution, 8.9 mL, 18 mmol) in THF (45 mL) which was cooled to −78° C. was added dropwise a solution of compound (VII-16) (2.60 g, 14.8 mmol) in THF (12 mL), and the mixture was stirred at −78° C. for 45 min. To the reaction mixture was added dropwise a solution of hexachloroethane (3.85 g, 16.3 mmol) in THF (12 mL), and the mixture was stirred at −78° C. for 30 min, warmed to room temperature and stirred for 1 hr. The reaction was discontinued by adding saturated aqueous ammonium chloride solution, and the mixture was extracted with ethyl acetate. The organic layer was washed successively with saturated aqueous ammonium chloride solution and saturated brine, and dried over anhydrous sodium sulfate. The solvent was evaporated under reduced pressure, and the residue was purified by silica gel column chromatography (n-hexane:ethyl acetate=97:3→85:15) to give compound (VII-17) (yield 2.18 g, 70%) as a pale-yellow solid.

Step 2

Compound (VII-17) (100 mg, 0.475 mmol), compound (VIa-2) (146 mg, 0.523 mmol), (A-$^{ta}$Phos)$_2$PdCl$_2$ (16.8 mg, 0.0240 mmol) and cesium carbonate (310 mg, 0.950 mmol) were dissolved in 1,4-dioxane (1.5 mL) and water (0.30 mL) mixed solution, and the mixture was stirred under microwave irradiation at 70° C. for 10 min. Water was added to the reaction mixture, and the mixture was extracted with chloroform. The solvent was evaporated under reduced pressure, and the residue was purified by silica gel column chromatography (NH silica gel, n-hexane:ethyl acetate=97:3→75:25) to give compound (I-97) (yield 138 mg, 79%) as a colorless oil.

Example 98

Production of 2-{[6-(1,1-difluoroethyl)pyridin-3-yl]oxy}-5'-fluoro-4'-methoxy-3,3'-bipyridine (I-98)

Compound (IV-97) (40.0 mg, 0.109 mmol) was dissolved in methanol (0.50 mL), sodium methoxide (8.9 mg, 0.16 mmol) was added and the mixture was stirred at 70° C. for 16 hr. Water was added to the reaction mixture, and the mixture was extracted with chloroform. The solvent was evaporated under reduced pressure, and the residue was purified by silica gel column chromatography (n-hexane:ethyl acetate=95:5→50:50) to give compound (IV-98) (yield 1.8 mg, 5%) as a colorless oil.

Example 99

Production of 2-{[6-(1,1-difluoroethyl)pyridin-3-yl]oxy}-5'-fluoro-4'-methyl-3,3'-bipyridine (I-99)

By a production method similar to that in compound (I-53), compound (I-99) (yield 9.3 mg, 13%) was obtained as a colorless oil from compound (IV-97) (76.5 mg, 0.209 mmol) and methylboronic acid (62.6 mg, 1.05 mmol).

Example 100

Production of 5'-chloro-2-{[6-(1,1-difluoroethyl)pyridin-3-yl]oxy}-4'-methoxy-3,3'-bipyridine (I-100)

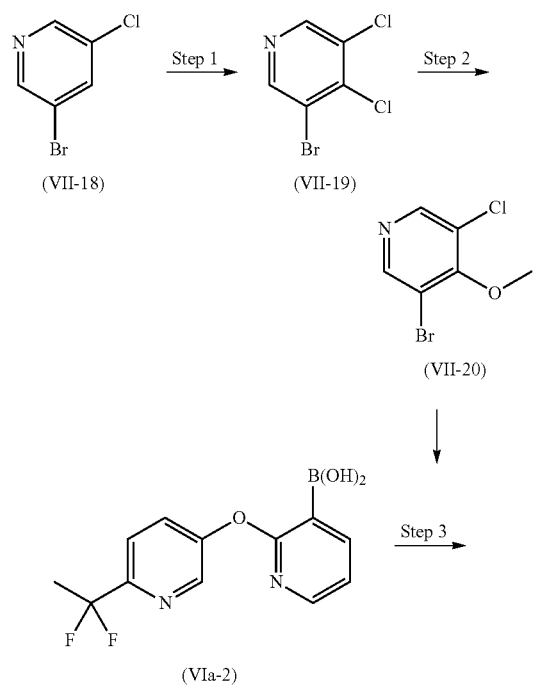

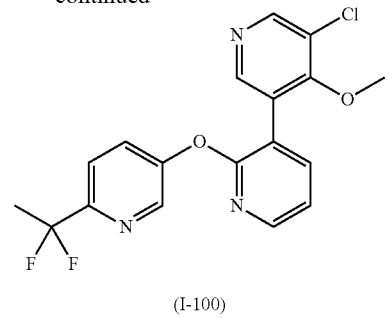

(I-100)

Step 1

To THF (9.0 mL) were successively added dropwise LDA (2.0 mol/L THF solution, 7.2 mL, 14 mmol) and compound (VII-18) (6.0 mol/L THF solution, 2.0 mL, 12 mmol) at −78° C., and the mixture was stirred for 45 min. Hexachloroethane (6.6 mol/L THF solution, 2.0 mL, 13.2 mmol) was added dropwise at −78° C., and the mixture was stirred for 30 min, warmed to room temperature and stirred for 1 hr. Saturated aqueous ammonium chloride solution was added, and the mixture was extracted with ethyl acetate. The organic layer was washed successively with saturated aqueous ammonium chloride solution and saturated brine, dried over anhydrous sodium sulfate. The solvent was evaporated under reduced pressure, and the residue was purified by silica gel column chromatography (n-hexane:ethyl acetate) to give compound (VII-19) (yield 2.30 g, 85%) as a yellow solid.

Step 2

Compound (VII-19) (1.00 mg, 4.41 mmol) was dissolved in THF (10 mL), sodium methoxide (28% methanol solution, 1.30 mL, 31.6 mmol) was added and the mixture was stirred at 70° C. for 1 hr. Water was added, the mixture was extracted with ethyl acetate, and the organic layer was dried over anhydrous sodium sulfate. The solvent was evaporated under reduced pressure to give compound (VII-20) (yield 950 mg, 97%) as a pale-brown solid.

Step 3

By a production method similar to that in compound (I-36), compound (I-100) (yield 2.45 mg, 53%) was obtained as a white solid from compound (VII-20) (2.70 g, 12.1 mmol) and compound (VIa-2) (4.08 g, 14.6 mmol).

Example 101

Production of 4-(2-{[6-(1,1-difluoroethyl)pyridin-3-yl]oxy}pyridin-3-yl)-3,5'-dimethylisothiazole (I-101)

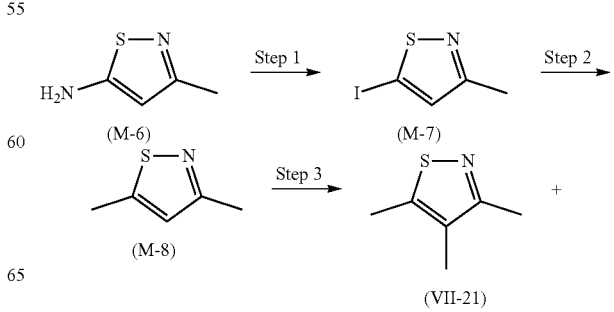

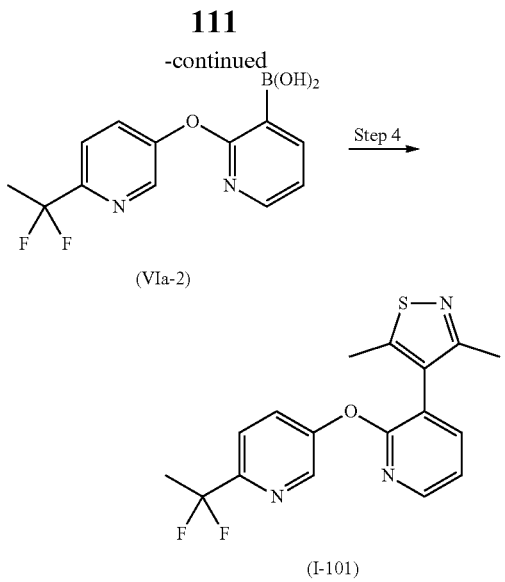

(VIa-2)

(I-101)

Step 1

Compound (M-6) was dissolved in concentrated sulfuric acid (5.0 mL) and water (50 mL), sodium nitrite (4.08 g, 59.1 mmol) dissolved in water (20 mL) was added, and the mixture was stirred at 0° C. for 30 min. Furthermore, potassium iodide (26.2 g, 158 mmol) dissolved in water (30 mL) was added and the mixture was stirred at room temperature for 3 hr. To the reaction mixture was added sodium carbonate, the mixture was extracted with ethyl acetate, and the organic layer was dried over anhydrous sodium sulfate. The solvent was evaporated under reduced pressure, and the residue was purified by silica gel column chromatography (n-hexane:ethyl acetate) to give compound (M-7) (yield 3.50 g, 40%).

Step 2

Compound (M-7) (400 mg, 1.78 mmol), methylboronic acid (1.06 g, 17.8 mmol), (A-$^{ta}$Phos)$_2$PdCl$_2$ (62.9 mg, 0.0888 mmol) and cesium carbonate (2.90 g, 8.89 mmol) were dissolved in 1,4-dioxane (1.0 mL) and water (0.1 mL) and the mixture was stirred under microwave irradiation at 120° C. for 30 min. The reaction mixture was allowed to cool, water was added, and the mixture was extracted with ethyl acetate. The organic layer was dried over anhydrous sodium sulfate, and filtered. The solvent was evaporated under reduced pressure, and the residue was purified by silica gel column chromatography (n-hexane:ethyl acetate) to give compound (M-8).

Step 3

Compound (M-8) (201 mg, 1.78 mmol) was dissolved in conc. nitric acid (2.0 mL), and iodine (673 mg, 2.65 mmol) was added and the mixture was stirred at 80° C. for 3 hr. The reaction mixture was neutralized with 4 mol/L aqueous sodium hydroxide solution, and the mixture was extracted with ethyl acetate. The organic layer was dried over sodium sulfate. The solvent was evaporated under reduced pressure, and the residue was purified by silica gel column chromatography (n-hexane) to give compound (VII-21) [yield 85.0 mg, 20% (2 steps)].

Step 4

By a production method similar to that in compound (I-36), compound (I-101) (yield 32.0 mg, 52%) was obtained as a white solid from compound (VII-21) (51.2 mg, 0.214 mmol) and compound (VIa-2) (50.0 mg, 0.179 mmol).

Example 102

Production of 4-2-{[6-(1,1-difluoroethyl)pyridin-3-yl]oxy}pyridin-3-yl)-3,5-dimethylisoxazole (I-102)

By a production method similar to that in compound (I-1), compound (I-102) (yield 12.7 mg, 40%) was obtained as a white solid from compound (IV-13) (30.0 mg, 0.0952 mmol) and 3,5-dimethylisoxazole-4-boronic acid (V-47) (16.1 mg, 0.114 mmol).

Example 103

Production of 5-(2-{[6-(1,1-difluoroethyl)pyridin-3-yl]oxy}-3-yl)-3-methylisoxazole (I-103)

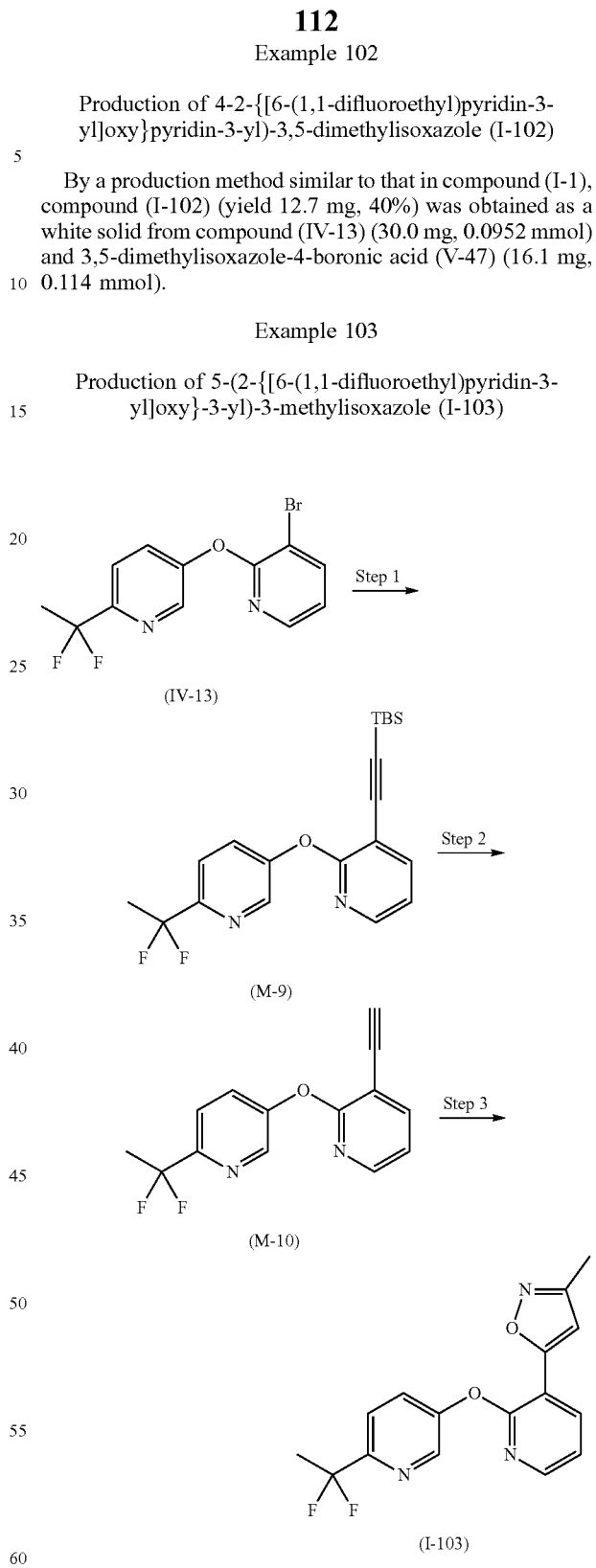

Step 1

To a solution of compound (IV-13) (230 mg, 0.730 mmol) in TEA (4.0 mL) was added TBS acetylene (307 mg, 2.19 mmol), copper iodide (13.9 mg, 0.0730 mmol) and PdCl$_2$ (dppf) (26.7 mg, 0.0360 mmol) were successively added, and the mixture was stirred under an argon atmosphere at 60° C. for 2 hr. The reaction mixture was filtered, and washed with ethyl acetate. The solvent was evaporated under reduced pressure, and the residue was purified by silica gel column chromatography (n-hexane:ethyl acetate=97:3→75:25) to give compound (M-9) (yield 225 mg, 82%) as a brown oil.

$^1$H-NMR (400 MHz, CDCl$_3$) δ: 0.80 (9H, s), 1.85 (3H, t, J=18.5 Hz), 6.84 (1H, dd, J=5.0, 8.2 Hz), 7.45 (1H, dd, J=2.7, 8.7 Hz), 7.51 (1H, d, J=0.6, 8.7 Hz), 7.65 (1H, dd, J=2.0, 7.5 Hz), 7.86 (1H, dd, J=2.0, 5.0 Hz), 8.33-8.36 (1H, m).

ESI-MS m/z: 333 [M+H]$^+$.

Step 2

Compound (M-9) (209 mg, 0.558 mmol) was dissolved in THF (3.0 mL), TBAF (0.67 mL, 0.670 mmol) was added, and the mixture was stirred at room temperature for 15 hr. The solvent was evaporated under reduced pressure, and the residue was filtered through silica gel, and washed with ethyl acetate. The solvent was evaporated under reduced pressure to give compound (M-10) (yield 139 mg, 96%) as a brown solid.

$^1$H-NMR (400 MHz, CDCl$_3$) δ: 2.05 (3H, t, J=18.4 Hz), 3.42 (1H, s), 7.06 (1H, dd, J=5.0, 7.8 Hz), 7.64 (1H, dd, J=2.7, 8.8 Hz), 7.72 (1H, d, J=0.6, 8.8 Hz), 7.89 (1H, dd, J=1.9, 7.4 Hz), 8.10 (1H, dd, J=1.9, 5.0 Hz), 8.52-8.56 (1H, m).

ESI-MS m/z: 261 [M+H]$^+$.

Step 3

Aldoxime (59 μL, 0.96 mmol) was dissolved in DMF (1.0 mL), NCS (154 mg, 1.15 mmol) was added, and the mixture was stirred at room temperature for 21 hr. Water was added, and the mixture was extracted with ethyl acetate. The organic layer was washed successively with water and saturated brine, and dried over anhydrous sodium sulfate. After filtration, the solvent was evaporated under reduced pressure to prepare aldoxime chloride, and ethanol (1.0 mL) was added to give an ethanol solution.

Compound (M-10) (50.0 mg, 0.192 mmol) was dissolved in ethanol (0.5 mL), TEA (0.13 mL, 0.961 mmol) and an ethanol solution of aldoxime chloride (1.0 mL, 0.96 mmol) were successively added, and the mixture was stirred at room temperature for 2 days. Water was added, and the mixture was extracted with ethyl acetate. The organic layer was washed with water, and dried over anhydrous sodium sulfate. The solvent was evaporated under reduced pressure, and the residue was purified by silica gel column chromatography (n-hexane:ethyl acetate=97:3→75:25) to give compound (I-103) (yield 46.9 mg, 77%) as a white solid.

Example 104

Production of 4-chloro-5-(2-{[6-(1,1-difluoroethyl)pyridin-3-yl]oxy}pyridin-3-yl)-3-methylisoxazole (I-104)

Compound (I-103) (20.0 mg, 0.0630 mmol) was dissolved in DMF (0.50 mL), NCS (10.1 mg, 0.0756 mmol) was added and the mixture was stirred at 70° C. for 24 hr. Water was added, and extracted with chloroform. The organic layer was washed with water, and dried over anhydrous sodium sulfate. The solvent was evaporated under reduced pressure, and the residue was purified by silica gel column chromatography (n-hexane:ethyl acetate=97:3→80:20) to give compound (I-104) (yield 10.8 mg, 49%) as a colorless oil.

Example 105

Production of 2-{[6-(1,1-difluoroethyl)pyridin-3-yl]oxy}-2'-pyrrolidin-1-yl)-3,3'-bipyridine (I-105)

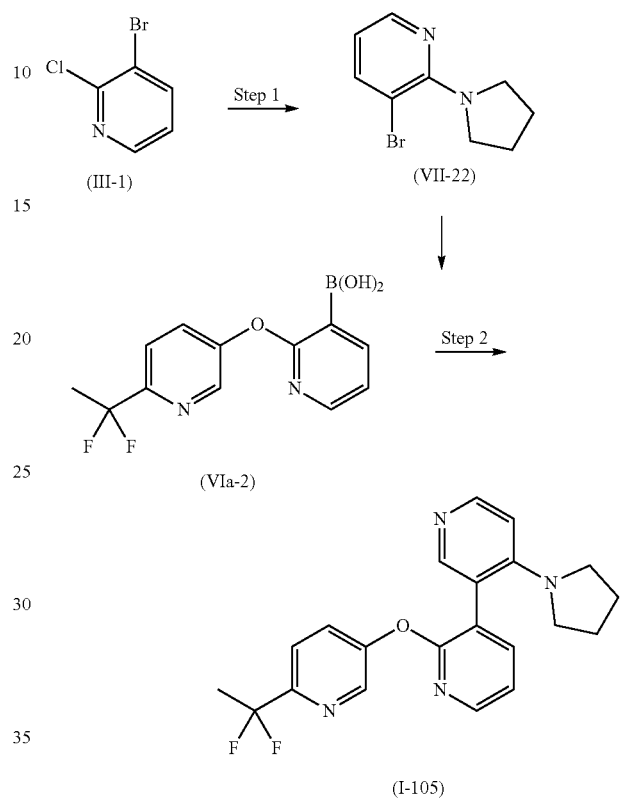

Step 1

To a solution of compound (III-1) (500 mg, 2.60 mmol) in DMF (15 mL) were added pyrrolidine (2.0 mL, 24.4 mmol and sodium hydride (120 mg, 5.20 mmol) was added and the mixture was stirred at 120° C. for 4 hr. The reaction mixture was allowed to cool, water was added, and the mixture was extracted with chloroform. The organic layer was washed successively with water and saturated brine, dried over anhydrous sodium sulfate, and filtered. The solvent was evaporated under reduced pressure, and the residue was purified by silica gel column chromatography (n-hexane:ethyl acetate=90:10→75:25) to give compound (VII-22) (yield 430 mg, 73%) as a colorless oil.

Step 2

By a production method similar to that in compound (I-36), compound (I-105) (yield 22.4 mg, 13%) was obtained as a colorless oil from compound (VII-22) (100 mg, 0.440 mmol) and compound (VIa-2) (185 mg, 0.661 mmol).

Example 106

Production of 2-{[6-(1,1-difluoroethyl)pyridin-3-yl]oxy}-2'-(1H-imidazol-1-yl)-3,3'-bipyridine (I-106)

Step 1

By a production method similar to that in compound (VII-22), 3-bromo-2-(1H-imidazol-1-yl)pyridine (VII-23)

(yield 466 mg, 80%) was obtained as a colorless oil from compound (III-1) (500 mg, 2.60 mmol) and imidazole (2.00 g, 29.4 mmol).

Step 2

Compound (VIa-2) (60.0 mg, 0.214 mmol), compound (VII-23) (32.0 mg, 0.143 mmol), Pd(PPH₃)₄ (16.5 mg, 0.0143 mmol) and tripotassium phosphate (60.6 mg, 0.286 mmol) were dissolved in n-butanol (0.50 mL), and the mixture was stirred under microwave irradiation at 120° C. for 30 min. Water was added to the reaction mixture, and the mixture was extracted with chloroform. The organic layer was washed successively with water and saturated brine, dried over anhydrous sodium sulfate, and filtered. The solvent was evaporated under reduced pressure, and the residue was purified by silica gel column chromatography (n-hexane:ethyl acetate=25:75→0:100) to give compound (I-106) (yield 4.8 mg, 96%) as a colorless oil.

Example 107

Production of 2-{[6-(1,1-difluoroethyl)pyridin-3-yl] oxy}-2'-(1H-pyrazol-1-yl)-3,3'-bipyridine (I-107)

Step 1

By a production method similar to that in compound (VII-22), 3-bromo-2-(1H-pyrazol-1-yl)pyridine (VII-24) (yield 507 mg, 87%) was obtained as a colorless oil from compound (III-1) (500 mg, 2.60 mmol) and pyrazole (2.00 g, 29.4 mmol).

Step 2

By a production method similar to that in compound (I-106), compound (I-107) (yield 4.3 mg, 8%) was obtained as a colorless oil from compound (VIa-2) (60.0 mg, 0.214 mmol) and compound (VII-24) (19.1 mg, 0.0955 mmol).

Example 108

Production of 4-(2-{[6-(1,1-difluoroethyl)pyridin-3-yl]oxy}pyridin-3-yl)quinoline (I-108)

By a production method similar to that in compound (I-36), compound (I-108) (yield 12.8 mg, 49%) was obtained as a colorless oil from 4-bromoquinoline (VII-25) (22.3 mg, 0.107 mmol) and compound (VIa-2) (20.0 mg, 0.0714 mmol).

Example 109

Production of 4-(2-{[6-(1,1-difluoroethyl)pyridin-3-yl]oxy}pyridin-3-yl)isoquinoline (I-109)

By a production method similar to that in compound (I-36), compound (I-109) (yield 19.5 mg, 56%) was obtained as a yellow oil from 4-bromoisoquinoline (VII-26) (24.7 mg, 0.143 mmol) and compound (VIa-2) (30.0 mg, 0.0952 mmol).

Example 110

Production of 5-(2-{[6-(1,1-difluoroethyl)pyridin-3-yl]oxy}pyridin-3-yl)quinoxaline (I-110)

By a production method similar to that in compound (I-36), compound (I-110) (yield 21.4 mg, 41%) was obtained as a white solid from 5-bromoquinoxaline (VII-2) (90.0 mg, 0.429 mmol) and compound (VIa-2) (40.0 mg, 0.143 mmol).

Example 111

Production of 8-(2-{[6-(1,1-difluoroethyl)pyridin-3-yl]oxy}pyridin-3-yl)pyrido[3,4-b]pyrazine (I-111)

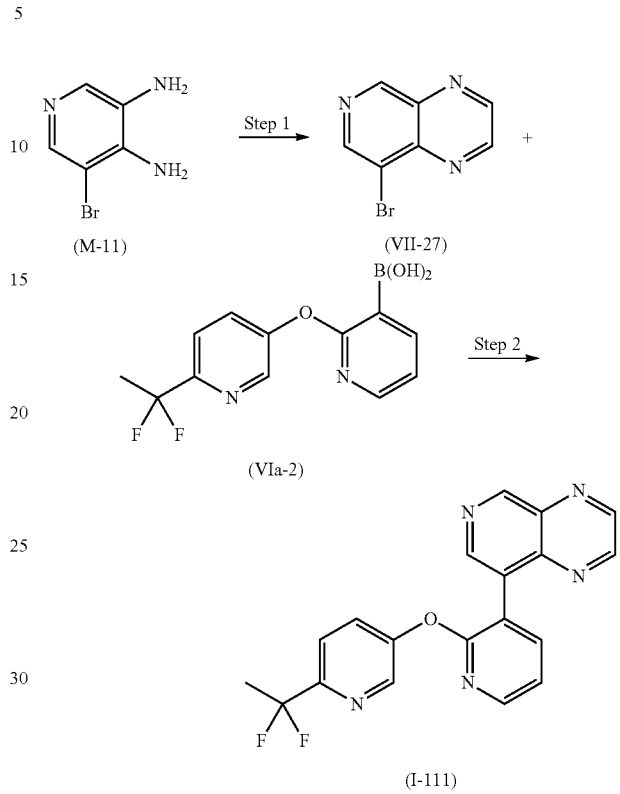

Step 1

3-bromopyridine-4,5-diamine (M-11) (1.0 g, 5.32 mmol) was dissolved in ethanol (21 mL), acetic acid (300 µL, 5.3 mmol) and glyoxal (4.9 mL, 43 mmol) were added, and the mixture was stirred at 100° C. for 14 hr. The reaction mixture was concentrated, and the residue was purified by silica gel column chromatography (n-hexane:ethyl acetate) to give compound (VII-27) (yield 721 mg, 65%) as a white solid.

Step 2

By a production method similar to that in compound (I-36), compound (I-111) (yield 17.8 mg, 46%) was obtained as a pale-yellow solid from 8-bromopyrido[3,4-b]pyrazine (VII-27) (27.1 mg, 0.129 mmol) and compound (VIa-2) (30.0 mg, 0.107 mmol).

Example 112

Production of 1-(2-{[6-(1,1-difluoroethyl)pyridin-3-yl]oxy}-3-yl)isoquinoline (I-112)

By a production method similar to that in compound (I-36), compound (I-112) (yield 167 mg, 64%) was obtained as a white solid from 1-bromoisoquinoline (VII-28) (22.3 mg, 0.107 mmol) and compound (VIa-2) (20.0 mg, 0.0714 mmol).

Example 113

Production of 4-(2-{[6-(1,1-difluoroethyl)pyridin-3-yl]oxy}-3-yl)benzo[d]oxazole (I-113)

By a production method similar to that in compound (I-36), compound (I-113) (yield 5.6 mg, 18%) was obtained as a white solid from 4-bromobenzo[d]oxazole (VII-29) (26.5 mg, 0.134 mmol) and compound (VIa-2) (25.0 mg, 0.0890 mmol).

Example 114

Production of 7-(2-{[6-(1,1-difluoroethyl)pyridin-3-yl]oxy}pyridin-3-yl)benzo[d]oxazole (I-114)

By a production method similar to that in compound (I-36), compound (I-114) (yield 3.2 mg, 10%) was obtained as a yellow oil from 7-bromobenzo[d]oxazole (VII-30) (26.5 mg, 0.134 mmol) and compound (VIa-2) (25.0 mg, 0.0890 mmol).

Example 115

Production of 7-(2-{[6-(1,1-difluoroethyl)pyridin-3-yl]oxy}pyridin-3-yl)pyrazolo[1,5-a]pyridine (I-115)

By a production method similar to that in compound (I-36), compound (I-115) (yield 800 mg, 32%) was obtained as a white solid from 7-bromopyrazolo[1,5-a]pyridine (VII-8) (1.26 mg, 6.41 mmol) and compound (VIa-2) (2.00 mg, 7.12 mmol).

Example 116

Production of 3-chloro-7-(2-{[6-(1,1-difluoroethyl)pyridin-3-yl]oxy}pyridin-3-yl)pyrazolo[1,5-a]pyridine (I-116)

Compound (I-115) (30.0 mg, 0.0851 mmol) was dissolved in DMF (280 μL), NCS (12.5 mg, 0.0937 mmol) was added, and the mixture was stirred at room temperature for 3 hr. Water was added, and the mixture was extracted with chloroform, and the organic layer was dried over anhydrous sodium sulfate. The solvent was evaporated under reduced pressure, and the residue was purified by silica gel column chromatography (n-hexane:ethyl acetate) to give compound (I-116) (yield 23.7 mg, 72%) as a white solid.

Example 117

Production of 5-{[3-(2-methoxyphenyl)pyridin-2-yl]oxy}-3-methyl-2-(trifluoromethyl)pyridine (I-117)

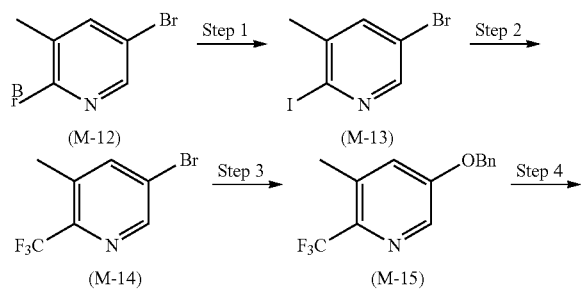

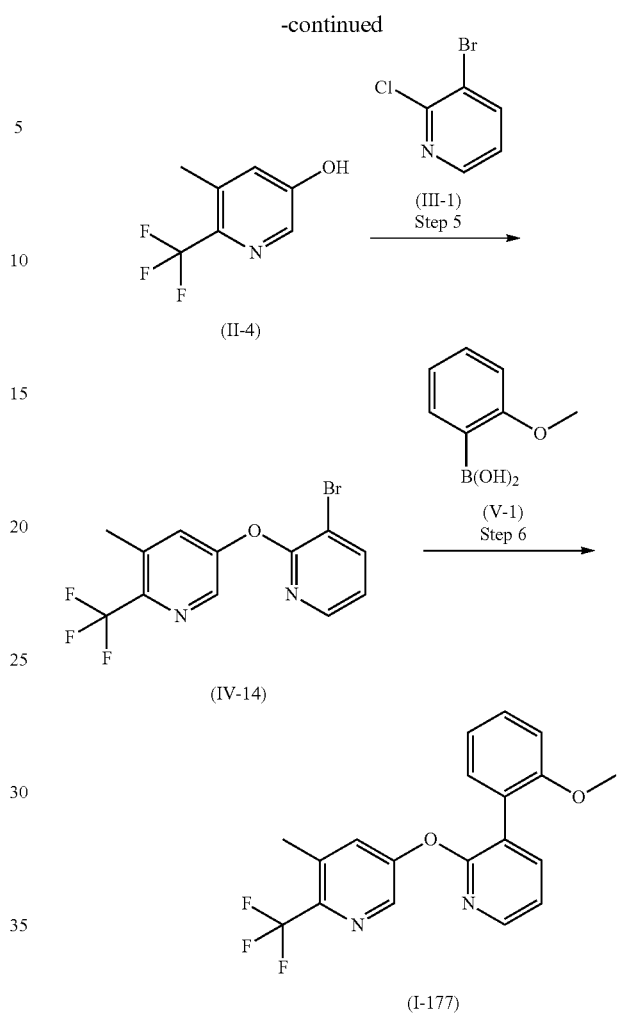

Step 1

To a solution of 2,5-dibromo-3-methylpyridine (M-12) (5.02 g, 20.0 mmol) in acetonitrile (50 mL) were added sodium iodide (12.0 g, 80.0 mmol) and acetyl chloride (2.85 mL, 40.0 mmol), and the mixture was stirred with heating under reflux for 24 hr. The reaction mixture was cooled, water was added, and neutralized (pH 8) with saturated aqueous sodium hydrogen carbonate solution. The mixture was extracted with ethyl acetate, and the organic layer was dried over anhydrous sodium sulfate, and filtered. The solvent was evaporated under reduced pressure, and the residue was purified by silica gel column chromatography (n-hexane:ethyl acetate=98:2→70:30) to give compound (M-13) (yield 5.76 g, 97%) as a red oil.

Step 2

A mixture of copper iodide (5.71 g, 30.0 mmol) and potassium fluoride (3.49 g, 60.0 mmol) was stirred under reduced pressure at 180° C. until it turned into green. The mixture was allowed to cool to room temperature, a solution of compound (M-13) (5.96 g, 20.0 mmol) and trimethylsilyltrifluoromethane (3.85 mL, 26.0 mmol) in NMP (30 mL) was added, and the mixture was stirred at 40° C. for 18 hr. The reaction mixture was added to aqueous ammonia solution, and the mixture was extracted with diethyl ether. The organic layer was dried over anhydrous sodium sulfate, and filtered. The solvent was evaporated under reduced pressure, and the residue was purified by distillation to give compound (M-14) (yield 3.95 g, 82%) as an oil.

119

Step 3

To a solution of compound (M-14) (3.95 g, 16.5 mmol) in benzyl alcohol (10.2 mL, 99.0 mmol) were added cesium carbonate (8.04 g, 24.7 mmol), 1,10-phenanthroline (297 mg, 1.65 mmol) and copper iodide (157 mg, 0.823 mmol) and the mixture was stirred at 120° C. for 19 hr. The reaction mixture was cooled, diluted with ethyl acetate, and filtered through Celite. The solvent was evaporated under reduced pressure, and the residue was purified by silica gel column chromatography (n-hexane:ethyl acetate=99:1→70:30) to give compound (M-15) (yield 3.84 g, 87%) as a pale-yellow oil.

Step 4

To a solution of compound (M-15) (3.84 g, 14.4 mmol) in ethyl acetate (20 mL) were added palladium hydroxide/carbon (115 mg), and the mixture was stirred under a hydrogen atmosphere at 5° C. for 5 hr. The reaction mixture was cooled, and filtered through Celite. The solvent was evaporated under reduced pressure, and the residue was purified by silica gel column chromatography (n-hexane:ethyl acetate=95:5→25:75) to give compound (II-4) (yield 2.32 g, 91%) as a white solid.

Step 5

To a solution of compound (II-4) (2.30 g, 13.0 mmol) and compound (III-1) (2.38 g, 12.4 mmol) in DMSO (8.0 mL) was added cesium carbonate (6.04 g, 18.6 mmol) was added and the mixture was stirred at 130° C. for 17 hr. The reaction mixture was cooled, water was added, and the mixture was extracted with ethyl acetate. The organic layer was washed successively with water and saturated brine, dried over anhydrous sodium sulfate, and filtered. The solvent was evaporated under reduced pressure, and the residue was purified by silica gel column chromatography (n-hexane:ethyl acetate=99:1→80:20) to give compound (IV-14) (yield 3.58 g, 87%) as a colorless oil.

Step 6

By a production method similar to that in compound (I-1), compound (I-117) (yield 28.2 mg, 87%) was obtained as a colorless oil from compound (IV-14) (30.0 mg, 0.0901 mmol) and 2-methoxyphenylboronic acid (V-1) (17.8 mg, 0.117 mmol).

Example 118

Production of 5-{[3-(4-fluoro-2-methoxyphenyl)pyridin-2-yl]oxy}-3-methyl-2-(trifluoromethyl)pyridine (I-118)

By a production method similar to that in compound (I-1), compound (I-118) (yield 28.6 mg, 84%) was obtained as a colorless oil from compound (IV-14) (30.0 mg, 0.0901 mmol) and 4-fluoro-2-methoxyphenylboronic acid (V-12) (19.9 mg, 0.117 mmol).

Example 119

Production of 5-fluoro-2-methoxy-2'-{[5-methyl-6-(trifluoromethyl)pyridin-3-yl]oxy}-3,3'-bipyridine (I-119)

By a production method similar to that in compound (I-1), compound (I-119) (yield 11.4 mg, 33%) was obtained as a colorless oil from compound (IV-14) (30.0 mg, 0.0901 mmol) and 5-fluoro-2-methoxypyridine-3-boronic acid (V-32) (20.0 mg, 0.117 mmol).

Example 120

Production of 2-(difluoromethyl)-5-{[2-(methoxyphenyl)pyridin-2-yl]oxy}-3-methylpyridine (I-120)

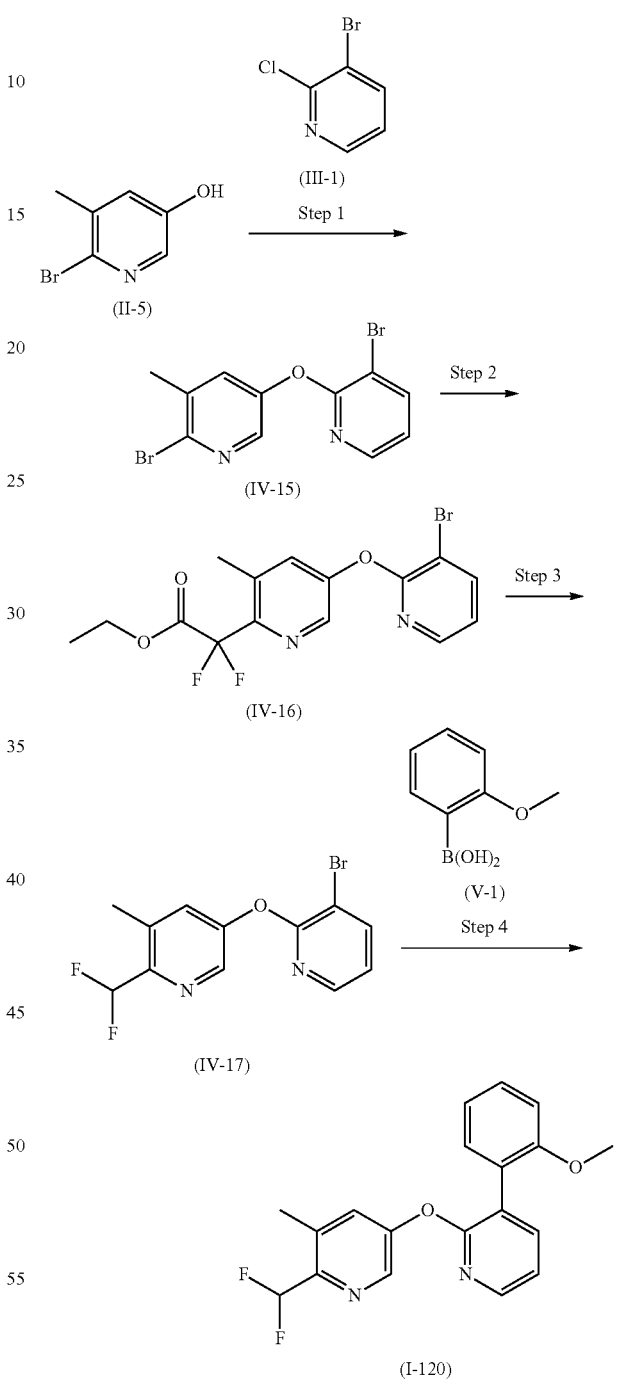

Step 1

To a solution of compound (III-1) (4.80 g, 24.9 mmol) and compound (II-5) (4.92 g, 26.2 mmol) in DMSO (24.9 mL) was added cesium carbonate (12.2 g, 37.4 mmol) and the mixture was stirred at 120° C. for 16 hr. The reaction mixture was allowed to cool to room temperature, added to water (100 mL), and the mixture was stirred under ice-cooling for 1 hr. The precipitated solid was collected by filtration, washed with water (25 mL×2), and dried under reduced pressure to give compound (IV-15) (yield 8.40 g, 98%) as a pale-brown solid.

Step 2

To a solution of compound (I-15) (3.85 g, 11.2 mmol) and ethyl 2-bromo-2,2-difluoroacetate (1.58 mL, 12.3 mmol) in DMSO (12 mL) was added copper (powder, <75 μm, 99.9%, 1.64 g, 25.7 mmol) was added and the mixture was stirred at 80° C. for 2 hr. The reaction mixture was ice-cooled, diluted with ethyl acetate (60 mL), saturated aqueous potassium dihydrogen phosphate solution was added and the mixture was stirred for 30 min. The reaction mixture was filtered through Celite, and the organic layer was separated. The organic layer was washed successively with water and saturated brine, dried over anhydrous sodium sulfate, and filtered. The solvent was evaporated under reduced pressure, and the residue was purified by silica gel column chromatography (n-hexane:ethyl acetate=95:5→70:30) to give compound (IV-16) (yield 2.53 g, 58%) as a colorless oil.

Step 3

To a solution of compound (I-16) (2.00 mg, 5.17 mmol) in NMP (10.0 mL) was added magnesium chloride hexahydrate (1.05 g, 5.17 mmol), and the mixture was stirred under microwave irradiation at 180° C. for 15 min. The reaction mixture was allowed to cool, water was added, and the mixture was extracted with ethyl acetate. The organic layer was washed successively with water and saturated brine, dried over anhydrous sodium sulfate, and filtered. The solvent was evaporated under reduced pressure, and the residue was purified by silica gel column chromatography (n-hexane:ethyl acetate=100:0→80:20) to give compound (IV-17) (yield 1.03 g, 63%) as a white solid.

Step 4

By a production method similar to that in compound (I-1), compound (I-120) (yield 29.8 mg, 91%) was obtained as a white solid from compound (IV-17) (30.0 mg, 0.0952 mmol) and 2-methoxyphenylboronic acid (V-1) (18.8 mg, 0.124 mmol).

Example 121

Production of 2-(difluoromethyl)-5-{[3-(4-fluoro-2-methoxyphenyl)pyridin-2-yl]oxy}-3-methylpyridine (I-121)

By a production method similar to that in compound (I-1), compound (I-121) (yield 673 mg, 86%) was obtained as a white solid from compound (IV-17) (683 mg, 2.17 mmol) and 4-fluoro-2-methoxyphenylboronic acid (V-12) (479 mg, 2.82 mmol).

Example 122

Production of 2-(difluoromethyl)-5-{[3-(5-fluoro-2-methoxyphenyl)pyridin-2-yl]oxy}-3-methylpyridine (I-122)

By a production method similar to that in compound (I-1), compound (I-122) (yield 30.0 mg, 87%) was obtained as a colorless oil from compound (IV-17) (30.0 mg, 0.0952 mmol) and 5-fluoro-2-methoxyphenylboronic acid (V-11) (21.0 mg, 0.124 mmol).

Example 123

Production of 2'-{[6-(difluoromethyl)-5-methylpyridin-3-yl]oxy}-2,6-dimethoxy-3,3'-bipyridine (I-123)

By a production method similar to that in compound (I-1), compound (I-123) (yield 32.3 mg, 91%) was obtained as a colorless oil from compound (IV-17) (30.0 mg, 0.0952 mmol) and 2,6-dimethoxypyridine-3-boronic acid (V-42) (22.7 mg, 0.124 mmol).

Example 124

Production of 2-[(6-ethylpyridin-3-yl)oxy]-3-(2-methoxyphenyl)pyridine (I-124)

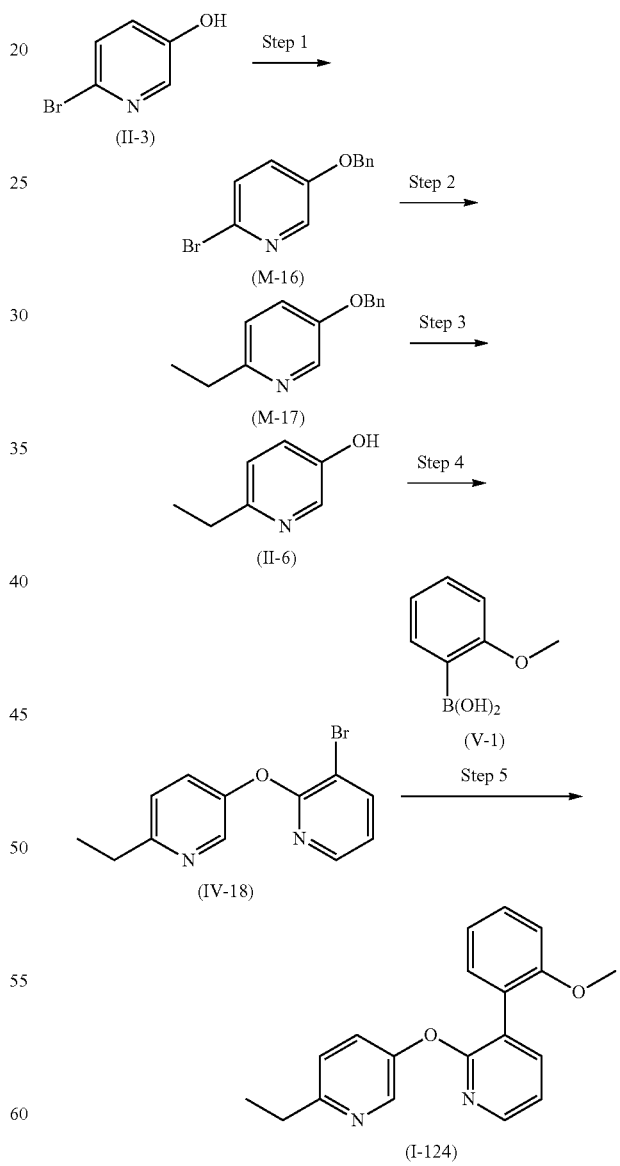

Step 1

Compound (II-3) (5.00 g, 28.7 mmol) was dissolved in DMF (30 mL), potassium carbonate (7.94 g, 57.5 mmol), benzyl bromide (4.1 mL, 35 mmol) and TBAI (531 mg, 1.44 mmol) were added under ice-cooling, and the mixture was warmed to room temperature and stirred for 1 hr. Water was added to the reaction mixture, and the mixture was extracted with ethyl acetate. The organic layer was washed successively with water and saturated brine, dried over anhydrous sodium sulfate, and filtered. The solvent was evaporated under reduced pressure. The residue was filtered through silica gel column chromatography (n-hexane:ethyl acetate=97:3→80:20) to give compound (M-16) (yield 6.97 g, 92%) as a white solid.

Step 2

Compound (M-16) (1.00 g, 3.79 mmol) was dissolved in THF (8.0 mL), PdCl$_2$(dppf).DCM (77.0 mg, 0.0950 mmol) and diethylzinc (1.0 mol/L THF solution, 5.7 mL, 5.7 mmol) were successively added, and the mixture was stirred at 70° C. for 4 hr. To the reaction mixture was added saturated aqueous sodium hydrogen carbonate solution, and the mixture was extracted with ethyl acetate. The organic layer was washed successively with saturated aqueous sodium hydrogen carbonate solution and saturated brine, dried over anhydrous sodium sulfate, and filtered. The solvent was evaporated under reduced pressure, and the residue was purified by silica gel column chromatography (NH silica gel, n-hexane:ethyl acetate=97:3→70:30) to give compound (M-17) (yield 338 mg, 42%) as a colorless oil.

Step 3

Compound (M-17) (338 mg, 1.59 mmol) was dissolved in THF (3.0 mL)/methanol (3.0 mL) mixed solution, 20% palladium hydroxide/carbon (33.8 mg) was added, and the mixture was stirred under a hydrogen atmosphere at room temperature for 1 hr. The mixture was filtered through Celite, and the solvent was evaporated under reduced pressure to give compound (II-6) (yield 176 mg, 90%) as a white solid.

Step 4

By a production method similar to that in compound (IV-1), compound (IV-18) (yield 344 mg, 86%) was obtained as a colorless oil from compound (II-6) (176 mg, 3.24 mmol) and compound (III-1) (330 mg, 1.72 mmol).

Step 5

By a production method similar to that in compound (I-1), compound (I-124) (yield 40.4 mg, 92%) was obtained as a colorless oil from compound (IV-18) (40.0 mg, 0.164 mmol) and 2-methoxyphenylboronic acid (V-1) (32.7 mg, 0.215 mmol).

Example 125

Production of 3-(2,3-dihydrobenzofuran-7-yl)-2-[(6-(ethylpyridin-3-yl)oxy]pyridine (I-125)

By a production method similar to that in compound (I-1), compound (I-125) (yield 34.0 mg, 75%) was obtained as a colorless oil from compound (IV-18) (40.0 mg, 0.164 mmol) and 2,3-dihydrobenzofuran-7-boronic acid (V-35) (35.2 mg, 0.215 mmol).

Example 126

Production of 2-[(6-ethylpyridin-3-yl)oxy]-2'-methoxy-3,3'-bipyridine (I-126)

By a production method similar to that in compound (I-1), compound (I-126) (yield 39.9 mg, 91%) was obtained as a colorless oil from compound (IV-18) (40.0 mg, 0.164 mmol) and 2-methoxypyridine-3-boronic acid (V-26) (32.9 mg, 0.215 mmol).

Example 127

Production of 2-[(6-ethylpyridin-3-yl)oxy]-4'-methoxy-3,3'-bipyridine (I-127)

Compound (IV-18) (40.0 mg, 0.164 mmol) 4-methoxypyridine-3-boronic acid monohydrate (V-28) (36.7 mg, 0.215 mmol), (A-$^{ta}$Phos)$_2$PdCl$_2$ (5.9 mg, 7.2 μmol) and TEA (73 μL, 0.717 mmol) were dissolved in n-butanol (0.60 mL), and the mixture was stirred under microwave irradiation at 120° C. for 30 min. Water was added to the reaction mixture, and the mixture was extracted with chloroform. The solvent was evaporated under reduced pressure from the organic layer, and the residue was purified by silica gel column chromatography (NH silica gel, n-hexane:ethyl acetate=97:3→70:30) to give compound (I-127) (yield 24.5 mg, 56%) as a colorless oil.

Example 128

Production of 2-[(6-cyclopropylpyridin-3-yl)oxy]-3-(2-methoxyphenyl)pyridine (I-128)

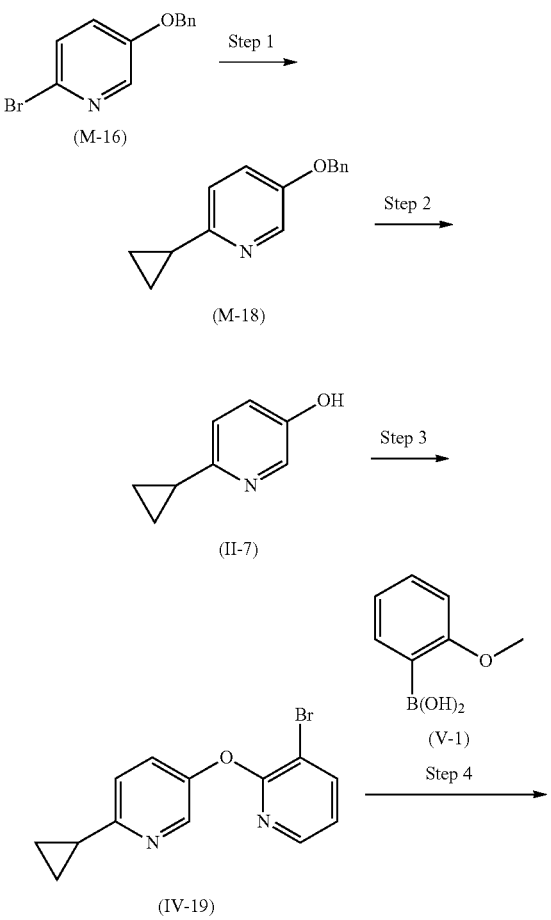

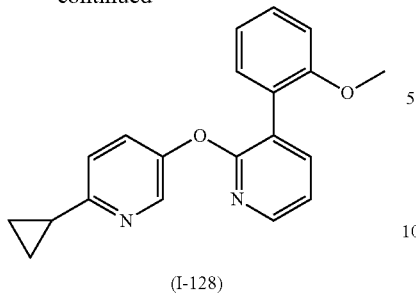

(I-128)

Step 1

Compound (M-16) (2.50 g, 9.47 mmol) was dissolved in THF (12 mL), c-PrZnBr (0.5 mol/L THF solution, 28 mL, 14 mmol) and Pd(PPh)$_4$ (219 mg, 0.189 mmol) were successively added, and the mixture was stirred at 70° C. for 2 hr. To the reaction mixture was added saturated aqueous sodium hydrogen carbonate solution, and the mixture was extracted with ethyl acetate. The organic layer was washed successively with saturated aqueous sodium hydrogen carbonate solution and saturated brine, dried over anhydrous sodium sulfate, and filtered. The solvent was evaporated under reduced pressure, and the residue was purified by silica gel column chromatography (n-hexane:ethyl acetate=97:3→80: 15) to give compound (M-18) (yield 1.70 g, 80%) as a colorless oil.

Step 2

By a production method similar to that in compound (II-6), compound (II-7) (yield 686 mg, 67%) was obtained as a white solid from compound (M-18) (1.70 g, 7.55 mmol).

Step 3

By a production method similar to that in compound (IV-1), compound (IV-19) (yield 580 mg, 90%) was obtained as a white solid from compound (II-7) (300 mg, 2.22 mmol) and compound (III-1) (513 mg, 2.66 mmol).

Step 4

By a production method similar to that in compound (I-1), compound (I-128) (yield 41.5 mg, 95%) was obtained as a white solid from compound (IV-19) (40.0 mg, 0.137 mmol) and 2-methoxyphenylboronic acid (V-1) (25.1 mg, 0.165 mmol).

Example 129

Production of 2-[(6-cyclopropylpyridin-3-yl)oxy]-3-(4-fluoro-2-methoxyphenyl)pyridine (I-129)

By a production method similar to that in compound (I-1), compound (I-129) (yield 16.3 mg, 35%) was obtained as a colorless oil from compound (IV-19) (40.0 mg, 0.137 mmol) and 4-fluoro-2-methoxyphenylboronic acid (V-12) (28.0 mg, 0.165 mmol).

Example 130

Production of 2-[(6-cyclopropylpyridin-3-yl)oxy]-2'-methoxy-3,3'-bipyridine (I-130)

By a production method similar to that in compound (I-1), compound (I-130) (yield 27.2 mg, 62%) was obtained as a colorless oil from compound (IV-19) (40.0 mg, 0.137 mmol) and 2-methoxypyridine-3-boronic acid (V-26) (25.2 mg, 0.165 mmol).

Example 131

Production of 2-[(5-chloro-6-cyclopropylpyridin-3-yl)oxy]-2'-methoxy-3,3'-bipyridine (I-131)

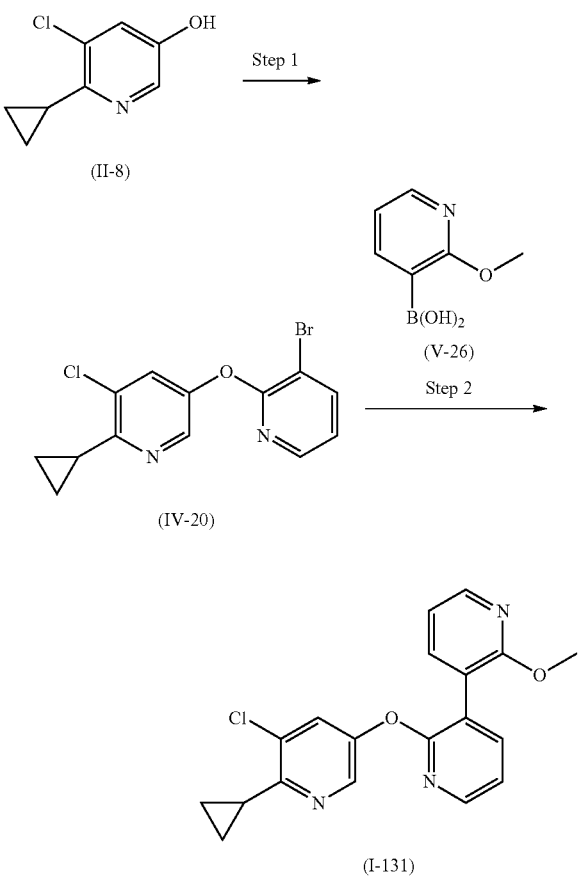

Step 1

By a production method similar to that in compound (IV-1), compound (IV-20) (yield 314.9 mg, 82%) was obtained as a colorless oil from compound (II-8) (200 mg, 1.18 mmol) and compound (III-1) (272 mg, 1.42 mmol).

Step 2

By a production method similar to that in compound (I-1), compound (I-131) (yield 25.3 mg, 58%) was obtained as a colorless oil from compound (IV-20) (40.0 mg, 0.123 mmol) and 2-methoxypyridine-3-boronic acid (V-26) (22.6 mg, 0.148 mmol).

Example 132

Production of 2-[(5-chloro-6-cyclopropylpyridin-3-yl)oxy]-4'-methoxy-3,3'-bipyridine (I-132)

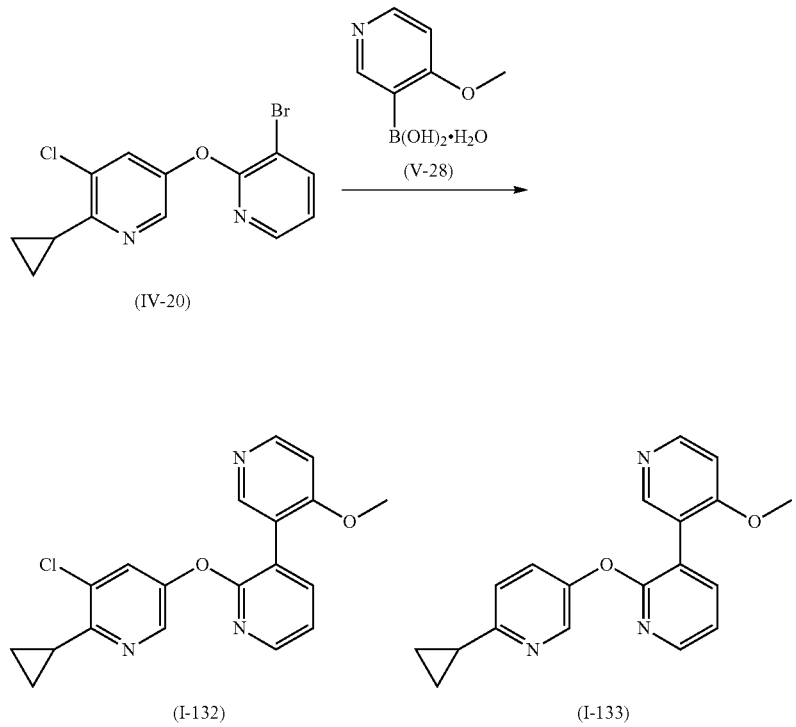

By a production method similar to that in compound (I-127), compound (I-132) (yield 11.1 mg, 20%) was obtained as a pale-yellow oil from compound (IV-20) (50.0 mg, 0.154 mmol) and 4-methoxypyridine-3-boronic acid monohydrate (V-28) (28.2 mg, 0.184 mmol).

Example 133

Production of 2-[(6-cyclopropylpyridin-3-yl)oxy]-4'-methoxy-3,3'-bipyridine (I-133)

Compound (I-133) (yield 13.2 mg, 27%) was obtained as a pale-yellow oil as a byproduct of the aforementioned compound (I-132).

Example 134

Production of 3-{[3-(2-methoxyphenyl)pyridin-2-yl]oxy}-5,6,7,8-tetrahydroquinoline (I-134)

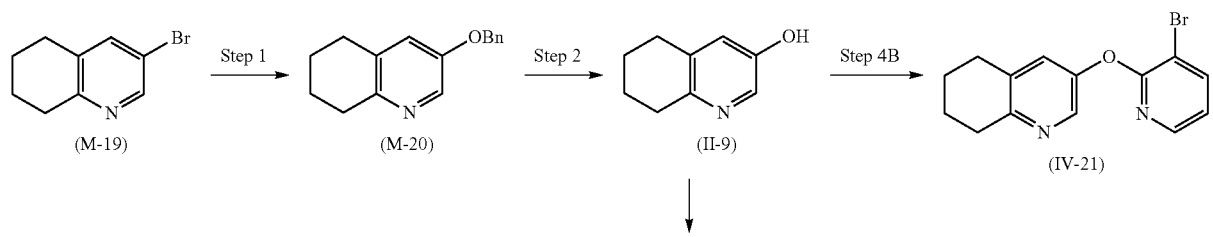

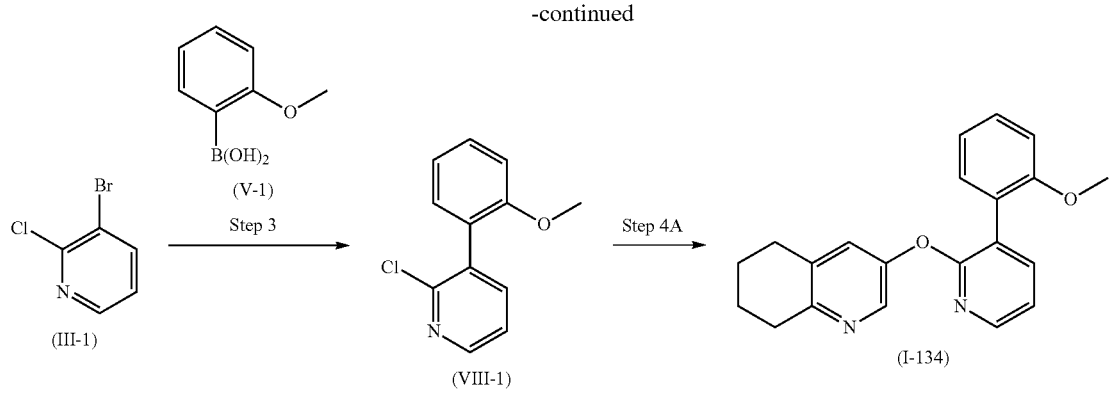

Step 1

Compound (M-19) (160 mg, 0.754 mmol), 1,10-phenanthroline (27.2 mg, 0.151 mmol) and cesium carbonate (492 mg, 1.51 mmol) were dissolved in benzyl alcohol (1.0 mL, 9.6 mmol), copper(I) iodide (14.37 mg, 0.075 mmol) was added, and the mixture was stirred under an argon atmosphere at 120° C. for 24 hr. The reaction mixture was allowed to cool, diluted with ethyl acetate, and filtered through Celite. The solvent was evaporated under reduced pressure, and the residue was purified by silica gel column chromatography (n-hexane:ethyl acetate=0:100→85:15) to give compound (M-20) (yield 155 mg, 86%).

Compound (M-19) can be synthesized according to a known method. Such method is described in, for example, J. Am. Chem. Soc. 2011; 133: 12285-12292.

Step 2

Compound (M-20) (140 mg, 0.585 mmol) was dissolved in ethanol (1.4 mL), 10% Pd/C (28.0 mg, 20 w/w %) was added, and the mixture was stirred under a hydrogen atmosphere at room temperature for 2 hr. The reaction mixture was diluted with ethanol, and filtered through Celite. The solvent was evaporated under reduced pressure, and the residue was dried under reduced pressure to give compound (II-9) (yield 82.0 mg, 94%).

Step 3

Compound (III-1) (700 mg, 3.64 mmol), 2-methoxyphenylboronic acid (V-1) (553 mg, 3.64 mmol), A-$^{ta}$Phos$_2$PdCl$_2$ (129 mg, 0.182 mmol) and cesium carbonate (2.37 g, 7.28 mmol) were dissolved in 1,4-dioxane and water (5:1, 12 mL), and the mixture was stirred at 70° C. for 4 hr. The reaction mixture was cooled, and extracted with ethyl acetate. The organic layer was washed successively with water and saturated brine, dried over anhydrous sodium sulfate, and filtered. The solvent was evaporated under reduced pressure, and the residue was purified by silica gel column chromatography (n-hexane:ethyl acetate) to give compound (VII-1) (yield 629 mg, 79%) as a colorless oil.

Step 4

Compound (VIII-1) (45.0 mg, 0.205 mmol) and compound (II-9) (30.1 mg, 0.202 mmol) were dissolved in NMP (1 mL), cesium carbonate (79.0 mg, 0.242 mmol) was added, and the mixture was stirred under microwave irradiation at 180° C. for 20 min. Water was added to the reaction mixture, and the mixture was extracted with ethyl acetate, and the organic layer was washed successively with water and saturated brine. The organic layer was dried over anhydrous sodium sulfate, and filtered, and the solvent was evaporated under reduced pressure. The residue was purified by silica gel column chromatography (n-hexane:ethyl acetate=60:40→85:15) to give compound (I-134) (yield 34.5 mg, 51%) as a brown oil.

Step 4B

By a production method similar to that in compound (IV-1), compound (IV-21) (yield 4.18 mg, 91%) was obtained from compound (II-9) (2.24 g, 15.0 mmol) and compound (III-1) (2.89 g, 15.0 mmol).

Example 135

Production of 3-{[2'-methoxy-(3,3'-bipyridin)-2-yl]oxy}-5,6,7,8-tetrahydroquinoline (I-135)

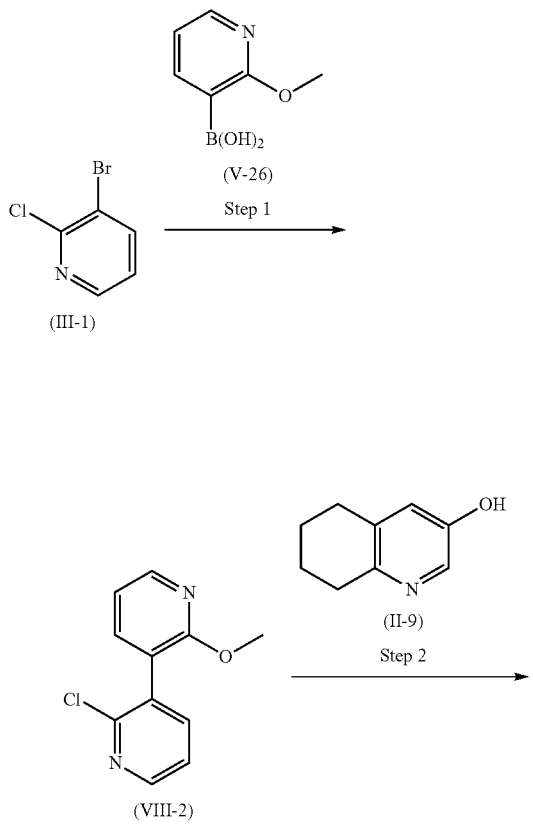

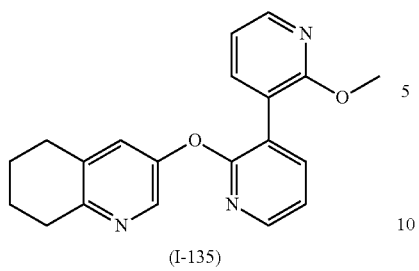

Step 1

By a production method similar to that in compound (VIII-1), compound (VIII-2) (865 mg, yield 75%) was obtained as a white solid from compound (III-1) (1.00 g, 5.20 mmol) and 2-methoxypyridine-3-boronic acid (V-26) (795 mg, 5.20 mmol).

Step 2

By a production method similar to that in compound (I-134), compound (I-135) (yield 30.4 mg, 45%) was obtained as a white solid from compound (VIII-2) (45.0 mg, 0.204 mmol) and compound (II-9) (30.1 mg, 0.202 mmol).

Example 136

Production of 3-{[3-(2-methoxyphenyl)pyridin-2-yl]oxy}-6,7,8,9-tetrahydro-5H-cyclohepta[b]pyridine (I-136)

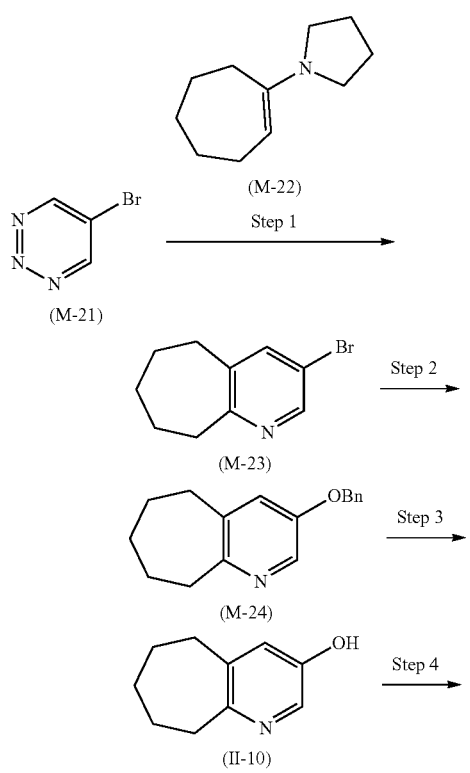

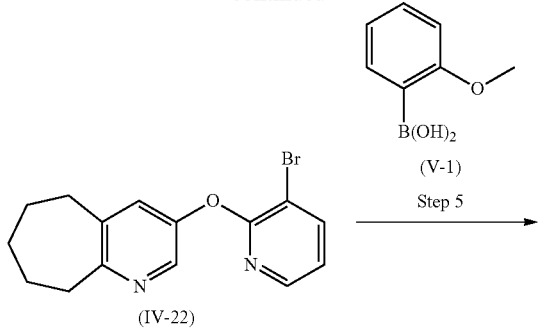

Step 1

Compound (M-21) (2.00 g, 12.5 mmol) was dissolved in chloroform (25.0 mL), 4 Å molecular sieve (400 mg, powder) was added, and compound (M-22) (3.10 g, 18.8 mmol) was added at 0° C., and the mixture was stirred at 0° C. for 5 min. After stirring at 70° C. for 40 min, the mixture was allowed to cool to room temperature. The solvent was evaporated under reduced pressure, and the residue was purified by silica gel column chromatography (n-hexane:ethyl acetate) to give compound (M-23) (yield 1.90 g, 67%).

Step 2

Compound (M-23) (1.70 g, 7.52 mmol), cesium carbonate (4.90 g, 15.0 mmol) and 1,10-phenanthroline (0.271 g, 1.50 mmol) was dissolved in benzyl alcohol (7.82 mL, 75 mmol), copper(I) iodide (0.143 g, 0.752 mmol) was added and the mixture was stirred at 120° C. for 24 hr. The reaction mixture was allowed to cool, diluted with ethyl acetate, filtered through Celite, and washed with ethyl acetate. The solvent was evaporated under reduced pressure from the filtrate and washing solution, and the residue was purified by silica gel column chromatography (n-hexane:ethyl acetate) to give compound (M-24) (yield 1.11 g, 58%).

Step 3

Compound (M-24) (1.06 g, 4.18 mmol) was dissolved in ethanol (10 mL), 10% Pd/C (0.212 g, 20 w/w %) was added, and the mixture was stirred under a hydrogen atmosphere at room temperature for 2 hr. The reaction mixture was diluted with ethanol, filtered through Celite, and washed with ethyl acetate. The solvent was evaporated under reduced pressure from the filtrate and washing solution, and the residue was dried under reduced pressure to give compound (II-10) (yield 0.665 mg, 97%) as a white solid.

Step 4

By a production method similar to that in compound (IV-1), compound (IV-22) (yield 1.15 g, 90%) was obtained from compound (II-10) (650 mg, 3.98 mmol).

Step 5

By a production method similar to that in compound (I-1), compound (I-136) (yield 38.7 mg, 89%) was obtained as a colorless oil from compound (IV-22) (40.0 mg, 0.125 mmol) and 2-methoxyphenylboronic acid (V-1) (25.4 mg, 0.163 mmol).

Example 137

Production of 3-{[3-(2,3-dihydrobenzyofuran-7-yl)pyridin-2-yl]oxy}-5,6,7,8-tetrahydroquinoline (I-137)

By a production method similar to that in compound (I-1), compound (I-137) (yield 33.6 mg, 99%) was obtained as a colorless oil from compound (IV-21) (30.0 mg, 0.098 mmol) and compound (V-35) (21.0 mg, 0.128 mmol).

Example 138

Production of 3-{[3-(2,3-dihydrobenzofuran-7-yl)pyridin-2-yl]oxy}-6,7-dihydro-5H-cyclopenta[b]pyridine (I-138)

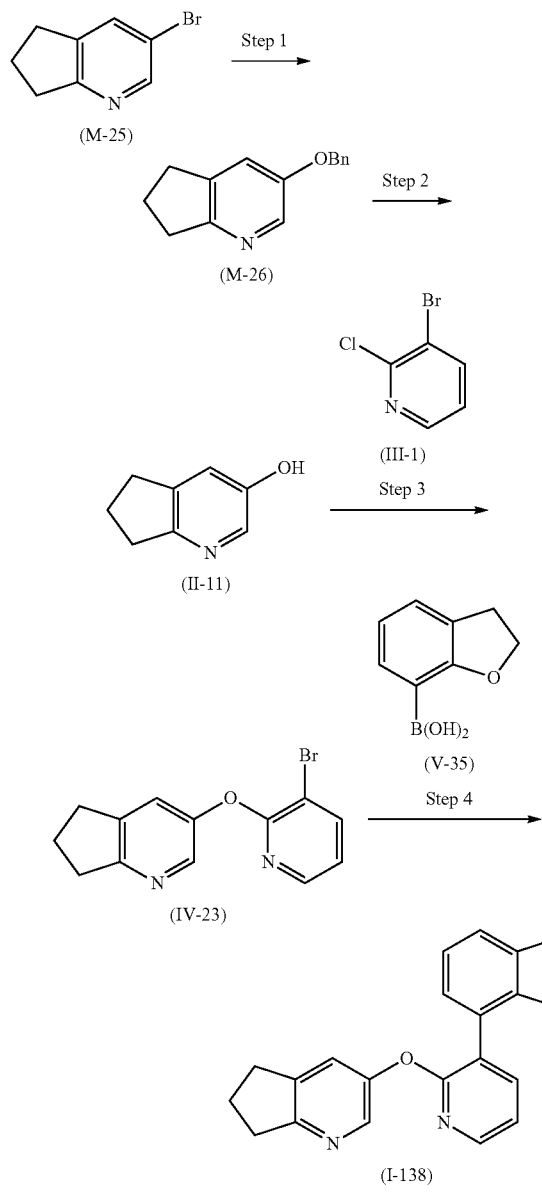

Step 1

By a production method similar to that in compound (M-24), compound (M-26) (yield 1.97 mg, 87%) was obtained as a white solid from compound (M-25) (2.00 g, 10.1 mmol).

Step 2

By a production method similar to that in compound (II-10), compound (II-11) (yield 1.04 g, 98%) was obtained as a white solid from compound (M-26) (1.77 g, 7.86 mmol).

Step 3

By a production method similar to that in compound (IV-1), compound (IV-23) (yield 1.64 g, 95%) was obtained from compound (II-11) (800 mg, 5.92 mmol) and compound (III-1) (1.14 g, 5.92 mmol).

Step 4

By a production method similar to that in compound (I-1), compound (I-138) (yield 223 mg, 98%) was obtained as a white solid from compound (IV-23) (200 mg, 0.687 mmol) and compound (V-35) (146 mg, 0.893 mmol).

Production of 8,8-difluoro-3-{[3-(2-methoxyphenyl)pyridin-2-yl]oxy}-5,6,7,8-tetrahydroquinoline (I-142)

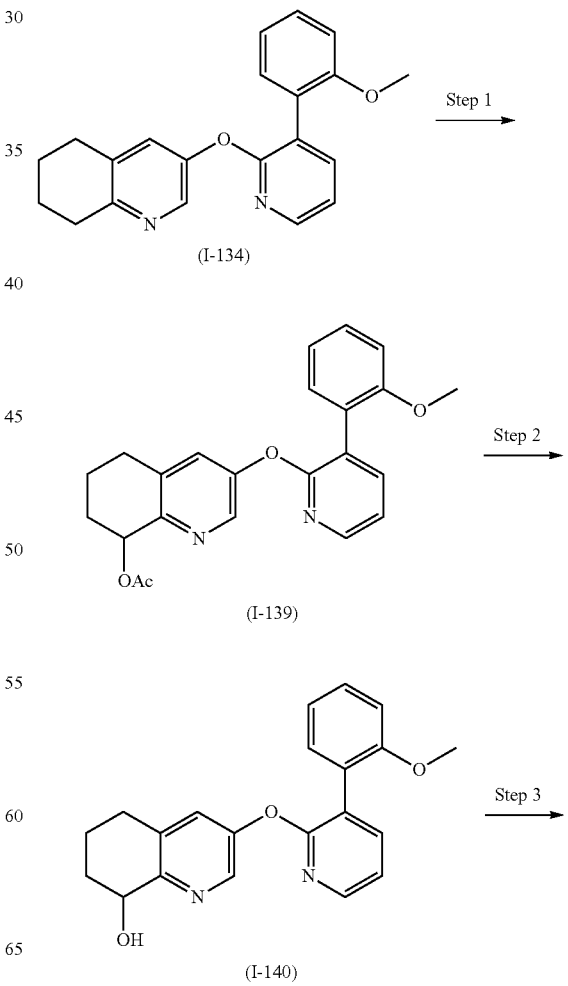

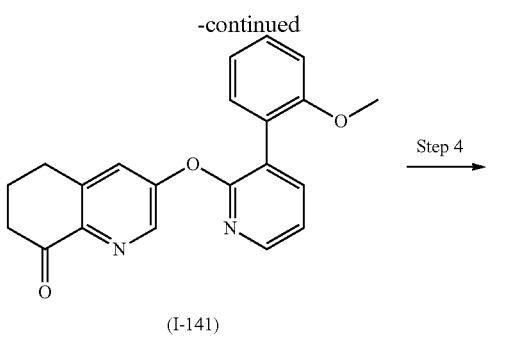

(I-141)

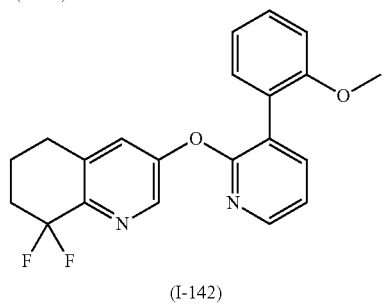

(I-142)

Example 139

Production of 3-{[3-(2-methoxyphenyl)pyridin-2-yl]oxy}-5,6,7,8-tetrahydroquinolin-8-yl acetate (I-139)

Compound (I-134) (300 mg, 0.903 mmol) was dissolved in DCM (3.0 mL), mCPBA (271 mg, 1.08 mmol) was added ice-cooling, and the mixture was stirred at room temperature overnight. The reaction mixture was allowed to cool, aqueous sodium sulfite solution and saturated aqueous sodium hydrogen carbonate solution were added, and the mixture was extracted with chloroform, and washed with saturated brine. The organic layer was dried over anhydrous sodium sulfate, and filtered, and the solvent was evaporated under reduced pressure to give a crude N-oxide compound. Crude N-oxide compound was dissolved in acetic anhydride (1.0 mL, 10.6 mmol), and the mixture was stirred at 60° C. for 11 hr. The reaction mixture was allowed to cool, diluted with ethyl acetate, and washed successively with saturated aqueous sodium hydrogen carbonate solution and saturated brine. The organic layer was dried over anhydrous sodium sulfate, and filtered, and the solvent was evaporated under reduced pressure. The residue was purified by silica gel column chromatography (n-hexane:ethyl acetate=70:30→30:70) to give compound (I-139) (yield 317 g, 90%) as a white solid.

Example 140

Production of 3-{[3-(2-methoxyphenyl)pyridin-2-yl]oxy}-5,6,7,8-tetrahydroquinolin-8-ol (I-140)

Compound (I-139) (295 g, 0.756 mmol) was dissolved in methanol (3 mL), potassium carbonate (313 mg, 2.23 mmol) was added, and the mixture was stirred at room temperature for 2 hr. The solvent was evaporated under reduced pressure, ethyl acetate and water were added. The organic layer was separated, wash with saturated brine, dried over anhydrous sodium sulfate, and filtered. The solvent was evaporated under reduced pressure, and the residue was purified by silica gel column chromatography (n-hexane:ethyl acetate=70:30→20:80) to give compound (I-140) (yield 184 g, 70%) as a white solid.

Example 141

Production of 3-{[3-(2-methoxyphenyl)pyridin-2-yl]oxy}-6,7-dihydroquinolin-8(5H)-one (I-141)

Compound (I-140) (111 mg, 0.319 mmol) was dissolved in DCM (2.0 mL), DMP (176 mg, 0.414 mmol) was added, and the mixture was stirred at room temperature for 7 hr. The reaction mixture was diluted with chloroform, and aqueous sodium sulfite solution and saturated aqueous sodium hydrogen carbonate solution were added. The organic layer was separated, washed with saturated brine, dried over anhydrous sodium sulfate, and filtered. The solvent was evaporated under reduced pressure, and the residue was purified by silica gel column chromatography (n-hexane:ethyl acetate=50:50→10:90) to give compound (I-141) (yield 103 g, 93%) as a pale-yellow solid.

Example 142

Production of 8,8-difluoro-3-{[3-(2-methoxyphenyl)pyridin-2-yl]oxy}-5,6,7,8-tetrahydroquinoline (I-142)

Compound (I-141) (30.0 mg, 0.0866 mmol) was dissolved in DCM (1.0 mL), Deoxo-Fluor (registered trademark) (76.0 µL, 0.371 mmol) was added, and the mixture was stirred at room temperature for 4 days. To the reaction mixture was slowly added water, and the mixture was extracted with chloroform. The organic layer was washed with saturated brine, dried over anhydrous sodium sulfate, and filtered. The solvent was evaporated under reduced pressure, and the residue was purified by silica gel column chromatography (n-hexane:ethyl acetate=90:10→20:80) to give compound (I-141) (yield 3.9 mg, 12%) as a white solid.

Example 143 and 144

Production of 3-{[3-(2-methoxyphenyl)pyridin-2-yl]oxy}-N,N-dimethyl-5,6,7,8-tetrahydroquinolin-8-amine (I-143)

Production of 3-{[3-(2-methoxyphenyl)pyridin-2-yl]oxy}-5,6-dihydroquinoline (I-144)

Compound (I-140) (30.0 mg, 0.086 mmol) and TEA (24.0 µL, 0.172 mmol) were dissolved in THF (1.0 mL), methanesulfonyl chloride (8.7 µL, 0.112 mmol) was added under ice-cooling, and the mixture was stirred at room temperature for 30 min. 50% Aqueous dimethylamine solution (36.0 µL) was added, and the mixture was further stirred at room temperature for 7 hr. 50% Aqueous dimethylamine solution (36.0 µL) was further added, and the mixture was stirred at room temperature for 17 hr. The mixture was extracted with ethyl acetate, and the organic layer was washed with water and saturated brine. The organic layer was dried over anhydrous sodium sulfate, and filtered, and the solvent was evaporated under reduced pressure. The residue was purified by silica gel column chromatography (chloroform:methanol=100:0→20:80), NH silica, n-hexane:ethyl acetate=70:30→30:70) to give compound (I-143) (yield 6.0 mg, 19%) and compound (I-144) (yield 0.9 mg, 3%) each as a colorless oil.

Example 145

Production of 2-{[6-(1,1-difluoro-2-methoxyethyl) pyridin-3-yl]oxy}-3-(2-methoxyphenyl)pyridine (I-145)

To a solution of compound (I-79) (30.0 mg, 0.0837 mmol) in DMF (0.55 mL) were successively added, under ice-cooling, 60% sodium hydride (4.4 mg, 0.092 mmol) and methyl iodide (5.8 µL, 0.092 mmol), and the mixture was stirred at room temperature for 14 hr. Water was added to the reaction mixture, and the mixture was extracted with ethyl acetate. The organic layer was washed successively with water and saturated brine, dried over anhydrous sodium sulfate, and filtered. The solvent was evaporated under reduced pressure, and the residue was purified by silica gel column chromatography (n-hexane:ethyl acetate) to give compound (I-145) (yield 20.8 mg, 67%) as a white solid.

Example 146

Production of 2,2-difluoro-2-(5-{[3-(2-methoxyphenyl)pyridin-2-yl]oxy}-pyridin-2-yl)-N-methylethanamine (I-146)

Compound (I-80) (500 mg, 1.02 mmol) was dissolved in DMF (3.3 mL), DIPEA (3.6 mL, 20 mmol), cesium carbonate (1.65 g, 5.10 mmol) and methylamine hydrochloride (344 mg, 5.10 mmol) were successively added at room temperature, and the mixture was heated to 60° C. and stirred for 15 hr. Water was added to the reaction mixture and the reaction mixture was extracted with ethyl acetate. The organic layer was washed successively with water and saturated brine, dried over anhydrous sodium sulfate, and filtered. The solvent was evaporated under reduced pressure, and the residue was purified by silica gel column chromatography (n-hexane:ethyl acetate) to give compound (I-146) (yield 260 g, 69%) as a colorless oil.

Example 147

Production of 2,2-difluoro-2-(5-{[3-(2-methoxyphenyl)pyridin-2-yl]oxy}-2-yl)-N,N-dimethylethanamine (I-147)

By a production method similar to that in compound (I-146), compound (I-147) (yield 31.1 mg, 79%) was obtained as a colorless oil from compound (I-80) (50.0 mg, 0.102 mmol) and dimethylamine hydrochloride (63.0 mg, 1.02 mmol).

Example 148

Production of 4-[2,2-difluoro-2-(5-{[3-(2-methoxyphenyl)pyridin-2-yl]oxy}pyridin-2-yl)-ethyl]morpholine (I-148)

By a production method similar to that in compound (I-146), compound (I-148) (yield 31.1 mg, 79%) was obtained as a colorless oil from compound (I-80) (50.0 mg, 0.102 mmol) and morpholine (44 µL, 0.51 mmol).

Example 149

Production of N-ethyl-2,2-difluoro-2-(5-{[3-(2-methoxyphenyl)pyridin-2-yl]oxy}-pyridin-2-yl)-N-methylethanamine (I-149)

Compound (I-80) (68.6 mg, 0.102 mmol) was dissolved in DMF (420 µL), pyridine (17 µL, 0.21 mmol) and methylethylamine (13 µL, 0.15 mmol) were successively added at room temperature, and the mixture was stirred at room temperature for 15 hr. Water was added to the reaction mixture, and the mixture was extracted with ethyl acetate. The organic layer was washed successively with water and saturated brine, dried over anhydrous sodium sulfate, and filtered. The solvent was evaporated under reduced pressure, and the residue was purified by silica gel column chromatography (n-hexane:ethyl acetate) to give compound (I-149) (yield 1.2 mg, 2%) as a colorless oil.

Example 150

Production of N-[2,2-difluoro-2-(5-{[3-(2-methoxyphenyl)pyridin-2-yl]oxy}pyridin-2-yl)ethyl]-N,O-dimethylhydroxylamine (I-150)

By a production method similar to that in compound (I-146), compound (I-150) (yield 41.0 mg, qunatitative) was obtained as a colorless oil from compound (I-80) (50.0 mg, 0.102 mmol) and N,O-dimethylhydroxylamine hydrochloride (49.7 mg, 0.510 mmol).

Example 151

Production of N-[2,2-difluoro-2-(5-{[3-(2-methoxyphenyl)pyridin-2-yl]oxy}-2-yl)-ethyl]-N-methylacetamide (I-151)

Compound (I-146) (30.0 mg, 0.0808 mmol) was dissolved in DCM (400 µL), DIPEA (42 µL, 0.24 mmol), and acetyl chloride (7.5 µL, 0.11 mmol) were added, and the mixture was stirred at room temperature for 15 hr. Water was added to the reaction mixture, and the mixture was extracted with chloroform. The extract was purified by silica gel column chromatography (n-hexane:ethyl acetate) to give compound (I-151) (yield 32.7 mg, 98%) as a colorless oil.

Example 152

Production of methyl [2,2-difluoro-2-(5-{[3-(2-methoxyphenyl)pyridin-2-yl]oxy}pyridin-2-yl)ethyl](methyl)carbamate (I-152)

By a production method similar to that in compound (I-151), compound (I-152) (yield 26.7 mg, 74%) was obtained as a colorless oil from compound (I-146) (30.0 mg, 0.0808 mmol) and methyl chloroformate (8.1 µL, 0.11 mmol).

Example 153

Production of 2-{(6-[1,1-difluoro-2-(4-methyl-1H-pyrazol-1-yl)ethyl]pyridin-3-yl}oxy)-3-(2-methoxyphenyl)pyridine (I-153)

By a production method similar to that in compound (I-146), compound (I-153) (yield 18.2 mg, 70%) was obtained as a colorless oil from compound (I-80) (30.0 mg, 0.0612 mmol) and 4-methyl-1H-pyrazole (50.2 mg, 0.612 mmol).

Example 154

Production of 2,2-difluoro-2-(5-{[3-(4-fluoro-2-methoxyphenyl)pyridin-2-yl]oxy}pyridin-2-yl)-ethanol (I-154)

By a production method similar to that in compound (I-1), compound (I-154) (yield 272 mg, 92%) was obtained as a colorless oil from compound (IV-10) (260 mg, 0.785 mmol) and 4-fluoro-2-methoxyphenylboronic acid (V-12) (160 mg, 0.942 mmol).

Example 155

Production of 2-{[6-(2-ethoxy-1,1-difluoroethyl)pyridin-3-yl]oxy}-3-(4-fluoro-2-methoxyphenyl)pyridine (I-155)

By a production method similar to that in compound (I-145), compound (I-155) (yield 26.2 mg, 81%) was obtained as a colorless oil from compound (I-154) (30.0 mg, 0.080 mmol) and ethyl bromide (7.1 μL, 0.096 mmol).

Reference Example 156

Production of 2,2-difluoro-2-(5-{[3-(4-fluoro-2-methoxyphenyl)pyridin-2-yl]oxy}pyridin-2-yl)ethyl trifluoromethanesulfonate (I-156)

By a production method similar to that in compound (I-80), compound (I-156) (yield 410 mg, 65%) was obtained as a pale-yellow oil from compound (I-154) (682 mg, 1.81 mmol) and trifluoromethanesulfonic anhydride (610 μL, 3.6 mmol).

Example 157

Production of 2-{(6-[1,1-difluoro-2-(1H-pyrazol-1-yl)ethyl]pyridin-3-yl)oxy}-3-(4-fluoro-2-methoxyphenyl)pyridine (I-157)

By a production method similar to that in compound (I-146), compound (I-157) (yield 9.3 mg, 36%) was obtained as a colorless oil from compound (I-156) (31.1 mg, 0.0612 mmol) and 1H-pyrazole (41.6 mg, 0.612 mmol).

Example 158

Production of 2-{(6-[1,1-difluoro-2-(1H-imidazol-1-yl)ethyl]pyridin-3-yl)oxy}-3-(4-fluoro-2-methoxyphenyl)pyridine (I-158)

By a production method similar to that in compound (I-146), compound (I-158) (yield 16.7 mg, 64%) was obtained as a colorless oil from compound (I-156) (31.1 mg, 0.0612 mmol) and 1H-imidazole (41.6 mg, 0.612 mmol).

Example 159

Production of 2-({6-[1,1-difluoro-2-(2-methoxyethoxy)ethyl]pyridin-3-yl}oxy)-3-(4-fluoro-2-methoxyphenyl)pyridine (I-159)

By a production method similar to that in compound (I-145), compound (I-159) (yield 15.0 mg, 45%) was obtained as a colorless oil from compound (I-154) (30.0 mg, 0.080 mmol) and 1-bromo-2-methoxyethane (9.0 μL, 0.096 mmol).

Example 160

Production of 2-({6-[1,1-difluoro-2-(2-propyl-1-yloxy)ethyl]pyridin-3-yl}oxy)-3-(2-methoxyphenyl)pyridine (I-160)

By a production method similar to that in compound (I-145), compound (I-160) (yield 15.9 mg, 48%) was obtained as a colorless oil from compound (I-79) (30.0 mg, 0.0761 mmol) and propargyl bromide (6.3 μL, 0.092 mmol).

Example 161

Production of 2-{[6-(1,1-difluoro-2-methoxyethyl)pyridin-3-yl]oxy}-3-(4-fluoro-2-methoxyphenyl)pyridine (I-161)

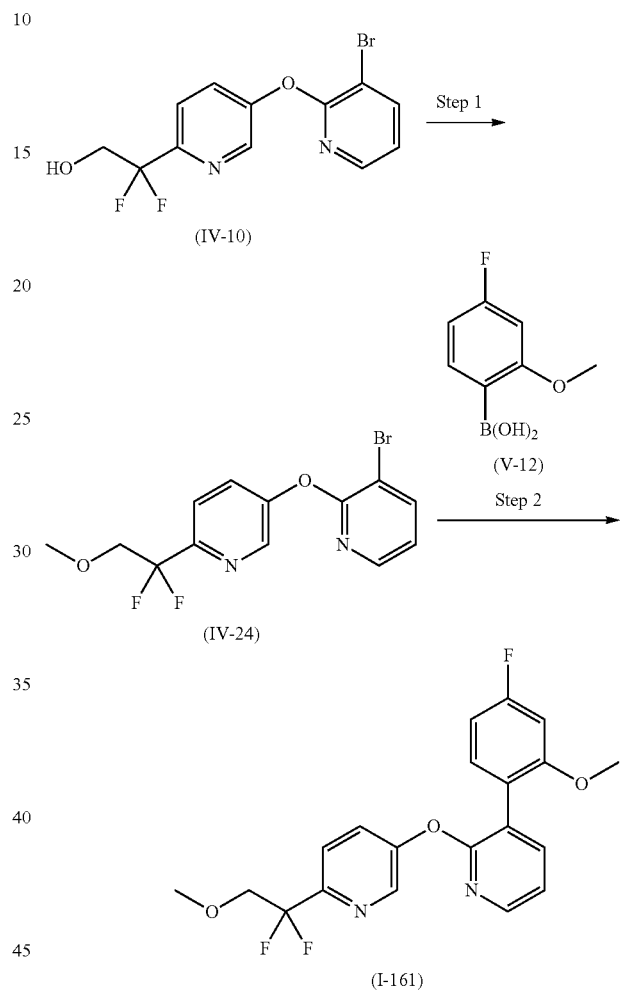

Step 1

By a production method similar to that in compound (I-145), compound (IV-24) (yield 84.5 mg, 81%) was obtained as a white solid from compound (IV-10) (100.0 mg, 0.302 mmol) and methyl iodide (21 μL, 0.332 mmol).

Step 2

By a production method similar to that in compound (I-1), compound (I-161) (yield 25.1 mg, 82%) was obtained as a white solid from compound (IV-24) (27.0 mg, 0.0782 mmol) and 4-fluoro-2-methoxyphenylboronic acid (V-12) (16.0 mg, 0.0939 mmol).

Example 162

Production of 2-{[6-(1,1-difluoro-2-methoxyethyl)pyridin-3-yl]oxy}-3-(5-fluoro-2-methoxyphenyl)pyridine (I-162)

By a production method similar to that in compound (I-1), compound (I-162) (yield 19.5 mg, 64%) was obtained as a colorless oil from compound (IV-24) (27.0 mg, 0.0782 mmol) and 5-fluoro-2-methoxyphenylboronic acid (V-11) (16.0 mg, 0.0939 mmol).

Example 163

Production of 3-(5-chloro-2-methoxyphenyl)-2-{[6-(1,1-difluoro-2-methoxyethyl)pyridin-3-yl]oxy}pyridine (I-163)

By a production method similar to that in compound (I-1), compound (I-163) (yield 31.4 mg, 89%) was obtained as a colorless oil from compound (IV-24) (30.0 mg, 0.0869 mmol) and 5-chloro-2-methoxyphenylboronic acid (V-23) (21.1 mg, 0.113 mmol).

Example 164

Production of 2-(5-{[3-(2,4-difluoro-5-methoxyphenyl)pyridin-2-yl]oxy}pyridin-2-yl)-2,2-difluoroethanol (I-164)

By a production method similar to that in compound (I-1), compound (I-164) (yield 246 mg, 86%) was obtained as a colorless oil from compound (IV-10) (400 mg, 1.21 mmol) and 2,4-difluoro-5-methoxyphenylboronic acid (V-41) (204 mg, 1.07 mmol).

Example 165

Production of 2-{[6-(1,1-difluoro-2-methoxyethyl)pyridin-3-yl]oxy}-3-(2,4-difluoro-5-methoxyphenyl)pyridine (I-165)

By a production method similar to that in compound (I-145), compound (I-165) (yield 36.4 mg, 92%) was obtained as a colorless oil from compound (I-164) (38.0 mg, 0.0964 mmol) and methyl iodide (7.8 µL, 0.13 mmol).

Example 166

Production of 2-{[6-(1,1-difluoro-2-methoxyethyl)pyridin-3-yl]oxy}-3-(2,3-dihydrobenzofuran-7-yl)pyridine (I-166)

By a production method similar to that in compound (I-1), compound (I-166) (yield 19.4 mg, 65%) was obtained as a colorless oil from compound (IV-24) (27.0 mg, 0.0782 mmol) and 2,3-dihydrobenzofuran-7-boronic acid (V-35) (15.4 mg, 0.0939 mmol).

Example 167

Production of 7-(2-{[6-(1,1-difluoro-2-methoxyethyl)pyridin-3-yl]oxy}pyridin-3-yl)pyrazolo[1,5-a]pyridine (I-166)

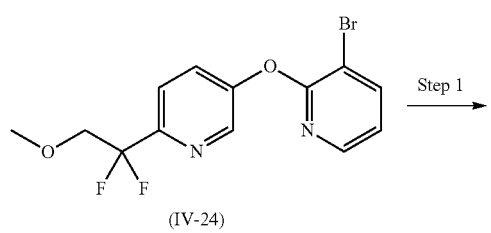

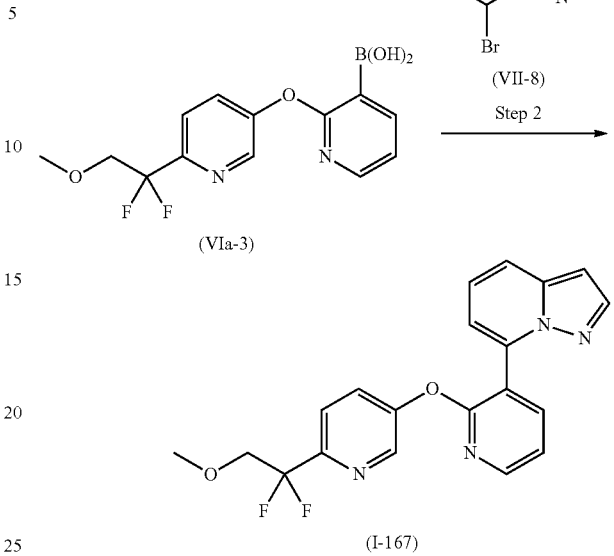

Step 1

Compound (IV-24) (150 mg, 0.435 mmol) was dissolved in THF (2.2 mL), iPrMgBr·LiCl (1.3 mol/L THF solution, 400 µL, 0.522 mmol) was added and the mixture was stirred for 30 min. Thereafter, under ice-cooling, triisopropyl borate (300 µL, 1.30 mmol) was added and the mixture was stirred for 1 hr. then, 1 mol/L hydrochloric acid (5 mL) was added and the mixture was stirred for 10 min. Water was added to the reaction mixture, and the mixture was extracted with ethyl acetate. The organic layer was washed successively with water and saturated brine, dried over anhydrous sodium sulfate, and filtered. The solvent was evaporated under reduced pressure to give compound (VIa-3) (yield 48.3 mg, 36%) as a white solid.

Step 2

By a production method similar to that in compound (I-36), compound (I-167) (yield 31.1 mg, 84%) was obtained as a colorless oil from 7-bromopyrazolo[1,5-a]pyridine (VIII-8) (30.3 mg, 0.145 mmol) and compound (VIa-3) (30.0 mg, 0.0968 mmol).

Example 168

Production of 5-(2-{[6-(1,1-difluoro-2-methoxyethyl)pyridin-3-yl]oxy}pyridin-3-yl)quinoxaline (I-168)

By a production method similar to that in compound (I-36), compound (I-168) (yield 20.3 mg, 67%) was obtained as a colorless oil from 5-bromoquinoxaline (VII-2) (24.3 mg, 0.115 mmol) and compound (VIa-3) (24.0 mg, 0.0774 mmol).

Example 169

Production of 8-(2-{[6-(1,1-difluoro-2-methoxyethyl)pyridin-3-yl]oxy}pyridin-3-yl)quinoline (I-169)

By a production method similar to that in compound (I-1), compound (I-169) (yield 20.3 mg, 59%) was obtained as a colorless oil from compound (IV-24) (30.0 mg, 0.0869 mmol) and 8-quinolineboronic acid (V-34) (19.6 mg, 0.113 mmol).

Example 170

Production of 5-(2-{[6-(1,1-difluoro-2-methoxy-ethyl)pyridin-3-yl]oxy}pyridin-3-yl)-7-fluoroquinoxaline (I-170)

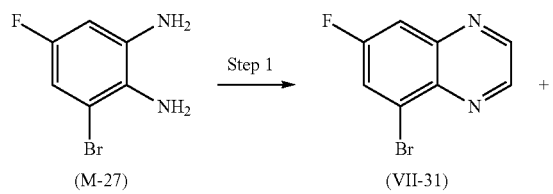

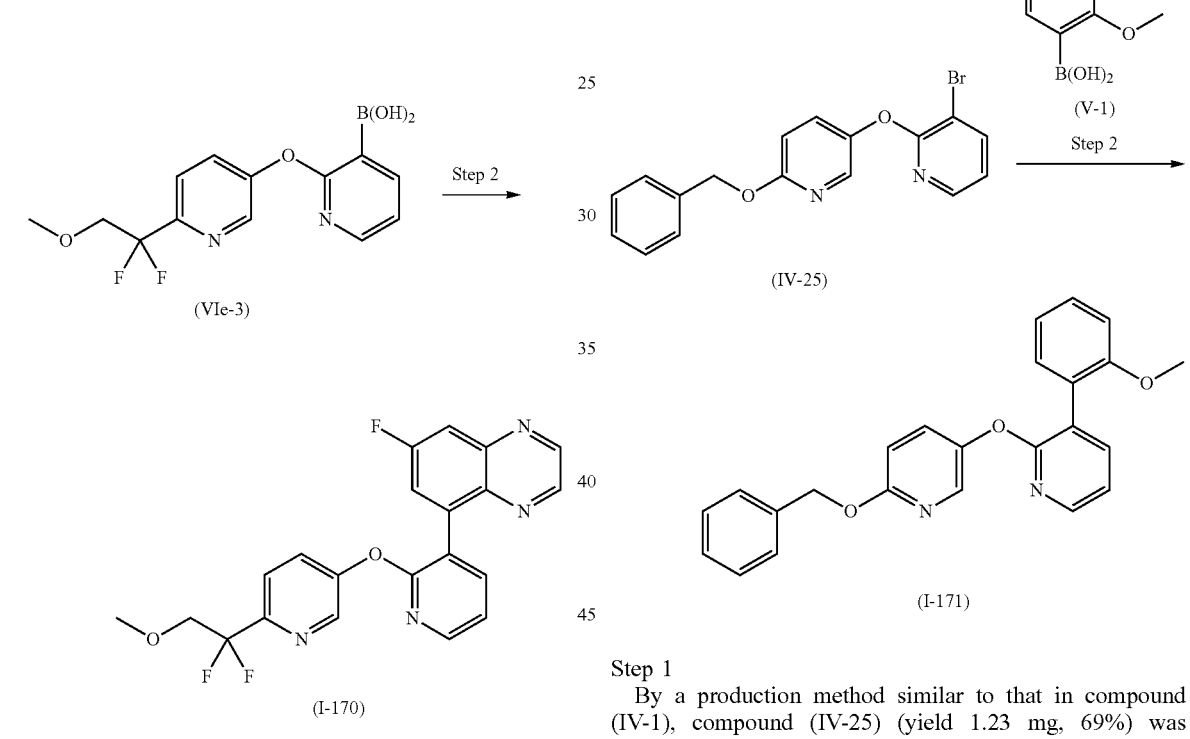

Step 1

By a production method similar to that in compound (VII-27), compound (VII-31) (yield 128 mg, 39%) was obtained as a colorless oil from 3-bromo-5-fluorobenzene-1,2-diamine (M-27) (300 mg, 1.46 mmol) and glyoxal (1.3 mL, 11 mmol).

Step 2

By a production method similar to that in compound (I-36), compound (I-170) (yield 11.4 mg, 29%) was obtained as a colorless oil from compound (VII-31) (32.9 mg, 0.145 mmol) and compound (VIa-3) (30.0 mg, 0.0968 mmol).

Example 171

Production of 2-{[6-(benzyloxy)pyridin-3-yl]oxy}-3-(2-methoxyphenyl)pyridine (I-171)

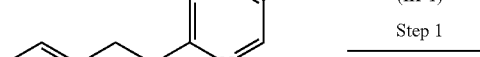

Step 1

By a production method similar to that in compound (IV-1), compound (IV-25) (yield 1.23 mg, 69%) was obtained from compound (III-1) (956 mg, 4.97 mmol) and 6-(benzyloxy)pyridin-3-ol (II-12) (1.00 g, 4.97 mmol).

Step 2

By a production method similar to that in compound (I-1), compound (I-171) (yield 750 mg, 93%) was obtained as a white solid from compound (IV-25) (751 mg, 2.10 mmol) and 2-methoxyphenylboronic acid (V-1) (639 mg, 4.20 mmol).

Example 172

Production of 5-{[3-(2-methoxyphenyl)pyridin-2-yl]oxy}pyridin-2-ol (I-172)

Compound (I-171) (300 mg, 0.780 mmol) was dissolved in ethanol (5.0 mL)/ethyl acetate (5.0 mL)/THF (5.0 mL) mixed solution, 20% palladium hydroxide/carbon (50.0 mg) was added, and the mixture was stirred under a hydrogen atmosphere at room temperature for 3 hr. The reaction mixture was filtered through Celite, and the filtrate was concentrated. The residue was purified by silica gel column chromatography (n-hexane:ethyl acetate) to give compound (I-172) (yield 175 mg, 76%).

Example 173

Production of 3-(2-methoxyphenyl)-2-[(6-phenethoxypyridin-3-yl)oxy]pyridine (I-173)

Compound (I-172) (40.0 mg, 0.136 mmol) was dissolved in DMF (2 mL), potassium carbonate (75.0 mg, 0.780 mmol) was added and the mixture was stirred for 20 hr. Furthermore, (2-bromoethyl)benzene was added, and the mixture was stirred at room temperature for 20 hr. Water was added to discontinue the reaction, and the mixture was extracted with ethyl acetate. The organic layer was washed with saturated brine, dried over anhydrous magnesium sulfate, and the solvent was evaporated under reduced pressure. The residue was purified by silica gel column chromatography (n-hexane:ethyl acetate) to give compound (I-173) (yield 23.9 mg, 44%) as a colorless oil.

Example 174

Production of 3-(2-methoxyphenyl)pyridin-2-{[6-(pyridin-3-ylmethoxy)pyridin-3-yl]oxy}pyridine (I-174)

By a production method similar to that in compound (I-173), compound (I-174) (yield 5.0 mg, 5%) was obtained as a colorless oil from compound (I-172) (74.0 mg, 0.251 mmol) and 3-(bromomethyl)pyridine hydrobromide (127 mg, 0.503 mmol).

Example 175

Production of 3-(2-methoxyphenyl)-2-{[6-(phenoxymethyl)pyridin-3-yl]oxy}pyridine (I-175)

Compound (I-70) (30.0 mg, 0.097 mmol) was dissolved in THF (0.5 mL), TEA (50 μL, 0.36 mmol) and methanesulfonyl chloride (10 μL, 0.10 mmol) were added under ice-cooling, and the mixture was stirred for 30 in (reaction mixture 1). Phenol (30.0 mg, 0.319 mmol) was dissolved in THF (0.5 mL), sodium hydride (16.0 mg, 0.333 mmol) was added, and the mixture was stirred at room temperature for 30 min (reaction mixture 2). To the reaction mixture 2 was added the reaction mixture 1, and the mixture was stirred at room temperature for 18 hr. Water was added to the reaction mixture, and the mixture was extracted chloroform. The organic layer was dried over magnesium sulfate, and the solvent was evaporated under reduced pressure. The residue was purified by silica gel column chromatography (n-hexane:ethyl acetate) to give compound (I-175) (yield 6.0 mg, 16%) as a yellow oil.

Example 176

Production of 2-{[6-(benzyloxy)pyridin-3-yl]oxy}-2'-methoxy-3,3'-bipyridine (I-176)

By a production method similar to that in compound (I-1), compound (I-176) (yield 685 mg, 80%) was obtained as a white solid from compound (IV-25) (795 mg, 2.23 mmol) and compound (V-26) (443 mg, 2.89 mmol).

Example 177

Production of 2-{[6-(benzyloxy)pyridin-3-yl]oxy}-4'-methoxy-3,3'-bipyridine (I-177)

By a production method similar to that in compound (I-1), compound (I-177) (yield 230 mg, 47%) was obtained as a colorless oil from compound (IV-25) (455 mg, 1.27 mmol) and compound (V-28) (253 mg, 1.66 mmol).

Example 178

Production of 5-{[3-(2-methoxyphenyl)pyridin-2-yl]oxy}-2-trifluoromethyl)pyrimidine (I-178)

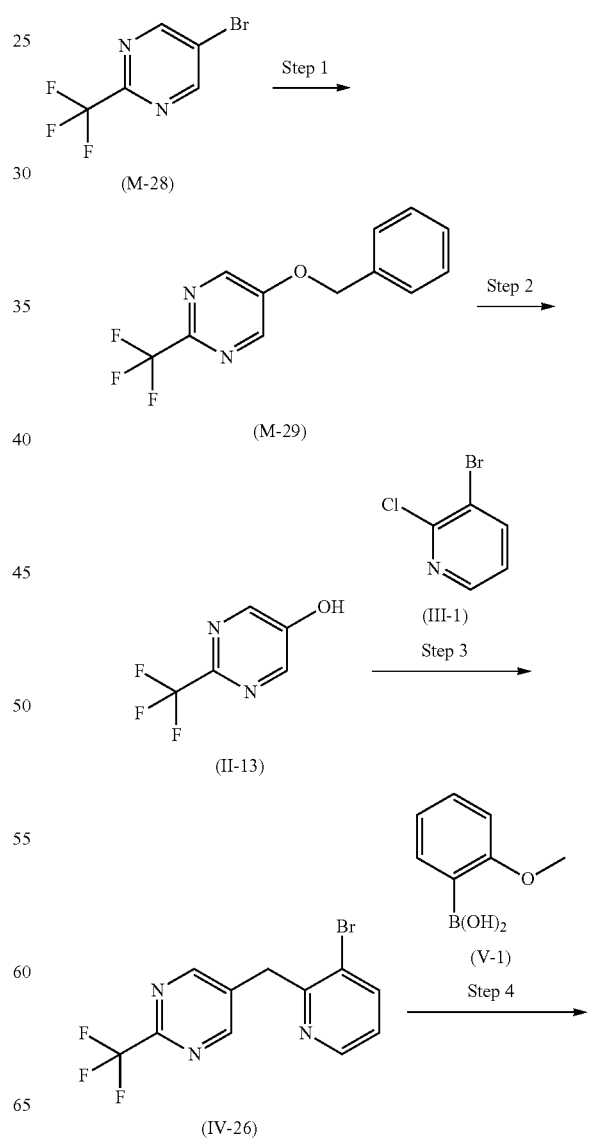

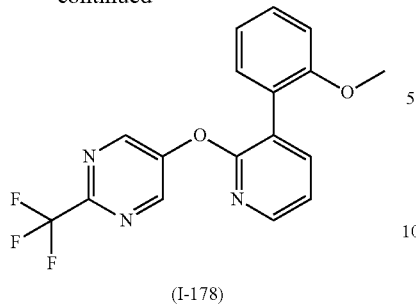

(I-178)

Step 1

To a solution of 5-bromo-2-trifluoromethylpyrimidine (M-28) (1.00 mg, 4.41 mmol) in benzyl alcohol (4.58 mL, 44.1 mmol) were added cesium carbonate (2.87 g, 8.81 mmol), 1,10-phenanthroline (159 mg, 0.81 mmol) and copper(I) iodide (84.0 mg, 0.441 mmol) was added and the mixture was stirred at 120° C. for 20 hr. The reaction mixture was cooled, diluted with ethyl acetate and filtered through Celite. The solvent was evaporated under reduced pressure, and the residue was purified by silica gel column chromatography (NH silica gel, n-hexane:ethyl acetate=95:5→80:20) to give compound (M-29) (yield 863 g, 77%) as a pale-yellow solid.

Step 2

To a solution of compound (M-29) (859 mg, 3.38 mmol) in ethanol (10.0 mL) was added 10% palladium/carbon (172 mg), and the mixture was stirred under a hydrogen atmosphere at room temperature for 3 hr. The mixture was diluted with ethanol, and filtered through Celite. The solvent was evaporated under reduced pressure to give compound (II-13) (yield 510 mg, 92%) as a pale-gray solid.

Step 3

To a solution of compound (II-13) (400 mg, 2.44 mmol) and compound (III-1) (469 mg, 2.44 mmol) in DMSO (5.0 mL) was added cesium carbonate (1.19 g, 3.66 mmol) and the mixture was stirred at 120° C. for 20 hr. The reaction mixture was cooled, water was added, and the mixture was extracted with ethyl acetate. The organic layer was washed successively with water and saturated brine, dried over anhydrous sodium sulfate, and filtered. The solvent was evaporated under reduced pressure, and the residue was purified by silica gel column chromatography (n-hexane:ethyl acetate=95:5→85:15) to give compound (IV-26) (yield 163 mg, 21%) as a yellow oil.

Step 4

By a production method similar to that in compound (I-1), compound (I-178) (yield 23.0 mg, 71%) was obtained as a colorless oil from compound (IV-26) (30.0 mg, 0.0937 mmol) and 2-methoxyphenylboronic acid (V-1) (18.5 mg, 0.122 mmol).

Example 179

Production of 5-{[3-(4-fluoro-2-methoxyphenyl)pyridin-2-yl]oxy}-2-(trifluoromethyl)pyrimidine (I-179)

By a production method similar to that in compound (I-1), compound (I-179) (yield 28.5 mg, 83%) was obtained as a colorless oil from compound (IV-26) (30.0 mg, 0.0937 mmol) and 4-fluoro-2-methoxyphenylboronic acid (V-12) (20.7 mg, 0.122 mmol).

Example 180

Production of 5-chloro-2-methoxy-2'-{[2-(trifluoromethyl)pyrimidin-5-yl]oxy}-3,3'-bipyridine (I-180)

By a production method similar to that in compound (I-1), compound (I-180) (yield 21.6 mg, 60%) was obtained as a colorless oil from compound (IV-26) (30.0 mg, 0.0937 mmol) and 5-chloro-2-methoxypyridine-3-boronic acid (V-31) (19.3 mg, 0.103 mmol).

Example 181

Production of 5-{[3-(2-methoxyphenyl)pyridin-2-yl]oxy}-2-(pentafluoroethyl)pyrimidine (I-181)

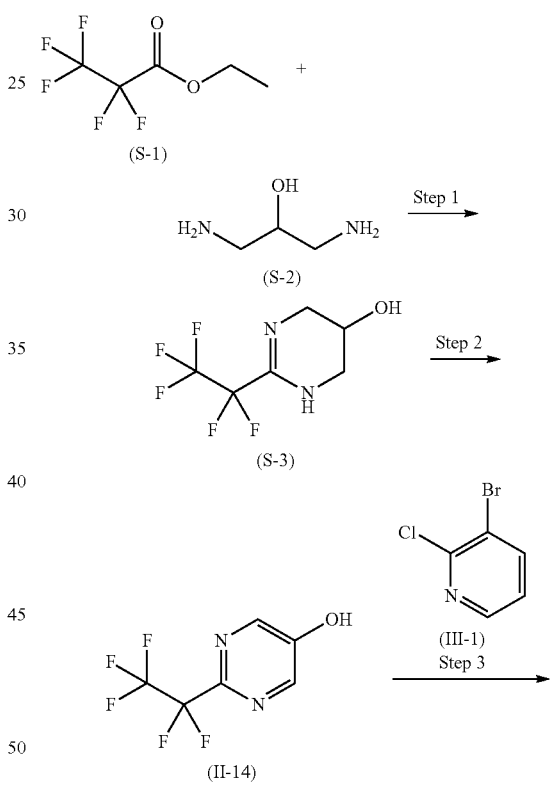

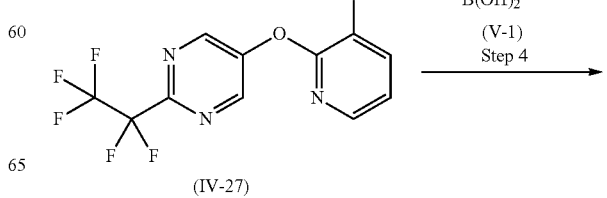

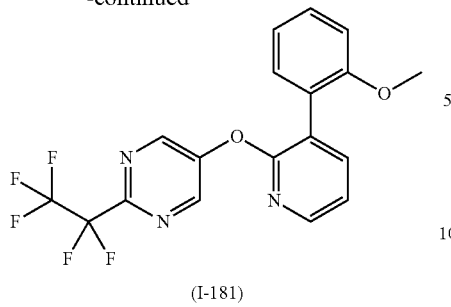

(I-181)

Step 1

To a solution of ethyl 2,2,3,3,3-pentafluoropropanoate (S-1) (7.69 g, 40.0 mmol) in p-xylene (30 mL) was added 1,3-diaminopropan-2-ol (S-2) (3.61 g, 40.0 mmol) and the mixture was stirred at 160° C. for 4 hr. The solvent was evaporated under reduced pressure to give compound (S-3) (yield 10.1 g) as a yellow oil.

Step 2

A solution of compound (S-3) (8.72 g, 29.8 mmol) in nitrobenzene (40 mL) was heated to 90° C., a methanol solution of 28% sodium methoxide (31.8 mL, 160 mmol) was gradually added, and the mixture was stirred while evaporating methanol for 3 hr. Thereafter, the mixture was further stirred at 120° C. for 1 hr. The reaction mixture was allowed to cool, water was added, and the mixture was extracted with ethyl acetate. The aqueous layer was washed with ethyl acetate, and adjusted to pH 4 with 6 mol/L hydrochloric acid. The mixture was extracted with ethyl acetate, and the organic layer was washed with saturated brine, dried over anhydrous sodium sulfate, and filtered. The solvent was evaporated under reduced pressure, and the residue was purified by silica gel column chromatography (n-hexane:ethyl acetate=90:10→30:70) to give compound (II-14) [yield 1.19 g, 14% (2 steps)] as a yellow oil.

Step 3

To a solution of compound (II-14) (1.00 g, 4.67 mmol) and compound (III-1) (899 mg, 4.67 mmol) in DMSO (10 mL) was added cesium carbonate (2.28 g, 7.01 mmol) and the mixture was stirred at 120° C. for 21 hr. Thereafter, the mixture was stirred at 140° C. for 9 hr. The reaction mixture was cooled, water was added, and the mixture was extracted with ethyl acetate. The organic layer was washed successively with water and saturated brine, dried over anhydrous sodium sulfate, and filtered. The solvent was evaporated under reduced pressure, and the residue was purified by silica gel column chromatography (n-hexane:ethyl acetate=95:5→85:15) to give compound (IV-27) (yield 163 g, 21%) as a yellow oil.

Step 4

By a production method similar to that in compound (I-1), compound (I-181) (yield 29.4 mg, 91%) was obtained as a colorless oil from compound (IV-27) (30.0 mg, 0.0811 mmol) and 2-methoxyphenylboronic acid (V-1) (16.0 mg, 0.105 mmol).

Example 182

Production of 5-{[3-(2-methoxyphenyl)pyridin-2-yl]oxy}-N-methyl-N-propylpyrimidin-2-amine (I-182)

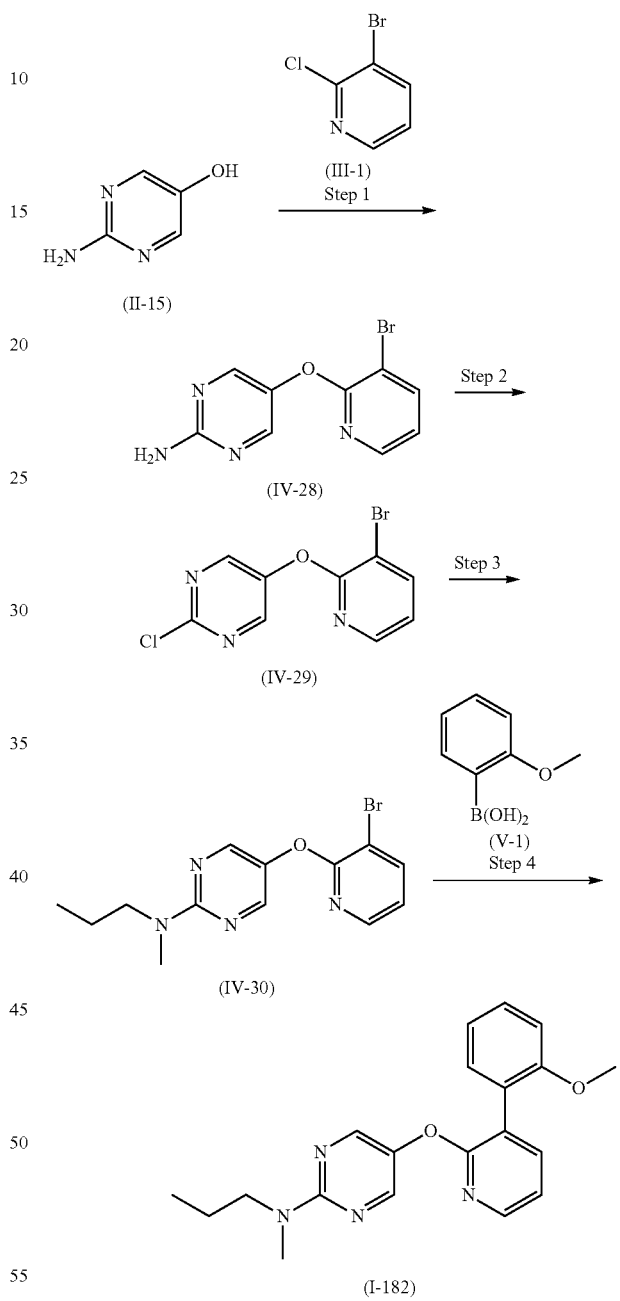

Step 1

By a production method similar to that in compound (IV-1), compound (IV-28) (yield 1.23 g, 46%) was obtained from compound (III-1) (2.32 g, 12.1 mmol) and 2-aminopyrimidin-5-ol (II-15) (1.12 g, 10.1 mmol).

Step 2

Compound (IV-28) (1.50 g, 5.62 mmol) was dissolved in DCM (5.0 mL), concentrated hydrochloric acid (5.0 mL, 58 mmol), and zinc(II) chloride (1.30 g, 9.55 mmol) were added, and the mixture was stirred under ice-cooling for 30 min. Sodium nitrite (659 mg, 9.55 mmol) was further added and the mixture was stirred for 3 hr. Ice water was added to discontinue the reaction, and the mixture was extracted with chloroform. The organic layer was washed with saturated brine, dried over anhydrous magnesium sulfate, and the solvent was evaporated under reduced pressure. The residue was purified by silica gel column chromatography (n-hexane:ethyl acetate) to give compound (IV-29) (yield 622 mg, 39%).

Step 3

Compound (IV-29) (100 mg, 0.349 mmol) was dissolved in NMP (1 mL), N-methylpropan-1-amine (128 mg, 1.75 mmol) and potassium carbonate (241 mg, 1.75 mmol) were added, and the mixture was stirred at 80° C. for 18 hr. Water was added to discontinue the reaction, and the mixture was extracted with ethyl acetate. The organic layer was washed with saturated brine, dried over anhydrous magnesium sulfate, and the solvent was evaporated under reduced pressure. The residue was purified by silica gel column chromatography (n-hexane:ethyl acetate) to give compound (IV-30) (yield 105 mg, 93%).

Step 4

By a production method similar to that in compound (I-1), compound (I-182) (yield 28.5 mg, quantitative) was obtained as a colorless oil from compound (IV-30) (26.0 mg, 0.0800 mmol) and compound (V-1) (18.3 mg, 0.121 mmol).

Example 183

Production of 5-{[2'-methoxy-(3,3'-bipyridin-2-yl]oxy}-N-methyl-N-propylpyrimidin-2-amine (I-183)

By a production method similar to that in compound (I-1), compound (I-183) (yield 25.8 mg, 91%) was obtained as a colorless oil from compound (IV-30) (26.0 mg, 0.0800 mmol) and compound (V-26) (18.5 mg, 0.121 mmol).

Example 184

Production of N-ethyl-5-{[3-(4-fluoro-2-methoxyphenyl)pyridin-2-yl]oxy}-N-methylpyrimidin-2-amine (I-184)

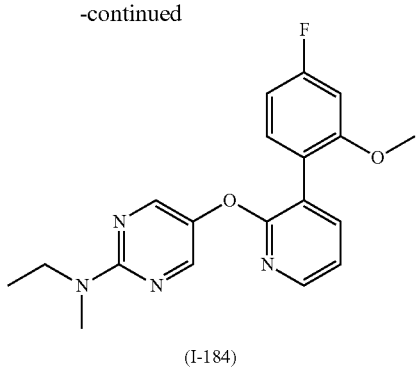

(I-184)

Step 1

By a production method similar to that in compound (IV-30), compound (IV-31) (yield 69.0 mg, 80%) was obtained from compound (IV-29) (80.0 mg, 0.279 mmol) and N-ethylmethylamine (83.0 mg, 1.40 mmol).

Step 2

By a production method similar to that in compound (I-1), compound (I-184) (yield 20.7 mg, 95%) was obtained as a colorless oil from compound (IV-31) (19.0 mg, 0.0615 mmol) and compound (V-12) (15.7 mg, 0.0922 mmol).

Example 185

Production of 5-{[3-(4-fluoro-2-methoxyphenyl)pyridin-2-yl]oxy}-N,N-dimethylpyrimidin-2-amine (I-185)

By a production method similar to that in compound (I-30), compound (I-185) (yield 17.6 mg, 88%) was obtained as a white solid from compound (I-191) (25.0 mg, 0.0591 mmol) and dimethylamine (53.3 mg, 0.591 mmol).

Example 186

Production of 2-(propylthio)-5-{[3-(4-fluoro-2-methoxyphenyl)pyridin-2-yl]oxy}-pyrimidine (IV-186)

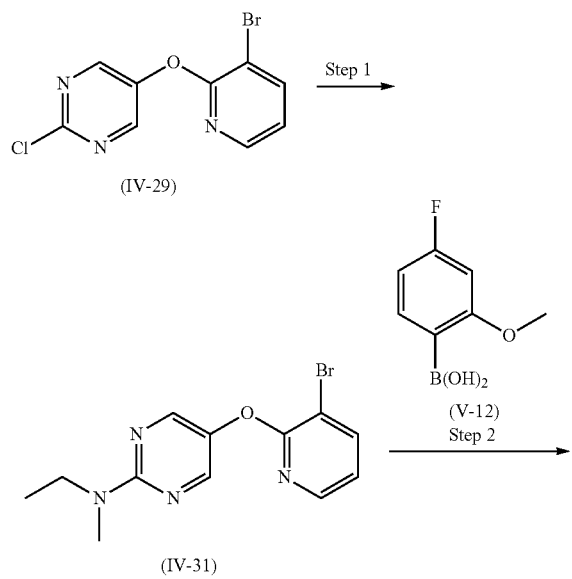

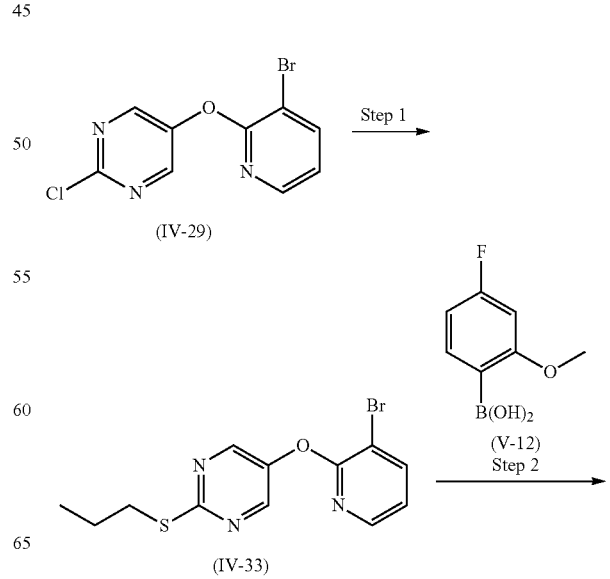

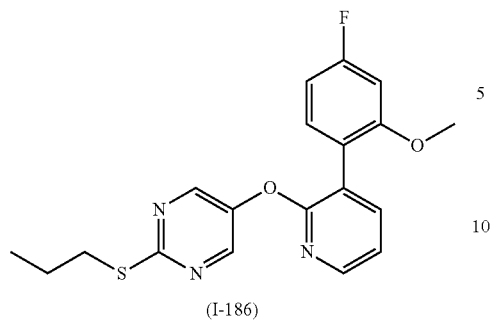

(I-186)

Step 1 propane-1-thiol (137 mg, 1.80 mmol) was dissolved in THF (1 mL), sodium hydride (72.0 mg, 1.80 mmol) was added, and the mixture was stirred at room temperature for 20 min. Furthermore, compound (IV-29) (172 mg, 0.600 mmol) was added and the mixture was stirred at 80° C. for 3 hr. Water was added to discontinue the reaction, and the mixture was extracted with ethyl acetate. The organic layer was washed with saturated brine, dried over anhydrous magnesium sulfate, and the solvent was evaporated under reduced pressure. The residue was purified by silica gel column chromatography (n-hexane:ethyl acetate) to give compound (IV-33) (yield 58.0 mg, 30%).

Step 2

By a production method similar to that in compound (I-1), compound (I-186) (yield 17.8 mg, 63%) was obtained from compound (IV-33) (25.0 mg, 0.0766 mmol) and compound (V-12) (19.5 mg, 0.115 mmol).

Example 187

Production of 2-ethoxy-5-{[3-(4-fluoro-2-methoxy-phenyl)pyridin-2-yl]oxy}pyrimidine (IV-187)

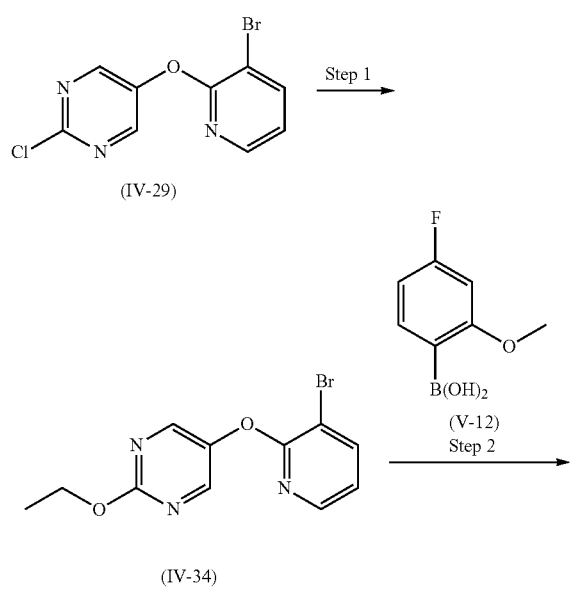

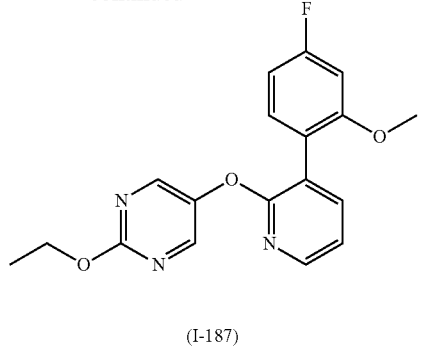

(I-187)

Step 1

Compound (IV-29) (100 mg, 0.349 mmol) was dissolved in THF (1.0 mL), 50% sodium hydride (16.8 mg, 0.419 mmol) was added and the mixture was stirred for 10 min. Furthermore, ethanol (24.4 µL, 0.419 mmol) was added, and the mixture was stirred at 80° C. for 4 hr. Water was added to discontinue the reaction, and the mixture was extracted with ethyl acetate. The organic layer was washed with saturated brine, dried over anhydrous magnesium sulfate, and the solvent was evaporated under reduced pressure. The residue was purified by silica gel column chromatography (n-hexane:ethyl acetate) to give compound (IV-34) (yield 48.0 mg, 46%).

Step 2

By a production method similar to that in compound (I-1), compound (I-187) (yield 18.7 mg, 95%) was obtained as a colorless oil from compound (IV-34) (17.0 mg, 0.0570 mmol) and compound (V-12) (14.6 mg, 0.0861 mmol).

Example 188

Production of 5-{[3-(4-fluoro-2-methoxyphenyl)pyridin-2-yl]oxy}-N-(2-methoxyethyl)-N-methylpyrimidin-2-amine (I-188)

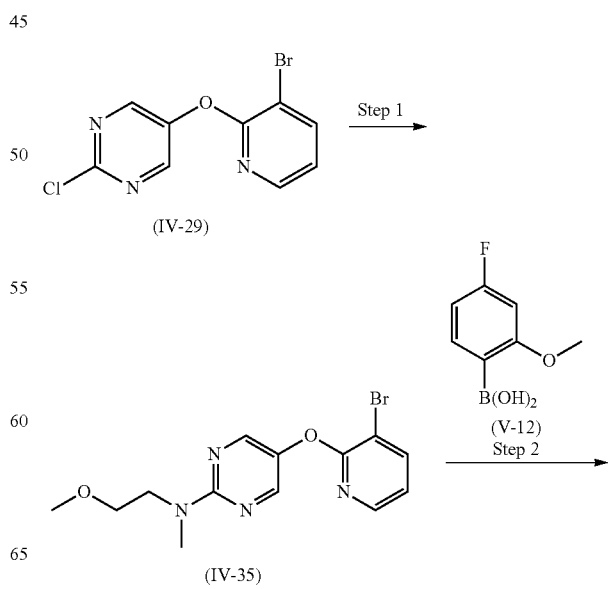

155
-continued

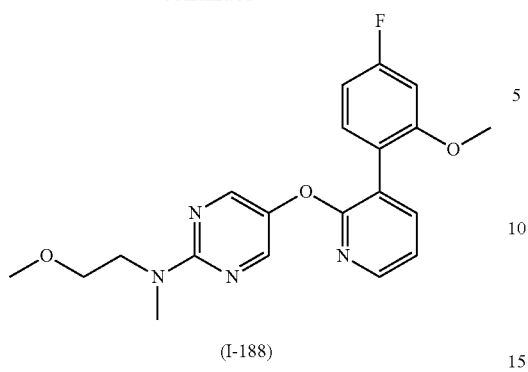

(I-188)

Step 1

By a production method similar to that in compound (IV-30), compound (IV-35) (yield 122 mg, quantitative) was obtained from compound (IV-29) (100 mg, 0.349 mmol) and 2-methoxy-N-methylethanamine (200 µL, 1.85 mmol).

Step 2

By a production method similar to that in compound (I-1), compound (I-188) (yield 25.2 mg, quantitative) was obtained as a colorless oil from compound (IV-35) (20.0 mg, 0.0590 mmol) and compound (V-12) (15.0 mg, 0.0884 mmol).

Example 189

Production of 2-[5-{[3-(4-fluoro-2-methoxyphenyl)pyridin-2-yl]oxy}-pyrimidin-2-yl)(methyl)amino]acetonitrile (IV-189)

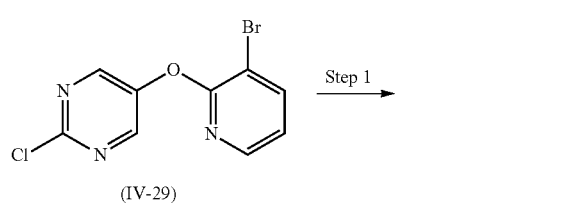

156
-continued

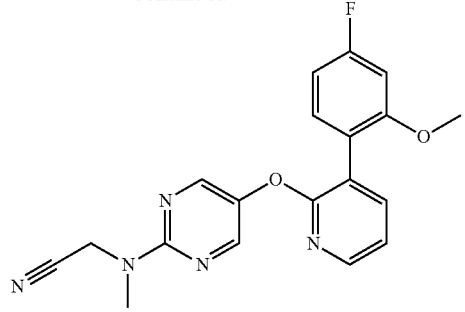

(I-189)

Step 1

Compound (IV-29) (100 mg, 0.349 mmol) was dissolved in DMA (1.0 mL), N,N-diisopropylethylamine (0.2 mL, 1.15 mmol) was added, 2-(methylamino)acetonitrile (200 mg, 2.96 mmol) was added, and the mixture was stirred at 100° C. Water was added to discontinue the reaction, and the mixture was extracted with chloroform. The organic layer was washed with saturated brine, dried over anhydrous magnesium sulfate, and the solvent was evaporated under reduced pressure. The residue was purified by silica gel column chromatography (n-hexane:ethyl acetate) to give compound (IV-36) (yield 73.0 mg, 65%).

Step 2

By a production method similar to that in compound (I-1), compound (I-189) (yield 18.1 mg, 79%) was obtained as a colorless oil from compound (IV-36) (20.0 mg, 0.0625 mmol) and compound (V-12) (16.5 mg, 0.0938 mmol).

Reference Example 190

Production of 5-{[3-(4-fluoro-2-methoxyphenyl)pyridin-2-yl]oxy}-pyrimidin-2-amine (IV-190)

By a production method similar to that in compound (I-1), compound (I-190) (yield 2.40 mg, 82%) was obtained from compound (IV-28) (2.50 g, 9.36 mmol) and compound (V-12) (2.36 g, 14.0 mmol).

Example 191

Production of 5-{[3-(4-fluoro-2-methoxyphenyl)pyridin-2-yl]oxy}-2-iodopyrimidine (I-191)

Compound (I-190) (3.50 g, 11.2 mmol) was dissolved in THF (9.6 mL), isoamyl nitrite (0.39 mL, 2.90 mmol), diiodomethane (0.78 mL, 9.65 mmol) and copper iodide (92.0 mg, 0.483 mmol) were successively added, and the mixture was stirred at 60° C. for 1 hr. The reaction mixture was allowed to cool, filtered through Celite, and the solvent was evaporated under reduced pressure. The residue was purified by amino silica gel column chromatography (n-hexane:ethyl acetate=95:5→60:40) to give compound (I-191) (yield 3.00 mg, 63%) as a pale-yellow oil.

Example 192

Production of methyl 2-[(5-{[3-(4-fluoro-2-methoxyphenyl)pyridin-2-yl]oxy}-pyrimidin-2-yl)(methyl)amino]acetate (I-192)

By a production method similar to that in compound (IV-30), compound (I-192) (yield 22.0 mg, 47%) was obtained as a colorless oil from compound (I-191) (50 mg, 0.118 mmol) and sarcosine methyl ester (82.0 mg, 0.590 mmol).

Example 193

Production of 5-{[3-(4-fluoro-2-methoxyphenyl)pyridin-2-yl]oxy}-N-methyl-N-(oxazol-4-ylmethyl)pyrimidin-2-amine (I-193)

By a production method similar to that in compound (IV-30), compound (I-193) (yield 24.6 mg, 85%) was obtained as a colorless oil from compound (I-191) (30.0 mg, 0.071 mmol) and N-methyl-1-(oxazol-4-yl)methanamine (30.0 mg, 0.268 mmol).

Example 194

Production of 5-{[3-(4-fluoro-2-methoxyphenyl)pyridin-2-yl]oxy}-N-methyl-N-(thiazol-2-ylmethyl)pyrimidin-2-amine (I-194)

Compound (I-191) (30.0 mg, 0.071 mmol) was dissolved in 1,4-dioxane (0.6 mL)/DMA (0.6 mL) mixed solution, N-methyl-1-(thiazol-2-yl)methanamine (20.0 mg, 0.156 mmol) and DIPEA (50 µL, 0.29 mmol) were added and the mixture was stirred at 120° C. for 2 hr. The reaction mixture was allowed to cool, water was added and the mixture was extracted with ethyl acetate. The organic layer was dried over anhydrous magnesium sulfate, and the solvent was evaporated under reduced pressure. The residue was purified by silica gel column chromatography (n-hexane:ethyl acetate) to give compound (I-194) (yield 3.3 mg, 11%) as a colorless oil.

Example 195

Production of ethyl 3-(5-{[3-(4-fluoro-2-methoxyphenyl)pyridin-2-yl]oxy}-pyrimidin-2-yl)propionate (I-195)

Compound (I-191) (300 mg, 0.709 mmol) was dissolved in THF solution (0.5 mol/L, 12 mL, 6.0 mmol) of 3-ethoxy-3-oxopropylzinc bromide, tetrakis(triphenylphosphine)palladium (82.0 mg, 0.071 mmol) was added and the mixture was stirred at room temperature for 18 hr. The solvent was evaporated under reduced pressure, and the residue was neutralized with hydrochloric acid, and the mixture was extracted with ethyl acetate. The organic layer was dried over anhydrous magnesium sulfate, and the solvent was evaporated under reduced pressure. The residue was purified by silica gel column chromatography (n-hexane:ethyl acetate) to give compound (I-195) (yield 200 mg, 71%) as a yellow oil.

Example 196

Production of ethyl 2-[(5-{[3-(4-fluoro-2-methoxyphenyl)pyridin-2-yl]oxy}-pyrimidin-2-yl)oxy]acetate (I-196)

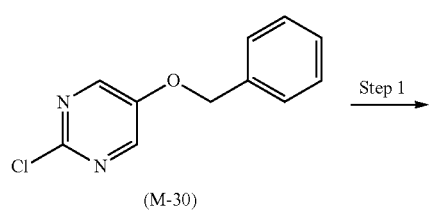

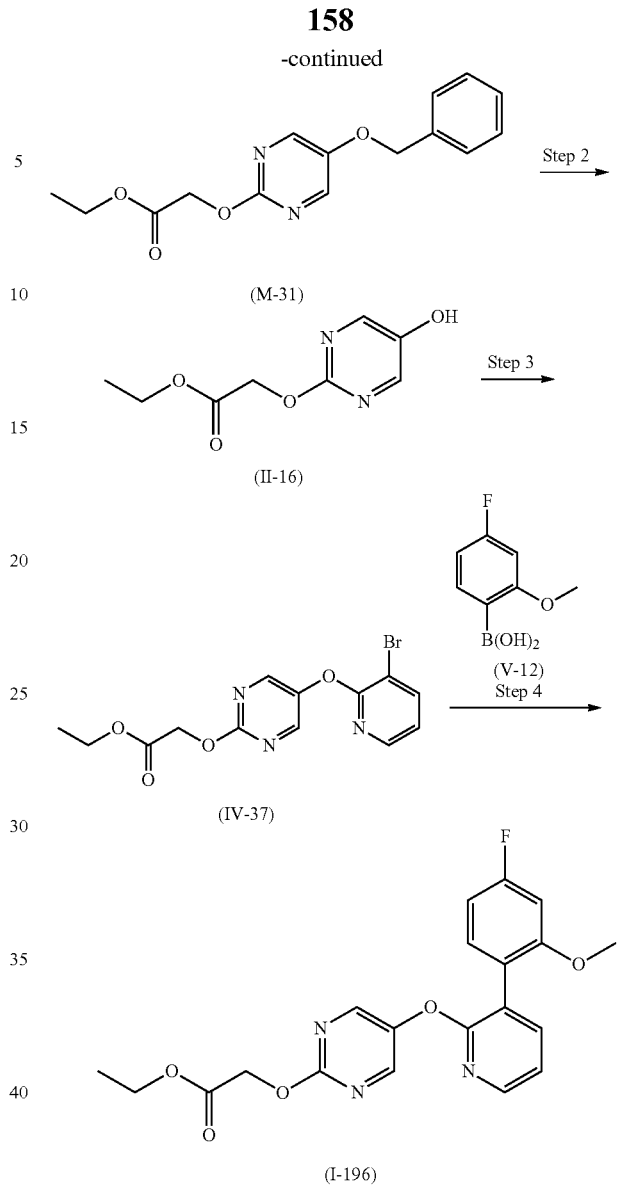

Step 1

Sodium hydride (400 mg, 8.33 mmol) was suspended in toluene (10 mL), ethyl 2-hydroxyacetate (0.70 mL, 7.40 mmol) was added and the mixture was stirred at room temperature for 30 min. To the reaction mixture was added (M-30) (1.00 g, 4.53 mmol), and the mixture was stirred at 60° C. for 18 hr. The reaction mixture was allowed to cool, saturated ammonium chloride solution was added and the mixture was extracted with ethyl acetate. The organic layer was dried over anhydrous magnesium sulfate, and the solvent was evaporated under reduced pressure. The residue was purified by silica gel column chromatography (n-hexane:ethyl acetate) to give compound (M-31) (yield 650 mg, 50%) as a colorless oil.

Step 2

Compound (M-31) (650 mg, 2.26 mmol) was dissolved in ethanol (10 mL), 10% Pd/C (300 mg) was added and the mixture was stirred under a hydrogen atmosphere (3 atm) for 16 hr. After filtration of the reaction mixture through Celite, the solvent was evaporated under reduced pressure to give compound (II-16) (440 mg, yield 98%) as a colorless oil.

Step 3

By a production method similar to that in compound (IV-1), compound (IV-37) (yield 180 mg, 23%) was obtained as a colorless oil from compound (III-1) (450 mg, 2.34 mmol) and compound (II-16) (440 mg, 2.22 mmol).

Step 4

By a production method similar to that in compound (I-1), compound (I-196) (yield 23.6 mg, 70%) was obtained as a colorless oil from compound (IV-37) (30.0 mg, 0.0847 mmol) and compound (V-12) (20.0 mg, 0.118 mmol).

Reference Example 197

Production of 5-{[3-(4-fluoro-2-methoxyphenyl)pyridin-2-yl]oxy}2-[(1-methyl-1H-pyrazol-4-yl)ethynyl]pyrimidine (IV-197)

Compound (I-191) (100 mg, 0.236 mmol) was dissolved in THF (5.0 mL), 1-methyl-4-ethynylpyrazole (75.2 mg, 0.709 mmol), PdCl$_2$(PPh$_3$)$_2$ (16.6 mg, 0.0236 mmol), copper iodide (9.0 mg, 0.047 mmol) and TEA (66 μL, 0.47 mmol) were added, and the mixture was stirred at room temperature overnight. Water was added to the reaction mixture, and the mixture was extracted with ethyl acetate. The organic layer was washed successively with water and saturated brine, dried over anhydrous sodium sulfate, and filtered. The solvent was evaporated under reduced pressure, and the residue was purified by silica gel column chromatography (n-hexane:ethyl acetate) to give compound (I-197) (yield 26.1 mg, 28%) as a yellow solid.

Example 198

Production of 5-{[3-(4-fluoro-2-methoxyphenyl)pyridin-2-yl]oxy}-2-[2-(1-methyl-1H-pyrazol-4-yl)ethyl]pyrimidine (IV-198)

Compound (I-197) (15.0 mg, 0.0374 mmol) was dissolved in ethanol (2.0 mL), 10% Pd/C (5.0 mg) was added and the mixture was stirred under a hydrogen atmosphere (3 atm) for 16 hr. The reaction mixture was filtered through Celite, the solvent was evaporated under reduced pressure, and the residue was purified by silica gel column chromatography (n-hexane:ethyl acetate) to give compound (I-198) (yield 6.5 mg, 43%) as a colorless oil.

Example 199

Production of 2-(4-chlorophenoxy)-3-(2-methoxyphenyl)pyridine (I-199)

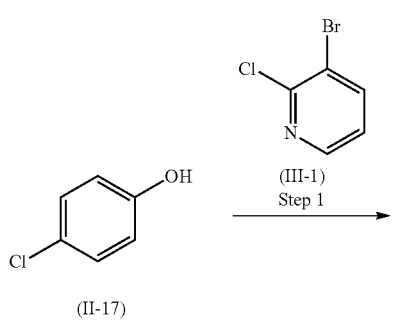

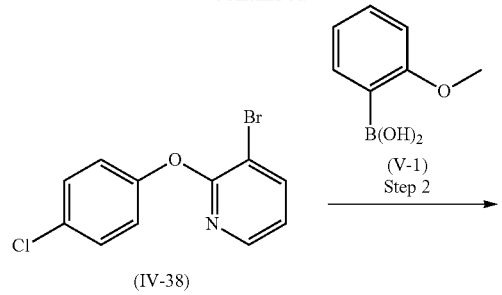

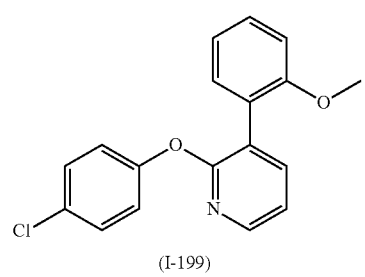

Step 1

Compound (III-1) (647 mg, 3.36 mmol) and 4-chlorophenol (II-17) (431 mg, 3.36 mmol) were dissolved in DMF (10 mL), potassium carbonate (557 mg, 4.03 mmol) were added and the mixture was stirred at 90° C. for 29 hr. The reaction mixture was cooled, water was added, and the mixture was extracted with ethyl acetate. The organic layer was washed successively with water and saturated brine, dried over anhydrous sodium sulfate, and filtered. The solvent was evaporated under reduced pressure, and the residue was purified by silica gel column chromatography (NH silica gel, n-hexane:ethyl acetate=100:0→85:15) to give compound (IV-38) (yield 107 mg, 11%) as a pale-yellow solid.

$^1$H-NMR (400 MHz, CDCl$_3$) δ: 6.91 (1H, dd, J=5.0, 7.8 Hz), 7.08-7.14 (2H, m), 7.34-7.41 (2H, m), 7.94 (1H, dd, J=1.8, 7.8 Hz), 8.06 (1H, dd, J=1.8, 5.0 Hz).

ESI-MS m/z: 284, 286, 288 [M+H]$^+$.

Step 2

By a production method similar to that in compound (I-1), compound (I-199) (yield 47.3 mg, 86%) was obtained as a white solid from compound (IV-38) (50.0 mg, 0.176 mmol) and 2-methoxyphenylboronic acid (V-1) (34.7 mg, 0.228 mmol).

Example 200

Production of 2-(4-chlorophenoxy)-3-(3-methoxyphenyl)pyridine (I-200)

By a production method similar to that in compound (I-1), compound (I-200) (yield 49.5 mg, 90%) was obtained as a colorless oil from compound (IV-38) (50.0 mg, 0.176 mmol) and 3-methoxyphenylboronic acid (V-2) (34.7 mg, 0.228 mmol).

Example 201

Production of 3-(2-methoxyphenyl)-2-[4-(trifluoromethyl)phenoxy]pyridine (I-201)

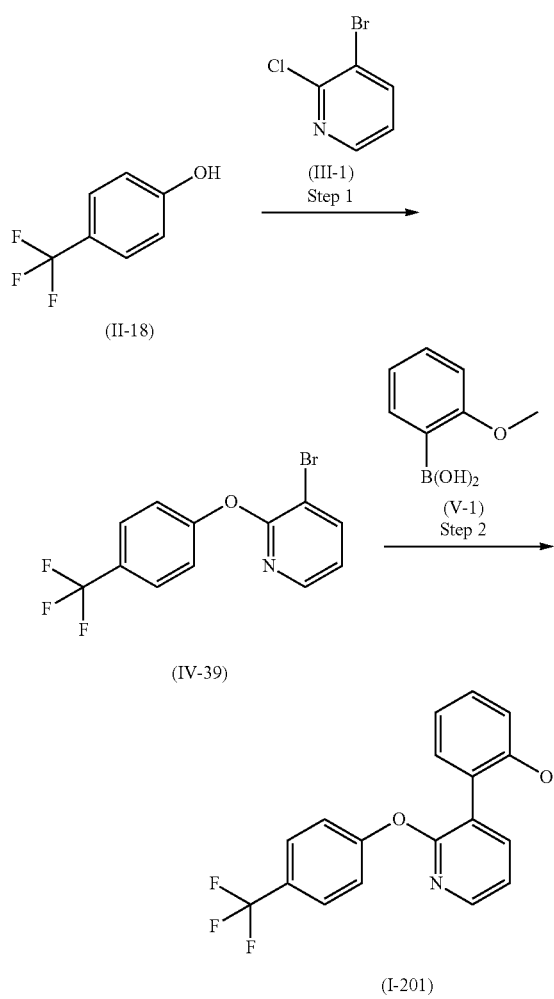

Step 1

By a production method similar to that in compound (IV-1), compound (IV-39) (yield 6.8 mg, 35%) was obtained as a white solid from 4-trifluoromethylphenol (II-18) (10.0 mg, 61.7 mmol) and compound (III-1) (14.3 mg, 74.0 mmol).

Step 2

By a production method similar to that in compound (I-1), compound (I-201) (yield 19.9 mg, 61%) was obtained as a colorless oil from compound (IV-39) (30.0 mg, 0.0943 mmol) and 2-methoxyphenylboronic acid (V-1) (17.2 mg, 0.113 mmol).

Example 202

Production of 2-methoxy-2'-[4-(trifluoromethyl)phenoxy]-3,3'-bipyridine (I-202)

By a production method similar to that in compound (I-1), compound (I-202) (yield 21.1 mg, 65%) was obtained as a colorless oil from compound (IV-39) (30.0 mg, 0.0943 mmol) and 2-methoxypyridine-3-boronic acid (V-26) (17.3 mg, 0.113 mmol).

Example 203

Production of 2,4-dimethoxy-2'-[4-(trifluoromethyl)phenoxy]-3,3'-bipyridine (IV-203)

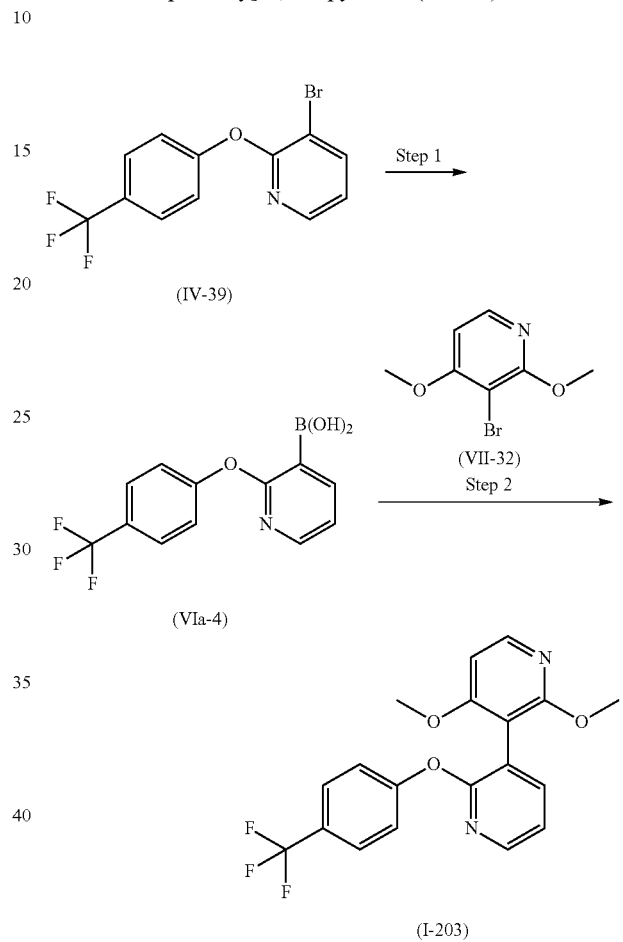

Step 1

To a solution of compound (IV-39) (1.50 g, 4.72 mmol) in THF (9.4 mL) was added 1.3 mol/L iPrMgBr.LiCl THF solution (7.3 mL, 9.4 mmol) and the mixture was stirred for 30 min. Thereafter, under ice-cooling, triisopropyl borate (3.4 mL, 14 mmol) was added and the mixture was stirred for 1 hr. Then, 1 mol/L hydrochloric acid (20 mL) was added and the mixture was stirred for 30 min. Water was added to the reaction mixture, and the mixture was extracted with ethyl acetate. The organic layer was washed with successively with water and saturated brine, dried over anhydrous sodium sulfate, and filtered. The solvent was evaporated under reduced pressure to give (VIa-4) (yield 1.20 g, 90%) as a pale-yellow solid.

Step 2

By a production method similar to that in compound (I-36), compound (I-203) (yield 34.3 mg, 86%) was obtained as a colorless oil from compound (VIa-4) (30.0 mg, 0.105 mmol) and 3-bromo-2,4-dimethoxypyridine (VII-32) (27.7 mg, 0.127 mmol).

Example 204

Production of 3'-methoxy-2-[4-(trifluoromethyl)phenoxy]-3,4'-bipyridine (IV-204)

By a production method similar to that in compound (I-1), compound (I-204) (yield 31.3 mg, 48%) was obtained as a colorless oil from compound (IV-39) (50.5 mg, 0.159 mmol) and 3-methoxypyridine-4-boronic acid (V-27) (29.1 mg, 0.190 mmol).

Example 205

Production of 3'-methoxy-2-[4-(trifluoromethyl)phenoxy]-3,4'-bipyridine (IV-205)

To 4-bromo-3-methylpyridine hydrobromide (24.6 mg, 0.118 mmol) was added 1.0 mol/L aqueous sodium hydroxide solution, and the mixture was extracted with chloroform. The organic layer was dried over anhydrous sodium sulfate, and filtered. The solvent was evaporated under reduced pressure to give 4-bromo-3-methylpyridine (VII-33) as a colorless oil.

The residue was dissolved in n-butanol (0.6 mL), (A-$^{ta}$Phos)$_2$PdCl$_2$ (4.2 mg, 0.0059 mmol), cesium carbonate (76.8 mg, 0.236 mmol) and compound (VIa-4) (50.0 mg, 0.079 mmol) were added, and the mixture was stirred under microwave irradiation at 120° C. for 30 min. Water was added to the reaction mixture, and the mixture was extracted with chloroform. The organic layer was dried over anhydrous sodium sulfate, and filtered. The solvent was evaporated under reduced pressure, and the residue was purified by silica gel column chromatography (n-hexane:ethyl acetate) to give compound (I-205) (yield 30.2 mg, 78%) as a colorless oil.

Example 206

Production of 4'-methyl-2-[4-(trifluoromethyl)phenoxy]-3,3'-bipyridine (IV-206)

By a production method similar to that in compound (I-1), compound (I-206) (yield 24.0 mg, 77%) was obtained as a white solid from compound (IV-39) (30.0 mg, 0.0943 mmol) and 4-methylpyridine-3-boronic acid (V-25) (19.5 mg, 0.139 mmol).

Example 207

Production of 4'-chloro-5'-fluoro-2-[4-(trifluoromethyl)phenoxy]-3,3'-bipyridine (IV-207)

By a production method similar to that in compound (I-36), compound (I-207) (yield 259 mg, 74%) was obtained as a colorless oil from compound (VIa-4) (296 mg, 1.05 mmol) and compound (VII-17) (200 mg, 0.950 mmol).

Example 208

Production of 5-fluoro-4'-methyl-2-[4-(trifluoromethyl)phenoxy]-3,3'-bipyridine (IV-208)

By a production method similar to that in compound (I-53), compound (I-208) (yield 21.5 mg, 67%) was obtained as a colorless oil from compound (I-207) (50.0 mg, 0.136 mmol) and methylboronic acid (48.7 mg, 0.814 mmol).

Example 209

Production of 5-fluoro-2-methoxy-2'-[4-(trifluoromethyl)phenoxy]-3,3'-bipyridine (I-209)

By a production method similar to that in compound (I-1), compound (I-209) (yield 13.4 mg, 39%) was obtained as a colorless oil from compound (IV-39) (30.0 mg, 0.0943 mmol) and 5-fluoro-2-methoxypyridine-3-boronic acid (V-32) (19.4 mg, 0.113 mmol).

Example 210

Production of 4'-methoxy-2-[4-(trifluoromethyl)phenoxy]-3,3'-bipyridine (IV-210)

Compound (IV-39) (2.50 g, 7.86 mmol), compound (V-28) (1.44 g, 9.43 mmol), (A-$^{ta}$Phos)$_2$PdCl$_2$ (278 mg, 0.393 mmol) and TEA (1.3 mL, 9.43 mmol) were dissolved in n-butanol (15 mL), and the mixture was stirred under microwave irradiation at 120° C. for 30 min. Water was added to the reaction mixture, and the mixture was extracted with ethyl acetate. The organic layer was washed successively with water and saturated brine, dried over anhydrous sodium sulfate, and filtered. The solvent was evaporated under reduced pressure, and the residue was purified by silica gel column chromatography (n-hexane:ethyl acetate) to give compound (I-210) (yield 1.42 g, 52%) as a white solid.

Example 211

Production of 5'-chloro-4'-methoxy-2-[4-(trifluoromethyl)phenoxy]-3,3'-bipyridine (I-211)

By a production method similar to that in compound (I-36), compound (I-211) (yield 31.3 mg, 48%) was obtained as a colorless oil from compound (VIa-4) (52.9 mg, 0.187 mmol) and compound (VII-20) (37.8 mg, 0.170 mmol).

Example 212

Production of 5'-fluoro-4'-methoxy-2-[4-(trifluoromethyl)phenoxy]-3,3'-bipyridine (IV-212)

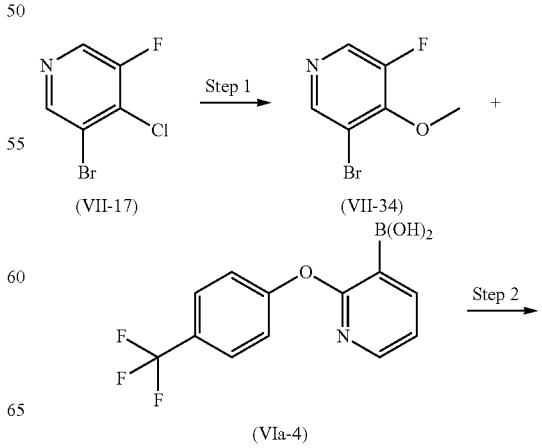

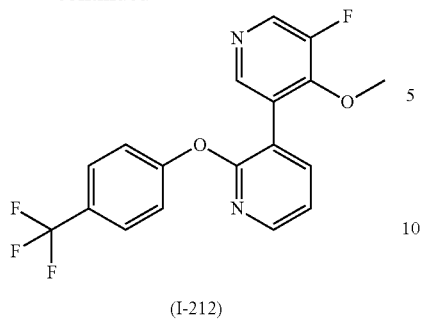

(I-212)

Step 1
By a production method similar to that in compound (VII-20), compound (VII-34) (yield 93.0 mg, 32%) was obtained as a colorless oil from compound (VII-17) (300 mg, 1.43 mmol) and sodium methoxide (28% methanol solution, 0.520 mL, 2.14 mmol).

Step 2
By a production method similar to that in compound (I-36), compound (I-212) (yield 18.7 mg, 24%) was obtained as a pale-yellow oil from compound (VIa-4) (74.2 mg, 0.262 mmol) and compound (VII-34) (45.0 mg, 0.218 mmol).

Example 213

Production of 6-methoxy-2'-[4-(trifluoromethyl)phenoxy]-2,3'-bipyridine (IV-213)

By a production method similar to that in compound (I-1), compound (I-213) (yield 17.5 mg, 54%) was obtained as a colorless oil from compound (IV-39) (30.0 mg, 0.0943 mmol) and 6-methoxypyridine-2-boronic acid (V-46) (21.3 mg, 0.139 mmol).

Reference Example 214

Production of 4'-methoxy-5-nitro-2-[4-(trifluoromethyl)phenoxy]-3,3'-bipyridine (I-214)

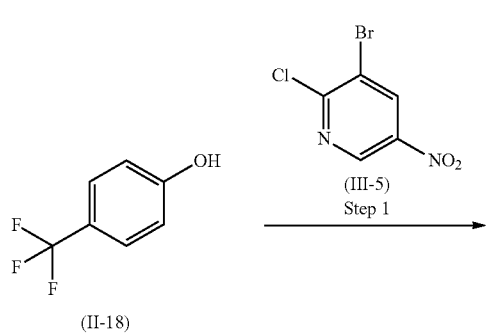

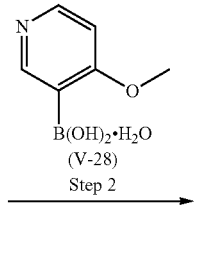

(IV-40)

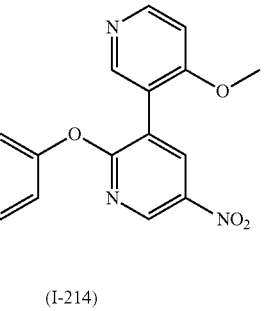

(I-214)

Step 1
By a production method similar to that in compound (IV-1), compound (IV-40) (yield 770 mg, 50%) was obtained as a pale-yellow solid from compound (III-6) (1.00 g, 4.21 mmol) and compound (II-18) (819 mg, 5.05 mmol).

Step 2
By a production method similar to that in compound (I-127), compound (I-214) (yield 208 mg, 48%) was obtained as a pale-yellow solid from compound (IV-40) (400 mg, 1.10 mmol) and 4-methoxypyridine-3-boronic acid monohydrate (V-28) (219 mg, 1.43 mmol).

Reference Example 215

Production of 4'-methoxy-2-[4-(trifluoromethyl)phenoxy]-3,3'-bipyridine-5-amine (I-215)

Compound (I-214) (189 mg, 0.483 mmol) was dissolved in methanol (1.6 mL) and ethyl acetate (0.8 mL), tin chloride dihydrate (436 mg, 1.93 mmol) was added, and the mixture was stirred at room temperature for 18 hr. The reaction mixture was concentrated, diluted with ethyl acetate, and washed successively with saturated aqueous sodium hydrogen carbonate solution and saturated brine. The organic layer was dried over anhydrous sodium sulfate, and filtered. Under reduced pressure, the solvent was evaporated, and the residue was purified by silica gel column chromatography (NH silica gel, n-hexane:ethyl acetate=60:40→10:90) to give compound (I-215) (yield 163 mg, 93%) as a pale-yellow solid.

Example 216

Production of 5-fluoro-4'-methoxy-2-[4-(trifluoromethyl)phenoxy]-3,3'-bipyridine (I-216)

To compound (I-215) (140 mg, 0.387 mmol) was added aqueous HBF$_4$ solution (1.6 mL, 0.387 mmol), sodium nitrite (29.4 mg, 0.426 mmol) dissolved in water (1.0 mL) was added at 0° C., and the mixture was stirred for 1 hr. The precipitate was collected by filtration, washed with water and n-hexane, and dried at room temperature under reduced pressure to give a brown solid. To this solid was added toluene (3.3 mL), and the mixture was stirred at 120° C. for 2 hr. The reaction mixture was concentrated, diluted with ethyl acetate, and washed successively with saturated aqueous sodium hydrogen carbonate solution and saturated brine. The organic layer was dried over anhydrous sodium sulfate, and filtered. Under reduce pressure, the solvent was evaporated, and the residue was purified by silica gel column chromatography (silica gel: eluent n-hexane:ethyl acetate=70:30→40:60) to give compound (I-216) (yield 35.0 mg, 25%) as a yellow oil.

Example 216

Production of 5-chloro-4'-methoxy-2-[4-(trifluoromethyl)phenoxy]-3,3'-bipyridine (I-217)

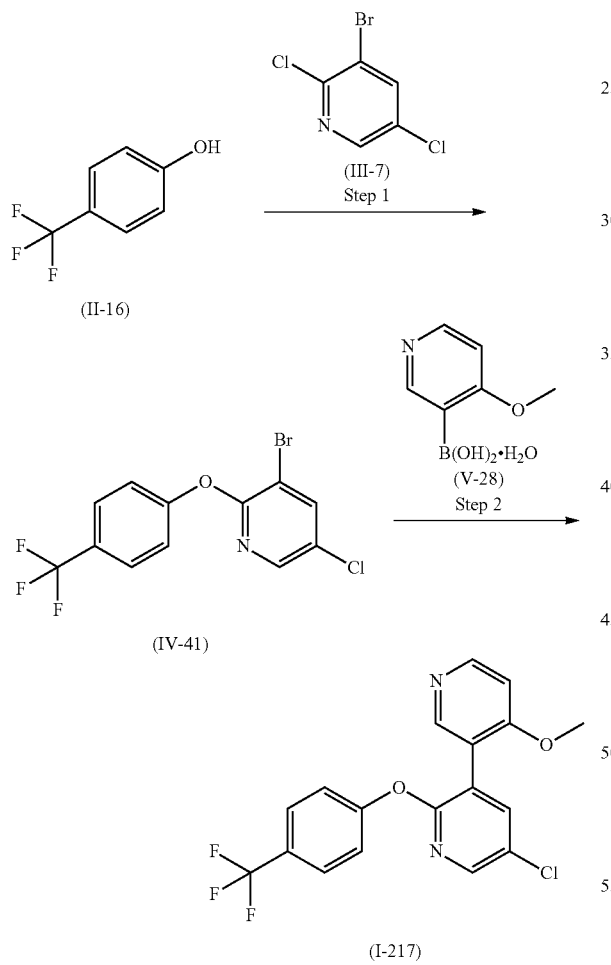

Step 1
By a production method similar to that in compound (IV-1), compound (IV-41) (yield 543 mg, 47%) was obtained as a colorless oil from compound (III-7) (500 mg, 2.20 mmol) and compound (II-18) (429 mg, 2.64 mmol).
Step 2
By a production method similar to that in compound (I-127), compound (I-217) (yield 26.0 mg, 23%) was obtained as a white solid from compound (IV-41) (100 mg, 0.284 mmol) and 4-methyoxypyridine-3-boronic acid monohydrate (V-28) (65.1 mg, 0.425 mmol).

Example 218

Production of 2-methoxy-3-{2-[4-(trifluoromethyl)phenoxy]pyridin-3-yl}pyrazine (I-218)

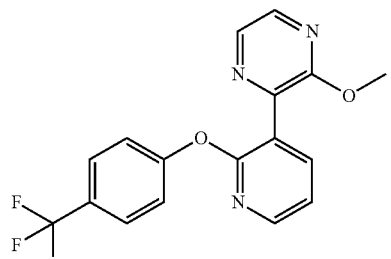

By a production method similar to that in compound (I-36), compound (I-218) (yield 11.2 mg, 30%) was obtained as a white solid from compound (VIa-4) (30.0 mg, 0.105 mmol) and 2-bromo-3-methoxypyrazine (VII-35) (24.0 mg, 0.127 mmol).

Example 219

Production of 4-methoxy-5-{2-[4-(trifluoromethyl)phenoxy]pyridin-3-yl}pyrimidine (IV-219)

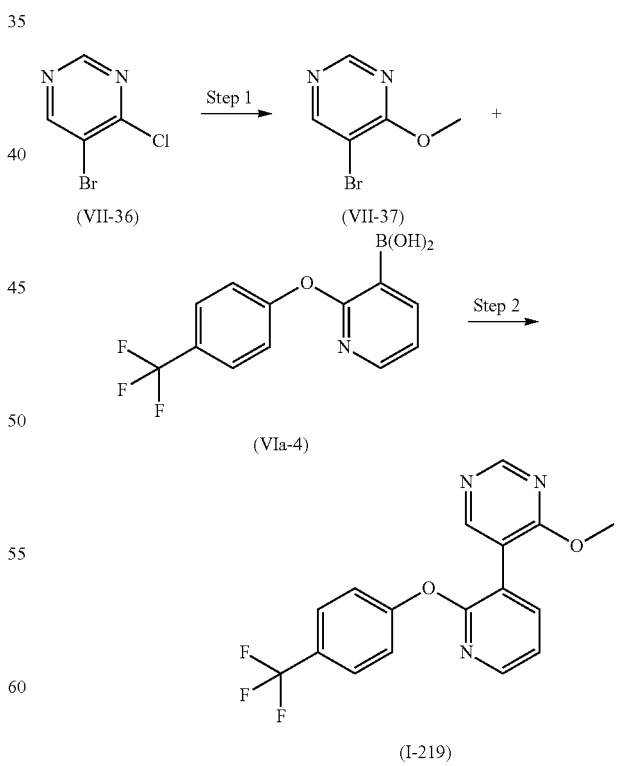

Step 1
Compound (VII-36) (9.90 g, 41.2 mmol) was dissolved in methanol (140 mL), 28% sodium methoxide methanol solution (24 mg, 120 mmol) was added and the mixture was stirred at 60° C. for 15 hr. The reaction mixture was allowed to cool, water was added, and the mixture was extracted with ethyl acetate. The organic layer was washed with saturated brine, dried over anhydrous sodium sulfate, and filtered. The solvent was evaporated under reduced pressure to give compound (VII-37) (yield 7.72 g, 79%) as a pale-yellow solid.

Step 2

By a production method similar to that in compound (I-36), compound (I-219) (yield 16.0 mg, 44%) was obtained as white solid from compound (VIa-4) (30.0 mg, 0.105 mmol) and compound (VII-37) (29.9 mg, 0.127 mmol).

Example 220

Production of 3-(5-chloro-1,3-dimethyl-1H-pyrazol-4-yl)-2-[4-(trifluoromethyl)phenoxy]pyridine (I-220)

Compound (IV-39) (100 mg, 0.314 mmol), 5-chloro-1,3-dimethyl-1H-pyrazole (41.0 mg, 0.314 mmol), Pd(Oac)$_2$ (1.4 mg, 0.0063 mmol) and potassium acetate (61.7 mg, 0.629 mmol) were dissolved in DMA (1.0 mL), and the mixture was stirred under microwave irradiation at 160° C. for 45 hr. Water was added to the reaction mixture, and the mixture was extracted with ethyl acetate. The organic layer was washed successively with water and saturated brine, dried over anhydrous sodium sulfate, and filtered. The solvent was evaporated under reduced pressure, and the residue was purified by silica gel column chromatography (n-hexane:ethyl acetate) to give compound (I-220) (yield 3.0 mg, 3%) as a colorless oil.

Example 221

Production of 3-(1-methyl-1H-pyrazol-5-yl)-2-[4-(trifluoromethyl)phenoxy]pyridine (I-221)

By a production method similar to that in compound (I-1), compound (I-221) (yield 440 mg, 44%) was obtained as a colorless oil from compound (IV-39) (1.00 g, 3.14 mmol) and 1-methyl-1H-pyrazole-5-boronic acid (V-48) (475 mg, 3.77 mmol).

Example 222

Production of 3-(4-chloro-1-methyl-1H-pyrazol-5-yl)-2-[4-(trifluoromethyl)phenoxy]pyridine (I-222)

Compound (I-221) (40.0 mg, 0.125 mmol) was dissolved in DMF (1.0 mL), NCS (20.1 mg, 0.150 mmol) was added and the mixture was stirred at 80° C. for 3 hr. Thereafter, water was added, and the mixture was extracted with ethyl acetate. The organic layer was dried over anhydrous sodium sulfate, and filtered. The solvent was evaporated under reduced pressure. The residue was purified by silica gel column chromatography (n-hexane:ethyl acetate) to give compound (I-222) (yield 32.0 mg, 72%) as a colorless oil.

Example 223

Production of 3-(5-methoxy-1-methyl-1H-pyrazol-4-yl)-2-[4-(trifluoromethyl)phenoxy]pyridine (I-223)

Step 1

5-Methoxy-1-methyl-1H-pyrazole (343 mg, 3.06 mmol) was dissolved in acetonitrile (5.0 mL), NIS (757 mg, 3.36 mmol) was added and the mixture was stirred at 70° C. for 1 hr. Saturated aqueous sodium hydrogen carbonate solution was added, and the mixture was extracted with ethyl acetate, and organic layer was dried over anhydrous sodium sulfate. The solvent was evaporated under reduced pressure, and the residue was purified by silica gel column chromatography (n-hexane:ethyl acetate) to give 4-iodo-5-methoxy-1-methyl-1H-pyrazole (VII-38) (yield 225 mg, 31%).

Step 2

Compound (VIa-4) (212 mg, 0.890 mmol), compound (VII-38) (210 mg, 0.742 mmol), (A-$^{ta}$Phos)$_2$PdCl$_2$ (26.3 mg, 0.037 mmol) and cesium carbonate (484 mg, 1.48 mmol) were dissolved in n-butanol (1.0 mL) and water (0.10 mL), and the mixture was stirred under microwave irradiation at 120° C. for 30 min. Water was added to the reaction mixture, and the mixture was extracted with ethyl acetate. The organic layer was washed successively with water and saturated brine, dried over anhydrous sodium sulfate, and filtered. The solvent was evaporated under reduced pressure, and the residue was purified by silica gel column chromatography (n-hexane:ethyl acetate) to give compound (I-223) (yield 35.0 mg, 14%) as a white solid.

Example 224

Production of 5-{2-[4-(trifluoromethyl)phenoxy]pyridin-3-yl}quinoxaline (I-224)

By a production method similar to that in compound (IV-36), compound (I-224) (yield 35.0 mg, 27%) was obtained as a white solid from compound (VIa-4) (100 mg, 0.353 mmol) and 5-bromoquinoxaline (VII-2) (73.9 mg, 0.353 mmol).

Example 225

Production of 8-{2-[4-(trifluoromethyl)phenoxy]pyridin-3-yl}-1,6-naphthyridine (I-225)

By a production method similar to that in compound (I-36), compound (I-225) (yield 15.4 mg, 44%) was obtained as a white solid from compound (VIa-4) (30.0 mg, 0.106 mmol) and 8-bromo-1,6-naphthyridine (VII-39) (26.9 mg, 0.129 mmol).

Example 226

Production of 4-{2-[4-(trifluoromethyl)phenoxy]pyridin-3-yl}-1,5-naphthyridine (I-226)

By a production method similar to that in compound (I-36), compound (I-226) (yield 7.7 mg, 20%) was obtained as a colorless oil from compound (VIa-4) (30.3 mg, 0.107 mmol) and 4-bromo-1,5-naphthyridine (VII-40) (26.9 mg, 0.129 mmol).

Example 227

Production of 8-{2-[4-(trifluoromethyl)phenoxy] pyridin-3-yl}pyrido[3,4-b]pyrazine (I-227)

By a production method similar to that in compound (I-36), compound (I-227) (yield 5.6 mg, 22%) was obtained as a yellow solid from compound (VIa-4) (30.0 mg, 0.106 mmol) and 8-bromopyrido[3,4-b]pyrazine (VII-27) (27.1 mg, 0.129 mmol).

Example 228

Production of 7-{2-[4-(trifluoromethyl)phenoxy] pyridin-3-yl}pyrazolo[1,5-a]pyridine (I-228)

By a production method similar to that in compound (I-1), compound (I-228) (yield 6.5 mg, 20%) was obtained as a colorless oil from compound (IV-39) (28.6 mg, 0.0899 mmol) and pyrazolo[1,5-a]pyridine-7-boronic acid (V-49) (29.2 mg, 0.180 mmol).

Example 229

Production of 8-{2-[4-(trifluoromethyl)phenoxy] pyridin-3-yl}imidazo[1,2-a]pyridine (I-229)

Step 1

2-Amino-3-bromopyridine (VII-41) (5.00 g, 28.9 mmol) was dissolved in ethanol (100 mL), sodium hydrogen carbonate (3.64 g, 43.3 mmol) and 2-chloroacetaldehyde (7.1 mL, 43 mmol) were added, and the mixture was stirred under refluxing with heating for 4 hr. The mixture was allowed to cool, and the solvent was evaporated under reduced pressure. Water was added, and the mixture was extracted with ethyl acetate. The organic layer was washed with saturated brine, dried over anhydrous sodium sulfate, and filtered. The solvent was evaporated under reduced pressure. The residue was purified by silica gel column chromatography (n-hexane:ethyl acetate=70:30→40:60) to give 8-bromoimidazo[1,2-a]pyridine (VII-42) (yield 5.71 g, quantitative).

Step 2

By a production method similar to that in compound (I-36), compound (I-229) (yield 12.2 mg, 17%) was obtained as a colorless oil from compound (VIa-4) (58.2 mg, 0.206 mmol) and compound (VII-42) (48.6 mg, 0.247 mmol).

Example 230

Production of 5-{2-[4-(trifluoromethyl)phenoxy] pyridin-3-yl}[1,2,4]triazolo[1,5-a]pyridine (I-230)

By a production method similar to that in compound (I-36), compound (I-230) (yield 2.0 mg, 3%) was obtained as a white solid from compound (VIa-4) (60.0 mg, 0.212 mmol) and 5-bromo[1,2,4]triazolo[1,5-a]pyridine (VII-9) (54.6 mg, 0.276 mmol).

Example 231

Production of 5-{2-[4-(trifluoromethyl)phenoxy] pyridin-3-yl}imidazo[1,2-a]pyrazine (I-231)

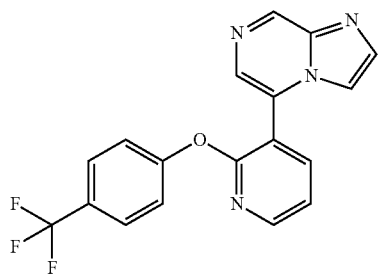

By a production method similar to that in compound (I-1), compound (I-231) (yield 11.8 mg, 30%) was obtained as a white solid from compound (VIa-4) (40.0 mg, 0.141 mmol) and 5-bromoimidazo[1,2-b]pyrazine (VII-43) (28.0 mg, 0.141 mmol).

Example 232

Production of 6-methyl-7-{2-[4-(trifluoromethyl) phenoxy]pyridin-3-yl}-2,3-dihydropyrazolo[1,5-b] oxazole (I-232)

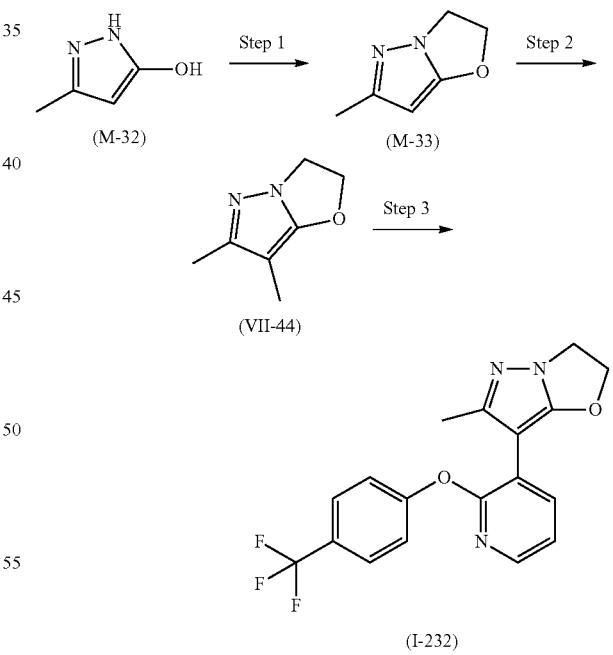

Step 1

Compound (M-32) (1.00 g, 10.2 mmol) and potassium carbonate (2.82 g, 20.4 mmol) were dissolved in acetonitrile (20 mL), TBAB (657 mg, 2.04 mmol) and 1,2-dibromoethane (2.87 g, 15.3 mmol) were added and the mixture was stirred at 50° C. for 14 hr. Thereafter, water was added, and the mixture was extracted with ethyl acetate. The organic layer was dried over anhydrous sodium sulfate, and filtered. The solvent was evaporated under reduced pressure to give a crude compound (M-33).

Step 2

Compound (M-33) was dissolved in acetonitrile (20 mL), NIS (2.29 g, 10.2 mmol) was added and the mixture was stirred at 70° C. for 1 hr. Thereafter, saturated aqueous sodium hydrogen carbonate solution was added, and the mixture was extracted with ethyl acetate. The organic layer was dried over anhydrous sodium sulfate, and filtered, and the solvent was evaporated under reduced pressure. The residue was purified by silica gel column chromatography (n-hexane:ethyl acetate) to give compound (VII-44) [yield 332 mg, 13% (2 steps)].

Step 3

By a production method similar to that in compound (I-1), compound (I-232) (yield 12.8 mg, 20%) was obtained as a white solid from compound (VIa-4) (50.0 mg, 0.177 mmol) and compound (VII-44) (53.0 mg, 0.212 mmol).

Example 233

Production of 2-methyl-3-{2-[4-(trifluoromethyl)phenoxy]pyridin-3-yl}-5,6,7,8-tetrahydropyrazolo[1,5-b][1,3]oxazepine (I-233)

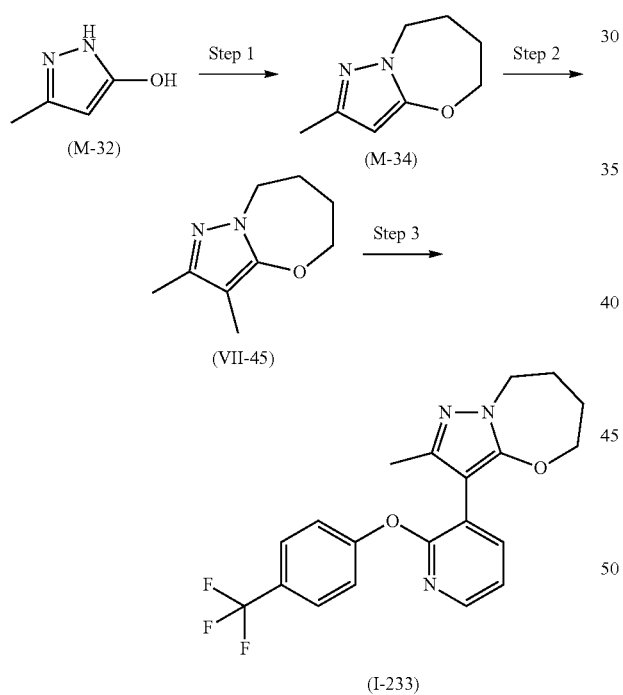

Step 1

Compound (M-32) (1.00 mg, 10.2 mmol) and potassium carbonate (4.23 g, 30.6 mmol) were dissolved in acetonitrile (30 mL), 1,4-diobromobutane (2.64 g, 12.2 mmol) was added and the mixture was stirred at 50° C. for 12 hr. Thereafter, water was added, and the mixture was extracted with ethyl acetate. The organic layer was dried over anhydrous sodium sulfate, and filtered, and the solvent was evaporated under reduced pressure. The residue was purified by silica gel column chromatography (n-hexane:ethyl acetate) to give compound (M-34).

Step 2

Compound (M-34) was dissolved in acetonitrile (30 mL), NIS (3.22 g, 14.3 mmol) was added and the mixture was stirred at 70° C. for 30 min. Thereafter, saturated aqueous sodium hydrogen carbonate solution was added, and the mixture was extracted with ethyl acetate. The organic layer was washed dried over anhydrous sodium sulfate, and filtered, and the solvent was evaporated under reduced pressure. The residue was purified by silica gel column chromatography (n-hexane:ethyl acetate) to give compound (VII-45) [yield 825 mg, 29% (2 steps)].

Step 3

By a production method similar to that in compound (I-36), compound (I-233) (yield 10.1 mg, 14%) was obtained as a colorless oil from compound (VIa-4) (61.1 mg, 0.216 mmol) and compound (VII-45) (50.0 mg, 0.180 mmol).

Example 234

Production of 2-(4-bromophenoxy)-4'-methoxy-3,3'-bipyridine (I-234)

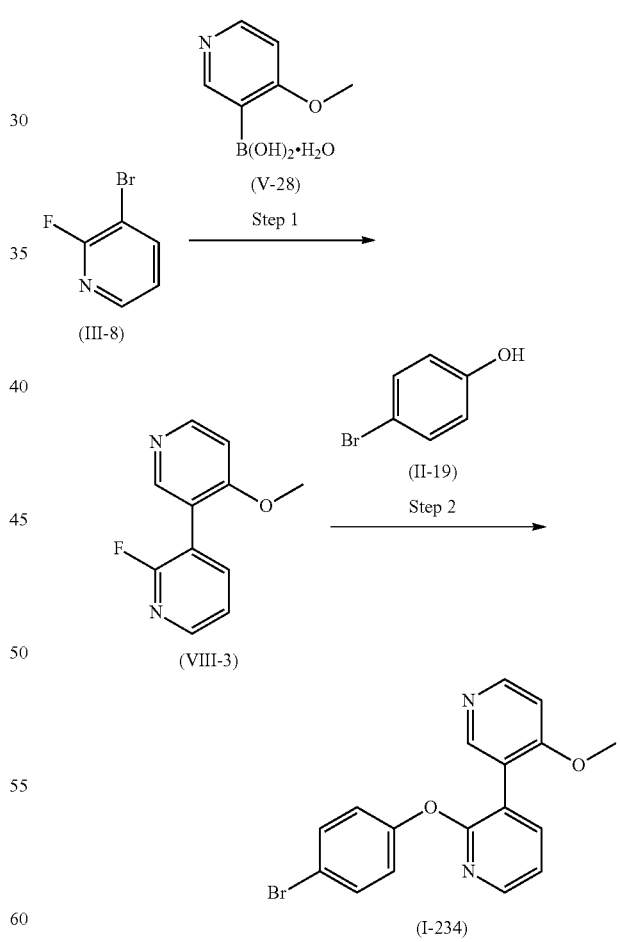

Step 1

By a production method similar to that in compound (VIII-1), bipyridyl compound (VIII-3) (yield 1.48 g, 50%) was obtained compound (III-8) (2.55 g, 14.5 mmol) and compound (V-28) (3.32 g, 21.7 mmol).

Step 2

Compound (VIII-3) (25.0 mg, 0.122 mmol) and 4-bromophenol (II-19) (63.5 mg, 0.367 mmol) were dissolved in NMP (0.50 mL), cesium carbonate (120 mg, 0.367 mmol) was added, and the mixture was stirred under microwave irradiation at 180° C. for 30 min. The reaction mixture was allowed to cool, 1 mol/L aqueous sodium hydroxide solution was added, and the mixture was extracted with ethyl acetate. The organic layer was washed with saturated brine, dried over anhydrous sodium sulfate, and filtered. The solvent was evaporated under reduced pressure, and the residue was purified by silica gel column chromatography (n-hexane:ethyl acetate) to give compound (I-234) (yield 13.2 mg, 30%) as a colorless oil.

Example 235

Production of 2-(4-chlorophenoxy)-4'-methoxy-3,3'-bipyridine (I-235)

By a production method similar to that in compound (I-1), compound (I-235) (yield 23.3 mg, 43%) was obtained as a colorless oil from compound (IV-38) (50.0 mg, 0.176 mmol) and compound (V-28) (32.3 mg, 0.211 mmol).

Example 236

Production of 2-(4-fluorophenoxy)-4'-methoxy-3,3'-bipyridine (I-236)

By a production method similar to that in compound (I-234), compound (I-236) (yield 24.0 mg, 55%) was obtained as a white solid from compound (VIII-3) (30.0 mg, 0.147 mmol) and 4-fluorophenol (II-20) (63.5 mg, 0.367 mmol).

Example 237

Production of 4'-methoxy-2-[4-(trifluoromethoxy)phenoxy]-3,3'-bipyridine (I-237)

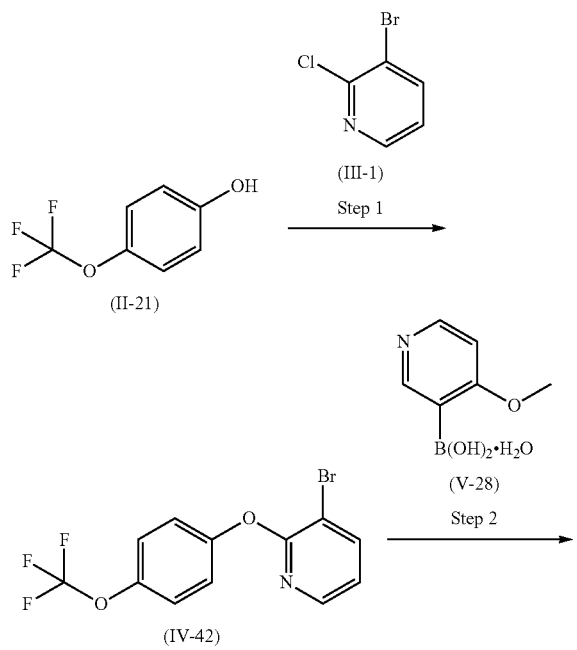

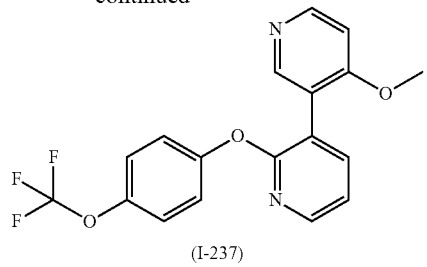

(I-237)

Step 1

By a production method similar to that in compound (IV-1), compound (IV-42) (yield 328 mg, 50%) was obtained as a white solid from compound (III-1) (455 mg, 2.36 mmol) and 4-(trifluoromethoxy)phenol (II-2) (350 mg, 1.97 mmol).

Step 2

By a production method similar to that in compound (I-1), compound (I-237) (yield 21.0 mg, 39%) was obtained as a colorless oil from compound (IV-42) (50.0 mg, 0.150 mmol) and compound (V-28) (34.4 mg, 0.224 mmol).

Example 238

Production of 2-[4-(difluoromethoxy)phenoxy]-4'-methoxy-3,3'-bipyridine (I-238)

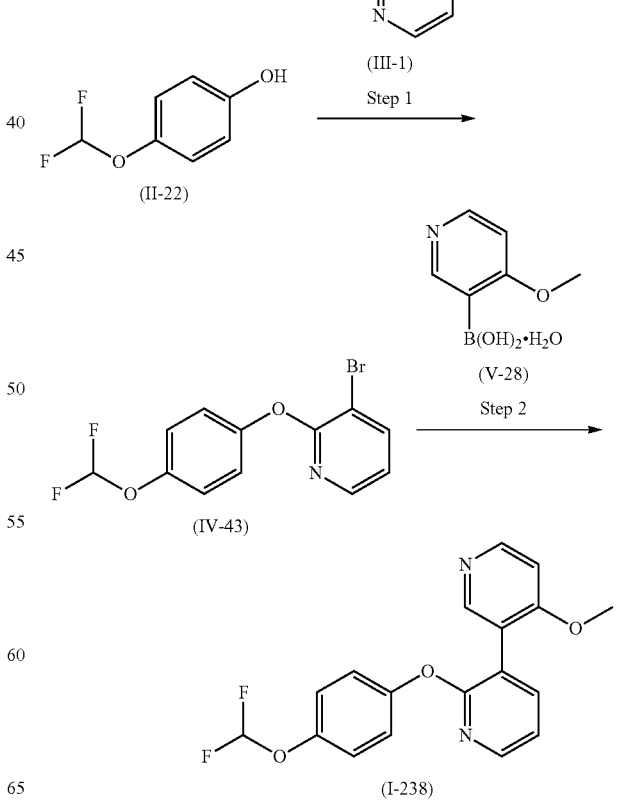

Step 1

By a production method similar to that in compound (IV-1), compound (IV-43) (yield 3.12 mg, 79%) was obtained from compound (III-1) (3.12 g, 12.5 mmol) and 4-(difluoromethoxy)phenol (II-22) (2.00 mg, 12.5 mmol).

Step 2

By a production method similar to that in compound (I-1), compound (I-238) (yield 7.3 mg, 6%) was obtained as a colorless oil from compound (IV-43) (112 mg, 0.354 mmol) and compound (V-28) (81.0 mg, 0.531 mmol).

Example 239

Production of 4'-methoxy-2-{4-[(trifluoromethyl)thio]phenoxy}-3,3'-bipyridine (I-239)

Example 240

Production of 4'-methoxy-2-[4-(pentafluorosulfanyl)phenoxy]-3,3'-bipyridine (I-240)

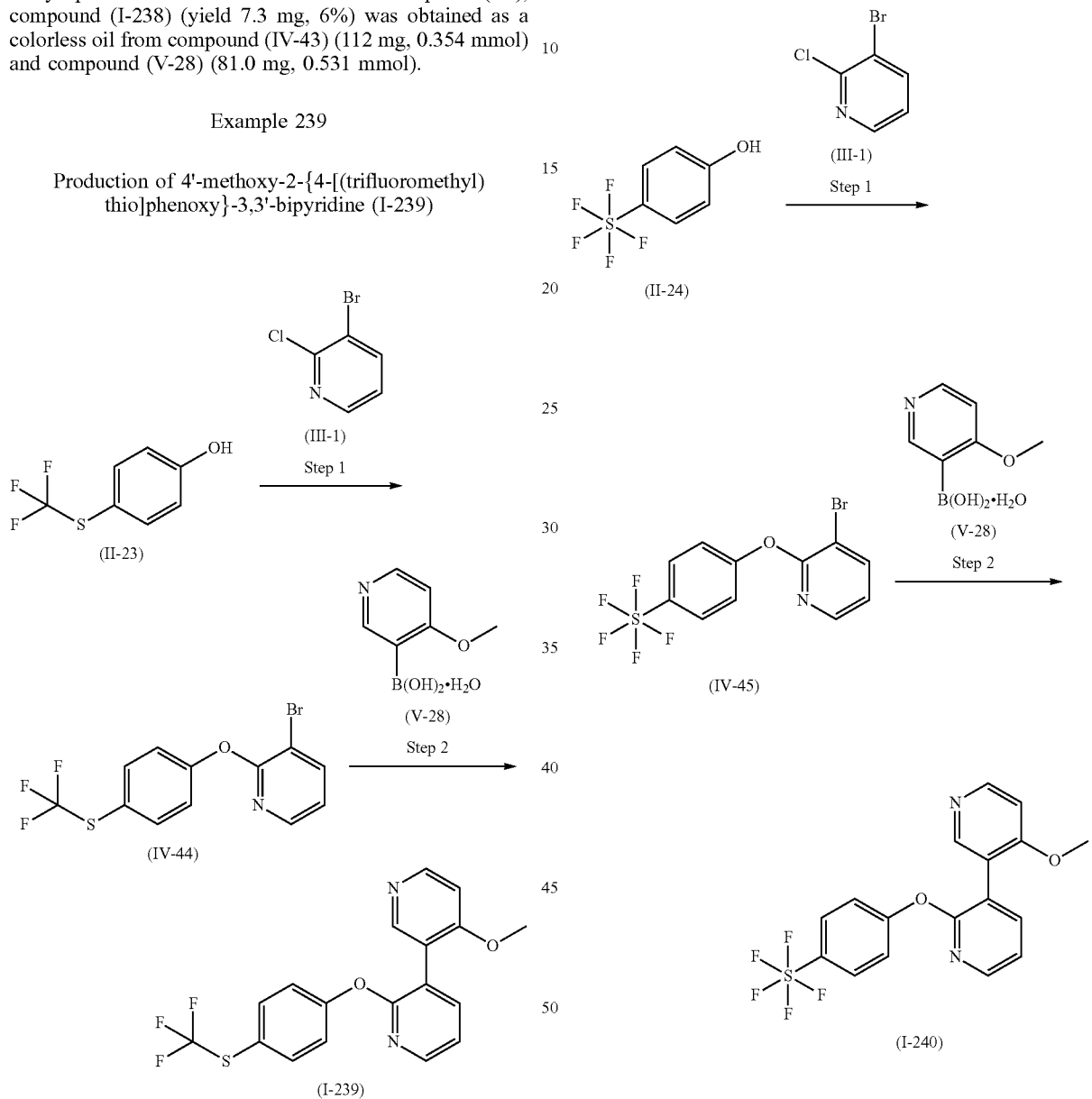

Step 1

By a production method similar to that in compound (IV-1), compound (IV-44) (yield 1.10 g, 61%) was obtained as a colorless oil from compound (III-1) (1.00 g, 5.20 mmol) and 4-(trifluoromethylthio)phenyl (II-23) (1.51 g, 7.79 mmol).

Step 2

By a production method similar to that in compound (I-1), compound (I-239) (yield 28.0 mg, 52%) was obtained as a colorless oil from compound (IV-44) (50.0 mg, 0.143 mmol) and compound (V-28) (36.6 mg, 0.214 mmol).

Step 1

By a production method similar to that in compound (IV-1), compound (IV-45) (yield 309 mg, 60%) was obtained as a white solid from compound (III-1) (315 mg, 1.64 mmol) and 4-(pentafluorosulfanyl)phenol (II-24) (300 mg, 1.36 mmol).

Step 2

By a production method similar to that in compound (I-1), compound (I-240) (yield 15.1 mg, 28%) was obtained as a colorless oil from compound (IV-45) (50.0 mg, 0.133 mmol) and compound (V-28) (34.1 mg, 0.199 mmol).

Example 241

Production of 4'-methoxy-2-[4-(methylthio)phenoxy]-3,3'-bipyridine (I-241)

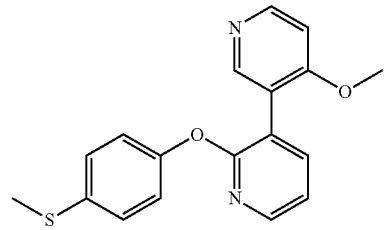

By a production method similar to that in compound (I-234), compound (I-241) (yield 24.0 mg, 55%) was obtained as a white solid from compound (VIII-3) (30.0 mg, 0.147 mmol) and 4-(methylthio)phenol (II-25) (63.5 mg, 0.367 mmol).

Example 242

Production of 4'-methoxy-2-(4-methoxyphenoxy)-3,3'-bipyridine (I-242)

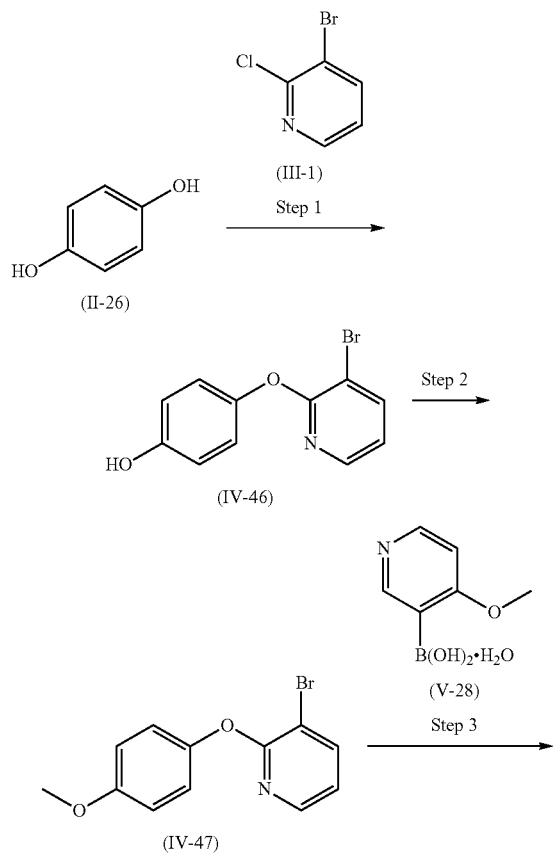

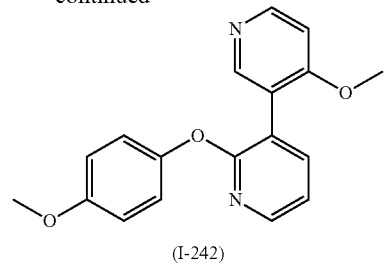

Step 1
By a production method similar to that in compound (IV-1), compound (IV-46) (yield 827 mg, 60%) was obtained as a white solid from compound (III-1) (1.00 g, 5.20 mmol) and hydroquinone (II-26) (1.14 g, 10.4 mmol).

Step 2
Compound (IV-46) (100 mg, 0.376 mmol) was dissolved in DMF (1.9 mL), sodium hydride (36.1 mg, 0.752 mmol) and methyl iodide (35.2 μL, 0.564 mmol) were successively added, and the mixture was stirred at room temperature for 1 hr. Water was added, and the mixture was extracted with ethyl acetate. The organic layer was washed successively with water and saturated brine, dried over anhydrous sodium sulfate, and filtered. The solvent was evaporated under reduced pressure, and the residue was purified by silica gel column chromatography (n-hexane:ethyl acetate) to give compound (IV-47) (yield 102 mg, 97%) as a white solid.

Step 3
By a production method similar to that in compound (I-1), compound (I-242) (yield 20.2 mg, 37%) was obtained as a white solid from compound (IV-47) (50.0 mg, 0.179 mmol) and compound (V-28) (54.8 mg, 0.358 mmol).

Example 243

Production of 4-{[4'-methoxy-(3,3'-bipyridin)-2-yl]oxy}benzonitrile (I-243)

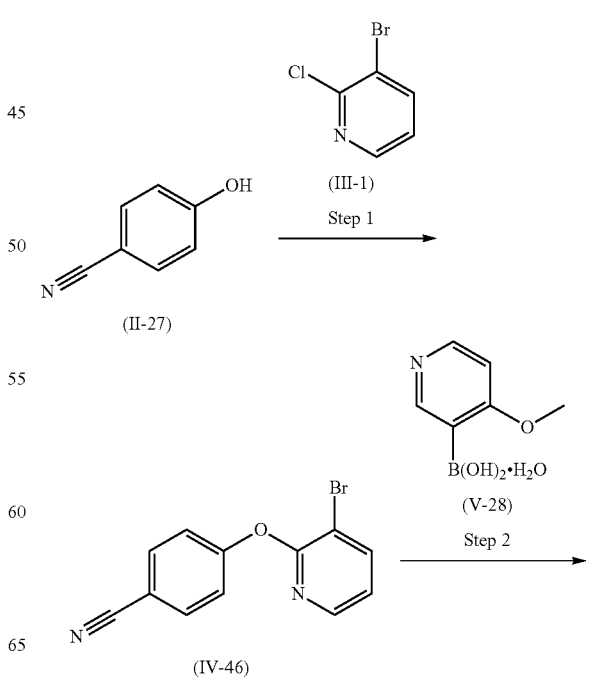

-continued

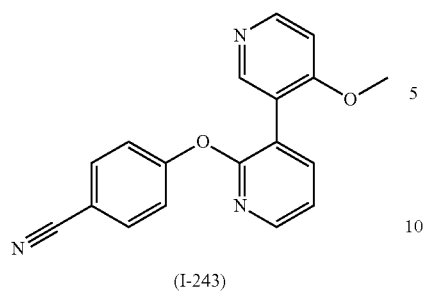

(I-243)

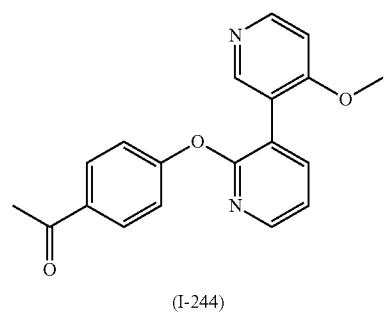

(I-244)

Step 1

By a production method similar to that in compound (IV-1), compound (IV-48) (yield 213 mg, 68%) was obtained from compound (III-1) (200 mg, 1.14 mmol) and 4-hydroxybenzonitrile (II-27) (149 mg, 1.25 mmol).

Step 2

By a production method similar to that in compound (I-1), compound (I-243) (yield 9.9 mg, 30%) was obtained as a white solid from compound (IV-48) (30.0 mg, 0.109 mmol) and compound (V-28) (25.0 mg, 0.164 mmol).

Step 1

By a production method similar to that in compound (IV-1), compound (IV-49) (yield 4.23 g, 85%) was obtained as a white solid from compound (III-1) (3.00 g, 17.0 mmol) and 4-hydroxyacetophenone (II-28) (2.79 mg, 20.5 mmol).

Step 2

By a production method similar to that in compound (I-1), compound (I-244) (yield 10.1 mg, 18%) was obtained as a white solid from compound (IV-49) (50.0 mg, 0.171 mmol) and compound (V-28) (39.3 mg, 0.257 mmol).

Example 244

Production of 1-(4-{[4'-methoxy-3,3'-bipyridin)-2-yl]oxy}phenyl)ethanone (I-244)

Example 245

Production of ethyl 4-{[4'-methoxy-3,3'-bipyridin)-2-yl]oxy}benzoate (I-245)

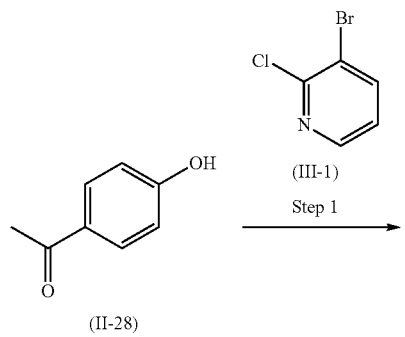

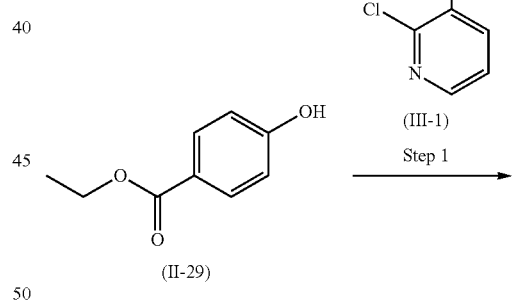

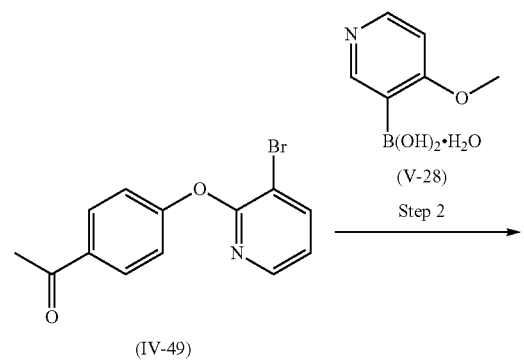

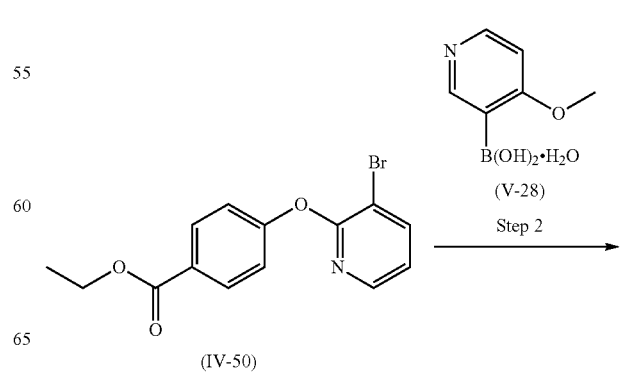

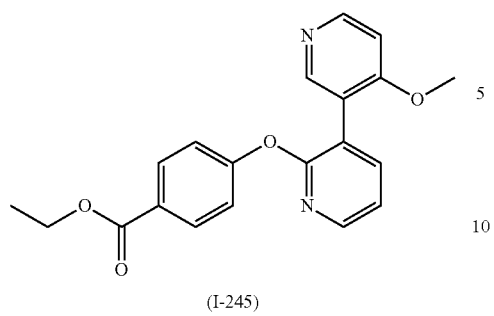

(I-245)

Step 1

By a production method similar to that in compound (IV-1), compound (IV-50) (yield 11.8 mg, 71%) was obtained as a white solid from compound (III-1) (10.0 g, 52.0 mmol) and ethyl 4-hydroxybenzoate (II-29) (10.4 g, 62.6 mmol).

Step 2

Compound (IV-50) (300 mg, 0.931 mmol), compound (V-28) (214 mg, 0.140 mmol) and (A-<sup>ta</sup>Phos)₂PdCl₂) (33.0 mg, 0.0470 mmol) were dissolved in 1,4-dioxane (2.5 mL), 3.7 mol/L aqueous cesium fluoride solution (0.50 mL, 1.86 mmol) was added, and the mixture was stirred under microwave irradiation at 120° C. for 30 min. Water was added to the reaction mixture, and the mixture was extracted with ethyl acetate. The organic layer was washed successively with water and saturated brine, dried over anhydrous sodium sulfate, and filtered. The solvent was evaporated under reduced pressure, and the residue was purified by silica gel column chromatography (NH silica gel, n-hexane:ethyl acetate=95:5→50:50) to give compound (I-245) (yield 101 mg, 31%) as a white solid.

Example 246

Production of ethyl 4-{[4'-methoxy-3,3'-bipyridin)-2-yl]oxy}benzaldehyde (I-246)

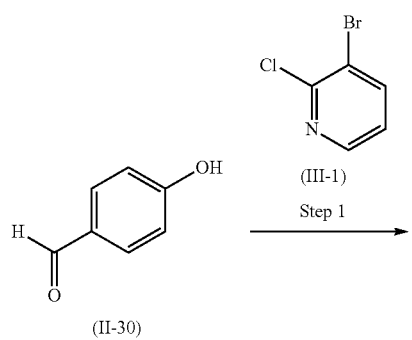

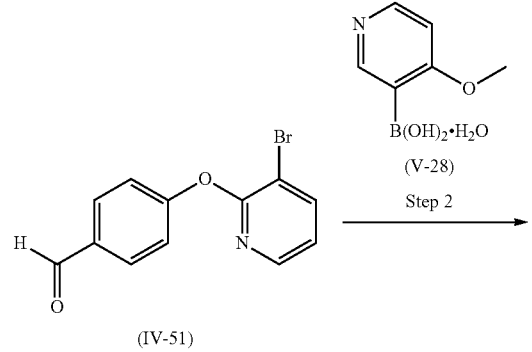

(IV-51)

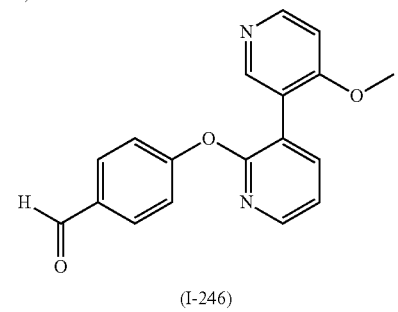

(I-246)

Step 1

By a production method similar to that in compound (IV-1), compound (IV-51) (yield 1.13 g, 23%) was obtained as a white solid from compound (III-1) (5.00 g, 26.0 mmol) and 4-hydroxybenzaldehyde (II-30) (2.11 g, 17.3 mmol).

Step 2

By a production method similar to that in compound (I-1), compound (I-246) (yield 493 mg, 45%) was obtained as a yellow oil from compound (IV-51) (1.00 mg, 3.60 mmol) and compound (V-28) (715 mg, 4.18 mmol).

Production of 4'-methoxy-2-[4-(2,2,2-trifluoroethyl)phenoxy]-3,3'-bipyridine (I-249)

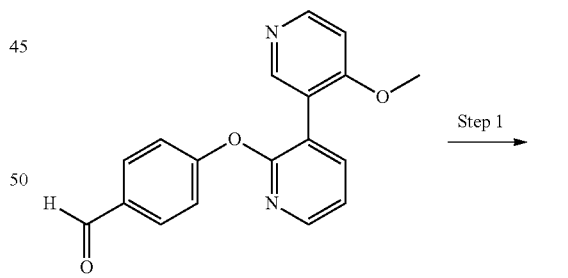

(I-246)

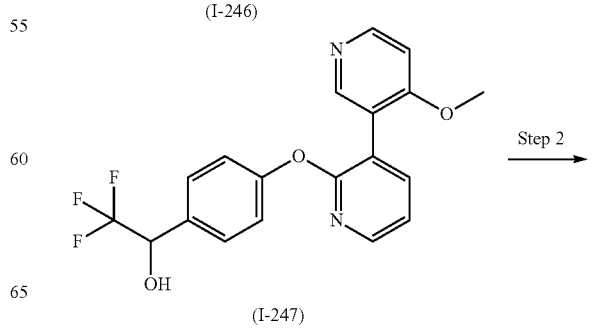

(I-247)

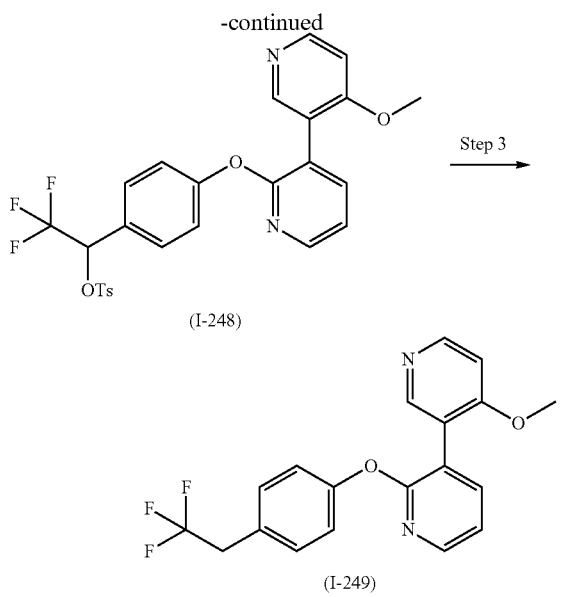

(I-248)

(I-249)

Example 247

Production of 2,2,2-trifluoro-1-(4-{[4'-methoxy-3,3'-bipyridin)-2-yl]oxy}phenyl)ethanol (I-247)

To a solution of compound (I-246) (200 mg, 0.653 mmol) in THF (2.0 mL) were successively added, under ice-cooling, trimethylsilyltrifluoromethane (115 μL, 0.778 mmol) and TBAF (65 μL, 0.065 mmol), and the mixture was warmed to room temperature and stirred for 6 hr. The reaction mixture was ice-cooled, trimethylsilyltrifluoromethane (30 μL, 0.203 mmol) and 1 mol/L THF solution of TBAF (0.65 mL, 0.59 mmol) were successively added, and the mixture was warmed to room temperature and stirred for 17 hr. 1 mol/L Hydrochloric acid (2.0 mL) was added, and the mixture was stirred at room temperature for 1 hr. to the reaction mixture was added saturated aqueous sodium hydrogen carbonate solution, and the mixture was extracted with ethyl acetate. The organic layer was washed with saturated brine, dried over anhydrous sodium sulfate, and filtered. The solvent was evaporated under reduced pressure, and the residue was purified by silica gel column chromatography (NH silica gel, n-hexane:ethyl acetate=50:50→0:100) to give compound (I-247) (yield 167 mg, 68%) as a white solid.

Example 248

Production of 2,2,2-trifluoro-1-(4-{[4'-methoxy-3,3'-bipyridin)-2-yl]oxy}phenyl)ethyl 4-methylbenzenesulfonate (I-248)

To a solution of compound (I-247) (100 mg, 0.266 mmol), DMAP (1.6 mg, 0.013 mmol) and TEA (74 μL, 0.53 mmol) in DCM (3.0 mL) was added, under ice-cooling, TsCl (55.7 mg, 0.292 mmol), and the mixture was stirred at room temperature for 5 days. Water was added to the reaction mixture, and the mixture was extracted with ethyl acetate. The organic layer was dried over anhydrous sodium sulfate, and filtered. The solvent was evaporated under reduced pressure, and the residue was purified by silica gel column chromatography (NH silica gel, n-hexane:ethyl acetate=40:60→0:100) to give compound (I-248) (yield 78.1 mg, 55%) as a white solid.

Example 249

Production of 4'-methoxy-2-[4-(2,2,2-trifluoroethyl)phenoxy]-3,3'-bipyridine (I-249)

Compound (I-248) (70.0 mg, 0.132 mmol) was dissolved in ethanol (3.0 mL), palladium hydroxide/carbon (Pd 20%) (14.0 mg) was added and the mixture was stirred under 0.3 MPa hydrogen atmosphere at room temperature for 2 hr. The reaction mixture was filtered through Celite. The solvent was evaporated under reduced pressure, and the residue was purified by silica gel column chromatography (NH silica gel, n-hexane:ethyl acetate=95:5→20:80) to give compound (I-249) (yield 30.9 mg, 65%) as a colorless oil.

Example 250

Production of (4-{[4'-methoxy-3,3'-bipyridin)-2-yl]oxy}phenyl)methanol (I-250)

Step 1
By a production method similar to that in compound (IV-1), compound (IV-52) (yield 682 mg, 60%) was obtained as a yellow oil from compound (III-1) (412 mg, 2.14 mmol) and 4-hydroxymethylphenol (II-31) (500 mg, 1.79 mmol).

Step 2
By a production method similar to that in compound (I-1), compound (I-250) (yield 98.0 mg, 45%) was obtained as a colorless oil from compound (IV-52) (200 mg, 0.714 mmol) and compound (V-28) (164 mg, 1.07 mmol).

Example 251

Production of 4'-methoxy-2-[4-(methoxymethyl)phenoxy]-3,3'-bipyridine (I-251)

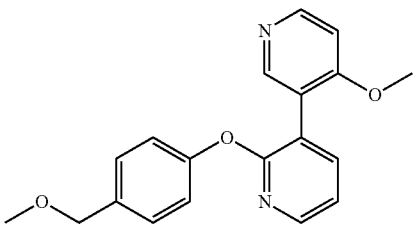

Compound (I-250) (30.0 mg, 0.097 mmol) was dissolved in DMF (1.0 mL), 50% sodium hydride (9.3 mg, 0.19 mmol) was added, and the mixture was stirred at room temperature for 5 min. To the reaction mixture was added methyl iodide (12 μL, 0.19 mmol) and the mixture was stirred at room temperature for 1 hr. Water was added to the reaction mixture, and the mixture was extracted with chloroform. The organic layer was dried over anhydrous sodium sulfate, and the solvent was evaporated under reduced pressure. The residue was purified by silica gel column chromatography (n-hexane:ethyl acetate=0:100→33:67) to give compound (I-251) (yield 3.2 mg, 10%) as a colorless oil.

Example 252

Production of 4'-methoxy-2-(p-tolyloxy)-3,3'-bipyridine (I-252)

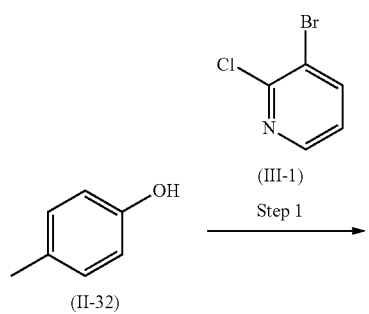

Example 253

Production of 2-(4-ethylphenoxy)-4'-methoxy-3,3'-bipyridine (I-253)

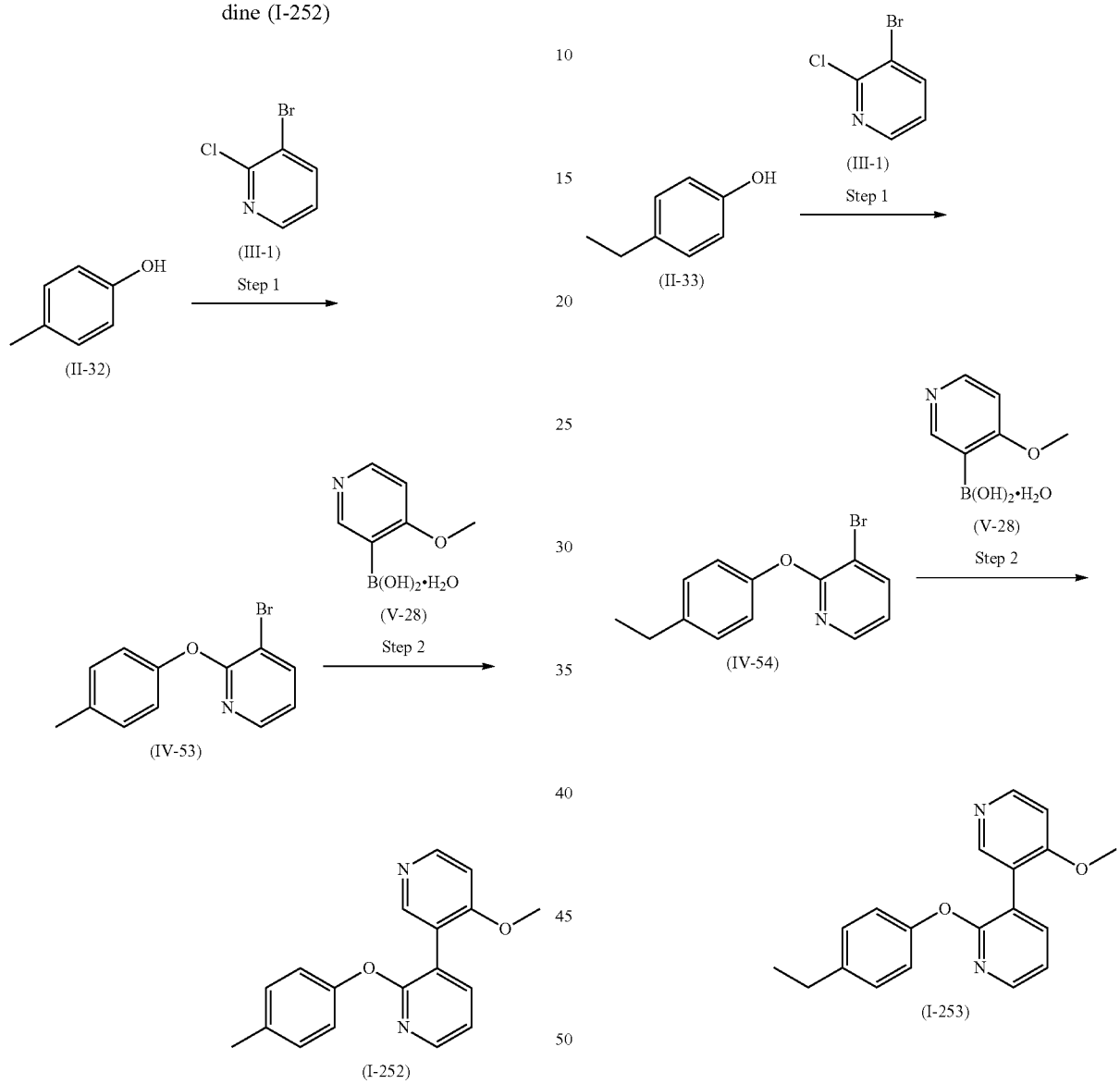

Step 1

By a production method similar to that in compound (IV-1), compound (IV-53) (yield 1.09 g, 78%) was obtained as a yellow oil from compound (III-1) (1.00 g, 5.25 mmol) and p-cresol (II-32) (0.62 mL, 5.8 mmol).

Step 2

By a production method similar to that in compound (I-1), compound (I-252) (yield 34.8 mg, 63%) was obtained as a colorless oil from compound (IV-53) (50.0 mg, 0.189 mmol) and compound (V-28) (43.4 mg, 0.284 mmol).

Step 1

By a production method similar to that in compound (IV-1), compound (IV-54) (yield 1.14 mg, 82%) was obtained as a white solid from compound (III-1) (1.00 g, 5.25 mmol) and 4-ethylphenol (II-33) (698 mg, 5.78 mmol).

Step 2

By a production method similar to that in compound (I-1), compound (I-253) (yield 10.5 mg, 19%) was obtained as a white solid from compound (IV-54) (50.0 mg, 0.180 mmol) and compound (V-28) (41.2 mg, 0.270 mmol).

Example 254

Production of 4'-methoxy-2-(4-propylphenoxy)-3,3'-bipyridine (I-254)

Example 255

Production of 2-(4-isopropylphenoxy)-4'-methoxy-3,3'-bipyridine (I-255)

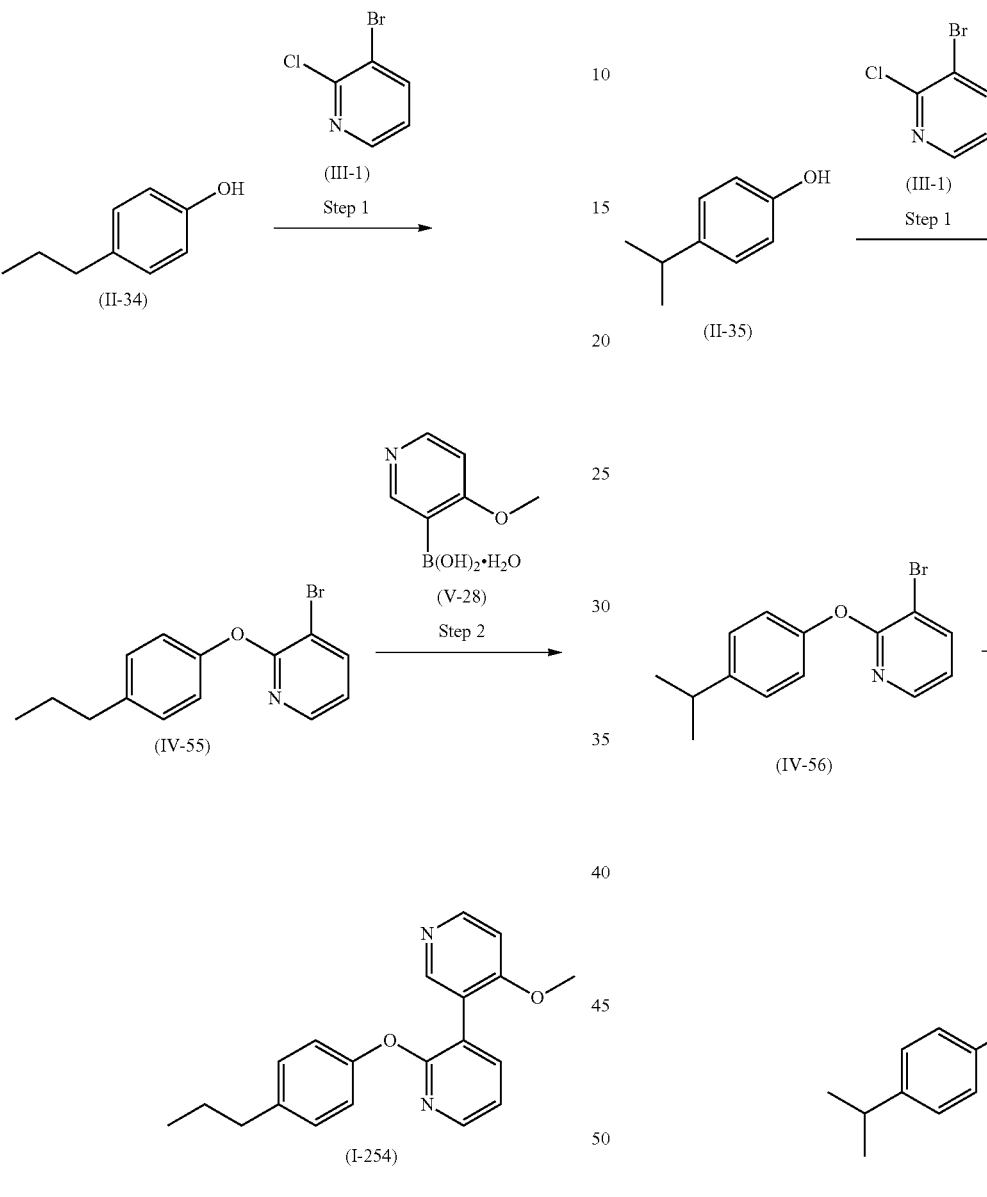

Step 1

By a production method similar to that in compound (IV-1), compound (IV-55) (yield 601 mg, 79%) was obtained as a colorless oil from compound (III-1) (500 mg, 2.60 mmol) and 4-propylphenol (II-34) (425 mg, 3.12 mmol).

Step 2

By a production method similar to that in compound (I-1), compound (I-254) (yield 34.4 mg, 63%) was obtained as a colorless oil from compound (IV-55) (50.0 mg, 0.171 mmol) and compound (V-28) (43.9 mg, 0.257 mmol).

Step 1

By a production method similar to that in compound (IV-1), compound (IV-56) (yield 1.93 g, 90%) was obtained as a white solid from 4-isopropylphenol (II-35) (1.00 g, 7.34 mmol) and compound (III-1) (1.41 g, 7.34 mmol).

Step 2

By a production method similar to that in compound (I-1), compound (I-255) (yield 23.8 mg, 43%) was obtained as a colorless oil from compound (IV-56) (50.0 mg, 0.171 mmol) and compound (V-28) (43.9 mg, 0.257 mmol).

Example 256

Production of 2-[4-(sec-butyl)phenoxy]-4'-methoxy-3,3'-bipyridine (I-256)

Example 257

Production of 2-(4-{[4'-methoxy-(3,3'-bipyridin-2-yl]oxy}phenyl)ethanol (I-257)

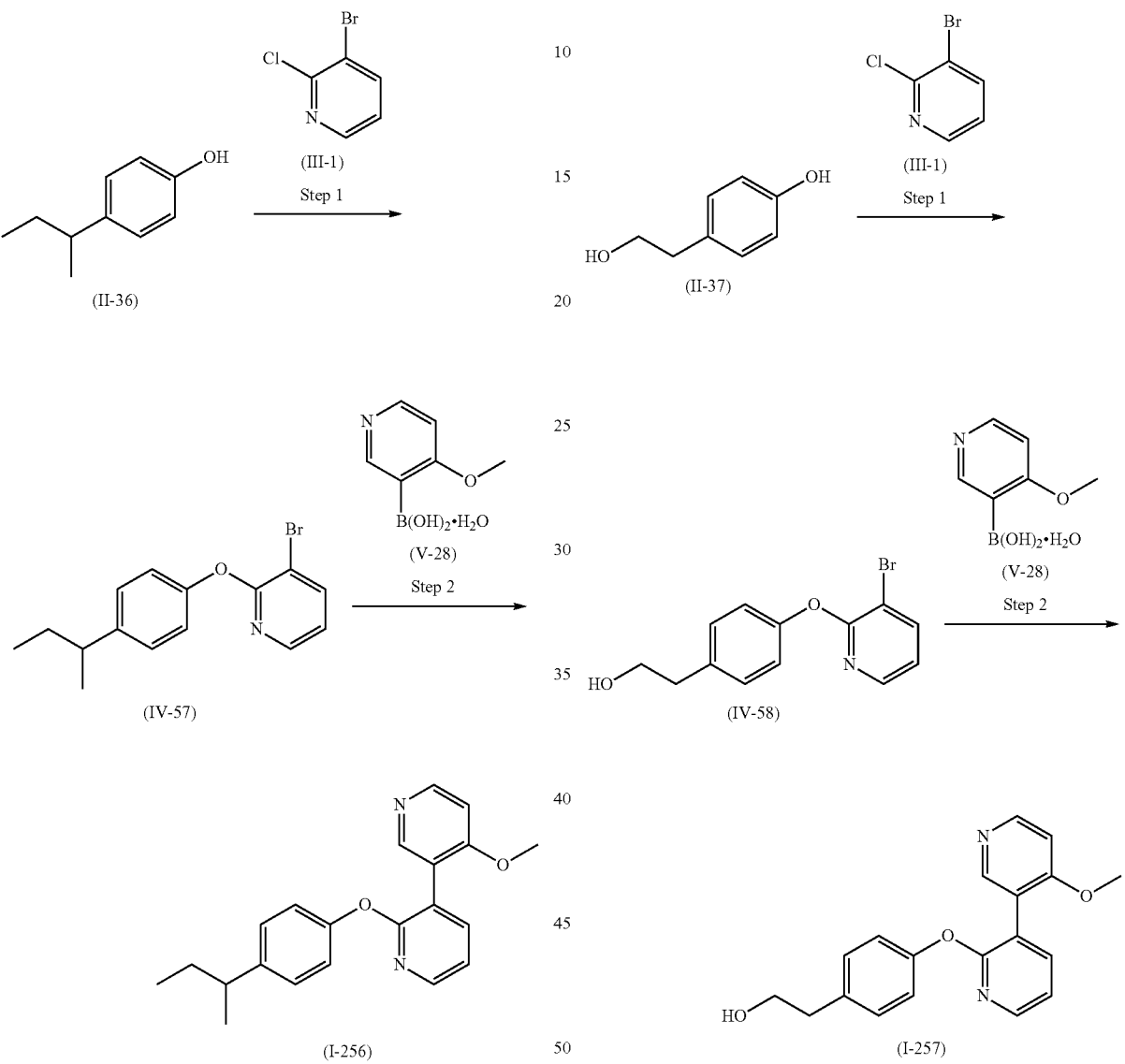

Step 1

By a production method similar to that in compound (IV-1), compound (IV-57) (yield 720 mg, 91%) was obtained as a colorless oil from compound (III-1) (500 mg, 2.60 mmol) and 4-sec-butylphenol (II-36) (468 mg, 3.12 mmol).

Step 2

By a production method similar to that in compound (I-1), compound (I-256) (yield 21.2 mg, 39%) was obtained as a colorless oil from compound (IV-57) (50.0 mg, 0.163 mmol) and compound (V-28) (41.9 mg, 0.245 mmol).

Step 1

By a production method similar to that in compound (IV-1), compound (IV-58) (yield 3.29 g, 98%) was obtained as a white solid from compound (III-1) (2.01 g, 11.4 mmol) and 4-(2-hydroxyethyl)phenol (II-37) (1.74 g, 12.6 mmol).

Step 2

By a production method similar to that in compound (I-1), compound (I-257) (yield 330 mg, 75%) was obtained as a colorless oil from compound (IV-58) (400 mg, 1.36 mmol) and compound (V-28) (312 mg, 2.04 mmol).

Example 258

Production of 4'-methoxy-2-(4-vinylphenoxy)-3,3'-bipyridine (I-258)

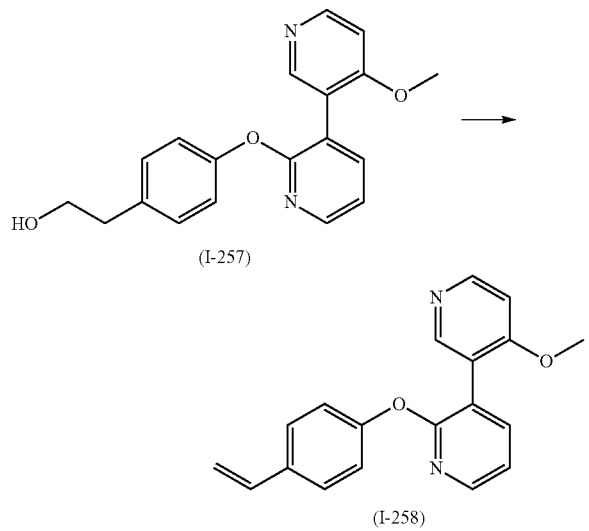

Compound (I-257) (22.0 mg, 0.0680 mmol) was dissolved in DCM (1.0 mL), TEA (29 μL, 0.205 mmol) and methanesulfonyl chloride (8.0 μL, 0.10 mmol) were successively added, and the mixture was stirred at room temperature for 30 min. Water was added to the reaction mixture, and the mixture was extracted with ethyl acetate. The organic layer was washed successively with water and saturated brine, dried over anhydrous sodium sulfate, and filtered. The solvent was evaporated under reduced pressure to give a mesylated product.

The obtained mesylated product was dissolved in ethanol (0.05 mL), cesium carbonate (44.5 mg, 0.136 mmol) was added, and the mixture was stirred at room temperature for 19 hr. Water was added to the reaction mixture, and the mixture was extracted with chloroform, and the solvent was evaporated under reduced pressure. The residue was purified by silica gel column chromatography (n-hexane:ethyl acetate) to give compound (I-248) [yield 5.8 mg, 28% (2 steps)] as a white solid.

Reference Example 259

Production of 4'-methoxy-2-{4-[(trimethylsilyl)ethynyl]phenoxy}-3,3'-bipyridine (I-259)

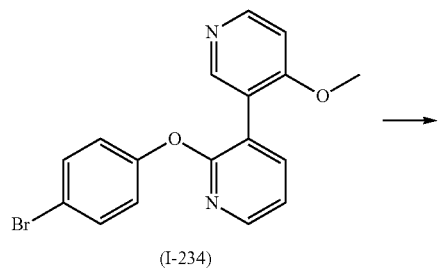

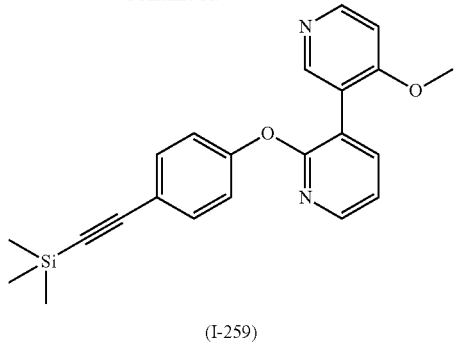

Compound (I-234) (300 mg, 0.840 mmol), copper iodide (16.0 mg, 0.0840 mmol) and PdCl$_2$(dppf) (34.3 mg, 0.0420 mmol) were suspended in TEA (3.0 mL), trimethylsilylacetylene (0.24 mL, 1.7 mmol) was added, and the mixture was stirred under microwave irradiation at 100° C. for 30 min. Thereafter, the mixture was stirred under microwave irradiation at 120° C. for 30 min. The reaction mixture was filtered through Celite, and the solvent was evaporated under reduced pressure. The residue was purified by silica gel column chromatography (NH silica gel, n-hexane:ethyl acetate=95:5→60:40) to give compound (I-259) (yield 297 mg, 94%) as an orange solid.

Example 260

Production of 2-(4-ethynylphenoxy)-4'-methoxy-3,3'-bipyridine (I-260)

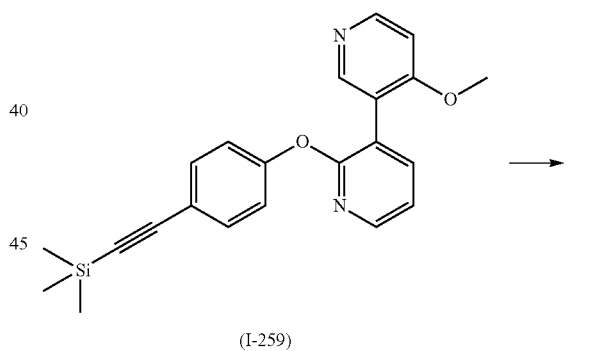

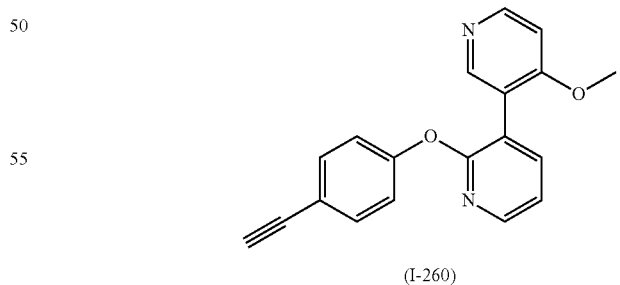

Compound (I-259) (285 mg, 0.761 mmol) was dissolved in THF (2.0 mL), TBAF (1.0 mol/L THF solution, 1.9 mL, 1.9 mmol) was added, and the mixture was stirred at room temperature for 1 hr. Thereafter, the mixture was stirred under microwave irradiation at 120° C. for 30 min. Water was added to the reaction mixture, and the mixture was extracted with ethyl acetate. The organic layer was washed successively with water and saturated brine, dried over anhydrous sodium sulfate, and filtered. The solvent was evaporated under reduced pressure, and the residue was purified by silica gel column chromatography (n-hexane: ethyl acetate=3:97→50:50) to give compound (I-260) (yield 67.8 mg, 30%) as a white solid.

Example 261

Production of 2-(4-cyclopropylphenoxy)-4'-methoxy-3,3'-bipyridine (I-261)

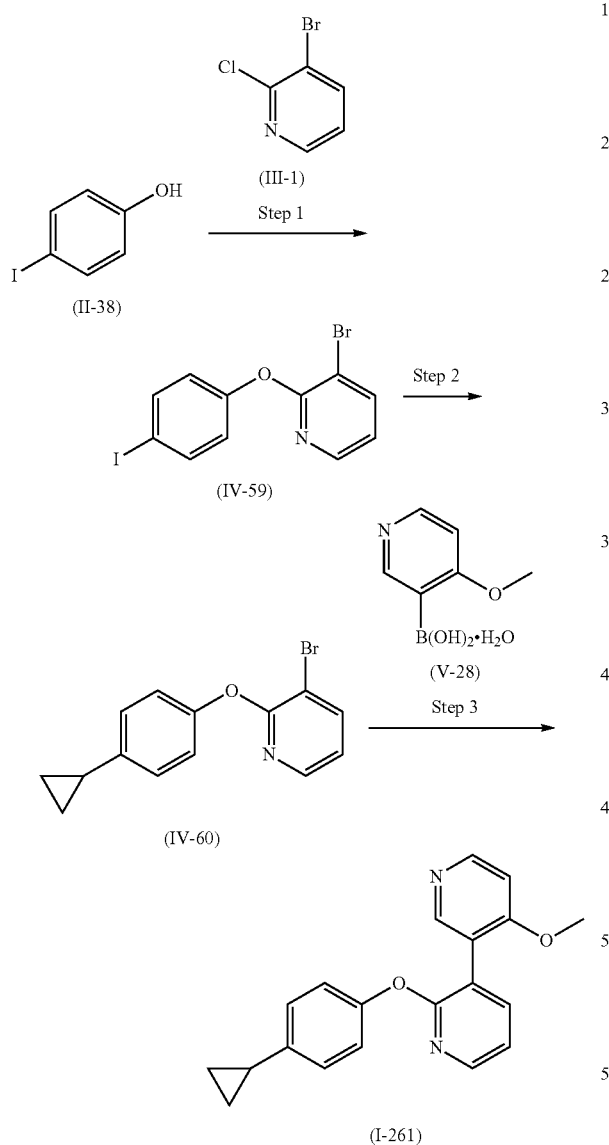

Step 1
By a production method similar to that in compound (IV-1), compound (IV-59) (yield 14.8 mg, 87%) was obtained as a compound (III-1) (9.62 g, 50.0 mmol) and 4-iodophenol (II-38) (10.0 g, 45.5 mmol).
Step 2
Compound (IV-59) (500 mg, 1.33 mmol) was dissolved in THF (2.0 mL), cyclopropylzinc bromide (0.5 mol/L THF solution, 2.9 mL, 1.5 mmol) and tetrakis(triphenylphosphine)palladium (77.0 mg, 0.0660 mmol) were successively added, and the mixture was stirred at room temperature for 3.5 hr. To the reaction mixture was added saturated aqueous sodium hydrogen carbonate solution, and the mixture was extracted with ethyl acetate. The organic layer was washed successively with saturated aqueous sodium hydrogen carbonate solution and saturated brine, dried over anhydrous sodium sulfate, and filtered. The solvent was evaporated under reduced pressure, and the residue was purified by silica gel column chromatography (n-hexane:ethyl acetate=97:3→80:20) to give compound (IV-60) (yield 172 mg, 45%) as a colorless oil.
Step 3
By a production method similar to that in compound (I-1), compound (I-261) (yield 14.4 mg, 33%) was obtained as a colorless oil from compound (IV-60) (40.0 mg, 0.138 mmol) and compound (V-28) (31.6 mg, 0.207 mmol).

Example 262

Production of 2-(3,4-dimethylphenoxy)-4'-methoxy-3,3'-bipyridine (I-262)

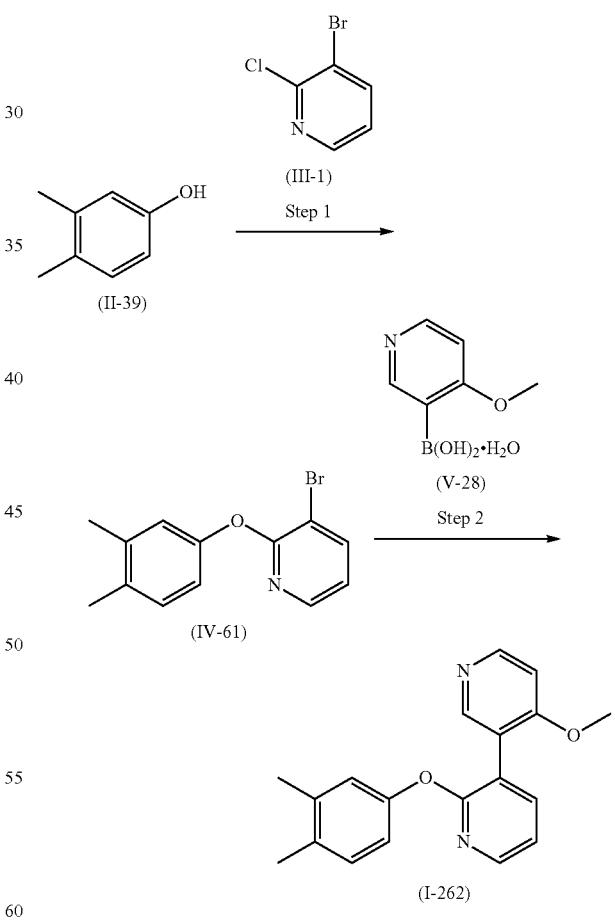

Step 1
By a production method similar to that in compound (IV-1), compound (IV-61) (yield 960 mg, 42%) was obtained as a colorless oil from compound (III-1) (1.57 mg, 8.18 mmol) and 3,4-dimethylphenol (II-39) (1.0 mg, 8.18 mmol).

Step 2

By a production method similar to that in compound (I-1), compound (I-262) (yield 12.3 mg, 11%) was obtained as a colorless oil from compound (IV-61) (100 mg, 0.360 mmol) and compound (V-28) (82.6 mg, 0.540 mmol).

Example 263

Production of 2-(4-ethyl-3-methylphenoxy)-4'-methoxy-3,3'-bipyridine (I-263)

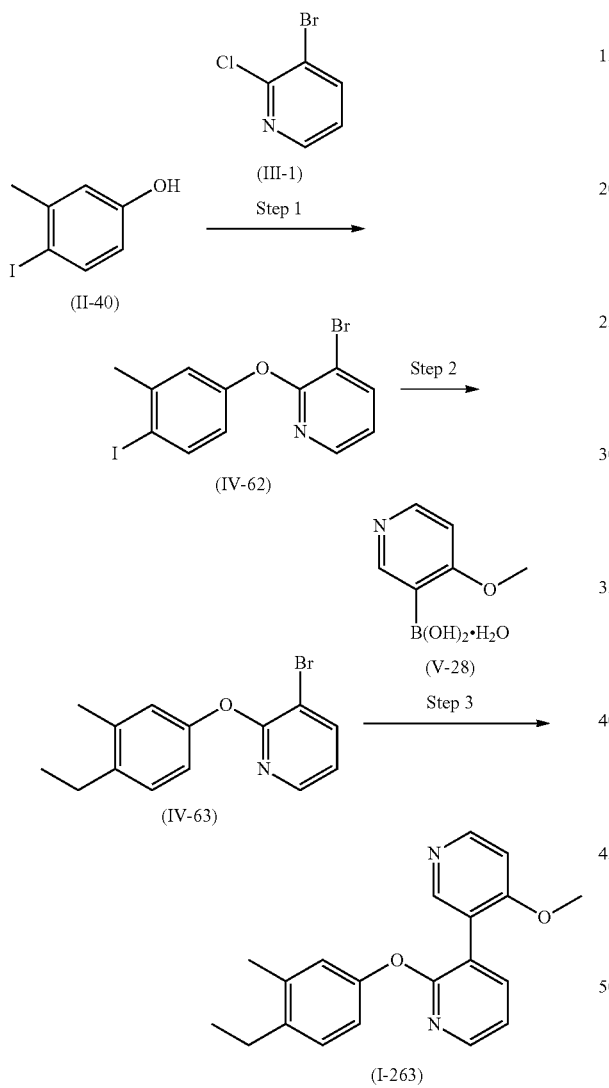

Step 1

By a production method similar to that in compound (IV-1), compound (IV-62) (yield 3.12 mg, 94%) was obtained as a white solid from compound (III-1) (1.97 g, 10.3 mmol) and 4-iodo-3-methylphenyl (II-40) (2.00 g, 8.55 mmol).

Step 2

Compound (IV-62) (515 mg, 1.32 mmol) was dissolved in THF (3.0 mL), PdCl$_2$(dppf)·DCM (53.9 mg, 0.0660 mmol) and diethylzinc (1.0 mol/L THF solution, 1.4 mL, 1.39 mmol) were successively added, and the mixture was stirred at room temperature for 2.5 hr. To the reaction mixture was added saturated aqueous sodium hydrogen carbonate solution, and the mixture was extracted with ethyl acetate. The organic layer was washed successively with saturated aqueous sodium hydrogen carbonate solution and saturated brine, dried over anhydrous sodium sulfate, and filtered. The solvent was evaporated under reduced pressure, and the residue was purified by silica gel column chromatography (n-hexane:ethyl acetate=97:3→85:15) to give compound (IV-63) (yield 309 mg, 80%) as a colorless oil.

Step 3

By a production method similar to that in compound (I-1), compound (I-263) (yield 13.8 mg, 25%) was obtained as a colorless oil from compound (IV-63) (50.0 mg, 0.171 mmol) and compound (V-28) (39.3 mg, 0.257 mmol).

Example 264

Production of 2-(3-ethyl-4-methylphenoxy)-4'-methoxy-3,3'-bipyridine (I-264)

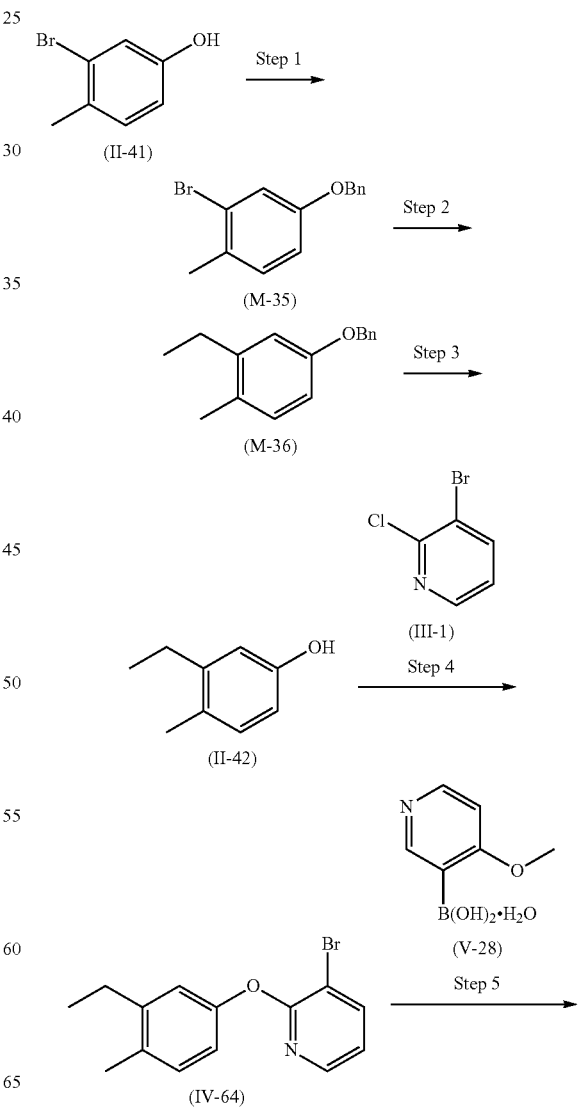

199
-continued

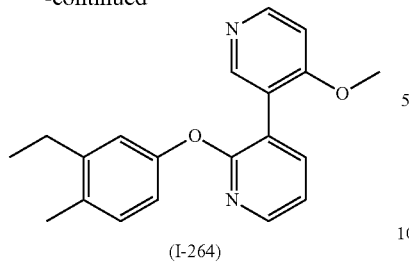

(I-264)

Step 1

3-Bromo-4-methylphenol (II-41) (500 mg, 2.67 mmol) was dissolved in DMF (3.0 mL), potassium carbonate (739 mg, 5.35 mmol), benzyl bromide (0.38 mL, 3.2 mmol) and TBAI (49.4 mg, 0.134 mmol) were successively added under ice-cooling, and the mixture was stirred at room temperature for 1 hr. Water was added to the reaction mixture, and the mixture was extracted with ethyl acetate. The organic layer was washed successively with water and saturated brine, dried over anhydrous sodium sulfate, and filtered. The solvent was evaporated under reduced pressure, and the residue was purified by silica gel column chromatography (n-hexane:ethyl acetate=97:3→85:15) to give a benzyloxy compound (M-35) (yield 635 mg, 88%) as a pale-yellow oil.

Step 2

By a production method similar to that in compound (IV-63), 4-(benzyloxy)-2-ethyl-1-methylbenzene (M-36) (yield 290 mg, 89%) was obtained as a colorless oil from benzyloxy compound (M-35) (400 mg, 1.44 mmol) and diethylzinc (1.0 mol/L THF solution, 2.2 mL, 2.2 mmol).

Step 3

4-(Benzyloxy)-2-ethyl-1-methylbenzene (M-36) (290 mg, 1.28 mmol) was dissolved in THF (2.0 mL) and methanol (2.0 mL), 20% palladium hydroxide/carbon (29.0 mg) was added and the mixture was stirred under a hydrogen atmosphere (1 atm) at room temperature for 17 hr. The solid reagent was removed by filtration through Celite and the solvent was evaporated under reduced pressure to give compound (II-42) (yield 175 mg, quantitative) as a pale-orange oil.

Step 4

By a production method similar to that in compound (IV-1), compound (IV-64) (yield 320 mg, 85%) was obtained as a colorless oil from compound (III-1) (297 mg, 1.54 mmol) and compound (II-42) (175 mg, 1.29 mmol).

Step 5

By a production method similar to that in compound (I-1), compound (I-264) (yield 36.7 mg, 67%) was obtained as a colorless oil from compound (IV-64) (50.0 mg, 0.171 mmol) and compound (V-28) (43.9 mg, 0.257 mmol).

200

Example 265

Production of 2-(3-ethylphenoxy)-4'-methoxy-3,3'-bipyridine (I-265)

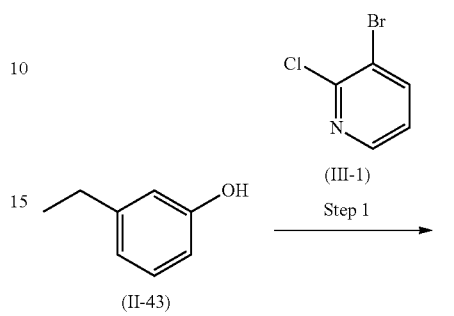

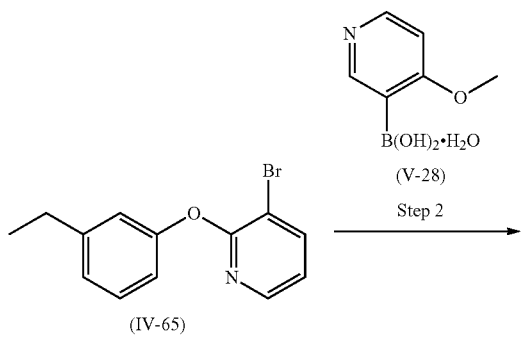

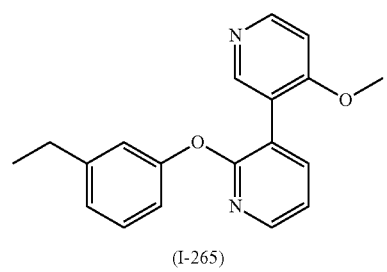

(I-265)

Step 1

By a production method similar to that in compound (IV-1), compound (IV-65) (yield 1.22 g, 84%) was obtained as a colorless oil from compound (III-1) (1.00 g, 5.20 mmol) and 3-ethylphenol (II-43) (0.75 mL, 6.2 mmol).

Step 2

By a production method similar to that in compound (I-1), compound (I-265) (yield 271 mg, 57%) was obtained as a white solid from compound (IV-65) (100 mg, 0.360 mmol) and compound (V-28) (82.0 mg, 0.539 mmol).

Example 266

Production of 2-[(2,3-dihydro-1H-inden-5-yl)oxy]-4'-methoxy-3,3'-bipyridine (I-266)

Example 267

Production of 4'-methoxy-[(5,6,7,8-tetrahydronaphthalen-2-yl)oxy]-3,3'-bipyridine (I-267)

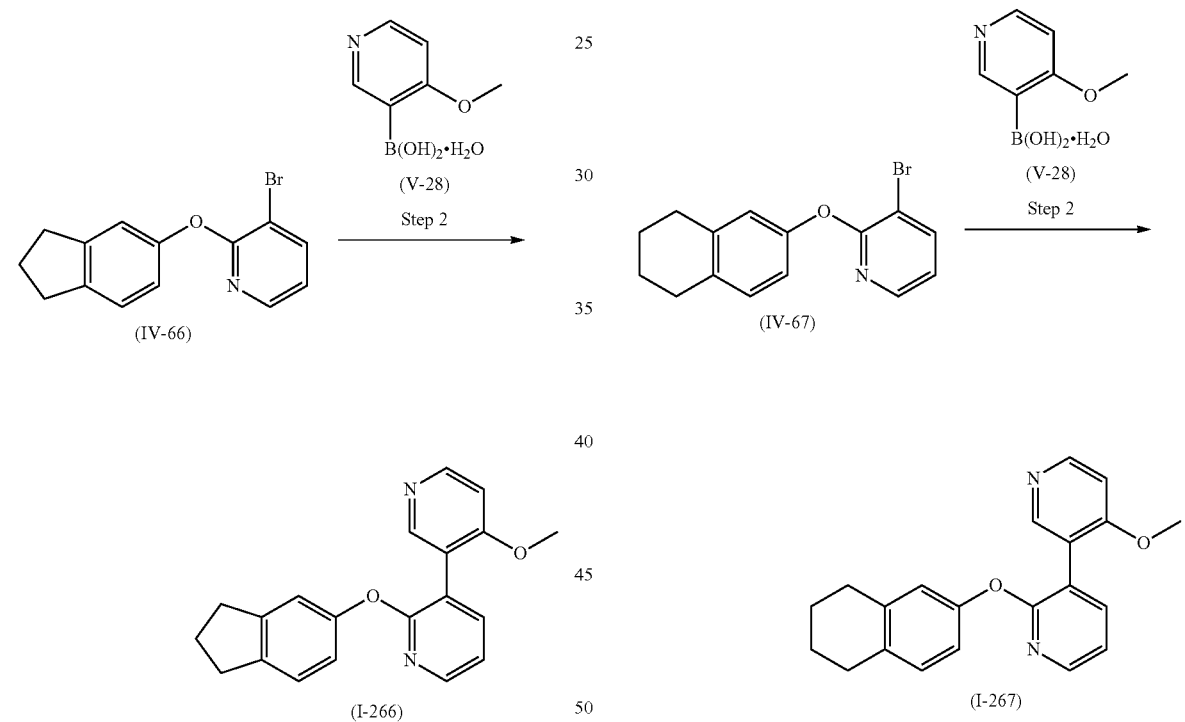

Step 1

By a production method similar to that in compound (IV-1), compound (IV-66) (yield 198 mg, 66%) was obtained from compound (II-44) (209 mg, 1.56 mmol) and compound (III-1) (200 mg, 1.04 mmol).

Step 2

By a production method similar to that in compound (I-1), compound (I-266) (yield 59 mg, quantitative) was obtained as a colorless oil from compound (IV-66) (50.0 mg, 0.172 mmol) and compound (V-28) (39.0 mg, 0.258 mmol).

Step 1

By a production method similar to that in compound (IV-1), compound (IV-67) (yield 6.15 g, 97%) was obtained as a pale-yellow oil from compound (III-1) (4.00 mg, 20.8 mmol) and 5,6,7,8-tetrahydronaphthalen-2-ol (II-45) (3.23 g, 21.8 mmol).

Step 2

By a production method similar to that in compound (I-1), compound (I-267) (yield 27.5 mg, 50%) was obtained as a colorless oil from compound (IV-67) (50.0 mg, 0.164 mmol) and compound (V-28) (30.2 mg, 0.197 mmol).

Example 268

Production of 3-(2-methoxyphenyl)-2-[(5,6,7,8-tetrahydronaphthalen-2-yl)oxy]pyridine (I-268)

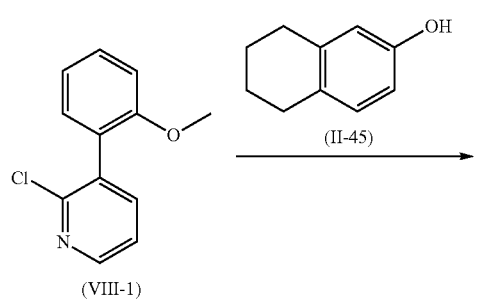

Compound (VIII-1) (50.0 mg, 0.288 mmol) (5,6,7,8-tetrahydronaphthalen-2-ol (II-45) (38.0 mg, 0.254 mmol) were dissolved in NMP (1 mL), cesium carbonate (90.0 mg, 0.276 mmol) was added and the mixture was stirred at 180° C. for 4 hr. The reaction mixture was cooled, water was added, and the mixture was extracted with ethyl acetate. The organic layer was washed with water, dried over anhydrous sodium sulfate, and filtered. The solvent was evaporated under reduced pressure, and the residue was purified by silica gel column chromatography (n-hexane:ethyl acetate=20:1) to give compound (I-268) (yield 17.0 mg, 23%) as an oil.

Example 269

Production of 2-methoxy-2'-[(5,6,7,8-tetrahydronaphthalen-2-yl)oxy]-3,3'-bipyridine (I-269)

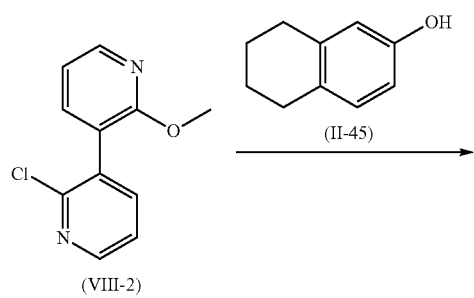

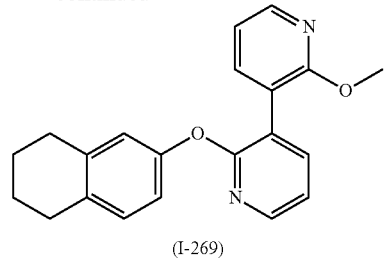

By a production method similar to that in compound (I-268), compound (I-269) (yield 40.0 mg, 53%) was obtained as an oil from compound (VIII-2) (50.0 mg, 0.227 mmol) and compound (II-45) (38.0 mg, 0.254 mmol).

Example 270

Production of 2-[(2,3-dihydro-1H-inden-5-yl)oxy]-2'-methoxy-3,3'-bipyridine (I-270)

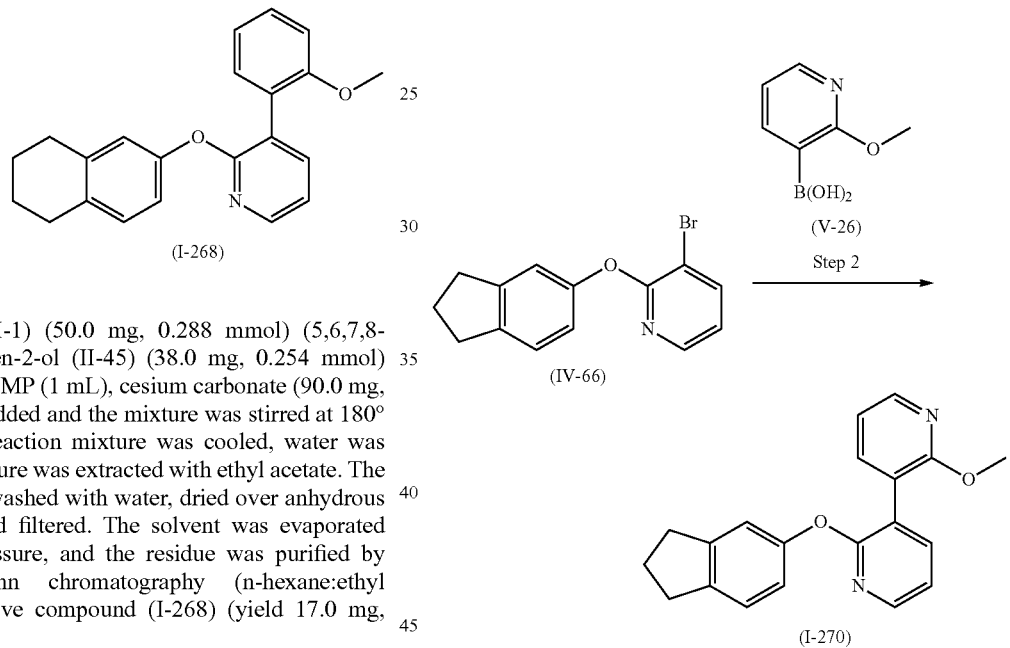

By a production method similar to that in compound (I-1), compound (I-270) (yield 99 mg, 90%) was obtained as a white solid from compound (IV-66) (100 mg, 0.345 mmol) and compound (V-26) (79.1 mg, 0.518 mmol).

Example 271

Production of 4'-methoxy-5-{2-[(5,6,7,8-tetrahydronaphthalen-2-yl)oxy]pyridin-3-yl}pyrimidine (I-271)

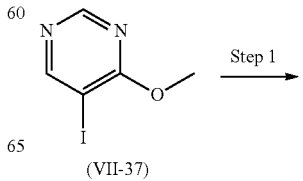

205

-continued

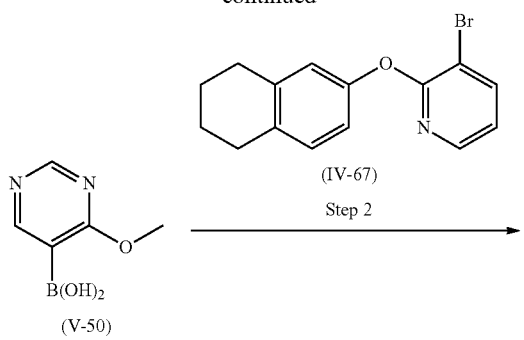

206

-continued

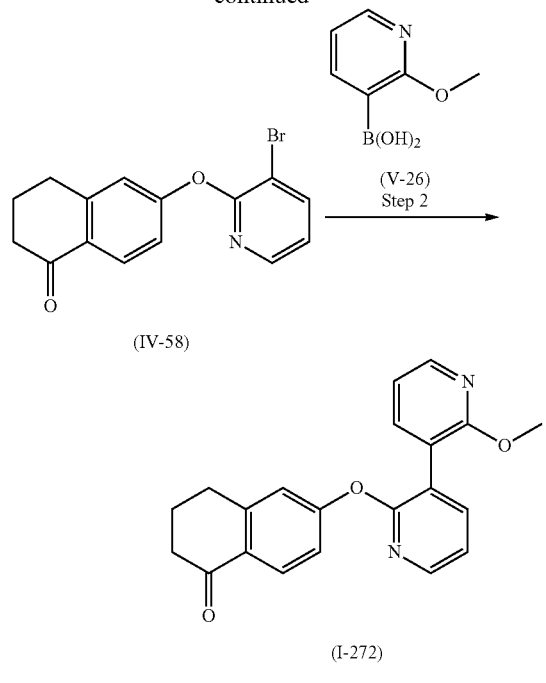

Step 1

By a production method similar to that in compound (VIa-4a), compound (V-50) (yield 180 mg, 14%) was obtained as a pale-yellow solid from compound (VII-37) (2.00 g, 8.47 mmol).

Step 2

By a production method similar to that in compound (I-1), compound (I-271) (yield 5.4 mg, 16%) was obtained as a colorless oil from compound (IV-67) (30.0 mg, 0.0960 mmol) and compound (V-50) (17.8 mg, 0.115 mmol).

Example 272

Production of 6-{[2'-methoxy-(3,3-bipyridin)-2-yl]oxy}-3,4-dihydronaphthalen-1(2H)-one (I-272)

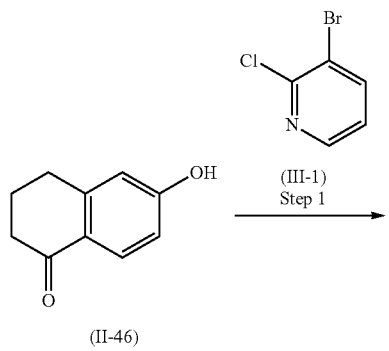

Step 1

Compound (III-1) (300 mg, 1.56 mmol), compound (II-46) (279 mg, 1.72 mmol), tris(dibenzylideneacetone)dipalladium (143 mg, 0.156 mmol), xantphos (271 mg, 0.468 mmol) and cesium carbonate (1.52 g, 4.68 mmol) were dissolved in 1,4-dioxane (5.0 mL), and the mixture was stirred at 90° C. for 16 hr. The reaction mixture was filtered, and the filtrate was diluted with ethyl acetate, and wash successively with saturated aqueous sodium hydrogen carbonate solution and saturated brine. The organic layer was washed dried over anhydrous sodium sulfate, and filtered, and the solvent was evaporated under reduced pressure. The residue was purified by silica gel column chromatography (n-hexane:ethyl acetate) to give compound (I-68) (yield 222 mg, 52%) as a pale-yellow white solid.

Step 2

By a production method similar to that in compound (I-1), compound (I-272) (yield 20 mg, 32%) was obtained as a white solid from compound (IV-68) (50.0 mg, 0.183 mmol) and compound (V-26) (41.8 mg, 0.275 mmol).

Example 273

Production of 7-{[3-(2-methoxyphenyl)pyridin-2-yl]oxy}-3,4-dihydronaphthalen-1(2H)-one (I-273)

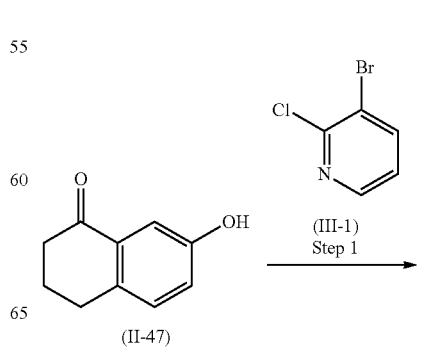

207

-continued

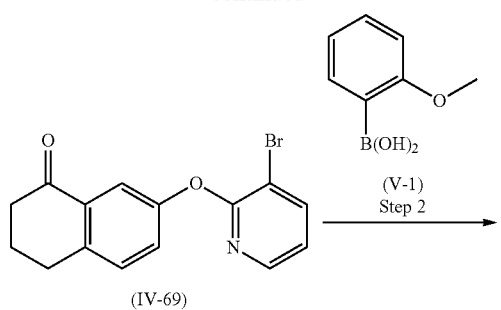

(IV-69)

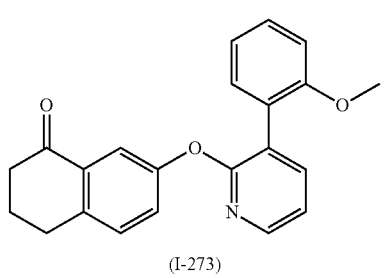

(I-273)

Step 1

By a production method similar to that in compound (IV-1), compound (IV-69) (yield 150 mg, 45%) was obtained from compound (III-1) (200 mg, 1.04 mmol) and compound (II-47) (253 mg, 1.56 mmol).

Step 2

By a production method similar to that in compound (I-1), compound (I-273) (yield 40 mg, 74%) was obtained as a colorless oil from compound (IV-69) (50.0 mg, 0.157 mmol) and compound (V-1) (36.0 mg, 0.236 mmol).

Example 274

Production of 2-[4-(2-ethoxyethyl)phenoxy]-4'-methoxy-3,3'-bipyridine (I-274)

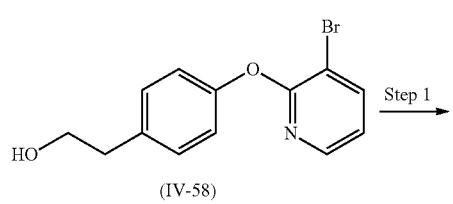

(IV-58)

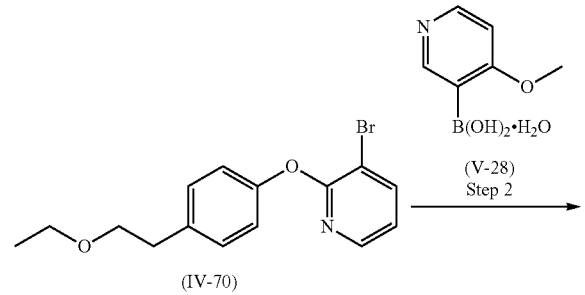

(IV-70)

208

-continued

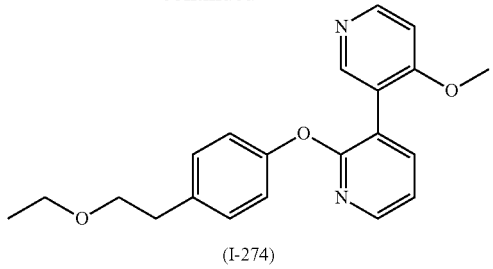

(I-274)

Step 1

By a production method similar to that in compound (IV-24), compound (IV-70) (yield 52.9 mg, 97%) was obtained from compound (IV-58) (50.0 mg, 0.170 mmol) and iodoethane (41 µL, 0.51 mmol).

Step 2

By a production method similar to that in compound (I-1), compound (I-274) (yield 23.8 mg, 43%) was obtained as a colorless oil from compound (IV-70) (52.9 mg, 0.164 mmol) and compound (V-28) (37.7 mg, 0.246 mmol).

Example 275

Production of 4'-methoxy-2-[4-(1-methoxy-2-methylpropan-2-yl)phenoxy]-3,3'-bipyridine (I-275)

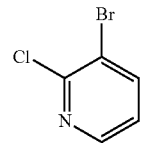

(II-48)

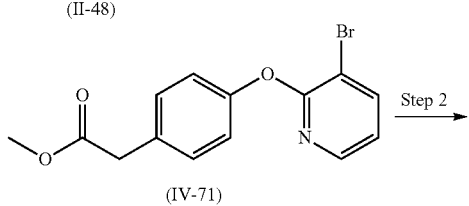

(IV-71)

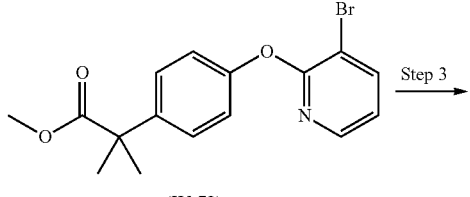

(IV-72)

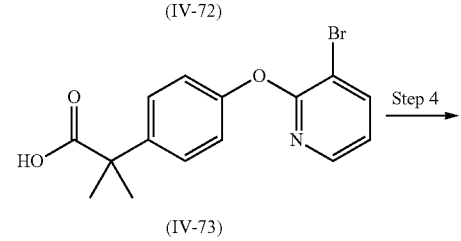

(IV-73)

209
-continued

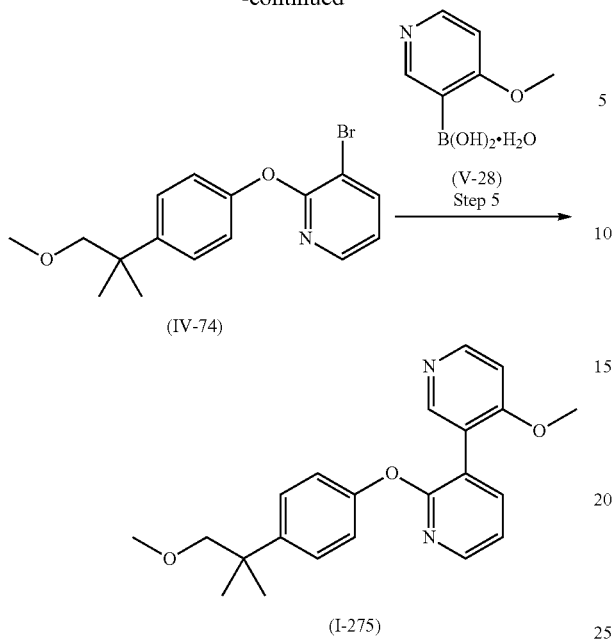

(IV-74)

(I-275)

Step 1
By a production method similar to that in compound (IV-1), compound (IV-71) (yield 330 mg, 20%) was obtained as a colorless oil from compound (III-1) (1.00 g, 5.20 mmol) and compound (II-48) (1.04 g, 6.24 mmol).

Step 2
Compound (IV-71) (330 mg, 1.02 mmol) was dissolved in DMF (5.0 mL), 50% sodium hydride (148 mg, 3.08 mmol) was added under ice-cooling, and the mixture was stirred under ice-cooling for 30 min. To the reaction mixture was added methyl iodide (0.19 mL, 3.1 mmol) under ice-cooling, and the mixture was stirred at room temperature for 2.5 hr. Water was added to the reaction mixture, and the mixture was extracted with ethyl acetate. The organic layer was washed successively with water and saturated brine, dried over anhydrous sodium sulfate, and filtered. The solvent was evaporated under reduced pressure, and the residue was purified by silica gel column chromatography (n-hexane: ethyl acetate=0:100→100:0) to give compound (IV-72) (yield 86.2 mg, 24%).

Step 3
To a solution of compound (IV-72) (86.0 mg, 0.246 mmol) in THF (4.0 mL) and methanol (4.0 mL) was added sodium borohydride (60.9 mg, 1.61 mmol), and the mixture was stirred at room temperature for 1 hr. After completion of the reaction, the solvent was evaporated under reduced pressure. The residue was purified by silica gel column chromatography (n-hexane:ethyl acetate=0:100→50:50) to give alcohol compound (IV-73) (yield 61.5 mg, 78%) as a colorless oil.

Step 4
By a production method similar to that in compound (IV-24), compound (IV-74) (yield 46.4 mg, 73%) was obtained from alcohol compound (IV-73) (61.0 mg, 0.189 mmol) and methyl iodide (18 μL, 0.28 mmol).

Step 5
By a production method similar to that in compound (I-1), compound (I-275) (yield 10.0 mg, 40%) was obtained as white solid from compound (IV-74) (23.0 mg, 0.0684 mmol) and compound (V-28) (15.8 mg, 0.103 mmol).

210

Example 276

Production of 4'-methoxy-2-{4-[1-(methoxymethyl)cyclopropyl]phenoxy}-3,3'-bipyridine (I-276)

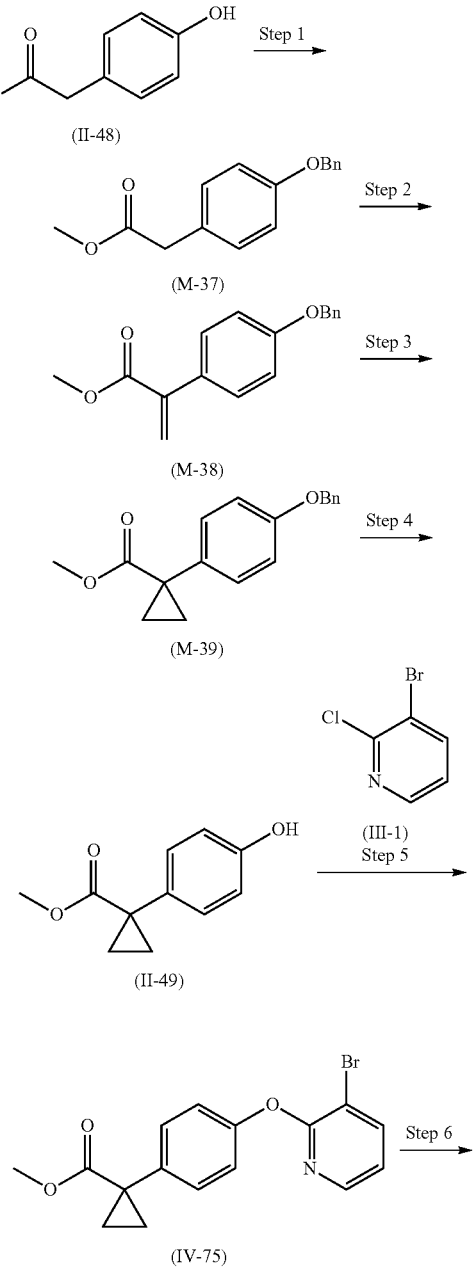

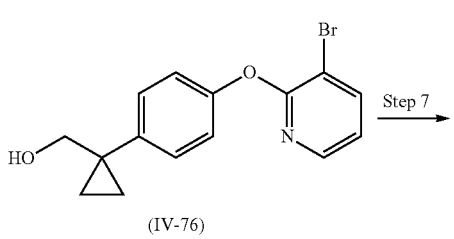

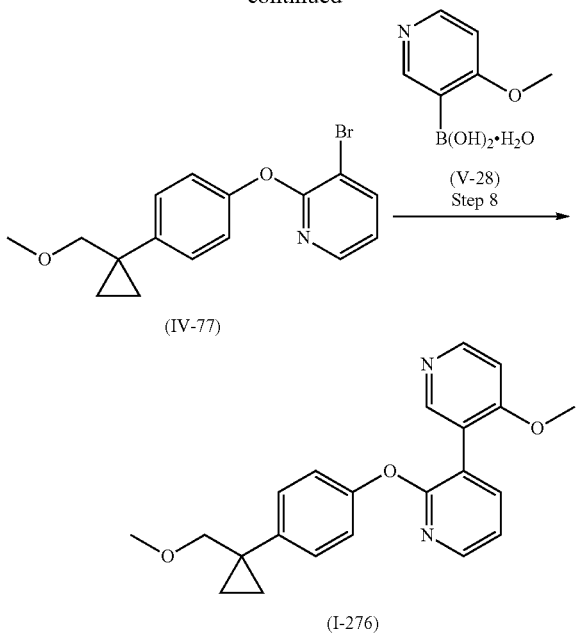

(IV-77)

(I-276)

Step 1

Compound (II-48) (3.00 g, 18.1 mmol) was dissolved in DMF (18 mL), potassium carbonate (5.00 g, 36.2 mmol), benzyl bromide (3.2 mL, 27.2 mmol) and TBAI (669 mg, 1.81 mmol) were successively added, and the mixture was stirred at room temperature for 1 hr. Water was added to the reaction mixture, and the mixture was extracted with ethyl acetate. The organic layer was washed successively with water and saturated brine, dried over anhydrous sodium sulfate, and filtered. The solvent was evaporated under reduced pressure, and the residue was purified by silica gel column chromatography (NH silica gel, n-hexane:ethyl acetate=97:3→85:15) to give compound (M-37) (yield 3.01 g, 65%) as a colorless oil.

Step 2

Compound (M-37) (930 mg, 3.63 mmol) was dissolved in toluene (12 mL), potassium carbonate (778 mg, 5.63 mmol), paraformaldehyde hydrate (172 mg, 5.45 mmol) and TBAI (67.2 mg, 0.182 mmol) were successively added, and the mixture was stirred at 80° C. for 18.5 hr. Water was added to the reaction mixture, and the mixture was extracted with ethyl acetate. The organic layer was washed successively with water and saturated brine, dried over anhydrous sodium sulfate, and filtered. The solvent was evaporated under reduced pressure, and the residue was purified by silica gel column chromatography (n-hexane:ethyl acetate=97:3→80: 20) to give compound (M-38) (yield 294 mg, 30%) as a colorless oil.

Step 3

Trimethylsulfonium iodide (315 mg, 1.43 mmol) was dissolved in DMSO (1.0 mL), KOt-Bu (185 mg, 1.65 mmol) was added, and the mixture was stirred at room temperature for 1 hr. To the reaction mixture was added a solution of compound (M-38) (294 mg, 1.10 mmol) in DMSO (3.0 mL), and the mixture was was stirred at room temperature for 17 hr. Water was added to the reaction mixture, and the mixture was extracted with ethyl acetate. The organic layer was washed successively with water and saturated brine, dried over anhydrous sodium sulfate, and filtered. The solvent was evaporated under reduced pressure, and the residue was purified by silica gel column chromatography (n-hexane: ethyl acetate=97:3→80:20) to give cyclopropyl compound (M-39) (yield 184 mg, 59%) as a colorless oil.

Step 4

The cyclopropyl compound (M-39) (184 mg, 0.652 mmol) was dissolved in ethanol (6.5 mL), palladium/carbon (36.8 mg) was added and the mixture was stirred under a hydrogen atmosphere (1 atm) at room temperature for 17 hr. The solid reagent was removed filtration, and the solvent was evaporated under reduced pressure to give compound (II-49) (yield 130 mg, quantitative) as a white solid.

Step 5

By a production method similar to that in compound (IV-1), compound (IV-75) (yield 227 mg, quantitative) was obtained as a colorless oil from compound (III-1) (188 mg, 0.978 mmol) and compound (II-49) (125 mg, 0.652 mmol).

Step 6

Compound (IV-75) (227 mg, 1.61 mmol) was dissolved in THF (4.0 mL) and ethanol (3.0 mL), lithium borohydride (3.0 mol/L THF solution, 0.33 mL, 0.98 mmol) was added under ice-cooling, and the mixture was stirred at room temperature for 18 hr. Thereafter, lithium borohydride (3.0 mol/L THF solution, 0.33 mg, 0.98 mmol) was further added under ice-cooling, and the mixture was stirred at room temperature for 3 hr. To the reaction mixture was added saturated aqueous ammonium chloride solution, and the mixture was extracted with ethyl acetate. The organic layer was washed successively with water and saturated aqueous ammonium chloride solution and saturated brine, dried over anhydrous sodium sulfate, and filtered. The solvent was evaporated under reduced pressure, and the residue was purified by silica gel column chromatography (n-hexane: ethyl acetate=90:10→50:50) to give compound (I-76) (yield 139 mg, 67%) as a colorless oil.

Step 7

By a production method similar to that in compound (IV-24), compound (IV-77) (yield 90.9 mg, 68%) was obtained as a white solid from compound (IV-76) (128 mg, 0.400 mmol) and methyl iodide (32 μL, 0.52 mmol).

Step 8

By a production method similar to that in compound (I-1), compound (I-276) (yield 21.4 mg, 66%) was obtained as a white solid from compound (IV-77) (30.0 mg, 0.0898 mmol) and compound (V-28) (20.6 mg, 0.135 mmol).

Example 277

Production of 2-[4-(benzyloxy)phenoxy]-2'-methoxy-3,3'-bipyridine (I-277)

By a production method similar to that in compound (I-268), compound (I-277) (yield 24.0 mg, 23%) was obtained as a solid from compound (VIII-2) (60.0 mg, 0.272 mmol) and 4-(benzyloxy)phenol (II-50) (59.0 mg, 0.298 mmol).

Example 278

Production of 4-{[4'-methoxy-3,3'-bipyridin)-2-yl]oxy}phenethyl propionate (I-278)

Compound (I-257) (40.1 mg, 0.124 mmol) was dissolved in DMF (0.62 mL), TEA (21 μL, 0.15 mmol) and propionyl chloride (13.8 mg, 0.149 mmol) were added and the mixture was stirred at room temperature for 30 min. Water was added to the reaction mixture, and the mixture was extracted with ethyl acetate. The organic layer was dried over anhydrous sodium sulfate, and filtered, and the solvent was evaporated under reduced pressure. The residue was purified by silica gel column chromatography (n-hexane:ethyl acetate) to give compound (I-278) (yield 29.1 mg, 62%) as a colorless oil.

Example 279

Production of methyl 3-(4-{[4'-methoxy-3,3'-bipyridin-2-yl]oxy}phenyl)propionate (I-279)

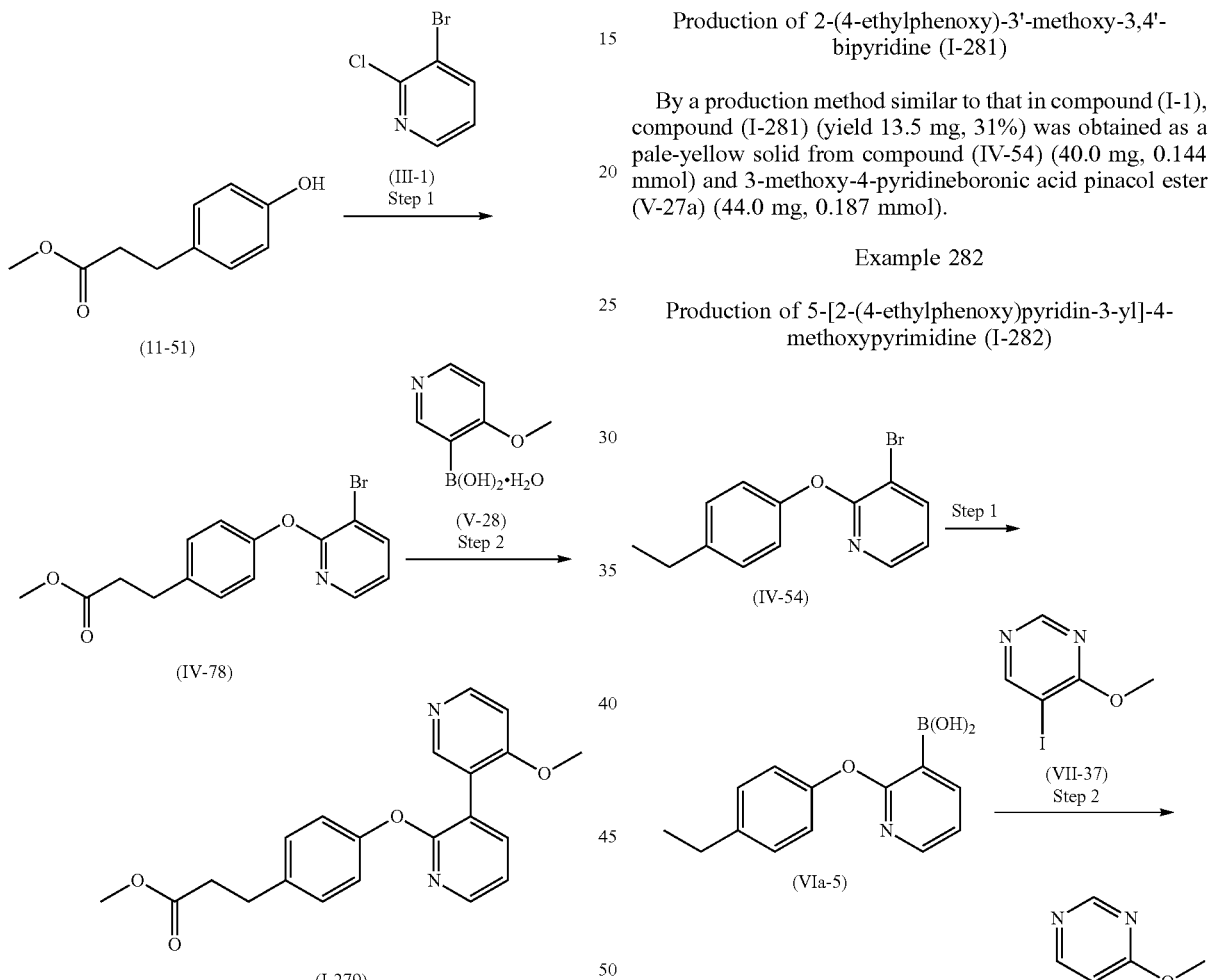

Step 1

By a production method similar to that in compound (IV-1), compound (IV-78) (yield 2.14 mg, 61%) was obtained as a colorless oil from compound (III-1) (2.00 g, 10.4 mmol) and methyl 3-(4-hydroxyphenyl)propionate (II-51) (2.81 g, 15.6 mmol).

Step 2

By a production method similar to that in compound (I-1), compound (I-279) (yield 14.9 mg, 27%) was obtained as a white solid from compound (IV-78) (50.0 mg, 0.149 mmol) and compound (V-28) (34.3 mg, 0.224 mmol).

Example 280

Production of 2-(4-ethylphenoxy)-2'-methoxy-3,3'-bipyridine (I-280)

By a production method similar to that in compound (I-1), compound (I-280) (yield 15.3 mg, 58%) was obtained as a white solid from compound (IV-54) (20.0 mg, 0.0856 mmol) and 2-methoxy-3-pyridineboronic acid (V-26) (19.6 mg, 0.128 mmol).

Example 281

Production of 2-(4-ethylphenoxy)-3'-methoxy-3,4'-bipyridine (I-281)

By a production method similar to that in compound (I-1), compound (I-281) (yield 13.5 mg, 31%) was obtained as a pale-yellow solid from compound (IV-54) (40.0 mg, 0.144 mmol) and 3-methoxy-4-pyridineboronic acid pinacol ester (V-27a) (44.0 mg, 0.187 mmol).

Example 282

Production of 5-[2-(4-ethylphenoxy)pyridin-3-yl]-4-methoxypyrimidine (I-282)

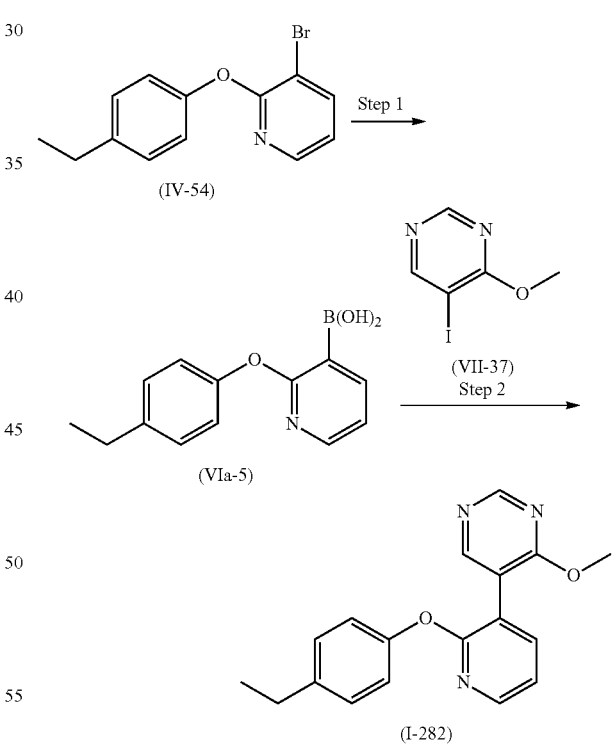

Step 1

Compound (IV-54) (1.00 g, 3.60 mmol) was dissolved in THF (3.0 mL), iPrMgCl.LiCl (1.3 mol/L THF solution, 5.5 Ml, 7.19 mmol) was added, and the mixture was stirred at room temperature for 30 min. Thereafter, B(OiPr)₃ (2.5 mL, 11 mmol) was added, and the mixture was stirred at room temperature for 1 hr. to the reaction mixture was added 1 mol/L hydrochloric acid (7.0 mL), and the mixture was extracted with ethyl acetate. The organic layer was washed with saturated brine, dried over anhydrous sodium sulfate. The solvent was evaporated under reduced pressure to give compound (VIa-5) (yield 851 mg, 97%) as a white solid.
Step 2

By a production method similar to that in compound (I-36), compound (I-282) (yield 27.1 mg, 54%) was obtained as a colorless oil from 5-iodo-4-methoxypyrimidine (VII-37) (50.5 mg, 0.214 mmol) and compound (VIa-5) (40.0 mg, 0.165 mmol).

Example 283

Production of 2-(4-ethylphenoxy)-5'-fluoro-4'-methoxy-3,3'-bipyridine (I-283)

A suspension of compound (VIII-34) (45.0 mg, 0.218 mmol), compound (VIa-5) (63.7 mg, 0.262 mmol), (A-$^{ta}$-Phos)$_2$PdCl$_2$ (7.7 mg, 11 μmol) and cesium carbonate (142 mg, 0.437 mmol) in 1,4-dioxane (0.60 mL)/water (0.12 mL) was stirred at 70° C. for 20 min. Water was added to the reaction mixture, and the mixture was extracted with chloroform. The solvent was evaporated under reduced pressure, and the residue was purified by silica gel column chromatography (n-hexane:ethyl acetate=97:3→70:30) to give compound (I-283) (yield 9.4 mg, 13%) as a colorless oil.

Example 284

Production of 5'-chloro-2-(4-ethylphenoxy)-4'-methoxy-3,3'-bipyridine (I-284)

By a production method similar to that in compound (I-283), compound (I-284) (yield 27.2 mg, 36%) was obtained as a colorless oil from compound (VII-20) (50.0 mg, 0.225 mmol) and compound (VIa-5) (65.6 mg, 0.270 mmol).

Example 285

Production of 5'-bromo-2-(4-ethylphenoxy)-4'-methoxy-3,3'-bipyridine (I-285)

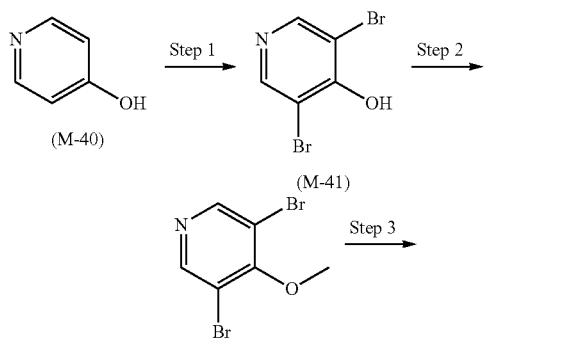

Step 1

4-Pyridinol (M-40) (20.0 g, 210 mmol) was suspended in carbon tetrachloride (400 mL), NBS (77.0 g, 431 mmol) were added, and the mixture was stirred under shading at room temperature for 24 hr. The solvent was evaporated under reduced pressure, and the residue was suspended in acetone (400 mL)/methanol (120 mL), and the mixture was stirred at room temperature for 30 min. The precipitated solid was collected by filtration and suspended in acetonitrile (1.0 L), and the suspension was stirred at room temperature for 1 hr. The solid were collected by filtration, and dried under reduced pressure to give compound (M-41) (yield 46.0 g, 86%) as a white solid.
Step 2

Compound (M-41) (10.0 mg, 39.5 mmol) was suspended in acetonitrile (50 mL), DIPEA (15 mL, 87 mmol) was added at room temperature, phosphoryl chloride (7.4 mL, 79 mmol) was added under ice-cooling, and the mixture was stirred with heating under reflux for 17 hr. The mixture was allowed to cool, and the reaction mixture was added dropwise to ice water, and neutralized with sodium carbonate (11.6 g, 138 mmol). Thereafter, the mixture was extracted with ethyl acetate, and the organic layer was washed with saturated brine, and dried over anhydrous sodium sulfate. The solvent was evaporated under reduced pressure to give a chloro compound (yield 10.6 g, 99%) as a brown solid. The chloro compound (10.6 g, 39.1 mmol) was dissolved in THF (70 mL), sodium methoxide (28% methanol solution, 14 mL, 59 mmol) was added, and the mixture was stirred at 60° C. for 30 min. The mixture was allowed to cool, water was added to the reaction mixture, and the mixture was extracted with ethyl acetate. The organic layer was washed successively with water and saturated brine, and dried over anhydrous sodium sulfate. The solvent was evaporated under reduced pressure to give compound (VII-46) (yield 9.21 mg, 88%) as a yellow solid.
Step 3

By a production method similar to that in compound (I-283), compound (I-285) (yield 60.4 mg, 38%) was obtained as a colorless oil from compound (VII-46) (132 mg, 0.494 mmol) and compound (VIa-5) (100 mg, 0.411 mmol).

Example 286

Production of 2-(4-ethylphenoxy)-4'-methoxy-5'-methyl-3,3'-bipyridine (I-286)

By a production method similar to that in compound (I-53), compound (I-286) (yield 17.3 mg, 52%) was obtained as a colorless oil from compound (I-285) (40.0 mg, 0.104 mmol) and methylboronoic acid (31.1 mg, 0.519 mmol).

Example 287

Production of 2'-(4-ethylphenoxy)-4-methoxy-(3,3'-bipyridine)-5-carbaldehyde (I-287)

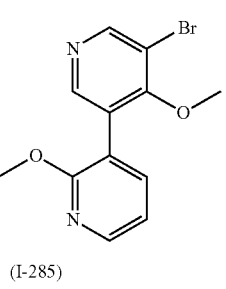

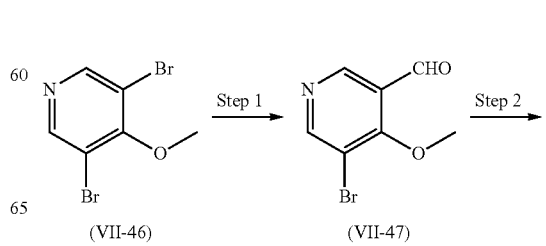

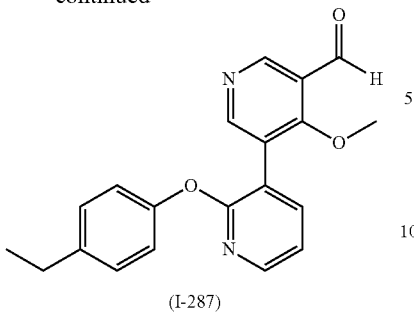

(I-287)

Step 1
Compound (VII-46) (100 mg, 0.369 mmol) was dissolved in THF (0.75 mL), iPrMgCl·LiCl (1.3 mol/L THF solution, 0.30 mL, 0.39 mmol) was added, and the mixture was stirred at room temperature for 30 min. Thereafter, DMF (100 μL, 1.1 mmol) was added, and the mixture was stirred at room temperature for 30 min. To the reaction mixture was added saturated aqueous ammonium chloride solution, and the mixture was extracted with chloroform. The organic layer was washed with saturated aqueous ammonium chloride solution, and dried over anhydrous sodium sulfate. The solvent was evaporated under reduced pressure, and the residue was purified by silica gel column chromatography (n-hexane:ethyl acetate=95:5→50:50) to give compound (VII-47) (yield 59.8 mg, 74%) as a white solid.

Step 2
By a production method similar to that in compound (I-283), compound (I-287) (yield 22.3 mg, 24%) was obtained as a pale-yellow oil from compound (VII-47) (59.6 mg, 0.276 mmol) and compound (VIa-5) (101 mg, 0.414 mmol).

Example 288

Production of 5'-(difluoromethyl)-2-(4-ethylphenoxy)-4'-methoxy-3,3'-bipyridine (I-288)

Compound (I-287) (20.0 mg, 0.600 mmol) was dissolved in DCM (1.0 mL), Deoxo-Fluor (registered trademark) (22 μL, 0.12 mmol) was added, and the mixture was stirred at room temperature for 1 hr. Water was added to the reaction mixture, and the mixture was extracted with chloroform. The solvent was evaporated under reduced pressure, and the residue was purified by silica gel column chromatography (n-hexane:ethyl acetate=95:5→50:50) to give compound (I-288) (yield 18.4 mg, 86%) as a colorless oil.

Example 289

Production of 2-(4-ethylphenoxy)-4'-methyl-3,3'-bipyridine (I-289)

By a production method similar to that in compound (I-1), compound (I-289) (yield 1.9 mg, 7%) was obtained as a colorless oil from compound (IV-54) (50.0 mg, 0.180 mmol) and 4-methylpyridine-3-boronic acid (V-25) (36.9 mg, 0.270 mmol).

Example 290

Production of 4'-chloro-2-(4-ethylphenoxy)-3,3'-bipyridine (I-290)

By a production method similar to that in compound (I-283), compound (I-290) (yield 95.9 mg, 55%) was obtained as a colorless oil from 3-bromo-4-chloropyridine (VII-48) (109 mg, 0.566 mmol) and compound (VIa-5) (165 mg, 0.680 mmol).

Example 291

Production of 4'-ethyl-2-(4-ethylphenoxy)-3,3'-bipyridine (I-291)

By a production method similar to that in compound (IV-63), compound (I-291) (yield 32.6 mg, 83%) was obtained as a colorless oil from compound (I-290) (40.0 mg, 0.129 mmol) and diethylzinc (1.0 mol/L THF solution, 0.19 mL, 0.19 mmol).

Example 292

Production of 7-[2-(4-ethylphenoxy)pyridin-3-yl]pyrazolo[1,5-a]pyridine (I-292)

By a production method similar to that in compound (I-1), compound (I-292) (yield 12.9 mg, 23%) was obtained as a white solid from compound (IV-54) (50.0 mg, 0.180 mmol) and pyrazolo[1,5-a]pyridine-7-boronic acid (V-49) (58.3 mg, 0.360 mmol).

Example 293

Production of 7-[2-(4-ethylphenoxy)pyridin-3-yl]-6-methylimidazo[1,2-a]pyridine (I-293)

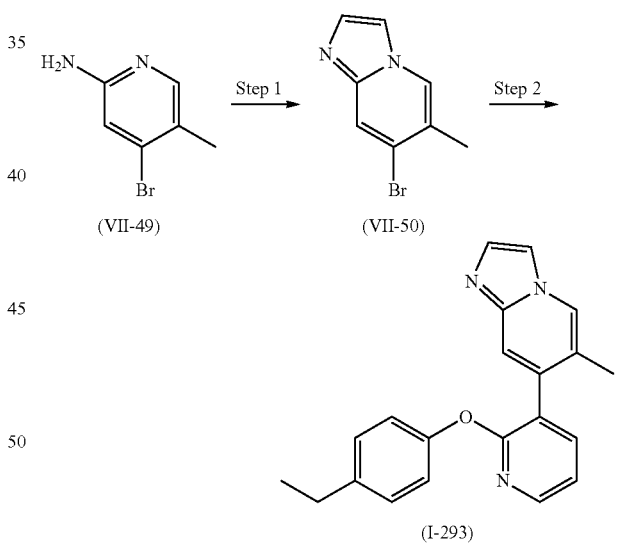

Step 1
Compound (VII-49) (200 mg, 1.07 mmol) was dissolved in ethanol (5.0 mL), sodium hydrogen carbonate (135 mg, 1.60 mmol) and 2-chloroacetaldehyde (0.27 mL, 1.6 mmol) were added and the mixture was stirred under refluxing with heating for 4 hr. The mixture was allowed to cool and the solvent was evaporated under reduced pressure. Water was added, and the mixture was extracted with ethyl acetate. The organic layer was washed with saturated brine, dried over anhydrous sodium sulfate, and filtered. The solvent was evaporated under reduced pressure. The residue was purified by silica gel column chromatography (n-hexane:ethyl acetate=50:50→0:100) to give compound (VII-50) (yield 213 mg, 94%) as a pale-brown solid.

Step 2

By a production method similar to that in compound (I-36), compound (I-293) (yield 30.6 mg, 57%) was obtained as a colorless oil from compound (VII-50) (41.7 mg, 0.197 mmol) and compound (VIa-5) (40.0 mg, 0.165 mmol).

Example 294

Production of 2-[4-(difluoromethyl)phenoxy]-4'-methoxy-3,3'-bipyridine (I-294)

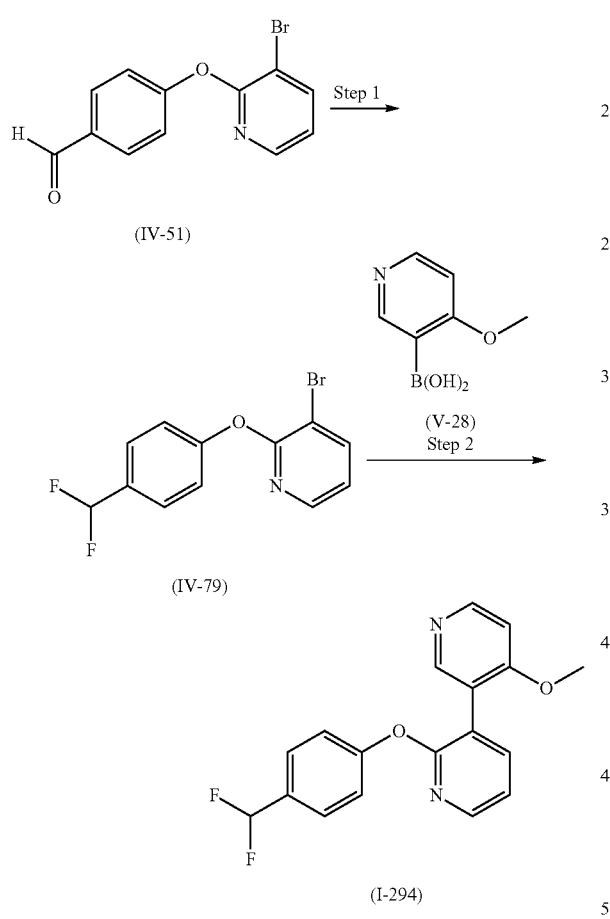

Step 1

To a solution of compound (IV-51) (500 mg, 1.80 mmol) was dissolved in DCM (15 mL) was added DAST (0.71 mL, 5.4 mmol), and the mixture was stirred at room temperature for 18 hr. Water was added to the reaction mixture, and the mixture was extracted with chloroform. The organic layer was washed with saturated brine, and dried over anhydrous sodium sulfate, and the solvent was evaporated under reduced pressure. The residue was purified by silica gel column chromatography (n-hexane:ethyl acetate) to give compound (IV-79) (yield 408 mg, 76%).

Step 2

By a production method similar to that in compound (I-1), compound (I-294) (yield 27.2 mg, 50%) was obtained as a white solid from compound (IV-79) (50.0 mg, 0.167 mmol) and compound (V-28) (38.2 mg, 0.250 mmol).

Example 295

Production of 2-[4-(difluoromethyl)-3-methylphenoxy]-4'-methoxy-3,3'-bipyridine (I-295)

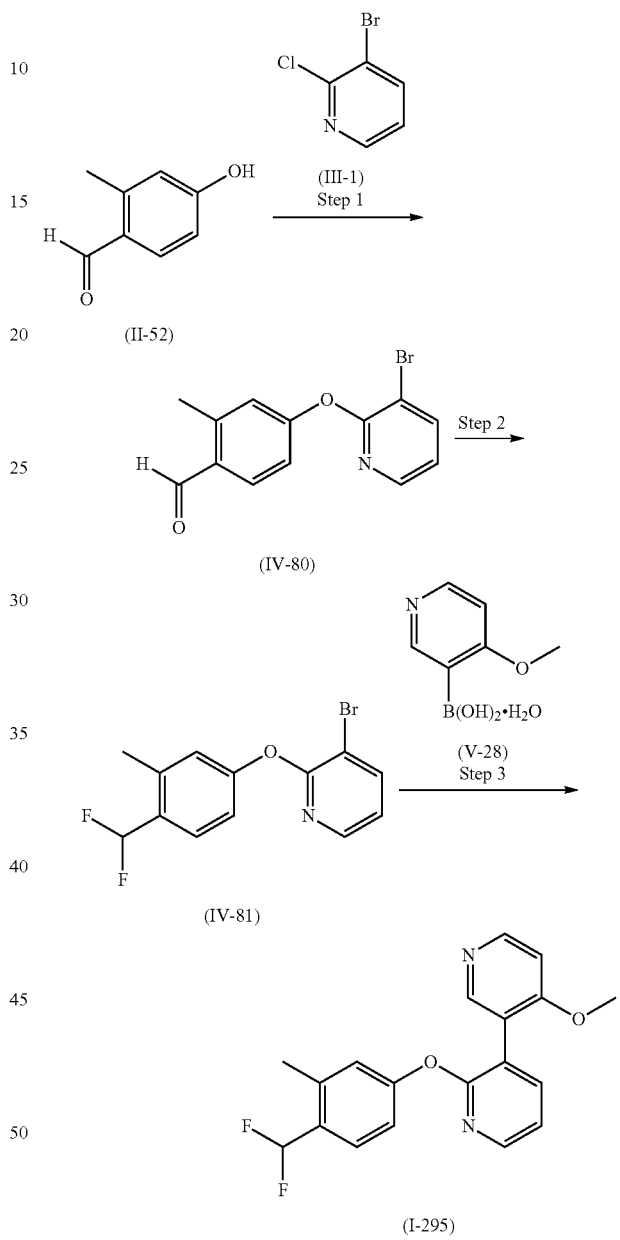

Step 1

By a production method similar to that in compound (IV-1), compound (IV-280) (yield 965 mg, 15%) was obtained as a white solid from compound (III-1) (6.35 mg, 33.0 mmol) and 4-hydroxy-2-methylbenzaldehyde (II-52) (3.00 g, 22.0 mmol).

Step 2

By a production method similar to that in compound (IV-79), compound (IV-81) (yield 655 mg, 69%) was obtained as a white solid from compound (IV-80) (771 mg, 2.64 mmol) and DAST (1.1 mL, 7.9 mmol).

221

Step 3
By a production method similar to that in compound (I-210), compound (I-295) (yield 25.0 mg, 77%) was obtained as a white solid from compound (IV-81) (30.0 mg, 0.167 mmol) and compound (V-28) (21.9 mg, 0.143 mmol).

Example 296

Production of 2-[4-(difluoromethyl)-3-ethylphenoxy]-4'-methoxy-3,3'-bipyridine (I-296)

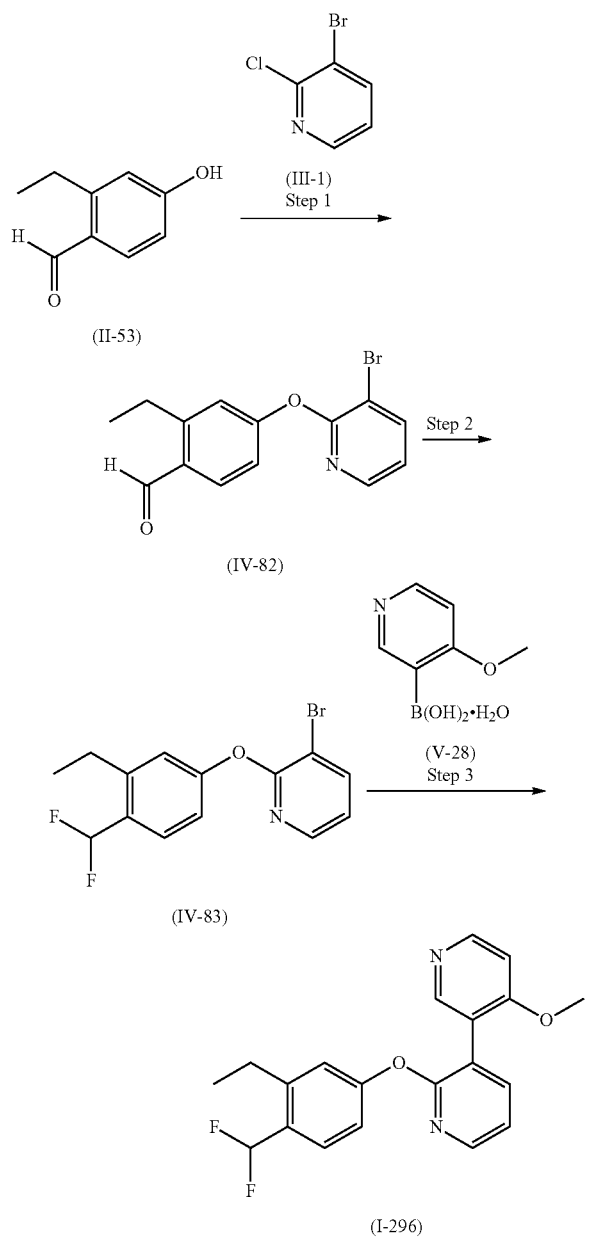

Step 1
To a solution of compound (III-1) (281 mg, 1.60 mmol) and 2-ethyl-4-hydroxybenzaldehyde (II-53) (200 mg, 1.33 mmol) in NMP (3.0 mL) was added cesium carbonate (651 mg, 2.00 mmol), and the mixture was stirred under microwave irradiation at 140° C. 30 min. The reaction mixture was cooled, water was added, and the mixture was extracted with ethyl acetate. The organic layer was washed successively with water and saturated brine, dried over anhydrous sodium sulfate, and filtered. The solvent was evaporated under reduced pressure, and the residue was purified by silica gel column chromatography (n-hexane:ethyl acetate=97:3→70:30) to give compound (IV-82) (yield 299 mg, 73%) as a colorless oil.

Step 2
By a production method similar to that in compound (IV-79), compound (IV-83) (yield 66.6 mg, 58%) was obtained as a colorless oil from compound (IV-82) (108 mg, 0.353 mmol) and Deoxo-Fluor (registered trademark) (0.20 mL, 1.1 mmol).

Step 3
By a production method similar to that in compound (I-210), compound (I-296) (yield 10.1 mg, 17%) was obtained as a white solid from compound (IV-83) (55.1 mg, 0.168 mmol) and compound (V-28) (43.1 mg, 0.252 mmol).

Example 297

Production of 2-[4-(1,1-difluoroethyl)-phenoxy]-4'-methoxy-3,3'-bipyridine (I-297)

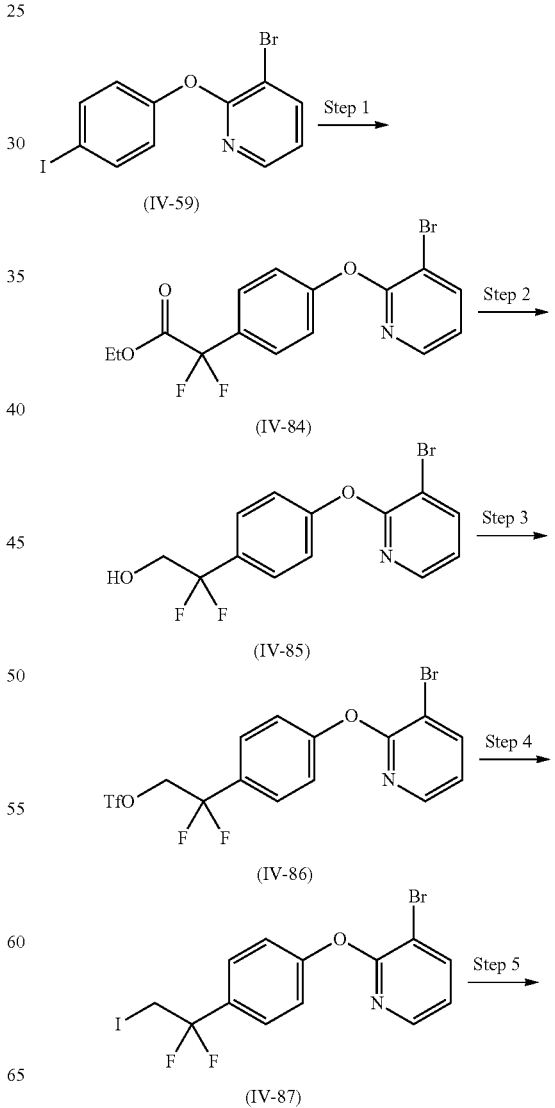

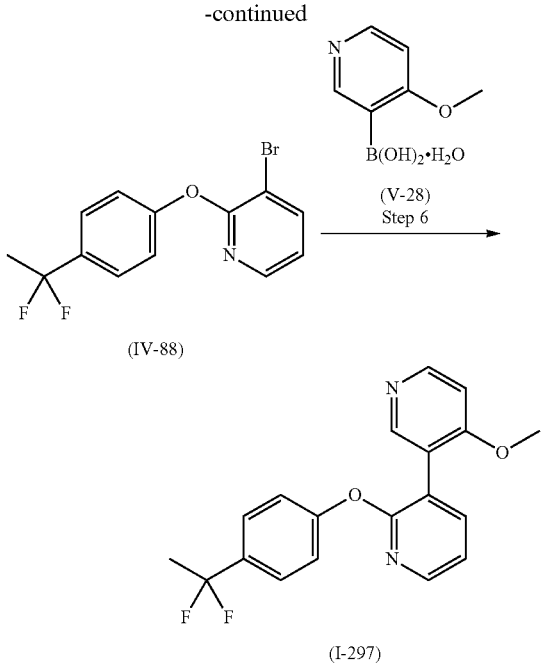

Step 1

A suspension of compound (IV-59) (5.46 g, 14.5 mmol), ethyl 2-bromo-2,2-difluoroacetate (2.95 g, 14.5 mmol), copper (powder, <75 μm, 99.9%, 2.12 g, 33.4 mmol) in DMSO (70 mL) was stirred at 80° C. for 2 hr. The reaction mixture was allowed to cool, saturated aqueous potassium monohydrogen phosphate solution was added, and the mixture was extracted with ethyl acetate. The organic layer was washed with saturated brine, dried over anhydrous sodium sulfate, and filtered. The solvent was evaporated under reduced pressure, and the residue was purified by silica gel column chromatography (n-hexane:ethyl acetate) to give compound (IV-84).

Step 2

Compound (IV-84) was dissolved in methanol (40 mL), sodium borohydride (549 mg, 14.5 mmol) was added under ice-cooling, and the mixture was stirred at room temperature for 1 hr. The reaction mixture was allowed to cool, water was added, and the mixture was extracted with ethyl acetate. The organic layer was washed with saturated brine, dried over anhydrous sodium sulfate, and filtered. The solvent was evaporated under reduced pressure, and the residue was purified by silica gel column chromatography (n-hexane: ethyl acetate) to give compound (IV-85) [(yield 1.17 g, 24%) (2 steps)].

Step 3

Compound (IV-85) (1.15 g, 3.48 mmol) and pyridine (1.7 mL, 21 mmol) were dissolved in DCM (5.0 mL), trifluoromethanesulfonic anhydride (1.8 mL, 10 mmol) was added under ice-cooling, and the mixture was stirred at room temperature for 12 hr. Water was added to the reaction mixture, and the mixture was extracted with ethyl acetate. The organic layer was dried over anhydrous sodium sulfate, and filtered. The solvent was evaporated under reduced pressure, and the residue was purified by silica gel column chromatography (n-hexane:ethyl acetate) to give compound (IV-86) (yield 1.25 g, 78%).

Step 4

Compound (IV-86) (1.18 g, 2.55 mmol) was dissolved in acetone (12 mL), sodium iodide (1.1 g, 12.8 mmol) was added, and the mixture was stirred at room temperature for 3 hr. Water was added to the reaction mixture, and the mixture was extracted with ethyl acetate. The organic layer was dried over anhydrous sodium sulfate, and filtered. The solvent was evaporated under reduced pressure, and the residue was purified by silica gel column chromatography (n-hexane:ethyl acetate) to give compound (IV-87) (yield 1.5 g, 93%).

Step 5

Compound (IV-87) (1.00 g, 2.27 mmol) was dissolved in THF (2.5 mL), tributyltin hydride (3.0 mL, 11 mmol) was added and the mixture was stirred at 60° C. for 3 hr. Water was added to the reaction mixture, and the mixture was extracted with ethyl acetate. The organic layer was dried over anhydrous sodium sulfate, and filtered. The solvent was evaporated under reduced pressure, and the residue was purified by silica gel column chromatography (n-hexane: ethyl acetate) to give compound (IV-88) (yield 75 mg, 11%) as a colorless oil.

Step 6

Compound (IV-88) (22.0 mg, 0.0700 mmol), compound (V-28) (16.1 mg, 0.105 mmol), (A-$^{ta}$Phos)$_2$PdCl$_2$ (2.5 mg, 0.004 mmol) and cesium carbonate (45.6 mg, 0.140 mmol) were suspended in n-butanol (1.0 mL)/water (0.1 mL) mixed solution, and the mixture was stirred under microwave irradiation at 120° C. for 20 min. Water was added to the reaction mixture, and the mixture was extracted with ethyl acetate. The organic layer was dried over anhydrous sodium sulfate, and filtered. The solvent was evaporated under reduced pressure, and the residue was purified by silica gel column chromatography (n-hexane:ethyl acetate) to give compound (I-297) (yield 17.0 g, 71%) as a white solid.

Example 298

Production of 2-[4-(1,1-difluoromethyl)phenoxy]-2'-methoxy-3,3'-bipyridine (I-298)

By a production method similar to that in compound (I-1), compound (I-298) (yield 37.0 mg, 85%) was obtained as a colorless oil from compound (IV-88) (40.0 mg, 0.127 mmol) and 2-methoxypyridine-3-boronic acid (V-26) (29.2 mg, 0.191 mmol).

Example 299

Production of 2-[4-(1,1-difluoroethyl)-phenoxy]-4'-methyl-3,3'-bipyridine (I-299)

By a production method similar to that in compound (I-1), compound (I-299) (yield 13.7 mg, 33%) was obtained as a colorless oil from compound (IV-88) (40.0 mg, 0.127 mmol) and 4-methylpyridine-3-boronic acid (V-25) (26.2 mg, 0.191 mmol).

Example 300

Production of 5'-chloro-2-[4-(1,1-difluoroethyl)-phenoxy]-4'-methyl-3,3'-bipyridine (I-300)

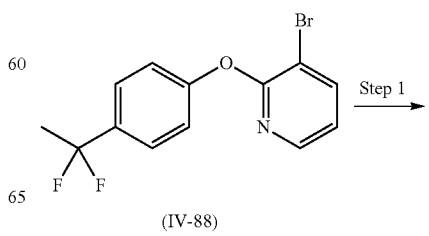

225

-continued

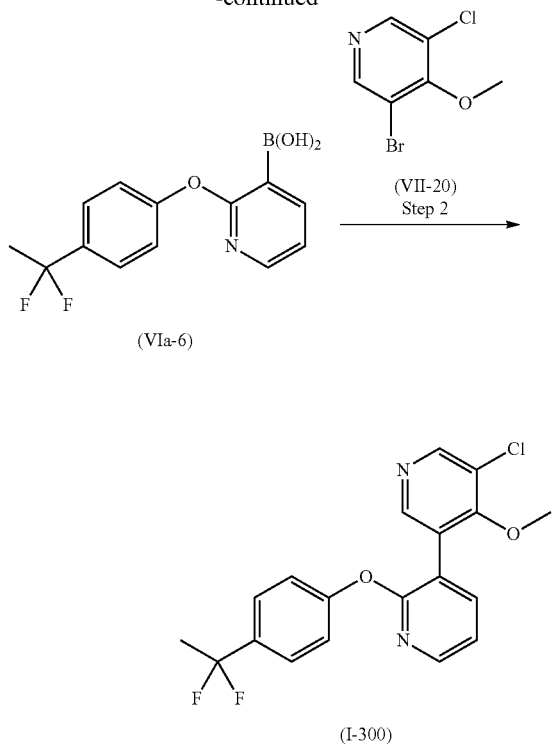

Step 1

To a solution of compound (IV-88) (600 mg, 1.90 mmol) in THF (4.0 mL) was added iPrMgBr.LiCl (1.3 mol/L THF solution, 2.00 mL, 2.60 mmol), and the mixture was stirred at room temperature for 30 min. Thereafter, under ice-cooling, triisopropyl borate (1.32 mL, 5.69 mmol) was added and the mixture was stirred for 10 min. 1 mol/L Hydrochloric acid was added, and the mixture was extracted with ethyl acetate. The organic layer was was washed successively with water and saturated brine, dried over anhydrous sodium sulfate, and filtered. The solvent was evaporated under reduced pressure to give compound (VIa-6) (yield 352 mg, 66%).

Step 2

By a production method similar to that in compound (I-36), compound (I-300) (yield 24.5 mg, 36%) was obtained as a colorless oil from compound (VIa-6) (40.0 mg, 0.180 mmol) and compound (VII-20) (60.2 mg, 0.216 mmol).

Example 301

Production of 2-[4-(1,1-difluoroethyl)-phenoxy]-5'-fluoro-4'-methoxy-3,3'-bipyridine (I-301)

By a production method similar to that in compound (I-36), compound (I-301) (yield 45.8 mg, 52%) was obtained as a colorless oil from compound (VIa-6) (50.0 mg, 0.243 mmol) and compound (VII-34) (74.5 mg, 0.267 mmol).

226

Example 302

Production of 2-[4-(1,1-difluoroethyl)-2-fluorophenoxy]-4'-methyl-3,3'-bipyridine (I-302)

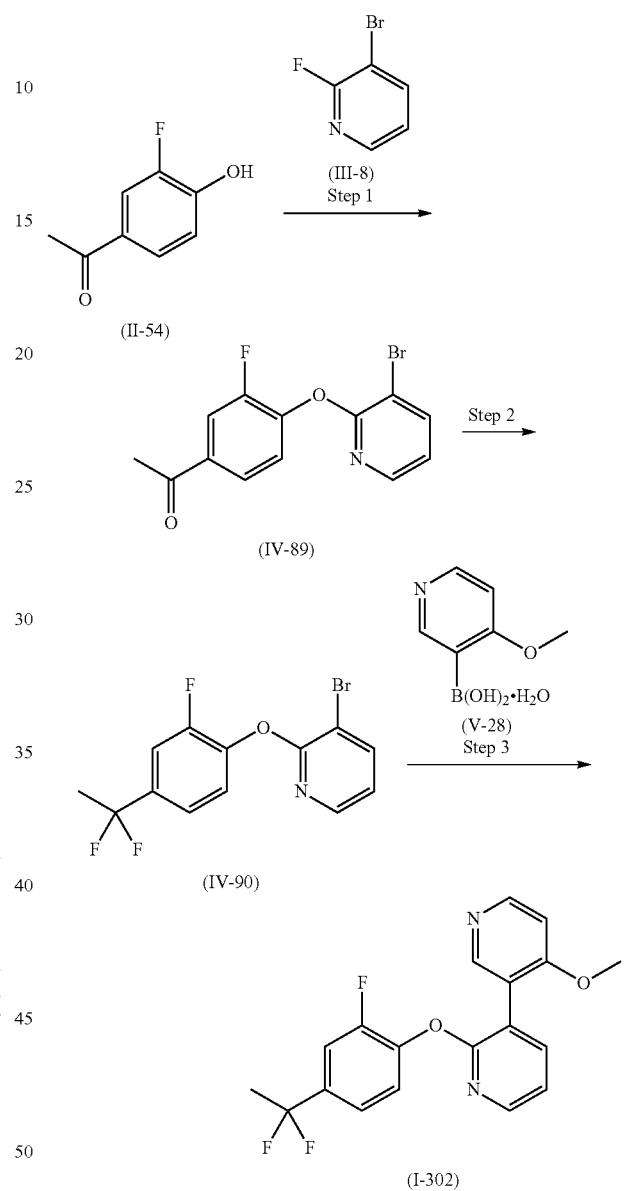

Step 1

Compound (III-8) (200 mg, 1.14 mmol) and compound (II-54) (193 mg, 1.25 mmol) were dissolved in NMP (2.0 mL), cesium carbonate (555 mg, 1.71 mmol) was added, and the mixture was stirred under microwave irradiation at 120° C. for 30 min. The mixture was cooled, water was added, and the mixture was extracted with ethyl acetate, dried over anhydrous sodium sulfate, and filtered. The solvent was evaporated under reduced pressure, and the residue was purified by silica gel column chromatography (n-hexane: ethyl acetate) to give compound (IV-89) (yield 192 mg, 55%).

Step 2

Compound (IV-89) (168 mg, 0.542 mmol) was dissolved in THF (1.0 mL), Deoxo-Fluor (registered trademark) (1.50 mL, 8.13 mmol) was added and the mixture was stirred at 70° C. for 36 hr. Water was added to the reaction mixture, and the mixture was extracted with ethyl acetate. The organic layer was dried over anhydrous sodium sulfate, and filtered. The solvent was evaporated under reduced pressure, and the residue was purified by silica gel column chromatography (n-hexane:ethyl acetate) to give compound (IV-90) (yield 99 mg, 55%).

Step 3

By a production method similar to that in compound (I-1), compound (I-302) (yield 36.1 mg, 74%) was obtained as a white solid from compound (IV-90) (45.0 mg, 0.135 mmol) and 4-methoxypyridine-3-boronic acid monohydrate (V-28) (31.1 mg, 0.203 mmol).

Example 303

Production of 2-[4-(1,1-difluoroethyl)-2-fluorophenoxy]-4'-methyl-3,3'-bipyridine (I-303)

By a production method similar to that in compound (I-1), compound (I-303) (yield 25.2 mg, 54%) was obtained as a colorless oil from compound (IV-90) (45.0 mg, 0.135 mmol) and 4-methoxypyridine-3-boronic acid (V-25) (27.8 mg, 0.203 mmol).

Example 304

Production of 2-[4-(1,1-difluoroethyl)-3-fluorophenoxy]-4'-methyl-3,3'-bipyridine (I-304)

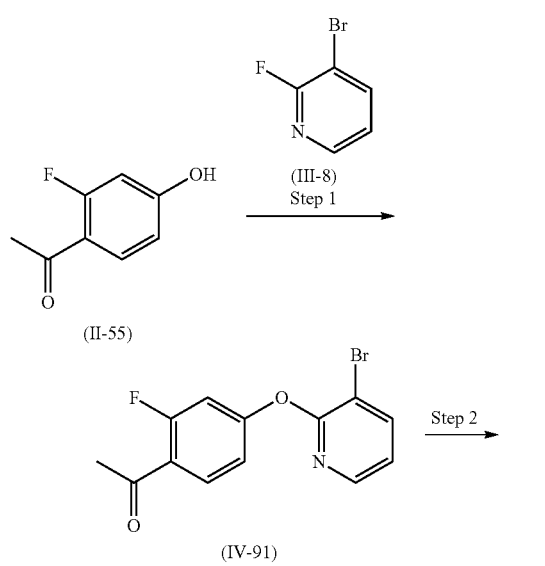

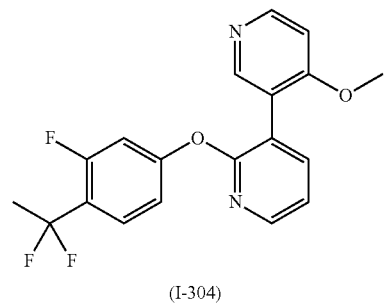

(I-304)

Step 1

By a production method similar to that in compound (IV-89), compound (IV-91) (yield 330 mg, 71%) was obtained from compound (III-8) (394 mg, 2.24 mmol) and compound (II-55) (230 mg, 1.49 mmol).

Step 2

By a production method similar to that in compound (IV-90), compound (IV-92) (yield 98 mg, 57%) was obtained from compound (IV-91) (160 mg, 0.516 mmol) and Deoxo-Fluor (registered trademark) (0.951 mL, 5.16 mmol).

Step 3

By a production method similar to that in compound (I-1), compound (I-304) (yield 36.1 mg, 74%) was obtained as a white solid from compound (IV-92) (45.0 mg, 0.135 mmol) and 4-methoxypyridine-3-boronic acid monohydrate compound (V-28) (31.1 mg, 0.203 mmol).

Example 305

Production of 2-[4-(1,1-difluoroethyl)-3-fluorophenoxy]-4'-methyl-3,3'-bipyridine (I-305)

By a production method similar to that in compound (I-1), compound (I-305) (yield 27.1 mg, 58%) was obtained as a colorless oil from compound (IV-92) (45.0 mg, 0.135 mmol) and 4-methylpyridine-3-boronic acid (V-25) (27.8 mg, 0.203 mmol).

Example 306

Production of 4-methyl-2-[4-(1,1,2-trifluoroethyl)-phenoxy]-3,3'-bipyridine (I-306)

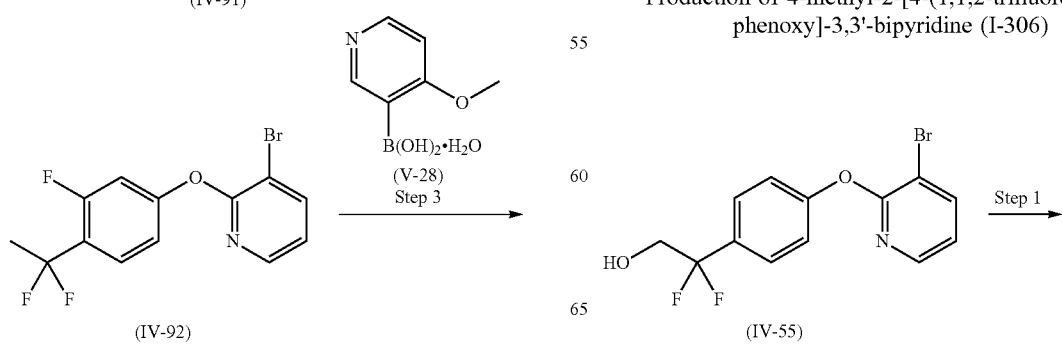

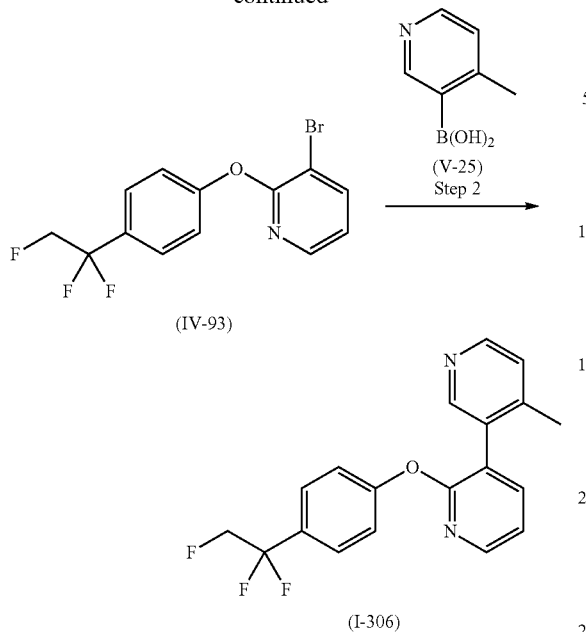

Step 1
Compound (IV-85) (300 mg, 0.909 mmol) was dissolved in DCM (3.0 mL), DAST (180 μL, 1.36 mmol) was added, and the mixture was stirred at room temperature for 3 hr. Water was added to the reaction mixture, and the mixture was extracted with ethyl acetate. The organic layer was dried over anhydrous sodium sulfate, and filtered. The solvent was evaporated under reduced pressure, and the residue was purified by silica gel column chromatography (n-hexane: ethyl acetate) to give compound (IV-93) (yield 112 mg, 37%).

Step 2
By a production method similar to that in compound (I-1), compound (I-306) (yield 19.3 mg, 37%) was obtained as a colorless oil from compound (IV-93) (50.0 mg, 0.151 mmol) and 4-methylpyridine-3-boronic acid (V-25) (30.9 mg, 0.226 mmol).

Example 307

Production of 7-{2-[4-(1,1-difluoroethyl)-phenoxy]pyridin-3-yl}pyrazolo[1,5-a]pyridine (I-307)

By a production method similar to that in compound (I-36), compound (I-307) (yield 11.2 mg, 15%) was obtained as a colorless oil from compound (VIa-6) (60.0 mg, 0.215 mmol) and 7-iodopyrazolo[1,5-a]pyridine (VII-51) (63.0 mg, 0.258 mmol).

Example 308

Production of 5-{2-[4-(1,1-difluoroethyl)-phenoxy]-3-yl}quinoxaline (I-308)

By a production method similar to that in compound (I-36), compound (I-308) (yield 9.6 mg, 12%) was obtained as a yellow oil from compound (VIa-6) (60.0 mg, 0.215 mmol) and 5-bromoquinoxaline (VII-2) (53.9 mg, 0.258 mmol).

Example 309

Production of 2-(2-methoxyphenyl)-3-{[6-(trifluoromethyl)pyridin-3-yl]oxy}pyrazine (I-309)

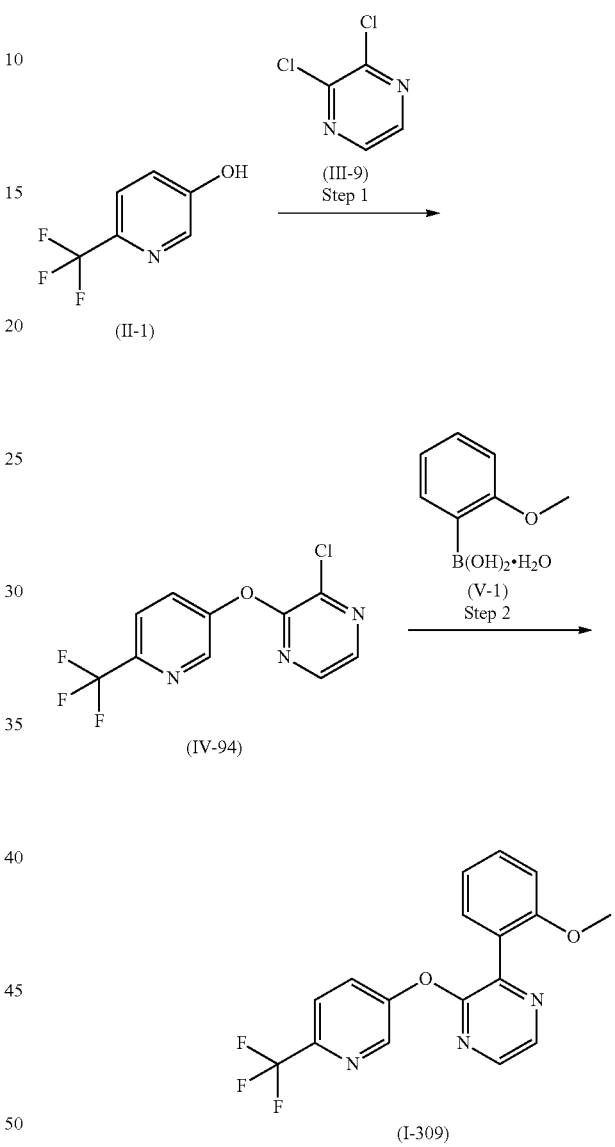

Step 1
By a production method similar to that in compound (IV-1), compound (IV-94) (yield 846 mg, 78%) was obtained as a white solid from compound (III-9) (500 mg, 3.36 mmol) and 6-(trifluoromethyl)pyridin-3-ol (II-1) (547 mg, 3.36 mmol).

Step 2
By a production method similar to that in compound (I-1), compound (I-309) (yield 62.0 mg, 98%) was obtained as a white solid from compound (IV-94) (50.0 mg, 0.181 mmol) and 2-methoxyphenylboronic acid (V-1) (35.8 mg, 0.236 mmol).

Example 310

Production of 5-(2-methoxyphenyl)-4-{[6-(trifluoromethyl)pyridin-3-yl]oxy}pyrimidine (I-310)

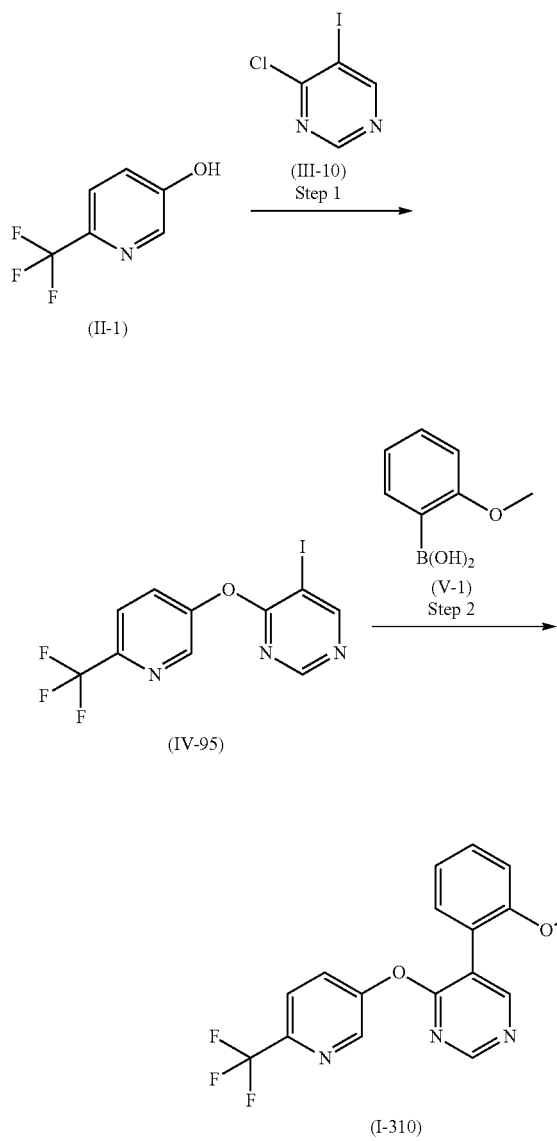

Example 311

Production of 4-(2-methoxyphenyl)-3-{[6-(trifluoromethyl)pyridin-3-yl]oxy}pyridazine (I-311)

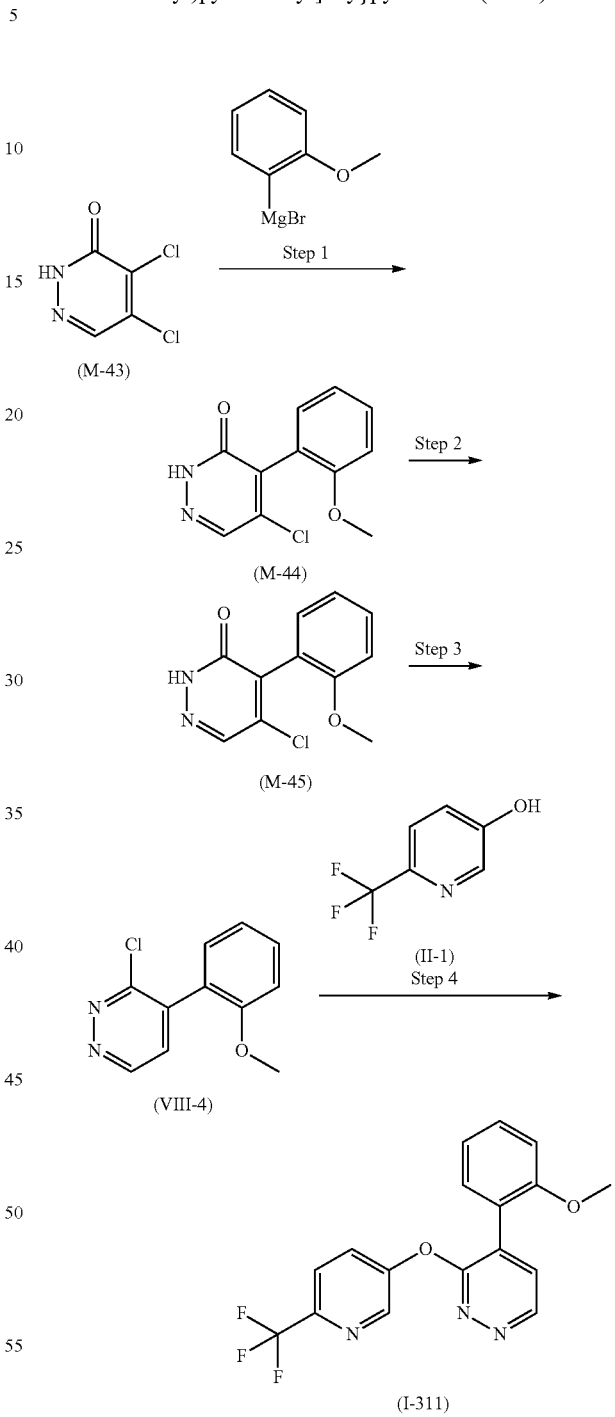

Step 1

By a production method similar to that in compound (IV-1), compound (IV-95) (yield 7.40 mg, 79%) was obtained as a white solid from compound (III-10) (6.18 mg, 25.7 mmol) and 6-(trifluoromethyl)pyridin-3-ol (II-1) (5.00 g, 30.8 mmol).

Step 2

By a production method similar to that in compound (I-1), compound (I-310) (yield 78.7 mg, 83%) was obtained as a colorless oil from compound (IV-95) (100 mg, 0.272 mmol) and 2-methoxyphenylboronic acid (V-1) (49.7 mg, 0.327 mmol).

Step 1

To a solution of 4,5-dichloropyridazinone (M-43) (100 mg, 0.606 mmol) in THF (3.5 mL) was added, under an argon atmosphere, 1.0 mol/L 2-methoxyphenylmagnesium bromide (1.50 mL, 1.50 mmol), and the mixture was heated under reflux for 3 hr. To the reaction mixture was added ammonium chloride solution, and the mixture was extracted with ethyl acetate. The organic layer was dried over magnesium sulfate, and the solvent was evaporated under reduced pressure. The residue was purified by silica gel column chromatography (n-hexane:ethyl acetate) to give compound (M-44) (yield 130 mg, 91%) as a white solid.

Step 2

Compound (M-44) (130 mg, 0.549 mmol) was dissolved in DMF (1.0 mL), 1.0 mol/L sodium hydroxide (1.4 mL, 1.40 mmol) and 10% Pd/C (10.0 mg, 7.7 wt %) were successively added, and the mixture was stirred under a hydrogen atmosphere (3 atm) for 18 hr. The reaction mixture was filtered through Celite, hydrochloric acid was added, and the mixture was extracted with ethyl acetate. The organic layer was dried over magnesium sulfate, and the solvent was evaporated under reduced pressure. The residue was purified by silica gel column chromatography (n-hexane:ethyl acetate) to give compound (M-45) (yield 60.0 mg, 54%) as a white solid.

Step 3

Compound (M-45) (60.0 mg, 0.297 mmol) was dissolved in phosphorus oxychloride (1.0 mL, 1.5 mmol), and the mixture was heated under reflux for 1 hr. To the reaction mixture were successively added ice and sodium hydrogen carbonate, and the mixture was extracted with ethyl acetate. The organic layer was dried over magnesium sulfate, and the solvent was evaporated under reduced pressure to give compound (VIII-4) (yield 65.0 mg, 99%) as a yellow oil.

Step 4

Compound (VIII-4) (30.0 mg, 0.136 mmol) and 6-trifluoromethylpyridin-3-ol (II-1) (25.0 mg, 0.153 mmol) were dissolved in N,N-dimethylacetamide (0.5 mL), cesium carbonate (70.0 mg, 0.215 mmol) was added, and the mixture was stirred under microwave irradiation at 120° C. for 30 min. Water was added to the reaction mixture, and the mixture was extracted with ethyl acetate. The organic layer was dried over magnesium sulfate, and the solvent was evaporated under reduced pressure. The residue was purified by silica gel column chromatography (n-hexane:ethyl acetate) to give compound (I-311) (yield 14.0 mg, 30%) as a yellow oil.

Example 312

Production of 4-{[6-(1,1-difluoroethyl)-pyridin-3-yl]oxy}-5-(2-methoxyphenyl)pyrimidine (I-312)

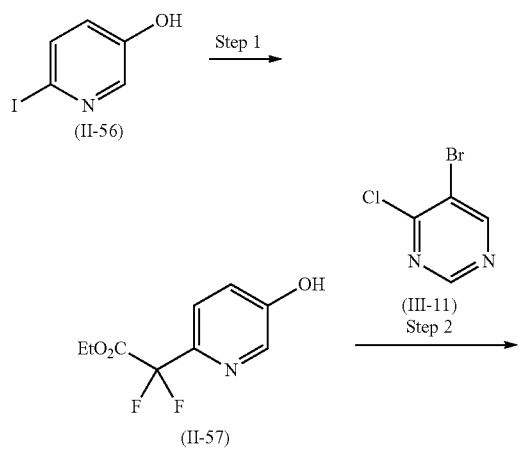

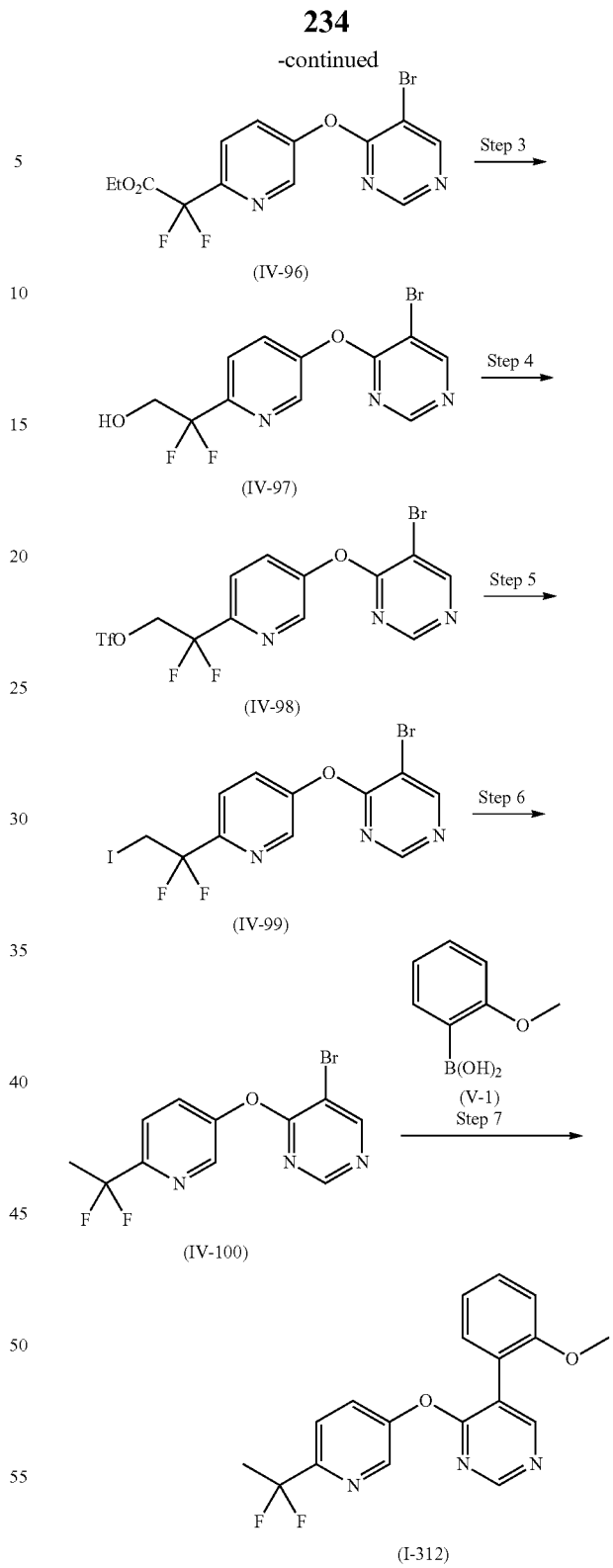

Step 1

Compound (II-56) (5.00 g, 28.7 mmol), copper (powder, <75 μm, 99.9%, 7.58 g, 37.4 mmol) and ethyl 2-bromo-2,2-difluoroacetate (4.16 g, 66.1 mmol) were dissolved in DMSO (70 mL), and the mixture was stirred at 70° C. for 2 hr. The reaction mixture was allowed to cool, saturated aqueous potassium monohydrogen phosphate solution was added, and the mixture was extracted with ethyl acetate. The organic layer was washed with saturated brine, dried over anhydrous sodium sulfate, and filtered. The solvent was evaporated under reduced pressure, and the residue was purified by silica gel column chromatography (n-hexane: ethyl acetate) to give compound (II-57) (yield 1.30 g, 21%).

Step 2

By a production method similar to that in compound (IV-1), compound (IV-96) (yield 6.90 g, 78%) was obtained from compound (II-57) (5.05 g, 26.1 mmol) and compound (II-11) (5.15 g, 23.7 mmol).

Step 3

Compound (IV-96) (16.4 g, 43.8 mmol) was dissolved in methanol (80 mL), sodium borohydride (6.63 g, 175 mmol) was added, and the mixture was stirred at room temperature for 10 min. The reaction mixture was allowed to cool, water was added, and the mixture was extracted with ethyl acetate. The organic layer was washed with saturated brine, dried over anhydrous sodium sulfate, and filtered. The solvent was evaporated under reduced pressure, and the residue was purified by silica gel column chromatography (n-hexane: ethyl acetate) to give compound (IV-97) (yield 6.30 g, 43%).

Step 4

By a production method similar to that in compound (I-80), compound (IV-98) (yield 7.40 g, 84%) was obtained from compound (IV-97) (6.30 g, 19.0 mmol) and trifluoromethanesulfonic anhydride (9.61 mL, 56.9 mmol).

Step 5

By a production method similar to that in compound (IV-12), compound (IV-99) (yield 6.70 g, 96%) was obtained from compound (IV-98) (7.30 g, 15.7 mmol) and sodium iodide (11.8 g, 79.0 mmol).

Step 6

By a production method similar to that in compound (I-82), Step 3, compound (IV-100) (yield 3.00 g, 63%) was obtained from compound (IV-99) (6.70 g, 15.2 mmol) and tributyltin hydride (13.2 g, 45.5 mmol).

Step 7

By a production method similar to that in compound (I-1), compound (I-312) (yield 45.0 g, 92%) was obtained as a white solid from compound (IV-100) (45.0 mg, 0.142 mmol) and 2-methoxyphenylboronic acid (V-1) (32.4 g, 0.214 mmol).

Example 313

Production of 3-(2-methoxyphenyl)-N-[6-trifluoroethyl)-pyridin-3-yl]pyridin-2-amine (I-313)

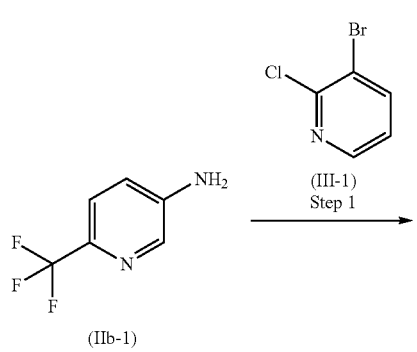

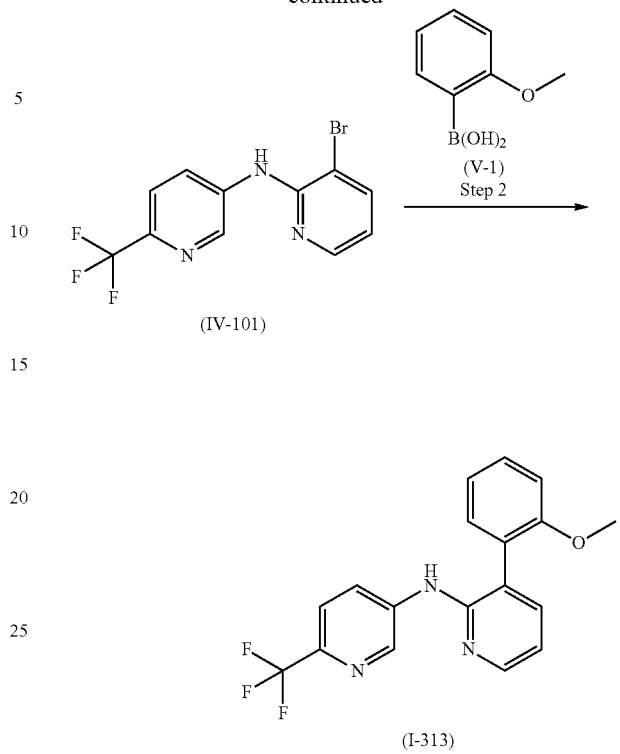

Step 1

Compound (III-1) (500 mg, 2.60 mmol) and 6-(trifluoromethyl)pyridin-3-amine (IIb-1) (463 mg, 2.86 mmol) were dissolved in IPA (5.0 mL), p-toluenesulfonic acid monohydrate (494 mg, 2.60 mmol) was added, and the mixture was stirred under microwave irradiation at 160° C. for 2 hr. The reaction mixture was allowed to cool, diluted with ethyl acetate, and washed successively with saturated aqueous sodium hydrogen carbonate solution and saturated brine. The organic layer was dried over anhydrous sodium sulfate, and filtered. The solvent was evaporated under reduced pressure, and the residue was purified by silica gel column chromatography (n-hexane:ethyl acetate=100: 0→80:20) to give compound (IV-101) (yield 188 mg, 23%) as a white solid.

$^1$H-NMR (400 MHz, CDCl$_3$) δ: 6.80 (1H, dd, J=5.0, 7.8 Hz), 7.25 (1H, br s), 7.65 (1H, d, J=8.2 Hz), 7.83 (1H, dd, J=1.8, 7.8 Hz), 8.22 (1H, dd, J=1.8, 5.0 Hz), 8.53 (1H, dd, J=2.7, 8.7 Hz), 8.78 (1H, d, J=1.8 Hz).

ESI-MS m/z: 318, 320 [M+H]$^+$.

Step 2

By a production method similar to that in compound (I-1), compound (I-313) (yield 32.4 g, 75%) was obtained as a pale-yellow solid from compound (IV-101) (40.0 mg, 0.126 mmol) and compound (V-1) (24.8 g, 0.163 mmol).

Example 324

Production of 2-(4-chlorophenoxy)-3-(naphthalen-1-yl)pyrazine (I-314)

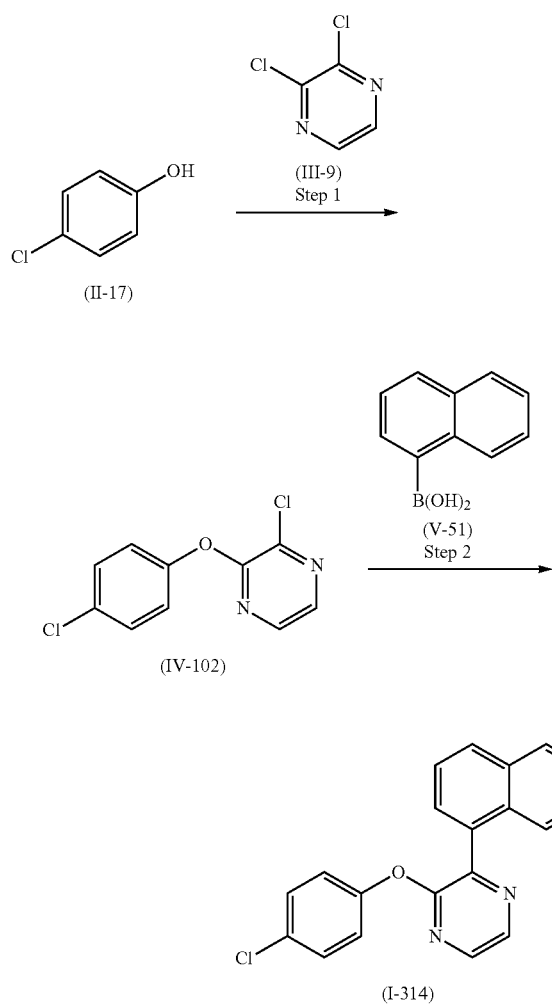

Step 1

2,3-Dichloropyrazine (III-9) (500 mg, 3.36 mmol) and 4-chlorophenol (II-17) (431 mg, 3.36 mmol) were dissolved in DMF (10 mL), potassium carbonate (557 mg, 4.03 mmol) was added and the mixture was stirred at 90° C. for 15 hr. The reaction mixture was allowed to cool, water was added, and the mixture was extracted with ethyl acetate. The organic layer was washed successively with water and saturated brine, and the solvent was evaporated under reduced pressure. The residue was purified by silica gel column chromatography (n-hexane:ethyl acetate=100:0→85:15) to give compound (IV-102) (yield 809 mg, quantitative) as a white solid.

Step 2

By a production method similar to that in compound (I-1), compound (I-314) (yield 33.0 g, 48%) was obtained as a solid from compound (IV-102) (50.0 mg, 0.207 mmol) and 1-naphthylboronic acid (V-51) (47.0 g, 0.273 mmol).

Example 315

Production of 2-(2-methoxyphenyl)-3-[(5,6,7,8-tetrahydronaphthalen-2-yl)oxy]pyrazine (I-315)

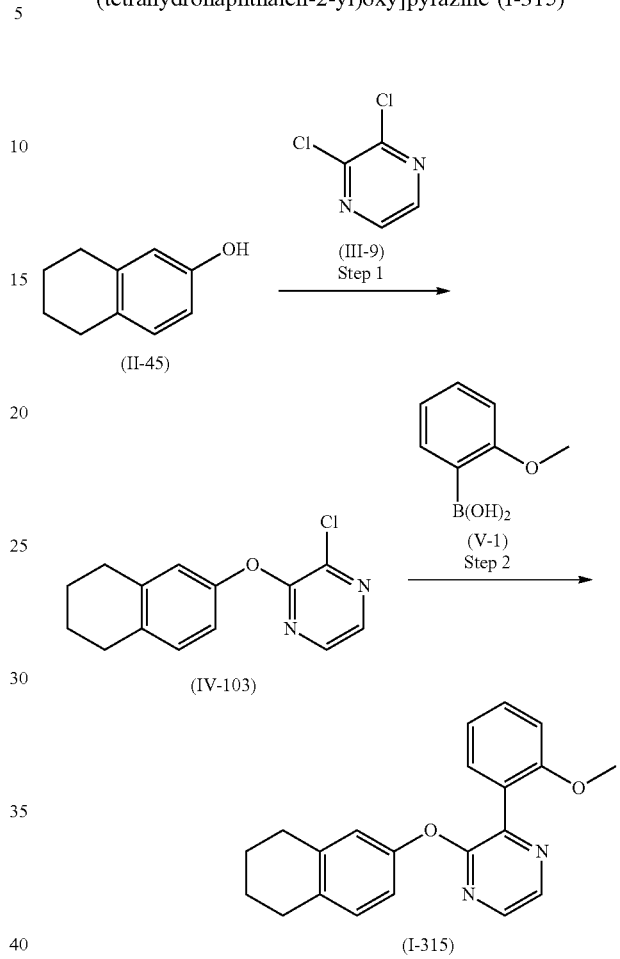

Step 1

By a production method similar to that in compound (IV-102), compound (IV-103) (yield 846 mg, 97%) was obtained as a colorless oil from compound (III-9) (500 mg, 3.36 mmol) and 5,6,7,8-tetrahydronaphthalen-2-ol (II-45) (497 mg, 3.36 mmol).

Step 2

By a production method similar to that in compound (I-1), compound (I-315) (yield 27.4 mg, 43%) was obtained as a colorless oil from compound (IV-103) (50.0 mg, 0.192 mmol) and 2-methoxyphenylboronic acid (V-1) (37.9 mg, 0.249 mmol).

Example 316

Production of 2-(2-methoxypyridin-3-yl)-3-[(5,6,7,8-tetrahydronaphthalen-2-yl)oxy]pyrazine (I-316)

By a production method similar to that in compound (I-1), compound (I-316) (yield 53.8 mg, 84%) was obtained as a colorless oil from compound (IV-103) (50.0 mg, 0.192 mmol) and 2-methoxypyridine-3-boronic acid (V-26) (38.1 g, 0.249 mmol).

Example 317

Production of 2-(4-methoxypyridin-3-yl)-3-[(5,6,7,8-tetrahydronaphthalen-2-yl)oxy]pyrazine (I-317)

By a production method similar to that in compound (I-1), compound (I-317) (yield 12.9 mg, 20%) was obtained as a colorless oil from compound (IV-103) (50.0 mg, 0.192 mmol) and 4-methoxypyridine-3-boronic acid (V-28a) (38.1 mg, 0.249 mmol).

Example 318

Production of 2-[4-(benzyloxy)phenoxy]-3-(2-methoxypyridin-3-yl)pyrazine (I-318)

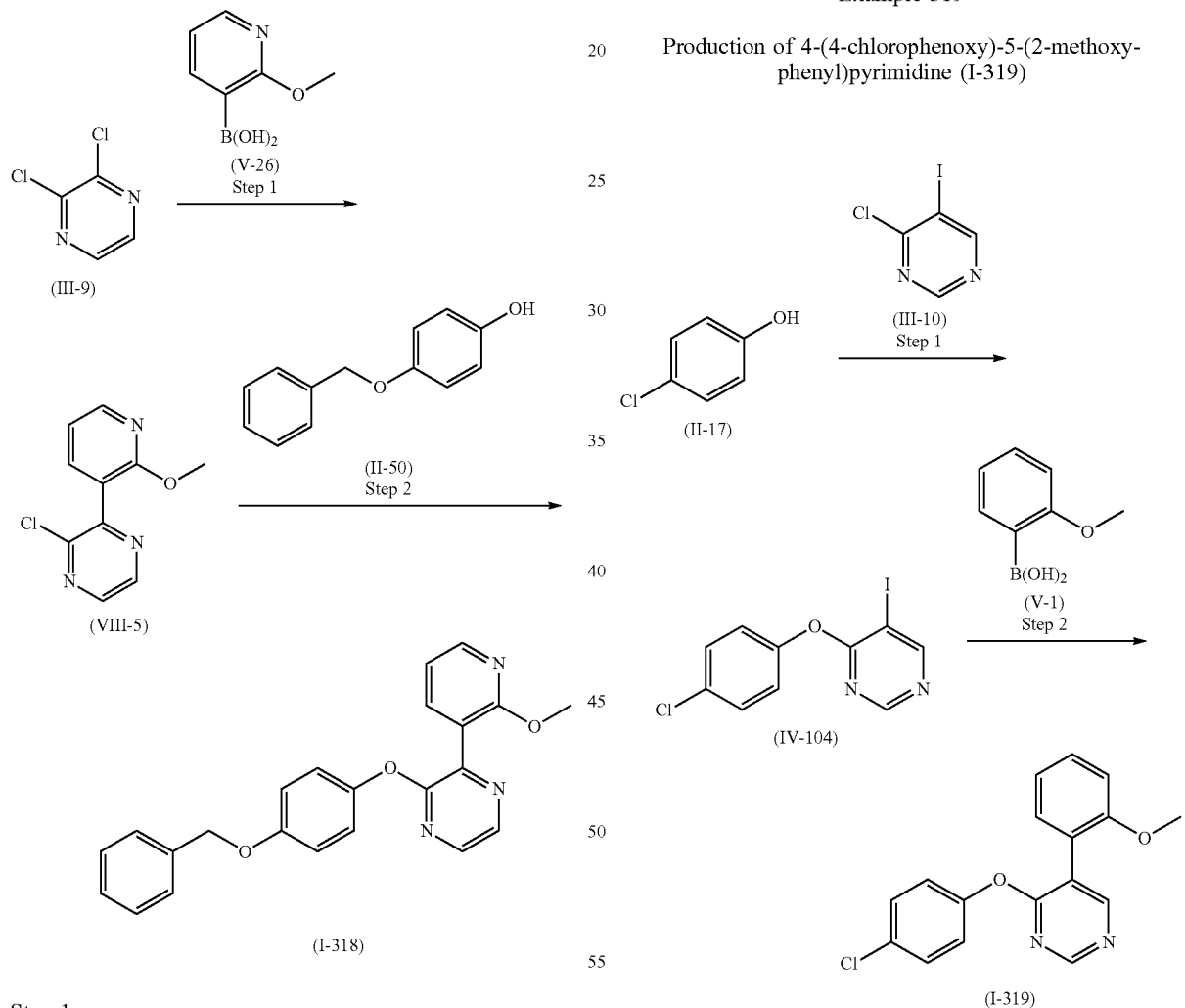

Step 1

2,3-Dichloropyrazine (III-9) (925 mg, 6.21 mmol), 2-methoxypyridine-3-boronic acid (V-26) (1.23 g, 8.07 mmol), (A-$^{ta}$Phos)$_2$PdCl$_2$ (221 mg, 0.312 mmol) and cesium carbonate (4.05 g, 12.4 mmol) were dissolved in 1,4-dioxane (30 mL) and water (6 mL), and the mixture was stirred at 90° C. for 1.5 hr. The reaction mixture was allowed to cool, water was added, and the mixture was extracted with ethyl acetate. The organic layer was washed successively with water and saturated brine, and filtered, and the solvent was evaporated under reduced pressure. The residue was purified by silica gel column chromatography (n-hexane:ethyl acetate=10:1) to give compound (VIII-5) (844 mg, yield 61%) as an oil.

Step 2

Compound (VIII-5) (65.0 mg, 0.293 mmol) and 4-benzyloxyphenol (II-50) (64.0 mg, 0.323 mmol) were dissolved in NMP (1.0 mL), cesium carbonate (115 mg, 0.383 mmol) was added and the mixture was stirred at 180° C. for 5 hr. The reaction mixture was allowed to cool, water was added, and the mixture was extracted with ethyl acetate. The organic layer was washed successively with water and saturated brine, dried over anhydrous sodium sulfate, and filtered. The solvent was evaporated under reduced pressure, and the residue was purified by silica gel column chromatography (n-hexane:ethyl acetate=5:1) to give compound (I-318) (yield 18.0 mg, 16%) as a solid.

Example 319

Production of 4-(4-chlorophenoxy)-5-(2-methoxyphenyl)pyrimidine (I-319)

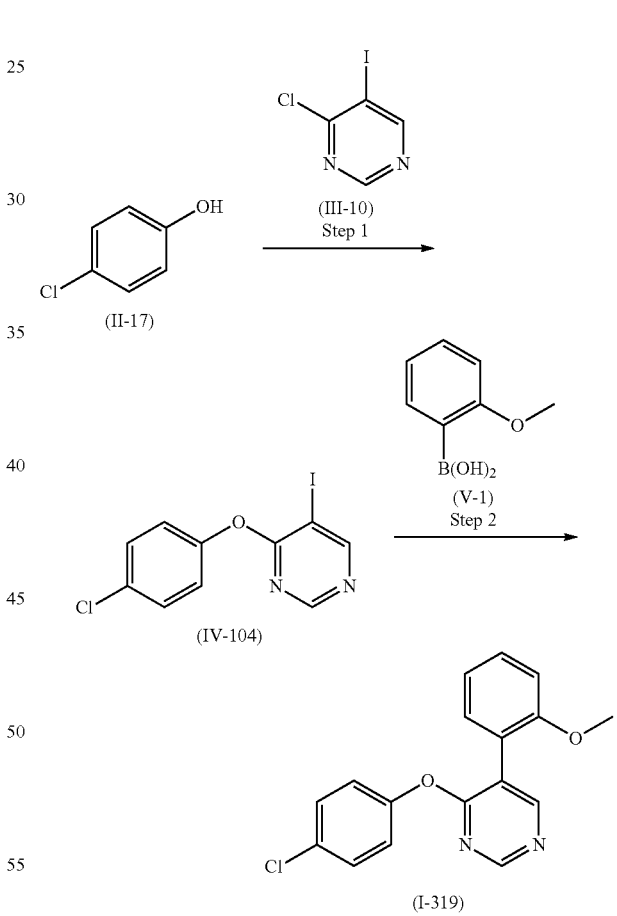

Step 1

By a production method similar to that in compound (IV-1), compound (IV-104) (yield 360 mg, 65%) was obtained as a white solid from compound (III-10) (400 mg, 1.66 mmol) and 4-chlorophenol (II-17) (257 mg, 2.00 mmol).

Step 2

By a production method similar to that in compound (I-1), compound (I-319) (yield 50.3 mg, quantitative) was obtained as a colorless oil from compound (IV-104) (48.9 mg, 0.147 mmol) and 2-methoxyphenylboronic acid (V-1) (26.8 mg, 0.175 mmol).

Example 320

Production of 4-(4-isopropylphenoxy)-5-(2-methoxyphenyl)pyrimidine (I-320)

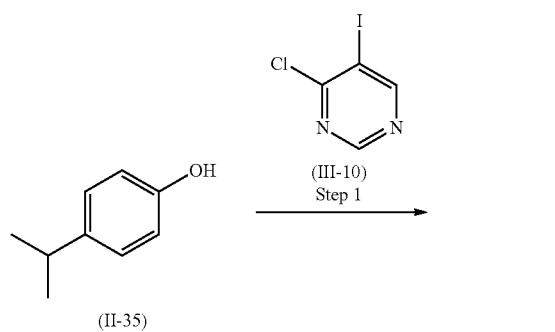

(I-320)

Example 321

Production of 5-(2-methoxyphenyl)-4-[4-(trifluoromethyl)phenoxy]pyrimidine (I-321)

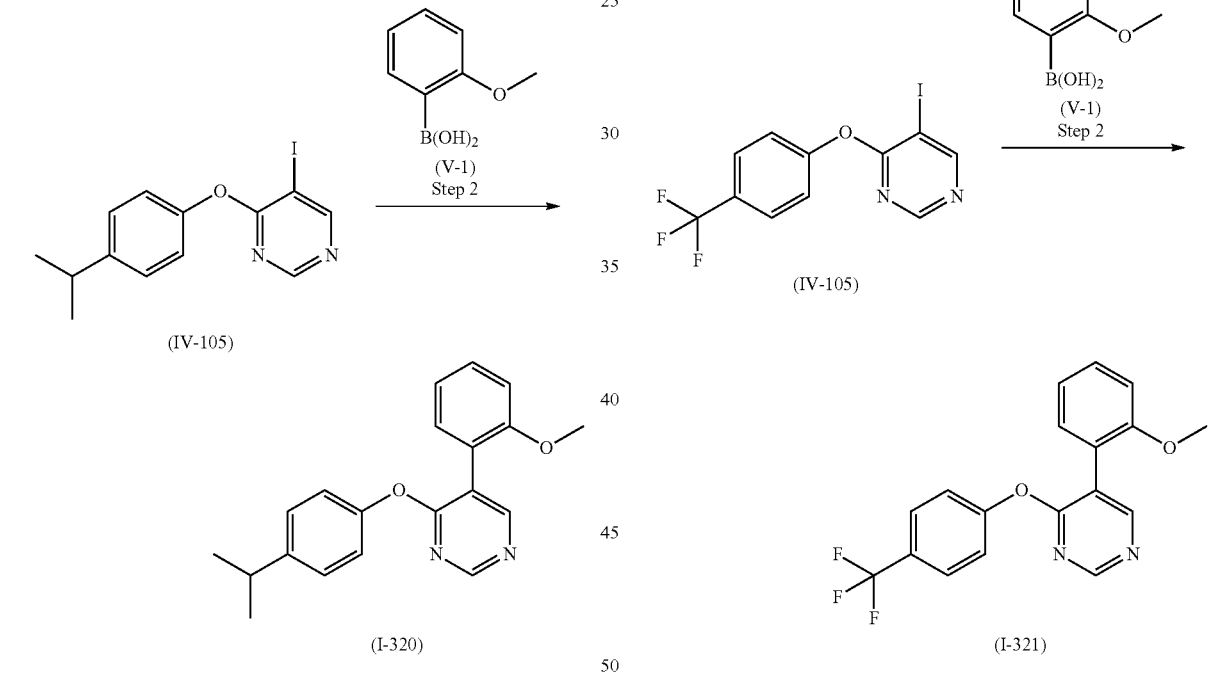

Step 1

By a production method similar to that in compound (IV-1), compound (IV-105) (yield 312 mg, 55%) was obtained as a colorless oil from compound (III-10) (400 mg, 1.66 mmol) and 4-isopropylphenol (II-35) (272 mg, 2.00 mmol).

Step 2

By a production method similar to that in compound (I-1), compound (I-320) (yield 51.3 mg, quantitative) was obtained as a colorless oil from compound (IV-105) (50.0 mg, 0.147 mmol) and 2-methoxyphenylboronic acid (V-1) (26.8 mg, 0.175 mmol).

Step 1

By a production method similar to that in compound (IV-1), compound (IV-106) (yield 1.20 g, 79%) was obtained as a white solid from compound (III-10) (1.00 mg, 4.16 mmol) and 4-(trifluoromethyl)phenol (II-18) (909 mg, 4.99 mmol).

Step 2

By a production method similar to that in compound (I-1), compound (I-321) (yield 36.0 mg, quantitative) was obtained as a colorless oil from compound (IV-106) (30.0 mg, 0.0838 mmol) and 2-methoxyphenylboronic acid (V-1) (18.7 mg, 0.123 mmol).

Example 322

Production of 4-[4-(difluoromethyl)phenoxy]-5-(2-methoxyphenyl)pyrimidine (I-322)

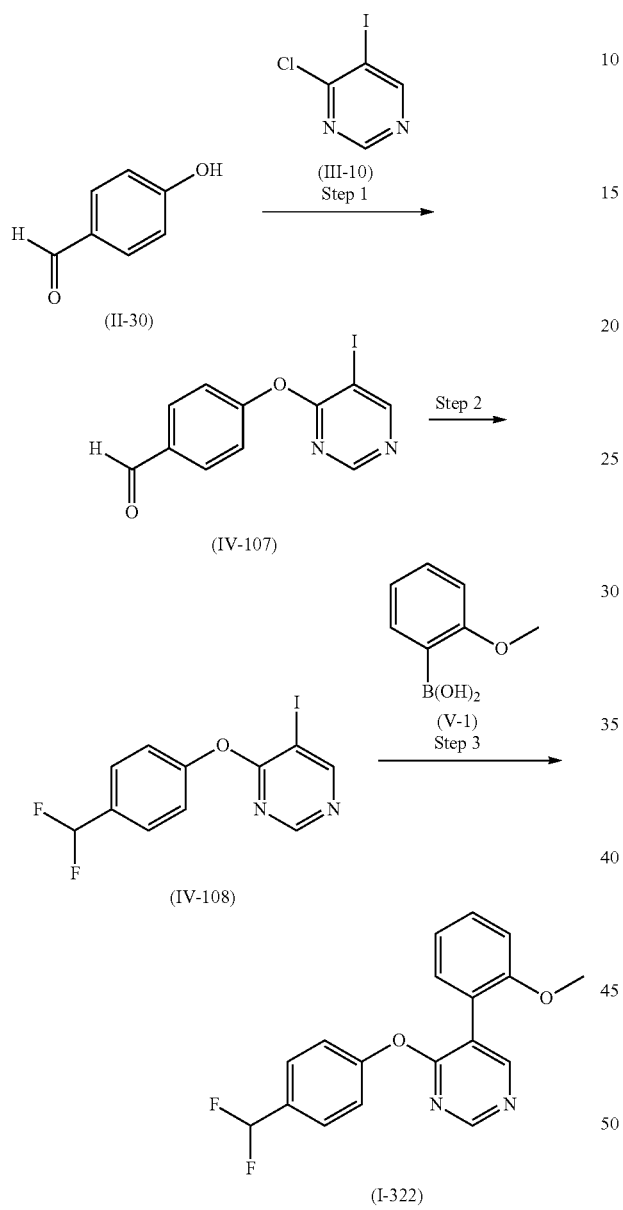

Step 1
Compound (III-10) (1.80 g, 7.49 mmol) and compound (II-30) (0.914 g, 7.49 mmol) were dissolved in DMSO (3.0 mL), cesium carbonate (407 mg, 1.25 mmol) was added, and the mixture was stirred under microwave irradiation at 80° C. for 30 min. The mixture was extracted with ethyl acetate and water, and the organic layer was washed successively with water and saturated brine, dried over anhydrous sodium sulfate, and filtered. The solvent was evaporated under reduced pressure, and the residue was purified by silica gel column chromatography (n-hexane:ethyl acetate) to give compound (IV-107) (yield 1.35 g, 55%) as a yellow solid.

Step 2
Compound (IV-107) (1.30 g, 3.99 mmol) was dissolved in DCM (10 mL), DAST (1.58 mL, 12.0 mmol) was added, and the mixture was stirred at room temperature for 15 hr. Water was added to the reaction mixture, and the mixture was extracted with chloroform. The organic layer was dried over anhydrous sodium sulfate, and filtered. The solvent was evaporated under reduced pressure, and the residue was purified by silica gel column chromatography (n-hexane:ethyl acetate) to give compound (IV-108) (yield 1.21 g, 87%).

Step 3
By a production method similar to that in compound (I-1), compound (I-322) (yield 21.0 mg, 56%) was obtained as a colorless oil from compound (IV-108) (40.0 mg, 0.115 mmol) and 2-methoxyphenylboronic acid (V-1) (26.2 mg, 0.172 mmol).

Example 323

Production of 4-[4-(difluoromethyl)-3-methylphenoxy]-5-(2-methoxyphenyl)pyrimidine (I-323)

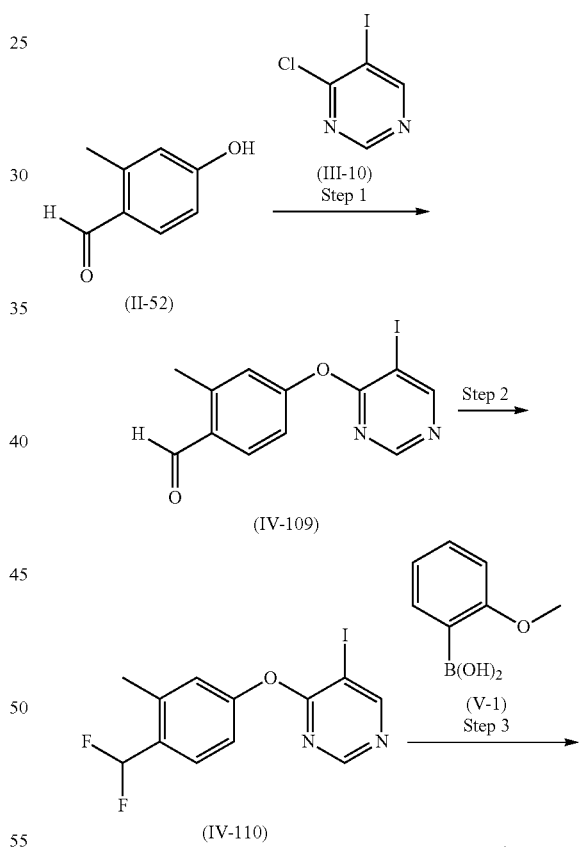

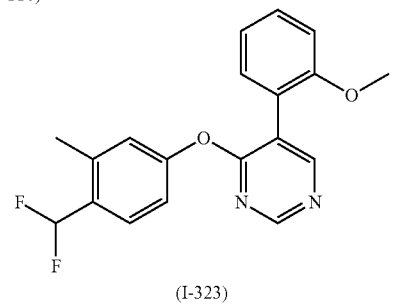

Step 1

By a production method similar to that in compound (IV-107), compound (IV-109) (yield 1.29 g, 69%) was obtained from compound (III-10) (1.32 mg, 5.49 mmol) and compound (II-52) (0.897 g, 6.59 mmol).

Step 2

By a production method similar to that in compound (IV-108), compound (IV-110) (yield 580 mg, 44%) was obtained from compound (IV-109) (1.25 g, 3.68 mmol) and DAST (2.43 mL, 18.4 mmol).

Step 3

By a production method similar to that in compound (I-1), compound (I-323) (yield 16.5 mg, 58%) was obtained as a white solid from compound (IV-110) (30.0 mg, 0.0830 mmol) and 2-methoxyphenylboronic acid (V-1) (18.9 mg, 0.124 mmol).

Example 324

Production of 4-{[6-difluoromethyl)-5-methylpyridin-3-yl]oxy}-5-(2,3-dihydrobenzofuran-7-yl)pyrimidine (I-324)

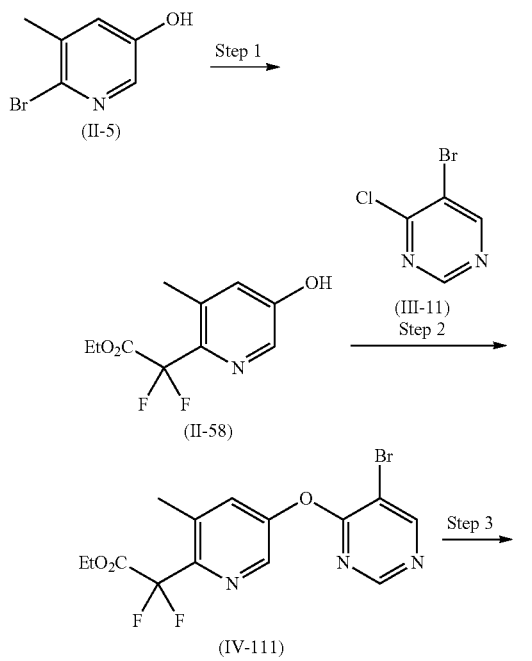

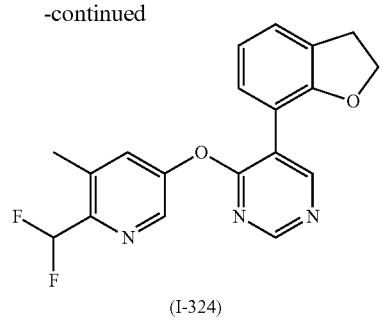

(I-324)

Step 1

By a production method similar to that in compound (II-57), compound (II-58) (yield 1.18 g, 48%) was obtained as a colorless oil from compound (II-5) (2.00 mg, 10.6 mmol) and ethyl 2-bromo-2,2-difluoroacetate (2.59 g, 12.7 mmol).

Step 2

By a production method similar to that in compound (IV-1), compound (IV-111) (yield 670 mg, 34%) was obtained as a colorless oil from compound (II-58) (1.18 g, 5.10 mmol) and compound (III-11) (987 mg, 5.10 mmol).

Step 3

By a production method similar to that in compound (IV-17), compound (IV-112) (yield 120 mg, 74%) was obtained as a white solid from compound (IV-111) (200 mg, 0.515 mmol) and magnesium chloride hexahydrate (241 mg, 1.19 mmol).

Step 4

By a production method similar to that in compound (I-1), compound (I-324) (yield 20.1 mg, 59%) was obtained as a colorless oil from compound (IV-112) (30.0 mg, 0.0949 mmol) and 2,3-dihydrobenzofuran-7-boronic acid (V-35) (32.4 mg, 0.214 mmol).

Example 325

Production of 5-(2,4-difluoro-5-methoxyphenyl)-4-{[6-(difluoromethyl)-5-methylpyridin-3-yl]oxy}pyrimidine (I-325)

By a production method similar to that in compound (I-1), compound (I-325) (yield 20.1 mg, 56%) was obtained as a colorless oil from compound (IV-112) (30.0 mg, 0.0949 mmol) and 2,4-difluoro-5-methoxyphenylboronic acid (V-41) (26.8 mg, 1.42 mmol).

Example 326

Production of 7-{4-[(2,3-dihydro-1H-inden-5-yl)oxy]pyrimidin-5-yl}pyrazolo[1,5-a]pyridine (I-326)

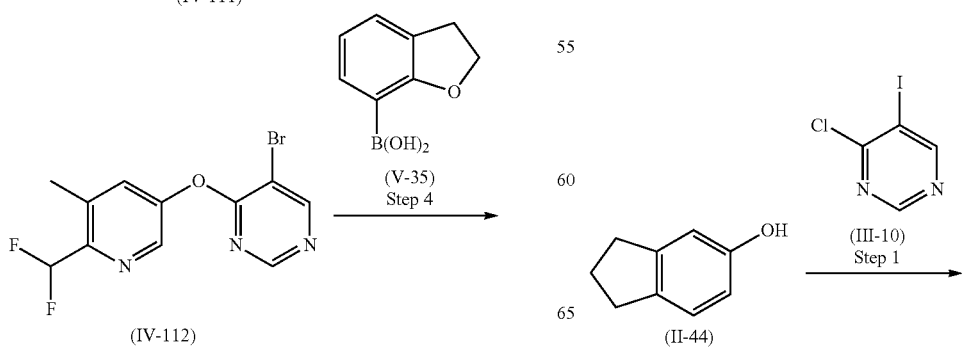

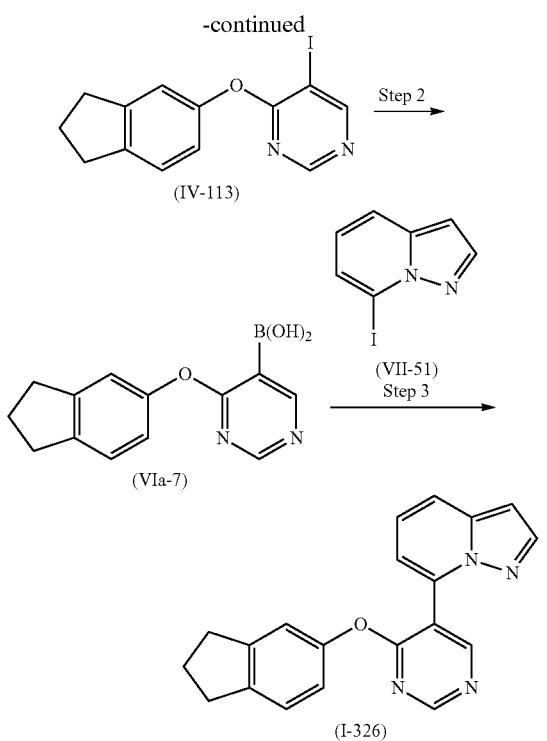

Step 1

By a production method similar to that in compound (IV-1), compound (IV-113) (yield 157 mg, 56%) was obtained as a white solid from compound (III-10) (200 mg, 0.832 mmol) and 2,3-dihydro-1H-inden-5-ol (II-44) (134 mg, 0.998 mmol).

Step 2

By a production method similar to that in compound (VIa-2), compound (VIa-7) (yield 80.8 mg, 90%) was obtained as a yellow solid from compound (IV-113) (119 mg, 0.352 mmol), 1.3 mol/L THF solution of iPrMgBr.LiCl (0.325 mL, 4.22 mmol) and triisopropyl borate (245 μL, 1.06 mmol).

Step 3

By a production method similar to that in compound (I-36), compound (I-326) (yield 36.0 mg, quantitative) was obtained as a colorless oil from compound (VIa-7) (50.0 mg, 0.195 mmol) and 7-iodopyrazolo[1,5-a]pyridine (VII-51) (39.7 mg, 0.163 mmol).

Example 327

Production of 5-(2,3-dihydrobenzofuran-7-yl)-4-{[6-(trifluoromethyl)pyridin-3-yl]oxy}pyrimidine (I-327)

By a production method similar to that in compound (I-1), compound (I-327) (yield 10.2 mg, 35%) was obtained as a colorless oil from compound (III-95) (30.0 mg, 0.0817 mmol) and 2,3-dihydrobenzofuran-7-boronic acid (V-35) (16.1 mg, 0.0981 mmol).

Example 328

Production of 5-(4,5-difluoro-2-methoxyphenyl)-4-{[6-(trifluoromethyl)pyridin-3-yl]oxy}pyrimidine (I-328)

By a production method similar to that in compound (I-1), compound (I-328) (yield 8.5 mg, 27%) was obtained as a colorless oil from compound (IV-95) (30.0 mg, 0.0817 mmol) and 4,5-difluoro-2-methoxyphenylboronic acid (V-40) (18.4 mg, 0.0981 mmol).

Example 329

Production of 5-(2,4-difluoro-5-methoxyphenyl)-4-{[6-(trifluoromethyl)pyridin-3-yl]oxy}pyrimidine (I-329)

By a production method similar to that in compound (I-1), compound (I-329) (yield 35.1 mg, 84%) was obtained as a colorless oil from compound (IV-95) (40.0 mg, 0.109 mmol) and 2,4-difluoro-5-methoxyphenylboronic acid (V-41) (26.6 mg, 0.142 mmol).

Example 330

Production of 5-(2-methoxypyridin-3-yl)-4-[4-(trifluoromethyl)phenoxy]pyrimidine (I-330)

By a production method similar to that in compound (I-1), compound (I-330) (yield 26.5 mg, 90%) was obtained as a colorless oil from compound (IV-106) (30.0 mg, 0.0838 mmol) and 2-methoxypyridine-3-boronic acid (V-26) (18.8 mg, 0.123 mmol).

Example 331

Production of 5-(5-chloro-4-methoxypyridin-3-yl)-4-[4-(trifluoromethyl)phenoxy]pyrimidine (I-331)

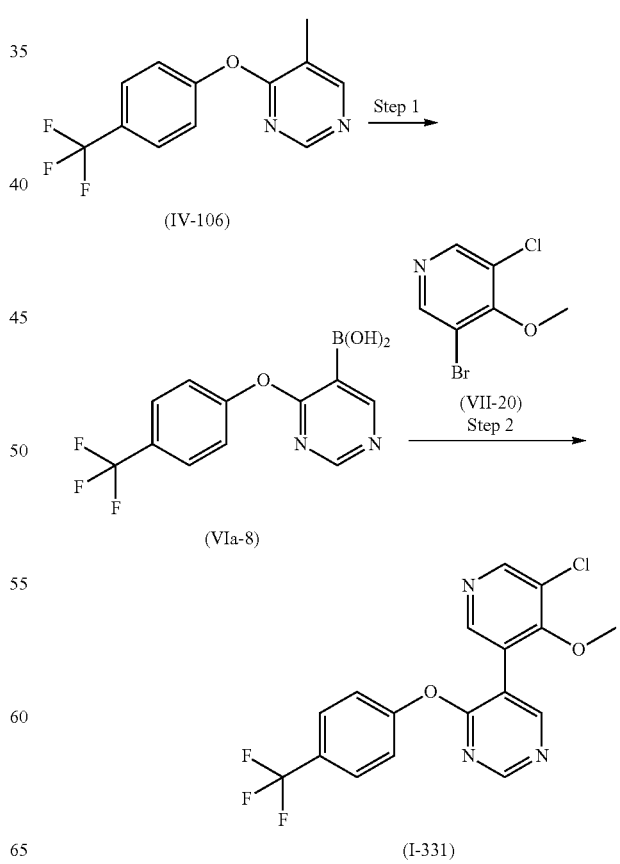

Step 1

By a production method similar to that in compound (VIa-2), compound (VIa-8) (yield 107 mg, 69%) was obtained as a pale-yellow solid from compound (IV-106) (200 mg, 0.515 mmol), 1.3 mol/L THF solution of iPrMg-Br.LiCl (504 μL, 0.655 mmol) and triisopropyl borate (380 μL, 1.64 mmol).

Step 2

By a production method similar to that in compound (I-36), compound (I-331) (yield 6.3 mg, 7%) was obtained as a colorless oil from compound (VIa-8) (50.0 mg, 0.225 mmol) and 3-bromo-5-chloro-4-methoxypyridine (VII-20) (77.0 mg, 0.270 mmol).

Example 332

Production of 7-{4-[4-(trifluoromethyl)phenoxy]pyrimidin-5-yl}pyrazolo[1,5-a]pyridine (I-332)

By a production method similar to that in compound (I-36), compound (I-332) (yield 1.30 mg, 23%) was obtained as a white solid from compound (VIa-8) (4.45 g, 15.7 mmol) and 7-iodopyrazolo[1,5-a]pyridine (VII-51) (3.82 g, 15.7 mmol).

Example 333

Production of 7-{4-[4-(1,1-difluoroethyl)phenoxy]pyrimidin-5-yl}pyrazolo[1,5-a]pyridine (I-333)

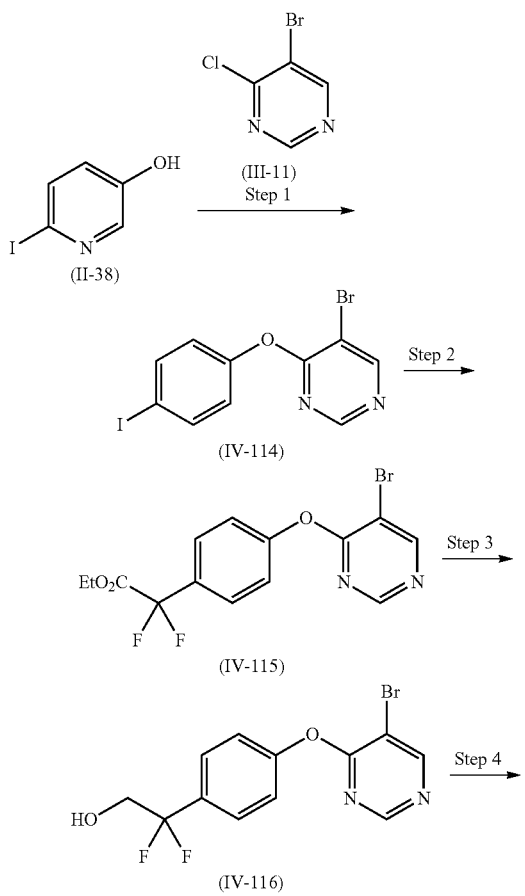

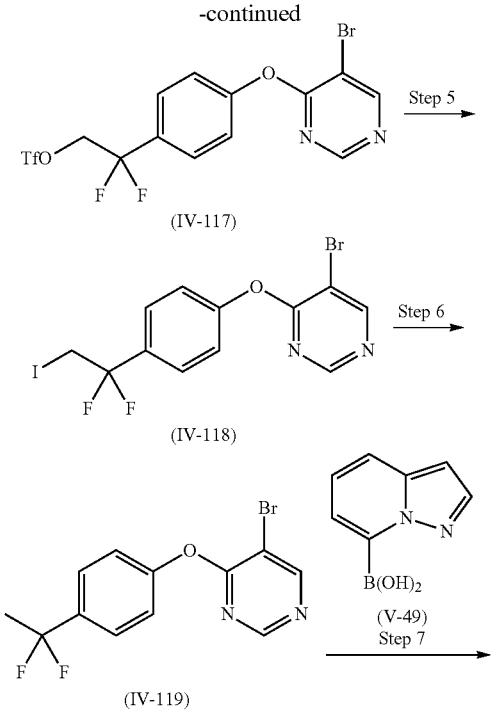

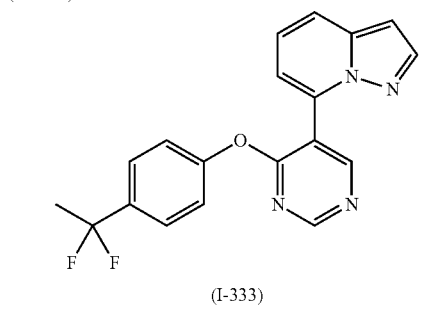

Step 1

By a production method similar to that in compound (IV-1), compound (IV-114) (yield 15.5 g, 80%) was obtained from compound (III-11) (10.0 g, 51.7 mmol) and 4-iodophenol (II-38) (13.7 g, 62.0 mmol).

Step 2

Compound (IV-114) (15.0 g, 39.7 mmol), ethyl 2-bromo-2,2-difluoroacetate (8.61 g, 39.7 mmol) and copper (powder, <75 μm, 99.9%, 5.75 g, 91.0 mmol) were dissolved in DMSO (50 mL), and the mixture was stirred at 70° C. for 12 hr. The reaction mixture was allowed to cool, saturated aqueous potassium monohydrogen phosphate solution was added, and the mixture was extracted with chloroform. The organic layer was washed with saturated brine, dried over anhydrous sodium sulfate, and filtered. The solvent was evaporated under reduced pressure, and the residue was purified by silica gel column chromatography (n-hexane:ethyl acetate) to give compound (IV-115).

Step 3

Compound (IV-115) was dissolved in THF (10 mL), sodium borohydride (1.21 g, 31.9 mmol) was added under ice-cooling, and the mixture was stirred at room temperature for 1 hr. The reaction mixture was allowed to cool, water was added, and the mixture was extracted with ethyl acetate. The organic layer was washed with saturated brine, dried over anhydrous sodium sulfate, and filtered. The solvent was evaporated under reduced pressure, and the residue was purified by silica gel column chromatography (n-hexane: ethyl acetate) to give compound (IV-116) [yield 905 mg, 23% (2 steps)].

Step 4

Compound (IV-116) (900 mg, 2.72 mmol) and pyridine (1.76 mL 21.7 mmol) were dissolved in DCM (5.0 mL), trifluoromethanesulfonic anhydride (1.84 mL, 10.9 mmol) was added under ice-cooling, and the mixture was stirred at room temperature for 3 hr. Water was added to the reaction mixture, and the mixture was extracted with ethyl acetate. The organic layer was dried over anhydrous sodium sulfate, and filtered. The solvent was evaporated under reduced pressure, and the residue was purified by silica gel column chromatography (n-hexane:ethyl acetate) to give compound (IV-117) (yield 682 mg, 54%).

Step 5

Compound (IV-117) (682 mg, 1.47 mmol) was dissolved in acetone (3.0 mL), sodium iodide (1.10 g, 7.36 mmol) was added, and the mixture was stirred at room temperature for 4 hr. Water was added to the reaction mixture, and the mixture was extracted with ethyl acetate. The organic layer was dried over anhydrous sodium sulfate, and filtered. The solvent was evaporated under reduced pressure, and the residue was purified by silica gel column chromatography (n-hexane:ethyl acetate) to give compound (IV-118) (yield 440 mg, 68%).

Step 6

Compound (IV-118) (435 mg, 0.986 mmol) was dissolved in THF (0.40 mL), tributyltin hydride (1.32 mL, 4.93 mmol) was added and the mixture was stirred at 70° C. for 2 hr. Water was added to the reaction mixture, and the mixture was extracted with ethyl acetate. The organic layer was dried over anhydrous sodium sulfate, and filtered. The solvent was evaporated under reduced pressure, and the residue was purified by silica gel column chromatography (n-hexane: ethyl acetate) to give compound (IV-119) (yield 265 mg, 85%) as a colorless oil.

Step 7

By a production method similar to that in compound (I-1), compound (I-333) (yield 13.0 mg, 23%) was obtained as a colorless oil from compound (IV-119) (50.0 mg, 0.159 mmol) and pyrazolo[1,5-a]pyridine-7-boronic acid (V-49) (51.4 mg, 0.317 mmol).

Example 334

Production of 4-{[6-(1,1-difluoroethyl)pyridin-3-yl] oxy}-5-(2,4-difluoro-5-methoxyphenyl)pyrimidine (I-334)

By a production method similar to that in compound (I-1), compound (I-334) (yield 41.2 mg, 86%) was obtained as a white solid from compound (IV-100) (40.0 mg, 0.127 mmol) and 2,4-difluoro-5-methoxyphenylboronic acid (V-41) (30.9 mg, 0.165 mmol).

Example 335

Production of 4-{[6-(1,1-difluoroethyl)pyridin-3-yl] oxy}-5-(2,3-dihydrobenzofuran-7-yl)pyrimidine (I-335)

By a production method similar to that in compound (I-1), compound (I-335) (yield 39.1 mg, 77%) was obtained as a white solid from compound (IV-100) (45.0 mg, 0.142 mmol) and 2,3-dihydrobenzofuran-7-boronic acid (V-35) (35.0 mg, 0.214 mmol).

Example 336

Production of 4-{[6-(1,1-difluoroethyl)pyridin-3-yl] oxy}-5-(4,5-difluoro-2-methoxyphenyl)pyrimidine (I-336)

By a production method similar to that in compound (I-1), compound (I-336) (yield 37.1 mg, 77%) was obtained as a white solid from compound (IV-100) (40.0 mg, 0.127 mmol) and 4,5-difluoro-2-methoxyphenylboronic acid (V-40) (30.9 mg, 0.165 mmol).

Reference Example 337

Production of 5-{[3-(2-methoxyphenyl)pyridin-2-yl] oxy}pyrimidin-2-amine (I-337)

By a production method similar to that in compound (I-1), compound (I-337) (yield 452 mg, 82%) was obtained as a white solid from compound (IV-28) (500 mg, 1.87 mmol) and 2-methoxyphenylboronic acid (V-1) (341 mg, 2.25 mmol).

Example 338

Production of 2-chloro-5-{[3-(2-methoxyphenyl) pyridin-2-yl]oxy}pyrimidine (I-338)

By a production method similar to that in compound (IV-29), compound (I-338) (yield 55.0 mg, 38%) was obtained as a white solid from compound (I-337) (136 mg, 0.462 mmol), zinc(II) chloride (107 mg, 0.786 mmol) and sodium nitrite (54.2 mg, 0.786 mmol).

Example 339

Production of N-benzyl-5-{[3-(2-methoxyphenyl) pyridin-2-yl]oxy}-N-methylpyrimidin-2-amine (I-339)

Compound (I-338) (23.0 g, 0.0733 mmol) was dissolved in DMF (1 mL), N-methyl-1-phenylmethanamine (26.7 mg, 0.220 mmol) and potassium carbonate (50.7 mg, 0.367 mmol) were added and the mixture was stirred at 100° C. for 18 hr. Water was added to discontinue the reaction, and the mixture was extracted with ethyl acetate. The organic layer was washed with saturated brine, dried over anhydrous magnesium sulfate, and the solvent was evaporated under reduced pressure. The residue was purified by silica gel column chromatography (n-hexane:ethyl acetate) to give compound (I-339) (yield 15.6 mg, 53%) as a colorless oil.

Example 340

Production of 5-{[3-(2,3-dihydrobenzofuran-7-yl) pyridin-2-yl]oxy}-N-ethyl-N-methylpyrimidin-2-amine (I-340)

By a production method similar to that in compound (I-1), compound (I-340) (yield 21.3 mg, 99%) was obtained as a colorless oil from compound (IV-31) (19.0 mg, 0.0615 mmol) and 2,3-dihydrobenzofuran-7-boronic acid (V-35) (51.1 mg, 0.0922 mmol).

Example 341

Production of 2-[4-(trifluoromethyl)phenoxy]-3-(1,3,5-trimethyl-1H-pyrazol-4-yl)pyridine (I-341)

By a production method similar to that in compound (I-1), compound (I-341) (yield 10.1 mg, 31%) was obtained as a white solid from compound (IV-39) (30.0 mg, 0.0943 mmol) and 1,3,5-trimethyl-1H-pyrazol-4-boronic acid pinacol ester (V-52) (26.7 mg, 0.113 mmol).

Example 342

Production of (2,4-dimethyl-5-{2-[4-(trifluoromethyl)phenoxy]pyridin-3-yl}thiazole (I-342)

By a production method similar to that in compound (I-1), compound (I-342) (yield 25.5 mg, 77%) was obtained as a colorless oil from compound (IV-39) (30.0 mg, 0.0943 mmol) and 2,4-dimethylthiazole-5-boronic acid pinacol ester (V-53) (27.1 mg, 0.113 mmol).

Example 343

Production of 5-(2-{[6-(1,1-difluoro-2-methoxyethyl)pyridin-3-yl]oxy}pyridin-3-yl)-[1,2,4]triazolo[1,5-a]pyridine (I-343)

By a production method similar to that in compound (I-36), compound (I-343) (yield 21.5 mg, 58%) was obtained as a colorless oil from compound 5-bromo[1,2,4]triazolo[1,5-a]pyridine (VII-9) (28.7 mg, 0.145 mmol) and compound (VIa-3) (30.0 mg, 0.0968 mmol).

Example 344

Production of ethyl 2-[(5-{[3-(2-methoxyphenyl)pyridin-2-yl]oxy}pyridin-2-yl)(methyl)amino]acetate (I-344)

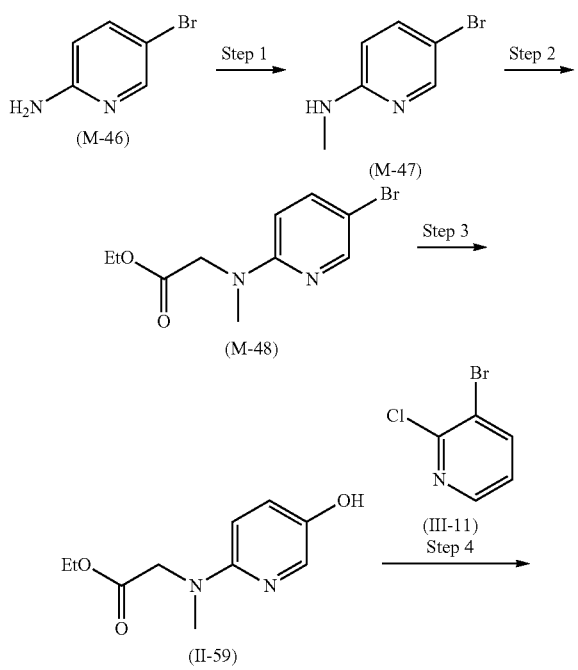

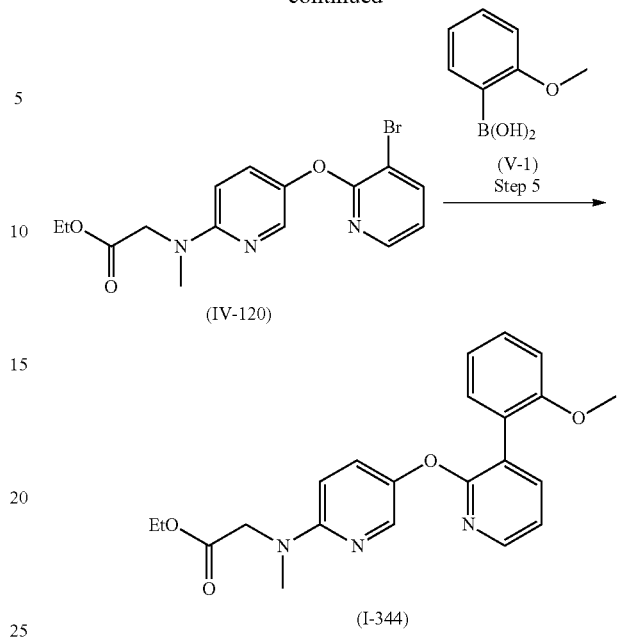

Step 1

By a production method similar to that in compound (I-47), compound (M-47) (yield 1.19 g, 22%) was obtained from 5-bromopyridin-2-amine (M-46) (5.00 g, 28.9 mmol) and methyl iodide (1.8 mL, 29 mmol).

Step 2

Compound (M-47) (1.19 g, 6.36 mmol) was dissolved in DMF (21 mL), sodium hydride (229 mg, 9.54 mmol) was added and the mixture was stirred under ice-cooling for 20 min. Ethyl bromoacetate (1.4 mL, 13 mmol) was added under ice-cooling, and the mixture was warmed to room temperature and stirred for 1 hr. The mixture was heated to 70° C. and stirred for 16 hr. Water was added, and the mixture was extracted with ethyl acetate. The organic layer was washed successively with water and saturated brine, and the organic layer was dried over anhydrous sodium sulfate. The solvent was evaporated under reduced pressure, and the residue was purified by silica gel column chromatography (n-hexane:ethyl acetate) to give compound (M-48) (yield 644 mg, 37%).

Step 3

Compound (M-48) (640 mg, 2.34 mmol) was dissolved in DMF (8.0 mL), bis(pinacolato)diboron (714 mg, 2.81 mmol), potassium acetate (689 mg, 7.02 mmol) and palladium acetate (26.3 mg, 0.117 mmol) were successively added, and the mixture was stirred at 80° C. for 16 hr. The resulting solid was removed by filtration, water was added, and the mixture was extracted with ethyl acetate. The organic layer was washed successively with water and saturated brine, dried over anhydrous sodium sulfate, and filtered. The solvent was evaporated under reduced pressure. The residue was dissolved in THF (12 mL) and water (12 mL), sodium perborate (1.30 g, 8.42 mmol) was added, and the mixture was stirred at room temperature for 13 hr. The reaction was discontinued by adding saturated aqueous ammonium chloride solution, and the mixture was extracted with ethyl acetate. The organic layer was washed successively with saturated aqueous ammonium chloride solution and saturated brine, and dried over anhydrous sodium sulfate. The solvent was evaporated under reduced pressure, and the residue was purified by silica gel column chromatography (n-hexane:ethyl acetate=95:5→50:50) to give compound (II-59) (yield 357 mg, 73%).

Step 4

By a production method similar to that in compound (IV-1), compound (IV-120) (yield 82.0 mg, 13%) was obtained from compound (III-1) (489 mg, 2.54 mmol) and compound (II-59) (356 mg, 1.69 mmol).

Step 5

By a production method similar to that in compound (I-1), compound (I-344) (yield 18.5 mg, 65%) was obtained as a pale-yellow solid from compound (IV-120) (26.7 mg, 0.0729 mmol) and 2-methoxyphenylboronic acid (V-1) (14.5 mg, 0.0948 mmol).

Example 345

Production of 2-[(2,3-dihydro-1H-inden-5-yl)oxy]-3-(2-methoxyphenyl)pyridine (I-345)

By a production method similar to that in compound (I-1), compound (I-345) (yield 115 mg, quantitative) was obtained as a colorless oil from compound (IV-66) (100 mg, 0.345 mmol) and 2-methoxyphenylboronic acid (V-1) (79.0 mg, 0.518 mmol).

Example 346

Production of 2-{[6-(trifluoromethyl)pyridin-3-yl]oxy}-3-(1,3,5-trimethyl-1H-pyrazol-4-yl)pyridine (I-346)

By a production method similar to that in compound (I-1), compound (I-346) (yield 21.2 mg, 39%) was obtained as a colorless oil from compound (IV-1) (50.0 mg, 0.157 mmol) and 1,3,5-trimethyl-1H-pyrazole-4-boronic acid pinacol ester (V-52) (48.1 mg, 0.204 mmol).

Example 347

Production of (2,2-difluoro-2-(5-{[2'-methoxy-(3,3'-bipyridin)-2-yl]oxy}pyridin-2-yl)ethanol (I-347)

By a production method similar to that in compound (I-1), compound (I-347) (yield 182 mg, 95%) was obtained as a colorless oil from compound (IV-10) (176 mg, 0.555 mmol) and 2-methoxypyridine-3-boronic acid (V-26) (127 mg, 0.833 mmol).

Example 348

Production of 2-{[6-(1,1-difluoro-2-methoxyethyl)pyridin-3-yl]oxy}-2'-methoxy-3,3'-bipyridine (I-348)

By a production method similar to that in compound (I-145), compound (I-348) (yield 15.5 mg, 50%) was obtained as a colorless oil from compound (I-347) (30.0 mg, 0.834 mmol) and methyl iodide (5.7 μL, 0.092 mmol).

Example 349

Production of 2-{[6-(1,1-difluoro-2-methoxyethyl)pyridin-3-yl]oxy}-4'-methoxy-3,3'-bipyridine (I-349)

By a production method similar to that in compound (I-1), compound (I-349) (yield 32.5 mg, 60%) was obtained as a colorless oil from compound (IV-24) (50.0 mg, 0.145 mmol) and 4-methoxypyridine-3-boronic acid (V-28a) (26.6 mg, 0.174 mmol).

Example 350

Production of 2-({6-[1,1-difluoro-2-(1H-pyrazol-1-yl)ethyl]pyridin-3-yl}oxy)-3-(2-methoxyphenyl)pyridine (I-350)

By a production method similar to that in compound (I-146), compound (I-350) (yield 35.6 mg, 85%) was obtained as a colorless oil from compound (I-80) (50.0 mg, 0.102 mmol) and 1H-pyrazole (69.4 mg, 1.02 mmol).

Example 351

Production of 2-({6-[1,1-difluoro-2-(1H-imidazol-1-yl)ethyl]pyridin-3-yl}oxy)-3-(2-methoxyphenyl)pyridine (I-351)

By a production method similar to that in compound (I-146), compound (I-351) (yield 33.1 mg, 79%) was obtained as a colorless oil from compound (I-80) (50.0 mg, 0.102 mmol) and 1H-imidazole (69.4 mg, 1.02 mmol).

Reference Example 352

Production of 5-{[2'-methoxy-(3,3'-bipyridin)-2-yl]oxy}-pyrimidin-2-amine (I-352)

By a production method similar to that in compound (I-1), compound (I-352) (yield 560 mg, quantitative) was obtained as a white solid from compound (IV-28) (500 mg, 1.87 mmol) and 2-methoxypyridine-3-boronic acid (V-26) (372 mg, 2.43 mmol).

Example 353

Production of 2-[(2-iodopyrimidin-5-yl)oxy]-2'-methoxy-(3,3'bipyridine (I-353)

By a production method similar to that in compound (I-191), compound (I-353) (yield 263 mg, 67%) was obtained as a pale-yellow oil from compound (I-352) (285 mg, 0.965 mmol), isoamyl nitrite (0.39 mL, 2.90 mmol) and diiodomethane (0.78 mL, 9.65 mmol).

Example 354

Production of methyl 2-[(5-{[2'-methoxy-(3,3'-bipyridin)-2-yl]oxy}-pyrimidin-2-yl)(methyl)amino]acetate (I-354)

Compound (I-353) (50.0 mg, 0.123 mmol) was dissolved in DMA (1.0 mL), DIPEA (100 μL, 0.581 mmol) and sarcosine methyl ester (30.0 mg, 0.215 mmol) were successively added, and the mixture was stirred at 100° C. overnight. Water was added to the reaction mixture, and the mixture was extracted with chloroform. The organic layer was washed successively with water and saturated brine, and dried over anhydrous sodium sulfate, and the solvent was evaporated under reduced pressure. The residue was purified by silica gel column chromatography (n-hexane:ethyl acetate) to give compound (I-354) (yield 35.0 mg, 75%) as a colorless oil.

Example 355

Production of 5'-chloro-2-[4-(difluoromethyl)phenoxy]-4'-methoxy-3,3'-bipyridine (I-355)

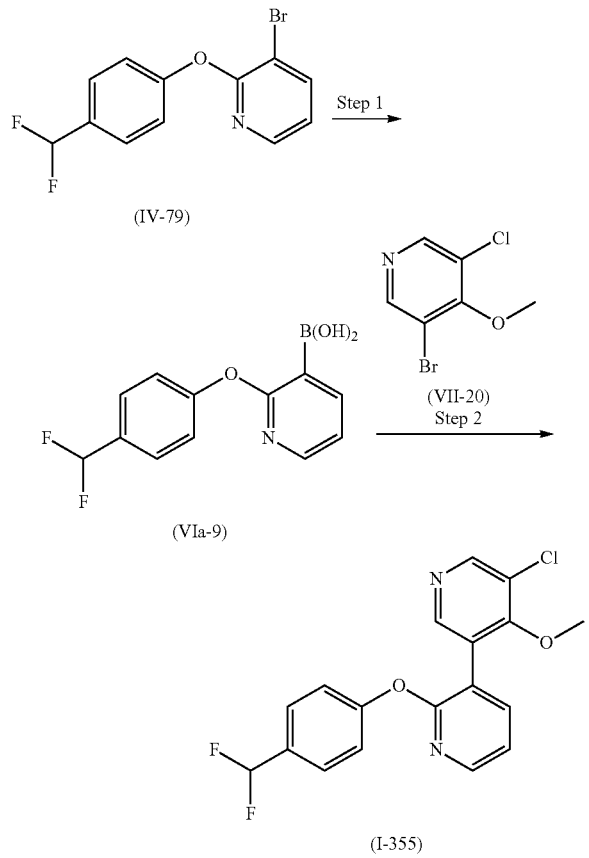

Step 1

By a production method similar to that in compound (VIa-6), compound (VIa-9) (yield 442 mg, quantitative) was obtained as a pale-yellow solid from compound (IV-79) (500 mg, 1.67 mmol) and iPrMgBr.LiCl (1.3 mol/L THF solution, 2.56 mL, 1.16 mmol) and triisopropyl borate (1.16 mL, 5.00 mmol).

Step 2

By a production method similar to that in compound (I-36), compound (I-355) (yield 41.6 mg, 51%) was obtained as a colorless oil from compound (VIa-9) (71.5 mg, 0.270 mmol) and compound (VII-20) (50.0 mg, 0.225 mmol).

Example 356

Production of 2-[4-(difluoromethyl)phenoxy]-5'-fluoro-4'-methoxy-3,3'-bipyridine (I-356)

By a production method similar to that in compound (I-36), compound (I-356) (yield 54.1 mg, 80%) was obtained as a colorless oil from compound (VIa-9) (61.7 mg, 0.233 mmol) and compound (VII-34) (40.0 mg, 0.194 mmol).

Example 357

Production of 4-(4-chlorophenoxy)-5-(4-methoxypyridin-3-yl)pyrimidine (I-357)

By a production method similar to that in compound (I-1), compound (I-357) (yield 36.1 mg, 78%) was obtained as a colorless oil from compound (IV-104) (48.9 mg, 0.147 mmol) and 4-methoxypyridine-3-boronic acid (V-28a) (44.9 mg, 0.294 mmol).

Example 358

Production of 7-{4-[4-(difluoromethyl)phenoxy]pyrimidin-5-yl)pyrazolo[1,5-a]-pyridine (I-358)

By a production method similar to that in compound (I-1), compound (I-358) (yield 46.0 mg, 95%) was obtained as a white solid from compound (IV-108) (50.0 mg, 0.144 mmol) and pyrazolo[1,5-a]pyridine-7-boronic acid (V-49) (58.2 mg, 0.359 mmol).

Example 359

Production of 4-{[6-(1,1-difluoroethyl)pyridin-3-yl]oxy}-5-(4-fluoro-2-methoxyphenyl)pyrimidine (I-359)

By a production method similar to that in compound (I-1), compound (I-359) (yield 21.5 mg, 42%) was obtained as a colorless oil from compound (IV-100) (45.0 mg, 0.142 mmol) and 4-fluoro-2-methoxyphenylboronic acid (V-12) (36.3 mg, 0.214 mmol).

Example 360

Production of 4-{[6-(1,1-difluoroethyl)pyridin-3-yl]oxy}-5-(5-fluoro-2-methoxyphenyl)pyrimidine (I-360)

By a production method similar to that in compound (I-1), compound (I-360) (yield 48.8 mg, 95%) was obtained as a white solid from compound (IV-100) (45.0 mg, 0.142 mmol) and 5-fluoro-2-methoxyphenylboronic acid (V-11) (36.3 mg, 0.214 mmol).

Example 361

Production of 4-{[6-(1,1-difluoro-2-methoxyethyl)pyridin-3-yl]oxy}-5-(2-methoxypyridin-3-yl)pyrimidine (I-361)

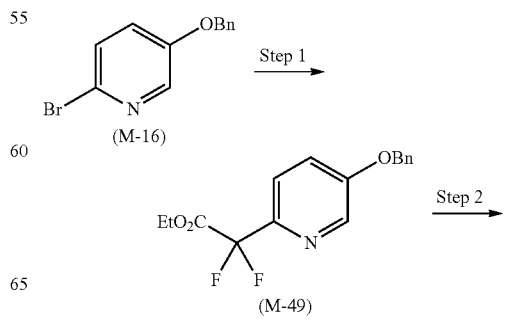

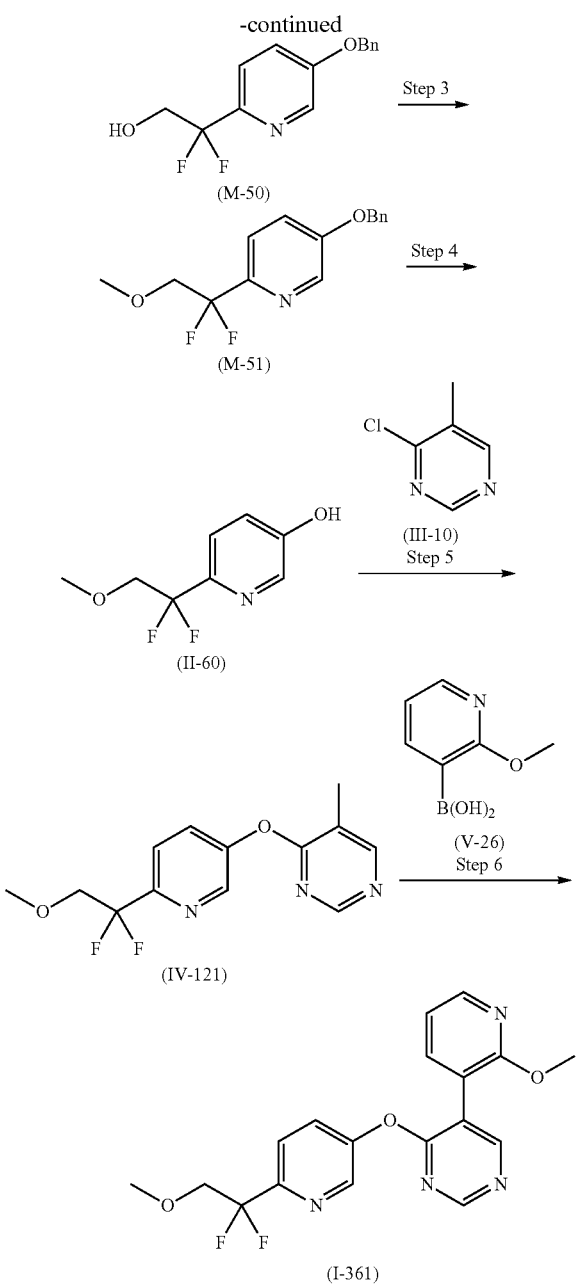

Step 1

Compound (M-16) (14.1 g, 53.4 mmol) and ethyl bromodifluoroacetate (10 mL, 80 mmol) were dissolved in DMSO (76 mL), copper (powder, <75 μm, 99.9%, 7.80 g, 123 mmol) was added and the mixture was stirred at 90° C. for 13 hr. The reaction mixture was cooled, and diluted with isopropyl acetate, saturated potassium dihydrogen phosphate solution was added, and the mixture was stirred for 30 min. The reaction mixture was extracted with ethyl acetate, the organic layer was washed successively with water and saturated brine, and the solvent was evaporated under reduced pressure. The residue was purified by silica gel column chromatography (n-hexane:ethyl acetate) to give compound (M-49) (yield 12.3 g, 75%) as a colorless oil.

Step 2

Compound (M-49) (12.3 g, 40.0 mmol) was dissolved in methanol (80 mL), sodium borohydride (4.64 g, 120 mmol) was added under ice-cooling, and the mixture was stirred at room temperature for 2 hr. To the reaction mixture was added saturated aqueous ammonium chloride solution, and the mixture was stirred for 1 hr, and extracted with ethyl acetate. The organic layer was washed successively with water and saturated brine, and the solvent was evaporated under reduced pressure. The residue was purified by silica gel column chromatography (n-hexane:ethyl acetate) to give compound (M-50) (yield 10.8 g, 99%) as a colorless oil.

Step 3

Compound (M-50) (10.8 g, 40.0 mmol) was dissolved in DMF (133 mL), 50% sodium hydride (2.11 g, 44.0 mmol) and methyl iodide (2.8 mL, 44 mmol) were successively added under ice-cooling, and the mixture was stirred at room temperature for 2 hr. Water was added to the reaction mixture, and the mixture was extracted with ethyl acetate. The organic layer was washed successively with water and saturated brine, and the solvent was evaporated under reduced pressure. The residue was purified by silica gel column chromatography (n-hexane:ethyl acetate) to give compound (M-51) (yield 11.2 g, quantitative) as a colorless oil.

Step 4

Compound (M-51) (11.2 g, 40.1 mmol) was dissolved in methanol (134 mL), 20% palladium hydroxide/carbon (1.12 g, 10 w/w %) was added, and the mixture was stirred under a hydrogen atmosphere at room temperature for 16 hr. The mixture was filtered through Celite, and the solvent was evaporated under reduced pressure, and the residue was purified by silica gel column chromatography (n-hexane: ethyl acetate) to give compound (II-60) (yield 11.2 g, quantitative) as a colorless oil.

Step 5

By a production method similar to that in compound (IV-1), compound (IV-121) (yield 134 mg, 17%) was obtained as a white solid from compound (III-10) (500 mg, 2.08 mmol) and compound (II-60) (375 mg, 1.98 mmol).

Step 6

By a production method similar to that in compound (I-1), compound (I-361) (yield 10.6 mg, 37%) was obtained as a colorless oil from compound (IV-121) (30.0 mg, 0.0763 mmol) and 2-methoxypyridine-3-boronic acid (V-26) (14.0 mg, 0.0915 mmol).

Example 362

Production of 5-(pyrazolo[1,5-a]pyridin-7-yl)-N-[4-(trifluoromethyl)phenyl]pyrimidin-4-amine (I-362)

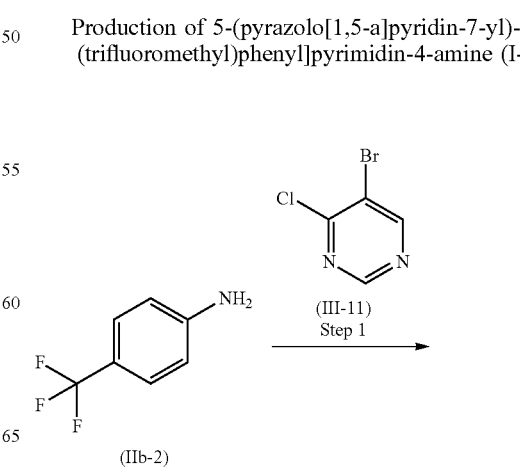

Step 1

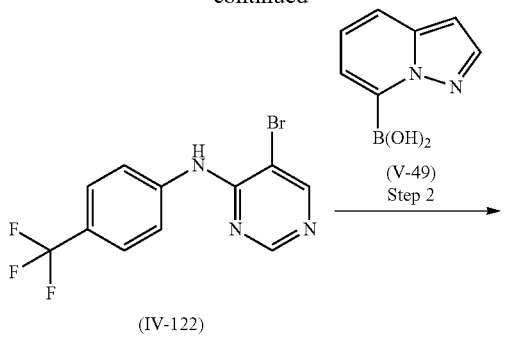

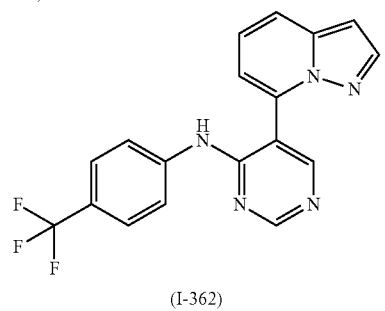

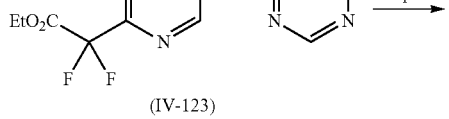

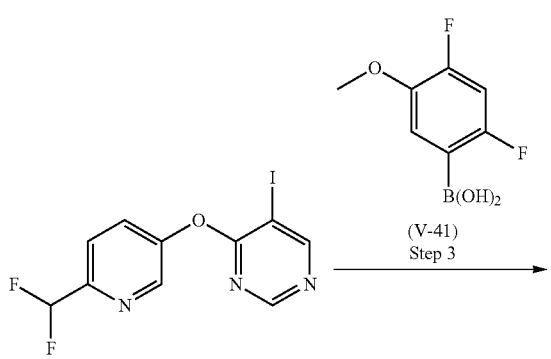

Step 1

Compound (III-11) (120 mg, 0.620 mmol) and compound (IIb-2) (150 mg, 0.931 mmol) were dissolved in NMP (2.0 mL), p-toluenesulfonic acid monohydrate (118 mg, 0.620 mmol) was added and the mixture was stirred at 60° C. for 2 hr. The reaction mixture was allowed to cool, water was added, and the mixture was extracted with ethyl acetate. The organic layer was dried over anhydrous sodium sulfate, and filtered. The solvent was evaporated under reduced pressure, and the residue was purified by silica gel column chromatography (n-hexane:ethyl acetate) to give compound (IV-122) (yield 100 mg, 51%).

Step 2

By a production method similar to that in compound (I-1), compound (I-362) (yield 49.0 mg, 73%) was obtained as a white solid from compound (IV-122) (60.0 mg, 0.189 mmol) and pyrazolo[1,5-a]pyridine-7-boronic acid (V-49) (61.1 mg, 0.377 mmol).

Example 363

Production of 5-(2,4-difluoro-5-methoxyphenyl)-4-{[6-(difluoromethyl)pyridin-3-yl]oxy}pyrimidine (I-363)

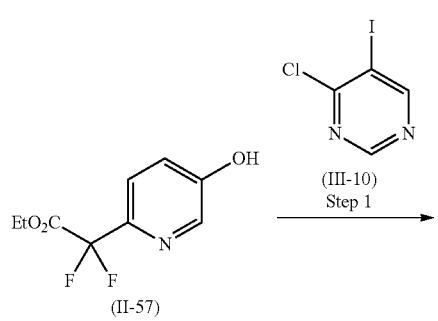

Step 1

By a production method similar to that in compound (IV-1), compound (IV-123) (yield 6.10 mg, 69%) was obtained as a pale-yellow solid from compound (II-57) (5.00 g, 23.0 mmol) and compound (III-10) (5.03 mg, 20.9 mmol).

Step 2

By a production method similar to that in compound (IV-17), compound (IV-124) (yield 301 mg, 36%) was obtained as a white solid from compound (IV-123) (1.00 g, 2.37 mmol) and magnesium chloride hexahydrate (241 mg, 1.19 mmol).

Step 3

By a production method similar to that in compound (I-1), compound (I-363) (yield 33.9 mg, 81%) was obtained as a colorless oil from compound (IV-124) (40.0 g, 0.115 mmol) and 2,4-difluoro-5-methoxyphenylboronic acid (V-41) (25.8 mg, 0.138 mmol).

Example 365

Production of 5-{[3-(2-methoxyphenyl)pyridin-2-yl]oxy}N,N-dimethylpyrimidin-2-amine (I-365)

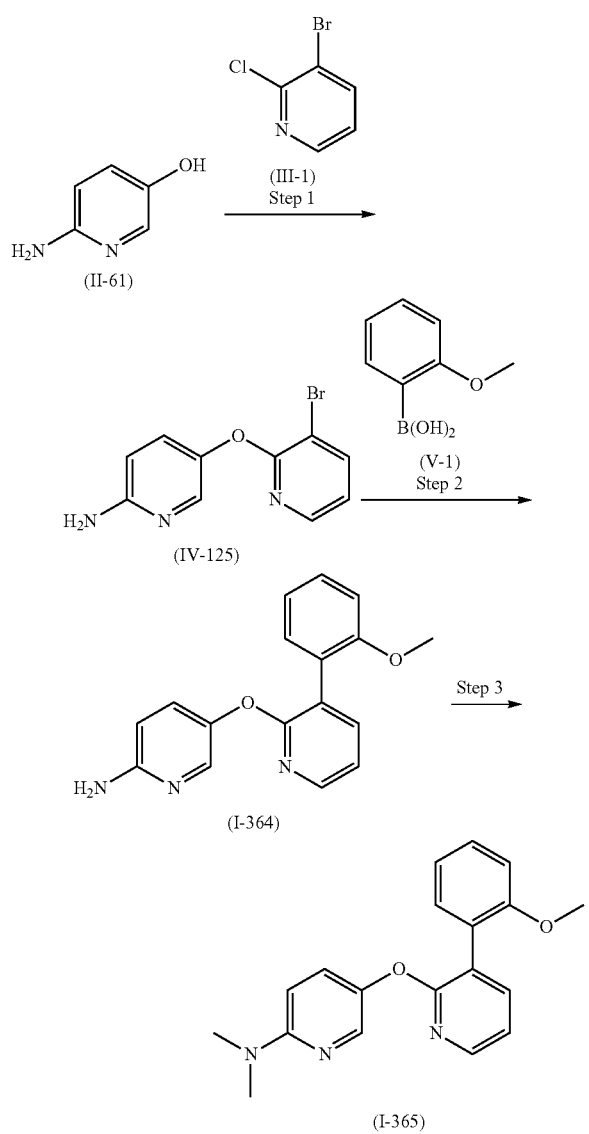

Step 1
By a production method similar to that in compound (IV-1), compound (IV-125) (yield 262 mg, 95%) was obtained as a pale-brown oil from compound (III-1) (200 mg, 1.04 mmol) and 2-aminopyridin-5-ol (II-61) (137 mg, 1.25 mmol).

Step 2
By a production method similar to that in compound (I-1), compound (I-364) (yield 210 mg, 73%) was obtained as a white solid from compound (IV-125) (260 mg, 0.977 mmol) and 2-methoxyphenylboronic acid (V-1) (223 mg, 1.47 mmol).

Step 3
Compound (I-364) (20.0 mg, 0.0628 mmol) was dissolved in acetonitrile (1.0 mL), formalin (56 μL, 0.68 mmol) and sodium triacetoxyborohydride (43.4 mg, 0.205 mmol) were added under ice-cooling, and the mixture was stirred at room temperature for 3 hr. Water was added to the reaction mixture, and the mixture was extracted with chloroform. The organic layer was dried over anhydrous sodium sulfate, and filtered, and the solvent was evaporated under reduced pressure. The residue was purified by silica gel column chromatography (n-hexane:ethyl acetate) to give compound (I-365) (yield 7.0 mg, 32%) as a yellow solid.

Example 366

Production of 2-[(6-chloropyridin-3-yl)oxy]-(3-(4-fluoro-2-methoxyphenyl)pyridine (I-366)

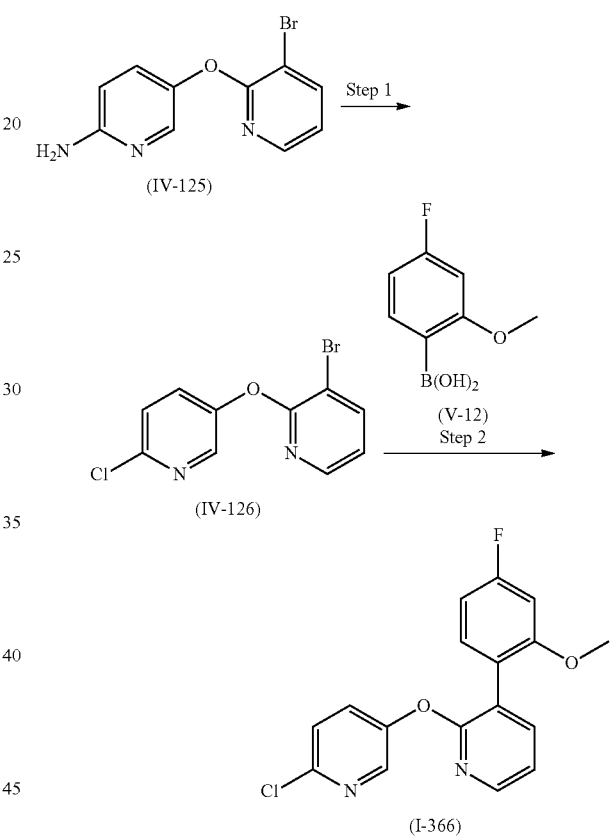

Step 1
Compound (IV-125) (500 mg, 1.88 mmol) was dissolved in DCM (4.0 mL), 6 mol/L hydrochloric acid (407 μL, 24.4 mmol) was added, zinc(II) chloride (512 mg, 3.76 mmol) was added under ice-cooling. The mixture was stirred under ice-cooling for 30 min. Sodium nitrite (259 mg, 3.76 mmol) was added under ice-cooling. The mixture was stirred under ice-cooling for 30 min. Sodium nitrite (259 mg, 3.76 mmol) was further added, and the mixture was stirred at room temperature for 41 hr. The reaction mixture was poured into ice-cold water, and the mixture was extracted with chloroform. The organic layer was dried over anhydrous magnesium sulfate, and filtered, and the solvent was evaporated under reduced pressure. The residue was purified by silica gel column chromatography to give compound (IV-126) (yield 250 mg, 47%).

Step 2
By a production method similar to that in compound (I-1), compound (I-366) (yield 115 mg, 86%) was obtained as an oil from compound (IV-126) (115 mg, 0.403 mmol) and 4-fluoro-2-methoxyphenylboronic acid (V-12) (75.0 mg, 0.444 mmol).

Example 367

Production of N-ethyl-5-{[3-(4-fluoro-2-methoxyphenyl)pyridin-2-yl]oxy}-N-methylpyridin-2-amine (I-367)

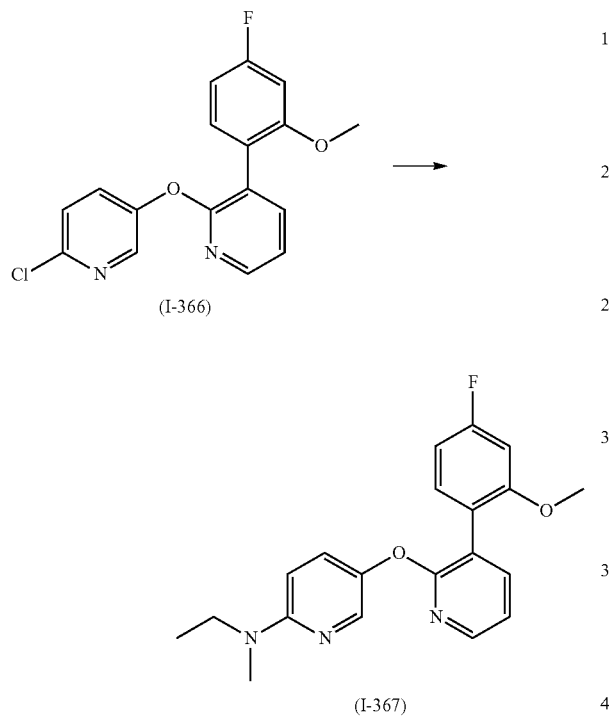

Compound (I-366) (50.0 mg, 0.151 mmol) was dissolved in toluene, N-methylethanamine (17.9 mg, 0.302 mL), sodium t-butoxide (29.1 mg, 0.302 mmol) and BINAP (9.4 mg, 0.0015 mmol) and Pd$_2$(dba)$_3$ (6.9 mg, 0.0076 mmol) were added and the mixture was stirred at 100° C. for 18 hr. Water was added to the reaction mixture, and the mixture was extracted with ethyl acetate. The organic layer was washed successively with water and saturated brine, dried over anhydrous magnesium sulfate, and filtered. The solvent was evaporated under reduced pressure, and the residue was purified by silica gel column chromatography to give compound (I-367) (yield 33.9 mg, 65%) as an oil.

Example 368

Production of 5-{[3-(4-fluoro-2-methoxyphenyl)pyridin-2-yl]oxy}-N-methyl-N-propylpyridin-2-amine (I-368)

By a production method similar to that in compound (I-367), compound (I-366) (yield 22.6 mg, 51%) was obtained as an oil from compound (IV-366) (39.7 mg, 0.120 mmol) and N-methyl-N-propylamine (24.1 μL, 17.6 mmol).

Example 369

Production of 5-{[3-(4-fluoro-2-methoxyphenyl)pyridin-2-yl]oxy}-N,N,3-trimethylpyrimidin-2-amine (I-369)

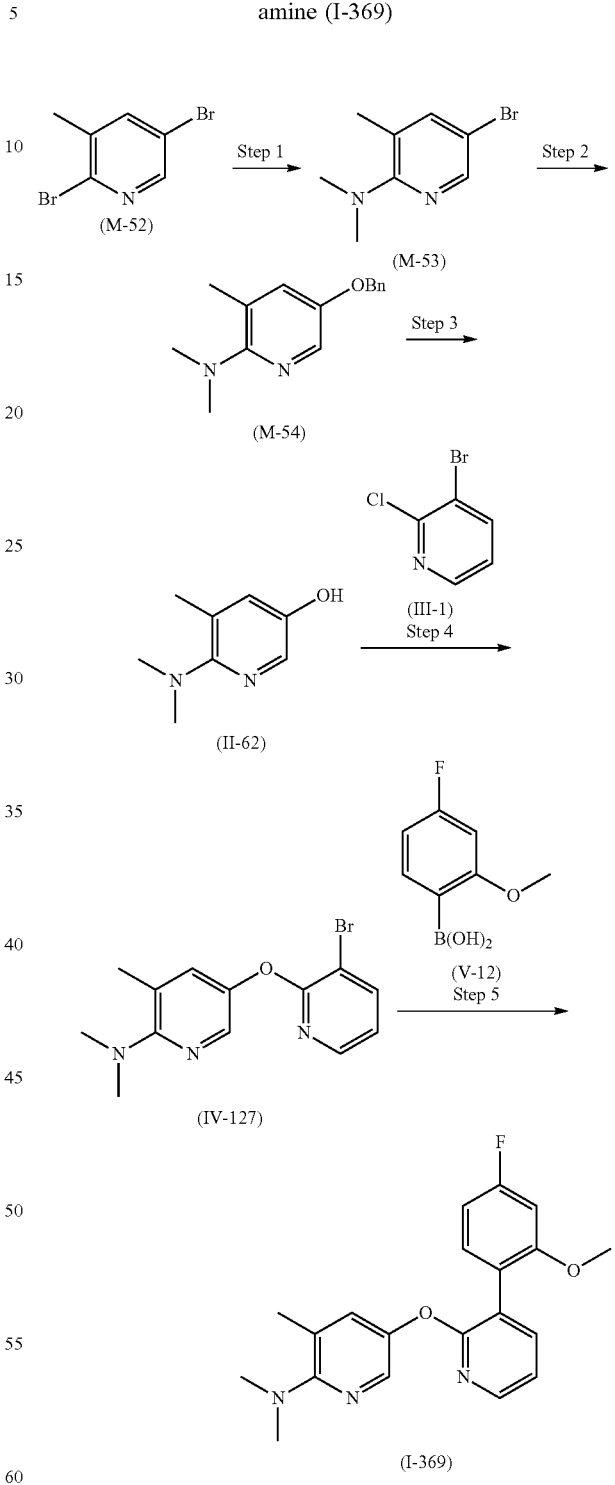

Step 1

Compound (M-52) (1.00 g, 3.99 mmol) was dissolved in aqueous dimethylamine solution (6.0 mL), and the mixture was stirred under microwave irradiation at 150° C. for 1 hr. Water was added to the reaction mixture, and the mixture was extracted with ethyl acetate. The organic layer was washed successively with water and saturated brine, dried over anhydrous sodium sulfate, and filtered. The solvent was evaporated under reduced pressure, and the residue was purified by silica gel column chromatography (n-hexane:ethyl acetate=100:0→80:20) to give compound (M-53) (yield 843 mg, 98%) as a colorless oil.

Step 2

Compound (M-53) (842 mg, 3.91 mmol) was dissolved in benzyl alcohol (4.1 mL), copper iodide (74.5 mg, 0.391 mmol), 1,10-phenanthroline (141 mg, 0.782 mmol) and cesium carbonate (2.55 g, 7.82 mmol) were successively added, and the mixture was stirred at 120° C. for 23 hr. The reaction mixture was filtered through Celite. The solvent was evaporated under reduced pressure, and the residue was purified by silica gel column chromatography (n-hexane:ethyl acetate=95:5→80:20) to give compound (M-54).

Step 3

Compound (M-54) was dissolved in ethanol (30 mL), 10% Pd/C (350 mg) was added, and the mixture was stirred under a hydrogen atmosphere at room temperature for 12 hr. The reaction mixture was filtered. The solvent was evaporated under reduced pressure, and the residue was purified by silica gel column chromatography (NH silica gel, n-hexane:ethyl acetate=80:20→10:90) to give compound (II-62) [yield 344 mg, 58% (2 steps)] as a white solid.

Step 4

Compound (II-62) (344 mg, 2.26 mmol) and compound (III-1) (652 mg, 3.39 mmol) were dissolved in DMSO (4.5 mL), cesium carbonate (1.47 g, 4.52 mmol) was added, and the mixture was stirred at 120° C. for 4 hr. The reaction mixture was cooled to room temperature, water was added, and the mixture was extracted with ethyl acetate. The organic layer was washed successively with water and saturated brine, dried over anhydrous sodium sulfate and filtered. The solvent was evaporated under reduced pressure, and the residue was purified by silica gel column chromatography (n-hexane:ethyl acetate=97:3→75:25) to give compound (IV-127) (yield 708 mg, quantitative) as a colorless oil.

Step 5

By a production method similar to that in compound (I-1), compound (I-369) (yield 43.8 mg, 77%) was obtained as a colorless oil from compound (IV-127) (50.0 mg, 0.162 mmol) and 4-fluoro-2-methoxyphenylboronic acid (V-12) (35.9 mg, 0.211 mmol).

Example 370

Production of 2-{[6-(difluoromethoxy)pyridin-3-yl]oxy}-3-(2-methoxyphenyl)pyridine (I-370)

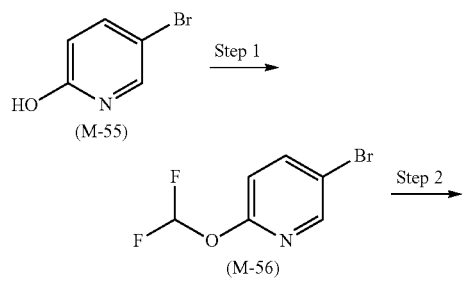

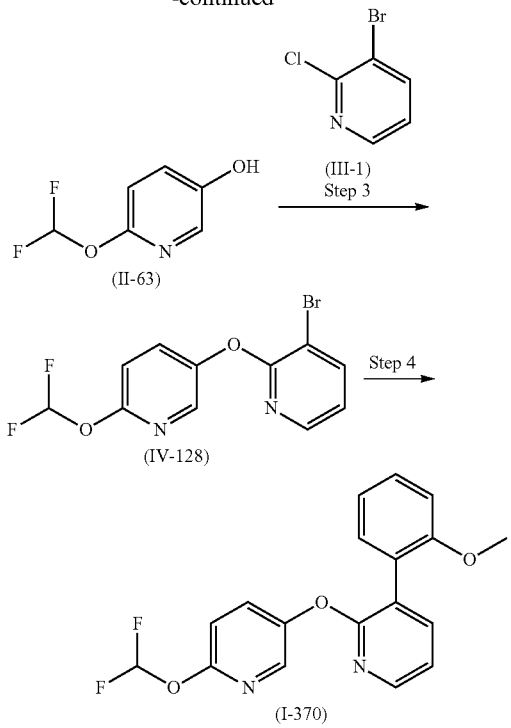

Step 1

Compound (M-55) (1.00 g, 5.75 mmol) was dissolved in acetonitrile (100 mL), sodium hydride (303 mg, 6.33 mmol) was added, and the mixture was stirred at room temperature for 15 min. 2,2-difluoro-2-(fluorosulfonyl)acetic acid (1.13 g, 6.33 mmol) was further added, and the mixture was stirred at room temperature for 15 min. Water was added to the reaction mixture, acetonitrile was evaporated under reduced pressure, and the mixture was extracted with ethyl acetate. The organic layer was washed successively with water and saturated brine, dried over anhydrous sodium sulfate and filtered. The solvent was evaporated under reduced pressure, and the residue was purified by silica gel column chromatography (n-hexane:ethyl acetate=100:0→90:10) to give compound (M-56) (yield 810 mg, 63%) as a colorless oil.

Step 2

Compound (M-56) (800 mg, 3.57 mmol) was dissolved in THF (5.0 mL), i-PrMgCl.LiCl (1.3 mol/L THF solution, 4.0 mL, 5.2 mmol) was added, and the mixture was stirred at room temperature for 1 hr. To the reaction mixture was added triisopropyl borate (1.5 mL, 6.5 mmol), and the mixture was stirred at room temperature for 2 hr. To the reaction mixture were added 1 mol/L aqueous sodium hydroxide solution (5.0 mL) and hydrogen peroxide (5.0 mL) and the mixture was stirred at room temperature for 2 hr. to the reaction mixture was added 2 mol/L hydrochloric acid, and the mixture was extracted with ethyl acetate. The organic layer was washed successively with water and saturated brine, dried over anhydrous sodium sulfate, and filtered. The solvent was evaporated under reduced pressure, and the residue was purified by silica gel column chromatography (n-hexane:ethyl acetate=100:0→70:30) to give compound (II-63) (yield 216 mg, 38%) as a colorless oil.

Step 3

By a production method similar to that in compound (IV-1), compound (IV-128) (yield 70.2 mg, 18%) was obtained as a colorless oil from compound (II-63) (200 mg, 1.24 mmol) and compound (III-1) (239 mg, 1.24 mmol).

Step 4

By a production method similar to that in compound (I-1), compound (I-370) (yield 5.1 mg, 23%) was obtained as a colorless oil from compound (IV-128) (20.0 mg, 0.0631 mmol) and 2-methoxyphenylboronic acid (V-1) (14.4 mg, 0.0946 mmol).

Example 371

Production of N-[(5-{[3-(2-methoxyphenyl)pyridin-2-yl]oxy}pyridin-2-yl)methyl]aniline (I-371)

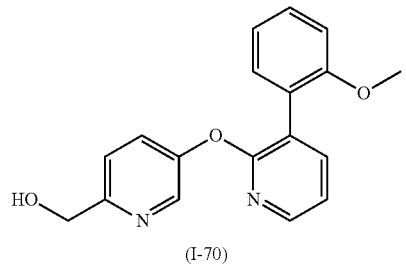

(I-70)

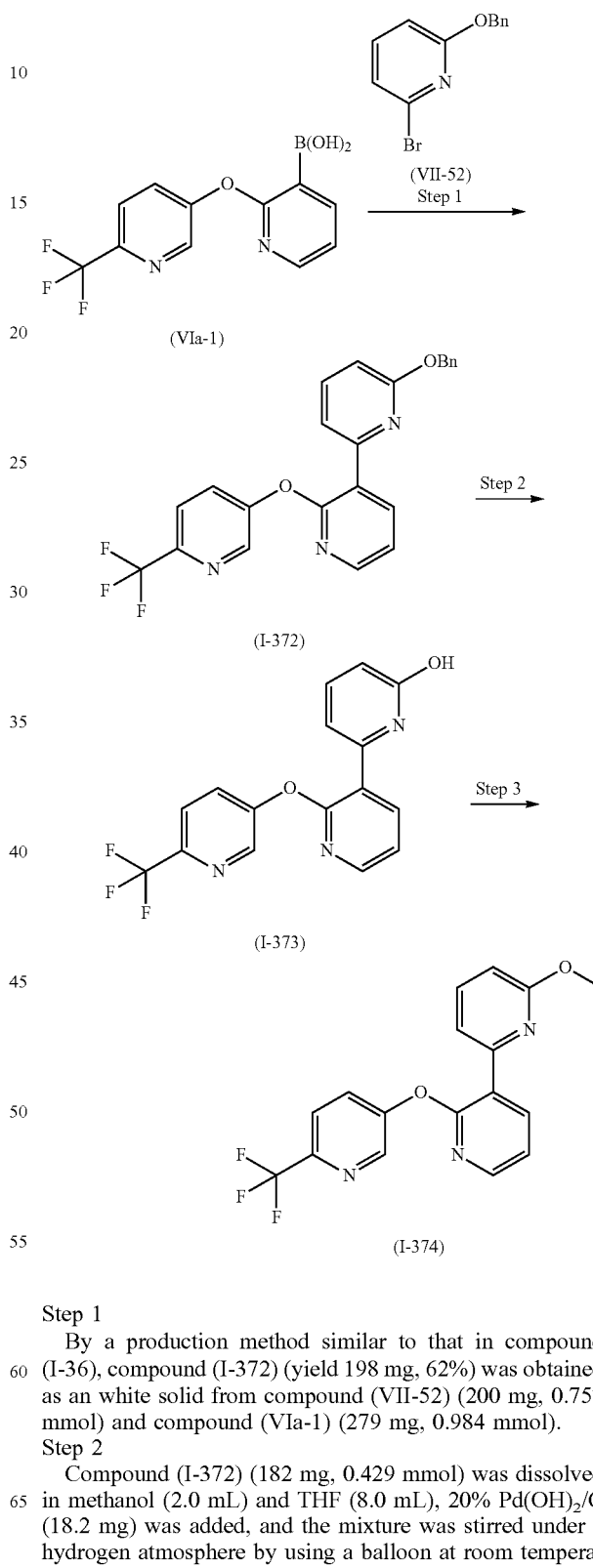

(I-371)

Compound (I-70) (30 mg, 0.097 mmol) was dissolved in DCM (0.60 mL), TEA (50 μL, 0.39 mmol) and methanesulfonyl chloride (10 μL, 0.13 mmol) were added under ice-cooling and the mixture was stirred for 30 min. Aniline (20 μL, 0.22 mmol) was added and the mixture was stirred at room temperature for 3 days. The reaction mixture was purified by silica gel column chromatography (NH silica gel, n-hexane:ethyl acetate=100:0→50:50) to give compound (I-371) (yield 11.1 mg, 30%) as a colorless oil.

Example 374

Production of 6-methoxy-2'-{[6-(trifluoromethyl)pyridin-3-yl]oxy}-2,3'-bipyridine (I-374)

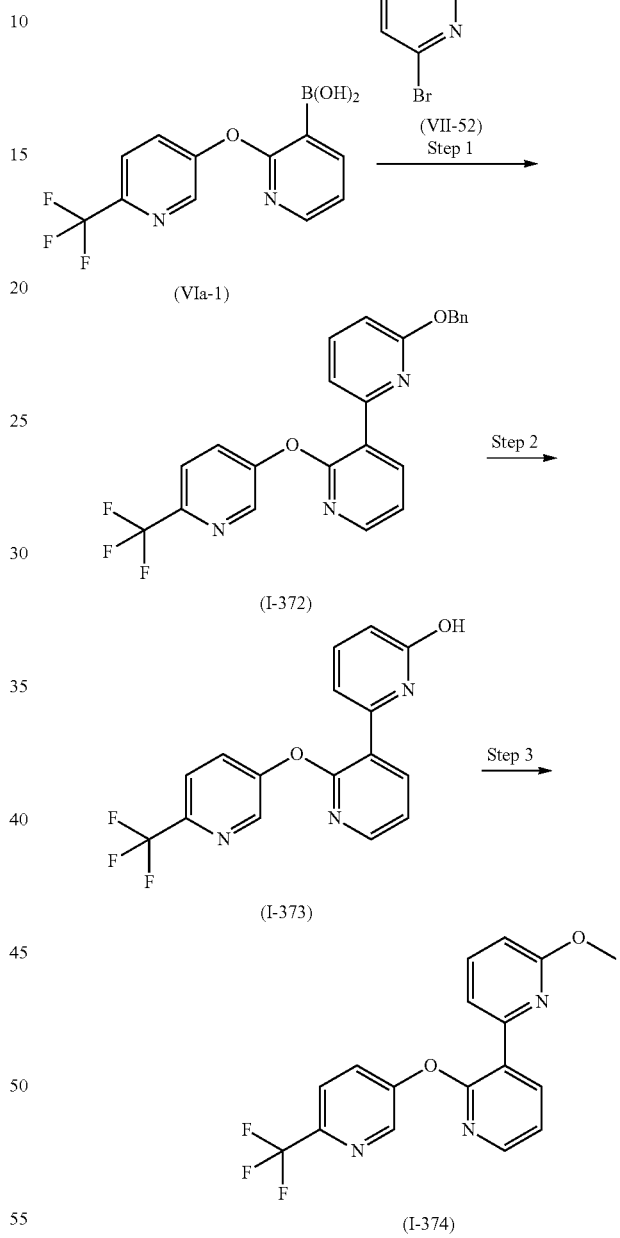

Step 1

By a production method similar to that in compound (I-36), compound (I-372) (yield 198 mg, 62%) was obtained as an white solid from compound (VII-52) (200 mg, 0.757 mmol) and compound (VIa-1) (279 mg, 0.984 mmol).

Step 2

Compound (I-372) (182 mg, 0.429 mmol) was dissolved in methanol (2.0 mL) and THF (8.0 mL), 20% Pd(OH)$_2$/C (18.2 mg) was added, and the mixture was stirred under a hydrogen atmosphere by using a balloon at room temperature for 16 hr. The mixture was filtered through Celite, and washed with ethyl acetate. The solvent was evaporated under reduced pressure, and the residue was purified by silica gel column chromatography (NH silica gel, chloroform:methanol=100:0→95:5) to give compound (I-373) (yield 143 mg, quantitative) as a white solid.

Step 3

Compound (I-373) (27.7 mg, 0.0831 mmol) was dissolved in DMF (1.0 mL), potassium carbonate (10.3 mg, 0.166 mmol) and methyl iodide (7.8 μL, 0.13 mmol) were successively added, and the mixture was stirred at room temperature for 13 hr. Water was added to the reaction mixture, and the mixture was extracted with ethyl acetate. The organic layer was washed successively with water and saturated brine, dried over anhydrous sodium sulfate and filtered. The solvent was evaporated under reduced pressure, and the residue was purified by silica gel column chromatography (NH silica gel, n-hexane:ethyl acetate=95:5→40:40) to give compound (I-374) (yield 9.1 g, 32%) as a colorless oil.

Example 375

Production of 2-chloro-7-(2-{[6-(trifluoromethyl)pyridin-3-yl]oxy}pyridin-3-yl)pyrazolo[1,5-a]pyridine (I-375)

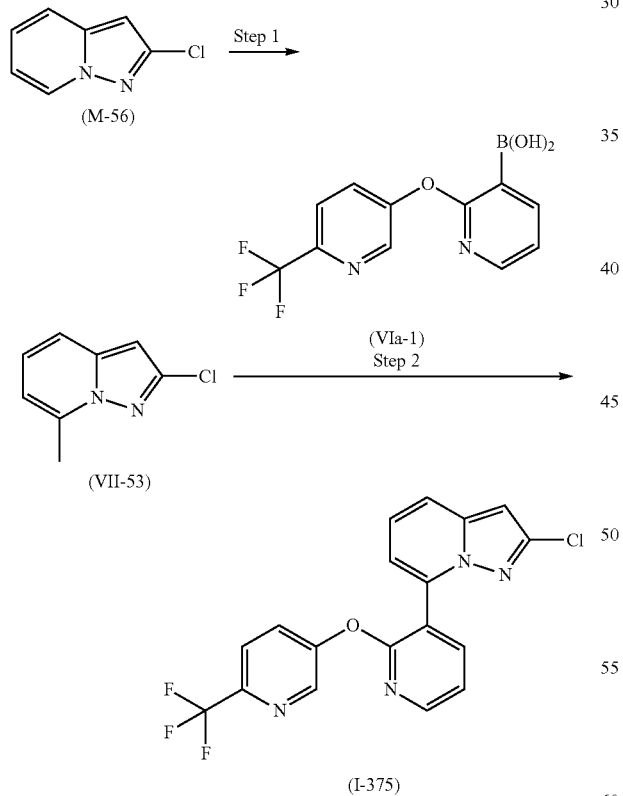

Step 1

To a solution of compound (M-56) (200 mg, 1.31 mmol) in THF (2.6 mL) was added n-butyllithium (1.6 mol/L n-hexane solution, 0.98 mL, 1.6 mmol) at −78° C., and the mixture was stirred at −78° C. for 30 min. To the reaction mixture was added 1,2-diiodoethane (443 mg, 1.57 mmol) at −78° C., and the mixture was stirred at −78° C. for 30 min. Thereafter, the mixture was gradually warmed to room temperature, saturated aqueous ammonium chloride solution was added to the reaction mixture, and the mixture was extracted with ethyl acetate. The organic layer was washed successively with saturated aqueous ammonium chloride solution and saturated brine, dried over anhydrous sodium sulfate and filtered. The solvent was evaporated under reduced pressure, and the residue was purified by silica gel column chromatography (n-hexane:ethyl acetate=97:3→80:20) to give compound (VII-53) (yield 258 g, 71%) as a beige solid.

Step 2

By a production method similar to that in compound (I-36), compound (I-375) (yield 12.6 mg, 18%) was obtained as a white solid from compound (VII-53) (50.0 mg, 0.180 mmol) and compound (VIa-1) (56.1 mg, 0.198 mmol).

Example 377

Production of 4-bromo-3-methyl-5-(2-{[6-(trifluoromethyl)pyridin-3-yl]oxy}pyridin-3-yl)isothiazole (I-377)

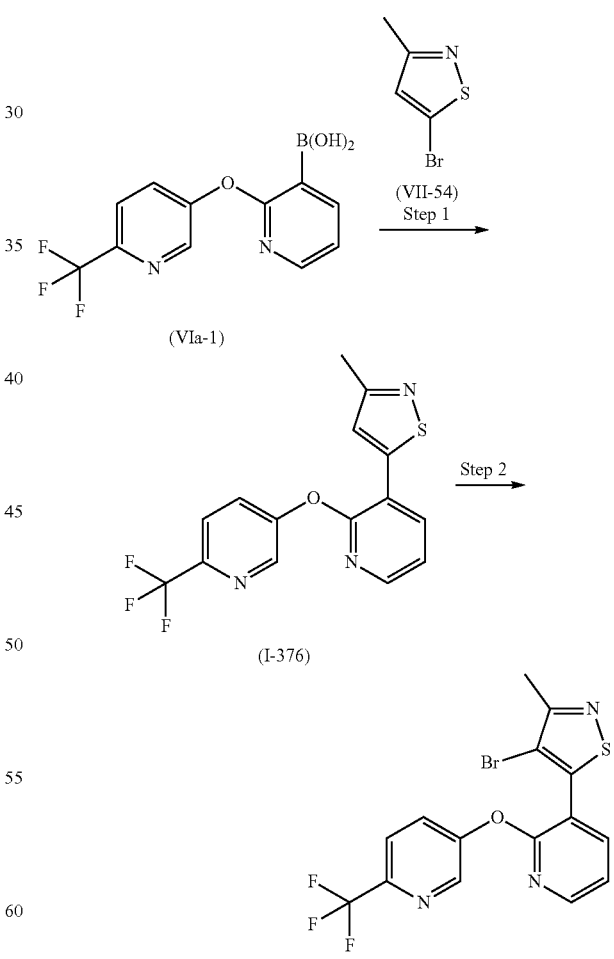

Step 1

By a production method similar to that in compound (I-36), compound (I-376) (yield 7.7 mg, 13%) was obtained as a white solid from 5-bromo-3-methylisothiazole (VII-54) (47.0 mg, 0.264 mmol) and compound (VIa-1) (50.0 mg, 0.176 mmol).

Step 2

Compound (I-376) (30.0 mg, 0.0890 mmol) was dissolved in acetic acid (1.0 mL), bromine (5.5 μL, 0.11 mmol) was added and the mixture was stirred at 100° C. for 3 hr. The reaction mixture was cooled to room temperature, saturated aqueous sodium hydrogen carbonate solution was added, and the mixture was extracted with ethyl acetate. The organic layer was dried over anhydrous sodium sulfate, and filtered. The solvent was evaporated under reduced pressure, and the residue was purified by silica gel column chromatography (n-hexane:ethyl acetate) to give compound (I-377) (yield 13.0 mg, 35%) as a white solid.

Example 378

Production of 5-{[3-(4-fluoro-2-methoxyphenyl)pyridin-2-yl]oxy}-2-(prop-1-en-2-yl)pyrimidine (I-378)

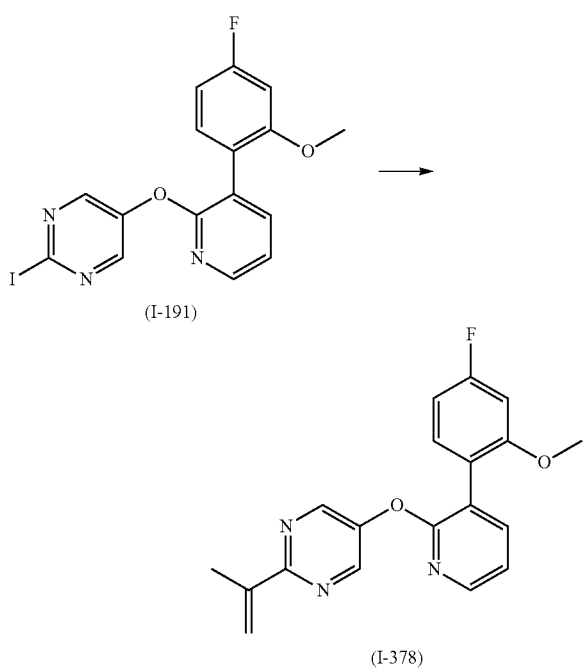

Compound (I-191) (100 mg, 0.236 mmol), isopropenylboronic acid pinacol ester (67 μL, 0.35 mmol), (A-$^{ta}$Phos)$_2$PdCl$_2$ (8.4 mg, 0.012 mmol) and cesium carbonate (154 mg, 0.472 mmol) were dissolved in 1,4-dioxane (1.0 mL) and water (0.20 mL), and the mixture was stirred under microwave irradiation at 120° C. for 30 min. Isopropenylboronic acid pinacol ester (44 μL, 0.24 mmol), and cesium carbonate (76.9 mg, 0.236 mmol) were successively added to the reaction mixture, and the mixture was stirred under microwave irradiation at 120° C. for 30 min. Water was added to the reaction mixture, and the mixture was extracted with ethyl acetate. The organic layer was washed successively with water and saturated brine, dried over anhydrous sodium sulfate and filtered. The solvent was evaporated under reduced pressure, and the residue was purified by silica gel column chromatography (NH silica gel, n-hexane:ethyl acetate=95:5→70:30) to give compound (I-378) (yield 61.4 g, 77%) as a pale-yellow oil.

Example 379

Production of 5-{[3-(4-fluoro-2-methoxyphenyl)pyridin-2-yl]oxy}-2-(1-methylcyclopropyl)pyrimidine (I-379)

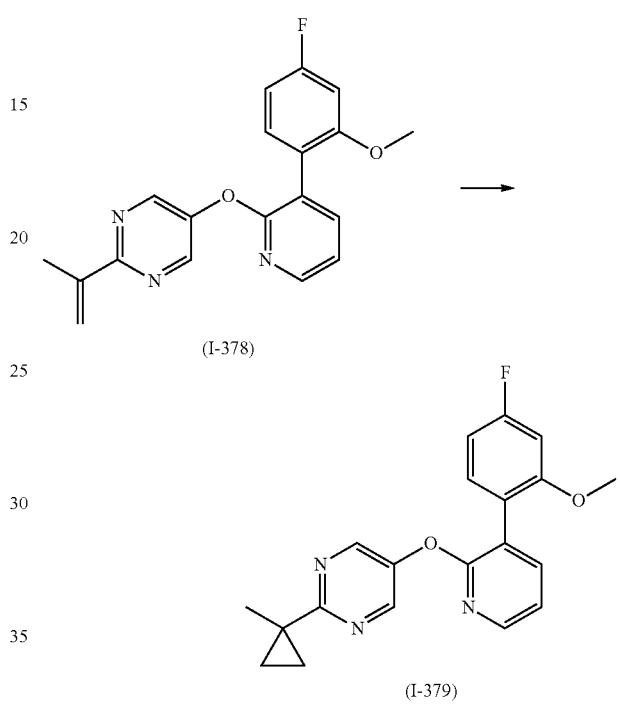

Trimethyloxosulfonium iodide (76.4 mg, 0.347 mmol) was dissolved in THF (0.40 mL) and DMSO (0.60 mL), potassium tert-butoxide (38.9 mg, 0.347 mmol) was added, and the mixture was stirred at room temperature for 30 min. Thereafter, to the reaction mixture was added a solution of compound (I-378) (77.9 mg, 0.231 mmol) in THF (0.60 mL), and the mixture was stirred at room temperature for 1 hr. Thereafter, the mixture was heated to 60° C. and stirred for 3 hr. The reaction mixture was cooled to room temperature, water was added, and the mixture was extracted with ethyl acetate. The organic layer was washed successively with water and saturated brine, dried over anhydrous sodium sulfate and filtered. The solvent was evaporated under reduced pressure, and the residue was purified by silica gel column chromatography (n-hexane:ethyl acetate=100:0→85:15) to give compound (I-379) (yield 28.7 mg, 35%) as a white solid.

Example 380

Production of 2-(benzyloxy)-5-{[3-(2-methoxyphenyl)pyridin-2-yl]oxy}pyrimidine (I-380)

Benzyl alcohol (63.0 μL, 0.606 mmol) was dissolved in DMF (1.0 mL), 60% sodium hydride (24.2 mg, 0.606 mmol) was added, and the mixture was stirred at room temperature for 30 min. Compound (I-338) (19.0 mg, 0.061 mmol) was added and the mixture was stirred at 100° C. for 18 hr. The reaction mixture was allowed to cool, water was added, and the mixture was extracted with ethyl acetate. The organic layer was washed successively with water and saturated brine, dried over anhydrous sodium sulfate and filtered. The solvent was evaporated under reduced pressure, and the residue was purified by silica gel column chromatography to give compound (I-380) (yield 13.2 mg, 57%) as an oil.

Example 381

Production of N-benzyl-5-{[2'-methoxy-(3,3'-bipyridin)-2-yl]oxy}-N-methylpyrimidin-2-amine (I-381)

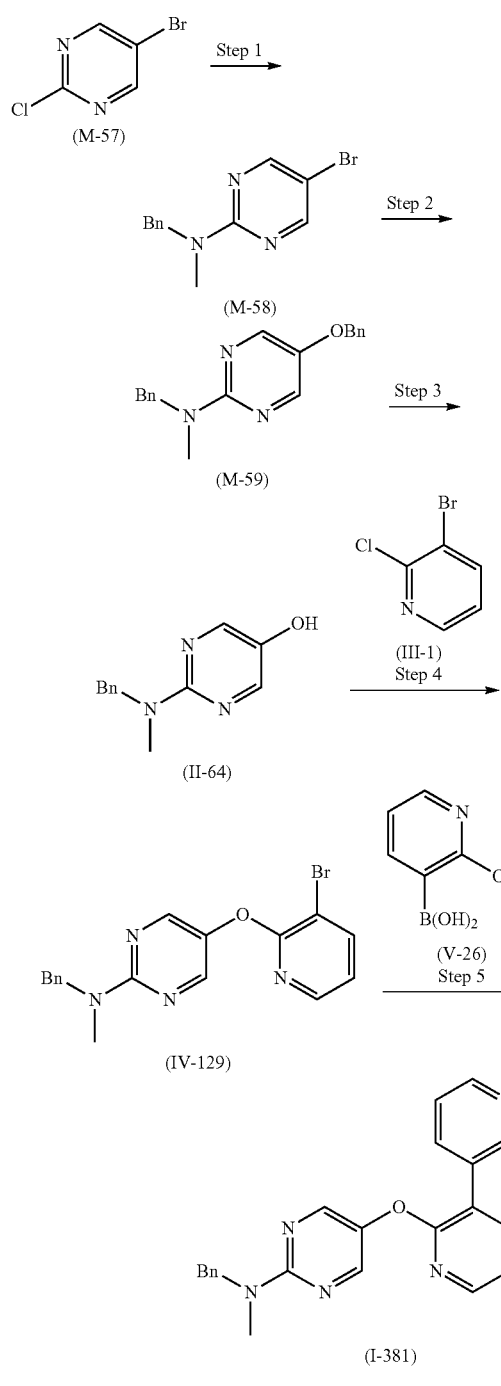

Step 1

5-Bromo-2-chloropyrimidine (M-57) (5.00 g, 25.8 mmol) was dissolved in IPA (10 mL), DIPEA (10 mL) and benzylmethylamine (4.50 mL, 34.9 mmol) were added and the mixture was stirred at 100° C. for 2 hr. The reaction solution was concentrated under reduced pressure, and the residue was purified by silica gel column chromatography (n-hexane:ethyl acetate=100:0→90:10) to give N-benzyl-5-bromo-N-methylpyrimidin-2-amine (M-58) (yield 7.15 g, 99%) as a white solid.

Step 2

By a production method similar to that in compound (M-53), compound (M-59) (yield 980 mg, 89%) was obtained as a yellow oil from compound (M-58) (1.00 g, 3.60 mmol).

Step 3

By a production method similar to that in compound (M-54), compound (II-64) (yield 340 mg, 49%) was obtained as a white solid from compound (M-59) (980 mg, 3.21 mmol).

Step 4

By a production method similar to that in compound (IV-1), compound (IV-129) (yield 580 mg, 99%) was obtained as a yellow oil from compound (III-1) (310 mg, 1.61 mmol) and compound (II-64) (340 mg, 1.58 mmol).

Step 5

By a production method similar to that in compound (I-1), compound (I-381) (yield 600 mg, 96%) was obtained as a colorless oil from compound (IV-129) (580 mg, 1.56 mmol) and 2-methoxypyridine-3-boronic acid (V-26) (300 mg, 1.96 mmol).

Example 384

Production of N-butyl-5-{[4'-methoxy-(3,3'-bipyridin-2-yl]oxy}-N-methylpyrimidin-2-amine (I-384)

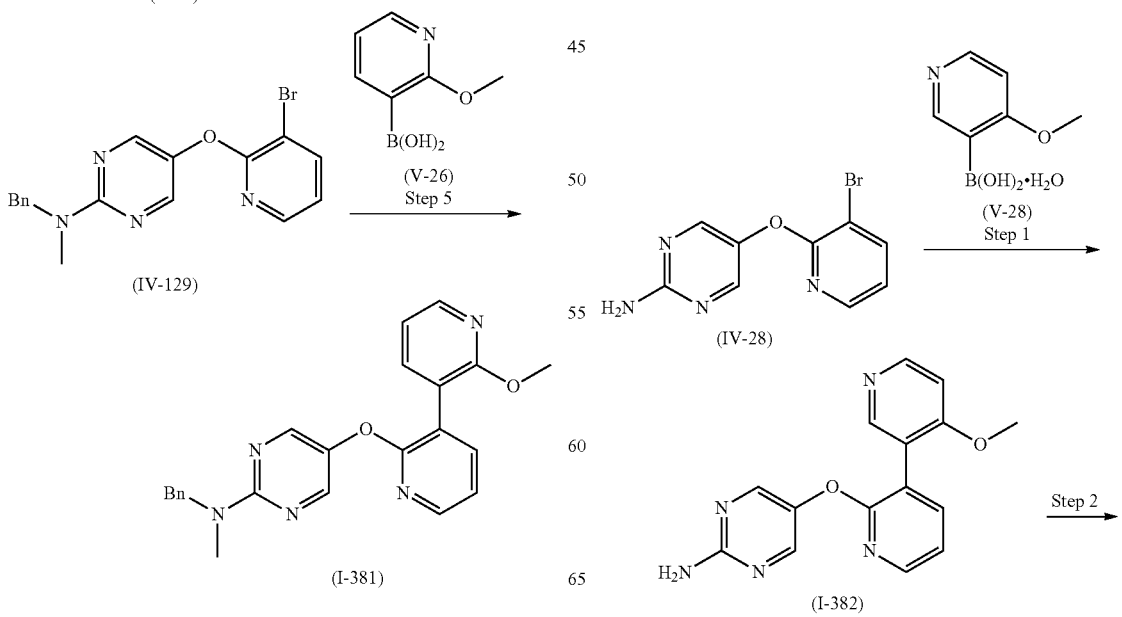

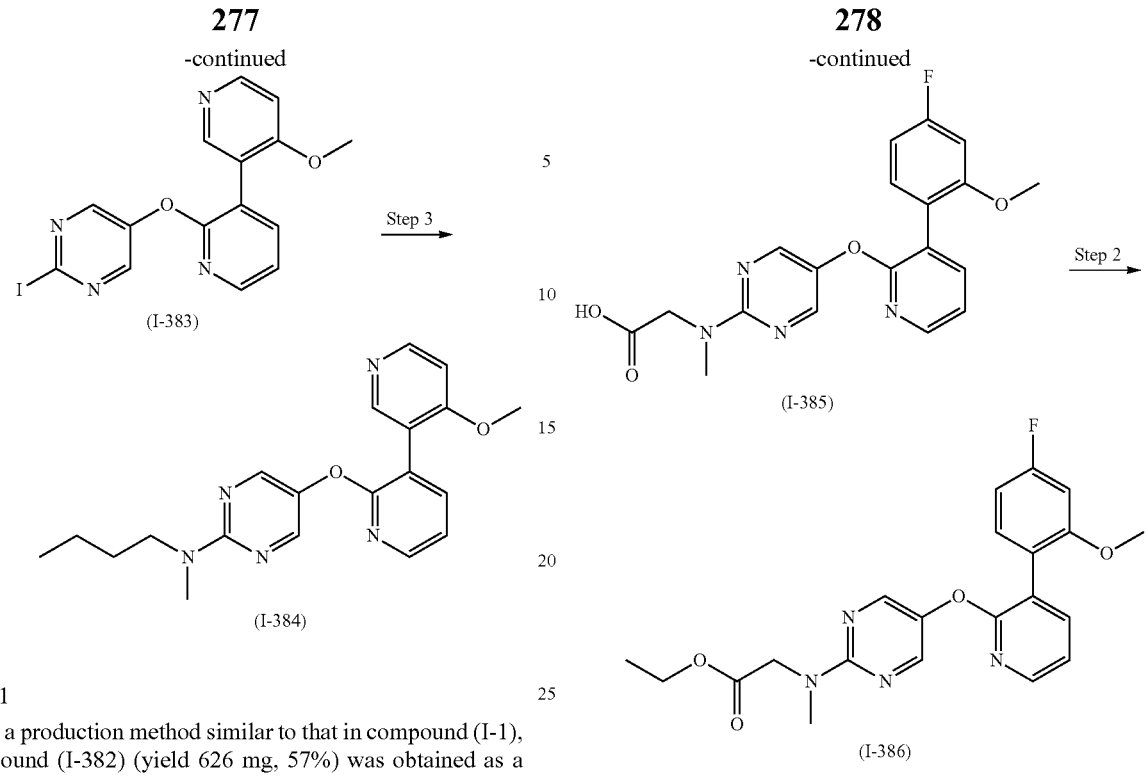

Step 1

By a production method similar to that in compound (I-1), compound (I-382) (yield 626 mg, 57%) was obtained as a white solid from compound (IV-28) (1.00 g, 3.74 mmol) and 4-methoxypyridine-3-boronic acid monohydrate (V-28) (858 mg, 5.61 mmol).

Step 2

By a production method similar to that in compound (I-191), compound (I-383) (yield 396 mg, 46%) was obtained from compound (I-382) (626 mg, 2.12 mmol).

Step 3

By a production method similar to that in compound (IV-30), compound (I-384) (yield 41.2 mg, 46%) was obtained as a colorless oil from compound (I-383) (100 mg, 0.246 mmol) and N-methyl-butylamine (0.29 mL, 2.5 mmol).

Example 386

Production of ethyl 2-[(5-{[3-(4-fluoro-2-methoxyphenyl)pyridin-2-yl]oxy}-pyrimidin-2-yl)(methyl)amino]acetate (I-386)

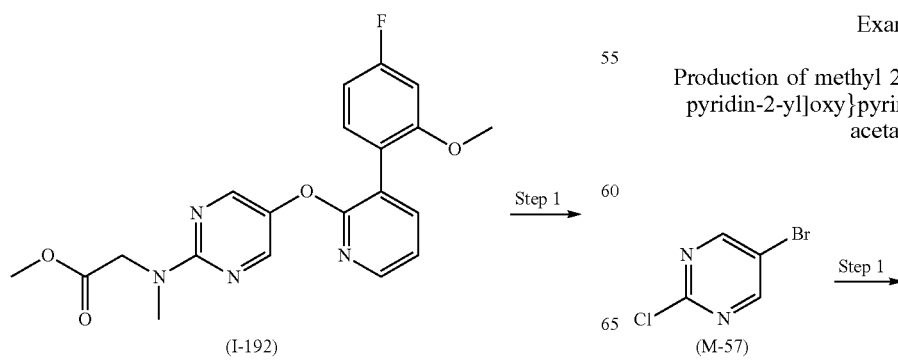

Step 1

Compound (I-192) (100 mg, 0.251 mmol) was dissolved in THF (1.5 mL) and methanol (1.5 mL), 4 mol/L aqueous sodium hydroxide solution (0.75 mL) was added, and the mixture was stirred at room temperature overnight. 1 mol/L Hydrochloric acid was added, and the mixture was washed with ethyl acetate. The aqueous layer was neutralized with 4 mol/L aqueous sodium hydroxide solution and extracted with chloroform. The organic layer was dried over anhydrous sodium sulfate. The solvent was evaporated under reduced pressure to give compound (I-385) (yield 93.0 mg, 96%) as a white solid.

Step 2

Compound (I-385) (30.0 mg, 0.0780 mmol) was dissolved in ethanol (1.0 mL), thionyl chloride (0.20 mL) was added and the mixture was heated under reflux overnight. The reaction mixture was allowed to cool, and the solvent evaporated under reduced pressure. The residue was neutralized with saturated aqueous sodium hydrogen carbonate solution, and extracted with chloroform. The organic layer was dried over anhydrous sodium sulfate. The solvent was evaporated under reduced pressure to give compound (I-386) (yield 18.0 mg, 57%) as a colorless oil.

Example 387

Production of methyl 2-[(5-{[3-(2-methoxyphenyl)pyridin-2-yl]oxy}pyrimidin-2-yl)(methyl)amino]acetate (I-387)

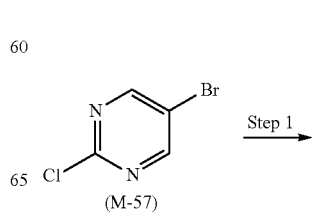

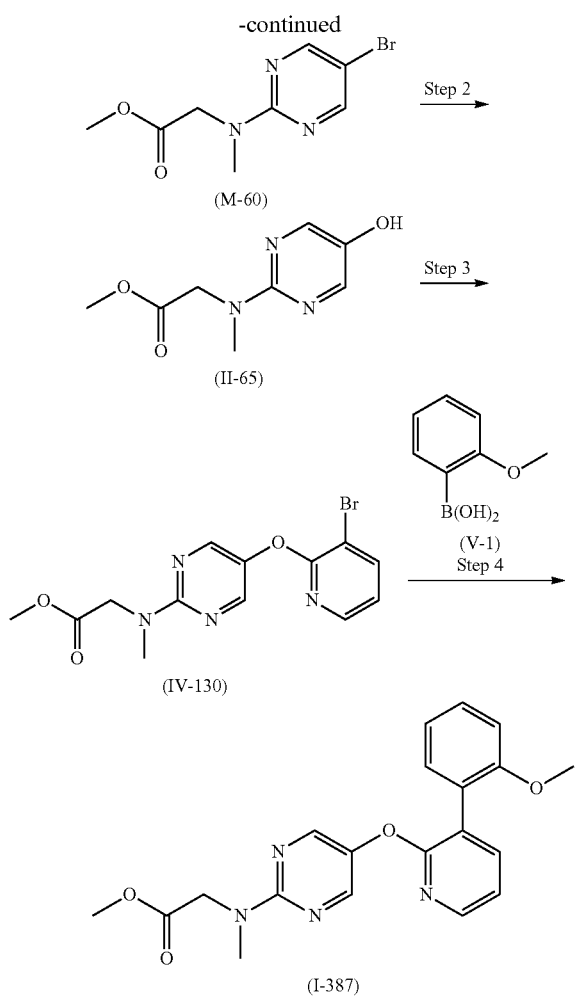

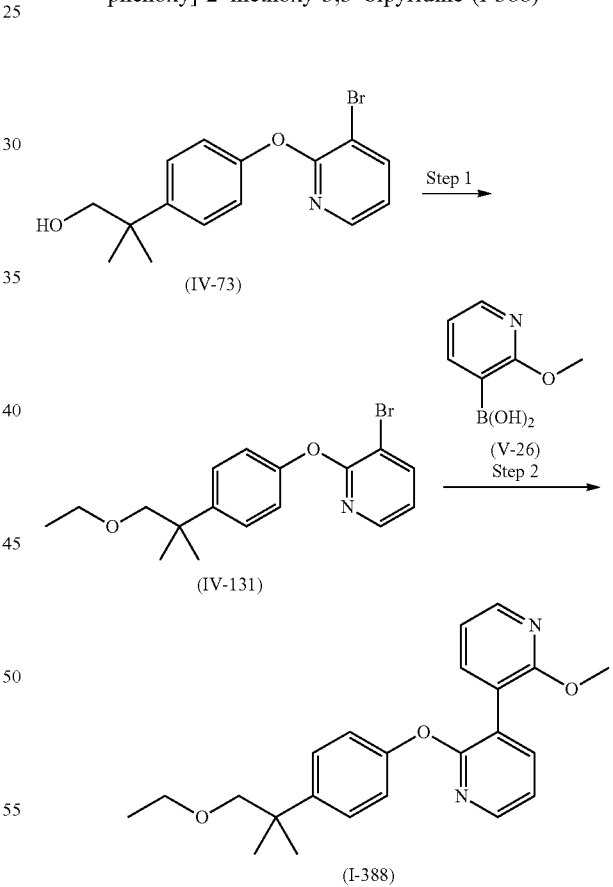

tion, and the mixture was extracted with ethyl acetate. The organic layer was washed successively with saturated aqueous ammonium chloride solution and saturated brine, and the organic layer was dried over anhydrous sodium sulfate. The solvent was evaporated under reduced pressure, and the residue was purified by silica gel column chromatography (n-hexane:ethyl acetate) to give compound (II-65) (yield 27.7 g, quantitative) as a white solid.

Step 3

By a production method similar to that in compound (IV-1), compound (IV-130) (yield 22.3 g, 45%) was obtained as a white solid from compound (III-1) (26.9 g, 140 mmol) and compound (II-65) (27.7 g, 140 mmol).

Step 4

By a production method similar to that in compound (I-1), compound (I-387) (yield 43.9 mg, quantitative) was obtained as a colorless oil from compound (IV-130) (40.0 mg, 0.113 mmol) and 2-methoxyphenylboronic acid (V-1) (25.8 mg, 0.170 mmol).

Example 388

Production of 2-[4-(1-ethoxy-2-methylpropan-2-yl)phenoxy]-2'-methoxy-3,3'-bipyridine (I-388)

Step 1

Compound (M-57) (30.0 g, 155 mmol) and sarcosine methyl ester (27.6 g, 310 mmol) was dissolved in DMF (155 mL), TEA (43 mL, 310 mmol) was added, and the mixture was heated under reflux at 100° C. overnight. The reaction mixture was allowed to cool, water was added to discontinue the reaction, and the mixture was extracted with ethyl acetate. The organic layer was washed with saturated brine, and dried over anhydrous magnesium sulfate, and the solvent was evaporated under reduced pressure. The residue was purified by silica gel column chromatography (n-hexane:ethyl acetate) to give compound (M-60) (yield 36.6 g, 91%) as a colorless oil.

Step 2

Compound (M-60) (36.6 g, 141 mmol) was dissolved in DMF (140 mL), bis(pinacolato)diboron (39.4 g, 155 mmol), cesium carbonate (91.9 g, 282 mmol) and palladium acetate (1.58 g, 7.05 mmol) were added, and the mixture was stirred at 80° C. overnight. The solid was removed by filtration, water was added to the reaction mixture, and the mixture was extracted with ethyl acetate. The organic layer was washed successively with water and saturated brine, dried over anhydrous sodium sulfate and filtered. The solvent was evaporated under reduced pressure. The residue was dissolved in THF (12 mL) and water (12 mL), sodium perborate (23.0 g, 282 mmol) was added, and the mixture was stirred at room temperature for 13 hr. Saturated aqueous ammonium chloride solution was added to discontinue the reac- Step 1

By a production method similar to that in compound (I-145), compound (IV-131) (yield 83.5 mg, 38%) was obtained as a colorless oil from compound (IV-73) (200 mg, 0.621 mmol) and ethyl bromide (70 μL, 0.93 mmol).

Step 2

By a production method similar to that in compound (I-1), compound (I-388) (yield 27.3 mg, 94%) was obtained as a white solid from compound (IV-131) (27.7 mg, 0.0771 mmol) and 2-methoxypyridine-3-boronic acid (V-26) (17.7 mg, 0.116 mmol).

Example 390

Production of 2-(4-ethynylphenoxy)-2'-methoxy-3,3'-bipyridine (I-390)

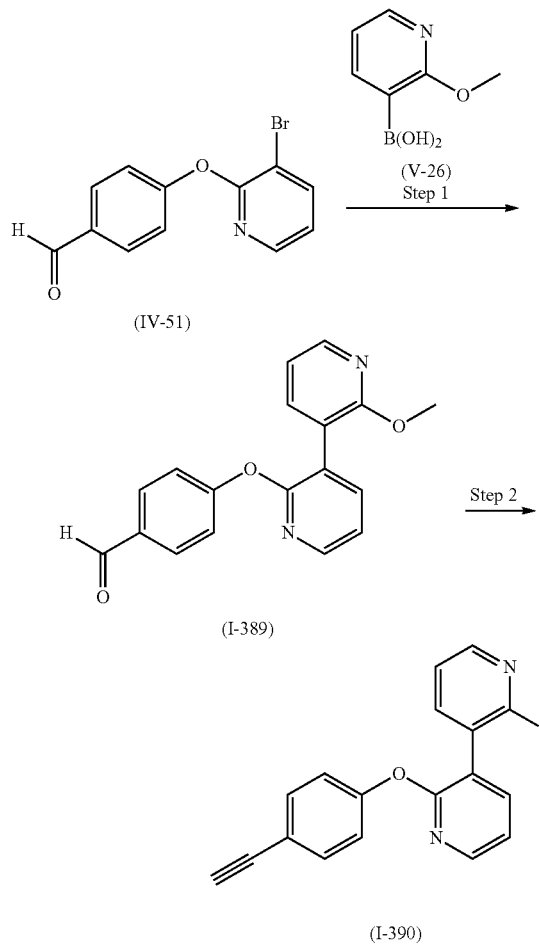

Step 1

By a production method similar to that in compound (I-1), compound (I-389) (yield 1.45 g, 88%) was obtained as a pale-yellow solid from compound (IV-51) (1.50 g, 5.39 mmol) and 2-methoxypyridine-3-boronic acid (V-26) (1.07 g, 7.01 mmol).

Step 2

Compound (I-389) (1.00 mg, 3.26 mmol) was dissolved in methanol (10 mL), potassium carbonate (901 mg, 6.52 mmol) and Ohira-Bestmann reagent (0.73 mL, 4.9 mmol) were successively added, and the mixture was stirred at room temperature for 2 hr. Water was added to the reaction mixture, and the mixture was extracted with chloroform. The organic layer was washed with water, dried over anhydrous sodium sulfate, and filtered. The solvent was evaporated under reduced pressure, and the residue was purified by silica gel column chromatography (n-hexane:ethyl acetate=97:3→75:25) to give compound (I-390) (yield 727 mg, 74%) as a pale-yellow oil.

Example 392

Production of 2-(4-ethyl-3-fluorophenoxy)-4'-methoxy-3,3'-bipyridine (I-392)

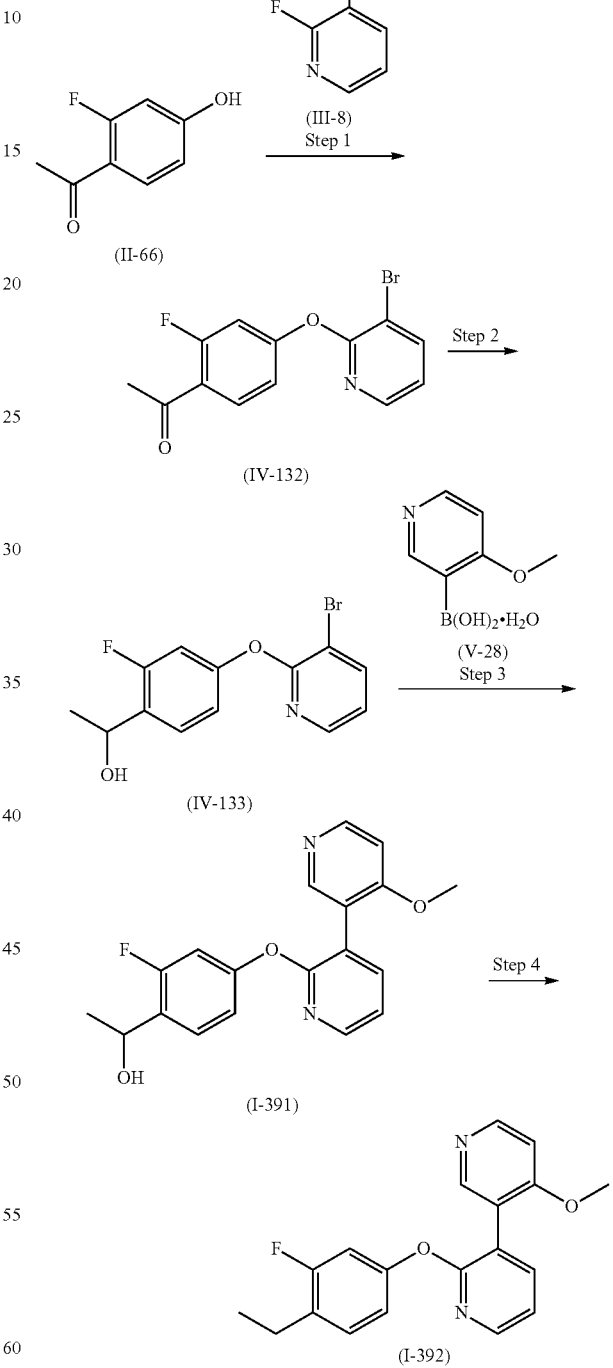

Step 1

Compound (III-8) (571 mg, 3.24 mmol) and 2-fluoro-4-hydroxyacetophenone (II-66) (500 mg, 3.24 mmol) was dissolved in NMP (5.0 mL), cesium carbonate (1.27 g, 3.89 mmol) was added and the mixture was stirred at 120° C. for 6 hr. The reaction mixture was allowed to cool, water was added, and the mixture was extracted with chloroform. The organic layer was dried over anhydrous sodium sulfate, and the solvent was evaporated under reduced pressure. The residue was purified by silica gel column chromatography (n-hexane:ethyl acetate=0:100→80:20) to give compound (IV-132) (yield 715 mg, 71%) as a colorless oil.

Step 2

To a solution of compound (IV-132) (500 mg, 1.61 mmol) in THF (4.0 mL), and methanol (4.0 mL) was added sodium borohydride (60.9 mg, 1.61 mmol), and the mixture was stirred at room temperature for 1 hr. After completion of the reaction, the solvent was evaporated under reduced pressure. The residue was purified by silica gel column chromatography (n-hexane:ethyl acetate=0:100→50:50) to give compound (IV-133) (yield 488 mg, 97%) as a white solid.

Step 3

By a production method similar to that in compound (I-127), compound (I-391) (yield 249 mg, 57%) was obtained as a colorless oil from compound (IV-133) (400 mg, 1.28 mmol) and 4-methoxypyridine-3-boronic acid monohydrate (V-28) (294 mg, 1.92 mmol).

Step 4

Compound (I-391) (30.0 mg, 0.0881 mmol) was dissolved in TFA (1.0 mL), triethylsilane (1.0 mL, 6.3 mmol) was added and the mixture was stirred at 50° C. overnight. The reaction mixture was allowed to cool, and the solvent was evaporated under reduced pressure. The residue was purified by silica gel column chromatography (n-hexane: ethyl acetate=0:100→30:70) to give compound (I-392) (yield 14.6 mg, 51%) as a colorless oil.

Example 394

Production of 2-(4-ethyl-2-fluorophenoxy)-4'-methoxy-3,3'-bipyridine (I-394)

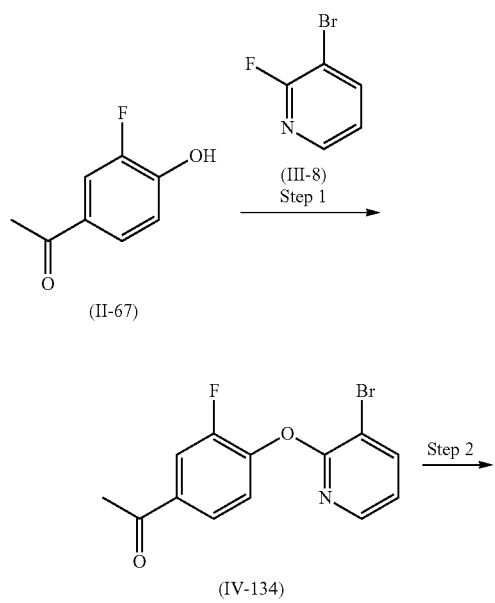

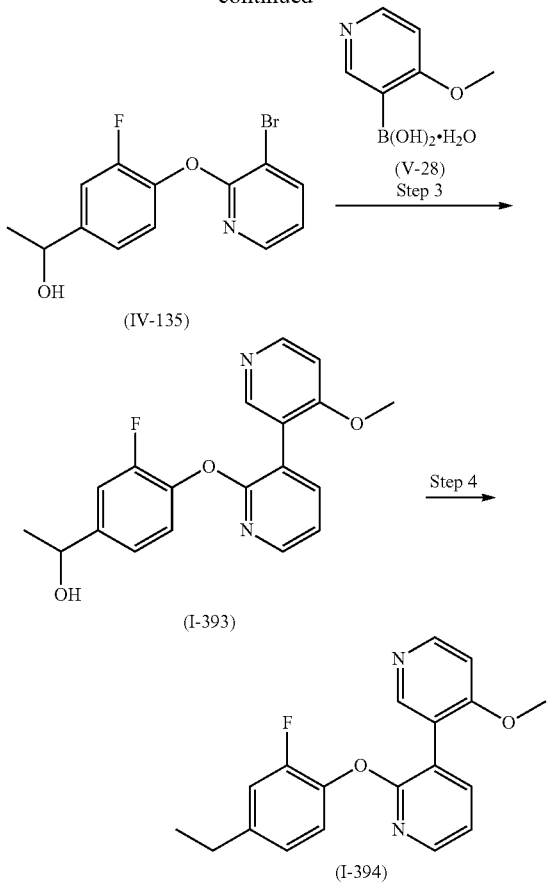

Step 1

Compound (III-8) (500 mg, 2.84 mmol), 3-fluoro-4-hydroxyacetophenone (II-67) (876 mg, 5.68 mmol) and cesium carbonate (1.85 g, 5.68 mmol) were dissolved in NMP (5 mL), and the mixture was stirred under microwave irradiation at 120° C. for 30 min. The reaction mixture was cooled, 1 mol/L aqueous sodium hydroxide solution was added and the mixture was extracted with ethyl acetate/n-hexane. The organic layer was dried over anhydrous sodium sulfate, and filtered. The solvent was evaporated under reduced pressure, and the residue was purified by silica gel column chromatography (n-hexane:ethyl acetate) to give compound (IV-134) (yield 465 mg, 53%).

Step 2

By a production method similar to that in compound (IV-133), compound (IV-135) (yield 438 mg, 95%) was obtained from compound (IV-134) (460 mg, 1.48 mmol).

Step 3

By a production method similar to that in compound (I-127), compound (I-393) (yield 271 mg, 57%) was obtained as a white solid from compound (IV-135) (438 mg, 1.40 mmol) and 4-methoxypyridine-3-boronic acid monohydrate (V-28) (322 mg, 2.11 mmol).

Step 4

Compound (I-393) (50.0 mg, 0.147 mmol) was dissolved in TFA (10 mL), triethylsilane (51.2 mg, 0.441 mmol) was added, and the mixture was stirred at 60° C. for 1 hr. Thereafter, the reaction solvent was evaporated under reduced pressure, saturated aqueous sodium hydrogen carbonate solution and ethyl acetate were added and the mixture was partitioned. The organic layer was was dried over

Example 396

Production of 2-[4-(2-ethoxyethyl)phenoxy]2'-methoxy-3,3'-bipyridine (I-396)

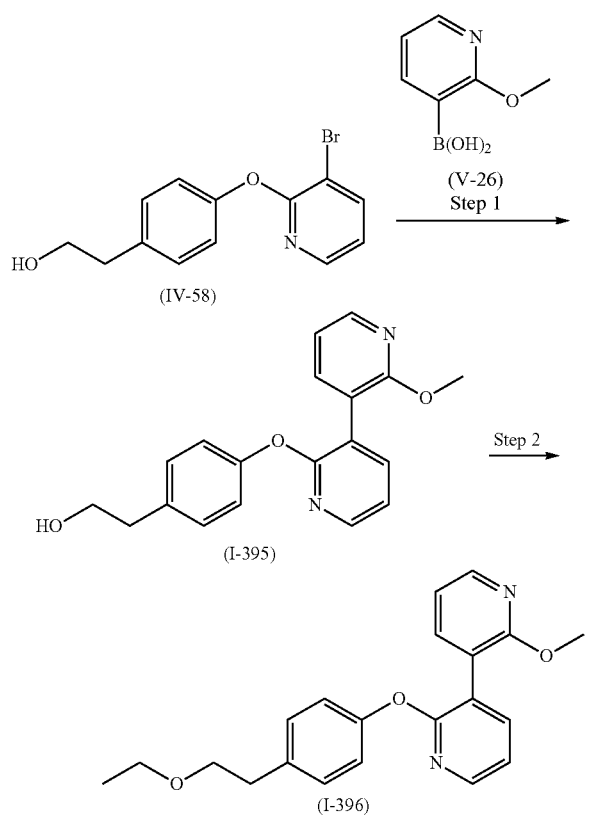

Step 1

By a production method similar to that in compound (I-1), compound (I-395) (yield 944 mg, 86%) was obtained as an orange oil from compound (IV-58) (1.00 g, 3.40 mmol) and 2-methoxypyridine-3-boronic acid (V-26) (676 mg, 4.42 mmol).

Step 2

By a production method similar to that in compound (I-145), compound (I-396) (yield 9.8 mg, 37%) was obtained as a colorless oil from compound (I-395) (30.0 mg, 0.0931 mmol) and ethyl bromide (10 μL, 0.14 mmol).

Example 397

Production of 4-{[(2'-methoxy)-(3,3'-bipyridin)-2-yl]oxy}phenethyl acetate (I-397)

Compound (I-395) (30.0 mg, 0.0931 mmol) was dissolved in DMF (1.0 mL), acetyl chloride (8.0 μL, 0.112 mmol) and DIPEA (24 μL, 0.140 mmol) were added, and the mixture was stirred at room temperature for 2 hr. Thereafter, sodium hydride (5.4 mg, 0.112 mmol) was added to the reaction mixture under ice-cooling, and the mixture was stirred at room temperature for 24 hr. Water was added to the reaction mixture, and the mixture was extracted with ethyl acetate. The organic layer was washed successively with water and saturated brine, dried over anhydrous sodium sulfate and filtered. The solvent was evaporated under reduced pressure, and the residue was purified by silica gel column chromatography (n-hexane:ethyl acetate) to give compound (I-397) (yield 4.9 mg, 15%) as a white solid.

Example 398

Production of 4-{[(2'-methoxy-(3,3'-bipyridin)-2-yl]oxy}phenethyl dimethylcarbamate (I-398)

By a production method similar to that in compound (I-397), compound (I-398) (yield 20.5 mg, 56%) was obtained as a colorless oil from compound (I-395) (30.0 mg, 0.0931 mmol) and dimethylcarbamoyl chloride (10 μL, 0.11 mmol).

Example 400

Production of 2-{4-[2-(1H-pyrazol-1-yl)ethyl]phenoxy}-2'-methoxy-3,3'-bipyridine (I-400)

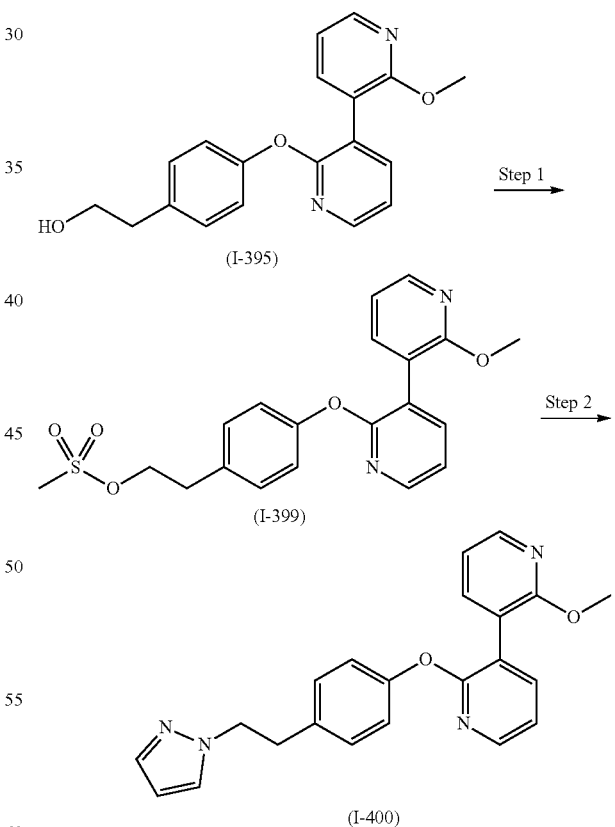

Step 1

Compound (I-395) (100 mg, 0.310 mmol) was dissolved in DCM (1.5 mL), TEA (0.13 mL, 0.93 mmol) and methanesulfonyl chloride (36 μL, 0.47 mmol) were added, and the mixture was stirred at room temperature for 10 min. Thereafter, water was added to the reaction mixture, and the mixture was extracted with ethyl acetate. The organic layer was washed successively with water and saturated brine, dried over anhydrous sodium sulfate, and filtered. The solvent was evaporated under reduced pressure to give compound (I-399) (yield 120 mg, 97%).

Step 2

Compound (I-399) (40.0 mg, 0.0999 mmol) was dissolved in DMF (0.50 mL), pyrazole (10.2 mg, 0.150 mmol) and cesium carbonate (65.1 mg, 0.200 mmol) were added, and the mixture was stirred at room temperature for 19 hr. Thereafter, water was added to the reaction mixture, and the mixture was extracted with ethyl acetate. The organic layer was washed successively with water and saturated brine, dried over anhydrous sodium sulfate, and filtered. The solvent was evaporated under reduced pressure, and the residue was purified by silica gel column chromatography (NH silica gel, n-hexane:ethyl acetate=97:3→60:40) to give compound (I-400) (yield 21.4 mg, 58%) as a colorless oil.

Example 401

Production of 2-methoxy-2'-{4-[2-(4-methyl-1H-pyrazol-1-yl)ethyl]phenoxy}-3,3'-bipyridine (I-401)

By a production method similar to that in compound (I-400), compound (I-401) (yield 13.1 mg, 34%) was obtained as a colorless oil from compound (I-399) (40.0 mg, 0.0999 mmol) and 4-methylpyrazole (12.3 mg, 0.150 mmol).

Example 404

Production of 2-{4-[2-(1-ethyl-1H-pyrazol-4-yl)ethyl]phenoxy}-2'-methoxy-3,3'-bipyridine (I-404)

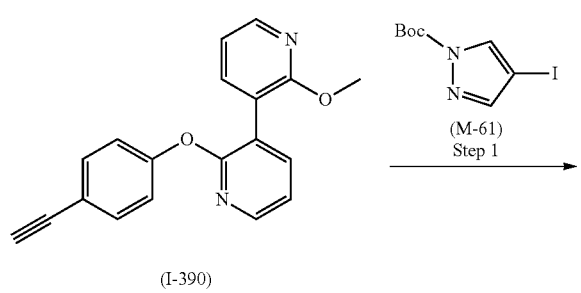

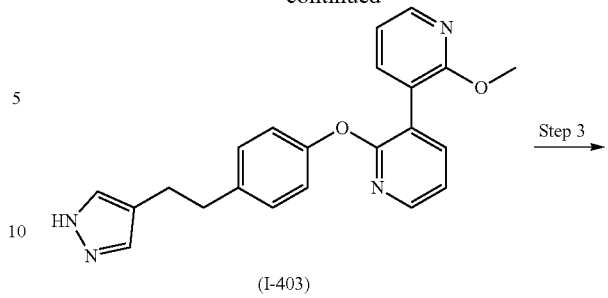

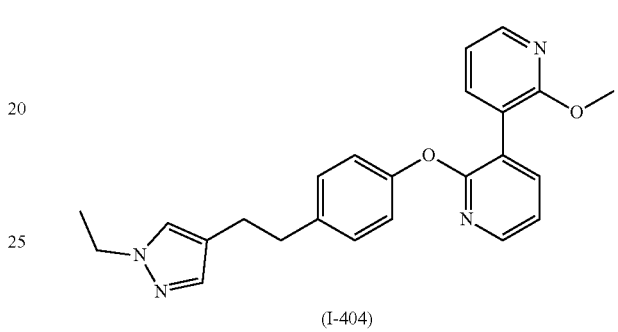

Step 1

Compound (I-390) (118 mg, 0.390 mmol) was dissolved in DMF (1.0 mL), compound (M-61) (138 mg, 0.468 mmol), Pd(PPh$_3$)$_4$ (13.7 mg, 0.0195 mmol), copper iodide (7.4 mg, 0.039 mmol) and TEA (1.0 mL) were successively added, and the mixture was stirred at room temperature for 13 hr. To the reaction mixture was added saturated aqueous ammonium chloride solution, and the mixture was extracted with chloroform. The organic layer was washed successively with saturated aqueous ammonium chloride solution and saturated brine. The solvent was evaporated under reduced pressure, and the residue was purified by silica gel column chromatography (n-hexane:ethyl acetate=97:3→60:40) to give compound (I-402) (yield 54.8 mg, 38%) as a white solid.

Step 2

Compound (I-402) (50.2 mg, 0.135 mmol) was dissolved in methanol (2.0 mL) and ethyl acetate (1.0 mL), 20% Pd(OH)$_2$/C (10.0 mg) was added, and the mixture was stirred under a hydrogen atmosphere by using a balloon at room temperature for 13 hr. The reaction mixture was filtered and the solvent was evaporated under reduced pressure. The residue was purified by silica gel column chromatography (NH silica gel, n-hexane:ethyl acetate=80:20→0:100) to give compound (I-403) (yield 33.8 mg, 67%) as a colorless oil.

Step 3

By a production method similar to that in compound (I-145), compound (I-404) (yield 12.9 mg, 60%) was obtained as a colorless oil from compound (I-403) (19.9 mg, 0.0534 mmol) and ethyl bromide (6.0 μL, 0.080 mmol).

Example 407

Production of 2-[4-(but-3-yn-1-yl)phenoxy]-2'-methoxy-3,3'-bipyridine (I-407)

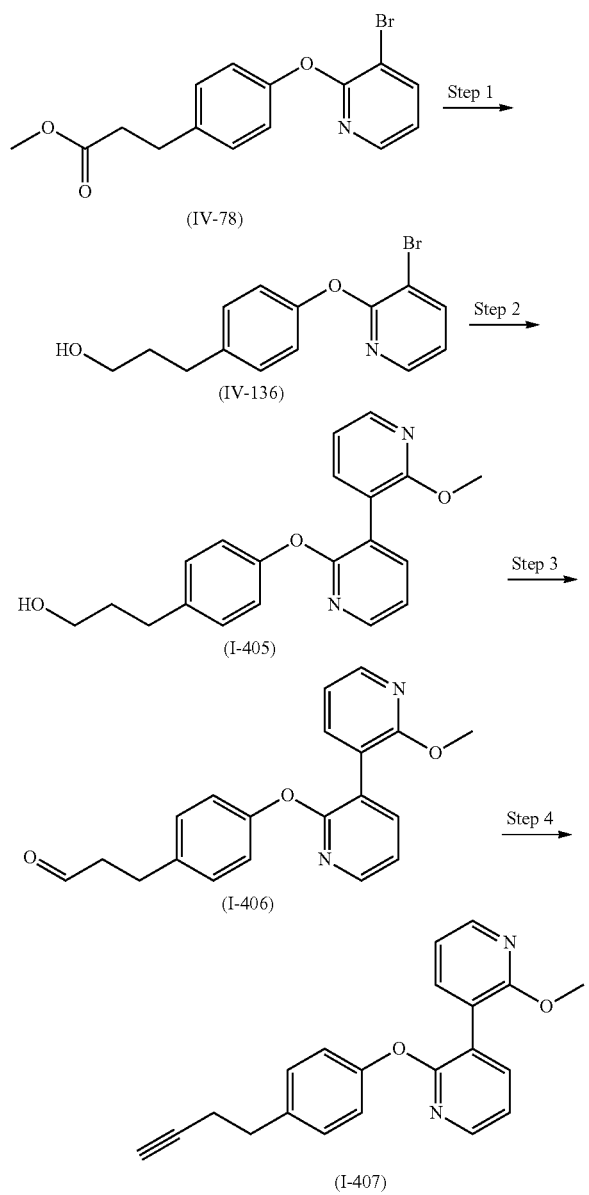

Step 1

To a solution of compound (IV-78) (1.50 g, 4.46 mmol) in THF (15 mL) was added lithium borohydride (3 mol/L THF solution, 1.5 mL, 4.5 mmol) under ice-cooling, and the mixture was stirred at room temperature for 10 hr. To the reaction mixture was added saturated aqueous ammonium chloride solution, and the mixture was extracted with ethyl acetate. The organic layer was washed successively with saturated aqueous ammonium chloride solution and saturated brine, dried over anhydrous sodium sulfate and filtered. The solvent was evaporated under reduced pressure, and the residue was purified by silica gel column chromatography (n-hexane:ethyl acetate=95:5→40:60) to give compound (IV-136) (yield 1.40 g, quantitative) as a colorless oil.

Step 2

By a production method similar to that in compound (I-1), compound (I-405) (yield 495 mg, 91%) was obtained as a yellow solid from compound (IV-136) (500 mg, 1.62 mmol) and 2-methoxypyridine-3-boronic acid (V-26) (323 mg, 2.11 mmol).

Step 3

Compound (I-405) (420 mg, 1.25 mmol) was dissolved in DCM (3.0 mL), DMP (797 mg, 1.88 mmol) was added, and the mixture was stirred at room temperature for 1 hr. Thereafter, aqueous saturated sodium thiosulfate solution was added to the reaction mixture, and the mixture was extracted with ethyl acetate. The organic layer was washed successively with saturated aqueous sodium thiosulfate solution and saturated brine, dried over anhydrous sodium sulfate, and filtered. The solvent was evaporated under reduced pressure, and the residue was purified by silica gel column chromatography (n-hexane:ethyl acetate=97:3→60:40) to give compound (I-406) (yield 193 mg, 46%) as a colorless oil.

Step 4

Compound (I-406) (152 mg, 0.453 mmol) was dissolved in methanol (2.0 mL), potassium carbonate (125 mg, 0.906 mmol) and Ohira-Bestmann reagent (0.10 mL, 0.680 mmol) were successively added, and the mixture was stirred at room temperature for 4.5 hr. Water was added to the reaction mixture, and the mixture was extracted with chloroform. The organic layer was washed with water, dried over anhydrous sodium sulfate, and filtered. The solvent was evaporated under reduced pressure, and the residue was purified by silica gel column chromatography (n-hexane:ethyl acetate) to give compound (I-407) (yield 142 mg, 95%) as a white solid.

Example 408

Production of 5-(4-{[2'-methoxy-(3,3'-bipyridin)-2-yl]oxy}phenethyl)-3-methylisoxazole (I-408)

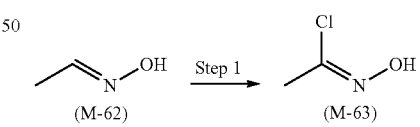

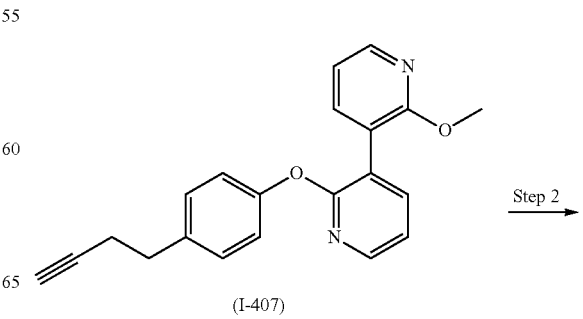

-continued

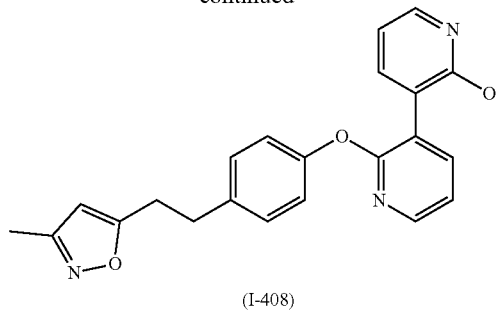

(I-408)

Step 1

Compound (M-62) (50 µL, 0.81 mmol) was dissolved in DMF (2.0 mL), NCS (130 mg, 0.976 mmol) was added, and the mixture was stirred at room temperature for 17 hr. Water was added, and the mixture was extracted with ethyl acetate. The organic layer was washed successively with water and saturated brine, dried over anhydrous sodium sulfate, and filtered. The solvent was evaporated under reduced pressure to give compound (M-63). Ethanol (1.0 mL) was added thereto to give an ethanol solution.

Step 2

Compound (I-407) (50.0 mg, 0.151 mmol) was dissolved in ethanol (1.0 mL), TEA (63 µL, 0.45 mmol) and compound (M-63) in the ethanol solution (1.0 mL, 0.81 mmol) were successively added, and the mixture was stirred at room temperature for 20 hr. Water was added to the reaction mixture, and the mixture was extracted with chloroform. The organic layer was washed with water, the solvent was evaporated under reduced pressure, and the residue was purified by silica gel column chromatography (NH silica gel, n-hexane:ethyl acetate=97:3→70:30) to give compound (I-408) (yield 21.8 mg, 37%) as a colorless oil.

Example 409

Production of methyl 3-(4-{[2'-methoxy-3,3'-bipyridin)-2-yl]oxy}phenyl)propionate (I-409)

By a production method similar to that in compound (I-1), compound (I-409) (yield 47.4 mg, 87%) was obtained as a white solid from compound (IV-78) (50.0 mg, 0.149 mmol) and 2-methoxypyridine-3-boronic acid (V-26) (34.3 mg, 0.224 mmol).

Example 411

Production of 5-(4-{[2'-methoxy-3,3'-bipyridin)-2-yl]oxy}phenethyl)-3-methyl-1,2,4-oxadiazole (I-411)

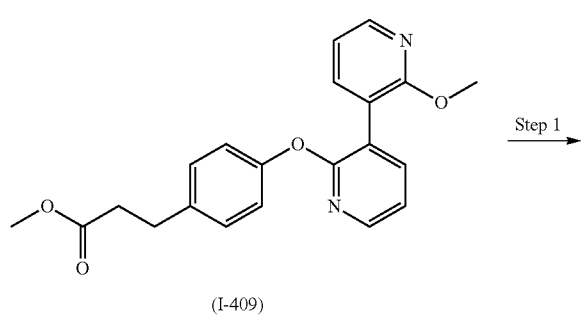

(I-409)

-continued

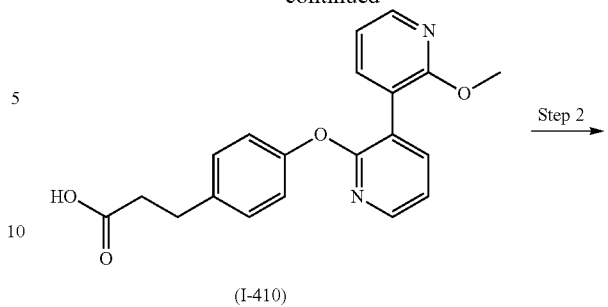

(I-410)

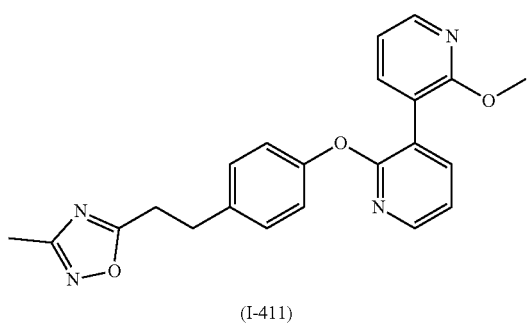

(I-411)

Step 1

Compound (I-409) (2.60 g, 7.14 mmol) was dissolved in methanol (12 mL) and THF (12 mL), 2 mol/L aqueous sodium hydroxide solution (7.2 mL, 14 mmol) was added, and the mixture was stirred at room temperature for 30 min. To the reaction mixture was added 2 mol/L hydrochloric acid (10 mL), and the mixture was extracted with ethyl acetate. The organic layer was washed with saturated brine, dried over anhydrous sodium sulfate and filtered. The solvent was evaporated under reduced pressure to give compound (I-410) (yield 2.50 g, quantitative) as a white solid.

Step 2

Compound (I-410) (50.0 mg, 0.143 mmol) was dissolved in DMF (1.0 mL), DIPEA (0.10 mL, 0.57 mmol) and HATU (81.4 mg, 0.22 mmol) were added, and the mixture was stirred at room temperature for 10 min. Thereafter, N'-hydroxyacetimidamide (21.2 mg, 0.286 mmol) was added to the reaction mixture, and the mixture was stirred at room temperature for 19 hr. Water was added to the reaction mixture, and the mixture was extracted with ethyl acetate. The organic layer was washed successively with water and saturated brine, dried over anhydrous sodium sulfate and filtered. The solvent was evaporated under reduced pressure, and the residue was dissolved in DMF (1.0 mL), and the mixture was stirred at 140° C. for 14 hr. Water was added to the reaction mixture, and the mixture was extracted with ethyl acetate. The organic layer was washed successively with water and saturated brine, dried over anhydrous sodium sulfate, and filtered. The solvent was evaporated under reduced pressure, and the residue was purified by silica gel column chromatography (n-hexane:ethyl acetate=95:5→60:40) to give compound (I-411) (yield 17.8 mg, 32%) as a colorless oil.

Example 412

Production of 7-{2-[4-(2-ethoxyethyl)phenoxy]pyridin-3-yl}pyrazolo[1,5-a]pyridine (I-412)

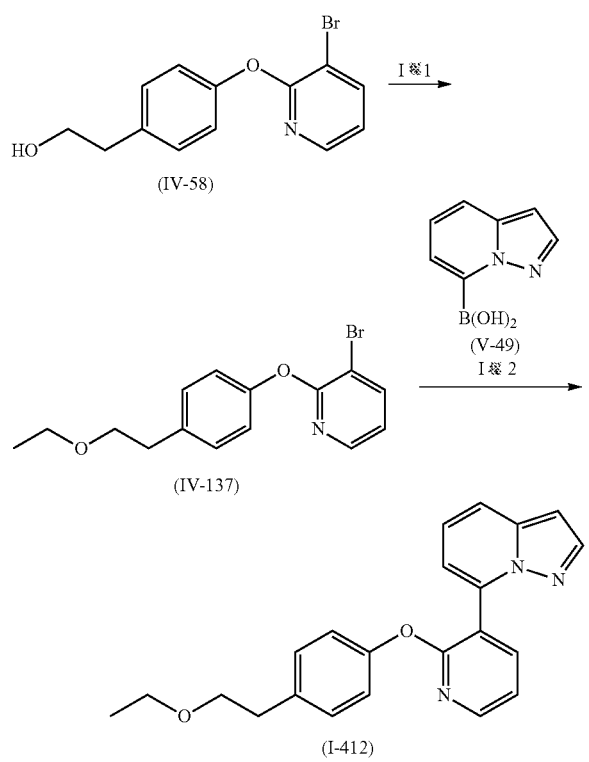

Step 1
By a production method similar to that in compound (I-145), compound (IV-137) (yield 286 mg, 87%) was obtained as a colorless oil from compound (IV-58) (300 mg, 1.02 mmol) and ethyl bromide (0.11 mL, 1.5 mmol).

Step 2
By a production method similar to that in compound (I-1), compound (I-412) (yield 3.0 mg, 9%) was obtained as a white solid from compound (IV-137) (30.0 mg, 0.0931 mmol) and pyrazolo[1,5-a]pyridine-7-boronic acid (V-49) (30.1 mg, 0.186 mmol).

Example 413

Production of 7-{2-[4-(1,1-difluoro-2-methoxyethyl)phenoxy]pyridin-3-yl}pyrazolo[1,5-a]pyridine (I-413)

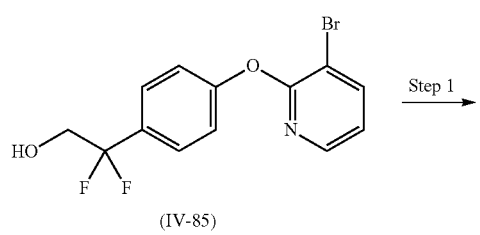

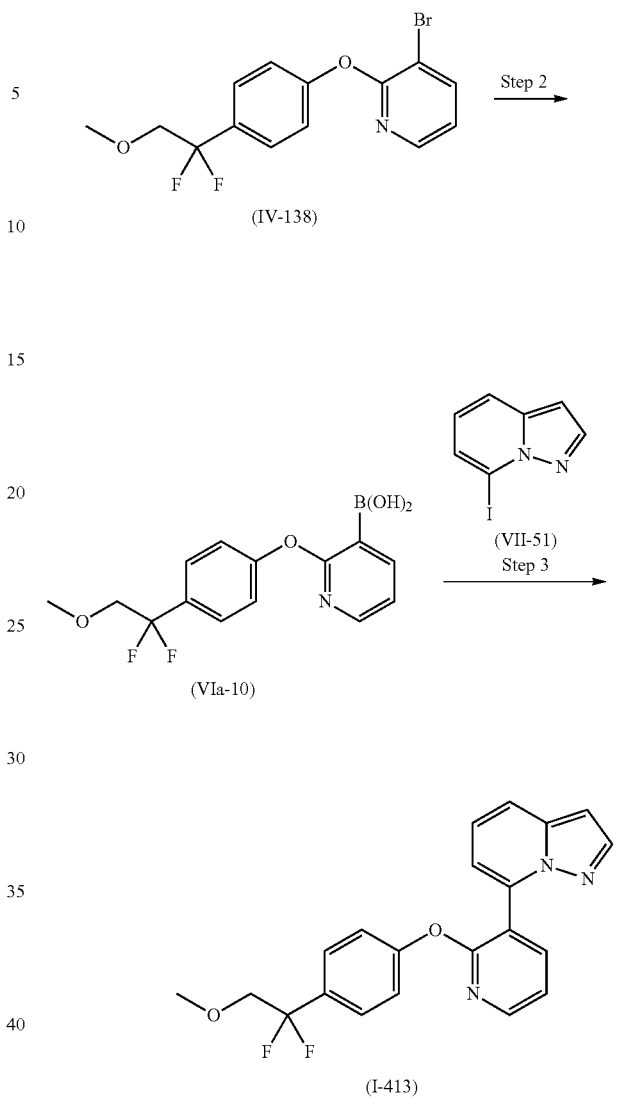

Step 1
By a production method similar to that in compound (I-145), compound (IV-138) (yield 410 mg, 79%) was obtained from compound (IV-85) (500 mg, 1.52 mmol) and methyl iodide (190 µL, 3.0 mmol).

Step 2
By a production method similar to that in compound (VIa-2), compound (VIa-10) (yield 188 mg, quantitative) was obtained as a yellow solid from compound (IV-138) (209 mg, 0.607 mmol), 1.3 mol/L THF solution of iPrMg-Br.LiCl (700 µL, 0.910 mmol) and triisopropyl borate (423 µL, 1.82 mmol).

Step 3
By a production method similar to that in compound (I-36), compound (I-413) (yield 28.0 mg, 38%) was obtained as a colorless oil from compound (VIa-10) (60.0 mg, 0.194 mmol) and 7-iodopyrazolo[1,5-a]pyridine (VII-51) (61.6 mg, 0.252 mmol).

Example 414

Production of ethyl 4-{[4'-chloro-(3,3'-bipyridin-2-yl]oxy}benzoate (I-414)

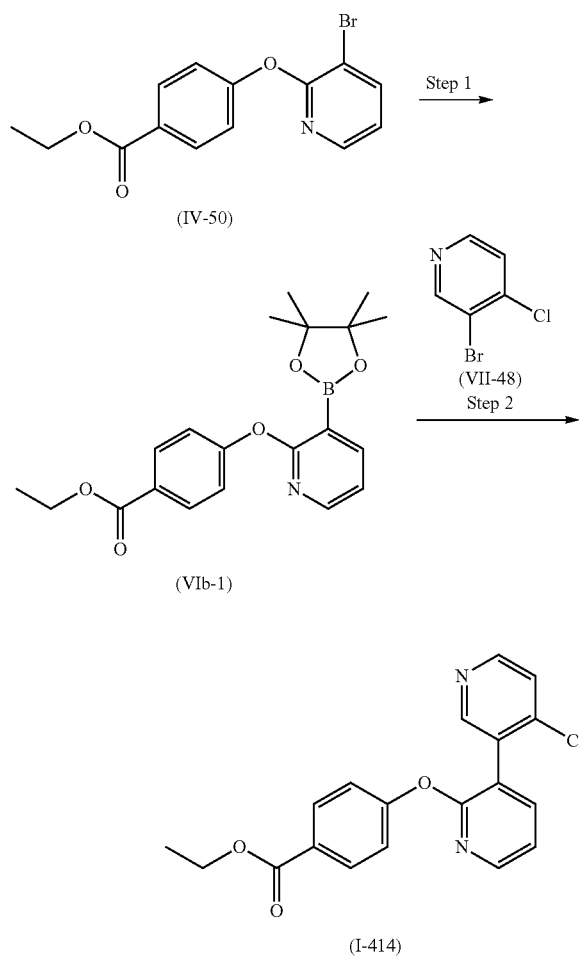

Step 1

A suspension of compound (IV-50) (1.50 g, 4.66 mmol), bis(pinacolato)diboron (2.36 g, 9.26 mmol), PdCl$_2$(dppf).DCM (190 mg, 0.233 mmol) and potassium acetate (1.37 g, 14.0 mmol) in 1,4-dioxane (15 mL) was stirred at 100° C. for 18 hr. The reaction mixture was cooled to room temperature, water was added, and the mixture was extracted with ethyl acetate. The organic layer was washed successively with water and saturated brine, dried over anhydrous sodium sulfate and filtered. The solvent was evaporated under reduced pressure, and the residue was purified by silica gel column chromatography (n-hexane: ethyl acetate=97:3→70:30) to give compound (VIb-1) (yield 749 mg, 44%) as a pale-yellow oil.

Step 2

By a production method similar to that in compound (I-36), compound (I-414) (yield 127 mg, 73%) was obtained as a colorless oil from compound (VII-48) (141 mg, 0.733 mmol) and compound (VIb-1) (300 mg, 0.488 mmol).

Example 415

Production of ethyl 4-{[4'-ethoxy-(3,3'-bipyridin)-2-yl]oxy}benzoate (I-415)

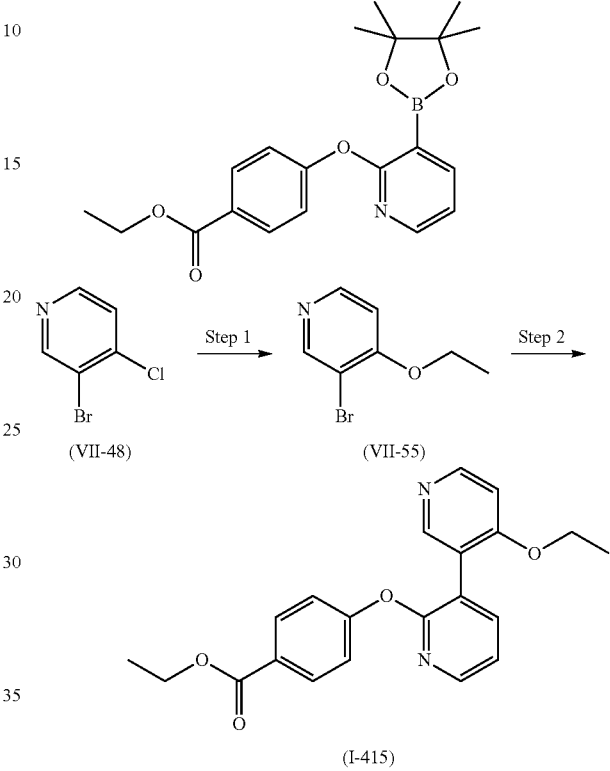

Step 1

To a solution of compound (VII-48) (300 mg, 1.56 mmol) in THF (5.0 mL) was added sodium ethoxide (20% ethanol solution, 1.8 mL, 4.6 mmol), and the mixture was stirred at 55° C. for 6 hr. The reaction mixture was cooled to room temperature, water was added, and the mixture was extracted with ethyl acetate. The organic layer was washed successively with water and saturated brine, dried over anhydrous sodium sulfate, and filtered. The solvent was evaporated under reduced pressure, and the residue was purified by silica gel column chromatography (NH silica gel, n-hexane:ethyl acetate=95:5→50:50) to give compound (VII-55) (yield 264 mg, 84%) as a yellow oil.

Step 2

Compound (VIb-1) (300 mg, 0.488 mmol), compound (VII-55) (148 mg, 0.732 mmol), (A-$^{ta}$Phos)$_2$PdCl$_2$ (17.3 mg, 0.0244 mmol), and cesium fluoride (148 mg, 0.974 mmol) were dissolved in 1,4-dioxane and (1.5 mL) and water (0.30 mL), and the mixture was stirred under microwave irradiation at 120° C. for 30 min. Water was added to the reaction mixture, and the mixture was extracted with ethyl acetate. The organic layer was washed successively with water and saturated brine, dried over anhydrous sodium sulfate, and filtered. The solvent was evaporated under reduced pressure, and the residue was purified by silica gel column chromatography (n-hexane:ethyl acetate) to give compound (I-415) (yield 162 mg, 91%) as a colorless oil.

Example 416

Production of ethyl 4-{[4'-ethyl-(3,3'-bipyridin-2-yl]oxy}benzoate (I-416)

To a solution of compound (I-414) (39.1 mg, 0.110 mmol) in THF (0.50 mL), were added PdCl$_2$(dppf).DCM (9.0 mg, 0.011 mmol) and diethylzinc (1.0 mol/L THF solution, 0.17 mL, 0.17 mmol), and the mixture was stirred at 70° C. for 1 hr. To the reaction mixture was added saturated aqueous sodium hydrogen carbonate solution, and the mixture was extracted with ethyl acetate. The organic layer was washed successively with saturated aqueous sodium hydrogen carbonate solution and saturated brine, dried over anhydrous sodium sulfate, and filtered. The solvent was evaporated under reduced pressure, and the residue was purified by silica gel column chromatography (n-hexane:ethyl acetate) to give compound (I-416) (yield 24.2 mg, 63%) as a colorless oil.

Example 418

Production of isopropyl 4-{[4'-methoxy-(3,3'-bipyridin-2-yl]oxy}benzoate (I-418)

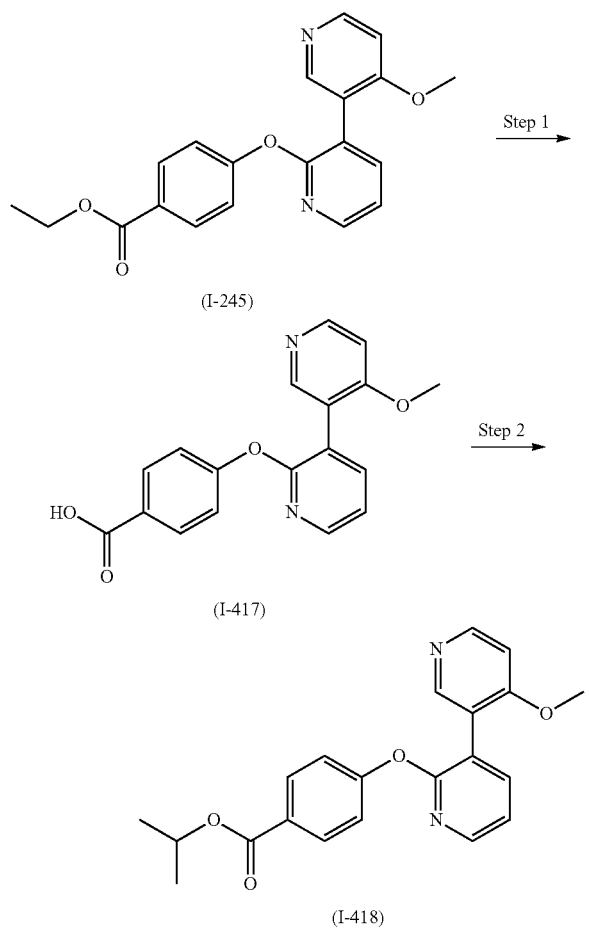

Step 1
Compound (I-245) (343 mg, 0.979 mmol) was dissolved in ethanol (2.0 mL), THF (2.0 mL), 4 mol/L aqueous sodium hydroxide solution (0.49 mL, 1.96 mmol) was added, and the mixture was stirred at room temperature for 16 hr. To the reaction mixture was added 5 mol/L hydrochloric acid (0.50 mL), and the mixture was extracted with ethyl acetate. The organic layer was washed with saturated brine, dried over anhydrous sodium sulfate, and filtered. The solvent was evaporated under reduced pressure, and the residue was purified by silica gel column chromatography (n-hexane:ethyl acetate) to give compound (I-417) (yield 250 mg, 79%) as a white solid.

Step 2
To a solution of compound (I-417) (23.0 mg, 0.0710 mmol) in DMF (0.90 mL) were successively added isopropyl alcohol (55 µL, 0.71 mmol) TEA (50 µL, 0.36 mmol), EDCI.HCl (20.5 mg, 0.107 mmol) and HOBt.H$_2$O (10.9 mg, 0.0710 mmol), and the mixture was stirred at 30° C. for 19 hr. Water was added to the reaction mixture, and the mixture was extracted with chloroform. The organic layer was washed with water, dried over anhydrous sodium sulfate, and filtered. The solvent was evaporated under reduced pressure, and the residue was purified by silica gel column chromatography (NH silica gel, n-hexane:ethyl acetate=95:5→50:50) to give compound (I-418) (yield 1.7 mg, 7%) as a colorless oil.

Example 419

Production of ethyl 4-{[4'-methyl-(3,3'-bipyridin-2-yl]oxy}benzoate (I-419)

By a production method similar to that in compound (I-1), compound (I-419) (yield 11.3 mg, 22%) was obtained as a colorless oil from compound (IV-50) (50.0 mg, 0.155 mmol) and 4-methylpyridine-3-boronic acid (V-25) (31.9 mg, 0.233 mmol).

Example 421

Production of 5-(4-{[4'-methyl-(3,3'-bipyridin-2-yl]oxy}phenyl)-3-methyl-1,2,4-oxadiazole (I-421)

-continued

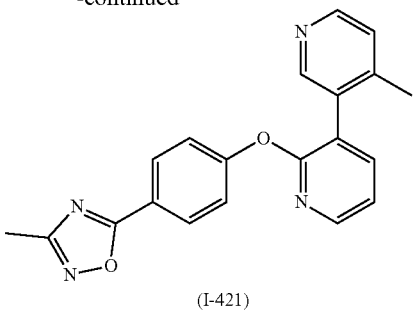

(I-421)

Step 1
By a production method similar to that in compound (I-417), compound (I-420) (yield 200 mg, 74%) was obtained as a white solid from compound (I-419) (297 mg, 0.888 mmol).

Step 2
By a production method similar to that in compound (I-411), compound (I-421) (yield 2.5 mg, 7%) was obtained as a white solid from compound (I-420) (30.0 mg, 0.0979 mmol) and N'-hydroxyacetimidamide (14.5 mg, 0.196 mmol).

Example 422

Production of 1-(4-{[4'-methyl-(3,3'-bipyridin-2-yl]oxy}phenyl)ethanone (I-422)

By a production method similar to that in compound (I-127), compound (I-422) (yield 747 mg, 72%) was obtained as a yellow solid from compound (IV-49) (1.00 mg, 3.42 mmol) and 4-methylpyridine-3-boronic acid (V-25) (703 mg, 5.13 mmol).

Example 423

Production of 2-methyl-5-(4-{[4'-methoxy-(3,3'-bipyridin-2-yl]oxy}phenyl)oxazole (I-423)

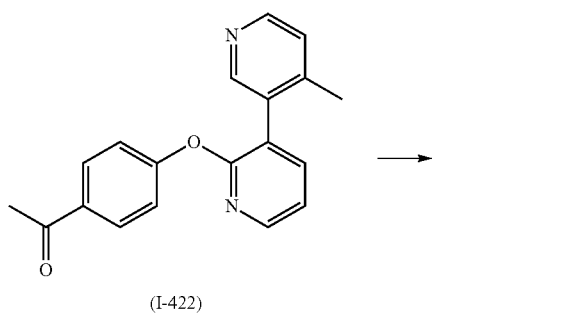

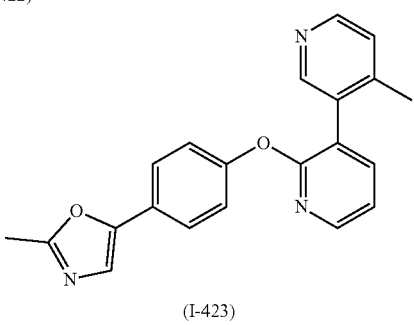

(I-423)

To a solution of thallium acetate (56.4 mg, 0.148 mmol) in acetonitrile (0.50 mL), was added trifluoromethanesulfonic acid (39 µL, 0.44 mmol), and the mixture was stirred at room temperature for 15 min. To the reaction mixture was added a solution of compound (I-422) (30.0 mg, 0.0986 mmol) in acetonitrile (1.0 mL) at 80° C., and the mixture was stirred for 2 hr. Water was added to the reaction mixture, and the mixture was extracted with ethyl acetate. The organic layer was washed successively with water and saturated brine, dried over anhydrous sodium sulfate, and filtered. The solvent was evaporated under reduced pressure, and the residue was purified by silica gel column chromatography (n-hexane:ethyl acetate) to give compound (I-423) (yield 9.7 mg, 29%) as a white solid.

Example 424

Production of 1-(4-{[4'-methyl-(3,3'-bipyridin-2-yl]oxy}phenyl)butane-1,3-dione (I-424)

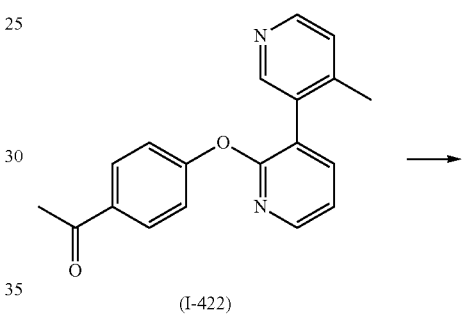

(I-422)

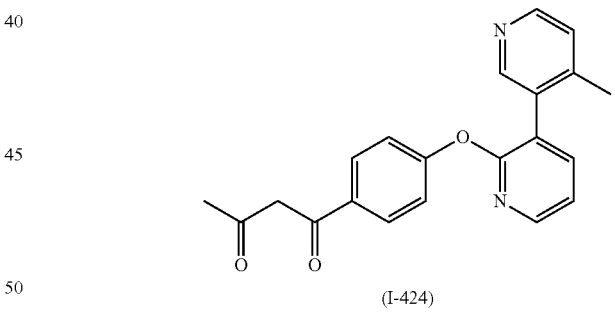

(I-424)

To a solution of compound (I-422) (100 mg, 0.329 mmol) in THF (1.5 mL), was added sodium hydride (65.7 mg, 1.64 mmol) under ice-cooling, and the mixture was stirred at room temperature for 15 min. To the reaction mixture was added ethyl acetate (0.13 mL, 1.3 mmol) at 45° C., and the mixture was stirred at 45° C. for 1 hr. Water was added to the reaction mixture, and the mixture was extracted with ethyl acetate. The organic layer was washed successively with water and saturated brine, dried over anhydrous sodium sulfate, and filtered. The solvent was evaporated under reduced pressure, and the residue was purified by silica gel column chromatography (n-hexane:ethyl acetate=80:20→20:80) to give compound (I-424) (yield 50.7 mg, 45%) as a white solid.

Example 425

Production of 3-methyl-5-(4-{[4'-methyl-(3,3'-bi-pyridin-2-yl]oxy}phenyl)isoxazole (I-425)

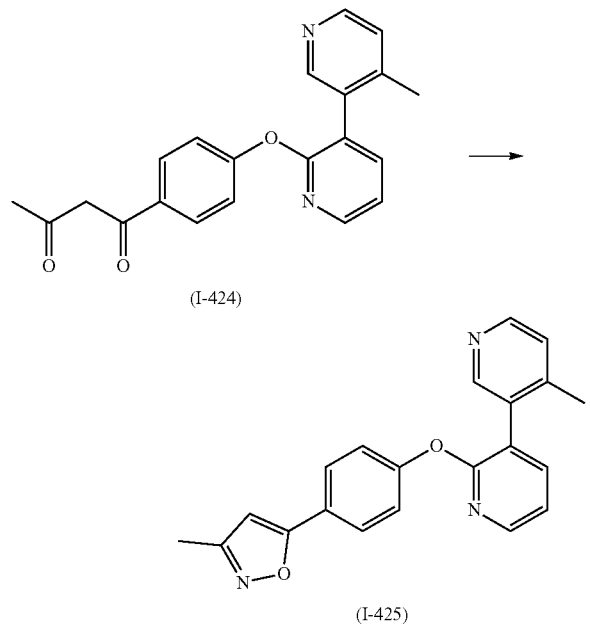

(I-424)

(I-425)

To a suspension of hydroxylamine hydrochloride (44.0 mg, 0.630 mmol) in IPA (0.50 mL), was added TEA (9.0 µL, 0.065 mmol), and the mixture was stirred at room temperature for 15 min. To the reaction mixture was added TFA (10 µL, 0.13 mmol), and the mixture was stirred at room temperature for 15 min. To the reaction mixture was added compound (I-424) (20.0 mg, 0.0577 mmol), and the mixture was stirred at 60° C. for 2 hr. Water was added to the reaction mixture, and the mixture was extracted with ethyl acetate. The organic layer was washed successively with water and saturated brine, dried over anhydrous sodium sulfate, and filtered. The solvent was evaporated under reduced pressure, and the residue was purified by silica gel column chromatography (NH silica gel, n-hexane:ethyl acetate=95:5→50:50) to give compound (I-425) (yield 13.1 mg, 66%) as a white solid.

Example 426

Production of 2-(4-iodophenoxy)-4'-methyl-(3,3'-bipyridine (I-426)

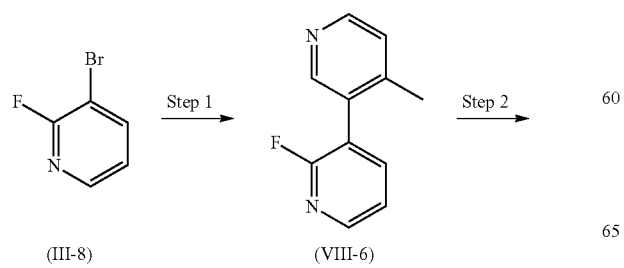

(III-8)   Step 1   (VIII-6)   Step 2

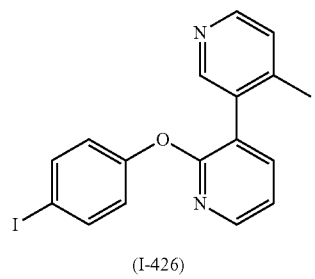

(I-426)

Step 1

By a production method similar to that in compound (I-127), compound (VIII-6) (yield 1.9 g, 59%) was obtained as a yellow oil from compound (III-8) (3.00 g, 17.0 mmol) and 4-methylpyridine-3-boronic acid (V-25) (3.96 g, 25.6 mmol).

Step 2

By a production method similar to that in compound (IV-1), compound (I-426) (yield 2.86 g, 73%) was obtained as a white solid from compound (VIII-6) (1.90 g, 10.1 mmol) and 4-iodophenol (II-38) (2.67 g, 12.1 mmol).

Example 428

Production of 5-methyl-2-(4-{[4'-methyl-(3,3'-bipyridin-2-yl]oxy}phenyl)thiazole (I-428)

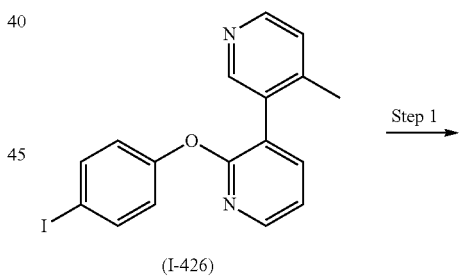

(I-426)   Step 1

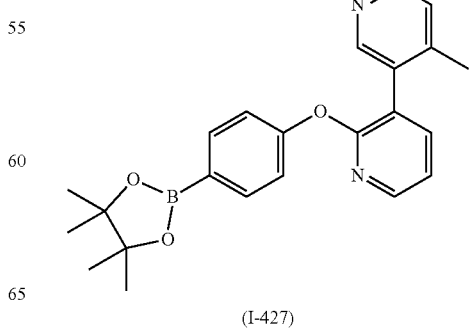

(I-427)   Step 2

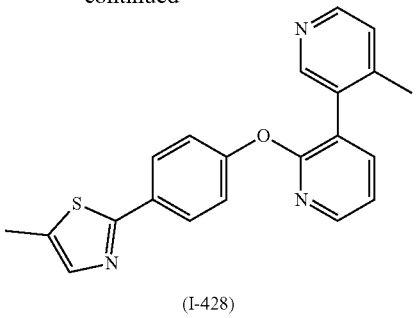

(I-428)

Step 1

Compound (I-426) (1.70 g, 4.38 mmol), bis(pinacolato) diboron (358 mg, 0.438 mmol), PdCl$_2$(dppf).DCM (358 mg, 0.438 mmol) and potassium acetate (1.29 g, 13.1 mmol) were dissolved in 1,4-dioxane (10 mL), and the mixture was stirred under microwave irradiation at 120° C. for 30 min. The reaction mixture was allowed to cool, water was added, and the mixture was extracted with ethyl acetate. The organic layer was washed successively with water and saturated brine, dried over anhydrous sodium sulfate, and filtered. The solvent was evaporated under reduced pressure, and the residue was purified by silica gel column chromatography (n-hexane:ethyl acetate) to give compound (I-427) (yield 1.64 g, 96%) as a brown solid.

Step 2

A suspension of compound (I-427) (50.0 mg, 0.129 mmol), 2-bromo-5-methylthiazole (34.4 mg, 0.193 mmol), (A-$^{ta}$Phos)$_2$PdCl$_2$ (4.6 mg, 6.5 μmol) and cesium carbonate (83.9 mg, 0.258 mmol) in 1,4-dioxane (1.0 mL) was stirred under microwave irradiation at 120° C. for 30 min. Water was added to the reaction mixture, and the mixture was extracted with ethyl acetate. The organic layer was washed successively with water and saturated brine, dried over anhydrous sodium sulfate, and filtered. The solvent was evaporated under reduced pressure, and the residue was purified by silica gel column chromatography (n-hexane: ethyl acetate=50:50→0:100) to give compound (I-428) (yield 7.8 mg, 17%) as a colorless oil.

Example 429

Production of 4'-methyl-2-[4-(pyrimidin-2-yl)phenoxy]-(3,3'-bipyridine (I-429)

By a production method similar to that in compound (I-428), compound (I-429) (yield 3.8 mg, 9%) was obtained as a colorless oil from compound (I-427) (50.0 mg, 0.129 mmol) and 2-bromopyrimidine (30.7 mg, 0.193 mmol).

Example 430

Production of 4'-methyl-2-[4-(pyridin-4-yl)phenoxy]-(3,3'-bipyridine (I-430)

Compound (I-427) (50.0 mg, 0.129 mmol), 4-iodopyridine (39.6 mg, 0.193 mmol), (A-$^{ta}$Phos)$_2$PdCl$_2$ (4.6 mg, 0.0064 mmol) and cesium fluoride (58.7 mg, 0.386 mmol) were dissolved in 1,4-dioxane (0.50 mL), and water (0.050 mL), and the mixture was stirred under microwave irradiation at 120° C. for 30 min. The reaction mixture was allowed to cool, water was added, and the mixture was extracted with ethyl acetate. The organic layer was washed with saturated brine, dried over anhydrous sodium sulfate, and filtered. The solvent was evaporated under reduced pressure, and the residue was purified by silica gel column chromatography (n-hexane:ethyl acetate) to give compound (I-430) (yield 13.8 mg, 32%) as a colorless oil.

Example 431

Production of 4'-methyl-2-[4-(pyridin-2-yl)phenoxy]-(3,3'-bipyridine (I-431)

By a production method similar to that in compound (I-430), compound (I-431) (yield 5.1 mg, 12%) was obtained as a colorless oil from compound (I-427) (50.0 mg, 0.129 mmol) and 2-bromopyridine (30.5 mg, 0.193 mmol).

Example 432

Production of 4'-methyl-2-[4-(4-methyl-1H-pyrazol-1-yl)phenoxy](3,3'-bipyridine (I-432)

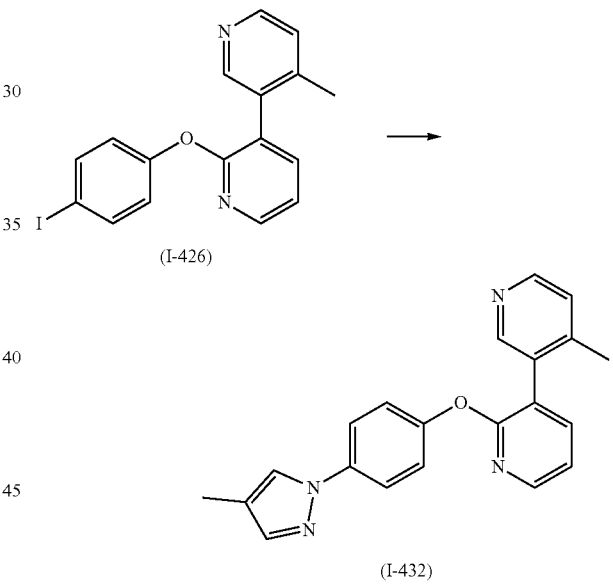

To a solution of compound (I-426) (30.0 mg, 0.0773 mmol) in toluene (1.0 mL) were successively added 4-methylpyrazole (12.9 mg, 0.157 mmol), copper iodide (1.5 mg, 0.0079 mmol), (1S,2S)—N,N'-dimethylcyclohexane-1,2-diamine (2.2 mg, 0.015 mmol) and potassium carbonate (32.0 mg, 0.232 mmol), and the mixture was stirred under microwave irradiation at 150° C. for 30 min. Thereafter, 4-methylpyrazole (12.9 mg, 0.157 mmol) and copper iodide (1.5 mg, 0.0079 mmol) were successively added to the reaction mixture, and the mixture was stirred under microwave irradiation at 160° C. for 30 min. Water was added to the reaction mixture, and the mixture was extracted with chloroform. The organic layer was washed with water, the solvent was evaporated under reduced pressure, and the residue was purified by silica gel column chromatography (NH silica gel, n-hexane:ethyl acetate=95:5→60:40) to give compound (I-432) (yield 3.4 mg, 13%) as a white solid.

Example 433

Production of 2-[4-(1H-pyrazol-1-yl)phenoxy]-4'-methyl-(3,3'-bipyridine (I-433)

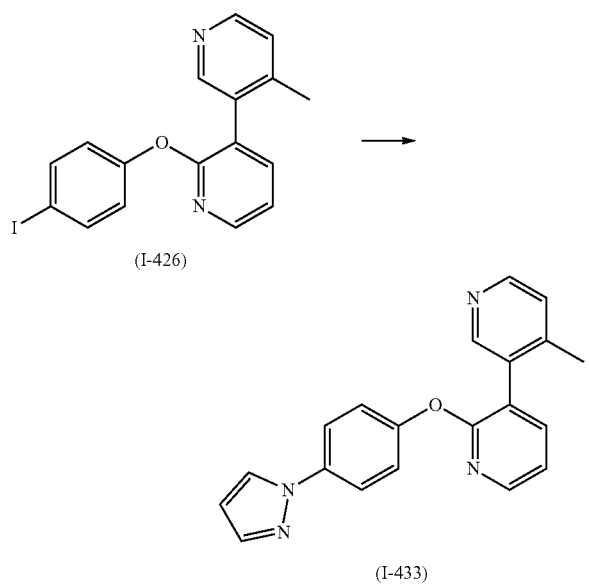

By a production method similar to that in compound (I-432), compound (I-433) (yield 2.0 mg, 5%) was obtained as a colorless oil from compound (I-426) (50.0 mg, 0.129 mmol) and pyrazole (17.5 mg, 0.257 mmol).

Example 434

Production of 2,2-difluoro-2-(4-{[2'-methoxy-(3,3'-bipyridin-2-yl]oxy}phenyl)ethanol (I-434)

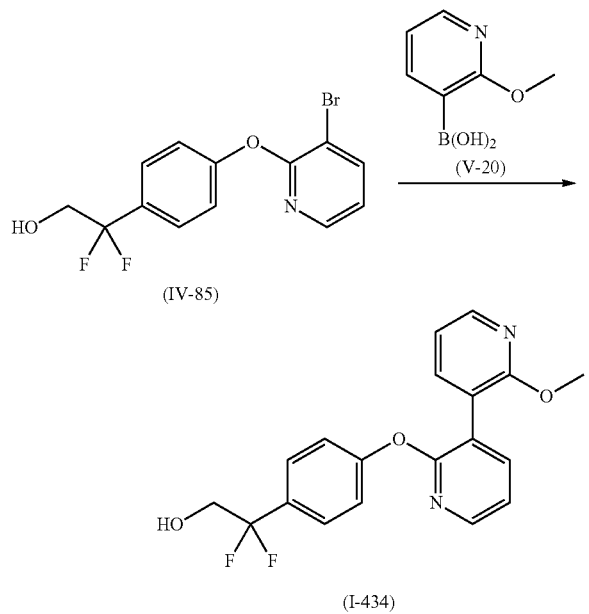

By a production method similar to that in compound (I-1), compound (I-434) (yield 136 mg, 84%) was obtained as a colorless oil from compound (IV-85) (150 mg, 0.454 mmol) and 2-methoxypyridine-3-boronic acid (V-26) (83.0 mg, 0.545 mmol).

Example 435

Production of 2-methoxy-2'-{[4-(trifluoromethyl)phenyl]thio}-(3,3'-bipyridine (I-435)

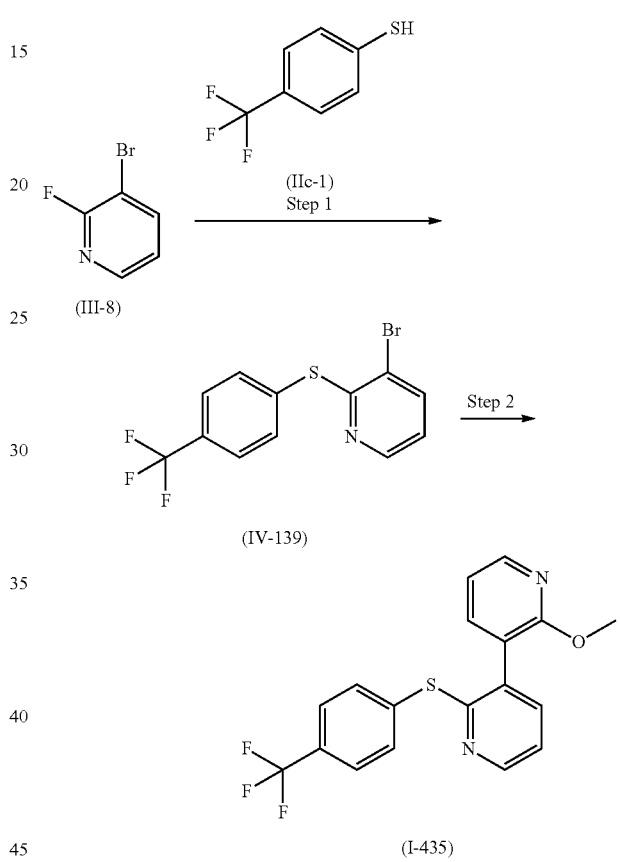

Step 1
By a production method similar to that in compound (IV-1), compound (IV-139) (yield 325 mg, 86%) was obtained as a white solid from 4-trifluoromethylthiophenol (IIc-1) (184 µL, 1.36 mmol) and compound (III-8) (200 mg, 1.14 mmol).

Step 2
By a production method similar to that in compound (I-1), compound (I-435) (yield 33.1 mg, 76%) was obtained as a colorless oil from compound (IV-139) (40.0 mg, 0.120 mmol) and 2-methoxypyridine-3-boronic acid (V-26) (27.5 mg, 0.180 mmol).

Example 436

Production of 3-(2-methoxyphenyl)-2-{[4-(trifluoromethyl)phenyl]thio}pyridine (I-436)

By a production method similar to that in compound (I-1), compound (I-436) (yield 116 mg, 77%) was obtained as a white solid from compound (IV-138) (40.0 mg, 0.120 mmol) and 2-methoxyphenylboronic acid (V-1) (94.1 mg, 0.619 mmol).

Example 439

Production of 3-(2-methoxyphenyl)-2-[4-(trifluoromethyl)benzyl]pyridine (I-439)

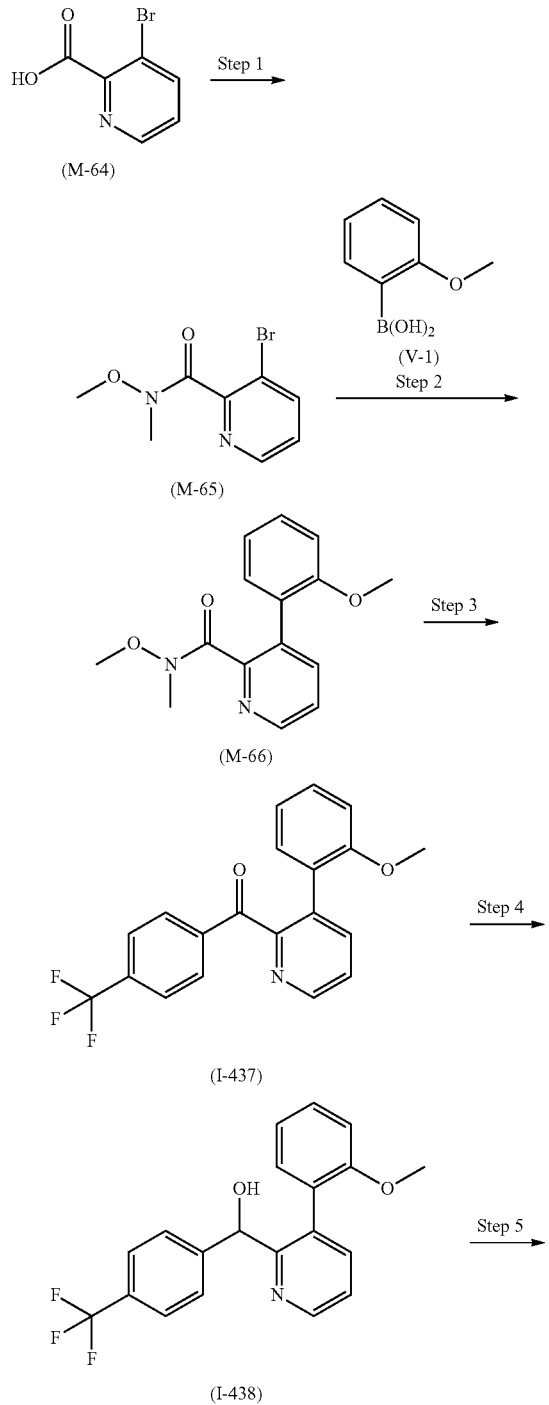

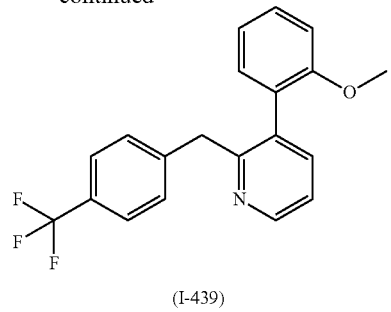

(I-439)

Step 1

3-Bromopicolinic acid (M-64) (2.02 g, 10.0 mmol) was dissolved in DCM (20.0 mL), DIPEA (5.19 mL, 30.0 mmol), HATU (4.56 g, 12.0 mmol) and N,O-dimethylhydroxylamine hydrochloride (1.17 g, 12.0 mmol) were added, and the mixture was stirred at room temperature for 20 hr. Water was added to the reaction mixture, and the mixture was extracted with chloroform. The organic layer was washed successively with water and saturated brine, dried over anhydrous sodium sulfate, and filtered. The solvent was evaporated under reduced pressure. The residue was purified by silica gel column chromatography (NH silica gel, n-hexane:ethyl acetate=80:20→20:80) to give compound (M-65) (yield 1.91 g, 78%) as a white solid.

Step 2

Compound (M-65) (1.00 g, 4.08 mmol), 2-methoxyphenylboronic acid (V-1) (806 mg, 5.30 mmol), (A-$^{ta}$Phos)$_2$PdCl$_2$ (144 mg, 0.204 mmol) and cesium carbonate (2.66 g, 8.16 mmol) were dissolved in 1,4-dioxane (10 mL) and water (1 mL), and the mixture was stirred under microwave irradiation at 120° C. for 30 min. Water was added to the reaction mixture, and the mixture was extracted with ethyl acetate. The organic layer was washed successively with water and saturated brine, dried over anhydrous sodium sulfate, and filtered. The solvent was evaporated under reduced pressure, and the residue was purified by silica gel column chromatography (NH silica gel, n-hexane:ethyl acetate=80:20→30:70) to give compound (M-66) (yield 947 mg, 85%) as a white solid.

Step 3

To a solution (2.5 mL) of 4-trifluoromethylbromobenzene (563 mg, 2.50 mmol) in THF were added magnesium powder (60.0 mg, 2.47 mmol) and iodine (1 grain), and the mixture was stirred at room temperature for 2 hr. The reaction mixture was ice-cooled, a solution of compound (M-66) (610 mg, 2.24 mmol) in THF (6.5 mL) was added, and the mixture was stirred at room temperature for 3 hr. To the reaction mixture was added saturated aqueous ammonium chloride solution, and the mixture was stirred for 30 min, and extracted with ethyl acetate. The organic layer was washed successively with water and saturated brine, dried over anhydrous sodium sulfate, and filtered. The solvent was evaporated under reduced pressure, and the residue was purified by silica gel column chromatography (n-hexane:ethyl acetate=100:0→70:30) to give compound (I-437) (yield 447 mg, 56%) as a white solid.

Step 4

To a solution of compound (I-437) (215 mg, 0.602 mmol) in methanol (4.0 mL) was added, under ice-cooling, sodium borohydride (46.0 mg, 1.22 mmol), and the mixture was stirred at room temperature for 1.5 hr. Water was added to the reaction mixture, and the mixture was extracted with ethyl acetate. The organic layer was washed successively with water and saturated brine, dried over anhydrous sodium sulfate, and filtered. The solvent was evaporated under reduced pressure, and the residue was purified by silica gel column chromatography (n-hexane:ethyl acetate=90:10→50:50) to give compound (I-438) (yield 217 mg, quantitative) as a colorless oil.

Step 5

Compound (I-438) (50.0 mg, 0.139 mmol) was dissolved in DCM (0.70 mL), TEA (29.1 µL, 0.209 mmol) and methanesulfonyl chloride (14.0 µL, 0.181 mmol) were added under ice-cooling and the mixture was stirred at for 30 min. The reaction mixture was ice-cooled, water was added, and the mixture was extracted with chloroform. The organic layer was dried over anhydrous sodium sulfate, and filtered, and the solvent was evaporated under reduced pressure. The residue was dissolved in methanol (1.0 mL), 10% Pd/C (15 mg) was added, and the mixture was stirred under a hydrogen atmosphere by using a balloon at room temperature for 18 hr. The mixture was filtered through Celite, and washed with methanol. The solvent was evaporated under reduced pressure, and the residue was purified by silica gel column chromatography (first time: silica gel, n-hexane:ethyl acetate=100:0→80:20) to give compound (I-439) (yield 8.8 mg, 18%) as a colorless oil.

By a production method similar to that in compound (I-1) (Suzuki-Miyaura cross coupling reaction), compound (I-440) to compound (I-502), compound (I-576) and compound (I-577) were synthesized. The structure and property value of each compound are shown in Table 54 to Table 61 and Table 71.

By a production method similar to that in compound (I-127) (Suzuki-Miyaura cross coupling reaction), compound (I-503) to compound (I-507) were synthesized. The structure and property value of each compound are shown in Table 61 and Table 62.

By a production method similar to that in compound (I-36) (Suzuki-Miyaura cross coupling reaction), compound (I-508) to compound (I-515) were synthesized. The structure and property value of each compound are shown in Table 62 and Table 63.

In the same manner as in compound (I-1), aryl halide compound (IV) was obtained by $S_N$ aryl reaction (Step 1), and compound (I-516) to compound (I-527) were synthesized by Suzuki-Miyaura cross coupling reaction (Step 2). The structure and property value of each compound are shown in Table 63 and Table 64.

In the same manner as in compound (I-318), a compound represented by the formula (VIII) was obtained by Suzuki-Miyaura cross coupling reaction (Step 1), and compound (I-528) to compound (I-532) were synthesized by $S_N$ aryl reaction with a compound represented by the formula (II). The structure and property value of each compound are shown in Table 65.

In the same manner as in compound (I-331), aryl halide compound (IV) was was led to boronic acid compound (VIa) or boronic acid ester compound (VIb) (Step 1), and compound (I-533) to compound (I-537) were synthesized by Suzuki-Miyaura cross coupling reaction with aryl halide (VII) (Step 2). The structure and property value of each compound are shown in Table 65 and Table 66.

By a production method similar to that in compound (I-175), compound (I-538) was synthesized. The structure and property value of each compound are shown in Table 66.

By a production method similar to that in compound (I-173) compound (I-539) was synthesized. The structure and property value of each compound are shown in Table 66.

By a production method similar to that in compound (I-145) compound (I-540) to compound (I-547) were synthesized. The structure and property value of each compound are shown in Table 66 and Table 67.

By a production method similar to that in compound (I-146), compound (I-548) and compound (I-549) were synthesized. The structure and property value of each compound are shown in Table 67.

By a production method similar to that in compound (IV-30), compound (I-550) to compound (I-554) and compound (I-578) were synthesized from halogen compound (I) by $S_N$ aryl reaction. The structure and property value of each compound are shown in Table 67, Table 68 and Table 67.

By a production method similar to that in compound (I-182), compound (I-555) to compound (I-565) were synthesized from various halogen compounds (IV) by amination (Step 1) and Suzuki-Miyaura cross coupling reaction (Step 2). The structure and property value of each compound are shown in Table 68 and Table 69.

By a production method similar to that in compound (I-186), compound (I-566) were synthesized. The structure and property value of the compound are shown in Table 69.

By a production method similar to that in compound (I-386), compound (I-567) was synthesized. The structure and property value of the compound are shown in Table 69.

By a production method similar to that in compound (I-222), compound (I-568) was synthesized by replacing NCS (reaction reagent) with NBS. The structure and property value of the compound are shown in Table 70.

By a production method similar to that in compound (I-198), compound (I-569) to compound (I-573), compound (I-570) and compound (I-580) were synthesized by Sonogashira cross coupling reaction (Step 1), followed by catalytic hydrogenation reaction (Step 2). The structure and property value of each compound are shown in Table 70 and Table 71.

By a production method similar to that in compound (I-326), compound (I-574) was synthesized from compound (III-10) by $S_N$ aryl reaction (Step 1), borylation (Step 2), followed by Suzuki-Miyaura cross coupling reaction (Step 3). The structure and property value of each compound are shown in Table 70.

By a production method similar to that in compound (I-178), compound (I-575) was synthesized in 4 steps from 5-bromo-2-t-butylpyrimidine. The structure and property value of the compound are shown in Table 70.

By a production method similar to that in compound (I-400), compound (I-581) was synthesized. The structure and property value of the compound are shown in Table 71.

By a production method similar to that in compound (I-52), compound (I-52) was synthesized by replacing NCS (reaction reagent) with SelectFlour (registered trademark). The structure and property value of each compound are shown in Table 71.

TABLE 1

| compound | structural formula | NMR | MS |
| --- | --- | --- | --- |
| I-1 | | $^1$H-NMR (400 MHz, CDCl$_3$) δ: 3.71 (3H, s), 6.97 (1H, d, J = 8.2 Hz), 7.07 (1H, dt, J = 0.9, 7.3 Hz), 7.20 (1H, dd, J = 5.0, 7.3 Hz), 7.32 (1H, dd, J = 1.8, 7.3 Hz), 7.40 (1H, ddd, J = 1.8, 7.3, 8.2 Hz), 7.61 (1H, dd, J = 2.7, 8.7 Hz), 7.68 (1H, d, J = 8.2 Hz), 7.75 (1H, dd, J = 1.8, 7.3 Hz), 8.17 (1H, dd, J = 2.3, 5.0 Hz), 8.51 (1H, d, J = 2.7 Hz). | ESI-MS m/z: 347 [M + H]$^+$. |
| I-2 | | $^1$H-NMR (400 MHz, CDCl$_3$) δ: 3.85 (3H, s), 6.96 (1H, dd, J = 1.8, 7.8 Hz), 7.15 (1H, dd, J = 1.8, 2.3 Hz), 7.17-7.24 (2H, m), 7.39 (1H, dd, J = 7.8, 8.2 Hz), 7.65 (1H, dd, J = 2.3, 8.7 Hz), 7.71 (1H, d, J = 8.2 Hz), 7.84 (1H, dd, J = 1.8, 7.3 Hz), 8.14 (1H, dd, J = 2.3, 5.0 Hz), 8.57 (1H, d, J = 2.3 Hz). | ESI-MS m/z: 347 [M + H]$^+$. |
| I-3 | | $^1$H-NMR (400 MHz, CDCl$_3$) δ: 7.14-7.30 (3H, m), 7.38-7.48 (2H, m), 7.66 (1H, dd, J = 2.3, 8.7 Hz), 7.71 (1H, d, J = 8.7 Hz), 7.80 (1H, dd, J = 1.8, 7.3 Hz), 8.19 (1H, dd, J = 2.3, 5.0 Hz), 8.58 (1H, d, J = 2.3 Hz). | ESI-MS m/z: 335 [M + H]$^+$. |
| I-4 | | $^1$H-NMR (400 MHz, CDCl$_3$) δ: 7.21 (1H, dd, J = 5.0, 7.3 Hz), 7.34-7.42 (3H, m), 7.47-7.54 (1H, m), 7.65 (1H, dd, J = 2.3, 8.2 Hz), 7.68-7.75 (2H, m), 8.20 (1H, dd, J = 1.8, 5.0 Hz), 8.55 (1H, d, J = 2.7 Hz). | ESI-MS m/z: 351, 353 [M + H]$^+$. |
| I-5 | | $^1$H-NMR (400 MHz, CDCl$_3$) δ: 7.21 (1H, dd, J = 5.0, 7.3 Hz), 7.26-7.32 (1H, m), 7.37 (1H, dd, J = 1.8, 7.8 Hz), 7.41-7.48 (2H, m), 7.65-7.71 (3H, m), 8.21 (1H, dd, J = 1.8, 5.0 Hz), 8.57 (1H, d, J = 1.8 Hz). | ESI-MS m/z: 394 [M + H]$^+$. |

TABLE 1-continued

| compound | structural formula | NMR | MS |
|---|---|---|---|
| I-6 | | ¹H-NMR (400 MHz, CDCl₃) δ: 7.00-7.09 (2H, m), 7.22 (1H, dd, J = 5.0, 7.8 Hz), 7.35-7.44 (1H, m), 7.65 (1H, dd, J = 2.3, 8.7 Hz), 7.71 (1H, d, J = 8.7 Hz), 7.81 (1H, dd, J = 1.8, 8.7 Hz), 8.22 (1H, dd, J = 1.8, 5.1 Hz), 8.55 (1H, d, J = 2.3 Hz). | ESI-MS m/z: 353 [M + H]⁺. |
| I-7 | | ¹H-NMR (400 MHz, CDCl₃) δ: 7.06-7.27 (4H, m), 7.66 (1H, dd, J = 2.3, 8.7 Hz), 7.72 (1H, d, J = 8.7 Hz), 7.78 (1H, dd, J = 1.8, 8.2 Hz), 8.20 (1H, dd, J = 1.8, 5.1 Hz), 8.56 (1H, d, J = 2.3 Hz). | ESI-MS m/z: 353 [M + H]⁺. |
| I-8 | | ¹H-NMR (400 MHz, CDCl₃) δ: 6.90-7.15 (2H, m), 7.20 (1H, dd, J = 5.1, 8.3 Hz), 7.41 (1H, dt, J = 6.4, 8.3 Hz), 7.65 (1H, dd, J = 2.3, 8.3 Hz), 7.71 (1H, d, J = 8.3 Hz), 7.76 (1H, dd, J = 1.4, 7.3 Hz), 8.19 (1H, dd, J = 1.8, 5.0 Hz), 8.55 (1H, d, J = 2.3 Hz). | ESI-MS m/z: 353 [M + H]⁺. |

TABLE 2

| compound | structural formula | NMR | MS |
|---|---|---|---|
| I-9 | | ¹H-NMR (400 MHz, CDCl₃) δ: 7.19-7.30 (4H, m), 7.66 (1H, dd, J = 2.3, 8.7 Hz), 7.72 (1H, d, J = 8.7 Hz), 7.79 (1H, dd, J = 1.8, 7.3 Hz), 8.21 (1H, dd, J = 1.8, 5.1 Hz), 8.57 (1H, d, J = 2.3 Hz). | ESI-MS m/z: 353 [M + H]⁺. |
| I-10 | | ¹H-NMR (400 MHz, CDCl₃) δ: 3.75 (3H, s), 6.77-6.85 (2H, m), 7.20 (1H, dd, J = 4.5, 7.3 Hz), 7.34 (1H, dd, J = 6.9, 8.2 Hz), 7.61 (1H, dd, J = 2.7, 8.3 Hz), 7.64 (1H, d, J = 8.2 Hz), 7.72 (1H, dd, J = 1.8, 7.3 Hz), 8.19 (1H, dd, J = 1.8, 4.6 Hz), 8.51 (1H, d, J = 2.3 Hz). | ESI-MS m/z: 365 [M + H]⁺. |

TABLE 2-continued

| compound | structural formula | NMR | MS |
| --- | --- | --- | --- |
| I-11 | | ¹H-NMR (400 MHz, CDCl₃) δ: 3.69 (3H, s), 6.89 (1H, dd, J = 4.1, 8.7 Hz), 7.04-7.12 (2H, m), 7.20 (1H, dd, J = 5.0, 7.3 Hz), 7.62 (1H, dd, J = 1.8, 7.8 Hz), 7.70 (1H, d, J = 8.2 Hz), 7.74 (1H, dd, J = 1.8, 7.3 Hz), 8.18 (1H, dd, J = 2.3. 5.0 Hz), 8.52 (1H, d, J = 2.3 Hz). | ESI-MS m/z: 365 [M + H]⁺. |
| I-12 | | ¹H-NMR (400 MHz, CDCl₃) δ: 3.70 (3H, s), 6.69 (1H, dd, J = 2.3, 10.9 Hz), 6.77 (1H, dd, J = 2.3, 8.3 Hz), 7.19 (1H, dd, J = 5.1, 7.1 Hz), 7.14-7.28 (1H, m), 7.61 (1H, dd, J = 2.8, 8.2 Hz), 7.70 (1H, d, J = 7.7 Hz), 7.72 (1H, dd, J = 1.8, 7.4 Hz), 8.17 (1H, dd, J = 1.8, 4.6 Hz), 8.50 (1H, d, J = 2.3 Hz). | ESI-MS m/z: 365 [M + H]⁺. |
| I-13 | | ¹H-NMR (400 MHz, CDCl₃) δ: 3.82 (3H, d, J = 2.3 Hz), 7.18-7.23 (4H, m), 7.63 (1H, dd, J = 2.8, 8.2 Hz), 7.70 (1H, d, J = 7.2 Hz), 7.75 (1H, dd, J = 2.3, 7.3 Hz), 8.18 (1H, dd, J = 1.9, 4.6 Hz), 8.54 (1H, d, J = 2.3 Hz). | ESI-MS m/z: 365 [M + H]⁺. |
| I-14 | | ¹H-NMR (400 MHz, CDCl₃) δ: 2.39 (3H, s), 7.20 (1H, dd, J = 5.0, 7.3 Hz), 7.24-7.28 (2H, m), 7.34 (1H, d, J = 8.2 Hz), 7.38-7.44 (1H, m), 7.64-7.68 (2H, m), 7.71 (1H, dd, J = 1.8, 7.3 Hz), 8.19 (1H, dd, J = 1.8, 5.0 Hz), 8.55-8.57 (1H, m). | ESI-MS m/z: 363 [M + H]⁺. |
| I-15 | | ¹H-NMR (400 MHz, CDCl₃) δ: 7.23-7.26 (1H, m), 7.48-7.52 (1H, m), 7.58-7.64 (2H, m), 7.71 (1H, d, J = 8.7 Hz), 7.75 (1H, d, J = 7.3 Hz), 7.80 (1H, dd, J = 1.8, 7.3 Hz), 8.09 (1H, d, J = 8.2 Hz), 8.17 (1H, dd, J = 1.8, 5.0 Hz), 8.49 (1H, d, J = 2.3 Hz). | ESI-MS m/z: 362 [M + H]⁺. |

TABLE 2-continued

| compound | structural formula | NMR | MS |
|---|---|---|---|
| I-16 | | $^1$H-NMR (400 MHz, CDCl$_3$) δ: 1.13 (3H, t, J = 7.6 Hz), 2.50-2.63 (2H, m), 7.18-7.23 (2H, m), 7.27-7.31 (1H, m), 7.34-7.41 (2H, m), 7.58 (1H, dd, J = 1.8, 8.2 Hz), 7.66-7.70 (2H, m), 8.17 (1H, dd, J = 1.8, 5.0 Hz), 8.49 (1H, d, J = 2.7 Hz). | ESI-MS m/z: 345 [M + H]$^+$. |

TABLE 3

| compound | structural formula | NMR | MS |
|---|---|---|---|
| I-17 | | $^1$H-NMR (400 MHz, CDCl$_3$) δ: 1.22 (3H, t, J = 6.9 Hz), 4.00 (2H, q, J = 6.9 Hz), 6.96 (1H, d, J = 8.2 Hz), 7.04 (1H, dd, J = 7.3, 8.2 Hz), 7.19 (1H, dd, J = 4.6, 7.3 Hz), 7.31 (1H, dd, J = 1.8, 7.3 Hz), 7.35-7.40 (1H, m), 7.62 (1H, dd, J = 2.3, 8.7 Hz), 7.68 (1H, d, J = 8.7 Hz), 7.76 (1H, dd, J = 2.3, 7.3 Hz), 8.16 (1H, dd, J = 1.8, 4.8 Hz), 8.52 (1H, d, J = 2.3 Hz). | ESI-MS m/z: 361 [M + H]$^+$. |
| I-18 | | $^1$H-NMR (400 MHz, CDCl$_3$) δ: 5.56 (1H, s), 6.96 (1H, d, J = 7.8 Hz), 7.03-7.08 (1H, m), 7.22-7.26 (1H, m), 7.31 (1H, d, J = 7.8 Hz), 7.64 (1H, dd, J = 1.8, 8.4 Hz), 7.68 (2H, d, J = 8.4 Hz), 7.82 (1H, dd, J = 2.3, 7.3 Hz), 8.20 (1H, dd, J = 1.8, 5.0 Hz), 8.53 (1H, d, J = 2.3 Hz). | ESI-MS m/z: 333 [M + H]$^+$. |
| I-19 | | $^1$H-NMR (400 MHz, CDCl$_3$) δ: 2.42 (3H, s), 7.21 (1H, dd, J = 5.0, 7.3 Hz), 7.34-7.40 (1H, m), 7.49-7.54 (1H, m), 7.59-7.65 (2H, m), 7.69 (1H, d, J = 9.6 Hz), 7.72 (1H, dd, J = 1.8, 7.3 Hz), 7.76-7.80 (1H, m), 8.13 (1H, dd, J = 1.8, 5.0 Hz), 8.47 (1H, d, J = 2.3 Hz). | ESI-MS m/z: 359 [M + H]$^+$. |
| I-20 | | $^1$H-NMR (400 MHz, CDCl$_3$) δ: 3.38 (3H, s), 7.21 (1H, dd, J = 5.0, 7.3 Hz), 7.38 (1H, dd, J = 1.0, 7.6 Hz), 7.50 (1H, ddd, J = 1.3, 7.6, 9.0 Hz), 7.61-7.73 (4H, m), 8.02 (1H, dd, J = 1.3, 7.6 Hz), 8.16 (1H, dd, J = 2.3, 5.0 Hz), 8.49 (1H, d, J = 2.3 Hz). | ESI-MS m/z: 375 [M + H]$^+$. |

TABLE 3-continued

| compound | structural formula | NMR | MS |
|---|---|---|---|
| I-21 | | $^1$H-NMR (400 MHz, CDCl$_3$) δ: 7.21 (1H, dd, J = 4.8, 7.3 Hz), 7.35-7.51 (4H, m), 7.62 (1H, dd, J = 2.3, 8.7 Hz), 7.71 (1H, d, J = 8.7 Hz), 7.74 (1H, dd, J = 1.8, 7.3 Hz), 8.20 (1H, dd, J = 1.8, 4.8 Hz), 8.52 (1H, d, J = 2.3 Hz). | ESI-MS m/z: 401 [M + H]$^+$. |
| I-22 | | $^1$H-NMR (400 MHz, CDCl$_3$) δ: 1.64 (1H, t, J = 5.5 Hz), 4.62 (2H, t, J =5.5 Hz), 7.21 (1H, dd, J = 5.5, 6.7 Hz), 7.28-7.32 (1H, m), 7.38-7.43 (1H, m), 7.45-7.50 (1H, m), 7.59-7.63 (2H, m), 7.69 (1H, d, J = 8.7 Hz), 7.74 (1H, dd, J = 2.3, 7.3 Hz), 8.18 (1H, dd, J = 1.3, 5.0 Hz), 8.50 (1H, d, J = 2.3 Hz). | ESI-MS m/z: 347 [M + H]$^+$. |
| I-23 | | $^1$H-NMR (400 MHz, CDCl$_3$) δ: 3.68 (3H, s), 6.88 (1H, d, J = 8.2 Hz), 7.17 (1H, dd, J = 5.1, 7.8 Hz), 7.28-7.36 (2H, m), 7.61 (1H, dd, J = 2.3, 8.2 Hz), 7.77-7.89 (2H, m), 8.15 (1H, dd, J = 1.8, 5.1 Hz), 8.50 (1H, d, J = 2.8 Hz). | ESI-MS m/z: 381, 383 [M + H]$^+$. |
| I-24 | | $^1$H-NMR (400 MHz, CDCl$_3$) δ: 2.51 (3H, s), 7.20-7.28 (2H, m), 7.58 (1H, dd, J = 1.8, 7.3 Hz), 7.62 (1H, dd, J = 2.3, 8.7 Hz), 7.68 (1H, dd, J = 5.0, 7.3 Hz), 7.71 (1H, d, J = 9.2 Hz), 8.21 (1H, dd, J = 1.8, 5.1 Hz), 8.52 (1H, d, J = 2.8 Hz), 8.58 (1H, dd, J = 1.8, 5.0 Hz). | ESI-MS m/z: 332 [M + H]$^+$. |

TABLE 4

| compound | structural formula | NMR | MS |
|---|---|---|---|
| I-25 | | $^1$H-NMR (400 MHz, CDCl$_3$) δ: 2.30 (3H, s), 7.21-7.30 (2H, m), 7.62 (1H, dd, J = 2.3, 8.7 Hz), 7.66-7.75 (2H, m), 8.22 (1H, dd, J = 1.8, 5.0 Hz), 8.44-8.60 (3H, m). | ESI-MS m/z: 332 [M + H]$^+$. |

TABLE 4-continued

| compound | structural formula | NMR | MS |
| --- | --- | --- | --- |
| I-26 | | ¹H-NMR (400 MHz, CDCl₃) δ: 3.87 (3H, s), 7.02 (1H, dd, J = 5.0, 7.3 Hz), 7.21 (1H, dd, J = 5.0, 7.3 Hz), 7.59-7.68 (2H, m), 7.71 (1H, d, J = 8.7 Hz), 7.77 (1H, dd, J = 1.8, 7.3 Hz), 8.19 (1H, dd, J = 2.3, 5.0 Hz), 8.24 (1H, dd, J = 1.8, 5.0 Hz), 8.53 (1H, d, J = 2.7 Hz). | ESI-MS m/z: 348 [M + H]⁺. |
| I-27 | | ¹H-NMR (400 MHz, CDCl₃) δ: 3.85 (3H, s), 7.23 (1H, dd, J = 4.6, 7.3 Hz), 7.28 (1H, d, J = 4.6 Hz), 7.63 (1H, dd, J = 2.3, 8.2 Hz), 7.72 (1H, d, J = 8.7 Hz), 7.77 (1H, dd, J = 1.8, 7.3 Hz), 8.22 (1H, dd, J = 1.8, 5.0 Hz), 8.38 (1H, d, J = 5.0 Hz), 8.40 (1H, s), 8.53 (1H, d, J = 2.7 Hz). | ESI-MS m/z: 348 [M + H]⁺. |
| I-28 | | ¹H-NMR (400 MHz, CDCl₃) δ: 3.80 (3H, s), 6.91 (1H, d, J = 5.5 Hz), 7.23 (1H, dd, J = 4.6, 7.3 Hz), 7.62 (1H, dd, J = 2.3, 8.2 Hz), 7.71 (1H, d, J = 8.2 Hz), 7.76 (1H, dd, J = 1.8, 7.3 Hz), 8.21 (1H, dd, J = 1.8, 4.6 Hz), 8.45 (1H, s), 8.52 (1H, d, J = 2.3 Hz), 8.56 (1H, d, J = 6.0 Hz). | ESI-MS m/z: 348 [M + H]⁺. |
| I-29 | | ¹H-NMR (400 MHz, CDCl₃) δ: 2.51 (3H, s), 3.84 (3H, s), 6.85 (1H, d, J = 7.3 Hz), 7.19 (1H, dd, J = 5.0, 7.3 Hz), 7.52 (1H, d, J = 7.3 Hz), 7.62 (1H, dd, J = 1.8, 8.7 Hz), 7.70 (1H, d, J = 8.7 Hz), 7.76 (1H, dd, J = 2.3, 7.3 Hz), 8.16 (1H, dd, J = 1.8, 5.0 Hz), 8.53 (1H, d J = 2.7 Hz). | ESI-MS m/z: 362 [M + H]⁺. |
| I-30 | | ¹H-NMR (400 MHz, CDCl₃) δ: 2.32 (3H, s), 3.83 (3H, s), 7.20 (1H, dd, J = 5.0, 7.3 Hz), 7.46 (1H, d, J = 2.3 Hz), 7.63 (1H, dd, J = 2.3, 8.7 Hz), 7.71 (1H, d, J = 8.7 Hz), 7.75 (1H, dd, J = 1.8, 7.3 Hz), 8.03 (1H, dd, J = 0.9, 2.3 Hz), 8.18 (1H, dd, J = 2.3, 5.0 Hz), 8.53 (1H, d, J = 2.7 Hz). | ESI-MS m/z: 362 [M + H]⁺. |

TABLE 4-continued

| compound | structural formula | NMR | MS |
| --- | --- | --- | --- |
| I-31 | | ¹H-NMR (400 MHz, CDCl₃) δ: 3.86 (3H, s), 7.22 (1H, dd, J = 5.0, 7.3 Hz), 7.62-7.67 (2H, m), 7.73 (1H, d, J = 8.2 Hz), 7.76 (1H, dd, J = 1.8, 7.3 Hz), 8.17 (1H, d, J = 2.7 Hz), 8.20 (1H, dd, J = 1.8, 5.0 Hz), 8.54 (1H, d, J = 2.7 Hz). | ESI-MS m/z: 382, 384 [M + H]⁺. |
| I-32 | | ¹H-NMR (400 MHz, CDCl₃) δ: 3.85 (3H, s), 7.22 (1H, dd, J = 5.0, 7.8 Hz), 7.47 (1H, dd, J = 2.7, 7.8 Hz), 7.63 (1H, dd, J = 2.3, 8.7 Hz), 7.72 (1H, d, J = 8.7 Hz), 7.78 (1H, dd, J = 1.8, 7.3 Hz), 8.07 (1H, d, J = 2.7 Hz), 8.20 (1H, dd, J = 2.3, 5.0 Hz), 8.54 (1H, d, J = 2.7 Hz). | ESI-MS m/z: 366 [M + H]⁺. |

TABLE 5

| compound | structural formula | NMR | MS |
| --- | --- | --- | --- |
| I-33 | | ¹H-NMR (400 MHz, CDCl₃) δ: 7.30 (1H, dd, J = 5.0, 7.3 Hz), 7.47-7.50 (1H, m), 7.55-7.59 (1H, m), 7.67 (1H, d, J = 8.7 Hz), 7.72 (1H, d, J = 7.3 Hz), 7.73-7.77 (1H, m), 7.83 (1H, dd, J = 1.8, 7.3 Hz), 8.09 (1H, dd, J = 1.4, 7.3 Hz), 8.29 (1H, dd, J = 1.8, 5.0 Hz), 8.47 (1H, d, J = 2.3 Hz), 8.54 (1H, d, J = 6.0 Hz), 9.35 (1H, s). | ESI-MS m/z: 368 [M + H]⁺. |
| I-34 | | ¹H-NMR (400 MHz, CDCl₃) δ: 7.29 (1H, dd, J = 5.0, 7.3 Hz), 7.40 (1H, dd, J = 4.1, 8.2 Hz), 7.62-7.70 (3H, m), 7.80 (1H, dd, J = 1.4, 7.3 Hz), 7.88-7.94 (2H, m), 8.20 (1H, dd, J = 1.8, 8.2 Hz), 8.26 (1H, dd, J = 1.8, 5.0 Hz), 8.50-8.53 (1H, m), 8.81 (1H, dd, J = 1.8, 4.1 Hz). | ESI-MS m/z: 368 [M + H]⁺. |
| I-35 | | ¹H-NMR (400 MHz, CDCl₃) δ: 3.27 (2H, t, J = 8.7 Hz), 4.51 (2H, t, J = 8.7 Hz), 6.96 (1H, d, J = 7.3 Hz), 7.19 (1H, dd, J = 4.6, 7.3 Hz), 7.22-7.29 (2H, m), 7.65 (1H, dd, J = 2.3, 8.2 Hz), 7.69 (1H, d, J = 8.2 Hz), 7.88 (1H, dd, J = 1.8, 7.3 Hz), 8.29 (1H, dd, J = 1.8, 5.0 Hz), 8.57 (1H, d, J = 2.3 Hz). | ESI-MS m/z: 359 [M + H]⁺. |

TABLE 5-continued

| compound | structural formula | NMR | MS |
|---|---|---|---|
| I-36 | | $^1$H-NMR (400 MHz, CDCl$_3$) δ: 7.30 (1H, dd, J = 5.0, 7.3 Hz), 7.42 (1H, dd, J = 4.1, 8.7 Hz), 7.54-7.59 (2H, m), 7.66 (1H, d, J = 8.2 Hz), 7.80-7.85 (2H, m), 8.01-8.05 (1H, m), 8.21 (1H, d, J = 8.7 Hz), 8.29 (1H, dd, J = 1.8, 5.0 Hz), 8.46 (1H, d, J = 2.3 Hz), 8.97 (1H, dd, J = 1.4, 4.1 Hz). | ESI-MS m/z: 368 [M + H]$^+$. |
| I-37 | | $^1$H-NMR (400 MHz, CDCl$_3$) δ: 7.29 (1H, dd, J = 5.0, 7.3 Hz), 7.60-7.69 (2H, m), 7.85-7.92 (3H, m), 8.21 (1H, dd, J = 1.8, 8.2 Hz), 8.27 (1H, dd, J = 1.8, 5.0 Hz), 8.51 (1H, d, J = 2.3 Hz), 8.75 (1H, d, J = 1.8 Hz), 8.85 (1H, d, J = 1.8 Hz). | ESI-MS m/z: 369 [M + H]$^+$. |
| I-38 | | $^1$H-NMR (400 MHz, CDCl$_3$) δ: 1.94 (2H, m), 3.35 (2H, t, J = 6.8 Hz), 3.99 (2H, t, J = 5.1 Hz), 6.94 (1H, t, J = 7.4 Hz), 7.09-7.15 (2H, m), 7.19 (1H, dd, J = 5.1, 7.8 Hz), 7.61 (1H, dd, J = 2.8, 7.8 Hz), 7.68-7.82 (2H, m), 8.16 (1H, dd, J = 1.8, 5.0 Hz), 8.52 (1H, d, J = 2.3 Hz). | ESI-MS m/z: 373 [M + H]$^+$. |
| I-39 | | $^1$H-NMR (400 MHz, CDCl$_3$) δ: 7.13 (1H, dd, J = 1.4, 7.4 Hz), 7.17-7.28 (3H, m), 7.69-7.78 (2H, m), 7.89 (1H, dd, J = 1.8, 7.3 Hz), 8.21 (1H, dd, J = 1.8, 5.1 Hz), 8.61 (1H, d, J = 2.3 Hz). | ESI-MS m/z: 397 [M + H]$^+$. |
| I-40 | | $^1$H-NMR (400 MHz, CDCl$_3$) δ: 2.61-2.66 (2H, m), 3.14-3.21 (2H, m), 7.18 (1H, dd, J = 5.0, 7.3 Hz), 7.29 (1H, d, J = 7.3 Hz), 7.53-7.57 (1H, m), 7.64-7.71 (3H, m), 7.76 (1H, dd, J = 2.7, 8.7 Hz), 8.17 (1H, dd, J = 1.8, 5.0 Hz), 8.49 (1H, d, J = 2.7 Hz). | ESI-MS m/z: 371 [M + H]$^+$. |

TABLE 6

| compound | structural formula | NMR | MS |
| --- | --- | --- | --- |
| I-41 | | $^1$H-NMR (400 MHz, CDCl$_3$) δ: 3.27 (2H, t, J = 8.7 Hz), 4.54 (2H, t, J = 8.7 Hz), 6.94-7.03 (2H, m), 7.19 (1H, dd, J = 7.3, 7.8 Hz), 7.67 (1H, dd, J = 2.7, 8.7 Hz), 7.72 (1H, d, J = 8.7 Hz), 7.88 (1H, dd, J = 1.8, 7.8 Hz), 8.15 (1H, dd, J = 1.8, 5.0 Hz), 8.57 (1H, d, J = 2.3 Hz). | ESI-MS m/z: 377 [M + H]$^+$. |
| I-42 | | $^1$H-NMR (400 MHz, CDCl$_3$) δ: 6.64 (1H, dd, J = 1.8, 3.2 Hz), 7.20-7.31 (4H, m), 7.56 (1H, dd, J = 1.8, 8.3 Hz), 7.65 (1H, d, J = 8.2 Hz), 7.72 (1H, d, J = 7.3 Hz), 7.96 (1H, dd, J = 1.8, 7.3 Hz), 8.22 (1H, dd, J = 2.3, 4.6 Hz), 8.33 (1H, br s), 8.48 (1H, d, J = 2.7 Hz). | ESI-MS m/z: 356 [M + H]$^+$. |
| I-43 | | $^1$H-NMR (400 MHz, CDCl$_3$) δ: 7.32 (1H, dd, J = 5.0, 7.3 Hz), 7.58-7.62 (2H, m), 7.67 (1H, d, J = 8.7 Hz), 7.75 (1H, d, J = 5.5 Hz), 7.80 (1H, dd, J = 7.3, 7.3 Hz), 7.86 (1H, dd, J = 1.8, 7.3 Hz), 7.93 (1H, d, J = 8.2 Hz), 8.30 (1H, dd, J = 1.8, 5.0 Hz), 8.46 (1H, d, J = 2.3 Hz), 8.59 (1H, d, J = 6.0 Hz), 9.14 (1H, s). | ESI-MS m/z: 368 [M + H]$^+$. |
| I-44 | | $^1$H-NMR (400 MHz, CDCl$_3$) δ: 6.62 (1H, d, J = 2.3 Hz), 6.91 (1H, dd, J = 1.4, 6.9 Hz), 7.23 (1H, dd, J = 6.9, 9.2 Hz), 7.28 (1H, d, J = 5.0, 7.8 Hz), 7.61-7.74 (3H, m), 7.91 (1H, d, J = 2.3 Hz), 8.02 (1H, dd, J = 1.8, 7.3 Hz), 8.29 (1H, dd, J = 1.8, 4.6 Hz), 8.55 (1H, d, J = 2.3 Hz). | ESI-MS m/z: 357 [M + H]$^+$. |
| I-45 | | $^1$H-NMR (400 MHz, CDCl$_3$) δ: 7.22 (1H, dd, J = 1.3, 7.3 Hz), 7.31 (1H, dd, J = 4.6, 7.3 Hz), 7.64-7.72 (3H, m), 7.87 (1H, dd, J = 1.3, 9.1 Hz), 8.05 (1H, dd, J = 1.8, 7.3 Hz), 8.31-8.34 (2H, m), 8.78 (1H, s). | ESI-MS m/z: 358 [M + H]$^+$. |

TABLE 6-continued

| compound | structural formula | NMR | MS |
|---|---|---|---|
| I-46 | | $^1$H-NMR (400 MHz, DMSO-d$_6$) δ: 7.26 (1H, dd, J = 4.6, 8.2 Hz), 7.41 (1H, dd, J = 5.0, 7.3 Hz), 8.01 (1H, d, J = 7.8 Hz), 8.05 (1H, dd, J = 2.3, 8.7 Hz), 8.26 (1H, dd, J = 1.8, 4.6 Hz), 8.31 (1H, dd, J = 1.8, 7.3 Hz), 8.46-8.49 (1H, m), 8.57 (1H, dd, J = 1.4, 4.6 Hz), 8.79 (1H, d, J = 2.3 Hz). | ESI-MS m/z: 358 [M + H]$^+$. |
| I-47 | | $^1$H-NMR (400 MHz, CDCl$_3$) δ: 4.27 (3H, s), 7.18 (1H, dd, J = 4.6, 8.2 Hz), 7.26-7.31 (1H, m), 7.68-7.71 (1H, m), 7.74 (1H, d, J = 8.7 Hz), 8.22-8.29 (3H, m), 8.59-8.63 (2H, m). | ESI-MS m/z: 372 [M + H]$^+$. |
| I-48 | | $^1$H-NMR (400 MHz, CDCl$_3$) δ: 2.69 (3H, s), 6.65 (1H, d, J = 2.3 Hz), 6.87 (1H, s), 7.30 (1H, dd, J = 5.0, 7.4 Hz), 7.71 (2H, d, J = 1.6 Hz), 8.03 (1H, d, J = 2.3 Hz), 8.10 (1H, dd, J = 1.9, 7.5 Hz), 8.32 (1H, dd, J = 1.9, 5.0 Hz), 8.54-8.60 (1H, m). | ESI-MS m/z: 372 [M + H]$^+$. |

TABLE 7

| compound | structural formula | NMR | MS |
|---|---|---|---|
| I-49 | | $^1$H-NMR (400 MHz, DMSO-d$_6$) δ: 7.00 (1H, dd, J = 1.4, 6.9 Hz), 7.33-7.39 (2H, m), 7.92 (1H, d, J = 9.0 Hz), 7.99 (2H, br s), 8.10 (1H, dd, J = 1.8, 4.9 Hz), 8.16 (1H, dd, J = 1.8, 7.4 Hz), 8.44 (1H, s), 8.73-8.79 (2H, m). | ESI-MS m/z: 357 [M + H]$^+$. |

TABLE 7-continued

| compound | structural formula | NMR | MS |
|---|---|---|---|
| I-50 | | $^1$H-NMR (400 MHz, CDCl$_3$) δ: 6.69 (1H, d, J = 3.7 Hz), 7.17 (1H, dd, J = 4.6, 7.8 Hz), 7.32 (1H, dd, J = 5.0, 7.8 Hz), 7.57 (1H, d, J = 3.7 Hz), 7.66-7.72 (2H, m), 8.00 (1H, dd, J = 1.4, 7.8 Hz), 8.17 (1H, dd, J = 1.8, 7.8 Hz), 8.19 (1H, dd, J = 1.8, 4.6 Hz), 8.33 (1H, dd, J = 1.8, 4.6 Hz), 8.59 (1H, s). | ESI-MS m/z: 357 [M + H]$^+$. |
| I-51 | | $^1$H-NMR (400 MHz, CDCl$_3$) δ: 6.96 (1H, dd, J = 1.3, 6.9 Hz), 7.28 (1H, dd, J = 4.9, 7.4 Hz), 7.32 (1H, dd, J = 6.9, 8.9 Hz), 7.65 (1H, dd, J = 1.3, 8.9 Hz), 7.67-7.70 (2H, m), 7.86 (1H, s), 7.98 (1H, dd, J = 1.9, 7.4 Hz), 8.30 (1H, dd, J = 1.9, 5.0 Hz), 8.51-8.57 (1H, m). | ESI-MS m/z: 391, 393 [M + H]$^+$. |
| I-52 | | $^1$H-NMR (400 MHz, CDCl$_3$) δ: 6.97 (1H, dd, J = 1.2, 6.9 Hz), 7.28 (1H, dd, J = 5.0, 7.4 Hz), 7.33 (1H, dd, J = 6.9, 8.9 Hz), 7.63 (1H, dd, J = 1.3, 8.9 Hz), 7.66-7.72 (2H, m), 7.89 (1H, s), 7.98 (1H, dd, J = 1.9, 7.4 Hz), 8.30 (1H, dd, J = 1.9, 5.0 Hz), 8.51-8.57 (1H, m). | ESI-MS m/z: 435, 437 [M + H]$^+$. |
| I-53 | | $^1$H-NMR (400 MHz, CDCl$_3$) δ: 2.34 (3H, s), 6.85 (1H, dd, J = 1.2, 6.8 Hz), 7.17, (1H, dd, J = 6.8, 8.9 Hz), 7.27 (1H, dd, J = 4.9, 7.4 Hz), 7.54 (1H, dd, J = 1.3, 8.9 Hz), 7.64-7.75 (3H, m), 7.99 (1H, dd, J = 1.9, 7.4 Hz), 8.28 (1H, dd, J = 1.9, 5.0 Hz), 8.54 (1H, d, J = 2.4 Hz). | ESI-MS m/z: 371 [M + H]$^+$. |
| I-54 | | $^1$H-NMR (400 MHz, CDCl$_3$) δ: 7.19 (1H, dd, J = 1.3, 7.1 Hz), 7.31 (1H, dd, J = 5.0, 7.4 Hz), 7.60 (1H, dd, J = 7.0, 8.9 Hz), 7.66 (1H, ddd, J = 0.5, 2.5, 8.6 Hz), 7.71 (1H, dd, J = 0.6, 8.6 Hz), 7.89 (1H, dd, J = 1.3, 8.9 Hz), 7.98 (1H, dd, J = 1.9, 7.4 Hz), 8.20 (1H, s), 8.33 (1H, dd, J = 1.9, 5.0 Hz), 8.54 (1H, d, J = 2.4 Hz). | ESI-MS m/z: 382 [M + H]$^+$. |

TABLE 7-continued

| compound | structural formula | NMR | MS |
| --- | --- | --- | --- |
| I-55 |  | $^1$H-NMR (400 MHz, CDCl$_3$) δ: 1.62-1.79 (4H, m), 1.90-2.00 (2H, m), 2.53-2.64 (1H, m), 3.91 (2H, d, J = 6.4 Hz), 6.98 (1H, d, J = 8.2 Hz), 7.04 (1H, t, J = 7.8 Hz), 7.15-7.20 (1H, m), 7.30-7.40 (2H, m), 7.60 (1H, dd, J = 2.3, 8.7 Hz), 7.67 (1H, d, J = 8.7 Hz), 7.78 (1H, dd, J = 1.8, 7.3 Hz), 8.15 (1H, dd, J = 1.8, 5.0 Hz), 8.50 (1H, d, J = 2.3 Hz). | ESI-MS m/z: 401 [M + H]$^+$. |
| I-56 |  | $^1$H-NMR (400 MHz, CDCl$_3$) δ: 2.40 (1H, t, J = 2.3 Hz), 4.64 (2H, d, J = 2.3 Hz), 7.07-7.14 (2H, m), 7.20 (1H, dd, J = 5.0, 7.3 Hz), 7.34 (1H, dd, J = 1.8, 7.8 Hz), 7.39-7.44 (1H, m), 7.64 (1H, dd, J = 2.3, 8.7 Hz), 7.68 (1H, d, J = 8.7 Hz), 7.76 (1H, dd, J = 1.8, 7.3 Hz), 8.18 (1H, dd, J = 1.8, 5.0 Hz), 8.55 (1H, d, J = 2.3 Hz). | ESI-MS m/z: 371 [M + H]$^+$. |

TABLE 8

| compound | structural formula | NMR | MS |
| --- | --- | --- | --- |
| I-57 |  | $^1$H-NMR (400 MHz, CDCl$_3$) δ: 0.12-0.19 (2H, m), 0.45-0.51 (2H, m), 1.00-1.10 (1H, m), 3.77 (2H, d, J = 6.9 Hz), 6.95 (1H, d, J = 8.2 Hz), 7.02-7.07 (1H, m), 7.19 (1H, dd, J = 5.0, 7.3 Hz), 7.30-7.38 (2H, m), 7.62-7.69 (2H, m), 7.77 (1H, dd, J = 1.8, 7.3 Hz), 8.17 (1H, dd, J = 1.8, 5.0 Hz), 8.55 (1H, d, J = 2.3 Hz). | ESI-MS m/z: 387 [M + H]$^+$. |
| I-58 |  | $^1$H-NMR (400 MHz, CDCl$_3$) δ: 1.54-1.63 (2H, m), 1.85-1.93 (2H, m), 3.43-3.50 (2H, m), 3.69-3.76 (2H, m), 4.44-4.50 (1H, m), 7.00 (1H, d, J = 8.9 Hz), 7.19 (1H, dd, J = 5.0, 7.3 Hz), 7.30-7.39 (2H, m), 7.62 (1H, dd, J = 2.3, 8.7 Hz), 7.68 (2H, d, J = 8.7 Hz), 7.76 (1H, dd, J = 1.8, 7.3 Hz), 8.16 (1H, dd, J = 1.8, 5.0 Hz), 8.50 (1H, d, J = 2.3 Hz). | ESI-MS m/z: 417 [M + H]$^+$. |
| I-59 |  | $^1$H-NMR (400 MHz, CDCl$_3$) δ: 0.61-0.70 (2H, m), 0.77-0.85 (2H, m), 1.71-1.79 (1H, m), 6.57 (1H, d, J = 4.6 Hz), 6.98 (1H, d, J = 7.3 Hz), 7.19-7.28 (2H, m), 7.31-7.36 (1H, m), 7.60 (1H, dd, J = 2.7, 8.7 Hz), 7.68 (1H, d, J = 8.7 Hz), 7.76 (1H, dd, J = 1.8, 7.3 Hz), 8.18 (1H, dd, J = 1.8, 4.6 Hz), 8.51 (1H, d, J = 2.7 Hz). | ESI-MS m/z: 357 [M + H]$^+$. |

TABLE 8-continued

| compound | structural formula | NMR | MS |
| --- | --- | --- | --- |
| I-60 | | $^1$H-NMR (CDCl$_3$) δ: 3.26 (3H, s), 4.36 (2H, s), 7.20 (1H, dd, J = 5.0, 7.3 Hz), 7.30 (1H, dd, J = 1.4, 7.3 Hz), 7.39 (1H, dt, J = 1.4, 7.3 Hz), 7.44 (1H, dt, J = 1.4, 7.3 Hz), 7.55 (1H, d, J = 7.3 Hz), 7.60 (1H, dd, J = 2.3, 7.3 Hz), 7.68 (1H, d, J = 7.3 Hz), 7.73 (1H, dd, J = 2.3, 7.3 Hz), 8.18 (1H, dd, J = 2.3, 5.0 Hz), 8.50 (1H, d, J = 2.3 Hz). | ESI-MS m/z: 361 [M + H]$^+$. |
| I-61 | | $^1$H-NMR (400 MHz, CDCl$_3$) δ: 3.68-3.74 (2H, br s), 6.82 (1H, d, J = 7.8 Hz), 6.84-6.89 (1H, m), 7.15-7.18 (1H, m), 7.20-7.26 (2H, m), 7.63 (1H, dd, J = 2.3, 8.7 Hz), 7.69 (1H, d, J = 8.7 Hz), 7.81 (1H, dd, J = 1.8, 7.3 Hz), 8.19 (1H, dd, J = 2.3, 5.0 Hz), 8.55 (1H, d, J = 2.3 Hz). | ESI-MS m/z: 332 [M + H]$^+$. |
| I-62 | | $^1$H-NMR (400 MHz, CDCl$_3$) δ: 3.24 (3H, s), 3.51 (3H, s), 6.06 (1H, t, J = 6.9 Hz), 6.82 (1H, dd, J = 3.2, 8.7 Hz), 7.15 (1H, dd, J = 2.3 6.9 Hz), 7.20 (1H, dd, J = 1.8, 6.9 Hz), 7.22-7.26 (1H, m), 7.33 (1H, d, J = 9.2 Hz), 7.36-7.39 (1H, m), 7.41-7.48 (2H, m), 7.97 (1H, d, J = 3.2 Hz). | ESI-MS m/z: 360 [M + H]$^+$. |
| I-63 | | $^1$H-NMR (400 MHz, CDCl$_3$) δ: 7.24 (1H, dd, J = 5.0, 7.4 Hz), 7.44 (1H, d, J = 7.3 Hz), 7.76 (1H, dd, J = 1.8, 7.3 Hz), 7.53-7.80 (5H, m), 7.99 (1H, d, J = 7.3 Hz), 8.20 (1H, dd, J = 1.8, 5.1 Hz), 8.49 (1H, d, J = 2.3 Hz), 10.0 (1H, s). | ESI-MS m/z: 345 [M + H]$^+$. |
| I-64 | | $^1$H-NMR (400 MHz, CDCl$_3$) δ: 3.02 (1H, s), 7.20 (1H, dd, J = 5.1, 7.3 Hz), 7.36-7.50 (3H, m), 7.60-7.72 (3H, m), 7.79 (1H, dd, J = 1.8, 7.3 Hz), 8.18 (1H, dd, J = 1.8, 5.1 Hz), 8.58 (1H, d, J = 2.3 Hz). | ESI-MS m/z: 341 [M + H]$^+$. |

TABLE 9

| compound | structural formula | NMR | MS |
| --- | --- | --- | --- |
| I-65 | | ¹H-NMR (400 MHz, CDCl₃) δ: 2.17 (3H, s), 3.71 (3H, s), 6.96 (1H, d, J = 8.2 Hz), 7.02-7.08 (2H, m), 7.18 (1H, dd, J = 1.8, 7.3 Hz), 7.35-7.41 (1H, m), 7.48-7.52 (1H, m), 7.62 (1H, d, J = 8.2 Hz), 8.05 (1H, d, J = 5.0 Hz), 8.41 (1H, d, J = 2.7 Hz). | ESI-MS m/z: 361 [M + H]⁺. |
| I-66 | | ¹H-NMR (400 MHz, CDCl₃) δ: 2.37 (3H, s), 3.67 (3H, s), 6.94 (1H, d, J = 8.7 Hz), 7.05 (1H, t, J = 7.3 Hz), 7.26-7.30 (1H, m), 7.36-7.41 (1H, m), 7.54-7.58 (2H, m), 7.66 (1H, d, J = 8.7 Hz), 7.99 (1H, br d), 8.48 (1H, d, J = 2.3 Hz). | ESI-MS m/z: 361 [M + H]⁺. |
| I-67 | | ¹H-NMR (400 MHz, CDCl₃) δ: 2.45 (3H, s), 3.66 (3H, s), 6.93 (1H, d, J = 8.2 Hz), 7.01-7.08 (2H, m), 7.26-7.29 (1H, m), 7.34-7.39 (1H, m), 7.48-7.52 (1H, dd, J = 2.3, 8.7 Hz), 7.64 (2H, d, J = 7.3 Hz), 8.50 (1H, d, J = 2.3 Hz). | ESI-MS m/z: 361 [M + H]⁺. |
| I-68 | | ¹H-NMR (400 MHz, CDCl₃) δ: 2.54 (3H, s), 3.78 (3H, s), 6.99 (1H, d, J = 8.2 Hz), 7.02-7.11 (2H, m), 7.15 (1H, d, J = 8.2 Hz), 7.30-7.41 (3H, m), 7.69 (1H, dd, J = 2.3, 7.3 Hz), 8.13 (1H, dd, J = 2.3, 4.8 Hz), 8.31 (1H, d, J = 2.7 Hz). | ESI-MS m/z: 293 [M + H]⁺. |
| I-69 | | ¹H-NMR (400 MHz, CDCl₃) δ: 2.15 (3H, s), 3.76 (3H, s), 5.20 (2H, s), 6.98 (1H, d, J = 8.2 Hz), 7.06 (1H, dt, J = 0.9, 7.5 Hz), 7.13 (1H, dd, J = 5.0, 7.3 Hz), 7.32-7.42 (3H, m), 7.48 (1H, dd, J = 2.8, 8.7 Hz), 7.72 (1H, dd, J = 1.8, 7.3 Hz), 8.14 (1H, dd, J = 1.8, 5.0 Hz), 8.41 (1H, d, J = 2.7 Hz). | ESI-MS m/z: 351 [M + H]⁺. |
| I-70 | | ¹H-NMR (400 MHz, CDCl₃) δ: 3.48 (1H, t, J = 5.0 Hz), 3.77 (3H, s), 4.75 (2H, d, J = 5.0 Hz), 6.99 (1H, d, J = 8.2 Hz), 7.07 (1H, t, J = 7.3 Hz), 7.13 (1H, dd, J = 5.0, 7.3 Hz), 7.24-7.28 (1H, m), 7.34 (1H, dd, J = 1.8, 7.8 Hz), 7.40 (1H, dt, J = 1.8, 1.3 Hz), 7.48 (1H, dd, J = 2.6, 8.2 Hz), 7.72 (1H, dd, J = 1.8, 7.3 Hz), 8.14 (1H, dd, J = 1.8, 5.0 Hz), 8.39 (1H, d, J = 2.7 Hz). | ESI-MS m/z: 309 [M + H]⁺. |

TABLE 9-continued

| compound | structural formula | NMR | MS |
|---|---|---|---|
| I-71 | 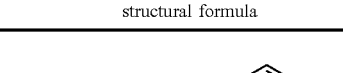 | ¹H-NMR (400 MHz, CDCl₃) δ: 3.68 (3H, s), 6.96 (1H, d, J = 8.2 Hz), 7.07 (1H, dt, J = 0.9, 7.3 Hz), 7.23 (1H, dd, J = 4.6, 7.3 Hz), 7.32 (1H, dd, J = 1.8, 7.3 Hz), 7.36-7.44 (1H, m), 7.57-7.64 (1H, m), 7.78 (1H, dd, J = 1.8, 7.3 Hz), 8.00 (1H, d, J = 8.7 Hz), 8.20 (1H, dd, J = 1.8, 5.0 Hz), 8.56 (1H, d, J = 2.7 Hz), 10.04 (1H, d, J = 0.9 Hz). | ESI-MS m/z: 307 [M + H]⁺. |
| I-72 |  | ¹H-NMR (400 MHz, CDCl₃) δ: 3.73 (3H, s), 6.65 (1H, t, J = 55.4 Hz), 6.98 (1H, d, J = 8.2 Hz), 7.07 (1H, dt, J = 0.9, 7.3 Hz), 7.18 (1H, dd, J = 4.6, 7.3 Hz), 7.33 (1H, dd, J = 1.8, 7.3 Hz), 7.40 (1H, dt, J = 1.8, 8.2 Hz), 7.59 (1H, dd, J = 2.3, 8.7 Hz), 7.65 (1H, d, J = 8.7 Hz), 7.74 (1H, dd, J = 1.8, 7.3 Hz), 8.17 (1H, dd, J = 1.8, 5.0 Hz), 8.45 (1H, d, J = 2.3 Hz). | ESI-MS m/z: 329 [M + H]⁺. |

TABLE 10

| compound | structural formula | NMR | MS |
|---|---|---|---|
| I-73 | 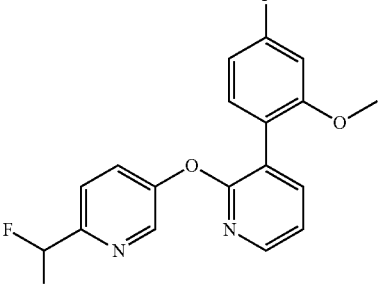 | ¹H-NMR (400 MHz, CDCl₃) δ: 3.72 (3H, s), 6.45 (1H, t, J = 55.4 Hz), 6.70 (1H, dd, J = 2.3, 11.0 Hz), 6.77 (1H, dt, J = 2.7, 8.2 Hz), 7.17 (1H, dd, J = 5.0, 7.3 Hz), 7.27 (1H, dd, J = 6.4, 8.2 Hz), 7.58 (1H, dd, J = 2.3, 8.2 Hz), 7.65 (1H, d, J = 8.2 Hz), 7.70 (1H, dd, J = 2.3, 7.3 Hz), 8.16 (1H, dd, J = 2.3, 5.0 Hz), 8.44 (1H, d, J = 2.7 Hz). | ESI-MS m/z: 347 [M + H]⁺. |
| I-74 | 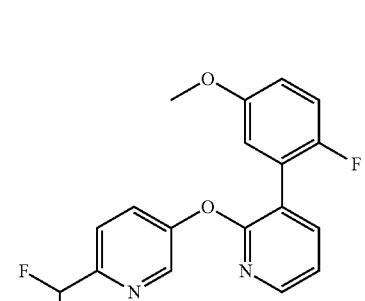 | ¹H-NMR (400 MHz, CDCl₃) δ: 3.83 (3H, s), 6.65 (1H, t, J = 55.4 Hz), 6.86-7.00 (2H, m), 7.09 (1H, t, J = 9.2 Hz), 7.19 (1H, dd, J = 4.6, 7.3 Hz), 7.64 (1H, dd, J = 2.3, 8.2 Hz), 7.67 (1H, d, J = 8.2 Hz), 7.78 (1H, dd, J = 1.8, 7.3 Hz), 8.18 (1H, dd, J = 1.8, 5.0 Hz), 8.49 (1H, d, J = 2.3 Hz). | ESI-MS m/z: 347 [M + H]⁺. |

TABLE 10-continued

| compound | structural formula | NMR | MS |
|---|---|---|---|
| I-75 | | ¹H-NMR (400 MHz, CDCl₃) δ: 3.93 (3H, s), 6.66 (1H, t, J = 55.4 Hz), 7.11-7.25 (4H, m), 7.63 (1H, dd, J = 2.3, 8.2 Hz), 7.69 (1H, d, J = 8.2 Hz), 7.80 (1H, dd, J = 1.8, 7.3 Hz), 8.14 (1H, dd, J = 1.8, 5.0 Hz), 8.50 (1H, d, J = 2.3 Hz). | ESI-MS m/z: 347 [M + H]⁺. |
| I-76 | | ¹H-NMR (400 MHz, CDCl₃) δ: 3.70 (3H, s), 6.65 (1H, t, J = 55.6 Hz), 6.79 (1H, dd, J = 6.6, 12.0 Hz), 7.13-7.21 (2H, m), 7.59 (1H, dd, J = 2.5, 8.5 Hz), 7.66 (1H, d, J = 8.6 Hz), 7.70 (1H, dd, J = 1.9, 7.4 Hz), 8.17 (1H, dd, J = 1.9, 4.9 Hz), 8.44 (1H, d, J = 2.2 Hz). | ESI-MS m/z: 365 [M + H]⁺. |
| I-77 | | ¹H-NMR (400 MHz, CDCl₃) δ: 3.91 (3H, s), 6.66 (1H, t, J = 55.4 Hz), 6.94-7.06 (2H, m), 7.20 (1H, dd, J = 5.0, 7.3 Hz), 7.63 (1H, dd, J = 2.8, 8.7 Hz), 7.68 (1H, d, J = 8.7 Hz), 7.77 (1H, dd, J = 1.8, 7.3 Hz), 8.19 (1H, dd, J = 1.8, 5.0 Hz), 8.49 (1H, d, J = 2.3 Hz). | ESI-MS m/z: 365 [M + H]⁺. |
| I-78 | | ¹H-NMR (400 MHz, CDCl₃) δ: 3.87 (3H, s), 3.96 (3H, s), 6.43 (1H, d, J = 7.8 Hz), 6.65 (1H, t, J = 55.4 Hz), 7.16 (1H, dd, J = 5.0, 7.3 Hz), 7.55-7.63 (2H, m), 7.66 (1H, d, J = 8.7 Hz), 7.75 (1H, dd, J = 1.8, 7.3 Hz), 8.13 (1H, dd, J = 2.3, 5.0 Hz), 8.46 (1H, d, J = 2.3 Hz). | ESI-MS m/z: 360 [M + H]⁺. |
| I-79 | | ¹H-NMR (400 MHz, CDCl₃) δ: 3.71 (3H, s), 3.74 (1H, t, J = 6.8 Hz), 4.12-422 (2H, m), 6.96 (1H, d, J = 7.8 Hz), 7.05 (1H, dt, J = 0.9, 7.3 Hz), 7.17 (1H, dd, J = 5.0, 7.4 Hz), 7.31 (1H, dd, J = 1.8, 7.8 Hz), 7.38 (1H, dt, J = 1.8, 7.8 Hz), 7.58 (1H, dd, J = 2.3, 8.3 Hz), 7.70 (1H, d, J = 8.2 Hz), 7.74 (1H, dd, J = 1.8, 7.3 Hz), 8.14 (1H, dd, J = 1.8, 5.0 Hz), 8.39 (1H, d, J = 2.3 Hz). | ESI-MS m/z: 359 [M + H]⁺. |

TABLE 10-continued

| compound | structural formula | NMR | MS |
|---|---|---|---|
| I-80 | 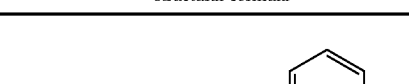 | $^1$H-NMR (400 MHz, CDCl$_3$) δ: 3.69 (3H, s), 5.11 (2H, t, J = 12.3 Hz), 6.96 (1H, d, J = 8.3 Hz), 7.05 (1H, d, J = 7.4 Hz), 7.19 (1H, dd, J = 1.8, 7.3 Hz), 7.31 (1H, dd, J = 1.8, 7.3 Hz), 7.37-3.41 (1H, m), 7.61 (1H, dd, J = 2.7, 8.7 Hz), 7.71-7.76 (2H, m), 8.17 (1H, d, J = 3.2 Hz), 8.41 (1H, d, J = 2.3 Hz). | — |

TABLE 11

| compound | structural formula | NMR | MS |
|---|---|---|---|
| I-81 |  | $^1$H-NMR (400 MHz, CDCl$_3$) δ: 2.02 (3H, t, J = 18.8 Hz), 3.73 (3H, s), 6.97 (1H, d, J = 8.2 Hz), 7.06 (1H, dt, J = 0.9, 7.4 Hz), 7.16 (1H, dd, J = 5.0, 7.3 Hz), 7.32 (1H, dd, J = 1.8, 7.3 Hz), 7.39 (1H, dt, J = 1.9, 7.3 Hz), 7.54 (1H, dd, J = 2.3, 7.3 Hz), 7.65 (1H, d, J = 8.7 Hz), 7.73 (1H, dd, J = 1.8, 7.3 Hz), 8.16 (1H, dd, J = 2.3, 5.1 Hz), 8.43 (1H, d, J = 2.3 Hz). | ESI-MS m/z: 343 [M + H]$^+$. |
| I-82 |  | $^1$H-NMR (400 MHz, CDCl$_3$) δ: 2.02 (3H, t, J = 18.3 Hz), 3.72 (3H, s), 6.70 (1H, dd, J = 2.3, 8.6 Hz), 6.76 (1H, dt, J = 2.3, 8.3 Hz), 7.16 (1H, dd, J = 5.1, 7.8 Hz), 7.27 (1H, dd, J = 6.8, 8.7 Hz), 7.53 (1H, dd, J = 2.7, 8.7 Hz), 7.65 (1H, d, J = 8.7 Hz), 7.70 (1H, dd, J = 2.3, 7.8 Hz), 8.16 (1H, dd, J = 1.8, 5.1 Hz), 8.42 (1H, d, J = 2.3 Hz). | ESI-MS m/z: 361 [M + H]$^+$. |
| I-83 |  | $^1$H-NMR (400 MHz, CDCl$_3$) δ: 2.02 (3H, t, J = 18.7 Hz), 3.71 (3H, s), 6.89 (1H, dd, J = 4.6, 9.6 Hz), 7.02-7.10 (2H, m), 7.16 (1H, dd, J = 5.0, 7.3 Hz), 7.54 (1H, dd, J = 2.7, 8.7 Hz), 7.66 (1H, d, J = 8.7 Hz), 7.72 (1H, dd, J = 1.8, 7.3 Hz), 8.17 (1H, dd, J = 1.8, 5.0 Hz), 8.44 (1H, d, J = 2.3 Hz). | ESI-MS m/z: 361 [M + H]$^+$. |

TABLE 11-continued

| compound | structural formula | NMR | MS |
|---|---|---|---|
| I-84 | | $^1$H-NMR (400 MHz, CDCl$_3$) δ: 2.02 (3H, t, J = 18.6 Hz), 3.68 (3H, s), 3.81 (3H, s), 6.88-6.94 (3H, m), 7.16 (1H, dd, J = 4.9, 7.4 Hz), 7.55 (1H, dd, J = 2.6, 8.6 Hz), 7.65 (1H, dd, J = 0.6, 8.6 Hz), 7.73 (1H, dd, J = 1.9, 7.4 Hz), 8.16 (1H, dd, J = 1.9, 4.9 Hz), 8.44 (1H, dd, J = 0.6, 2.6 Hz). | ESI-MS m/z: 373 [M + H]$^+$. |
| I-85 | | $^1$H-NMR (400 MHz, CDCl$_3$) δ: 2.03 (3H, t, J = 18.8 Hz), 3.91 (3H, s), 6.97 (1H, dd, J = 9.2, 11.0 Hz), 7.02 (1H, dd, J = 6.9, 9.2 Hz), 7.18 (1H, dd, J = 5.0, 7.3 Hz), 7.58 (1H, dd, J = 2.7, 8.7 Hz), 7.68 (1H, d, J = 8.7 Hz), 7.76 (1H, dd, J = 1.8, 7.3 Hz), 8.18 (1H, dd, J = 1.8, 5.0 Hz), 8.46 (1H, d, J = 2.3 Hz). | ESI-MS m/z: 379 [M + H]$^+$. |
| I-86 | | $^1$H-NMR (400 MHz, CDCl$_3$) δ: 2.01 (3H, t, J = 18.6 Hz), 6.60 (1H, t, J = 55.0 Hz), 7.19 (1H, dd, J = 5.0, 7.3 Hz), 7.30 (1H, m), 7.52-7.58 (3H, m), 7.66 (1H, dd, J = 0.5, 8.6 Hz), 7.69 (1H, dd, J = 1.8, 4.9 Hz), 7.77 (1H, dd, J = 2.6, 6.4 Hz), 8.21 (1H, dd, J = 1.9, 5.0 Hz), 8.42 (1H, d, J = 2.7 Hz). | ESI-MS m/z: 363 [M + H]$^+$. |
| I-87 | | $^1$H-NMR (400 MHz, CDCl$_3$) δ: 2.04 (3H, t, J = 18.6 Hz), 7.22 (1H, dd, J = 4.9, 7.4 Hz), 7.29 (1H, dt, J = 1.0, 8.5 Hz), 7.37 (1H, dd, J = 0.5, 7.8 Hz), 7.68-7.74 (3H, m), 7.78 (1H, dd, J = 1.9, 7.4 Hz), 8.23 (1H, dd, J = 1.9, 4.9 Hz), 8.50-8.51 (1H, m). | ESI-MS m/z: 356 [M + H]$^+$. |
| I-88 | | $^1$H-NMR (400 MHz, CDCl$_3$) δ: 2.03 (3H, t, J = 18.8 Hz), 3.89 (3H, s), 7.01 (1H, dd, J = 5.0, 7.3 Hz), 7.17 (1H, dd, J = 4.6, 7.3 Hz), 7.56 (1H, dd, J = 2.7, 8.7 Hz), 7.64 (1H, dd, J = 1.8, 7.3 Hz), 7.67 (1H, d, J = 8.7 Hz), 7.75 (1H, dd, J = 1.8, 7.4 Hz), 8.17 (1H, dd, J = 1.8, 5.0 Hz), 8.23 (1H, dd, J = 1.8, 5.0 Hz), 8.45 (1H, d, J = 2.3 Hz). | ESI-MS m/z: 344 [M + H]$^+$. |

TABLE 12

| compound | structural formula | NMR | MS |
| --- | --- | --- | --- |
| I-89 | | ¹H-NMR (400 MHz, CDCl₃) δ: 2.03 (3H, t, J = 18.6 Hz), 3.86 (3H, s), 7.19 (1H, dd, J = 5.0, 7.3 Hz), 7.29 (1H, d, J = 8.3 Hz), 7.56 (1H, dd, J = 2.7, 8.7 Hz), 7.67 (1H, dd, J = 0.6, 8.7 Hz), 7.75 (1H, dd, J = 1.8, 7.3 Hz), 8.21 (1H, dd, J = 1.8, 5.0 Hz), 8.36 (1H, d, J = 5.0 Hz), 8.39 (1H, s), 8.44 (1H, dd, J = 0.6, 2.7 Hz). | ESI-MS m/z: 344 [M + H]⁺. |
| I-90 | | ¹H-NMR (400 MHz, CDCl₃) δ: 2.02 (3H, t, J = 18.6 Hz), 3.81 (3H, s), 6.90 (1H, d, J = 5.7 Hz), 7.19 (1H, dd, J = 5.0, 7.3 Hz), 7.54 (1H, dd, J = 2.7, 8.7 Hz), 7.66 (1H, dd, J = 0.6, 8.7 Hz), 7.74 (1H, dd, J = 1.9, 7.3 Hz), 8.19 (1H, dd, J = 1.8, 5.0 Hz), 8.43 (1H, dd, J = 0.6, 2.7 Hz), 8.45 (1H, s), 8.55 (1H, d, J = 5.7 Hz). | ESI-MS m/z: 344 [M + H]⁺. |
| I-91 | | ¹H-NMR (400 MHz, CDCl₃) δ: 2.02 (3H, t, J = 18.6 Hz), 2.30 (3H, s), 7.21 (1H, dd, J = 5.0, 7.3 Hz), 7.23 (1H, d, J = 5.0 Hz), 7.54 (1H, dd, J = 2.7, 8.7 Hz), 7.66 (1H, dd, J = 0.7, 8.7 Hz), 7.67 (1H, dd, J = 1.8, 7.3 Hz), 8.21 (1H, dd, J = 1.8, 5.0 Hz), 8.42 (1H, dd, J = 0.6, 2.7 Hz), 8.47 (1H, s), 8.51 (1H, d, J = 5.0 Hz). | ESI-MS m/z: 328 [M + H]⁺. |
| I-92 | | ¹H-NMR (400 MHz, CDCl₃) δ: 2.04 (3H, t, J = 18.6 Hz), 7.23 (1H, dd, J = 4.9, 7.4 Hz), 7.45 (1H, dd, J = 5.0, 6.0 Hz), 7.60 (1H, dd, J = 2.6, 8.6 Hz), 7.71 (1H, dd, J = 0.6, 8.6 Hz), 7.82 (1H, ddd, J = 0.8, 1.9, 7.4 Hz), 8.24 (1H, dd, J = 1.9, 4.9 Hz), 8.49 (1H, d, J = 2.2 Hz), 8.54 (1H, d, J = 4.6 Hz), 8.59 (1H, d, J = 1.6 Hz). | ESI-MS m/z: 332 [M + H]⁺. |
| I-93 | | ¹H-NMR (400 MHz, CDCl₃) δ: 2.04 (3H, t, J = 18.6 Hz), 2.42 (3H, s), 7.21 (1H, dd, J = 4.9, 7.4 Hz), 7.60 (1H, dd, J = 2.6, 8.6 Hz), 7.69-7.71 (1H, m), 7.76-7.78 (1H, m), 7.81 (1H, dd, J = 1.9, 7.4 Hz), 8.17 (1H, dd, J = 1.9, 4.9 Hz), 8.48-8.49 (2H, m), 8.68 (1H, d, J = 1.9 Hz). | ESI-MS m/z: 328 [M + H]⁺. |

TABLE 12-continued

| compound | structural formula | NMR | MS |
|---|---|---|---|
| I-94 | | ¹H-NMR (400 MHz, CDCl₃) δ: 2.02 (3H, t, J = 18.8 Hz), 3.88 (3H, s), 3.96 (3H, s), 6.42 (1H, d, J = 8.7 Hz), 7.14 (1H, dd, J = 5.0, 7.3 Hz), 7.55 (1H, dd, J = 2.7, 8.7 Hz), 7.58 (1H, d, J = 8.7 Hz), 7.66 (1H, d, J = 8.7 Hz), 7.74 (1H, dd, J = 1.8, 7.3 Hz), 8.12 (1H, dd, J = 1.8, 5.0 Hz), 8.47 (1H, d, J = 2.7 Hz). | ESI-MS m/z: 374 [M + H]⁺. |
| I-95 | | ¹H-NMR (400 MHz, CDCl₃) δ: 2.05 (3H, t, J = 18.6 Hz), 4.01 (3H, s), 6.76 (1H, dd, J = 1.5, 7.4 Hz), 7.23 (1H, dd, J = 4.8, 7.6 Hz), 7.61 (1H, dd, J = 2.6, 8.6 Hz), 7.64-7.72 (3H, m), 8.15 (1H, dd, J = 2.0, 4.8 Hz), 8.51-8.53 (2H, m). | ESI-MS m/z: 344 [M + H]⁺. |
| I-96 | | ¹H-NMR (400 MHz, CDCl₃) δ: 2.03 (3H, t, J = 18.6 Hz), 3.70 (3H, s), 3.89 (3H, s), 6.78 (1H, d, J = 8.9 Hz), 7.21 (1H, dd, J = 4.9, 7.4 Hz), 7.32 (1H, d, J = 8.9 Hz), 7.57 (1H, dd, J = 2.6, 8.6 Hz), 7.66 (1H, dd, J = 0.6, 8.6 Hz), 7.94 (1H, dd, J = 2.0, 7.4 Hz), 8.20 (1H, dd, J = 2.0, 4.9 Hz), 8.47 (1H, dd, J = 0.6, 2.6 Hz). | ESI-MS m/z: 374 [M + H]⁺. |

TABLE 13

| compound | structural formula | NMR | MS |
|---|---|---|---|
| I-97 | | ¹H-NMR (400 MHz, CDCl₃) δ: 2.03 (3H, t, J = 18.6 Hz), 7.23 (1H, dd, J = 5.0, 7.4 Hz), 7.59 (1H, dd, J = 2.6, 8.6 Hz), 7.68-7.70 (1H, m), 7.74 (1H, dd, J = 1.9, 7.4 Hz), 8.26 (1H, dd, J = 1.9, 5.0 Hz), 8.45 (1H, s), 8.47-8.48 (1H, m), 8.57 (1H, br s). | ESI-MS m/z: 366, 368 [M + H]⁺. |

TABLE 13-continued

| compound | structural formula | NMR | MS |
| --- | --- | --- | --- |
| I-98 | | ¹H-NMR (400 MHz, CDCl₃) δ: 2.03 (3H, t, J = 19.0 Hz), 4.06 (3H, d, J = 4.6 Hz), 7.19 (1H, dd, J = 4.9, 7.4 Hz), 7.56 (1H, dd, J = 2.6, 8.6 Hz), 7.68-7.73 (2H, m), 8.21 (1H, dd, J = 1.9, 4.9 Hz), 8.29 (1H, br s), 8.45-8.46 (2H, m). | ESI-MS m/z: 362 [M + H]⁺. |
| I-99 | | ¹H-NMR (400 MHz, CDCl₃) δ: 2.03 (3H, t, J = 18.6 Hz), 2.25 (3H, d, J = 2.0 Hz), 7.22 (1H, dd, J = 5.0, 7.4 Hz), 7.55 (1H, dd, J = 2.7, 8.6 Hz), 7.68-7.73 (2H, m), 8.23 (1H, dd, J = 1.9, 5.0 Hz), 8.32 (1H, s), 8.43-8.44 (2H, m). | ESI-MS m/z: 346 [M + H]⁺. |
| I-100 | | ¹H-NMR (400 MHz, CDCl₃) δ: 2.03 (3H, t, J = 18.6 Hz), 3.82 (3H, s), 7.21 (1H, dd, J = 4.9, 7.4 Hz), 7.57 (1H, dd, J = 2.6, 8.6 Hz), 7.68-7.70 (1H, m), 7.76 (1H, dd, J = 1.9, 7.4 Hz), 8.22 (1H, dd, J = 1.9, 4.9 Hz), 8.45-8.46 (2H, m), 8.59 (1H, s). | ESI-MS m/z: 378, 380 [M + H]⁺. |
| I-101 | | ¹H-NMR (400 MHz, CDCl₃) δ: 2.03 (3H, t, J = 18.6 Hz), 2.37 (3H, s), 2.43 (3H, s), 7.21 (1H, dd, J = 4.9, 7.4 Hz), 7.54 (1H, dd, J = 2.6, 8.6 Hz), 7.62 (1H, dd, J = 2.0, 7.4 Hz), 7.68 (1H, dd, J = 0.6, 8.6 Hz), 8.21 (1H, dd, J = 1.9, 4.9 Hz), 8.42 (1H, dd, J = 0.6, 2.6 Hz). | ESI-MS m/z: 348 [M + H]⁺. |
| I-102 | | ¹H-NMR (400 MHz, CDCl₃) δ: 2.03 (3H, t, J = 18.7 Hz), 2.27 (3H, s), 2.41 (3H, s), 7.18 (1H, dd, J = 5.0, 7.3 Hz), 7.56 (1H, dd, J = 5.0, 7.3 Hz), 7.62 (1H, dd, J = 1.8, 7.3 Hz), 7.76 (1H, dd, J = 0.5, 8.6 Hz), 8.17 (1H, dd, J = 1.8, 5.0 Hz), 8.45 (1H, dd, J = 0.5, 2.7 Hz). | ESI-MS m/z: 332 [M + H]⁺. |

TABLE 13-continued

| compound | structural formula | NMR | MS |
|---|---|---|---|
| I-103 | 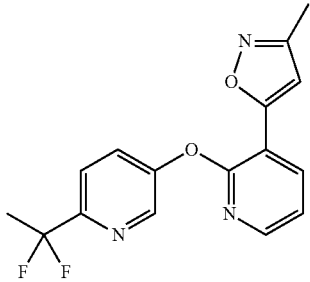 [SMILES: Cc1cc(-c2cccnc2Oc2ccc(C(C)(F)F)nc2)on1] | $^1$H-NMR (400 MHz, CDCl$_3$) δ: 2.06 (3H, t, J = 18.6 Hz), 2.39 (3H, s), 6.76 (1H, s), 7.22 (1H, dd, J = 4.9, 7.7 Hz), 7.65 (1H, dd, J = 2.6, 8.6 Hz), 7.75 (1H, dd, J = 0.6, 8.7 Hz), 8.16 (1H, dd, J = 1.9, 5.0 Hz), 8.39 (1H, dd, J = 1.9, 7.7 Hz), 8.54-8.57 (1H, m). | ESI-MS m/z: 318 [M + H]$^+$. |
| I-104 | 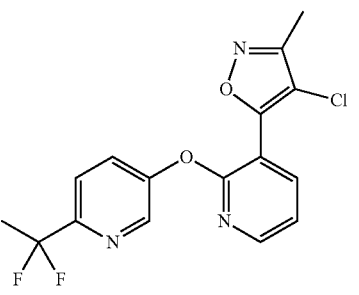 [SMILES: Cc1noc(-c2cccnc2Oc2ccc(C(C)(F)F)nc2)c1Cl] | $^1$H-NMR (400 MHz, CDCl$_3$) δ: 2.05 (3H, t, J = 18.6 Hz), 2.38 (3H, s), 7.23 (1H, dd, J = 4.9, 7.8 Hz), 7.65 (1H, dd, J = 2.6, 8.5 Hz), 7.70-7.75 (1H, m), 8.06 (1H, dd, J = 1.9, 7.8 Hz), 8.26 (1H, dd, J = 1.9, 4.9 Hz), 8.53-8.57 (1H, m). | ESI-MS m/z: 352, 354 [M + H]$^+$. |

TABLE 14

| compound | structural formula | NMR | MS |
|---|---|---|---|
| I-105 | 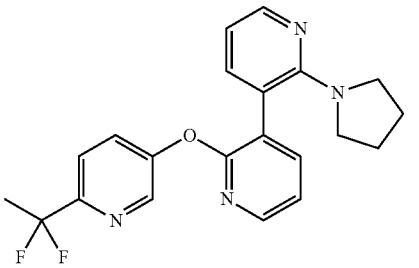 [SMILES: CC(F)(F)c1ccc(Oc2ncccc2-c2cccnc2N2CCCC2)cn1] | $^1$H-NMR (400 MHz, CDCl$_3$) δ: 1.79-1.83 (4H, m), 2.02 (3H, t, J = 18.6 Hz), 3.17-3.20 (4H, m), 6.70 (1H, dd, J = 4.9, 7.3 Hz), 7.14 (1H, dd, J = 4.9, 7.4 Hz), 7.42 (1H, dd, J = 1.9, 7.4 Hz), 7.56 (1H, dd, J = 2.6, 8.6 Hz), 7.67 (1H, dd, J = 0.6, 8.6 Hz), 7.71 (1H, dd, J = 1.9, 7.4 Hz), 8.12 (1H, dd, J = 1.9, 4.9 Hz), 8.22 (1H, dd, J = 1.9, 4.8 Hz), 8.43 (1H, d, J = 2.1 Hz). | ESI-MS m/z: 383 [M + H]$^+$. |
| I-106 | 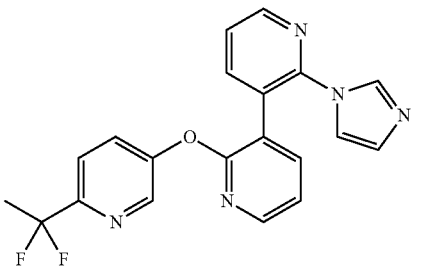 [SMILES: CC(F)(F)c1ccc(Oc2ncccc2-c2cccnc2-n2ccnc2)cn1] | $^1$H-NMR (400 MHz, CDCl$_3$) δ: 2.00 (3H, t, J = 18.6 Hz), 7.05-7.10 (3H, m), 7.21 (1H, dd, J = 5.0, 7.4 Hz), 7.48 (1H, dd, J = 4.8, 7.6 Hz), 7.60 (1H, dd, J = 0.5, 8.6 Hz), 7.72 (1H, t, J = 1.0 Hz), 7.80 (1H, dd, J = 1.9, 7.4 Hz), 7.89 (1H, dd, J = 1.8, 7.6 Hz), 8.11 (1H, dd, J = 0.5, 2.6 Hz), 8.17 (1H, dd, J = 1.9, 4.9 Hz), 8.63 (1H, dd, J = 1.8, 4.8 Hz). | ESI-MS m/z: 380 [M + H]$^+$. |
| I-107 | 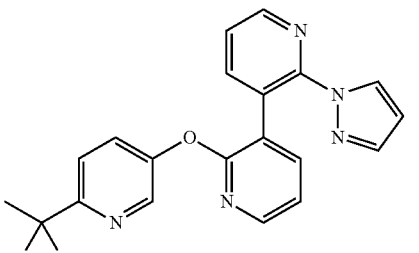 | $^1$H-NMR (400 MHz, CDCl$_3$) δ: 1.98 (3H, t, J = 18.6 Hz), 6.37 (1H, dd, J = 1.7, 2.6 Hz), 7.17-7.22 (2H, m), 7.40 (1H, dd, J = 4.8, 7.6 Hz), 7.48-7.50 (1H, m), 7.55 (1H, dd, J = 0.6, 8.6 Hz), 7.77 (1H, dd, J = 1.9, 7.3 Hz), 7.84 (1H, dd, J = 1.8, 7.6 Hz), 8.06-8.07 (1H, m), 8.11 (1H, dd, J = 1.9, 5.0 Hz), 8.29 (1H, dd, J = 0.7, 2.6 Hz), 8.55 (1H, dd, J = 1.8, 4.8 Hz). | ESI-MS m/z: 380 [M + H]$^+$. |

TABLE 14-continued

| compound | structural formula | NMR | MS |
|---|---|---|---|
| I-108 | 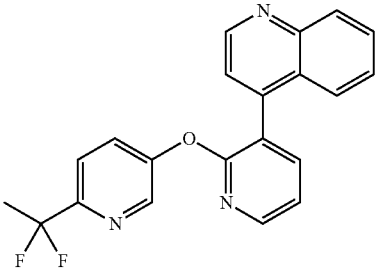 [SMILES: CC(F)(F)c1ccc(Oc2ncccc2-c2ccnc3ccccc23)cn1] | ¹H-NMR (400 MHz, CDCl₃) δ: 2.00 (3H, t, J = 18.6 Hz), 7.28 (1H, dd, J = 4.9, 7.3 Hz), 7.46 (1H, d, J = 4.4 Hz), 7.51 (1H, dd, J = 2.7, 8.6 Hz), 7.54-7.59 (1H, m), 7.62-7.66 (1H, m), 7.70-7.74 (1H, m), 7.76 (1H, ddd, J = 1.5, 7.8, 8.6 Hz), 7.81 (1H, dd, J = 1.9, 7.3 Hz), 8.20-8.25 (1H, m), 8.31 (1H, dd, J = 1.9, 4.9 Hz), 8.37-8.40 (1H, m), 9.03 (1H, d, J = 4.4 Hz). | ESI-MS m/z: 364 [M + H]⁺. |
| I-109 | 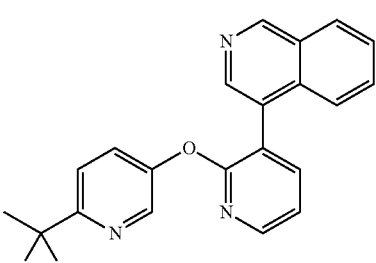 | ¹H-NMR (400 MHz, CDCl₃) δ: 1.92 (3H, t, J = 18.6 Hz), 7.26-7.29 (1H, m), 7.51 (1H, dd, J = 2.7, 8.6 Hz), 7.61-7.73 (4H, m), 7.84 (1H, dd, J = 1.9, 7.4 Hz), 8.06-8.10 (1H, m), 8.29 (1H, dd, J = 1.9, 5.0 Hz), 8.36-8.39 (1H, m), 8.57 (1H, br s), 9.20-9.53 (1H, m). | ESI-MS m/z: 364 [M + H]⁺. |
| I-110 | 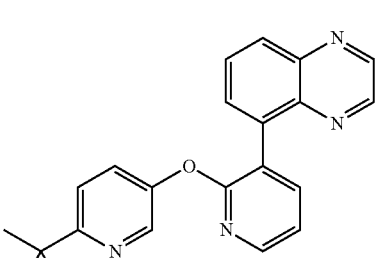 | ¹H-NMR (400 MHz, CDCl₃) δ: 2.05 (3H, t, J = 18.8 Hz), 7.22-7.30 (2H, m), 7.57 (1H, dd, J = 2.3, 8.7 Hz), 7.63 (1H, dd, J = 0.9, 8.7 Hz), 7.83-7.91 (3H, m), 8.20 (1H, dd, J = 2.3, 4.6 Hz), 8.42 (1H, dd, J = 1.8, 5.0 Hz), 8.77 (1H, d, J = 1.8 Hz), 8.85 (1H, d, J = 1.8 Hz). | ESI-MS m/z: 365 [M + H]⁺. |
| I-111 | 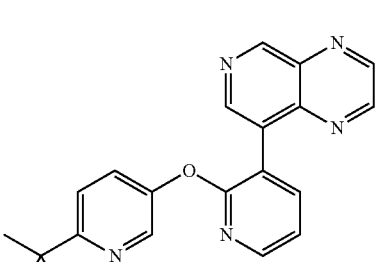 | ¹H-NMR (400 MHz, CDCl₃) δ: 2.01 (3H, t, J = 18.8 Hz), 7.29 (1H, dd, J = 5.0, 7.3 Hz), 7.57 (1H, dd, J = 2.7, 8.7 Hz), 7.65 (1H, dd, J = 0.6, 8.7 Hz), 7.91 (1H, dd, J = 1.8, 7.3 Hz), 8.30 (1H, dd, J = 1.8, 5.0 Hz), 8.43 (1H, dd, J = 0.6, 2.7 Hz), 8.95 (1H, s), 8.96 (1H, d, J = 1.8 Hz), 8.97 (1H, d, J = 1.8 Hz), 9.64 (1H, s). | ESI-MS m/z: 366 [M + H]⁺. |
| I-112 | 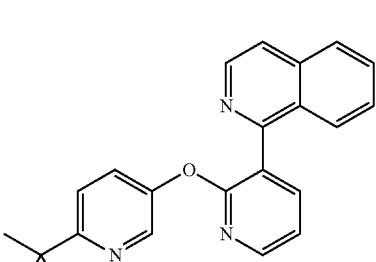 | ¹H-NMR (400 MHz, CDCl₃) δ: 1.99 (3H, t, J = 18.7 Hz), 7.29 (1H, dd, J = 5.0, 7.3 Hz), 7.52 (1H, dd, J = 2.7, 8.7 Hz), 7.56-7.63 (2H, m), 7.70-7.76 (2H, m), 7.83-7.87 (1H, m), 7.92 (1H, br d, J = 8.3 Hz), 7.97 (1H, dd, J = 2.0, 7.3 Hz), 8.31 (1H, dd, J = 1.9, 5.0 Hz), 8.35-8.38 (1H, m), 8.65 (1H, d, J = 5.8 Hz). | ESI-MS m/z: 364 [M + H]⁺. |

TABLE 15

| compound | structural formula | NMR | MS |
| --- | --- | --- | --- |
| I-113 | | ¹H-NMR (400 MHz, CDCl₃) δ: 2.03 (3H, t, J = 18.6 Hz), 7.24 (1H, dd, J = 2.0, 4.5 Hz), 7.50 (1H, t, J = 7.9 Hz), 7.62-7.68 (4H, m), 8.08 (1H, dd, J = 1.9, 7.4 Hz), 8.11 (1H, s), 8.21 (1H, dd, J = 1.9, 4.9 Hz), 8.51 (1H, d, J = 1.8 Hz). | ESI-MS m/z: 354 [M + H]⁺. |
| I-114 | | ¹H-NMR (400 MHz, CDCl₃) δ: 2.04 (3H, t, J = 18.6 Hz), 7.24 (1H, dd, J = 2.6, 7.5 Hz), 7.50 (1H, t, J = 7.8 Hz), 7.59-7.63 (2H, m), 7.69 (1H, d, J = 8.6 Hz), 7.86 (1H, dd, J = 1.1, 8.0 Hz), 7.98 (1H, dd, J = 1.9, 7.4 Hz), 8.11 (1H, s), 8.23 (1H, dd, J = 1.9, 4.9 Hz), 8.51 (1H, d, J = 2.0 Hz). | ESI-MS m/z: 354 [M + H]⁺. |
| I-115 | | ¹H-NMR (400 MHz, CDCl₃) δ: 2.01 (3H, t, J = 18.6 Hz), 6.61 (1H, d, J = 2.3 Hz), 6.91 (1H, dd, J = 1.2, 6.9 Hz), 7.21-7.26 (2H, m), 7.62-7.66 (3H, m), 7.92 (1H, d, J = 2.3 Hz), 8.01 (1H, dd, J = 1.9, 7.4 Hz), 8.29 (1H, dd, J = 1.9, 5.0 Hz), 8.46 (1H, s). | ESI-MS m/z: 353 [M + H]⁺. |
| I-116 | | ¹H-NMR (400 MHz, CDCl₃) δ: 2.02 (3H, t, J = 18.3 Hz), 6.96 (1H, dd, J = 1.2, 6.8 Hz), 7.25 (1H, dd, J = 5.0, 7.3 Hz), 7.30 (1H, dd, J = 6.9, 8.7 Hz), 7.60-7.66 (3H, m), 7.87 (1H, s), 7.97 (1H, dd, J = 1.8, 7.3 Hz), 8.28 (1H, dd, J = 1.8, 5.0 Hz), 8.45 (1H, d, J = 2.7 Hz). | ESI-MS m/z: 387, 389 [M + H]⁺. |
| I-117 | | ¹H-NMR (400 MHz, CDCl₃) δ: 2.48 (3H, d, J = 1.8 Hz), 3.72 (3H, s), 6.97 (1H, d, J = 8.2 Hz), 7.07 (1H, dt, J = 0.9, 7.3 Hz), 7.19 (1H, dd, J = 5.0, 7.8 Hz), 7.32 (1H, dd, J = 1.8, 7.3 Hz), 7.36-7.44 (2H, m), 7.75 (1H, dd, J = 1.8, 7.3 Hz), 8.18 (1H, dd, J = 1.8, 5.0 Hz), 8.30 (1H, d, J = 2.3 Hz). | ESI-MS m/z: 361 [M + H]⁺. |

TABLE 15-continued

| compound | structural formula | NMR | MS |
| --- | --- | --- | --- |
| I-118 | | $^1$H-NMR (400 MHz, CDCl$_3$) δ: 2.49 (3H, d, J = 1.8 Hz), 3.71 (3H, s), 6.70 (1H, dd, J = 2.3, 10.5 Hz), 6.77 (1H, dt, J = 2.3, 8.2 Hz), 7.19 (1H, dd, J = 5.0, 7.3 Hz), 7.26 (1H, t, J = 7.3 Hz), 7.40 (1H, d, J = 2.3 Hz), 7.71 (1H, dd, J = 1.8, 7.3 Hz), 8.17 (1H, dd, J = 2.3, 5.0 Hz), 8.30 (1H, d, J = 2.3 Hz). | ESI-MS m/z: 379 [M + H]$^+$. |
| I-119 | | $^1$H-NMR (400 MHz, CDCl$_3$) δ: 2.51 (3H, s), 3.86 (3H, s), 7.21 (1H, dd, J = 5.0, 7.3 Hz), 7.43 (1H, s), 7.47 (1H, dd, J = 2.7, 8.2 Hz), 7.78 (1H, dd, J = 1.8, 7.8 Hz), 8.07 (1H, d, J = 2.7 Hz), 8.20 (1H, dd, J = 1.8, 5.0 Hz), 8.33 (1H, d, J = 2.3 Hz). | ESI-MS m/z: 380 [M + H]$^+$. |
| I-120 | | $^1$H-NMR (400 MHz, CDCl$_3$) δ: 2.50 (3H, t, J = 1.8 Hz), 3.73 (3H, s), 6.68 (1H, t, J = 54.5 Hz), 6.97 (1H, d, J = 8.2 Hz), 7.06 (1H, dt, J = 0.9, 7.3 Hz), 7.17 (1H, dd, J = 4.6, 7.3 Hz), 7.32 (1H, dd, J = 1.8, 7.3 Hz), 7.35 (1H, d, J = 2.3 Hz), 7.39 (1H, ddd, J = 1.8, 7.3, 8.2 Hz), 7.74 (1H, dd, J = 1.8, 7.3 Hz), 8.17 (1H, dd, J = 1.8, 5.0 Hz), 8.24 (1H, d, J = 2.3 Hz). | ESI-MS m/z: 343 [M + H]$^+$. |

TABLE 16

| compound | structural formula | NMR | MS |
| --- | --- | --- | --- |
| I-121 | | $^1$H-NMR (400 MHz, CDCl$_3$) δ: 2.51 (3H, s), 3.72 (3H, s), 6.69 (1H, t, J = 54.5 Hz), 6.70 (1H, dd, J = 2.3, 11.0 Hz), 6.77 (1H, dt, J = 2.8, 8.2 Hz), 7.17 (1H, dd, J = 5.0, 7.3 Hz), 7.23-7.30 (1H, m), 7.35 (1H, d, J = 2.3 Hz), 7.70 (1H, dd, J = 1.8, 7.3 Hz), 8.17 (1H, dd, J = 1.8, 5.0 Hz), 8.23 (1H, d, J = 2.3 Hz). | ESI-MS m/z: 361 [M + H]$^+$. |

TABLE 16-continued

| compound | structural formula | NMR | MS |
|---|---|---|---|
| I-122 | 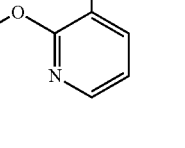 | ¹H-NMR (400 MHz, CDCl₃) δ: 2.51 (3H, t, J = 1.8 Hz), 3.71 (3H, s), 6.69 (1H, t, J = 54.5 Hz), 6.85-6.94 (1H, m), 7.02-7.12 (2H, m), 7.17 (1H, dd, J = 5.0, 7.3 Hz), 7.36 (1H, d, J = 2.3 Hz), 7.72 (1H, dd, J = 1.8, 7.3 Hz), 8.18 (1H, dd, J = 1.8, 5.0 Hz), 8.24 (1H, d, J = 2.3 Hz). | ESI-MS m/z: 361 [M + H]⁺. |
| I-123 | 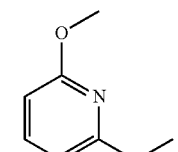 | ¹H-NMR (400 MHz, CDCl₃) δ: 2.51 (3H, s), 3.87 (3H, s), 3.96 (3H, s), 6.42 (1H, d, J = 8.2 Hz), 6.69 (1H, t, J = 54.5 Hz), 7.15 (1H, dd, J = 4.6, 7.3 Hz), 7.36 (1H, d, J = 2.3 Hz), 7.57 (1H, d, J = 7.8 Hz), 7.75 (1H, dd, J = 2.3, 7.8 Hz), 8.14 (1H, dd, J = 1.8, 5.0 Hz), 8.25 (1H, d, J = 2.3 Hz). | ESI-MS m/z: 374 [M + H]⁺. |
| I-124 | 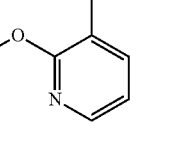 | ¹H-NMR (400 MHz, CDCl₃) δ: 1.31 (3H, t, J = 7.6 Hz), 2.82 (2H, t, J = 7.6 Hz), 3.78 (3H, s), 6.97-6.99 (1H, m), 7.04-7.08 (1H, m), 7.10 (1H, dd, J = 4.9, 7.3 Hz), 7.16 (1H, d, J = 8.5 Hz), 7.34 (1H, dd, J = 1.7, 7.5 Hz), 7.36-7.41 (2H, m), 7.70 (1H, dd, J = 2.0, 7.3 Hz), 8.13 (1H, dd, J = 2.0, 4.9 Hz), 8.34 (1H, d, J = 2.5 Hz). | ESI-MS m/z: 307 [M + H]⁺. |
| I-125 | 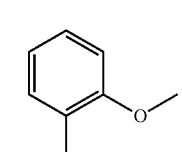 | ¹H-NMR (400 MHz, CDCl₃) δ: 1.31 (3H, t, J = 7.6 Hz), 2.83 (2H, t, J = 7.6 Hz), 3.28 (2H, t, J = 8.7 Hz), 4.57 (2H, t, J = 8.7 Hz), 6.94 (1H, dd, J = 7.5, 7.5 Hz), 7.09 (1H, dd, J = 4.9, 7.4 Hz), 7.17 (1H, d, J = 8.4 Hz), 7.22-7.24 (1H, m), 7.29-7.31 (1H, m), 7.43 (1H, dd, J = 2.8, 8.4 Hz), 7.84 (1H, dd, J = 2.0, 7.4 Hz), 8.11 (1H, dd, J = 2.0, 4.9 Hz), 8.39 (1H, d, J = 2.6 Hz). | ESI-MS m/z: 319 [M + H]⁺. |
| I-126 | 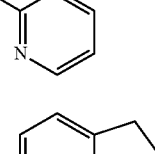 | ¹H-NMR (400 MHz, CDCl₃) δ: 1.31 (3H, t, J = 7.6 Hz), 2.83 (2H, t, J = 7.6 Hz), 3.93 (3H, s), 7.00 (1H, dd, J = 5.0, 7.3 Hz), 7.11 (1H, dd, J = 4.9, 7.4 Hz), 7.18 (1H, d, J = 8.4 Hz), 7.39 (1H, dd, J = 2.8, 8.4 Hz), 7.67 (1H, dd, J = 1.9, 7.3 Hz), 7.72 (1H, dd, J = 1.9, 7.4 Hz), 8.15 (1H, dd, J = 1.9, 4.9 Hz), 8.22 (1H, dd, J = 1.9, 5.0 Hz), 8.34 (1H, d, J = 2.8 Hz). | ESI-MS m/z: 308 [M + H]⁺. |
| I-127 | 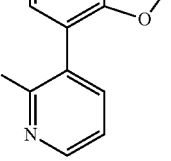 | ¹H-NMR (400 MHz, CDCl₃) δ: 1.31 (3H, t, J = 7.6 Hz), 2.83 (2H, t, J = 7.6 Hz), 3.85 (3H, s), 6.91 (1H, d, J = 5.9 Hz), 7.13 (1H, dd, J = 5.0, 7.4 Hz), 7.18 (1H, d, J = 8.4 Hz), 7.38 (1H, dd, J = 2.8, 8.4 Hz), 7.70 (1H, dd, J = 1.9, 7.4 Hz), 8.18 (1H, dd, J = 1.9, 7.4 Hz), 8.33 (1H, d, J = 2.8 Hz), 8.46 (1H, s), 8.54 (1H, d, J = 5.8 Hz). | ESI-MS m/z: 308 [M + H]⁺. |

TABLE 16-continued

| compound | structural formula | NMR | MS |
|---|---|---|---|
| I-128 | 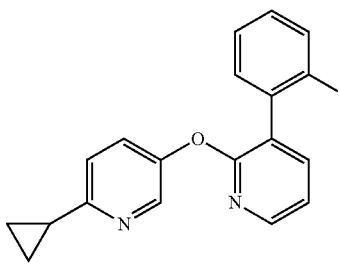 | $^1$H-NMR (400 MHz, CDCl$_3$) δ: 0.93-1.00 (4H, m), 2.00-2.06 (1H, m), 3.78 (3H, s), 6.97-7.00 (1H, m), 7.03-7.12 (3H, m), 7.31-7.34 (2H, m), 7.36-7.40 (1H, m), 7.68 (1H, dd, J = 1.9, 7.3 Hz), 8.12 (1H, dd, J = 1.9, 4.9 Hz), 8.26 (1H, d, J = 2.4 Hz). | ESI-MS m/z: 319 [M + H]$^+$. |

TABLE 17

| compound | structural formula | NMR | MS |
|---|---|---|---|
| I-129 | 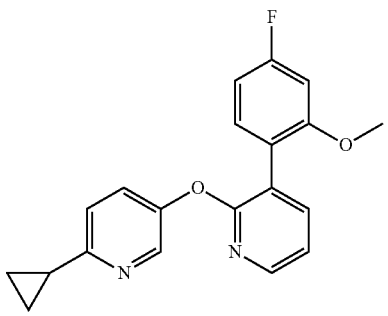 [SMILES: COc1cc(F)ccc1-c1cccnc1Oc1ccc(C2CC2)nc1] | $^1$H-NMR (400 MHz, CDCl$_3$) δ: 0.93-0.99 (4H, m), 2.00-2.06 (1H, m), 3.76 (3H, s), 6.70 (1H, dd, J = 2.4, 10.9 Hz), 6.73-6.78 (1H, m), 7.08 (1H, dd, J = 4.9, 7.3 Hz), 7.11-7.13 (1H, m), 7.27-7.32 (2H, m), 7.65 (1H, dd, J = 1.9, 7.3 Hz), 8.12 (1H, dd, J = 1.9, 4.9 Hz), 8.24 (1H, d, J = 2.6 Hz). | ESI-MS m/z: 337 [M + H]$^+$. |
| I-130 | 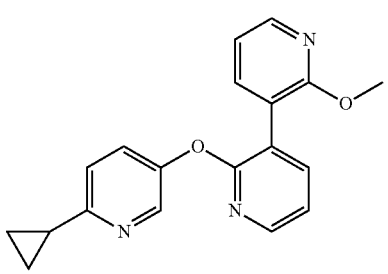 [SMILES: COc1ncccc1-c1cccnc1Oc1ccc(C2CC2)nc1] | $^1$H-NMR (400 MHz, CDCl$_3$) δ: 0.94-0.99 (4H, m), 2.00-2.07 (1H, m), 3.93 (3H, s), 7.00 (1H, dd, J = 5.0, 7.3 Hz), 7.10 (1H, dd, J = 4.9, 7.4 Hz), 7.12-7.14 (1H, m), 7.32 (1H, dd, J = 2.7, 8.5 Hz), 7.67 (1H, dd, J = 1.9, 7.3 Hz), 7.71 (1H, dd, J = 2.0, 7.4 Hz), 8.14 (1H, dd, J = 2.0, 4.9 Hz), 8.22 (1H, dd, J = 1.9, 5.0 Hz), 8.26-8.27 (1H, m). | ESI-MS m/z: 320 [M + H]$^+$. |
| I-131 | 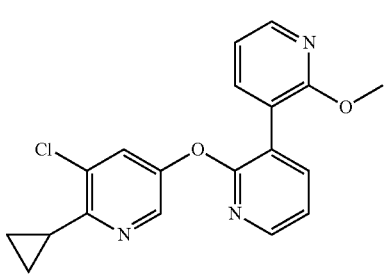 [SMILES: COc1ncccc1-c1cccnc1Oc1cnc(C2CC2)c(Cl)c1] | $^1$H-NMR (400 MHz, CDCl$_3$) δ: 0.98-1.09 (4H, m), 2.44-2.51 (1H, m), 3.92 (3H, s), 7.00 (1H, dd, J = 5.0, 7.3 Hz), 7.14 (1H, dd, J = 4.9, 7.4 Hz), 7.44 (1H, d, J = 2.4 Hz), 7.64 (1H, dd, J = 1.9, 7.2 Hz), 7.72 (1H, dd, J = 1.9, 7.4 Hz), 8.16 (1H, dd, J = 1.9, 4.6 Hz), 8.18 (1H, d, J = 2.4 Hz), 8.22 (1H, dd, J = 1.9, 5.0 Hz). | ESI-MS m/z: 354, 356 [M + H]$^+$. |
| I-132 | 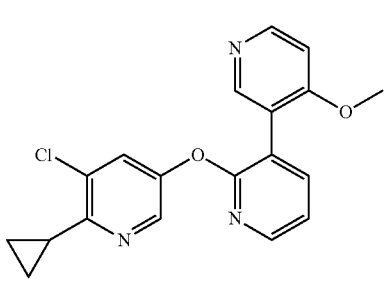 [SMILES: COc1ccncc1-c1cccnc1Oc1cnc(C2CC2)c(Cl)c1] | $^1$H-NMR (400 MHz, CDCl$_3$) δ: 0.98-1.09 (4H, m), 2.44-2.51 (1H, m), 3.84 (3H, s), 6.90 (1H, d, J = 5.8 Hz), 7.15 (1H, dd, J = 4.9, 7.4 Hz), 7.44 (1H, d, J = 2.4 Hz), 7.70 (1H, dd, J = 2.0, 7.4 Hz), 8.16 (1H, d, J = 2.4 Hz), 8.18 (1H, dd, J = 2.0, 5.0 Hz), 8.44 (1H, s), 8.54 (1H, d, J = 5.8 Hz). | ESI-MS m/z: 354, 356 [M + H]$^+$. |

TABLE 17-continued

| compound | structural formula | NMR | MS |
|---|---|---|---|
| I-133 | 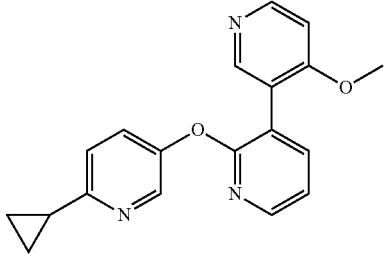 | $^1$H-NMR (400 MHz, CDCl$_3$) δ: 0.94-0.99 (4H, m), 2.01-2.07 (1H, m), 3.85 (3H, s), 6.90 (1H, d, J = 5.8 Hz), 7.10-7.14 (2H, m), 7.32 (1H, dd, J = 2.7, 8.5 Hz), 7.69 (1H, dd, J = 2.0, 7.4 Hz), 8.16 (1H, dd, J = 2.0, 5.0 Hz), 8.25 (1H, d, J = 2.7 Hz), 8.46 (1H, s), 8.54 (1H, d, J = 5.8 Hz). | ESI-MS m/z: 320 [M + H]$^+$. |
| I-134 | 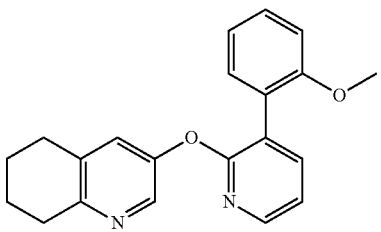 [SMILES: COc1ccccc1-c1cccnc1Oc1cnc2c(c1)CCCC2] | $^1$H-NMR (400 MHz, CDCl$_3$) δ: 1.74-1.95 (4H, m), 2.76 (2H, t, J = 6.4 Hz), 2.90 (2H, t, J = 6.4 Hz), 3.78 (3H, s), 6.98 (1H, d, J = 8.2 Hz), 7.02-7.12 (2H, m), 7.14 (1H, d, J = 2.3 Hz), 7.33 (1H, dd, J = 1.8, 7.8 Hz), 7.37 (1H, ddd, J = 1.8, 7.8, 8.2 Hz), 7.69 (1H, dd, J = 1.8, 7.3 Hz), 8.14 (1H, dd, J = 1.8, 5.0 Hz), 8.19 (1H, d, J = 2.7 Hz). | ESI-MS m/z: 333 [M + H]$^+$. |
| I-135 | 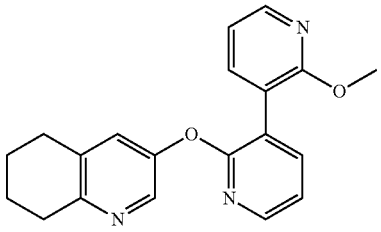 [SMILES: COc1ncccc1-c1cccnc1Oc1cnc2c(c1)CCCC2] | $^1$H-NMR (400 MHz, CDCl$_3$) δ: 1.75-1.94 (4H, m), 2.78 (2H, t, J = 6.4 Hz), 2.91 (2H, t, J = 6.4 Hz), 3.93 (3H, s), 7.00 (1H, dd, J = 5.0, 7.3 Hz), 7.10 (1H, dd, J = 5.0, 7.3 Hz), 7.15 (1H, d, J = 2.7 Hz), 7.67 (1H, dd, J = 1.8, 7.3 Hz), 7.72 (1H, dd, J = 1.8, 7.3 Hz), 8.16 (1H, dd, J = 1.8, 5.0 Hz), 8.19 (1H, d, J = 2.7 Hz), 8.21 (1H, dd, J = 1.8, 5.0 Hz). | ESI-MS m/z: 334 [M + H]$^+$. |
| I-136 | 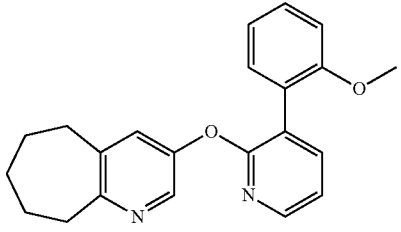 [SMILES: COc1ccccc1-c1cccnc1Oc1cnc2c(c1)CCCCC2] | $^1$H-NMR (400 MHz, CDCl$_3$) δ: 1.60-1.75 (4H, m), 1.80-1.92 (2H, m), 2.70-2.79 (2H, m), 2.97-3.07 (2H, m), 3.77 (3H, s), 6.98 (1H, d, J = 8.2 Hz), 7.05 (1H, dt, J = 0.9, 7.3 Hz), 7.10 (1H, dd, J = 5.0, 7.3 Hz), 7.17 (1H, d, J = 2.3 Hz), 7.33 (1H, dd, J = 1.8, 7.3 Hz), 7.38 (1H, ddd, J = 1.8, 7.3, 8.2 Hz), 7.70 (1H, dd, J = 2.3, 7.3 Hz), 8.11 (1H, d, J = 2.3 Hz), 8.15 (1H, dd, J = 2.3, 5.0 Hz). | ESI-MS m/z: 347 [M + H]$^+$. |

TABLE 18

| compound | structural formula | NMR | MS |
|---|---|---|---|
| I-137 | 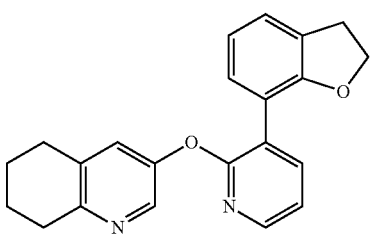 [SMILES: c1cnc(Oc2cnc3c(c2)CCCC3)c(-c2cccc3c2OCC3)c1] | $^1$H-NMR (400 MHz, CDCl$_3$) δ: 1.74-1.96 (4H, m), 2.78 (1H, t, J = 6.0 Hz), 2.91 (2H, t, J = 6.0 Hz), 3.28 (2H, t, J = 8.7 Hz), 4.58 (2H, t, J = 8.7 Hz), 6.94 (1H, t, J = 7.3 Hz), 7.09 (1H, dd, J = 4.6, 7.3 Hz), 7.19 (1H, d, J = 2.3 Hz), 7.23 (1H, dd, J = 1.4, 7.3 Hz), 7.31 (1H, d, J = 7.8 Hz), 7.84 (1H, dd, J = 1.8, 7.3 Hz), 8.12 (1H, dd, J = 1.8, 5.0 Hz), 8.24 (1H, d, J = 2.7 Hz). | ESI-MS m/z: 345 [M + H]$^+$. |

TABLE 18-continued

| compound | structural formula | NMR | MS |
|---|---|---|---|
| I-138 | 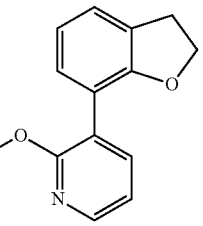 | ¹H-NMR (400 MHz, CDCl₃) δ: 2.11-2.23 (2H, m), 2.90-3.03 (4H, m), 3.28 (2H, t, J = 8.7 Hz), 4.58 (2H, t, J = 8.7 Hz), 6.94 (1H, t, J = 7.3 Hz), 7.09 (1H, dd, J = 5.0, 7.3 Hz), 7.23 (1H, dd, J = 0.9, 7.3 Hz), 7.29-7.35 (2H, m), 7.84 (1H, dd, J = 1.8, 7.3 Hz), 8.11 (1H, dd, J = 1.8, 5.0 Hz), 8.20 (1H, d, J = 2.3 Hz). | ESI-MS m/z: 331 [M + H]⁺. |
| I-139 | 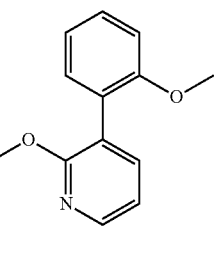 | ¹H-NMR (400 MHz, CDCl₃) δ: 1.74-2.24 (7H, m), 2.69-2.94 (2H, m), 3.76 (3H, s), 5.96 (1H, t, J = 4.1 Hz), 6.97 (1H, d, J = 8.2 Hz), 7.05 (1H, dt, J = 0.9, 7.3 Hz), 7.13 (1H, dd, J = 5.0, 7.3 Hz), 7.23 (1H, d, J = 2.7 Hz), 7.32 (1H, dd, J = 1.8, 7.8 Hz), 7.38 (1H, ddd, J = 1.4, 7.3, 8.2 Hz), 7.72 (1H, dd, J = 1.8, 7.3 Hz), 8.15 (1H, dd, J = 1.8, 5.0 Hz), 8.31 (1H, d, J = 2.7 Hz). | ESI-MS m/z: 391 [M + H]⁺. |
| I-140 | 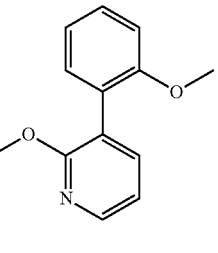 | ¹H-NMR (400 MHz, CDCl₃) δ: 1.71-1.88 (2H, m), 1.96-2.06 (1H, m), 2.20-2.34 (1H, m), 2.72-2.90 (2H, m), 3.70-3.83 (4H, m), 4.66-4.75 (1H, m), 6.98 (1H, d, J = 8.2 Hz), 7.06 (1H, ddd, J = 0.9, 7.3, 7.8 Hz), 7.12 (1H, dd, J = 5.0, 7.3 Hz), 7.20 (1H, d, J = 2.3 Hz), 7.33 (1H, dd, J = 1.8, 7.3 Hz), 7.39 (1H, ddd, J = 1.4, 7.8, 8.2 Hz), 7.71 (1H, dd, J = 1.8, 7.3 Hz), 8.15 (1H, dd, J = 1.8, 5.0 Hz), 8.24 (1H, d, J = 2.3 Hz). | ESI-MS m/z: 349 [M + H]⁺. |
| I-141 | 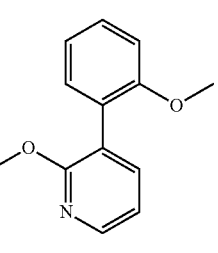 | ¹H-NMR (400 MHz, CDCl₃) δ: 2.19 (2H, quin, J = 6.4 Hz), 2.78 (2H, t, J = 6.0 Hz), 3.01 (2H, t, J = 6.0 Hz), 3.69 (3H, s), 6.96 (1H, d, J = 8.2 Hz), 7.06 (1H, dt, J = 0.9, 7.3 Hz), 7.21 (1H, dd, J = 4.6, 7.3 Hz), 7.31 (1H, dd, J = 1.4, 7.3 Hz), 7.36-7.43 (2H, m), 7.76 (1H, dd, J = 1.8, 7.3 Hz), 8.19 (1H, dd, J = 1.8, 5.0 Hz), 8.47 (1H, d, J = 2.7 Hz). | ESI-MS m/z: 347 [M + H]⁺. |
| I-142 | 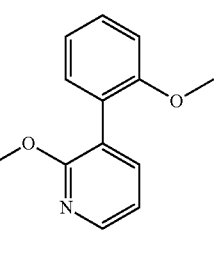 | ¹H-NMR (400 MHz, CDCl₃) δ: 1.96-2.10 (2H, m), 2.28-2.48 (2H, m), 2.81-2.90 (2H, m), 3.74 (3H, s), 6.97 (1H, d, J = 8.2 Hz), 7.06 (1H, dt, J = 0.9, 7.8 Hz), 7.17 (1H, dd, J = 5.0, 7.3 Hz), 7.28 (1H, s), 7.32 (1H, dd, J = 1.8, 7.3 Hz), 7.39 (1H, ddd, J = 1.8, 7.8, 8.2 Hz), 7.73 (1H, dd, J = 1.8, 7.3 Hz), 8.16 (1H, dd, J = 1.8, 5.0 Hz), 8.41 (1H, d, J = 2.3 Hz). | ESI-MS m/z: 369 [M + H]⁺. |

TABLE 18-continued

| compound | structural formula | NMR | MS |
|---|---|---|---|
| I-143 | | $^1$H-NMR (400 MHz, CDCl$_3$) δ: 1.64-1.78 (1H, m), 1.82-2.10 (3H, m), 2.36 (6H, s), 2.64-2.90 (2H, m), 3.76 (3H, s), 3.85 (1H, dd, J = 5.0, 8.2 Hz), 6.97 (1H, d, J = 8.2 Hz), 7.05 (1H, dt, J = 0.9, 7.3 Hz), 7.11 (1H, dd, J = 5.0, 7.3 Hz), 7.16 (1H, d, J = 2.7 Hz), 7.33 (1H, dd, J = 1.4, 7.3 Hz), 7.37 (1H, dt, J = 1.4, 7.3 Hz), 7.77 (1H, dd, J = 2.3, 7.3 Hz), 8.15 (1H, dd, J = 1.8, 5.0 Hz), 8.31 (1H, d, J = 2.7 Hz). | ESI-MS m/z: 376 [M + H]$^+$. |
| I-144 | | $^1$H-NMR (400 MHz, CDCl$_3$) δ: 2.30-2.40 (2H, m), 8.25 (2H, t, J = 8.2 Hz), 3.77 (3H, s), 6.21-6.29 (1H, m), 6.58-6.66 (1H, m), 6.98 (1H, d, J = 8.2 Hz), 7.06 (1H, dt, J = 0.9, 7.3 Hz), 7.11 (1H, dd, J = 5.0, 7.3 Hz), 7.19 (1H, d, J = 1.8 Hz), 7.33 (1H, dd, J = 1.4, 7.3 Hz), 7.39 (1H, ddd, J = 1.8, 7.3, 8.2 Hz), 7.70 (1H, dd, J = 2.3, 7.3 Hz), 8.13-8.30 (2H, m). | ESI-MS m/z: 331 [M + H]$^+$. |

TABLE 19

| compound | structural formula | NMR | MS |
|---|---|---|---|
| I-145 | | $^1$H-NMR (400 MHz, CDCl$_3$) δ: 3.45 (3H, s), 3.72 (3H, s), 4.07 (2H, t, J = 13.3 Hz), 6.96 (1H, d, J = 8.2 Hz), 7.06 (1H, t, J = 7.4 Hz), 7.17 (1H, dd, J = 4.5, 7.4 Hz), 7.31 (1H, dd, J = 1.8, 7.4 Hz), 7.39 (1H, dt, J = 1.8, 7.8 Hz), 7.55 (1H, dd, J = 2.7, 8.7 Hz), 7.67 (1H, d, J = 8.7 Hz), 7.74 (1H, dd, J = 1.8, 7.3 Hz), 8.16 (1H, dd, J = 2.4, 4.6 Hz), 8.45 (1H, d, J = 2.3 Hz). | ESI-MS m/z: 373 [M + H]$^+$. |
| I-146 | | $^1$H-NMR (400 MHz, CDCl$_3$) δ: 2.50 (3H, s), 3.40 (2H, t, J = 14.7 Hz), 3.71 (3H, s), 6.96 (1H, d, J = 8.3 Hz), 7.04 (1H, dt, J = 0.9, 7.3 Hz), 7.15 (1H, dd, J = 4.6, 7.3 Hz), 7.31 (1H, dd, J = 1.8, 7.3 Hz), 7.36-7.40 (1H, m), 7.55 (1H, dd, J = 2.3, 8.3 Hz), 7.67 (1H, d, J = 8.7 Hz), 7.73 (1H, dd, J = 1.8, 7.3 Hz), 8.14 (1H, dd, J = 1.8, 5.0 Hz), 8.44 (1H, d, J = 2.3 Hz). | ESI-MS m/z: 372 [M + H]$^+$. |
| I-147 | | $^1$H-NMR (400 MHz, CDCl$_3$) δ: 2.35 (6H, t, J = 7.3 Hz), 3.17 (2H, t, J = 14.7 Hz), 3.72 (3H, s), 6.96 (1H, d, J = 8.3 Hz), 7.05 (1H, dt, J = 0.9, 7.3 Hz), 7.17 (1H, dd, J = 5.0, 7.3 Hz), 7.31 (1H, dd, J = 1.8, 7.3 Hz), 7.40 (1H, dd, J = 1.8, 7.3 Hz), 7.54 (1H, dd, J = 2.7, 8.7 Hz), 7.67 (1H, d, J = 8.7 Hz), 7.74 (1H, dd, J = 1.8, 7.3 Hz), 8.15 (1H, dd, J = 1.8, 5.0 Hz), 8.44 (1H, d, J = 2.7 Hz). | ESI-MS m/z: 386 [M + H]$^+$. |

TABLE 19-continued

| compound structural formula | | NMR | MS |
|---|---|---|---|
| I-148 | (structure) | ¹H-NMR (400 MHz, CDCl₃) δ: 2.61 (4H, t, J = 4.6 Hz), 3.21 (2H, t, J = 14.7 Hz), 3.61 (4H, t, J = 4.6 Hz), 3.71 (3H, s), 6.97 (1H, d, J = 8.2 Hz), 7.06 (1H, dt, J = 0.9, 7.3 Hz), 7.17 (1H, dd, J = 4.6, 7.3 Hz), 7.32 (1H, dd, J = 1.8, 7.3 Hz), 7.39 (1H, dt, J = 1.8, 7.8 Hz), 7.55 (1H, dd, J = 2.8, 8.7 Hz), 7.64 (1H, d, J = 8.7 Hz), 7.73 (1H, dd, J = 2.3, 7.8 Hz), 8.16 (1H, dd, J = 1.8, 5.0 Hz), 8.45 (1H, d, J = 2.3 Hz). | ESI-MS m/z: 428 [M + H]⁺. |
| I-149 | (structure) | ¹H-NMR (400 MHz, CDCl₃) δ: 0.97 (3H, t, J = 7.3 Hz), 2.38 (3H, s), 2.55 (2H, q, J = 7.3 Hz), 3.20 (2H, t, J = 14.6 Hz), 3.73 (3H, s), 6.97 (1H, d, J = 8.7 Hz), 7.06 (1H, dt, J = 1.8, 7.3 Hz), (1H, dd, J = 5.0, 7.3 Hz), 7.32 (1H, dd, J = 1.9, 7.3 Hz), 7.37-7.41 (1H, m), 7.53 (1H, dd, J = 2.3, 8.7 Hz), 7.66 (1H, d, J = 8.3 Hz), 7.73 (1H, dd, J = 1.8, 7.3 Hz), 8.15 (1H, dd, J = 1.8, 4.8 Hz), 8.44 (1H, d, J = 2.7 Hz). | ESI-MS m/z: 400 [M + H]⁺. |
| I-150 | (structure) | ¹H-NMR (400 MHz, CDCl₃) δ: 2.65 (3H, s), 3.37 (3H, s), 3.55 (2H, t, J = 13.7 Hz), 3.71 (3H, s), 6.96 (1H, d, J = 8.2 Hz), 7.05 (1H, dt, J = 0.9, 7.3 Hz), 7.16 (1H, dd, J = 4.6, 7.3 Hz), 7.32 (1H, dd, J = 1.8, 7.3 Hz), 7.36-7.43 (1H, m), 7.55 (1H, dd, J = 2.8, 8.7 Hz), 7.67 (1H, d, J = 8.7 Hz), 7.73 (1H, dd, J = 1.8, 7.3 Hz), 8.15 (1H, dd, J = 1.8, 5.0 Hz), 8.45 (1H, d, J = 2.3 Hz). | ESI-MS m/z: 402 [M + H]⁺. |
| I-151 | (structure) | ¹H-NMR (400 MHz, CDCl₃) δ: 2.12 (1.5H, s), 2.13 (1.5H, s), 2.99 (1.5H, s), 3.17 (1.5H, s), 3.71 (1.5H, s), 3.72 (1.5H, s), 4.12-4.22 (2H, m), 6.94-7.00 (1H, m), 7.04-7.08 (1H, m), 7.15-7.21 (1H, m), 7.29-7.33 (1H, m), 7.36-7.44 (1H, m), 7.53-7.60 (1H, m), 7.64-7.69 (1H, m), 7.72-7.78 (1H, m), 8.16 (1H, dd, J = 1.8, 5.0 Hz), 8.44 (0.5H, d, J = 2.3 Hz), 8.46 (0.5H, d, J = 2.3 Hz). | ESI-MS m/z: 414 [M + H]⁺. |
| I-152 | (structure) | ¹H-NMR (400 MHz, CDCl₃) δ: 3.02 (3H, s), 3.59 (1.5H, s), 3.71 (1.5H, s), 3.71 (1.5H, s), 3.72 (1.5H, s), 4.04-4.21 (2H, m), 6.97 (1H, d, J = 8.2 Hz), 7.05 (1H, dt, J = 0.9, 7.3 Hz), 7.16 (1H, dd, J = 5.0, 7.3 Hz), 7.31 (1H, dd, J = 1.8, 8.3 Hz), 7.39 (1H, dt, J = 1.8, 8.3 Hz), 7.55 (1H, dd, J = 2.7, 8.7 Hz), 7.60-7.67 (1H, m), 7.73 (1H, dd, J = 1.8, 7.3 Hz), 8.13 (1H, d, J = 5.1 Hz), 8.45 (1H, br s). | ESI-MS m/z: 430 [M + H]⁺. |

TABLE 20

| compound | structural formula | NMR | MS |
|---|---|---|---|
| I-153 | | ¹H-NMR (400 MHz, CDCl₃) δ: 2.03 (3H, s), 3.70 (3H, s), 4.91 (2H, t, J = 13.7 Hz), 6.97 (1H, d, J = 8.3 Hz), 7.06 (1H, dt, J = 0.9, 7.3 Hz), 7.18 (1H, dd, J = 5.0, 7.3 Hz), 7.25 (1H, s), 7.31 (1H, s), 7.32 (1H, dd, J = 1.8, 7.3 Hz), 7.39 (1H, dt, J = 1.9, 7.3 Hz), 7.52 (1H, dd, J = 2.8, 8.7 Hz), 7.57 (1H, dd, J = 1.9, 8.7 Hz), 7.74 (1H, dd, J = 1.8, 7.4 Hz), 8.16 (1H, dd, J = 1.8, 5.0 Hz), 8.48 (1H, d, J = 2.3 Hz). | ESI-MS m/z: 423 [M + H]⁺. |
| I-154 | | ¹H-NMR (400 MHz, CDCl₃) δ: 3.71 (3H, s), 3.76 (1H, t, J = 6.9 Hz), 4.16 (2H, m), 6.69 (1H, dd, J = 2.3, 10.9 Hz), 6.75 (1H, dt, J = 2.3, 8.3 Hz), 7.16 (1H, dd, J = 5.0, 7.3 Hz), 7.25 (1H, dd, J = 6.9, 8.3 Hz), 7.58 (1H, dd, J = 2.7, 8.7 Hz), 7.68-7.72 (2H, m), 8.13 (1H, dd, J = 1.8, 5.1 Hz), 8.38 (1H, d, J = 2.3 Hz). | ESI-MS m/z: 377 [M + H]⁺. |
| I-155 | | ¹H-NMR (400 MHz, CDCl₃) δ: 1.17 (3H, t, J = 7.3 Hz), 3.62 (2H, q, J = 7.3 Hz), 3.71 (3H, s), 4.10 (2H, t, J = 13.3 Hz), 6.69 (1H, dd, J = 2.3, 10.5 Hz), 6.76 (1H, dt, J = 2.3, 8.3 Hz), 7.17 (1H, dd, J = 5.0, 7.3 Hz), 7.26 (1H, dd, J = 6.8, 8.3 Hz), 7.54 (1H, dd, J = 2.8, 8.7 Hz), 7.68 (1H, d, J = 8.3 Hz), 7.69 (1H, dd, J = 1.8, 7.3 Hz), 8.16 (1H, dd, J = 1.8, 5.0 Hz), 8.44 (1H, d, J = 2.3 Hz). | ESI-MS m/z: 405 [M + H]⁺. |
| I-156 | | ¹H-NMR (400 MHz, CDCl₃) δ: 3.69 (3H, s), 5.11 (2H, t, J = 12.3 Hz), 6.69 (1H, dd, J = 2.3, 10.9 Hz), 6.76 (1H, dt, J = 2.3, 8.3 Hz), 7.19 (1H, dd, J = 5.1, 7.3 Hz), 7.24-7.28 (1H, m), 7.61 (1H, dd, J = 2.3, 8.7 Hz), 7.71 (1H, dd, J = 1.8, 7.3 Hz), 7.74 (1H, d, J = 8.7 Hz), 8.17 (1H, dd, J = 1.8, 5.0 Hz), 8.42 (1H, d, J = 2.3 Hz). | — |
| I-157 | | ¹H-NMR (400 MHz, CDCl₃) δ: 3.62 (3H, s), 4.94 (2H, t, J = 13.3 Hz), 6.18 (1H, t, J = 2.3 Hz), 6.62 (1H, dd, J = 2.3, 11.0 Hz), 6.70 (1H, dt, J = 2.3, 8.2 Hz), 7.11 (1H, dd, J = 4.6, 7.3 Hz), 7.19 (1H, dd, J = 6.4, 8.2 Hz), 7.37-7.53 (4H, m), 7.64 (1H, dd, J = 2.3, 7.4 Hz), 8.10 (1H, dd, J = 1.8, 5.0 Hz), 8.41 (1H, d, J = 2.3 Hz). | ESI-MS m/z: 427 [M + H]⁺. |

TABLE 20-continued

| compound | structural formula | NMR | MS |
|---|---|---|---|
| I-158 | | $^1$H-NMR (400 MHz, CDCl$_3$) δ: 3.62 (3H, s), 4.73 (2H, t, J = 13.3 Hz), 6.63 (1H, dd, J = 2.3, 11.0 Hz), 6.69 (1H, dt, J = 2.3, 8.3 Hz), 6.84 (1H, br s), 6.90-6.92 (1H, m), 7.11 (1H, dd, J = 5.0, 7.3 Hz), 7.17-7.20 (1H, m), 7.45-7.51 (2H, m), 7.63 (1H, dd, J = 2.3, 7.3 Hz), 7.91 (1H, br s), 8.09 (1H, dd, J = 1.8, 5.0 Hz), 8.40 (1H, d, J = 2.3 Hz). | ESI-MS m/z: 427 [M + H]$^+$. |
| I-159 | | $^1$H-NMR (400 MHz, CDCl$_3$) δ: 3.34 (3H, s), 3.49-3.53 (2H, m), 3.71 (3H, s), 3.71-3.76 (2H, m), 4.18 (2H, t, J = 13.3 Hz), 6.69 (1H, dd, J = 2.3, 10.5 Hz), 6.76 (1H, dt, J = 2.3, 8.3 Hz), 7.16 (1H, dd, J = 5.0, 7.3 Hz), 7.24-7.29 (1H, m), 7.54 (1H, dd, J = 2.7, 8.7 Hz), 7.68 (1H, d, J = 8.2 Hz), 7.70 (1H, dd, J = 2.3, 7.4 Hz), 8.16 (1H, dd, J = 1.8, 5.0 Hz), 8.44 (1H, d, J = 2.3 Hz). | ESI-MS m/z: 435 [M + H]$^+$. |
| I-160 | | $^1$H-NMR (400 MHz, CDCl$_3$) δ: 2.47 (1H, t, J = 2.3 Hz), 3.71 (3H, s), 4.22 (2H, t, J = 13.3 Hz), 4.26 (2H, d, J = 2.3 Hz), 6.96 (1H, d, J = 8.3 Hz), 7.06 (1H, dt, J = 0.9, 7.3 Hz), 7.18 (1H, dd, J = 5.0, 8.3 Hz), 7.32 (1H, dd, J = 1.8, 7.3 Hz), 7.39 (1H, dt, J = 1.8, 8.2 Hz), 7.56 (1H, dd, J = 2.7, 8.7 Hz), 7.68 (1H, d, J = 8.3 Hz), 7.74 (1H, dd, J = 1.8, 7.3 Hz), 8.16 (1H, dd, J = 1.8, 5.0 Hz), 8.45 (1H, d, J = 2.3 Hz). | ESI-MS m/z: 397 [M + H]$^+$. |

TABLE 21

| compound | structural formula | NMR | MS |
|---|---|---|---|
| I-161 | 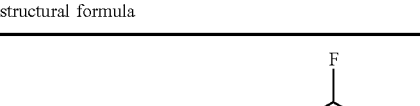 | $^1$H-NMR (400 MHz, CDCl$_3$) δ: 3.44 (3H, s), 3.71 (3H, s), 4.07 (2H, t, J = 13.3 Hz), 6.69 (1H, dd, J = 2.3, 10.5 Hz), 6.76 (1H, dt, J = 2.3, 8.3 Hz), 7.17 (1H, dd, J = 5.0, 7.3 Hz), 7.26 (1H, dd, J = 6.2, 8.7 Hz), 7.54 (1H, dd, J = 2.7, 8.7 Hz), 7.68 (1H, d, J = 7.3 Hz), 7.70 (1H, dd, J = 1.8, 5.3 Hz), 8.16 (1H, dd, J = 1.8, 4.6 Hz), 8.44 (1H, d, J = 2.3 Hz). | ESI-MS m/z: 391 [M + H]$^+$. |

TABLE 21-continued

| compound structural formula | | NMR | MS |
|---|---|---|---|
| I-162 | 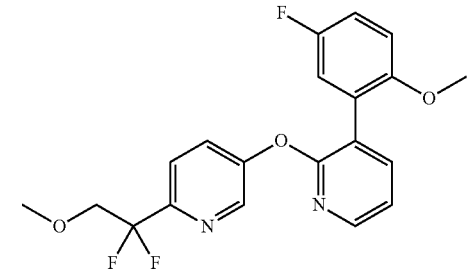 | ¹H-NMR (400 MHz, CDCl₃) δ: 3.44 (3H, s), 3.69 (3H, s), 4.09 (2H, t, J = 13.3 Hz), 6.88 (1H, dd, J = 4.6, 8.6 Hz), 7.05-7.13 (2H, m), 7.17 (1H, dd, J = 4.6, 7.3 Hz), 7.56 (1H, dd, J = 1.8, 8.7 Hz), 7.69 (1H, d, J = 8.7 Hz), 7.72 (1H, dd, J = 1.8, 7.3 Hz), 8.16 (1H, dd, J = 1.8, 5.1 Hz), 8.46 (1H, d, J = 2.3 Hz). | ESI-MS m/z: 391 [M + H]⁺. |
| I-163 | 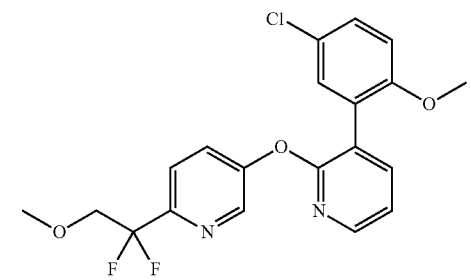 | ¹H-NMR (400 MHz, CDCl₃) δ: 3.45 (3H, s), 3.71 (3H, s), 4.08 (2H, t, J = 13.3 Hz), 6.89 (1H, d, J = 8.7 Hz), 7.18 (1H, dd, J = 4.6, 7.3 Hz), 7.30 (1H, d, J = 2.7 Hz), 7.34 (1H, dd, J = 2.7, 8.7 Hz), 7.57 (1H, dd, J = 2.7, 8.7 Hz), 7.67-7.74 (2H, m), 8.17 (1H, dd, J = 2.3, 5.0 Hz), 8.46 (1H, d, J = 2.3 Hz). | ESI-MS m/z: 407, 409 [M + H]⁺. |
| I-164 | 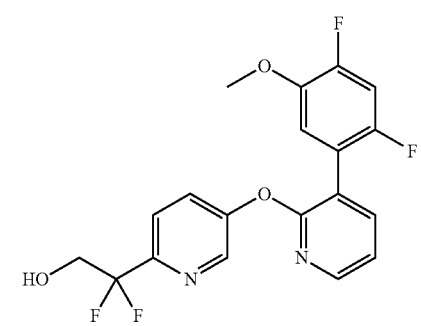 [SMILES: COc1cc(-c2cccnc2Oc2ccc(C(F)(F)CO)nc2)c(F)cc1F] | ¹H-NMR (400 MHz, CDCl₃) δ: 3.33 (1H, t, J = 6.9 Hz), 3.91 (3H, s), 4.20-4.29 (2H, m), 6.95-7.03 (2H, m), 7.20 (1H, dd, J = 5.0, 7.3 Hz), 7.64 (1H, dd, J = 2.7, 8.7 Hz), 7.75-7.78 (2H, m), 8.19 (1H, dd, J = 1.8, 5.0 Hz), 8.44 (1H, d, J = 2.7 Hz). | — |
| I-165 | 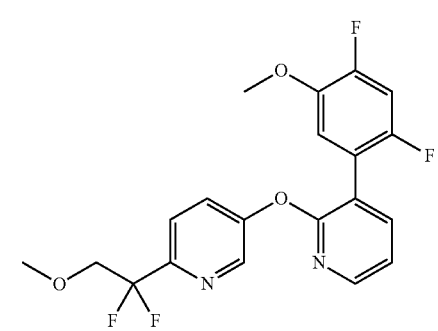 [SMILES: COCC(F)(F)c1ccc(Oc2ncccc2-c2cc(OC)c(F)cc2F)cn1] | ¹H-NMR (400 MHz, CDCl₃) δ: 3.45 (3H, s), 3.90 (3H, s), 4.08 (2H, t, J = 13.3 Hz), 6.94-7.05 (2H, m), 7.19 (1H, dd, J = 4.6, 7.3 Hz), 7.60 (1H, dd, J = 2.7, 8.7 Hz), 7.71 (1H, d, J = 8.7 Hz), 7.76 (1H, dd, J = 1.8, 7.3 Hz), 8.19 (1H, dd, J = 1.8, 5.0 Hz), 8.49 (1H, d, J = 2.7 Hz). | ESI-MS m/z: 409 [M + H]⁺. |
| I-166 | 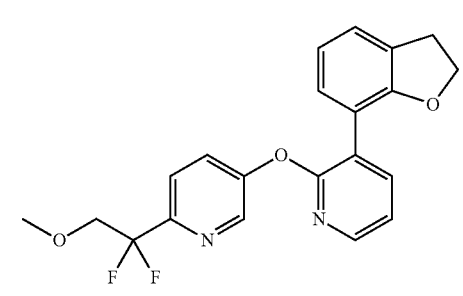 [SMILES: COCC(F)(F)c1ccc(Oc2ncccc2-c2cccc3c2OCC3)cn1] | ¹H-NMR (400 MHz, CDCl₃) δ: 3.26 (2H, t, J = 8.7 Hz), 3.42 (3H, s), 4.09 (2H, t, J = 13.3 Hz), 4.52 (2H, t, J = 8.7 Hz), 6.94 (1H, t, J = 7.3 Hz), 7.16 (1H, dd, J = 5.0, 7.3 Hz), 7.21-7.30 (2H, m), 7.60 (1H, dd, J = 2.3, 8.7 Hz), 7.69 (1H, d, J = 8.7 Hz), 7.87 (1H, dd, J = 1.8, 7.3 Hz), 8.15 (1H, dd, J = 1.8, 5.0 Hz), 8.50 (1H, d, J = 2.3 Hz). | ESI-MS m/z: 385 [M + H]⁺. |

TABLE 21-continued

| compound | structural formula | NMR | MS |
|---|---|---|---|
| I-167 | | ¹H-NMR (400 MHz, CDCl₃) δ: 3.43 (3H, s), 4.05 (2H, t, J = 13.3 Hz), 6.61 (1H, d, J = 2.3 Hz), 6.91 (1H, dd, J = 0.9, 6.7 Hz), 7.19-7.28 (2H, m), 7.60-7.71 (3H, m), 7.91 (1H, d, J = 2.3 Hz), 8.01 (1H, dd, J = 1.8, 7.3 Hz), 8.28 (1H, dd, J = 1.8, 5.1 Hz), 8.48 (1H, d, J = 2.3 Hz). | ESI-MS m/z: 383 [M + H]⁺. |
| I-168 | | ¹H-NMR (400 MHz, CDCl₃) δ: 3.43 (3H, s), 4.05 (2H, t, J = 13.3 Hz), 7.26 (1H, dd, J = 5.0, 7.3 Hz), 7.58 (1H, dd, J = 2.3, 8.7 Hz), 7.67 (1H, d, J = 8.7 Hz), 7.84-7.90 (2H, m), 8.20 (1H, dd, J = 2.3, 7.8 Hz), 8.27 (1H, dd, J = 1.8, 5.0 Hz), 8.44 (1H, d J = 2.7 Hz), 8.69 (1H, d, J = 1.8 Hz), 8.76 (1H, d, J = 1.4 Hz), 8.85 (1H, d J = 1.8 Hz). | ESI-MS m/z: 395 [M + H]⁺. |

TABLE 22

| compound | structural formula | NMR | MS |
|---|---|---|---|
| I-169 | | ¹H-NMR (400 MHz, CDCl₃) δ: 3.43 (3H, s), 4.04 (2H, t, J = 13.3 Hz), 7.24-7.28 (1H, m), 7.40 (1H, dd, J = 4.1, 8.2 Hz), 7.60-7.67 (3H, m), 7.80 (1H, dd, J = 1.4, 6.7 Hz), 7.88-7.92 (2H, m), 8.20 (1H, dd, J = 1.8, 8.2 Hz), 8.25 (1H, dd, J = 1.8, 5.0 Hz), 8.44 (1H, d, J = 1.8 Hz), 8.83 (1H, d, J = 1.8, 4.1 Hz). | ESI-MS m/z: 394 [M + H]⁺. |
| I-170 | | ¹H-NMR (400 MHz, CDCl₃) δ: 3.43 (3H, s), 4.05 (2H, t, J = 13.3 Hz), 7.28 (1H, dd, J = 5.0, 7.3 Hz), 7.58 (1H, dd, J = 2.7, 8.7 Hz), 7.65-7.74 (2H, m), 7.88 (1H, dd, J = 1.8, 7.3 Hz), 8.22 (1H, dd, J = 5.5, 9.2 Hz), 8.29 (1H, dd, J = 1.8, 5.0 Hz), 8.44 (1H, d, J = 2.3 Hz), 8.80 (1H, d, J = 1.8 Hz), 8.85 (1H, d, J = 1.8 Hz). | ESI-MS m/z: 413 [M + H]⁺. |
| I-171 | | ¹H-NMR (400 MHz, CDCl₃) δ: 3.81 (3H, s), 5.35 (2H, s), 6.82 (1H, d, J = 9.2 Hz), 7.00 (1H, d, J = 5.0 Hz), 7.04-7.09 (2H, m), 7.30-7.47 (8H, m), 7.68 (1H, dd, J = 1.8, 6.9 Hz), 7.99 (1H, d, J = 2.7 Hz), 8.12 (1H, dd, J = 1.8, 4.6 Hz). | ESI-MS m/z: 385 [M + H]⁺. |

TABLE 22-continued

| compound | structural formula | NMR | MS |
|---|---|---|---|
| I-172 | | $^1$H-NMR (400 MHz, CDCl$_3$) δ: 3.80 (3H, s), 6.58 (1H, d, J = 10.1 Hz), 7.00 (1H, d, J = 8.3 Hz), 7.04-7.11 (2H, m), 7.25 (1H, d, J = 2.7 Hz), 7.36-7.42 (2H, m), 7.67 (1H, dd, J = 2.3, 7.3 Hz), 8.13 (1H, dd, J = 1.8, 5.0 Hz). | ESI-MS m/z: 295 [M + H]$^+$. |
| I-173 | | $^1$H-NMR (400 MHz, CDCl$_3$) δ: 3.08 (2H, t, J = 6.9 Hz), 3.80 (3H, s), 4.49 (2H, t, J = 7.3 Hz), 6.73 (1H, d, J = 9.2 Hz), 6.99 (1H, d, J = 8.2 Hz), 7.04-7.08 (2H, m), 7.21-7.24 (1H, m), 7.28-7.41 (7H, m), 7.67 (1H, dd, J = 1.8, 7.3 Hz), 7.95 (1H, d, J = 2.7 Hz), 8.11 (1H, dd, J = 2.3, 5.0 Hz). | ESI-MS m/z: 399 [M + H]$^+$. |
| I-174 | | $^1$H-NMR (400 MHz, CDCl$_3$) δ: 3.80 (3H, s), 5.38 (2H, s), 6.81 (1H, d, J = 8.4 Hz), 7.00 (1H, d, J = 8.4 Hz), 7.04-7.10 (2H, m), 7.33-7.44 (4H, m), 7.69 (1H, dd, J = 1.9, 7.3 Hz), 7.79 (1H, d, J = 7.4 Hz), 7.98 (1H, d, J = 2.4 Hz), 8.12 (1H, dd, J = 1.9, 5.0 Hz), 8.56 (1H, s), 8.71 (1H, s). | ESI-MS m/z: 386 [M + H]$^+$. |
| I-175 | | $^1$H-NMR (400 MHz, CDCl$_3$) δ: 3.76 (3H, s), 5.20 (2H, s), 6.95-7.00 (3H, m), 7.06 (1H, t, J = 7.3 Hz), 7.13 (1H, dd, J = 4.6, 7.3 Hz), 7.28-7.55 (7H, m), 7.72 (1H, dd, J = 2.3, 7.3 Hz), 8.15 (1H, dd, J = 2.3, 5.0 Hz), 8.42 (1H, d, J = 2.3 Hz). | ESI-MS m/z: 385 [M + H]$^+$. |
| I-176 | | $^1$H-NMR (400 MHz, CDCl$_3$) δ: 3.95 (3H, s), 5.36 (2H, s), 6.84 (1H, d, J = 8.7 Hz), 7.01 (1H, t, J = 6.1 Hz), 7.10 (1H, t, J = 6.2 Hz), 7.30-7.47 (6H, m), 7.67-7.72 (2H, m), 8.00 (1H, d, J = 2.8 Hz), 8.15 (1H, dd, J = 1.9, 5.1 Hz), 8.23 (1H, dd, J = 1.8, 5.0 Hz). | ESI-MS m/z: 386 [M + H]$^+$. |

TABLE 23

| compound | structural formula | NMR | MS |
|---|---|---|---|
| I-177 | 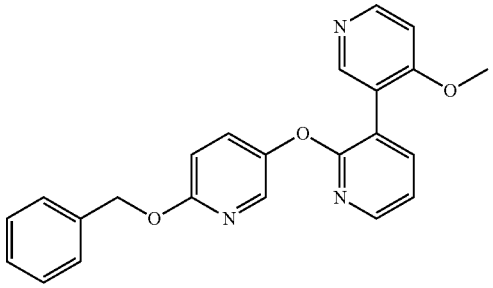 [SMILES: COc1ccccc1-c1cccnc1Oc1ccc(OCc2ccccc2)nc1] | ¹H-NMR (400 MHz, CDCl₃) δ: 3.87 (3H, s), 5.36 (2H, s), 6.83 (1H, d, J = 8.8 Hz), 6.92 (1H, d, J = 5.8 Hz), 7.11 (1H, t, J = 6.1 Hz), 7.30-7.52 (6H, m), 7.68 (1H, dd, J = 2.7, 7.4 Hz), 7.98 (1H, d, J = 2.8 Hz), 8.17 (1H, dd, J = 1.6, 4.9 Hz), 8.47 (1H, s), 8.54 (1H, d, J = 5.6 Hz). | ESI-MS m/z: 386 [M + H]⁺. |
| I-178 | 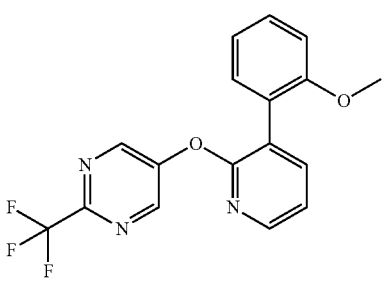 | ¹H-NMR (400 MHz, CDCl₃) δ: 3.72 (3H, s), 6.98 (1H, d, J = 8.2 Hz), 7.09 (1H, dt, J = 0.9, 7.3 Hz), 7.20-7.29 (1H, m), 7.32 (1H, dd, J = 1.8, 7.3 Hz), 7.42 (1H, dt, J = 1.8, 8.2 Hz), 7.78 (1H, dd, J = 1.8, 7.3 Hz), 8.17 (1H, dd, J = 1.8, 4.6 Hz), 8.72 (2H, s). | ESI-MS m/z: 348 [M + H]⁺. |
| I-179 | 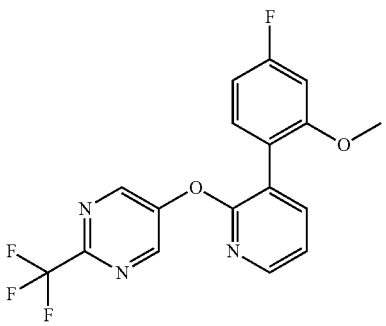 | ¹H-NMR (400 MHz, CDCl₃) δ: 3.72 (3H, s), 6.71 (1H, dd, J = 2.3, 10.5 Hz), 6.79 (1H, dt, J = 2.3, 8.2 Hz), 7.22-7.31 (2H, m), 7.75 (1H, dd, J = 1.8, 7.3 Hz), 8.17 (1H, dd, J = 1.8, 4.6 Hz), 8.73 (2H, s). | ESI-MS m/z: 366 [M + H]⁺. |
| I-180 | 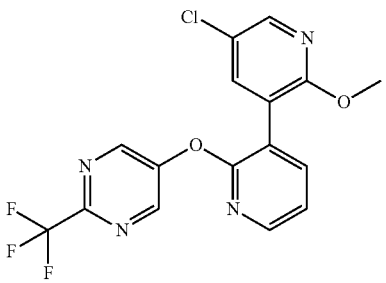 [SMILES: COc1ncc(Cl)cc1-c1cccnc1Oc1cnc(C(F)(F)F)nc1] | ¹H-NMR (400 MHz, CDCl₃) δ: 3.87 (3H, s), 7.23-7.29 (1H, m), 7.64 (1H, d, J = 2.7 Hz), 7.78 (1H, dd, J = 1.8, 7.3 Hz), 8.16-8.23 (2H, m), 8.76 (2H, s). | ESI-MS m/z: 383, 385 [M + H]⁺. |
| I-181 | 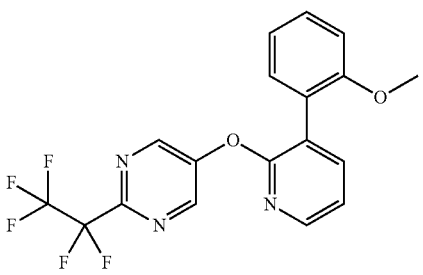 [SMILES: COc1ccccc1-c1cccnc1Oc1cnc(C(F)(F)C(F)(F)F)nc1] | ¹H-NMR (400 MHz, CDCl₃) δ: 3.70 (3H, s), 6.98 (1H, d, J = 8.2 Hz), 7.08 (1H, dt, J = 0.9, 7.3 Hz), 7.23-7.29 (1H, m), 7.32 (1H, dd, J = 1.8, 7.3 Hz), 7.42 (1H, dt, J = 1.8, 8.2 Hz), 7.78 (1H, dd, J = 1.8, 7.3 Hz), 8.18 (1H, dd, J = 1.8, 4.6 Hz), 8.75 (2H, s). | ESI-MS m/z: 398 [M + H]⁺. |

TABLE 23-continued

| compound structural formula | | NMR | MS |
|---|---|---|---|
| I-182 | (structure) | ¹H-NMR (400 MHz, CDCl₃) δ: 0.93 (3H, t, J = 7.3 Hz), 1.53-1.69 (2H, m), 3.14 (3H, s), 3.56 (2H, t, J = 7.8 Hz), 3.83 (3H, s), 7.00 (1H, d, J = 8.2 Hz), 7.05-7.08 (2H, m), 7.34 (1H, dd, J = 1.8, 7.8 Hz), 7.38-7.42 (1H, m), 7.66 (1H, dd, J = 1.8, 7.3 Hz), 8.10 (1H, dd, J = 1.8, 4.6 Hz), 8.18 (2H, s). | ESI-MS m/z: 351 [M + H]⁺. |
| I-183 | (structure) | ¹H-NMR (400 MHz, CDCl₃) δ: 0.93 (3H, t, J = 7.3 Hz), 1.59-1.60 (2H, m), 3.14 (3H, s), 3.57 (2H, t, J = 7.3 Hz), 3.97 (3H, s), 7.00-7.03 (1H, m), 7.06-7.09 (1H, m), 7.66-7.69 (2H, m), 8.12 (1H, dd, J = 1.8, 5.0 Hz), 8.18 (2H, s), 8.23 (1H, dd, J = 1.8, 5.0 Hz). | ESI-MS m/z: 352 [M + H]⁺. |
| I-184 | (structure) | ¹H-NMR (400 MHz, CDCl₃) δ: 1.18 (3H, t, J = 6.8 Hz), 3.13 (3H, s), 3.67 (2H, q, J = 6.8 Hz), 3.81 (3H, s), 6.71-6.79 (2H, m), 7.04-7.08 (1H, m), 7.26-7.30 (1H, m), 7.62 (1H, dd, J = 1.8, 7.3 Hz), 8.10 (1H, dd, J = 1.8, 5.0 Hz), 8.17 (2H, s). | ESI-MS m/z: 355 [M + H]⁺. |

TABLE 24

| compound structural formula | | NMR | MS |
|---|---|---|---|
| I-185 | (structure) | ¹H-NMR (400 MHz, CDCl₃) δ: 3.19 (6H, s), 3.81 (3H, s), 6.71-6.80 (2H, m), 7.04-7.07 (1H, m), 7.28-7.30 (1H, m), 7.62 (1H, dd, J = 1.8, 7.3 Hz), 8.10 (1H, dd, J = 1.8, 5.0 Hz), 8.18 (2H, s). | ESI-MS m/z: 341 [M + H]⁺. |

TABLE 24-continued

| compound | structural formula | NMR | MS |
|---|---|---|---|
| I-186 | | $^1$H-NMR (400 MHz, CDCl$_3$) δ: 1.06 (3H, t, J = 7.3 Hz), 1.78 (2H, sext, J = 7.3 Hz), 3.13 (2H, t, J = 7.3 Hz), 3.77 (3H, s), 6.70-6.80 (2H, m), 7.14 (1H, dd, J = 5.0, 7.3 Hz), 7.27 (1H, dd, J = 6.4, 8.2 Hz), 7.67 (1H, dd, J = 1.8, 7.3 Hz), 8.12 (1H, dd, J = 1.8, 5.0 Hz), 8.39 (2H, s). | ESI-MS m/z: 372 [M + H]$^+$. |
| I-187 | | $^1$H-NMR (400 MHz, CDCl$_3$) δ: 1.44 (3H, t, J = 6.9 Hz), 3.79 (3H, s), 4.41 (2H, q, J = 6.9 Hz), 6.71-6.80 (2H, m), 7.10-7.14 (1H, m), 7.28-7.30 (1H, m), 7.66 (1H, dd, J = 1.8, 7.3 Hz), 8.10 (1H, dd, J = 1.8, 5.0 Hz), 8.35 (2H, s). | ESI-MS m/z: 342 [M + H]$^+$. |
| I-188 | | $^1$H-NMR (400 MHz, CDCl$_3$) δ: 3.21 (3H, s), 3.36 (3H, s), 3.61 (2H, t, J = 6.0 Hz), 3.80-3.82 (5H, m), 6.71-6.79 (2H, m), 7.06 (1H, dd, J = 5.0, 7.3 Hz), 7.28 (1H, dd, J = 6.7, 8.7 Hz), 7.62 (1H, dd, J = 1.8, 7.3 Hz), 8.10 (1H, dd, J = 1.8, 5.0 Hz), 8.17 (2H, s). | ESI-MS m/z: 385 [M + H]$^+$. |
| I-189 | | $^1$H-NMR (400 MHz, CDCl$_3$) δ: 3.28 (3H, s), 3.81 (3H, s), 4.59 (2H, s), 6.72-6.80 (2H, m), 7.10 (1H, dd, J = 5.0, 7.3 Hz), 7.28 (1H, dd, J = 6.4, 8.2 Hz), 7.65 (1H, dd, J = 1.8, 7.3 Hz), 8.10 (1H, dd, J = 1.8, 5.0 Hz), 8.23 (2H, s). | ESI-MS m/z: 366 [M + H]$^+$. |
| I-190 | | $^1$H-NMR (400 MHz, CDCl$_3$) δ: 3.80 (3H, s), 4.93 (2H, br s), 6.72-6.79 (2H, m), 7.07-7.10 (1H, m), 7.26-7.29 (1H, m), 7.64 (1H, d, J = 7.3 Hz), 8.10 (1H, d, J = 4.8 Hz), 8.16 (2H, s). | ESI-MS m/z: 313 [M + H]$^+$. |

TABLE 24-continued

| compound | structural formula | NMR | MS |
|---|---|---|---|
| I-191 | | ¹H-NMR (400 MHz, CDCl₃) δ: 3.73 (3H, s), 6.71 (1H, dd, J = 2.3, 11.0 Hz), 6.75-6.81 (1H, m), 7.20 (1H, dd, J = 4.6, 7.3 Hz), 7.25 (1H, dd, J = 6.4, 8.3 Hz), 7.70 (1H, dd, J = 1.8, 7.3 Hz), 8.13 (1H, dd, J = 1.8, 5.0 Hz), 8.36 (2H, s). | ESI-MS m/z: 424 [M + H]⁺. |
| I-192 | | ¹H-NMR (400 MHz, CDCl₃) δ: 3.25 (3H, s), 3.74 (3H, s), 3.80 (3H, s), 4.38 (2H, s), 6.71-6.79 (2H, m), 7.07 (1H, dd, J = 5.0, 7.3 Hz), 7.26-7.29 (1H, m), 7.62 (1H, dd, J = 1.8, 7.3 Hz), 8.09 (1H, dd, J = 1.8, 5.0 Hz), 8.19 (2H, s). | ESI-MS m/z: 399 [M + H]⁺. |

TABLE 25

| compound | structural formula | NMR | MS |
|---|---|---|---|
| I-193 | | ¹H-NMR (400 MHz, CDCl₃) δ: 3.23 (3H, s), 3.81 (3H, s), 4.80 (2H, s), 6.72 (1H, dd, J = 2.3, 11.0 Hz), 6.77 (1H, dt, J = 2.3, 8.2 Hz), 7.06 (1H, dd, J = 5.0, 7.3 Hz), 7.28 (1H, dd, J = 6.9, 8.2 Hz), 7.57 (1H, s), 7.62 (1H, dd, J = 1.8, 7.3 Hz), 7.84 (1H, s), 8.09 (1H, dd, J = 1.8, 5.0 Hz), 8.20 (2H, s). | ESI-MS m/z: 408 [M + H]⁺. |
| I-194 | | ¹H-NMR (400 MHz, CDCl₃) δ: 3.26 (3H, s), 3.81 (3H, s), 5.16 (2H, s), 6.74 (1H, dd, J = 2.3, 11.0 Hz), 6.77 (1H, dt, J = 2.3, 8.2 Hz), 7.08 (1H, dd, J = 5.0, 7.3 Hz), 7.25 (1H, d, J = 3.2 Hz), 7.28 (1H, dd, J = 6.9, 8.2 Hz), 7.63 (1H, dd, J = 1.8, 7.3 Hz), 7.73 (1H, d, J = 3.2 Hz), 8.11 (1H, dd, J = 1.8, 5.0 Hz), 8.24 (2H, s). | ESI-MS m/z: 424 [M + H]⁺. |

TABLE 25-continued

| compound structural formula | | NMR | MS |
|---|---|---|---|
| I-195 | 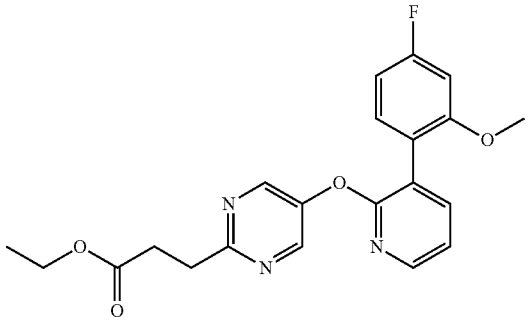 [SMILES: CCOC(=O)COc1ncc(Oc2ncccc2-c2ccc(F)cc2OC)cn1] | ¹H-NMR (400 MHz, CDCl₃) δ: 1.24 (3H, t, J = 7.3 Hz), 2.88 (2H, t, J = 7.3 Hz), 3.31 (2H, t, J = 7.3 Hz), 3.76 (3H, s), 4.15 (2H, q, J = 7.3 Hz), 6.71 (1H, dd, J = 2.3, 11.0 Hz), 6.77 (1H, dt, J = 2.3, 8.2 Hz), 7.15 (1H, dd, J = 5.0, 7.3 Hz), 7.27 (1H, dd, J = 6.9, 8.2 Hz), 7.68 (1H, dd, J = 1.8, 7.3 Hz), 8.12 (1H, dd, J = 1.8, 5.0 Hz), 8.50 (2H, s). | ESI-MS m/z: 398 [M + H]⁺. |
| I-196 | 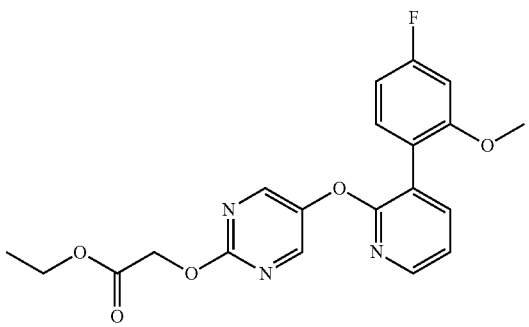 | ¹H-NMR (400 MHz, CDCl₃) δ: 1.27 (3H, t, J = 7.3 Hz), 3.78 (3H, s), 4.23 (2H, q, J = 7.3 Hz), 4.92 (2H, s), 6.72 (1H, dd, J = 2.3, 11.0 Hz), 6.77 (1H, dt, J = 2.3, 8.2 Hz), 7.12 (1H, dd, J = 5.0, 7.3 Hz), 7.27 (1H, dd, J = 6.9, 8.2 Hz), 7.66 (1H, dd, J = 1.8, 7.3 Hz), 8.10 (1H, dd, J = 1.8, 5.0 Hz), 8.35 (2H, s). | ESI-MS m/z: 400 [M + H]⁺. |
| I-197 | 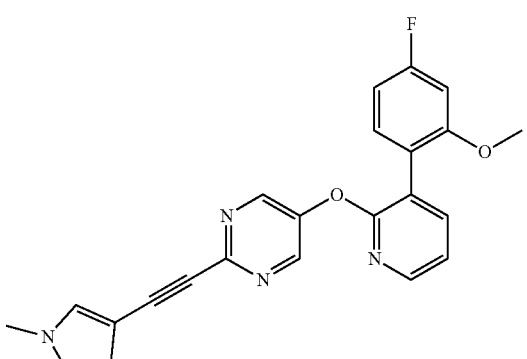 | ¹H-NMR (400 MHz, CDCl₃) δ: 3.74 (3H, s), 3.93 (3H, s), 6.72 (1H, d, J = 11.0 Hz), 6.75-6.81 (1H, m), 7.25-7.29 (1H, m), 7.27 (1H, t, J = 6.9 Hz), 7.67 (1H, s), 7.71 (1H, d, J = 7.3 Hz), 7.75 (1H, s), 8.15-8.16 (1H, m), 8.56 (2H, s). | ESI-MS m/z: 402 [M + H]⁺. |
| I-198 | 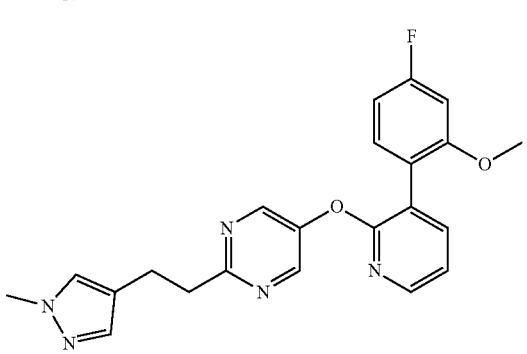 | ¹H-NMR (400 MHz, CDCl₃) δ: 2.99-3.03 (2H, m), 3.20-3.23 (2H, m), 3.76 (3H, s), 3.84 (3H, s), 6.72 (1H, dd, J = 2.3, 11.0 Hz), 6.78 (1H, dt, J = 2.3, 8.2 Hz), 7.14-7.17 (2H, m), 7.28-7.31 (2H, m), 7.69 (1H, dd, J = 1.8, 7.3 Hz), 8.13 (1H, dd, J = 1.8, 5.0 Hz), 8.51 (2H, s). | ESI-MS m/z: 406 [M + H]⁺. |
| I-199 | 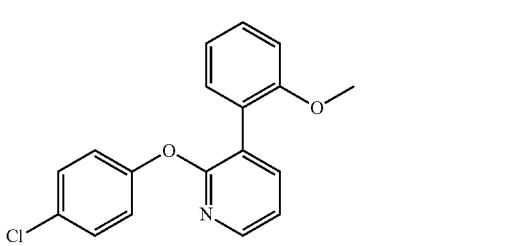 | ¹H-NMR (400 MHz, CDCl₃) δ: 3.75 (3H, s), 6.97 (1H, d, J = 8.2 Hz), 7.01-7.07 (3H, m), 7.09 (1H, dd, J = 5.0, 7.3 Hz), 7.27-7.34 (3H, m), 7.38 (1H, ddd, J = 1.8, 7.3, 8.2 Hz), 7.69 (1H, dd, J = 1.8, 7.3 Hz), 8.16 (1H, dd, J = 1.8, 5.0 Hz). | ESI-MS m/z: 312, 314 [M + H]⁺. |

TABLE 25-continued

| compound | structural formula | NMR | MS |
|---|---|---|---|
| I-200 | 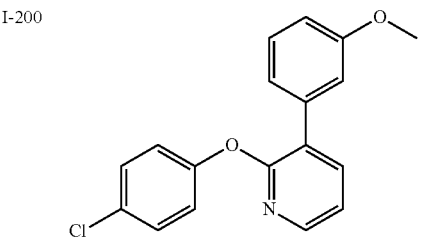 | ¹H-NMR (400 MHz, CDCl₃) δ: 3.84 (3H, s), 6.93 (1H, ddd, J = 0.9, 2.3, 8.2 Hz), 7.04-7.09 (2H, m), 7.11 (1H, dd, J = 5.0, 7.8 Hz), 7.18 (1H, dd, J = 1.8, 2.3 Hz), 7.19-7.23 (1H, m), 7.30-7.40 (3H, m), 7.77 (1H, dd, J = 1.8, 7.3 Hz), 8.14 (1H, dd, J = 1.8, 4.6 Hz). | ESI-MS m/z: 312, 314 [M + H]⁺. |

TABLE 26

| compound | structural formula | NMR | MS |
|---|---|---|---|
| I-201 | 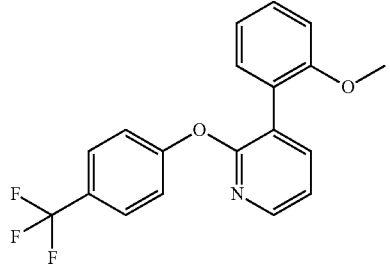 [SMILES: COc1ccccc1-c1cccnc1Oc1ccc(C(F)(F)F)cc1] | ¹H-NMR (400 MHz, CDCl₃) δ: 3.71 (3H, s), 6.96 (1H, d, J = 7.4 Hz), 7.03-7.07 (1H, m), 7.10-7.16 (1H, m), 7.18 (2H, d, J = 8.7 Hz), 7.32 (1H, dd, J = 1.8, 7.3 Hz), 7.34-7.40 (1H, m), 7.60 (2H, d, J = 8.7 Hz), 7.73 (1H, dd, J = 1.8, 7.3 Hz), 8.18 (1H, dd, J = 1.8, 5.0 Hz). | ESI-MS m/z: 346 [M + H]⁺. |
| I-202 | 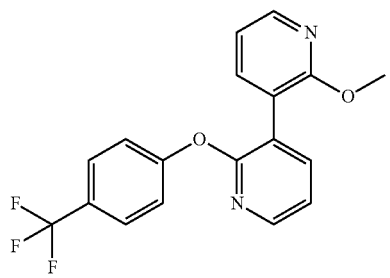 | ¹H-NMR (400 MHz, CDCl₃) δ: 3.87 (3H, s), 6.99 (1H, dd, J = 5.0, 7.3 Hz), 7.16 (1H, dd, J = 5.0, 7.4 Hz), 7.19 (2H, d, J = 7.5 Hz), 7.62 (2H, d, J = 7.5 Hz), 7.64 (1H, d, J = 2.0, 7.4 Hz), 7.75 (1H, d, J = 2.0, 7.4 Hz), 8.14-8.23 (2H, m). | ESI-MS m/z: 347 [M + H]⁺. |
| I-203 | 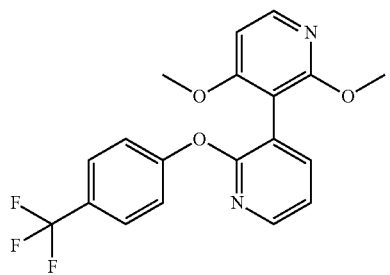 [SMILES: COc1ccnc(OC)c1-c1cccnc1Oc1ccc(C(F)(F)F)cc1] | ¹H-NMR (400 MHz, CDCl₃) δ: 3.76 (3H, s), 3.86 (3H, s), 6.61 (1H, d, J = 6.0 Hz), 7.13-7.16 (3H, m), 7.59 (2H, d, J = 8.7 Hz), 7.70 (1H, dd, J = 1.8, 7.3 Hz), 8.12 (1H, d, J = 5.0 Hz), 8.20 (1H, dd, J = 1.8, 5.0 Hz). | ESI-MS m/z: 377 [M + H]⁺. |
| I-204 | 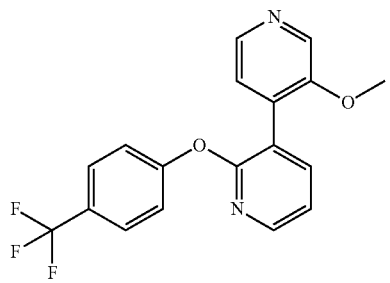 [SMILES: COc1cnccc1-c1cccnc1Oc1ccc(C(F)(F)F)cc1] | ¹H-NMR (400 MHz, CDCl₃) δ: 3.84 (3H, s), 7.18 (1H, dd, J = 4.9, 7.4 Hz), 7.18-7.20 (2H, m), 7.28 (1H, d, J = 4.7 Hz), 7.62-7.64 (2H, m), 7.75 (1H, dd, J = 1.9, 7.3 Hz), 8.24 (1H, dd, J = 1.9, 4.9 Hz), 8.35 (1H, d, J = 4.7 Hz), 8.38 (1H, s). | ESI-MS m/z: 347 [M + H]⁺. |

TABLE 26-continued

| compound | structural formula | NMR | MS |
|---|---|---|---|
| I-205 | | ¹H-NMR (400 MHz, CDCl₃) δ: 2.28 (3H, s), 7.17-7.20 (4H, m), 7.62-7.65 (3H, m), 8.24 (1H, dd, J = 1.9, 4.9 Hz), 8.51 (1H, d, J = 4.9 Hz), 8.55 (1H, s). | ESI-MS m/z: 331 [M + H]⁺. |
| I-206 | | ¹H-NMR (400 MHz, CDCl₃) δ: 2.30 (3H, s), 7.15-7.25 (4H, m), 7.61-7.63 (2H, d, J = 8.5 Hz), 7.57 (1H, dd, J = 1.9, 7.4 Hz), 8.24 (1H, dd, J = 1.9, 4.9 Hz), 8.46 (1H, s), 8.50 (1H, d, J = 5.0 Hz). | ESI-MS m/z: 331 [M + H]⁺. |
| I-207 | | ¹H-NMR (400 MHz, CDCl₃) δ: 7.20-7.25 (3H, m), 7.63-7.65 (2H, m), 7.73 (1H, dd, J = 1.9, 7.4 Hz), 8.28 (1H, dd, J = 1.9, 5.0 Hz), 8.45 (1H, s), 8.55 (1H, s). | ESI-MS m/z: 369, 371 [M + H]⁺. |
| I-208 | | ¹H-NMR (400 MHz, CDCl₃) δ: 2.25 (3H, d, J = 1.9 Hz), 7.16-7.23 (3H, m), 7.63-7.65 (2H, m), 7.75 (1H, dd, J = 2.0, 7.4 Hz), 8.25 (1H, dd, J = 2.0, 5.0 Hz), 8.31 (1H, s), 8.43 (1H, s). | ESI-MS m/z: 349 [M + H]⁺. |

TABLE 27

| compound | structural formula | NMR | MS |
|---|---|---|---|
| I-209 | | ¹H-NMR (400 MHz, CDCl₃) δ: 3.86 (3H, s), 7.17 (1H, dd, J = 5.0, 7.3 Hz), 7.20 (2H, d, J = 8.7 Hz), 7.47 (1H, dd, J = 2.7, 7.8 Hz), 7.63 (2H, d, J = 8.3 Hz), 7.76 (1H, dd, J = 2.3, 7.3 Hz), 8.05 (1H, d, J = 2.8 Hz), 8.22 (1H, dd, J = 1.8, 5.0 Hz). | ESI-MS m/z: 365 [M + H]⁺. |
| I-210 | | ¹H-NMR (400 MHz, CDCl₃) δ: 3.87 (3H, s), 6.99 (1H, dd, J = 5.0, 7.3 Hz), 7.16 (1H, dd, J = 5.0, 7.3 Hz), 7.16-7.21 (2H, m), 7.60-7.64 (2H, m), 7.65 (1H, dd, J = 1.9, 7.3 Hz), 7.75 (1H, dd, J = 1.8, 7.3 Hz), 8.19-8.23 (2H, m). | ESI-MS m/z: 347 [M + H]⁺. |
| I-211 | | ¹H-NMR (400 MHz, CDCl₃) δ: 3.81 (3H, s), 7.17-7.22 (3H, m), 7.63-7.65 (2H, m), 7.75 (1H, dd, J = 2.0, 7.4 Hz), 8.25 (1H, dd, J = 2.0, 5.0 Hz), 8.44 (1H, s), 8.58 (1H, s). | ESI-MS m/z: 381, 383 [M + H]⁺. |
| I-212 | | ¹H-NMR (400 MHz, CDCl₃) δ: 4.04 (3H, d, J = 4.6 Hz), 7.16-7.21 (3H, m), 7.62-7.65 (2H, m), 7.70 (1H, dd, J = 1.9, 8.6 Hz), 8.23 (1H, dd, J = 1.9, 5.0 Hz), 8.29 (1H, s), 8.43 (1H, d, J = 4.5 Hz). | ESI-MS m/z: 365 [M + H]⁺. |
| I-213 | | ¹H-NMR (400 MHz, CDCl₃) δ: 4.00 (3H, s), 6.74 (1H, dd, J = 1.0, 8.0 Hz), 7.20-7.28 (3H, m), 7.63-7.70 (4H, m), 8.19 (1H, dd, J = 1.9, 4.8 Hz), 8.52 (1H, dd, J = 1.9, 7.5 Hz). | ESI-MS m/z: 347 [M + H]⁺. |

TABLE 27-continued

| compound | structural formula | NMR | MS |
|---|---|---|---|
| I-214 | 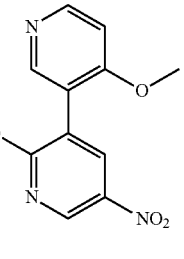 | $^1$H-NMR (400 MHz, CDCl$_3$) δ: 3.89 (3H, s), 6.97 (1H, d, J = 5.8 Hz), 7.22-7.24 (2H, m), 7.69-7.71 (2H, m), 8.53 (2H, m), 8.61 (1H, d, J = 5.8 Hz), 9.06 (1H, d, J = 2.8 Hz). | ESI-MS m/z: 392 [M + H]$^+$. |
| I-215 | 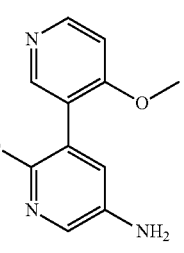 | $^1$H-NMR (400 MHz, CDCl$_3$) δ: 3.68 (5H, s), 6.83 (1H, d, J = 5.8 Hz), 7.06-7.08 (2H, m), 7.11 (1H, d, J = 3.0 Hz), 7.54-7.56 (2H, m), 7.76 (1H, d, J = 3.0 Hz), 8.39 (1H, s), 8.49 (1H, d, J = 5.8 Hz). | ESI-MS m/z: 362 [M + H]$^+$. |
| I-216 | 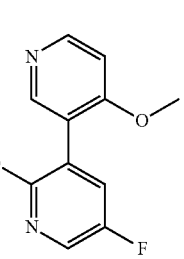 | $^1$H-NMR (400 MHz, CDCl$_3$) δ: 3.79 (3H, s), 6.90 (1H, d, J = 5.8 Hz), 7.14-7.16 (2H, m), 7.53 (1H, dd, J = 3.0, 7.8 Hz), 7.60-7.63 (2H, m), 8.07 (1H, d, J = 3.0 Hz), 8.46 (1H, s), 8.55 (1H, d, J = 5.8 Hz). | ESI-MS m/z: 365 [M + H]$^+$. |

TABLE 28

| compound | structural formula | NMR | MS |
|---|---|---|---|
| I-217 | 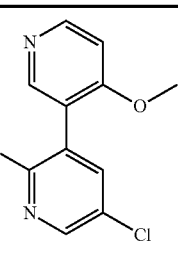 | $^1$H-NMR (400 MHz, CDCl$_3$) δ: 3.81 (3H, s), 6.90 (1H, d, J = 5.8 Hz), 7.16-7.18 (2H, m), 7.62-7.64 (2H, m), 7.72 (1H, d, J = 2.6 Hz), 8.15 (1H, d, J = 2.6 Hz), 8.45 (1H, s), 8.55 (1H, d, J = 5.8 Hz). | ESI-MS m/z: 381, 383 [M + H]$^+$. |
| I-218 | 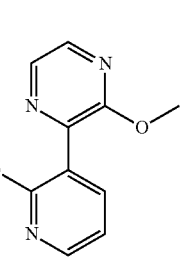 | $^1$H-NMR (400 MHz, CDCl$_3$) δ: 3.88 (3H, s), 7.20-7.31 (3H, m), 7.64 (2H, d, J = 8.7 Hz), 7.93 (1H, dd, J = 1.8, 7.3 Hz), 8.15 (1H, d, J = 2.7 Hz), 8.25-8.30 (2H, m). | ESI-MS m/z: 348 [M + H]$^+$. |

TABLE 28-continued

| compound | structural formula | NMR | MS |
| --- | --- | --- | --- |
| I-219 | | $^1$H-NMR (400 MHz, CDCl$_3$) δ: 3.96 (3H, s), 7.19 (1H, dd, J = 2.7, 7.3 Hz), 7.20 (2H, d, J = 8.3 Hz), 7.64 (2H, d, J = 8.3 Hz), 7.77 (1H, dd, J = 1.8, 7.3 Hz), 8.24 (1H, dd, J = 1.8, 5.0 Hz), 8.53 (1H, s), 8.82 (1H, s). | ESI-MS m/z: 348 [M + H]$^+$. |
| I-220 | | $^1$H-NMR (400 MHz, CDCl$_3$) δ: 2.25 (3H, s), 3.85 (3H, s), 7.14 (1H, dd, J = 4.9, 7.4 Hz), 7.20-7.22 (2H, m), 7.62-7.64 (2H, m), 7.67 (1H, dd, J = 2.0, 7.4 Hz), 8.18 (1H, dd, J = 2.0, 4.9 Hz). | ESI-MS m/z: 368, 370 [M + H]$^+$. |
| I-221 | | $^1$H-NMR (400 MHz, CDCl$_3$) δ: 3.89 (3H, s), 6.38 (1H, d, J = 1.9 Hz), 7.17 (1H, dd, J = 5.0, 7.4 Hz), 7.21-7.23 (2H, m), 7.56 (1H, d, J = 1.9 Hz), 7.64-7.66 (2H, m), 7.75 (1H, dd, J = 1.9, 7.4 Hz), 8.24 (1H, dd, J =1.9, 4.9 Hz). | ESI-MS m/z: 320 [M + H]$^+$. |
| I-222 | | $^1$H-NMR (400 MHz, CDCl$_3$) δ: 3.85 (3H, s), 7.23 (1H, dd, J = 4.9, 7.4 Hz), 7.22-7.24 (2H, m), 7.54 (1H, s), 7.64-7.67 (2H, m), 7.79 (1H, dd, J = 2.0, 7.4 Hz), 8.30 (1H, dd, J = 2.0, 4.9 Hz). | ESI-MS m/z: 354, 356 [M + H]$^+$. |
| I-223 | | $^1$H-NMR (400 MHz, CDCl$_3$) δ: 3.76 (3H, s), 3.83 (3H, s), 7.12 (1H, dd, J = 4.8, 7.5 Hz), 7.23-7.25 (2H, m), 7.64-7.66 (2H, m), 7.72 (1H, s), 7.97 (1H, dd, J = 1.9, 7.5 Hz), 8.07 (1H, dd, J = 1.9, 4.8 Hz). | ESI-MS m/z: 350 [M + H]$^+$. |

TABLE 28-continued

| compound | structural formula | NMR | MS |
|---|---|---|---|
| I-224 | | ¹H-NMR (400 MHz, CDCl₃) δ: 7.18-7.20 (2H, m), 7.25 (1H, dd, J = 4.9, 7.4 Hz), 7.56-7.58 (2H, m), 7.85-7.88 (3H, m), 8.17-8.21 (1H, m), 8.30 (1H, dd, J = 1.9, 4.9 Hz), 8.77 (1H, d, J = 1.8 Hz), 8.85 (1H, d, J = 1.8 Hz). | ESI-MS m/z: 368 [M + H]⁺. |

TABLE 29

| compound | structural formula | NMR | MS |
|---|---|---|---|
| I-225 | | ¹H-NMR (400 MHz, CDCl₃) δ: 7.20-7.23 (2H, m), 7.26 (1H, dd, J = 5.0, 7.3 Hz), 7.54 (1H, dd, J = 4.2, 8.3 Hz), 7.57-7.59 (2H, m), 7.92 (1H, dd, J = 1.9, 7.3 Hz), 8.31 (1H, dd, J = 1.9, 5.0 Hz), 8.35 (1H, dd, J = 1.8, 8.3 Hz), 8.86 (1H, s), 9.03 (1H, dd, J = 1.8, 4.3 Hz), 9.33 (1H, s). | ESI-MS m/z: 368 [M + H]⁺. |
| I-226 | | ¹H-NMR (400 MHz, CDCl₃) δ: 7.21-7.23 (2H, m), 7.26 (1H, dd, J = 5.0, 7.3 Hz), 7.58-7.59 (2H, m), 7.65 (1H, dd, J = 4.1, 8.5 Hz), 7.74 (1H, d, J = 4.3 Hz), 7.93 (1H, dd, J = 1.9, 7.3 Hz), 8.32 (1H, dd, J = 1.9, 4.9 Hz), 8.46 (1H, dd, J = 1.8, 8.5 Hz), 8.92 (1H, dd, J = 1.8, 4.2 Hz), 9.07 (1H, d, J = 4.3 Hz). | ESI-MS m/z: 368 [M + H]⁺. |
| I-227 | | ¹H-NMR (400 MHz, CDCl₃) δ: 7.19-7.22 (2H, m), 7.26 (1H, dd, J = 5.0, 7.4 Hz), 7.59-7.61 (2H, m), 7.91 (1H, dd, J = 1.8, 7.4 Hz), 8.31 (1H, dd, J = 1.8, 5.0 Hz), 8.96 (2H, d, J = 6.8 Hz), 8.96-8.98 (1H, m), 9.63 (1H, s). | ESI-MS m/z: 369 [M + H]⁺. |

TABLE 29-continued

| compound | structural formula | NMR | MS |
|---|---|---|---|
| I-228 | | $^1$H-NMR (400 MHz, CDCl$_3$) δ: 6.61 (1H, d, J = 2.3 Hz), 6.91 (1H, dd, J = 1.3, 6.8 Hz), 7.18-7.25 (4H, m), 7.58-7.60 (2H, m), 7.62 (1H, dd, J = 1.4, 8.7 Hz), 7.93 (1H, d, J = 2.3 Hz), 8.02 (1H, dd, J = 1.8, 7.3 Hz), 8.30 (1H, dd, J = 1.8, 5.0 Hz). | ESI-MS m/z: 356 [M + H]$^+$. |
| I-229 | | $^1$H-NMR (400 MHz, CDCl$_3$) δ: 6.89 (1H, t, J = 6.9 Hz), 7.21-7.27 (3H, m), 7.46 (1H, dd, J = 1.2, 7.0 Hz), 7.61 (2H, d, J = 8.4 Hz), 7.66-7.68 (2H, m), 8.17 (1H, dd, J = 1.2, 6.8 Hz), 8.23 (1H, dd, J = 1.9, 4.9 Hz), 8.31 (1H, dd, J = 1.9, 7.3 Hz). | ESI-MS m/z: 356 [M + H]$^+$. |
| I-230 | | $^1$H-NMR (400 MHz, CDCl$_3$) δ: 7.21-7.27 (4H, m), 7.62-7.67 (3H, m), 7.85 (1H, dd, J = 1.0, 9.0 Hz), 8.05 (1H, dd, J = 1.9, 7.4 Hz), 8.33-8.35 (2H, m). | ESI-MS m/z: 357 [M + H]$^+$. |
| I-231 | | $^1$H-NMR (400 MHz, CDCl$_3$) δ: 7.19-7.21 (2H, m), 7.30 (1H, dd, J = 5.0, 7.4 Hz), 7.57-7.58 (1H, m), 7.63-7.65 (2H, m), 7.88 (1H, d, J = 1.1 Hz), 7.95-7.99 (2H, m), 8.39 (1H, dd, J = 1.9, 5.0 Hz), 9.18 (1H, d, J = 0.4 Hz). | ESI-MS m/z: 357 [M + H]$^+$. |
| I-232 | | $^1$H-NMR (400 MHz, CDCl$_3$) δ: 2.31 (3H, s), 4.29 (2H, d, J = 8.3 Hz), 5.03 (2H, t, J = 8.3 Hz), 7.09 (1H, dd, J = 4.9, 7.4 Hz), 7.22-7.24 (2H, m), 7.62-7.65 (2H, m), 7.68 (1H, dd, J = 1.9, 7.4 Hz), 8.08 (1H, d, J = 1.9, 4.9 Hz). | ESI-MS m/z: 362 [M + H]$^+$. |

TABLE 30

| compound | structural formula | NMR | MS |
|---|---|---|---|
| I-233 | | ¹H-NMR (400 MHz, CDCl₃) δ: 1.24-1.32 (4H, m), 2.22 (3H, s), 3.96-3.98 (2H, m), 4.18-4.21 (2H, m), 7.11 (1H, dd, J = 4.9, 7.4 Hz), 7.19-7.21 (2H, m), 7.62-7.64 (3H, m), 8.11 (1H, dd, J = 2.0, 4.9 Hz). | ESI-MS m/z: 390 [M + H]⁺. |
| I-234 | | ¹H-NMR (400 MHz, CDCl₃) δ: 3.82 (3H, s), 6.90 (1H, d, J = 5.8 Hz), 6.96-7.00 (2H, m), 7.12 (1H, dd, J = 4.9, 7.3 Hz), 7.45-7.48 (2H, m), 7.70 (1H, dd, J = 2.0, 7.4 Hz), 8.20 (1H, dd, J = 2.0, 4.9 Hz), 8.45 (1H, s), 8.53 (1H, d, J = 5.8 Hz). | ESI-MS m/z: 357, 359 [M + H]⁺. |
| I-235 | | ¹H-NMR (400 MHz, CDCl₃) δ: 3.82 (3H, s), 6.89 (1H, d, J = 5.8 Hz), 7.00-7.04 (2H, m), 7.12 (1H, dd, J = 5.0, 7.3 Hz), 7.30-7.34 (2H, m), 7.69 (1H, dd, J = 1.9, 7.3 Hz), 8.19 (1H, dd, J = 1.9, 5.0 Hz), 8.45 (1H, s), 8.52 (1H, d, J = 5.8 Hz). | ESI-MS m/z: 313, 315 [M + H]⁺. |
| I-236 | | ¹H-NMR (400 MHz, CDCl₃) δ: 3.84 (3H, s), 6.90 (1H, d, J = 5.8 Hz), 7.04-7.06 (4H, m), 7.10 (1H, dd, J = 5.0, 7.3 Hz), 7.68 (1H, dd, J = 2.0, 7.4 Hz), 8.18 (1H, dd, J = 2.0, 5.0 Hz), 8.46 (1H, s), 8.53 (1H, d, J = 5.8 Hz). | ESI-MS m/z: 297 [M + H]⁺. |
| I-237 | | ¹H-NMR (400 MHz, CDCl₃) δ: 3.82 (3H, s), 6.89 (1H, d, J = 5.5 Hz), 7.09-7.16 (3H, m), 7.19-7.24 (2H, m), 7.71 (1H, d, J = 7.3 Hz), 8.21 (1H, dd, J = 2.0, 4.9 Hz), 8.45 (1H, s), 8.53 (1H, d, J = 5.0 Hz). | ESI-MS m/z: 363 [M + H]⁺. |
| I-238 | | ¹H-NMR (400 MHz, CDCl₃) δ: 3.84 (3H, s), 6.48 (1H, t, J = 73.7 Hz), 6.91 (1H, d, J = 6.0 Hz), 7.06-7.16 (4H, m), 7.10 (1H, dd, J = 1.8, 7.3 Hz), 8.20 (1H, dd, J = 1.8, 4.6 Hz), 8.46 (1H, s), 8.46 (1H, s), 8.53 (1H, d, J = 5.5 Hz). | ESI-MS m/z: 345 [M + H]⁺. |

TABLE 30-continued

| compound | structural formula | NMR | MS |
|---|---|---|---|
| I-239 | | $^1$H-NMR (400 MHz, CDCl$_3$) δ: 3.76 (3H, s), 6.87 (1H, d, J = 5.8 Hz), 7.12-7.14 (2H, m), 7.19 (1H, dd, J = 4.9, 7.4 Hz), 7.62-7.64 (2H, m), 7.74 (1H, dd, J = 2.0, 7.4 Hz), 8.24 (1H, dd, J = 2.0, 4.9 Hz), 8.44 (1H, s), 8.53 (1H, d J = 5.8 Hz). | ESI-MS m/z: 379 [M + H]$^+$. |
| I-240 | | $^1$H-NMR (400 MHz, CDCl$_3$) δ: 3.78 (3H, s), 6.89 (1H, d, J = 5.8 Hz), 7.14-7.16 (2H, m), 7.20 (1H, dd, J = 4.9, 7.4 Hz), 7.72-7.77 (3H, m), 8.24 (1H, dd, J = 2.0, 7.4 Hz), 8.44 (1H, s), 8.53 (1H, d, J = 5.8 Hz). | ESI-MS m/z: 405 [M + H]$^+$. |

TABLE 31

| compound | structural formula | NMR | MS |
|---|---|---|---|
| I-241 | | $^1$H-NMR (400 MHz, CDCl$_3$) δ: 2.47 (3H, s), 3.83 (3H, s), 6.90 (1H, d, J = 5.8 Hz), 7.01-7.04 (2H, m), 7.10 (1H, dd, J = 5.0, 7.3 Hz), 7.27-7.31 (2H, m), 7.69 (1H, dd, J = 2.0, 7.4 Hz), 8.20 (1H, dd, J = 2.0, 5.0 Hz), 8.45 (1H, s), 8.52 (1H, d, J = 5.9 Hz). | ESI-MS m/z: 325 [M + H]$^+$. |
| I-242 | | $^1$H-NMR (400 MHz, CDCl$_3$) δ: 3.80 (3H, s), 3.86 (3H, s), 6.84-6.91 (3H, m), 7.00-7.03 (2H, m), 7.06 (1H, dd, J = 4.8, 7.3 Hz), 7.66 (1H, dd, J = 1.9, 7.3 Hz), 8.18 (1H, dd, J = 1.9, 4.8 Hz), 8.46 (1H, s), 8.52 (1H, d, J = 5.7 Hz). | ESI-MS m/z: 309 [M + H]$^+$. |
| I-243 | | $^1$H-NMR (400 MHz, CDCl$_3$) δ: 3.76 (3H, s), 6.89 (1H, d, J = 5.8 Hz), 7.16-7.19 (2H, m), 7.21 (1H, dd, J = 4.9, 7.4 Hz), 7.64-7.67 (2H, m), 7.76 (1H, dd, J = 1.9, 7.4 Hz), 8.24 (1H, dd, J = 1.9, 4.9 Hz), 8.44 (1H, s), 8.54 (1H, d, J = 5.1 Hz). | ESI-MS m/z: 304 [M + H]$^+$. |

TABLE 31-continued

| compound | structural formula | NMR | MS |
| --- | --- | --- | --- |
| I-244 | | ¹H-NMR (400 MHz, CDCl₃) δ: 2.59 (3H, s), 3.77 (3H, s), 6.89 (1H, d, J = 5.8 Hz), 7.13-7.17 (2H, m), 7.18 (1H, dd, J = 4.9, 7.4 Hz), 7.74 (1H, dd, J = 2.0, 7.4 Hz), 7.97-8.00 (2H, m), 8.24 (1H, dd, J = 2.0, 4.90 Hz), 8.45 (1H, s), 8.53 (1H, d, J = 5.8 Hz). | ESI-MS m/z: 321 [M + H]⁺. |
| I-245 | | ¹H-NMR (400 MHz, CDCl₃) δ: 1.38 (3H, t, J = 7.1 Hz), 3.77 (3H, s), 4.36 (2H, q, J = 7.1 Hz), 6.88 (1H, d, J = 5.8 Hz), 7.10-7.14 (2H, m), 7.17 (1H, dd, J = 4.9, 7.4 Hz), 7.73 (1H, dd, J = 2.0, 7.4 Hz), 8.04-8.09 (2H, m), 8.24 (1H, dd, J = 2.0, 4.9 Hz), 8.45 (1H, s), 8.53 (1H, d, J = 5.8 Hz). | ESI-MS m/z: 351 [M + H]⁺. |
| I-246 | | ¹H-NMR (400 MHz, CDCl₃) δ: 3.75 (3H, s), 6.88 (1H, d, J = 5.8 Hz), 7.19-7.24 (3H, m), 7.76 (1H, dd, J = 1.9, 7.4 Hz), 7.88-7.91 (2H, m), 8.26 (1H, dd, J = 1.9, 4.9 Hz), 8.45 (1H, s), 8.53 (1H, d, J = 5.8 Hz), 9.96 (1H, s). | ESI-MS m/z: 307 [M + H]⁺. |
| I-247 | | ¹H-NMR (400 MHz, CDCl₃) δ: 3.65 (1H, br s), 3.80 (3H, s), 4.95 (1H, q, J = 6.8 Hz), 6.88 (1H, d, J = 5.8 Hz), 7.09-7.12 (2H, m), 7.14 (1H, dd, J = 5.0, 7.4 Hz), 7.44-7.46 (2H, m), 7.71 (1H, dd, J = 2.0, 7.4 Hz), 8.21 (1H, dd, J = 2.0, 5.0 Hz), 8.42 (1H, s), 8.49 (1H, d, J = 5.8 Hz). | ESI-MS m/z: 377 [M + H]⁺. |
| I-248 | | ¹H-NMR (400 MHz, CDCl₃) δ: 2.39 (3H, s), 3.75 (3H, s), 5.66 (1H, q, J = 6.3 Hz), 6.87 (1H, d, J = 5.8 Hz), 7.01-7.04 (2H, m), 7.17 (1H, dd, J = 4.9, 7.4 Hz), 7.25-7.27 (2H, m), 7.31-7.33 (2H, m), 7.66-7.69 (2H, m), 7.73 (1H, dd, J = 2.0, 7.4 Hz), 8.24 (1H, dd, J = 2.0, 5.0 Hz), 8.43 (1H, s), 8.52 (1H, d, J = 5.8 Hz). | ESI-MS m/z: 531 [M + H]⁺. |

TABLE 32

| compound | structural formula | NMR | MS |
|---|---|---|---|
| I-249 | | $^1$H-NMR (400 MHz, CDCl$_3$) δ: 3.35 (2H, q, J = 10.8 Hz), 3.81 (3H, s), 6.88 (1H, d, J = 5.8 Hz), 7.05-7.09 (2H, m), 7.12 (1H, dd, J = 5.0, 7.4 Hz), 7.27-7.29 (2H, m), 7.70 (1H, dd, J = 2.0, 7.4 Hz), 8.21 (1H, dd, J = 2.0, 5.0 Hz), 8.45 (1H, s), 8.52 (1H, d, J = 5.8 Hz). | ESI-MS m/z: 361 [M + H]$^+$. |
| I-250 | | $^1$H-NMR (400 MHz, CDCl$_3$) δ: 3.84 (3H, s), 4.68 (2H, s), 6.90 (1H, d, J = 5.8 Hz), 7.06-7.11 (3H, m), 7.35-7.38 (2H, m), 7.69 (1H, dd, J = 1.9, 7.3 Hz), 8.19 (1H, dd, J = 1.9, 5.0 Hz), 8.46 (1H, s), 8.51 (1H, d, J = 5.8 Hz). | ESI-MS m/z: 309 [M + H]$^+$. |
| I-251 | | $^1$H-NMR (400 MHz, CDCl$_3$) δ: 3.38 (3H, s), 3.82 (3H, s), 4.44 (2H, s), 6.89 (1H, d, J = 5.8 Hz), 7.05-7.11 (3H, m), 7.31-7.36 (2H, m), 7.68 (1H, dd, J = 2.0, 7.3 Hz), 8.19 (1H, dd, J = 2.0, 4.9 Hz), 8.45-8.57 (2H, m). | ESI-MS m/z: 323 [M + H]$^+$. |
| I-252 | | $^1$H-NMR (400 MHz, CDCl$_3$) δ: 2.33 (3H, s), 3.85 (3H, s), 6.90 (1H, d, J = 6.0 Hz), 6.95-7.00 (2H, m), 7.07 (1H, dd, J = 5.0, 7.3 Hz), 7.14-7.19 (2H, m), 7.66 (1H, dd, J = 1.8, 7.3 Hz), 8.19 (1H, dd, J = 1.8, 5.0 Hz), 8.46 (1H, s), 8.52 (1H, d, J = 6.0 Hz). | ESI-MS m/z: 293 [M + H]$^+$. |
| I-253 | | $^1$H-NMR (400 MHz, CDCl$_3$) δ: 1.23 (3H, t, J = 7.6 Hz), 2.64 (2H, q, J = 7.6 Hz), 3.84 (3H, s), 6.89 (1H, d, J = 5.8 Hz), 6.98-7.01 (2H, m), 7.07 (1H, dd, J = 5.0, 7.3 Hz), 7.17-7.20 (2H, m), 7.67 (1H, dd, J = 2.0, 7.3 Hz), 8.19 (1H, dd, J = 2.0, 5.0 Hz), 8.46 (1H, s), 8.51 (1H, d, J = 5.8 Hz). | ESI-MS m/z: 307 [M + H]$^+$. |
| I-254 | | $^1$H-NMR (400 MHz, CDCl$_3$) δ: 0.95 (3H, t, J = 7.3 Hz), 1.63 (2H, sext, J = 7.3 Hz), 2.57 (2H, t, J = 7.3 Hz), 3.84 (3H, s), 6.89 (1H, d, J = 5.8 Hz), 6.98-7.01 (2H, m), 7.07 (1H, dd, J = 5.0, 7.3 Hz), 7.16-7.20 (2H, m), 7.67 (1H, dd, J = 2.0, 7.3 Hz), 8.19 (1H, dd, J = 2.0, 5.0 Hz), 8.46 (1H, s), 8.51 (1H, d, J = 5.8 Hz). | ESI-MS m/z: 321 [M + H]$^+$. |

TABLE 32-continued

| compound | structural formula | NMR | MS |
|---|---|---|---|
| I-255 | | $^1$H-NMR (400 MHz, CDCl$_3$) δ: 1.24 (6H, d, J = 6.9 Hz), 2.90 (1H, sep, J = 6.9 Hz), 3.84 (3H, s), 6.89 (1H, d, J = 5.8 Hz), 6.98-7.01 (2H, m), 7.08 (1H, dd, J = 5.0, 7.3 Hz), 7.19-7.23 (2H, m), 7.67 (1H, dd, J = 2.0, 7.3 Hz), 8.20 (1H, dd, J = 2.0, 5.0 Hz), 8.46 (1H, s), 8.51 (1H, d, J = 5.8 Hz). | ESI-MS m/z: 321 [M + H]$^+$. |
| I-256 | | $^1$H-NMR (400 MHz, CDCl$_3$) δ: 0.83 (3H, t, J = 7.4 Hz), 1.22 (3H, d, J = 7.3 Hz), 1.55-1.60 (2H, m), 2.59 (1H, sext, J = 7.3 Hz), 3.84 (3H, s), 6.88 (1H, d, J = 5.8 Hz), 6.97-7.01 (2H, m), 7.09 (1H, dd, J = 5.0, 7.3 Hz), 7.14-7.17 (2H, m), 7.67 (1H, dd, J = 2.0, 7.3 Hz), 8.20 (1H, dd, J = 2.0, 5.0 Hz), 8.46 (1H, s), 8.51 (1H, d, J = 5.8 Hz). | ESI-MS m/z: 335 [M + H]$^+$. |

TABLE 33

| compound | structural formula | NMR | MS |
|---|---|---|---|
| I-257 | | $^1$H-NMR (400 MHz, CDCl$_3$) δ: 2.86 (2H, t, J = 6.4 Hz), 3.84 (3H, s), 3.86 (2H, t, J = 6.4 Hz), 6.89 (1H, d, J = 6.1 Hz), 7.01-7.05 (2H, m), 7.09 (1H, dd, J = 5.0, 7.3 Hz), 7.21-7.26 (2H, m), 7.68 (1H, dd, J = 1.8, 7.3 Hz), 8.19 (1H, dd, J = 1.8, 5.0 Hz), 8.45 (1H, s), 8.51 (1H, d, J = 6.1 Hz). | ESI-MS m/z: 323 [M + H]$^+$. |
| I-258 | | $^1$H-NMR (400 MHz, CDCl$_3$) δ: 3.83 (1H, s), 5.20 (1H, dd, J = 0.9, 10.9 Hz), 5.67 (1H, dd, J = 0.9, 17.6 Hz), 6.70 (1H, dd, J = 10.9, 17.6 Hz), 6.89 (1H, d, J = 5.8 Hz), 7.02-7.06 (2H, m), 7.10 (1H, dd, J = 5.0, 7.3 Hz), 7.39-7.42 (2H, m), 7.69 (1H, dd, J = 2.0, 7.3 Hz), 8.20 (1H, dd, J = 2.0, 5.0 Hz), 8.46 (1H, s), 8.52 (1H, d, J = 5.8 Hz). | ESI-MS m/z: 305 [M + H]$^+$. |
| I-259 | | $^1$H-NMR (400 MHz, CDCl$_3$) δ: 0.24 (9H, s), 3.78 (3H, s), 6.88 (1H, d, J = 5.8 Hz), 6.99-7.03 (2H, m), 7.14 (1H, dd, J = 4.9, 7.4 Hz), 7.43-7.47 (2H, m), 7.70 (1H, dd, J = 1.9, 7.4 Hz), 8.21 (1H, dd, J = 1.9, 4.9 Hz), 8.44 (1H, s), 8.52 (1H, d, J = 5.8 Hz). | ESI-MS m/z: 375 [M + H]$^+$. |

TABLE 33-continued

| compound | structural formula | NMR | MS |
|---|---|---|---|
| I-260 | | $^1$H-NMR (400 MHz, CDCl$_3$) δ: 3.03 (1H, s), 3.79 (3H, s), 6.88 (1H, d, J = 5.8 Hz), 7.02-7.06 (2H, m), 7.14 (1H, dd, 4.9, 7.4 Hz), 7.46-7.51 (2H, m), 7.71 (1H, dd, J = 1.9, 7.4 Hz), 8.22 (1H, dd, J = 1.9, 4.9 Hz), 8.44 (1H, s), 8.52 (1H, d, J = 5.8 Hz). | ESI-MS m/z: 303 [M + H]$^+$. |
| I-261 | | $^1$H-NMR (400 MHz, CDCl$_3$) δ: 0.64-0.68 (2H, m), 0.88-0.95 (2H, m), 1.85-1.92 (1H, m), 3.84 (3H, s), 6.88 (1H, d, J = 5.8 Hz), 6.95-7.00 (2H, m), 7.05-7.08 (3H, m), 7.67 (1H, dd, J = 2.0, 7.3 Hz), 8.19 (1H, dd, J = 2.0, 5.0 Hz), 8.46 (1H, s), 8.51 (1H, d, J = 5.8 Hz) | ESI-MS m/z: 319 [M + H]$^+$. |
| I-262 | | $^1$H-NMR (400 MHz, CDCl$_3$) δ: 2.23 (3H, s), 2.24 (3H, s), 3.86 (3H, s), 6.82 (1H, dd, J = 2.5, 8.0 Hz), 6.87 (1H, d, J = 2.3 Hz), 6.89 (1H, d, J = 5.5 Hz), 7.06 (1H, dd, J = 5.0, 7.3 Hz), 7.12 (1H, d, J = 7.3 Hz), 7.66 (1H, dd, J = 1.8, 7.3 Hz), 8.19 (1H, dd, J = 1.8, 5.0 Hz), 8.47 (1H, s), 8.51 (1H, s). | ESI-MS m/z: 307 [M + H]$^+$. |
| I-263 | | $^1$H-NMR (400 MHz, CDCl$_3$) δ: 1.20 (3H, t, J = 7.6 Hz), 2.27 (3H, s), 2.59 (2H, q, J = 7.6 Hz), 3.85 (3H, s), 6.85-6.89 (3H, m), 7.06 (1H, dd, J = 5.0, 7.3 Hz), 7.12-7.15 (1H, m), 7.66 (1H, dd, J = 1.9, 7.3 Hz), 8.20 (1H, dd, J = 1.9, 5.0 Hz), 8.46 (1H, s), 8.51 (1H, d, J = 5.8 Hz). | ESI-MS m/z: 321 [M + H]$^+$. |
| I-264 | | $^1$H-NMR (400 MHz, CDCl$_3$) δ: 1.19 (3H, t, J = 7.5 Hz), 2.26 (3H, s), 2.60 (2H, q, J = 7.5 Hz), 3.86 (3H, s), 6.82 (1H, dd, J = 2.5, 8.1 Hz), 6.88-6.90 (2H, m), 7.06 (1H, dd, J = 4.9, 7.3 Hz), 7.12 (1H, d, J = 8.1 Hz), 7.66 (1H, dd, J = 1.9, 7.3 Hz), 8.18 (1H, dd, J = 1.9, 4.9 Hz), 8.47 (1H, s), 8.51 (1H, d, J = 5.8 Hz). | ESI-MS m/z: 321 [M + H]$^+$. |

TABLE 34

| compound | structural formula | NMR | MS |
| --- | --- | --- | --- |
| I-265 | | ¹H-NMR (400 MHz, CDCl₃) δ: 1.23 (3H, t, J = 6.4 Hz), 2.64 (2H, q, J = 6.4 Hz), 3.84 (3H, s), 6.88-6.91 (3H, m), 6.98-7.00 (1H, m), 7.08 (1H, dd, J = 4.9, 7.4 Hz), 7.23-7.27 (1H, m), 7.68 (1H, dd, J = 2.0, 7.4 Hz), 8.20 (1H, dd, J = 2.0, 4.9 Hz), 8.47 (1H, s), 8.51 (1H, d, J = 5.8 Hz). | ESI-MS m/z: 307 [M + H]⁺. |
| I-266 | | ¹H-NMR (400 MHz, CDCl₃) δ: 2.08 (2H, quin, J = 7.3 Hz), 2.85-2.93 (4H, m), 3.86 (3H, s), 6.84 (1H, dd, J = 2.3, 8.2 Hz), 6.89 (1H, d, J = 5.5 Hz), 6.94 (1H, d, J = 2.3 Hz), 7.06 (1H, dd, J = 4.6, 7.3 Hz), 7.19 (1H, d, J = 7.8 Hz), 7.66 (1H, dd, J = 1.8, 7.3 Hz), 8.20 (1H, dd, J = 1.8, 5.0 Hz), 8.47 (1H, s), 8.52 (1H, d, J = 5.5 Hz). | ESI-MS m/z: 319 [M + H]⁺. |
| I-267 | | ¹H-NMR (400 MHz, CDCl₃) δ: 1.77 (4H, q, J = 3.3 Hz), 2.74 (4H, t, J = 3.3 Hz), 3.85 (3H, s), 6.78-6.82 (2H, m), 6.89 (1H, d, J = 5.8 Hz), 7.04-7.08 (1H, m), 7.66 (2H, dd, J = 2.0, 7.3 Hz), 8.18 (1H, dd, J = 2.0, 5.0 Hz), 8.46 (1H, s), 8.51 (1H, d, J = 5.8 Hz). | ESI-MS m/z: 333 [M + H]⁺. |
| I-268 | | ¹H-NMR (400 MHz, CDCl₃) δ: 1.70-1.84 (4H, m), 2.67-2.80 (4H, m), 3.79 (3H, s), 6.74-6.88 (2H, m), 6.97 (1H, d, J = 8.7 Hz), 7.00-7.10 (3H, m), 7.30-7.38 (2H, m), 7.66 (1H, dd, J = 1.8, 7.3 Hz), 8.15 (1H, dd, J = 1.8, 5.0 Hz). | ESI-MS m/z: 332 [M + H]⁺. |
| I-269 | | ¹H-NMR (400 MHz, CDCl₃) δ: 1.70-1.86 (4H, m), 2.65-2.83 (4H, m), 3.94 (3H, s), 6.75-6.84 (2H, m), 6.94-7.00 (1H, m), 7.00-7.10 (2H, m), 7.60-7.75 (2H, m), 8.10-8.21 (2H, m). | ESI-MS m/z: 333 [M + H]⁺. |
| I-270 | | ¹H-NMR (400 MHz, CDCl₃) δ: 2.08 (2H, quin, J = 7.3 Hz), 2.84-2.92 (4H, m), 3.95 (3H, s), 6.85 (1H, dd, J = 2.3, 8.2 Hz), 6.94-7.00 (3H, m), 7.05 (1H, dd, J = 5.0, 7.3 Hz), 7.19 (1H, d, J = 7.7 Hz), 7.67-7.72 (2H, m), 8.15-8.21 (1H, m). | ESI-MS m/z: 319 [M + H]⁺. |

TABLE 34-continued

| compound | structural formula | NMR | MS |
|---|---|---|---|
| I-271 | | ¹H-NMR (400 MHz, CDCl₃) δ: 1.71-1.82 (4H, m), 2.74 (4H, m), 4.01 (3H, s), 6.78-6.83 (2H, m), 7.05-7.07 (1H, m), 7.07 (1H, dd, J = 5.0, 7.3 Hz), 7.70 (1H, dd, J = 1.8, 7.3 Hz), 8.20 (1H, dd, J = 2.3, 5.0, Hz), 8.55 (1H, s), 8.80 (1H, s). | ESI-MS m/z: 334 [M + H]⁺. |
| I-272 | | ¹H-NMR (400 MHz, CDCl₃) δ: 2.13 (2H, quint., J = 6.0 Hz), 2.63 (2H, t, J = 6.0 Hz), 2.94 (2H, t, J = 6.0 Hz), 3.86 (3H, s), 6.94-7.02 (3H, m), 7.14-7.19 (1H, m), 7.64 (1H, dd, J = 1.8, 7.3 Hz), 7.76 (1H, dd, J = 1.8, 7.3 Hz), 8.06 (1H, d, J = 8.7 Hz), 8.20 (1H, dd, J = 1.8, 5.0 Hz), 8.23 (1H, dd, J = 1.8, 5.0 Hz). | ESI-MS m/z: 347 [M + H]⁺. |

TABLE 35

| compound | structural formula | NMR | MS |
|---|---|---|---|
| I-273 | | ¹H-NMR (400 MHz, CDCl₃) δ: 2.08-2.16 (2H, m), 2.62 (2H, t, J = 6.0 Hz), 2.92 (2H, t, J = 6.0 Hz), 3.70 (3H, s), 6.93-7.07 (4H, m), 7.16 (1H, dd, J = 5.0, 7.3 Hz), 7.31 (1H, d, J = 7.8 Hz), 7.37 (1H, t, J = 8.2 Hz), 7.74 (1H, dd, J = 1.8, 7.8 Hz), 8.04 (1H, d, J = 8.7 Hz), 8.21 (1H, dd, J = 1.8, 5.0 Hz). | ESI-MS m/z: 346 [M + H]⁺. |
| I-274 | | ¹H-NMR (400 MHz, CDCl₃) δ: 1.20 (3H, t, J = 7.0 Hz), 2.88 (2H, t, J = 7.3 Hz), 3.51 (2H, q, J = 7.0 Hz), 3.63 (2H, t, 7.3 Hz), 3.84 (3H, s), 6.89 (1H, d, J = 5.8 Hz), 6.98-7.02 (2H, m), 7.08 (1H, dd, J = 5.0, 7.3 Hz), 7.20-7.23 (2H, m), 7.67 (1H, dd, J = 1.9, 7.3 Hz), 8.19 (1H, dd, J = 1.9, 5.0 Hz), 8.46 (1H, s), 8.51 (1H, d, J = 5.8 Hz). | ESI-MS m/z: 351 [M + H]⁺. |
| I-275 | | ¹H-NMR (400 MHz, CDCl₃) δ: 1.32 (6H, s), 3.31 (3H, s), 3.37 (2H, s), 3.84 (3H, s), 6.88 (1H, d, J = 6.0 Hz), 7.00-7.04 (2H, m), 7.09 (1H, dd, J = 5.0, 7.3 Hz), 7.34-7.38 (2H, m), 7.68 (1H, dd, J = 2.3, 7.3 Hz), 8.20 (1H, dd, J = 2.3, 5.0 Hz), 8.45 (1H, s), 8.51 (1H, d, J = 6.0 Hz). | ESI-MS m/z: 365 [M + H]⁺. |

TABLE 35-continued

| compound | structural formula | NMR | MS |
|---|---|---|---|
| I-276 | | ¹H-NMR (400 MHz, CDCl₃) δ: 0.83-0.89 (4H, m), 3.30 (3H, s), 3.45 (2H, s), 3.83 (3H, s), 6.88 (1H, d, J = 5.5 Hz), 6.98-7.02 (2H, m), 7.09 (1H, dd, J = 5.0, 7.3 Hz), 7.30-7.34 (2H, m), 7.68 (1H, dd, J = 1.8, 7.3 Hz), 8.20 (1H, dd, J = 1.8, 5.0 Hz), 8.45 (1H, s), 8.51 (1H, d, J = 5.5 Hz). | ESI-MS m/z: 363 [M + H]⁺. |
| I-277 | | ¹H-NMR (400 MHz, CDCl₃) δ: 3.94 (3H, s), 5.04 (2H, s), 6.91-7.10 (6H, m), 7.28-7.48 (5H, m), 7.64-7.72 (2H, m), 8.16 (1H, dd, J = 1.8, 5.0 Hz), 8.20 (1H, dd, J = 1.8, 5.0 Hz). | ESI-MS m/z: 385 [M + H]⁺. |
| I-278 | | ¹H-NMR (400 MHz, CDCl₃) δ: 1.13 (3H, t, J = 7.3 Hz), 2.32 (2H, q, J = 7.3 Hz), 2.93 (2H, t, J = 6.8 Hz), 3.84 (3H, s), 4.28 (2H, t, J = 6.8 Hz), 6.91 (1H, d, J = 4.6 Hz), 7.00-7.03 (2H, d, J = 8.7 Hz), 7.09 (1H, dd, J = 5.0, 7.3 Hz), 7.20-7.24 (2H, d, J = 8.3 Hz), 7.68 (1H, dd, J = 1.8, 7.3 Hz), 8.19 (1H, dd, J = 1.8, 5.0 Hz), 8.40-8.60 (2H, m). | ESI-MS m/z: 379 [M + H]⁺. |
| I-279 | | ¹H-NMR (400 MHz, CDCl₃) δ: 2.63 (2H, t, J = 7.3 Hz), 2.94 (2H, t, J = 7.3 Hz), 3.68 (3H, s), 3.84 (3H, s), 6.89 (1H, d, J = 6.0 Hz), 6.99-7.03 (2H, m), 7.09 (1H, dd, J = 4.6, 7.3 Hz), 7.18-7.22 (2H, m), 7.68 (1H, dd, J = 1.8, 7.3 Hz), 8.19 (1H, dd, J = 1.8, 4.6 Hz), 8.46 (1H, s), 8.52 (1H, d, J = 6.0 Hz). | ESI-MS m/z: 365 [M + H]⁺. |
| I-280 | | ¹H-NMR (400 MHz, CDCl₃) δ: 1.24 (3H, t, J = 7.6 Hz), 2.64 (2H, q, J = 7.6 Hz), 3.93 (3H, s), 6.96-7.03 (3H, m), 7.06 (1H, dd, J = 4.9, 7.3 Hz), 7.17-7.21 (2H, m), 7.67-7.72 (2H, m), 8.17 (1H, dd, J = 1.9, 7.3 Hz), 8.19 (1H, dd, J = 1.9, 4.9 Hz). | ESI-MS m/z: 307 [M + H]⁺. |

TABLE 36

| compound | structural formula | NMR | MS |
|---|---|---|---|
| I-281 | | ¹H-NMR (400 MHz, CDCl₃) δ: 1.24 (3H, t, J = 7.6 Hz), 2.64 (2H, q, J = 7.6 Hz), 3.90 (3H, s), 6.99-7.02 (2H, m), 7.07 (1H, dd, J = 5.0, 7.4 Hz), 7.18-7.21 (2H, m), 7.31 (1H, dd, J = 0.4, 4.8 Hz), 7.69 (1H, dd, J = 2.0, 7.4 Hz), 8.20 (1H, dd, J = 2.0, 5.0 Hz), 8.33 (1H, d, J = 4.8 Hz), 8.38 (1H, s). | ESI-MS m/z: 307 [M + H]⁺. |
| I-282 | | ¹H-NMR (400 MHz, CDCl₃) δ: 1.24 (3H, t, J = 7.6 Hz), 2.65 (2H, q, J = 7.6 Hz), 4.00 (3H, s), 6.99-7.02 (2H, m), 7.08 (1H, dd, J = 5.0, 7.4 Hz), 7.19-7.21 (2H, m), 7.70 (1H, dd, J = 2.0, 7.4 Hz), 8.21 (1H, dd, J = 2.0, 5.0 Hz), 8.54 (1H, s), 8.80 (1H, s). | ESI-MS m/z: 308 [M + H]⁺. |
| I-283 | | ¹H-NMR (400 MHz, CDCl₃) δ: 1.24 (3H, t, J = 7.6 Hz), 2.65 (2H, q, J = 7.6 Hz), 4.07 (3H, d, J = 4.4 Hz), 6.99-7.01 (2H, m), 7.08 (1H, dd, J = 5.0, 7.4 Hz), 7.19-7.21 (2H, m), 7.64 (1H, dd, J = 2.0, 7.4 Hz), 8.20 (1H, dd, J = 2.0, 5.0 Hz), 8.29 (1H, s), 8.41 (1H, d, J = 4.3 Hz). | ESI-MS m/z: 325 [M + H]⁺. |
| I-284 | | ¹H-NMR (400 MHz, CDCl₃) δ: 1.24 (3H, t, J = 7.6 Hz), 2.65 (2H, q, J = 7.6 Hz), 3.83 (3H, s), 6.99-7.02 (2H, m), 7.10 (1H, dd, J = 5.0, 7.3 Hz), 7.19-7.21 (2H, m), 7.69 (1H, dd, J = 2.0, 7.3 Hz), 8.22 (1H, dd, J = 2.0, 5.0 Hz), 8.45 (1H, s), 8.55 (1H, s). | ESI-MS m/z: 341, 343 [M + H]⁺. |
| I-285 | | ¹H-NMR (400 MHz, CDCl₃) δ: 1.23 (3H, t, J = 7.6 Hz), 2.65 (2H, q, J = 7.6 Hz), 3.75 (3H, s), 6.99-7.02 (2H, m), 7.10 (1H, dd, J = 5.0, 7.3 Hz), 7.19-7.21 (2H, m), 7.71 (1H, dd, J = 2.0, 7.3 Hz), 8.22 (1H, dd, J = 2.0, 5.0 Hz), 8.49 (1H, s), 8.68 (1H, s). | ESI-MS m/z: 385, 387 [M + H]⁺. |
| I-286 | | ¹H-NMR (400 MHz, CDCl₃) δ: 1.23 (3H, t, J = 7.6 Hz), 2.31 (3H, s), 2.64 (2H, q, J = 7.6 Hz), 3.62 (3H, s), 7.00-7.02 (2H, m), 7.08 (1H, dd, J = 5.0, 7.3 Hz), 7.18-7.20 (2H, m), 7.70 (1H, dd, J = 2.0, 7.3 Hz), 8.20 (1H, dd, J = 2.0, 5.0 Hz), 8.38 (1H, s), 8.41 (1H, s). | ESI-MS m/z: 321 [M + H]⁺. |

TABLE 36-continued

| compound | structural formula | NMR | MS |
|---|---|---|---|
| I-287 | | $^1$H-NMR (400 MHz, CDCl$_3$) δ: 1.24 (3H, t, J = 7.6 Hz), 2.65 (2H, q, J = 7.6 Hz), 3.80 (3H, s), 6.99-7.02 (2H, m), 7.13 (1H, dd, J = 5.0, 7.3 Hz), 7.20-7.22 (2H, m), 7.73 (1H, dd, J = 2.0, 7.3 Hz), 8.25 (1H, dd, J = 2.0, 5.0 Hz), 8.71 (1H, s), 8.97 (1H, s), 10.48 (1H, s). | ESI-MS m/z: 335 [M + H]$^+$. |
| I-288 | | $^1$H-NMR (400 MHz, CDCl$_3$) δ: 1.24 (3H, t, J = 7.6 Hz), 2.65 (2H, q, J = 7.6 Hz), 3.65 (3H, s), 7.02 (1H, t, J = 64.3 Hz), 6.99-7.02 (2H, m), 7.12 (1H, dd, J = 5.0, 7.3 Hz), 7.20-7.22 (2H, m), 7.74 (1H, dd, J = 2.0, 7.3 Hz), 8.24 (1H, dd, J = 2.0, 5.0 Hz), 8.68 (1H, s), 8.76 (1H, s). | ESI-MS m/z: 357 [M + H]$^+$. |

TABLE 37

| compound | structural formula | NMR | MS |
|---|---|---|---|
| I-289 | | $^1$H-NMR (400 MHz, CDCl$_3$) δ: 1.23 (3H, t, J = 7.6 Hz), 2.32 (3H, s), 2.64 (2H, q, J = 6.4 Hz), 6.97-6.99 (2H, m), 7.10 (1H, dd, J = 5.0, 7.3 Hz), 7.17-7.22 (3H, m), 7.60 (1H, dd, J = 2.0, 7.3 Hz), 8.21 (1H, dd, J = 2.0, 5.0 Hz), 8.46 (1H, s), 8.48 (1H, d, J = 5.0 Hz). | ESI-MS m/z: 291 [M + H]$^+$. |
| I-290 | | $^1$H-NMR (400 MHz, CDCl$_3$) δ: 1.23 (3H, t, J = 7.6 Hz), 2.64 (2H, q, J = 7.6 Hz), 7.01-7.04 (2H, m), 7.10 (1H, dd, J = 5.0, 7.3 Hz), 7.19-7.21 (2H, m), 7.44 (1H, d, J = 5.3 Hz), 7.66 (1H, dd, J = 1.9, 7.3 Hz), 8.24 (1H, dd, J = 1.9, 5.0 Hz), 8.52 (1H, d, J = 5.3 Hz), 8.62 (1H, s). | ESI-MS m/z: 311, 313 [M + H]$^+$. |
| I-291 | | $^1$H-NMR (400 MHz, CDCl$_3$) δ: 1.17 (3H, t, J = 7.6 Hz), 1.23 (3H, t, J = 7.6 Hz), 2.61-2.66 (4H, m), 6.95-6.98 (2H, m), 7.08 (1H, dd, J = 5.0, 7.3 Hz), 7.17-7.19 (2H, m), 7.25-7.26 (1H, m), 7.59 (1H, dd, J = 2.0, 7.3 Hz), 8.21 (1H, dd, J = 2.0, 5.0 Hz), 8.44 (1H, s), 8.53 (1H, d, J = 5.2 Hz). | ESI-MS m/z: 305 [M + H]$^+$. |

TABLE 37-continued

| compound | structural formula | NMR | MS |
|---|---|---|---|
| I-292 | | $^1$H-NMR (400 MHz, CDCl$_3$) δ: 1.22 (3H, t, J = 7.6 Hz), 2.61 (2H, q, J = 7.6 Hz), 6.60 (1H, d, J = 2.3 Hz), 6.95 (1H, dd, J = 1.4, 6.8 Hz), 7.00-7.05 (2H, m), 7.12-7.16 (3H, m), 7.20 (1H, dd, J = 6.8, 8.7 Hz), 7.61 (1H, dd, J = 1.4, 8.7 Hz), 7.96 (1H, d, J = 2.3 Hz), 8.00 (1H, dd, J = 1.8, 7.3 Hz), 8.27 (1H, d, J = 2.3, 5.0 Hz). | ESI-MS m/z: 316 [M + H]$^+$. |
| I-293 | | $^1$H-NMR (400 MHz, CDCl$_3$) δ: 1.22 (3H, t, J = 7.6 Hz), 2.25 (3H, d, J = 0.9 Hz), 2.63 (2H, q, J = 7.6 Hz), 6.97-7.01 (2H, m), 7.09 (1H, dd, J = 5.0, 7.3 Hz), 7.17-7.23 (2H, m), 7.53-7.54 (2H, m), 7.61-7.64 (2H, m), 8.01 (1H, t, J = 1.0 Hz), 8.21 (1H, dd, J = 2.0, 5.0 Hz). | ESI-MS m/z: 330 [M + H]$^+$. |
| I-294 | | $^1$H-NMR (400 MHz, CDCl$_3$) δ: 3.80 (3H, s), 6.64 (1H, t, J = 56.8 Hz), 6.89 (1H, d, J = 6.0 Hz), 7.17 (3H, m), 7.49-7.52 (2H, m), 7.73 (1H, dd, J = 1.8, 7.3 Hz), 8.22 (1H, dd, J = 1.8, 5.0 Hz), 8.46 (1H, s), 8.54 (1H, d, J = 5.5 Hz). | ESI-MS m/z: 329 [M + H]$^+$. |
| I-295 | | $^1$H-NMR (400 MHz, CDCl$_3$) δ: 2.41 (3H, s), 3.81 (3H, s), 6.73 (1H, t, J = 55.4 Hz), 6.89 (1H, d, J = 6.0 Hz), 6.94-6.99 (2H, m), 7.14 (1H, dd, J = 5.0, 7.3 Hz), 7.49 (1H, d, J = 8.2 Hz), 7.71 (1H, dd, J = 1.8, 7.3 Hz), 8.22 (1H, dd, J = 1.8, 5.0 Hz), 8.45 (1H, s), 8.52 (1H, d, J = 6.0 Hz). | ESI-MS m/z: 343 [M + H]$^+$. |
| I-296 | | $^1$H-NMR (400 MHz, CDCl$_3$) δ: 1.24 (3H, t, J = 7.5 Hz), 2.75 (2H, q, J = 7.5 Hz), 3.81 (3H, s), 6.77 (1H, t, J = 55.7 Hz), 6.89 (1H, d, J = 5.8 Hz), 6.97-7.01 (2H, m), 7.14 (1H, dd, J = 4.9, 7.4 Hz), 7.50-7.54 (1H, m), 7.72 (1H, dd, J = 1.9, 7.4 Hz), 8.22 (1H, dd, J = 1.9, 4.9 Hz), 8.46 (1H, s), 8.53 (1H, d, J = 5.8 Hz). | ESI-MS m/z: 357 [M + H]$^+$. |

TABLE 38

| compound | structural formula | NMR | MS |
|---|---|---|---|
| I-297 | | ¹H-NMR (400 MHz, CDCl₃) δ: 1.92 (3H, t, J = 18.1 Hz), 3.80 (3H, s), 6.89 (1H, d, J = 5.8 Hz), 7.11-7.14 (2H, m), 7.14 (1H, dd, J = 4.9, 7.4 Hz), 7.48-7.52 (2H, m), 7.72 (1H, dd, J = 2.0, 7.4 Hz), 8.22 (1H, dd, J = 2.0, 5.0 Hz), 8.45 (1H, s), 8.53 (1H, d, J = 5.8 Hz). | ESI-MS m/z: 343 [M + H]⁺. |
| I-298 | | ¹H-NMR (400 MHz, CDCl₃) δ: 1.92 (3H, t, J = 18.1 Hz), 3.89 (3H, s), 6.98 (1H, dd, J = 5.0, 7.3 Hz), 7.13 (1H, dd, J = 5.0, 7.4 Hz), 7.13-7.15 (2H, m), 7.49-7.51 (2H, m), 7.65 (1H, dd, J = 2.0, 7.3 Hz), 7.73 (1H, dd, J = 2.0, 7.4 Hz), 8.19 (1H, dd, J = 2.0, 3.9 Hz), 8.20 (1H, dd, J = 2.0, 4.0 Hz). | ESI-MS m/z: 343 [M + H]⁺. |
| I-299 | | ¹H-NMR (400 MHz, CDCl₃) δ: 1.92 (3H, t, J = 18.1 Hz), 2.31 (3H, s), 7.10-7.13 (2H, d, J = 8.8 Hz), 7.16 (1H, dd, J = 5.0, 7.3 Hz), 7.22 (1H, d, J = 5.0 Hz), 7.49-7.52 (2H, d, J = 8.8 Hz), 7.64 (1H, dd, J = 2.0, 7.3 Hz), 8.23 (1H, dd, J = 1.9, 5.0 Hz), 8.46 (1H, s), 8.50 (1H, d, J = 5.0 Hz). | ESI-MS m/z: 327 [M + H]⁺. |
| I-300 | | ¹H-NMR (400 MHz, CDCl₃) δ: 1.92 (3H, t, J = 18.1 Hz), 3.82 (3H, s), 7.11-7.18 (3H, m), 7.52 (2H, d, J = 8.9 Hz), 7.74 (1H, dd, J = 2.0, 7.4 Hz), 8.25 (1H, dd, J = 2.0, 4.9 Hz), 8.44 (1H, s), 8.57 (1H, s). | ESI-MS m/z: 377, 379 [M + H]⁺. |
| I-301 | | ¹H-NMR (400 MHz, CDCl₃) δ: 1.93 (3H, t, J = 18.1 Hz), 4.04 (3H, d, J = 4.6 Hz), 7.12-7.17 (3H, m), 7.52 (2H, d, J = 8.9 Hz), 7.69 (1H, dd, J = 1.9, 7.4 Hz), 8.22 (1H, dd, J = 1.9, 4.9 Hz), 8.28 (1H, s), 8.43 (1H, d, J = 4.4 Hz). | ESI-MS m/z: 361 [M + H]⁺. |

TABLE 38-continued

| compound | structural formula | NMR | MS |
| --- | --- | --- | --- |
| I-302 | | $^1$H-NMR (400 MHz, CDCl$_3$) δ: 1.99 (3H, dt, J = 1.1, 18.5 Hz), 3.79 (3H, s), 6.87-6.93 (3H, m), 7.19 (1H, dd, J = 4.9, 7.4 Hz), 7.51 (1H, t, J = 8.4 Hz), 7.74 (1H, dd, J = 1.9, 7.4 Hz), 8.24 (1H, dd, J = 2.0, 4.9 Hz), 8.43 (1H, s), 8.53 (1H, d, J = 5.8 Hz). | ESI-MS m/z: 361 [M + H]$^+$. |
| I-303 | | $^1$H-NMR (400 MHz, CDCl$_3$) δ: 1.98 (3H, dt, J = 1.1, 18.6 Hz), 2.29 (3H, s), 6.87-6.90 (1H, m), 6.90-6.92 (1H, m), 7.20 (1H, dd, J = 4.9, 7.4 Hz), 7.22-7.24 (1H, m), 7.51 (1H, t, J = 8.3 Hz), 7.67 (1H, dd, J = 1.9, 7.3 Hz), 8.26 (1H, dd, J = 2.0, 4.9 Hz), 8.44 (1H, s), 8.50 (1H, d, J = 5.0 Hz). | ESI-MS m/z: 345 [M + H]$^+$. |
| I-304 | | $^1$H-NMR (400 MHz, CDCl$_3$) δ: 1.92 (3H, t, J = 18.1 Hz), 3.87 (3H, s), 6.92 (1H, d, J = 5.8 Hz), 7.13 (1H, dd, J = 5.0, 7.3 Hz), 7.19-7.23 (1H, m), 7.26-7.34 (2H, m), 7.71 (1H, dd, J = 1.9, 7.3 Hz), 8.15 (1H, dd, J = 1.9, 5.0 Hz), 8.49 (1H, s), 8.54 (1H, d, J = 5.8 Hz). | ESI-MS m/z: 361 [M + H]$^+$. |

TABLE 39

| compound | structural formula | NMR | MS |
| --- | --- | --- | --- |
| I-305 | | $^1$H-NMR (400 MHz, CDCl$_3$) δ: 1.92 (3H, t, J = 18.1 Hz), 2.33 (3H, s), 7.16 (1H, dd, J = 5.0, 7.3 Hz), 7.17-7.25 (1H, m), 7.23 (1H, td, J = 0.6, 5.1 Hz), 7.27-7.34 (2H, m), 7.64 (1H, dd, J = 1.9, 7.3 Hz), 8.18 (1H, dd, J = 1.9, 5.0 Hz), 8.48 (1H, s), 8.51 (1H, d, J = 5.0 Hz). | ESI-MS m/z: 345 [M + H]$^+$. |
| I-306 | | $^1$H-NMR (400 MHz, CDCl$_3$) δ: 2.31 (3H, s), 4.62 (2H, td, J = 12.2, 46.6 Hz), 7.17-7.22 (2H, m), 7.17-7.19 (2H, m), 7.52-7.54 (2H, m), 7.66 (1H, dd, J = 1.9, 7.4 Hz), 8.24 (1H, dd, J = 2.0, 5.0 Hz), 8.46 (1H, s), 8.50 (1H, d, J = 5.0 Hz). | ESI-MS m/z: 345 [M + H]$^+$. |

TABLE 39-continued

| compound | structural formula | NMR | MS |
|---|---|---|---|
| I-307 | | $^1$H-NMR (400 MHz, CDCl$_3$) δ: 1.90 (3H, t, J = 18.1 Hz), 6.61 (1H, d, J = 2.3 Hz), 6.92 (1H, dd, J = 1.2, 6.9 Hz), 7.17-7.19 (2H, d, J = 8.9 Hz), 7.18-7.22 (2H, m), 7.46-7.49 (2H, m), 7.61 (1H, dd, J = 1.3, 8.9 Hz), 7.94 (1H, d, J = 2.3 Hz), 8.02 (1H, dd, J = 2.0, 7.4 Hz), 8.30 (1H, dd, J = 2.0, 5.0 Hz). | ESI-MS m/z: 352 [M + H]$^+$. |
| I-308 | | $^1$H-NMR (400 MHz, CDCl$_3$) δ: 1.90 (3H, t, J = 18.1 Hz), 7.12-7.15 (2H, m), 7.21 (1H, dd, J = 5.0, 7.3 Hz), 7.45-7.47 (2H, m), 7.85 (1H, dd, J = 2.0, 7.3 Hz), 7.87 (1H, d, J = 1.3 Hz), 7.88 (1H, s), 8.16-8.20 (1H, m), 8.29 (1H, dd, J = 1.9, 4.9 Hz), 8.79 (1H, d, J = 1.8 Hz), 8.85 (1H, d, J = 1.8 Hz). | ESI-MS m/z: 364 [M + H]$^+$. |
| I-309 | | $^1$H-NMR (400 MHz, CDCl$_3$) δ: 3.74 (3H, s), 7.00 (1H, d, J = 7.8 Hz), 7.14 (1H, dt, J = 0.9, 7.8 Hz), 7.48 (1H, ddd, J = 1.8, 7.3, 7.8 Hz), 7.53 (1H, dd, J = 1.8, 7.8 Hz), 7.66 (1H, dd, J = 2.7, 8.7 Hz), 7.74 (1H, d, J = 8.2 Hz), 8.10 (1H, d, J = 2.7 Hz), 8.49 (1H, d, J = 2.3 Hz), 8.56 (1H, d, J = 2.7 Hz). | ESI-MS m/z: 348 [M + H]$^+$. |
| I-310 | | $^1$H-NMR (400 MHz, CDCl$_3$) δ: 3.82 (3H, s), 7.03 (1H, d, J = 8.3 Hz), 7.09 (1H, dd, J = 1.0, 8.4 Hz), 7.36 (1H, dd, J = 1.7, 7.5 Hz), 7.46 (1H, dt, J = 0.9, 7.5 Hz), 7.69 (1H, dd, J = 2.5, 8.5 Hz), 7.75 (1H, d, J = 2.5 Hz), 8.56 (1H, d, J = 2.6 Hz), 8.65 (1H, s), 8.74 (1H, s). | ESI-MS m/z: 348 [M + H]$^+$. |
| I-311 | | $^1$H-NMR (CDCl$_3$) δ: 3.78 (3H, s), 7.02 (1H, d, J = 8.2 Hz), 7.11 (1H, t, J = 7.3 Hz), 7.36 (1H, dd, J = 1.8, 7.3 Hz), 7.48 (1H, dt, J = 1.8, 7.3 Hz), 7.54 (1H, d, J = 4.6 Hz), 7.72-7.77 (2H, m), 8.57 (1H, d, J = 1.8 Hz), 9.05 (1H, d, J = 4.6 Hz). | ESI-MS m/z: 348 [M + H]$^+$. |

TABLE 39-continued

| compound | structural formula | NMR | MS |
|---|---|---|---|
| I-312 | | $^1$H-NMR (400 MHz, CDCl$_3$) δ: 2.04 (3H, t, J = 18.9 Hz), 3.83 (3H, s), 7.03 (1H, dd, J = 0.7, 8.4 Hz), 7.10 (1H, dt, J = 1.0, 7.5 Hz), 7.37 (1H, dd, J = 1.7, 7.5 Hz), 7.43-7.48 (1H, m), 7.60 (1H, dd, J = 2.6, 8.6 Hz), 7.72 (1H, dd, J = 0.6, 8.6 Hz), 8.48 (1H, dd, J = 0.5, 2.6 Hz), 8.63 (1H, s), 8.73 (1H, s). | ESI-MS m/z: 344 [M + H]$^+$. |

TABLE 40

| compound | structural formula | NMR | MS |
|---|---|---|---|
| I-313 | | $^1$H-NMR (400 MHz, CDCl$_3$) δ: 3.84 (3H, s), 6.72 (1H, br s), 6.98 (1H, dd, J = 4.6, 7.3 Hz), 7.09 (1H, d, J = 8.2 Hz), 7.14 (1H, t, J = 7.8 Hz), 7.28 (1H, dd, J = 1.8, 7.8 Hz), 7.42-7.62 (3H, m), 8.30 (1H, dd, J = 1.8, 5.0 Hz), 8.41-8.49 (2H, m). | ESI-MS m/z: 346 [M + H]$^+$. |
| I-314 | | $^1$H-NMR (400 MHz, CDCl$_3$) δ: 7.00-7.05 (2H, m), 7.27-7.37 (2H, m), 7.45-7.55 (2H, m), 7.60 (1H, t, J = 7.3 Hz), 7.71 (1H, d, J = 6.9 Hz), 7.76 (1H, dd, J = 0.8, 7.3 Hz), 7.93 (1H, dd, J = 2.3, 6.9 Hz), 7.98 (1H, d, J = 8.2 Hz), 8.17 (1H, d, J = 2.7 Hz), 8.48 (1H, d, J = 2.7 Hz). | ESI-MS m/z: 333, 335 [M + H]$^+$ |
| I-315 | | $^1$H-NMR (400 MHz, CDCl$_3$) δ: 1.73-1.84 (4H, m), 2.69-2.81 (4H, m), 3.82 (3H, s), 6.79-6.87 (2H, m), 7.00 (1H, d, J = 8.2 Hz), 7.04-7.14 (2H, m), 7.43 (1H, dt, J = 1.8, 7.3 Hz), 7.50 (1H, dd, J = 1.8, 7.8 Hz), 8.07 (1H, d, J = 2.7 Hz), 8.32 (1H, d, J = 2.7 Hz). | ESI-MS m/z: 333 [M + H]$^+$. |
| I-316 | | $^1$H-NMR (400 MHz, CDCl$_3$) δ: 1.74-1.85 (4H, m), 2.71-2.81 (4H, m), 3.96 (3H, s), 6.82 (1H, d, J = 2.3 Hz), 6.85 (1H, dd, J = 2.7, 8.2 Hz), 7.05 (1H, dd, J = 5.0, 6.9 Hz), 7.09 (1H, d, J = 8.2 Hz), 7.83 (1H, dd, J = 1.8, 7.3 Hz), 8.10 (1H, d, J = 2.7 Hz), 8.27 (1H, dd, J = 1.8, 5.0 Hz), 8.32 (1H, d, J = 2.7 Hz). | ESI-MS m/z: 334 [M + H]$^+$. |

TABLE 40-continued

| compound | structural formula | NMR | MS |
|---|---|---|---|
| I-317 | | $^1$H-NMR (400 MHz, CDCl$_3$) δ: 1.74-1.86 (4H, m), 2.71-2.81 (4H, m), 3.88 (3H, s), 6.80 (1H, d, J = 2.3 Hz), 6.83 (1H, dd, J = 2.7, 8.2 Hz), 6.92 (1H, d, J = 5.5 Hz), 7.09 (1H, d, J = 7.8 Hz), 8.12 (1H, d, J = 2.7 Hz), 8.35 (1H, d, J = 2.7 Hz), 8.58 (1H, d, J = 6.0 Hz), 8.62 (1H, s). | ESI-MS m/z: 334 [M + H]$^+$. |
| I-318 | | $^1$H-NMR (400 MHz, CDCl$_3$) δ: 3.97 (3H, s), 5.06 (2H, s), 6.97-7.10 (5H, m), 7.31-7.47 (5H, m), 7.84 (1H, dd, J = 1.8, 7.3 Hz), 8.09 (1H, d, J = 2.7 Hz), 8.28 1H, dd, J = 1.8, 5.0 Hz), 8.33 (1H, d, J = 2.7 Hz). | ESI-MS m/z: 386 [M + H]$^+$. |
| I-319 | | $^1$H-NMR (400 MHz, CDCl$_3$) δ: 3.82 (3H, s), 7.01-7.09 (4H, m), 7.33-7.46 (4H, m), 8.57 (1H, s), 8.72 (1H, s). | ESI-MS m/z: 313, 315 [M + H]$^+$. |
| I-320 | | $^1$H-NMR (400 MHz, CDCl$_3$) δ: 1.25 (6H, d, J = 6.9 Hz), 2.94 (1H, sep, J = 6.8 Hz), 3.82 (3H, s), 6.94-7.09 (4H, m), 7.25 (2H, d, J = 8.2 Hz), 7.30-7.42 (2H, m), 8.55 (1H, s), 8.72 (1H, s). | ESI-MS m/z: 321 [M + H]$^+$. |

TABLE 41

| compound | structural formula | NMR | MS |
|---|---|---|---|
| I-321 | | $^1$H-NMR (400 MHz, CDCl$_3$) δ: 3.81 (3H, s), 7.01 (1H, d, J = 8.3 Hz), 7.09 (1H, dt, J = 1.0, 7.3 Hz), 7.25 (2H, d, J = 8.3 Hz), 7.36 (1H, dd, J = 1.8, 7.3 Hz), 7.44 (1H, dt, J = 1.8, 7.3 Hz), 7.67 (2H, d, J = 8.3 Hz), 8.61 (1H, s), 8.74 (1H, s). | ESI-MS m/z: 347 [M + H]$^+$. |

TABLE 41-continued

| compound | structural formula | NMR | MS |
| --- | --- | --- | --- |
| I-322 | | $^1$H-NMR (400 MHz, CDCl$_3$) δ: 3.82 (3H, s), 6.66 (1H, t, J = 56.5 Hz), 7.02 (1H, d, J = 8.3 Hz), 7.09 (1H, dt, J = 1.0, 7.5 Hz), 7.21-7.23 (2H, m), 7.37 (1H, dd, J = 1.7, 7.5 Hz), 7.41-7.46 (1H, m), 7.55-7.57 (2H, m), 8.60 (1H, s), 8.73 (1H, s). | ESI-MS m/z: 329 [M + H]$^+$. |
| I-323 | | $^1$H-NMR (400 MHz, CDCl$_3$) δ: 2.44 (3H, s), 3.82 (3H, s), 6.75 (1H, t, J = 55.4 Hz), 6.99-7.05 (3H, m), 7.08 (1H, dt, J = 1.0, 7.5 Hz), 7.36 (1H, dd, J = 1.7, 7.5 Hz), 7.40-7.46 (1H, m), 7.55 (1H, d, J = 8.4 Hz), 8.59 (1H, s), 8.75 (1H, s). | ESI-MS m/z: 343 [M + H]$^+$. |
| I-324 | | $^1$H-NMR (400 MHz, CDCl$_3$) δ: 2.55 (3H, s), 3.31 (2H, t, J = 8.7 Hz), 4.61 (2H, t, J = 8.7 Hz), 6.72 (1H, t, J = 54.5 Hz), 6.98 (1H, t, J = 7.5 Hz), 7.28-7.31 (2H, m), 7.46 (1H, d, J = 2.3 Hz), 8.33 (1H, d, J = 2.3 Hz), 8.71 (1H, s), 8.77 (1H, s). | ESI-MS m/z: 356 [M + H]$^+$. |
| I-325 | | $^1$H-NMR (400 MHz, CDCl$_3$) δ: 2.56 (3H, s), 3.93 (3H, s), 6.72 (1H, t, J = 54.5 Hz), 7.00-7.05 (2H, m), 7.45 (1H, d, J = 2.3 Hz), 8.32 (1H, d, J = 2.3 Hz), 8.66 (1H, s), 8.77 (1H, s). | ESI-MS m/z: 380 [M + H]$^+$. |
| I-326 | | $^1$H-NMR (400 MHz, CDCl$_3$) δ: 2.09 (2H, quint, J = 7.6 Hz), 2.85-2.94 (4H, m), 6.64 (1H, d, J = 2.3 Hz), 6.89-6.93 (1H, m), 6.96 (1H, dd, J = 1.2, 6.9 Hz), 6.99-7.03 (1H, m), 7.19-7.24 (2H, m), 7.66 (1H, dd, J = 1.2, 9.0 Hz), 7.98 (1H, d, J = 2.3 Hz), 8.87 (2H, br s). | ESI-MS m/z: 329 [M + H]$^+$. |

TABLE 41-continued

| compound | structural formula | NMR | MS |
|---|---|---|---|
| I-327 | | $^1$H-NMR (400 MHz, CDCl$_3$) δ: 3.31 (2H, d, J = 8.7 Hz), 4.60 (2H, d, J = 8.7 Hz), 6.99 (1H, t, J = 7.4 Hz), 7.28-7.32 (2H, m), 7.72 (1H, dd, J = 2.3, 8.6 Hz), 7.77 (1H, d, J = 8.6 Hz), 8.61 (1H, d, J = 2.3 Hz), 8.71 (1H, s), 8.78 (1H, s). | ESI-MS m/z: 360 [M + H]$^+$. |
| I-328 | | $^1$H-NMR (400 MHz, CDCl$_3$) δ: 3.79 (3H, s), 6.86 (1H, dd, J = 6.5, 12.0 Hz), 7.23 (1H, dd, J = 8.6, 10.2 Hz), 7.68 (1H, dd, J = 2.5, 8.6 Hz), 7.77 (1H, d, J = 8.6 Hz), 8.56 (1H, d, J = 2.5 Hz), 8.62 (1H, s), 8.75 (1H, s). | ESI-MS m/z: 384 [M + H]$^+$. |

TABLE 42

| compound | structural formula | NMR | MS |
|---|---|---|---|
| I-329 | | $^1$H-NMR (400 MHz, CDCl$_3$) δ: 3.94 (3H, s), 7.01-7.06 (2H, m), 7.72 (1H, dd, J = 2.4, 8.5 Hz), 7.79 (1H, d, J = 8.5 Hz), 8.60 (1H, d, J = 2.4 Hz), 8.68 (1H, s), 8.78 (1H, s). | ESI-MS m/z: 384 [M + H]$^+$. |
| I-330 | | $^1$H-NMR (400 MHz, CDCl$_3$) δ: 3.96 (3H, s), 7.04 (1H, dd, J = 5.0, 7.3 Hz), 7.25 (2H, d, J = 8.3 Hz), 7.68-7.71 (3H, m), 8.27 (1H, dd, J = 2.3, 5.0 Hz), 8.64 (1H, s), 8.75 (1H, s). | ESI-MS m/z: 348 [M + H]$^+$. |

TABLE 42-continued

| compound | structural formula | NMR | MS |
|---|---|---|---|
| I-331 | | $^1$H-NMR (400 MHz, CDCl$_3$) δ: 3.92 (3H, s), 7.23-7.28 (2H, m), 7.70-7.72 (2H, m), 8.48 (1H, s), 8.64 (2H, m), 8.81 (1H, s). | ESI-MS m/z: 382, 384 [M + H]$^+$. |
| I-332 | | $^1$H-NMR (400 MHz, CDCl$_3$) δ: 6.65 (1H, d, J = 2.2 Hz), 6.95 (1H, dd, J = 1.2, 6.8 Hz), 7.24 (1H, dd, J = 6.8, 8.3 Hz), 7.30 (2H, d, J = 8.3 Hz), 7.66 (2H, d, J = 8.3 Hz), 7.70 (1H, d, J = 1.3 Hz), 7.96 (1H, d, J = 2.3 Hz), 8.87 (1H, s), 8.88 (1H, s). | ESI-MS m/z: 357 [M + H]$^+$. |
| I-333 | | $^1$H-NMR (400 MHz, CDCl$_3$) δ: 1.92 (3H, t, J = 18.1 Hz), 6.65 (1H, d, J = 2.3 Hz), 6.96 (1H, dd, J = 1.2, 6.8 Hz), 7.21-7.24 (2H, m), 7.24 (1H, d, J = 8.9 Hz), 7.53-7.55 (2H, m), 7.68 (1H, dd, J = 1.3, 8.9 Hz), 7.97 (1H, d, J = 2.3 Hz), 8.87 (1H, s), 8.88 (1H, s). | ESI-MS m/z: 353 [M + H]$^+$. |
| I-334 | | $^1$H-NMR (400 MHz, CDCl$_3$) δ: 2.05 (3H, t, J = 18.6 Hz), 3.94 (3H, s), 7.01-7.06 (2H, m), 7.64 (1H, dd, J = 2.6, 8.6 Hz), 7.75 (1H, dd, J = 0.6, 8.6 Hz), 8.51 (1H, dd, J = 0.5, 2.6 Hz), 8.66 (1H, s), 8.77 (1H, s). | ESI-MS m/z: 380 [M + H]$^+$. |
| I-335 | | $^1$H-NMR (400 MHz, CDCl$_3$) δ: 2.05 (3H, t, J = 18.6 Hz), 3.31 (2H, t, J = 8.7 Hz), 4.61 (2H, t, J = 8.8 Hz), 6.99 (1H, t, J = 7.6 Hz), 7.27-7.32 (2H, m), 7.65 (1H, dd, J = 2.6, 8.6 Hz), 7.73 (1H, dd, J = 0.6, 8.6 Hz), 8.52 (1H, dd, J = 0.6, 2.6 Hz), 8.71 (1H, s), 8.77 (1H, s). | ESI-MS m/z: 356 [M + H]$^+$. |

TABLE 42-continued

| compound | structural formula | NMR | MS |
| --- | --- | --- | --- |
| I-336 | | $^1$H-NMR (400 MHz, CDCl$_3$) δ: 2.05 (3H, t, J = 18.6 Hz), 3.80 (3H, s), 6.85 (1H, dd, J = 6.6, 11.9 Hz), 7.23 (1H, dd, J = 8.7, 10.2 Hz), 7.60 (1H, dd, J = 2.6, 8.6 Hz), 7.74 (1H, dd, J = 0.6, 8.6 Hz), 8.47 (1H, dd, J = 0.6, 2.6 Hz), 8.60 (1H, s), 8.74 (1H, s). | ESI-MS m/z: 380 [M + H]$^+$. |

TABLE 43

| compound | structural formula | NMR | MS |
| --- | --- | --- | --- |
| I-337 | | $^1$H-NMR (400 MHz, DMSO-d$_6$) δ: 3.78 (3H, s), 6.58 (2H, s), 7.05 (1H, t, J = 7.3 Hz), 7.12 (1H, d, J = 7.9 Hz), 7.17-7.20 (1H, m), 7.36 (1H, dd, J = 1.8, 7.3 Hz), 7.40 (1H, t, J = 8.2 Hz), 7.73 (1H, dd, J = 1.8, 7.3 Hz), 8.06 (2H, s), 8.08 (1H, dd, J = 1.8, 4.5 Hz). | ESI-MS m/z: 295 [M + H]$^+$. |
| I-338 | | $^1$H-NMR (400 MHz, CDCl$_3$) δ: 3.75 (3H, s), 6.99 (1H, d, J = 8.2 Hz), 7.06-7.10 (1H, m), 7.21 (1H, dd, J = 5.0, 7.3 Hz), 7.32 (1H, dd, J = 1.8, 7.3 Hz), 7.40-7.45 (1H, m), 7.74 (1H, dd, J = 1.8, 7.3 Hz), 8.14 (1H, dd, J = 1.8, 5.0 Hz), 8.50 (2H, s). | ESI-MS m/z: 314, 316 [M + H]$^+$. |
| I-339 | | $^1$H-NMR (400 MHz, CDCl$_3$) δ: 3.13 (3H, s), 3.82 (3H, s), 4.90 (2H, s), 7.00 (1H, d, J = 8.3 Hz), 7.04-7.09 (2H, m), 7.24-7.35 (6H, m), 7.40 (1H, t, J = 7.6 Hz), 7.66 (1H, dd, J = 1.3, 7.3 Hz), 8.11 (1H, d, J = 3.5 Hz), 8.22 (2H, s). | ESI-MS m/z: 399 [M + H]$^+$. |
| I-340 | | $^1$H-NMR (400 MHz, CDCl$_3$) δ: 1.18 (3H, t, J = 6.8 Hz), 3.14 (3H, s), 3.30 (2H, t, J = 8.7 Hz), 3.68 (2H, q, J = 6.9 Hz), 4.60 (2H, t, J = 8.7 Hz), 6.96 (1H, t, J = 7.8 Hz), 7.05-7.08 (1H, m), 7.23-7.32 (2H, m), 7.79 (1H, d, J = 7.3 Hz), 8.09 (1H, d, J = 4.6 Hz), 8.23 (2H, s). | ESI-MS m/z: 349 [M + H]$^+$. |

TABLE 43-continued

| compound | structural formula | NMR | MS |
|---|---|---|---|
| I-341 | | $^1$H-NMR (400 MHz, CDCl$_3$) δ: 2.20 (3H, s), 2.21 (3H, s), 3.78 (3H, s), 7.13 (1H, dd, J = 5.0, 7.3 Hz), 7.18 (2H, d, J = 8.7 Hz), 7.59 (1H, dd, J = 1.8, 7.3 Hz), 7.82 (2H, d, J = 8.7 Hz), 8.14 (1H, dd, J = 1.8, 5.0 Hz). | ESI-MS m/z: 348 [M + H]$^+$. |
| I-342 | | $^1$H-NMR (400 MHz, CDCl$_3$) δ: 2.42 (3H, s), 2.70 (3H, s), 7.14 (1H, dd, J = 5.0, 7.3 Hz), 7.23 (2H, d, J = 8.4 Hz), 7.65 (2H, d, J = 8.7 Hz), 7.76 (1H, dd, J = 1.8, 7.3 Hz), 8.17 (1H, dd, J = 1.8, 4.6 Hz). | ESI-MS m/z: 351 [M + H]$^+$. |
| I-343 | | $^1$H-NMR (400 MHz, CDCl$_3$) δ: 3.44 (3H, s), 4.07 (2H, t, J = 13.3 Hz), 7.22 (1H, dd, J = 0.9, 7.3 Hz), 7.27 (1H, dd, J = 5.0, 7.3 Hz), 7.62-7.74 (3H, m), 7.86 (1H, dd, J = 0.9, 8.7 Hz), 8.04 (1H, dd, J = 1.8, 7.3 Hz), 8.32 (1H, dd, J = 1.8, 5.0 Hz), 8.33 (1H, s), 8.51 (1H, d, J = 2.7 Hz). | ESI-MS m/z: 384 [M + H]$^+$. |
| I-344 | | $^1$H-NMR (400 MHz, CDCl$_3$) δ: 1.25 (3H, t, J = 7.3 Hz), 3.10 (3H, s), 3.81 (3H, s), 4.18 (2H, q, J = 7.3 Hz), 4.32 (3H, s), 6.56 (1H, d, J = 9.2 Hz), 6.98-7.08 (3H, m), 7.30-7.40 (3H, m), 7.65 (1H, dd, J = 1.8, 7.3 Hz), 7.96 (1H, d, J = 2.8 Hz), 8.10 (1H, dd, J = 1.8, 5.0 Hz). | ESI-MS m/z: 394 [M + H]$^+$. |

TABLE 44

| compound | structural formula | NMR | MS |
|---|---|---|---|
| I-345 | | $^1$H-NMR (400 MHz, CDCl$_3$) δ: 2.08 (2H, quin, J = 7.3 Hz), 2.83-2.91 (4H, m), 3.80 (3H, s), 6.85 (1H, dd, J = 2.3, 8.2 Hz), 6.94-7.06 (4H, m), 7.18 (1H, d, J = 8.2 Hz), 7.32-7.39 (2H, m), 7.67 (1H, dd, J = 1.9, 7.3 Hz), 8.15 (1H, dd, J = 2.3, 5.0 Hz). | ESI-MS m/z: 318 [M + H]$^+$. |

TABLE 44-continued

| compound | structural formula | NMR | MS |
|---|---|---|---|
| I-346 | 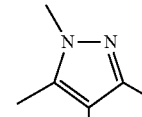 | ¹H-NMR (400 MHz, CDCl₃) δ: 2.21 (6H, s), 3.80 (3H, s), 7.18 (1H, dd, J = 4.6, 7.3 Hz), 7.58-7.66 (2H, m), 7.71 (1H, d, J = 8.7 Hz), 8.12 (1H, dd, J = 1.8, 5.0 Hz), 8.53 (1H, d, J = 2.3 Hz). | ESI-MS m/z: 349 [M + H]⁺. |
| I-347 | 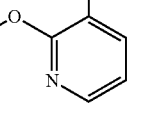 | ¹H-NMR (400 MHz, CDCl₃) δ: 3.85 (1H, t, J = 7.3 Hz), 3.87 (3H, s), 4.20 (2H, dt, J = 7.3, 12.8 Hz), 7.01 (1H, dd, J = 5.0, 7.3 Hz), 7.18 (1H, dd, J = 5.0, 7.3 Hz), 7.60 (1H, dd, J = 2.3, 8.7 Hz), 7.65 (1H, dd, J = 2.3, 7.4 Hz), 7.72 (1H, d, J = 8.7 Hz), 7.76 (1H, dd, J = 1.8, 7.3 Hz), 8.16 (1H, dd, J = 1.8, 5.1 Hz), 8.22 (1H, dd, J = 1.8, 5.1 Hz), 8.41 (1H, d, J = 2.8 Hz). | ESI-MS m/z: 360 [M + H]⁺. |
| I-348 | 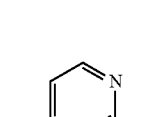 | ¹H-NMR (400 MHz, CDCl₃) δ: 3.45 (3H, s), 3.88 (3H, s), 4.07 (2H, t, J = 13.3 Hz), 7.01 (1H, dd, J = 5.1, 6.9 Hz), 7.18 (1H, dd, J = 5.1, 7.3 Hz), 7.57 (1H, dd, J = 2.3, 8.7 Hz), 7.65 (1H, dd, J = 1.8, 7.3 Hz), 7.70 (1H, d, J = 8.7 Hz), 7.76 (1H, dd, J = 1.8, 7.3 Hz), 8.18 (1H, dd, J = 1.8, 5.1 Hz), 8.22 (1H, dd, J = 1.8, 5.1 Hz), 8.47 (1H, d, J = 2.3 Hz). | ESI-MS m/z: 374 [M + H]⁺. |
| I-349 | 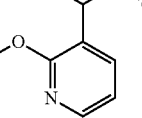 | ¹H-NMR (400 MHz, CDCl₃) δ: 3.45 (3H, s), 3.80 (3H, s), 4.08 (2H, t, J = 13.3 Hz), 6.90 (1H, d, J = 6.0 Hz), 7.20 (1H, dd, J = 5.0, 7.3 Hz), 7.56 (1H, dd, J = 2.7, 8.7 Hz), 7.70 (1H, d, J = 9.2 Hz), 7.75 (1H, dd, J = 2.7, 7.3 Hz), 8.20 (1H, dd, J = 1.8, 5.0 Hz), 8.42-8.48 (2H, m), 8.53 (1H, d, J = 5.5 Hz). | ESI-MS m/z: 374 [M + H]⁺. |
| I-350 | 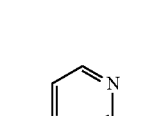 | ¹H-NMR (400 MHz, CDCl₃) δ: 3.70 (3H, s), 5.00 (2H, t, J = 13.7 Hz), 6.24 (1H, t, J = 2.3 Hz), 6.96 (1H, d, J = 2.3 Hz), 7.00 (1H, dt, J = 0.9, 7.3 Hz), 7.18 (1H, dd, J = 5.0, 7.3 Hz), 7.31 (1H, dd, J = 1.8, 7.3 Hz), 7.39 (1H, dt, J = 1.8, 8.3 Hz), 7.44 (1H, d, J = 2.3 Hz), 7.49-7.53 (2H, m), 7.56 (1H, d, J = 8.7 Hz), 7.74 (1H, dd, J = 2.3, 7.3 Hz), 8.17 (1H, dd, J = 1.8, 5.0 Hz), 8.48 (1H, d, J = 2.3 Hz). | ESI-MS m/z: 409 [M + H]⁺. |
| I-351 | 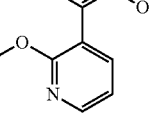 | ¹H-NMR (400 MHz, CDCl₃) δ: 3.68 (3H, s), 4.79 (2H, t, J = 13.3 Hz), 6.90 (1H, s), 6.95-7.01 (2H, m), 7.06 (1H, dt, J = 0.9, 7.3 Hz), 7.19 (1H, dd, J = 5.0, 7.3 Hz), 7.31 (1H, dd, J = 1.8, 7.3 Hz), 7.39 (1H, dt, J = 1.8, 8.3 Hz), 7.45 (1H, s), 7.52 (1H, dd, J = 2.3, 8.7 Hz), 7.56 (1H, d, J = 8.3 Hz), 7.74 (1H, dd, J = 1.8, 7.3 Hz), 8.17 (1H, dd, J = 1.8, 5.0 Hz), 8.48 (1H, d, J = 2.3 Hz). | ESI-MS m/z: 409 [M + H]⁺. |

TABLE 44-continued

| compound | structural formula | NMR | MS |
|---|---|---|---|
| I-352 | 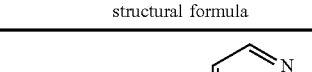 | $^1$H-NMR (400 MHz, DMSO-$d_6$) δ: 3.88 (3H, s), 6.61 (2H, s), 7.10-7.13 (1H, m), 7.20-7.23 (1H, m), 7.84 (2H, dt, J = 1.8, 7.8 Hz), 8.09 (2H, s), 8.11 (1H, dd, J = 1.8, 4.6 Hz), 8.23 (1H, dd, J = 2.2, 5.0 Hz). | ESI-MS m/z: 296 [M + H]$^+$. |

TABLE 45

| compound | structural formula | NMR | MS |
|---|---|---|---|
| I-353 |  | $^1$H-NMR (400 MHz, CDCl$_3$) δ: 3.89 (3H, s), 7.03 (1H, dd, J = 5.0, 6.9 Hz), 7.21 (1H, dd, J = 5.0, 7.3 Hz), 7.64 (1H, dd, J = 1.8, 7.3 Hz), 7.76 (1H, dd, J = 2.0, 7.3 Hz), 8.15 (1H, dd, J = 1.8, 5.0 Hz), 8.25 (1H, dd, J = 1.8, 5.0 Hz), 8.39 (2H, s). | ESI-MS m/z: 407 [M + H]$^+$ |
| I-354 |  | $^1$H-NMR (400 MHz, CDCl$_3$) δ: 3.26 (3H, s), 3.74 (3H, s), 3.96 (3H, s), 4.38 (2H, s), 7.01 (1H, dd, J = 5.0, 7.3 Hz), 7.09 (1H, dd, J = 5.0, 7.3 Hz), 7.65-7.70 (2H, m), 8.11 (1H, dd, J = 1.8, 5.0 Hz), 8.21 (2H, s), 8.23 (1H, dd, J = 1.8, 5.0 Hz). | ESI-MS m/z: 382 [M + H]$^+$. |
| I-355 |  | $^1$H-NMR (400 MHz, CDCl$_3$) δ: 3.82 (3H, s), 6.65 (1H, t, J = 56.6 Hz), 7.15-7.20 (3H, m), 7.52-7.54 (2H, m), 7.74 (1H, dd, J = 1.9, 7.4 Hz), 8.24 (1H, dd, J = 1.9, 4.9 Hz), 8.44 (1H, s), 8.57 (1H, s). | ESI-MS m/z: 363, 365 [M + H]$^+$. |
| I-356 |  | $^1$H-NMR (400 MHz, CDCl$_3$) δ: 4.05 (3H, d, J = 4.6 Hz), 6.65 (1H, t, J = 56.8 Hz), 7.14-7.19 (3H, m), 7.52-7.54 (2H, m), 7.69 (1H, dd, J = 1.9, 7.4 Hz), 8.22 (1H, dd, J = 1.9, 4.9 Hz), 8.29 (1H, s), 8.43 (1H, d, J = 4.4 Hz). | ESI-MS m/z: 347 [M + H]$^+$. |

TABLE 45-continued

| compound | structural formula | NMR | MS |
|---|---|---|---|
| I-357 | | $^{1}$H-NMR (400 MHz, CDCl$_3$) δ: 3.96 (3H, s), 6.95 (1H, d, J = 5.9 Hz), 7.06 (2H, d, J = 8.4 Hz). 7.39 (2H, d, J = 8.4 Hz), 8.49 (1H, s), 8.56-8.59 (2H, m), 8.76 (1H, s). | ESI-MS m/z: 314, 316 [M + H]$^+$. |
| I-358 | | $^{1}$H-NMR (400 MHz, CDCl$_3$) δ: 6.65 (1H, s), 6.65 (1H, t, J = 58.1 Hz), 6.96 (1H, dd, J = 1.2, 6.8 Hz), 7.21-7.29 (3H, m), 7.53-7.56 (2H, m), 7.68 (1H, dd, J = 1.3, 8.9 Hz), 7.97 (1H, d, J = 2.3 Hz), 8.86 (1H, s), 8.87 (1H, s). | ESI-MS m/z: 339 [M + H]$^+$. |
| I-359 | | $^{1}$H-NMR (400 MHz, CDCl$_3$) δ: 2.05 (3H, t, J = 18.5 Hz), 3.82 (3H, s), 6.76 (1H, dd, J = 2.4, 10.7 Hz), 6.81 (1H, dt, J = 2.4, 8.3 Hz), 7.32 (1H, dd, J = 6.5, 8.4 Hz), 7.60 (1H, dd, J = 2.6, 8.6 Hz), 7.73 (1H, dd, J = 0.6, 8.6 Hz), 8.47 (1H, dd, J = 0.6, 2.6 Hz), 8.60 (1H, s), 8.73 (1H, s). | ESI-MS m/z: 362 [M + H]$^+$. |
| I-360 | | $^{1}$H-NMR (400 MHz, CDCl$_3$) δ: 2.05 (3H, t, J = 18.6 Hz), 3.80 (3H, s), 6.96 (1H, dd, J = 4.3, 9.0 Hz), 7.10-7.17 (2H, m), 7.61 (1H, dd, J = 2.6, 8.6 Hz), 7.73 (1H, dd, J = 0.6, 8.6 Hz), 8.47 (1H, dd, J = 0.6, 2.6 Hz), 8.63 (1H, s), 8.74 (1H, s). | ESI-MS m/z: 362 [M + H]$^+$. |

TABLE 46

| compound | structural formula | NMR | MS |
|---|---|---|---|
| I-361 | | $^{1}$H-NMR (400 MHz, CDCl$_3$) δ: 3.46 (3H, s), 3.97 (3H, s), 4.09 (2H, t, J = 13.2 Hz), 7.04-7.07 (1H, dd, J = 5.0, 7.3 Hz), 7.63 (1H, dd, J = 2.7, 8.7 Hz), 7.69 (1H, dd, J = 1.8, 7.3 Hz), 7.77 (1H, d, J = 8.7 Hz), 8.28 (1H, dd, J = 1.8, 5.0 Hz), 8.51 (1H, dd, J = 2.3 Hz), 8.66 (1H, s), 8.75 (1H, s). | ESI-MS m/z: 375 [M + H]$^+$. |

TABLE 46-continued

| compound | structural formula | NMR | MS |
|---|---|---|---|
| I-362 | | ¹H-NMR (400 MHz, CDCl₃) δ: 6.78 (1H, d, J = 2.4 Hz), 6.96 (1H, dd, J = 1.2, 6.9 Hz), 7.32 (1H, dd, J = 7.0, 8.9 Hz), 7.55 (4H, s), 7.76 (1H, dd, J = 1.2, 8.9 Hz), 8.15 (1H, d, J = 2.4 Hz), 8.22 (1H, br s), 8.59 (1H, s), 8.89 (1H, s). | ESI-MS m/z: 356 [M + H]⁺. |
| I-363 | | ¹H-NMR (400 MHz, CDCl₃) δ: 3.94 (3H, s), 6.68 (1H, t, J = 55.5 Hz), 7.00-7.07 (2H, m), 7.69 (1H, dd, J = 2.4, 8.6 Hz), 7.74 (1H, d, J = 8.5 Hz), 8.53 (1H, d, J = 2.4 Hz), 8.67 (1H, s), 8.77 (1H, s). | ESI-MS m/z: 366 [M + H]⁺. |
| I-365 | | ¹H-NMR (400 MHz, CDCl₃) δ: 3.07 (6H, s), 3.83 (3H, s), 6.53 (1H, d, J = 9.2 Hz), 6.99-7.08 (3H, m), 7.26-7.40 (3H, m), 7.65 (1H, dd, J = 1.4, 7.3 Hz), 8.01 (1H, d, J = 1.8 Hz), 8.12 (1H, dd, J = 1.8, 4.6 Hz). | ESI-MS m/z: 322 [M + H]⁺. |
| I-366 | | ¹H-NMR (400 MHz, CDCl₃) δ: 3.74 (3H, s), 6.71 (1H, dd, J = 2.3, 10.5 Hz), 6.77 (1H, dt, J = 2.3, 10.3 Hz), 7.13-7.16 (1H, m), 7.25-7.28 (1H, m), 7.32 (1H, d, J = 8.7 Hz), 7.45 (1H, dd, J = 2.7, 8.2 Hz), 7.68 (1H, dd, J = 1.8, 7.3 Hz), 8.14 (1H, dd, J = 1.8, 4.6 Hz), 8.20 (1H, d, J = 3.2 Hz). | ESI-MS m/z: 331 [M + H]⁺. |
| I-367 | | ¹H-NMR (400 MHz, CDCl₃) δ: 1.15 (3H, t, J = 7.9 Hz), 3.02 (3H, s), 3.56 (2H, q, J = 7.3 Hz), 3.81 (3H, s), 6.70-6.78 (2H, m), 7.00-7.04 (1H, m), 7.24-7.31 (2H, m), 7.61 (1H, dd, J = 1.8, 7.3 Hz), 7.98 (1H, d, J = 3.2 Hz), 8.12 (1H, dd, J = 1.8, 5.0 Hz). | ESI-MS m/z: 354 [M + H]⁺. |

TABLE 46-continued

| compound | structural formula | NMR | MS |
|---|---|---|---|
| I-368 | | $^1$H-NMR (400 MHz, CDCl$_3$) δ: 0.92 (3H, t, J = 7.3 Hz), 1.61 (2H, sext., J = 7.8 Hz), 3.03 (3H, s), 3.43 (2H, t, J = 7.8 Hz), 3.81 (1H, s), 6.48 (1H, d, J = 9.2 Hz), 6.70-6.78 (2H, m), 7.00-7.04 (1H, m), 7.23-7.31 (2H, m), 7.61 (1H, dd, J = 1.8, 7.4 Hz), 7.97 (1H, d, J = 2.3 Hz), 8.12 (1H, dd, J = 1.8, 5.0 Hz). | ESI-MS m/z: 368 [M + H]$^+$. |
| I-369 | | $^1$H-NMR (400 MHz, CDCl$_3$) δ: 2.89 (3H, s), 2.81 (6H, s), 3.78 (3H, s), 6.68-6.78 (2H, m), 7.06 (1H, dd, J = 5.0, 7.3 Hz), 7.19 (1H, d, J = 2.3 Hz), 7.26-7.30 (1H, m), 7.64 (1H, dd, J = 1.8, 7.3 Hz), 7.95 (1H, d, J = 2.7 Hz), 8.14 (1H, dd, J = 1.8, 5.0 Hz). | ESI-MS m/z: 354 [M + H]$^+$. |

TABLE 47

| compound | structural formula | NMR | MS |
|---|---|---|---|
| I-370 | | $^1$H-NMR (400 MHz, CDCl$_3$) δ : 3.78 (3H, s), 6.91 (1H, dd, J = 0.5, 8.8 Hz), 6.99 (1H, dd, J = 0.8, 8.3 Hz), 7.07 (1H, dt, J = 1.0, 7.5 Hz), 7.12 (1H, dd, J = 4.9, 7.4 Hz), 7.33 (1H, dd, J = 1.7, 7.5 Hz), 7.39 (1H, dt, J = 1.9, 7.6 Hz), 7.40 (1H, t, J = 73.2 Hz), 7.52 (1H, dd, J = 2.9, 8.8 Hz), 7.70 (1H, dd, J = 1.9, 7.3 Hz), 8.00 (1H, d, J = 2.8 Hz), 8.12 (1H, dd, J = 1.9, 4.9 Hz). | ESI-MS m/z: 345 [M + H]$^+$. |
| I-371 | | $^1$H-NMR (400 MHz, CDCl$_3$,) δ: 3.76 (3H, s), 4.45 (2H, s), 4.75 (1H, br s), 6.68 (2H, d, J = 8.2 Hz), 6.72 (1H, t, J = 7.3 Hz), 6.98 (1H, d, J = 8.2 Hz), 7.06 (1H, t, J = 7.3 Hz), 7.12 (1H, dd, J = 5.0, 7.3 Hz), 7.18 (2H, t, J = 7.3 Hz), 7.31-7.44 (4H, m), 7.71 (1H, dd, J = 1.8, 7.3 Hz), 8.14 (1H, dd, J = 1.8, 5.0 Hz), 8.40 (1H, d, J = 2.7 Hz). | ESI-MS m/z: 384 [M + H]$^+$. |
| I-374 | | $^1$H-NMR (400 MHz, CDCl$_3$), δ: 4.00 (3H, s), 6.74-6.80 (1H, m), 7.26 (1H, dd, J = 5.0, 7.3 Hz), 7.64-7.70 (3H, m), 7.74 (1H, d, J = 7.3 Hz), 8.26 (1H, dd, J = 1.8, 5.0 Hz), 8.52 (1H, dd, J = 1.8, 7.3 Hz), 8.62 (1H, d, J = 2.4 Hz). | ESI-MS m/z: 348 [M + H]$^+$. |

TABLE 47-continued

| compound | structural formula | NMR | MS |
|---|---|---|---|
| I-375 | 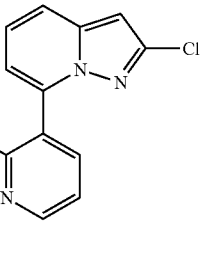 | $^1$H-NMR (400 MHz, CDCl$_3$) δ: 6.96 (1H, d, J = 6.4 Hz), 7.26-7.34 (2H, m), 7.63-7.68 (3H, m), 7.85 (1H, s), 7.97-7.99 (1H, m), 8.29-8.32 (1H, m), 8.54 (1H, s). | ESI-MS m/z: 391, 393 [M + H]$^+$. |
| I-377 | 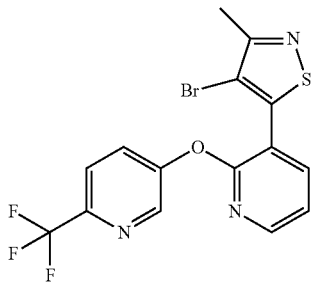 [SMILES: Cc1nsc(-c2cccnc2Oc2ccc(C(F)(F)F)nc2)c1Br] | $^1$H-NMR (400 MHz, CDCl$_3$) δ: 2.60 (3H, s), 7.25 (1H, dd, J = 4.9, 7.5 Hz), 7.70-7.77 (2H, m), 8.05 (1H, dd, J = 1.9, 7.5 Hz), 8.23 (1H, dd, J = 1.9, 4.9 Hz), 8.63 (1H, d, J = 2.2 Hz). | ESI-MS m/z: 416, 418 [M + H]$^+$. |
| I-378 | 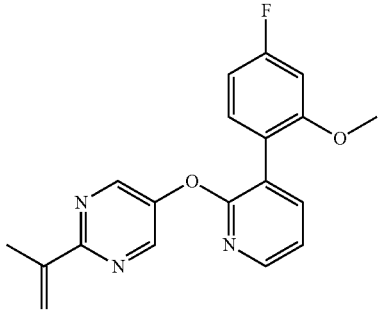 [SMILES: C=C(C)c1ncc(Oc2ncccc2-c2ccc(F)cc2OC)cn1] | $^1$H-NMR (400 MHz, CDCl$_3$) δ: 2.26 (3H, s), 3.37 (3H, s), 5.49-5.51 (1H, m), 6.35 (1H, br s), 6.72 (1H, dd, J = 2.3, 10.0 Hz), 6.78 (1H, ddd, J = 2.7, 8.2, 8.2 Hz), 7.16 (1H, dd, J = 4.6, 7.3 Hz), 7.26-7.31 (1H, m), 7.69 (1H, dd, J = 1.8, 7.3 Hz), 8.12 (1H, dd, J = 1.8, 4.6 Hz), 8.55 (2H, m). | ESI-MS m/z: 338 [M + H]$^+$. |
| I-379 | 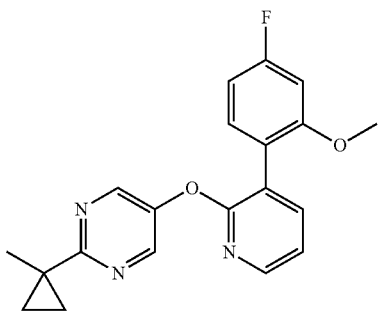 | $^1$H-NMR (400 MHz, CDCl$_3$) δ: 0.88-0.92 (2H, m), 1.24-1.28 (1H, m), 1.35-1.37 (2H, m), 3.77 (3H, s), 6.72 (1H, dd, J = 2.3, 11.0 Hz), 6.77 (1H, ddd, J = 2.3 8.2, 8.2 Hz), 7.13 (1H, dd, J = 4.6, 7.3 Hz), 7.26-7.30 (1H, m), 7.67 (1H, dd, J = 1.8, 7.3 Hz), 8.11 (1H, dd, J = 1.8, 4.6 Hz), 8.43 (2H, s). | ESI-MS m/z: 352 [M + H]$^+$. |
| I-380 | 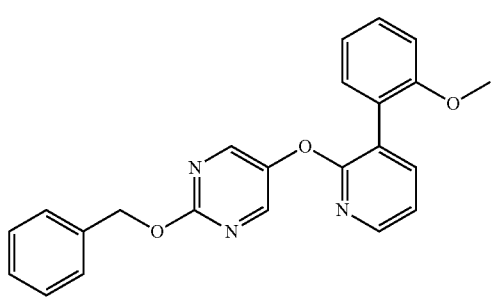 [SMILES: COc1ccccc1-c1cccnc1Oc1cnc(OCc2ccccc2)nc1] | $^1$H-NMR (400 MHz, CDCl$_3$) δ: 3.79 (3H, s), 5.43 (2H, s), 7.01 (1H, d, J = 8.3 Hz), 7.08 (1H, dt, J = 0.9, 7.3), 7.13 (1H, m), 7.29-7.43 (5H, m), 7.49 (2H, d, J = 6.9 Hz), 7.70 (1H, dd, J = 2.3, 7.3 Hz), 8.11 (1H, dd, J = 1.8, 5.0 Hz), 8.38 (2H, s). | ESI-MS m/z: 386 [M + H]$^+$. |

TABLE 48

| compound | structural formula | NMR | MS |
|---|---|---|---|
| I-381 | | $^1$H-NMR (400 MHz, CDCl$_3$) δ : 3.14 (3H, s), 3.97 (3H, s), 4.91 (2H, s), 7.01 (1H, dd, J = 5.0, 6.9 Hz), 7.09 (1H, dd, J = 5.0, 6.9 Hz), 7.23-7.34 (5H, m), 7.66-7.70 (2H, m), 8.13 (1H, dd, J = 1.8, 5.0 Hz), 8.22 (2H, s), 8.23 (1H, dd, J = 1.8, 5.0 Hz). | ESI-MS m/z: 400 [M + H]$^+$. |
| I-384 | | $^1$H-NMR (400 MHz, CDCl$_3$) δ : 0.95 (3H, t, J = 7.3 Hz), 1.31-1.40 (2H, m), 1.56-1.64 (2H, m), 3.14 (3H, s), 3.60 (2H, J = 7.3 Hz), 3.89 (3H, s), 6.92 (1H, d, J = 5.9 Hz), 7.10 (1H, dd, J = 5.0, 7.3 Hz), 7.66 (1H, dd, J = 2.3, 7.3 Hz), 8.14-8.17 (3H, m), 8.46 (1H, s), 8.55 (1H, d, J = 5.5 Hz). | ESI-MS m/z: 366 [M + H]$^+$. |
| I-386 | | $^1$H-NMR (400 MHz, CDCl$_3$) δ : 1.26 (3H, t, J = 7.3 Hz), 3.25 (3H, s), 4.20 (2H, q, J = 7.3 Hz), 4.36 (2H, s), 6.70-6.79 (2H, m), 7.06 (1H, dd, J = 5.0, 7.3 Hz), 7.27 (1H, dd, J = 6.4, 8.2 Hz), 7.62 (1H, dd, J = 1.8, 7.3 Hz), 8.09 (1H, dd, J = 1.8, 5.0 Hz), 8.19 (2H, s). | ESI-MS m/z: 413 [M + H]$^+$. |
| I-387 | | $^1$H-NMR (400 MHz, CDCl$_3$) δ : 3.25 (3H, s), 3.73 (3H, s), 3.81 (3H, s), 4.38 (2H, s), 7.00 (1H, d, J = 8.2 Hz), 7.05-7.09 (2H, m), 7.32-7.34 (1H, m), 7.37-7.42 (1H, m), 7.66 (1H, dd, J = 1.8, 7.3 Hz), 8.08-8.10 (1H, m), 8.20 (2H, s). | ESI-MS m/z: 381 [M + H]$^+$. |
| I-388 | | $^1$H-NMR (400 MHz, CDCl$_3$) δ : 1.14 (3H, t, J = 6.8 Hz), 1.32 (6H, s), 3.39 (2H, s), 3.44 (2H, q, J = 6.8 Hz), 3.93 (3H, s), 6.95 7.09 (4H, M), 7.36-7.40 (2H, m), 7.68 (1H, dd, J = 1.8, 7.3 Hz), 7.72 (1H, dd, J = 1.8, 7.3 Hz), 8.17-8.20 (2H, m). | ESI-MS m/z: 379 [M + H]$^+$. |

TABLE 48-continued

| compound | structural formula | NMR | MS |
|---|---|---|---|
| I-390 | | ¹H-NMR (400 MHz, CDCl₃) δ : 3.03 (1H, s), 3.88 (3H, s), 6.98 (1H, dd, J = 5.0, 7.3 Hz), 7.03-7.06 (2H, m), 7.13 (1H, dd, J = 5.0, 7.3 Hz), 7.47-7.52 (2H, m), 7.64 (1H, dd, J = 1.8, 7.3 Hz), 7.73 (1H, dd, J = 1.8, 7.3 Hz), 8.18-8.22 (2H, m). | ESI-MS m/z: 303 [M + H]⁺. |
| I-392 | | ¹H-NMR (400 MHz, CDCl₃) δ : 1.24 (3H, t, J = 7.6 Hz), 2.64 (2H, q, J = 7.6 Hz), 3.88 (3H, s), 6.91 (1H, d, J = 5.8 Hz), 6.95-7.09 (4H, m), 7.68 (1H, dd, J = 2.0, 7.3 Hz), 8.15 (1H), dd, J = 1.9, 5.0, Hz), 8.50 (1H, s), 8.52 (1H, d, J = 5.8 Hz). | ESI-MS m/z: 325 [M + H]⁺. |
| I-394 | | ¹H-NMR (400 MHz, CDCl₃) δ : 1.22 (3H, t, J = 7.6 Hz), 2.64 (2H, q, J = 7.6 Hz), 3.83 (3H, s), 6.77-6.82 (1H, m), 6.80 (1H, s), 6.89 (1H, d, J = 5.8 Hz), 7.12 (1H, dd, J = 4.9, 7.3 Hz), 7.17 (1H, t, J = 8.5 Hz), 7.69 (1H, dd, J = 1.9, 7.3 Hz), 8.21 (1H, dd, J = 1.9, 4.9 Hz), 8.44 (1H, s), 8.52 (1H, d, J = 5.8 Hz). | ESI-MS m/z: 325 [M + H]⁺. |

TABLE 49

| compound | structural formula | NMR | MS |
|---|---|---|---|
| I-396 | | ¹H-NMR (400 MHz, CDCl₃) δ : 1.21 (3H, t, J = 6.8 Hz), 2.88 (2H, t, J = 7.3 Hz), 3.51 (2H, q, J = 6.8 Hz), 3.63 (2H, t, J = 7.3 Hz), 3.93 (3H, s), 6.99 (1H, dd, J = 5.0, 7.3 Hz), 6.99-7.04 (2H, m), 7.07 (1H, dd, J = 5.0 7.3 Hz), 7.20-7.24 (2H, m), 7.67 (1H, dd, J = 1.8, 7.3 Hz), 7.71 (1H, dd, J =1.8, 7.3 Hz), 8.16 (1H, dd, J = 1.8, 5.0 Hz), 8.19 (1H, dd, J = 1.8, 5.0 Hz). | ESI-MS m/z: 325 [M + H]⁺. |
| I-397 | | ¹H-NMR (400 MHz, CDCl₃) δ : 2.04 (3H, s), 2.93 (2H, t, J = 7.3 Hz), 3.92 (3H, s), 4.28 (2H, t, J = 7.3 Hz), 6.98 (1H, dd, J = 5.0, 7.3 Hz), 7.02-7.05 (2H, m), 7.08 (1H, dd, J = 5.0, 7.3 Hz), 7.20-7.24 (2H, m), 7.67 (1H, dd, J = 1.8, 7.3 Hz), 7.72 (1H, dd, J = 1.8, 7.3 Hz), 8.17 (1H, dd, J = 1.8, 5.0 Hz), 8.20 (1H, dd, J = 1.8, 5.0 Hz). | ESI-MS m/z: 365 [M + H]⁺. |

TABLE 49-continued

| compound | structural formula | NMR | MS |
| --- | --- | --- | --- |
| I-398 | | ¹H-NMR (400 MHz, CDCl₃) δ : 2.86-2.95 (8H, m), 3.92 (3H, s), 4.27 (2H, t, J = 7.3 Hz), 6.98 (1H, dd, J = 5.0, 7.3 Hz), 7.01-7.05 (2H, m), 7.08 (1H, dd, J = 5.0, 7.3 Hz), 7.21-7.24 (2H, m), 7.67 (1H, dd, J = 1.8, 7.3 Hz), 7.71 (1H, dd, J = 1.8, 7.3 Hz), 8.17 (1H, dd, J = 1.8, 5.0 Hz), 8.19 (1H, dd, J = 1.8, 5.0 Hz). | ESI-MS m/z: 394 [M + H]⁺. |
| I-400 | | ¹H-NMR (400 MHz, CDCl₃) δ : 3.15 (2H, t, J = 7.3 Hz), 3.91 (3H, s), 4.34 (2H, t, J = 7.3 Hz), 6.18 (1H, dd, J = 1.8,1.8 Hz), 6.96-7.02 (3H, m), 7.06-7.10 (3H, m), 7.21 (1H, d, J = 1.8 Hz), 7.53 (1H, d, J = 1.8 Hz), 7.66 (1H, dd, J = 1.8, 7.3 Hz), 7.71 (1H, dd, J = 1.8, 7.3 Hz), 8.16 (1H, dd, J = 1.8, 5.0 Hz), 8.20 (1H, dd, J = 1.8, 5.0 Hz). | ESI-MS m/z: 373 [M + H]⁺. |
| I-401 | | ¹H-NMR (400 MHz, CDCl₃) δ : 2.03 (3H, s), 3.12 (2H, t, J = 7.3 Hz), 3.92 (3H, s), 4.26 (2H, t, J = 7.3 Hz), 6.97-7.03 (4H, m), 7.06-7.12 (3H, m), 7.32 (1H, s), 7.67 (1H, dd, J = 1.8, 7.3 Hz), 7.71 (1H, dd, J = 1.8, 7.3 Hz), 8.16 (1H, dd, J = 1.8, 5.0 Hz). | ESI-MS m/z: 387 [M + H]⁺. |
| I-404 | | ¹H-NMR (400 MHz, CDCl₃) δ : 1.45 (3H, t, J = 7.3 Hz), 2.74-2.79 (2H, m), 2.82-2.88 (2H, m), 3.94 (3H, s), 4.11 (2H, q, J = 7.3 Hz), 6.99 (1H, dd, J =5.0, 7.3 Hz), 6.99-7.04 (2H, m), 7.07 (1H, dd, J = 5.0, 7.3 Hz), 7.11 (1H, s), 7.15-7.19 (2H, m), 7.33 (1H, s), 7.68 (1H, dd, J = 1.8, 7.3 Hz), 7.71 (1H, dd, J = 1.8, 7.3 Hz), 8.17 (1H, dd, J = 1.8, 5.0 Hz), 8.20 (1H, dd, J = 1.8, 5.0 Hz). | ESI-MS m/z: 401 [M + H]⁺. |
| I-407 | | ¹H-NMR (400 MHz, CDCl₃) δ : 1.98 (1H, t, J = 2.7 Hz), 2.46-2.51 (2H, dt, J = 2.7, 7.3 Hz), 2.84 (2H, t, J = 7.3 Hz), 3.93 (3H, s), 6.98 (1H, dd, J = 5.0, 7.3 Hz), 7.01-7.05 (2H, m), 7.08 (1H, dd, J = 5.0, 7.3 Hz), 7.20-7.25 (2H, m), 7.67 (1H, dd, J = 1.8, 7.3 Hz), 7.71 (1H, dd, J = 1.8, 7.3 Hz), 8.17 (1H, dd, J = 1.8, 5.0 Hz), 8.20 (1H, dd, J = 1.8, 5.0 Hz). | ESI-MS m/z: 331 [M + H]⁺. |

TABLE 49-continued

| compound | structural formula | NMR | MS |
|---|---|---|---|
| I-408 | | $^1$H-NMR (400 MHz, CDCl$_3$) δ : 2.25 (3H, s), 2.97-3.04 (4H, m), 3.92 (3H, s), 5.78 (1H, s), 6.98 (1H, dd, J = 5.0, 7.3 Hz), 7.01-7.05 (2H, m), 7.08 (1H, dd, J = 5.0, 7.3 Hz), 7.16-7.19 (2H, m), 7.67 (1H, dd, J = 1.8, 7.3 Hz), 7.71 (1H, dd, J = 1.8, 7.3 Hz), 8.17 (1H, dd, J = 1.8, 5.0 Hz), 8.20 (1H, dd, J = 1.8, 5.0 Hz). | ESI-MS m/z: 388 [M + H]$^+$. |

TABLE 50

| compound | structural formula | NMR | MS |
|---|---|---|---|
| I-409 | | $^1$H-NMR (400 MHz, CDCl$_3$) δ : 2.65 (2H, t, J = 7.3 Hz), 2.94 (2H, t, J = 7.3 Hz), 3.68 (3H, s), 3.92 (3H, s), 6.98 (1H, dd, J = 5.0 7.3 Hz), 7.00-7.04 (2H, m), 7.08 (1H, dd J = 5.0, 7.3 Hz), 7.18-7.23 (2H, m), 7.68 (1H, dd, J = 1.8 7.3 Hz), 7.71 (1H, dd, J = 1.8 7.3 Hz), 8.17 (1H, dd, J = 1.8, 5.0 Hz), 8.19 (1H, dd, J = 1.8, 5.0 Hz). | ESI-MS m/z: 365 [M + H]$^+$. |
| I-411 | | $^1$H-NMR (400 MHz, CDCl$_3$) δ : 2.38 (3H, s), 3.11-3.19 (4H, s), 3.92 (3H, s), 6.98 (1H, dd, J = 5.0, 7.3 Hz), 7.02-7.05 (2H, m), 7.08 (1H, dd, J = 5.0, 7.3 Hz), 7.19-7.23 (2H, m), 7.67 (1H, dd, J = 1.8, 7.3 Hz), 7.71 (1H, dd, J = 1.8, 7.3 Hz), 8.17 (1H, dd, J = 1.8, 5.0 Hz), 8.20 (1H, dd, J = 1.8, 5.0 Hz). | ESI-MS m/z: 389 [M + H]$^+$. |
| I-412 | | $^1$H-NMR (400 MHz, CDCl$_3$) δ : 1.19 (3H, t, J = 7.3 Hz), 2.86 (2H, t, J = 7.3 Hz), 3.50 (2H, q, J = 7.3 Hz), 3.61 (2H, t, J = 7.3 Hz), 6.61 (1H, dd, J = 2.3 Hz), 6.93 (1H, dd, J = 1.4, 6.9 Hz), 7.04-7.08 (2H, m), 7.15 (1H, dd, J = 5.0, 7.3 Hz), 7.18-7.22 (3H, m), 7.60 (1H, dd, J = 1.4, 8.3 Hz), 7.96 (1H, d, J = 2.3 Hz), 8.00 (1H, dd, J = 1.8, 7.3 Hz) 8.28 (1H, dd, J = 1.8, 5.0 Hz). | ESI-MS m/z: 360 [M + H]$^+$. |
| I-413 | | $^1$H-NMR (400 MHz, CDCl$_3$) δ : 3.43 (3H, s), 3.78 (2H, t, J = 13.2 Hz), 6.61 (1H, d, J = 2.3 Hz), 6.91 (1H, dd, J = 1.2, 6.9 Hz), 7.18-7.22 (4H, m), 7.47-7.50 (2H, m), 7.61 (1H, dd, J = 1.3, 8.9 Hz), 7.94 (1H, d, J = 2.3 Hz), 8.02 (1H, dd, J = 2.0, 7.4 Hz), 8.30 (1H, dd, J = 2.0, 5.0 Hz). | ESI-MS m/z: 382 [M + H]$^+$. |

TABLE 50-continued

| compound | structural formula | NMR | MS |
| --- | --- | --- | --- |
| I-414 | | ¹H-NMR (400 MHz, CDCl₃) δ : 1.38 (3H, t, J = 7.1 Hz), 4.35 (2H, t, J = 7.1 Hz), 7.14-7.20 (3H, m), 7.45-7.46 (1H, m), 7.71 (1H, dd, J = 1.9, 7.4 Hz), 8.05-8.09 (2H, m), 8.26 (1H, dd, J = 1.9, 4.9 Hz), 8.53 (1H, d, J = 5.4 Hz), 8.61 (1H, s). | ESI-MS m/z: 355, 357 [M + H]⁺. |
| I-415 | | ¹H-NMR (400 MHz, CDCl₃) δ : 1.27 (3H, t, J = 7.0 Hz), 1.38 (3H, t, J = 7.1 Hz), 4.08 (2H, q, J = 7.0 Hz), 4.36 (2H, q, J = 7.1 Hz), 6.86 (1H, d, J = 5.8 Hz), 7.12-7.18 (3H, m), 7.73 (1H, dd, J = 1.9, 7.4 Hz), 8.03-8.07 (2H, m), 8.23 (1H, dd, J = 1.9, 4.9 Hz), 8.43 (1H, s), 8.49 (1H, d, J = 5.8 Hz). | ESI-MS m/z: 365 [M + H]⁺. |
| I-416 | | ¹H-NMR (400 MHz, CDCl₃) δ : 1.16 (3H, t, J = 7.6 Hz), 1.38 (3H, t, J = 7.1 Hz), 2.59-2.64 (2H, m), 4.36 (2H, q, J = 7.1 Hz), 7.08-7.12 (2H, m), 7.17 (1H, dd, J = 4.9, 7.3 Hz), 7.26-7.29 (1H, m), 7.65 (1H, dd, J = 1.9, 7.3 Hz), 8.03-8.07 (2H, m), 8.24 (1H, dd, J = 1.9, 4.9 Hz), 8.44 (1H, s), 8.55 (1H, d, J = 5.1 Hz). | ESI-MS m/z: 349 [M + H]⁺. |
| I-418 | | ¹H-NMR (400 MHz, CDCl₃) δ : 1.35 (6H, d, J = 6.2 Hz), 3.78 (3H, s), 5.24 (1H, quint, J = 6.2 Hz), 6.89 (1H, d, J = 5.7 Hz), 7.10-7.13 (2H, m), 7.17 (1H, dd, J = 4.9, 7.4 Hz), 7.73 (1H, dd, J = 1.9, 7.4 Hz), 8.03-8.06 (2H, m), 8.23 (1H, dd, J = 1.9, 4.9 Hz), 8.45 (1H, s), 8.52-8.55 (1H, m). | ESI-MS m/z: 365 [M + H]⁺. |

TABLE 51

| compound | structural formula | NMR | MS |
| --- | --- | --- | --- |
| I-419 | | ¹H-NMR (400 MHz, CDCl₃) δ : 1.38 (3H, t, J = 7.1 Hz), 1.61 (3H, s), 2.31 (H, t, J = 6.0 Hz), 4.36 (2H, q, J =7.1 Hz), 7.09-7.13 (2H, m), 7.18 (1H, dd, J = 4.9, 7.3 Hz), 7.22 (1H, d, J = 5.1 Hz), 7.66 (1H, dd, J = 1.9, 7.3 Hz), 8.04-8.07 (2H, m), 8.24 (1H, dd, J = 1.9, 4.9 Hz), 8.45 (1H, s), 8.50 (1H, d, J = 5.1 Hz). | ESI-MS m/z: 335 [M + H]⁺. |

TABLE 51-continued

| compound | structural formula | NMR | MS |
|---|---|---|---|
| I-421 | | ¹H-NMR (400 MHz, CDCl₃) δ : 2.24 (3H, s), 2.39 (3H, s), 7.12-7.17 (3H, m), 7.61 (1H, dd, J = 2.0, 7.4 Hz), 7.92-7.98 (2H, m), 8.03-8.07 (2H, m) 8.19 (1H, dd, J = 2.0, 4.9 Hz), 8.41-8.50 (1H, m). | ESI-MS m/z: 345 [M + H]⁺. |
| I-422 | | ¹H-NMR (CDCl₃) δ : 2.33 (3H, s), 2.61 (3H, s), 7.15-7.18 (2H, m), 7.22 (1H, dd, J = 4.9, 7.3 Hz), 7.25 (1H, d, J = 5.1 Hz), 7.69 (1H, dd, J = 1.9, 7.3 Hz), 7.99-8.02 (2H, m), 8.27 (1H, dd, J = 1.9, 4.9 Hz), 8.48 (1H, s), 8.53 (1H, d, J = 5.1 Hz). | ESI-MS m/z: 305 [M + H]⁺. |
| I-423 | | ¹H-NMR (400 MHz, CDCl₃) δ : 2.35 (3H, s), 2.54 (3H, s), 7.12-7.19 (4H, m), 7.25 (1H, d, J = 5.0 Hz), 7.61-7.64 (2H, m), 7.66 (1H, dd, J = 2.0, 7.3 Hz), 8.26 (1H, dd, J = 2.0, 5.0 Hz), 8.50 (1H, s), 8.53 (1H, d, J = 5.0 Hz). | ESI-MS m/z: 334 [M + H]⁺. |
| I-424 | | ¹H-NMR (CDCl₃) δ : 2.19 (3H, s), 2.31 (3H, s), 6.13 (1H, s), 7.12-7.16 (2H, m), 7.22 (1H, dd, J = 4.9, 7.4 Hz), 7.22-7.23 (1H, m), 7.66 (1H, dd, J = 1.9, 7.4 Hz), 7.88-7.92 (2H, m), 8.25 (1H, dd, J = 1.9, 4.9 Hz), 8.46 (1H, s), 8.50 (1H, d, J = 5.1 Hz). | ESI-MS m/z: 347 [M + H]⁺. |
| I-425 | | ¹H-NMR (400 MHz, CDCl₃) δ : 2.35 (3H, s), 2.37 (3H, s), 6.33 (1H, s), 7.16-7.21 (3H, m), 7.25 (1H, d, J = 5.0 Hz), 7.68 (1H, dd, J = 1.9, 7.3 Hz), 7.76-7.80 (2H, m), 8.26 (1H, dd, J = 1.9, 4.9 Hz), 8.50 (1H, s), 8.53 (1H, d, J = 5.0 Hz). | ESI-MS m/z: 344 [M + H]⁺. |

TABLE 51-continued

| compound | structural formula | NMR | MS |
|---|---|---|---|
| I-426 | | $^1$H-NMR (400 MHz, CDCl$_3$) δ : 2.30 (3H, s), 6.83-6.87 (2H, m), 7.14 (1H, dd, J =5.0, 7.3 Hz), 7.22 (1H, d, J = 5.0 Hz), 7.63 (1H, dd, J = 2.0, 7.3 Hz), 7.64-7.68 (2H, m), 8.21 (1H, dd, J = 1.9, 4.9 Hz), 8.45 (1H, s), 8.50 (1H, d, J = 5.0 Hz). | ESI-MS m/z: 389 [M + H]$^+$. |
| I-428 | | $^1$H-NMR (400 MHz, CDCl$_3$) δ : 2.33 (3H, s), 2.50 (3H, d, J = 1.2 Hz), 7.12-7.17 (3H, m), 7.23 (1H, d, J = 5.1 Hz), 7.47 (1H, m), 7.64 (1H, dd, J = 2.0, 7.3 Hz), 7.87-7.91 (2H, m), 8.24 (1H, dd, J = 1.9, 4.9 Hz), 8.47 (1H, s), 8.50 (1H, d, J = 5.0 Hz). | ESI-MS m/z: 360 [M + H]$^+$. |

TABLE 52

| compound | structural formula | NMR | MS |
|---|---|---|---|
| I-429 | | $^1$H-NMR (400 MHz, CDCl$_3$) δ : 2.34 (3H, s), 7.15-7.20 (4H, m), 7.23 (1H, d, J = 5.0 Hz), 7.65 (1H, dd, J = 2.0, 7.3 Hz), 8.25 (1H, dd, J = 1.9, 7.3 Hz), 8.45-8.51 (4H, m), 8.78 (1H, s), 8.79 (1H, s). | ESI-MS m/z: 341 [M + H]$^+$. |
| I-430 | | $^1$H-NMR (400 MHz, CDCl$_3$) δ : 2.34 (3H, s), 7.12-7.22 (3H, m), 7.24 (1H, d, J = 5.0 Hz), 7.47-7.49 (2H, m), 7.63-7.67 (3H, m), 8.26 (1H, dd, J = 2.0, 5.0 Hz), 8.49 (1H, s), 8.51 (1H, d, J = 5.0 Hz), 8.64-8.65 (2H, m). | ESI-MS m/z: 340 [M + H]$^+$. |
| I-431 | | $^1$H-NMR (400 MHz, CDCl$_3$) δ : 2.27 (3H, s), 7.06-7.15 (4H, m), 7.16 (1H, d, J = 4.9 Hz), 7.57 (1H, dd, J = 2.0, 7.3 Hz), 7.61-7.69 (2H, m), 7.92-7.96 (2H, m), 8.18 (1H, dd, J = 1.9, 4.9 Hz), 8.42 (1H, s), 8.43 (1H, d, J = 5.0 Hz), 8.59-8.61 (1H, m). | ESI-MS m/z: 340 [M + H]$^+$. |

TABLE 52-continued

| compound | structural formula | NMR | MS |
|---|---|---|---|
| I-432 | | $^1$H-NMR (400 MHz, CDCl$_3$) δ : 2.08 (3H, s), 2.26 (3H, s), 7.06-7.09 (3H, m), 7.17 (1H, d, J = 5.1 Hz), 7.44 (1H, s), 7.55-7.58 (4H, m), 8.16 (1H, dd, J = 1.9, 4.9 Hz), 8.41 (1H, s), 8.44 (1H, d, J = 5.0 Hz). | ESI-MS m/z: 343 [M + H]$^+$. |
| I-433 | | $^1$H-NMR (400 MHz, CDCl$_3$) δ : 2.27 (3H, s), 6.39 (1H, dd, J = 1.8, 2.4 Hz), 7.06-7.12 (3H, m), 7.17 1H, d, J = 5.0 Hz), 7.57 (1H, dd, J = 2.0, 7.3 Hz), 7.60-7.64 (3H, m), 7.81 (1H, dd, J = 0.5, 2.5 Hz), 8.16 (1H, dd, J = 1.9, 4.9 Hz), 8.41 (1H, s), 8.44 (1H, d, J = 5.0 Hz). | ESI-MS m/z: 329 [M + H]$^+$. |
| I-434 | | $^1$H-NMR (400 MHz, CDCl$_3$) δ : 3.38 (1H, t, J =6.9 Hz), 3.83 (2H, dt, J =6.9, 13.7 Hz), 3.88 (3H, s), 6.98 (1H, dd, J = 5.0, 7.3 Hz), 7.12-7.15 (3H, m), 7.48-7.50 (2H, m), 7.65 (1H, dd, J = 1.8, 7.3 Hz), 7.74 (1H, dd, J = 1.8, 7.3 Hz), 8.14 (1H, dd, J = 1.8, 5.0 Hz), 8.19 (1H, dd, J = 1.8, 5.0 Hz). | ESI-MS m/z: 359 [M + H]$^+$. |
| I-435 | | $^1$H-NMR (400 MHz, CDCl$_3$) δ : 3.91 (3H, s), 6.98 (1H, dd, J = 5.0, 7.2 Hz), 7.22 (1H, dd, J = 4.8, 7.6 Hz), 7.45-7.56 (6H, m), 8.24 (1H, dd, J = 1.9, 5.0 Hz), 8.45 (1H, dd, J = 1.8, 4.8 Hz). | ESI-MS m/z: 363 [M + H]$^+$. |
| I-436 | | $^1$H-NMR (400 MHz, CDCl$_3$) δ : 3.80 (3H, s), 7.00 (1H, dd, J = 0.7, 8.3 Hz), 7.08 (1H, dt, J = 1.0, 7.5 Hz), 7.23 (1H, dd, J = 4.8, 7.6 Hz), 7.26-7.30 (1H, m), 7.42-7.46 (1H, m), 7.49-7.51 (2H, m), 7.53-7.56 (2H, m), 7.58 (1H, dd, J = 1.9, 7.6 Hz), 8.46 (1H, dd, J = 1.8, 4.8 Hz). | ESI-MS m/z: 362 [M + H]$^+$. |

TABLE 53

| compound | structural formula | NMR | MS |
|---|---|---|---|
| I-437 | | $^1$H-NMR (400 MHz, CDCl$_3$) δ : 3.25 (3H, s), 6.79 (1H, d, J = 8.0 Hz), 7.08 (1H, dt, J = 0.8, 7.5 Hz), 7.31-7.36 (2H, m), 7.53 (1H, dd, J = 4.8, 7.8 Hz), 7.71-7.73 (2H, m), 7.83 (1H, dd, J = 1.5, 7.8 Hz), 8.05-8.07 (2H, m), 8.61 (1H, dd, J = 1.5, 4.7 Hz). | ESI-MS m/z: 358 [M + H]$^+$. |
| I-438 | | $^1$H-NMR (400 MHz, CDCl$_3$) δ : 3.12 (1.5H, s), 3.84 (1.5H, s), 5.69-5.73 (1H, m), 5.92-6.02 (1H, m), 6.47-6.48 (0.5H, m), 6.63-6.65 (0.5H, m), 6.78-6.86 (2.5H, m), 7.0-7.04 (1H, m), 7.18-7.20 (0.5H, m), 7.28-7.38 (4H, m), 7.50 (1H, m), 8.62 (1H, dd, J = 1.3, 4.8 Hz). | ESI-MS m/z: 360 [M + H]$^+$. |
| I-439 | | $^1$H-NMR (400 MHz, CDCl$_3$) δ : 3.59 (3H, s), 4.07 (2H, q, J = 12.8 Hz), 6.91 (1H, d, J = 8.2 Hz), 6.96-7.05 (4H, m), 7.23 (1H, dd, J = 4.9, 7.6 Hz), 7.35-7.40 (3H, m), 7.50 (1H, dd, J = 1.8, 7.6 Hz), 8.57 (1H, dd, J = 1.8, 4.9 Hz). | ESI-MS m/z: 344 [M + H]$^+$. |

TABLE 54

| compound | starting material yield | structural formula | NMR | MS |
|---|---|---|---|---|
| I-440 | starting material: IV-68 yield: 37% | | $^1$H-NMR (400 MHz, CDCl$_3$) δ 1.09-2.05 (2H, m), 2.62 (2H, t, J = 6.4 Hz), 2.92 (2H, t, J = 6.0 Hz), 3.70 (3H, s), 6.94-7.06 (4H, m), 7.16 (1H, dd, J = 5.0, 7.3 Hz), 7.30 (1H, dd, J = 1.8, 7.3 Hz), 7.34-7.39 (1H, m), 7.74 (1H, dd, J = 1.8, 7.3 Hz), 8.04 (1H, s), 8.21 (1H, dd, J = 1.8, 5.0 Hz). | ESI-MS m/z: 346 [M + H]$^+$. |
| I-441 | starting material: IV-1 yield: 28% | | $^1$H-NMR (400 MHz, CDCl$_3$) δ 3.73 (3H, s), 6.89 (1H, d, J = 8.3 Hz), 7.12 (1H, d, J = 8.3 Hz), 7.22 (1H, d, J = 5.1, 7.3 Hz), 7.31 (1H, t, J = 8.2 Hz), 7.60 (1H, dd, J = 2.3, 8.7 Hz), 7.65-7.71 (2H, m), 8.20 (1H, dd, J = 1.8, 5.0 Hz), 8.49 (1H, d, J = 2.3 Hz). | ESI-MS m/z: 381 383 [M + H]$^+$. |

TABLE 54-continued

| compound | starting material yield | structural formula | NMR | MS |
|---|---|---|---|---|
| I-442 | starting material: IV-42 yield: 37% | | $^1$H-NMR (400 MHz, CDCl$_3$) δ 3.93 (3H, s), 6.99 (1H, d, J = 5.0 7.3 Hz), 7.10-7.15 (3H, m), 7.21-7.23 (2H, m), 7.65 (1H, dd, J = 2.3, 7.3 Hz), 7.73 (1H, dd, J = 2.3, 7.3 Hz), 818-8.22 (2H, m). | ESI-MS m/z: 363 [M + H]$^+$. |
| I-443 | starting material: IV-79 yield: 82% | | $^1$H-NMR (400 MHz, CDCl$_3$) δ 3.89 (3H, s), 6.64 (1H, d, J = 56.8 Hz), 7.00 (1H, t, J = 6.2 Hz), 7.13-7.19 (3H, m), 7.52 (2H, d, J = 8.7 Hz), 7.66 (1H, dd, J = 1.8, 7.3 Hz), 7.74 (1H, dd, J = 1.8, 7.3 Hz), 8.19-8.22 (2H, m). | ESI-MS m/z: 329 [M + H]$^+$. |
| I-444 | starting material: IV-79 yield: 89% | | $^1$H-NMR (400 MHz, CDCl$_3$) δ 3.73 (3H, s), 6.63 (1H, d, J = 56.8 Hz), 6.97 (1H, d, J = 8.2 Hz), 7.05 (1H, t, J = 7.3 Hz), 7.11-7.18 (3H, m), 7.33 (1H, dd, J = 1.8, 7.8 Hz), 7.38 (1H, dt, J = 1.8, 8.2 Hz), 7.38 (1H, dt, J = 1.8, 8.2 Hz), 7.50 (2H, d, J = 8.7 Hz), 7.72 (1H, dd, J = 1.8, 7.3 Hz), 8.18 (1H, dd, J = 1.8, 5.0 Hz). | ESI-MS m/z: 328 [M + H]$^+$. |
| I-445 | starting material: IV-43 yield: 85% | | $^1$H-NMR (400 MHz, CDCl$_3$) δ 3.77 (3H, s), 6.47 (1H, t, J = 74.2 Hz), 6.98 (1H, d, J = 8.2 Hz), 7.03-7.13 (6H, m), 7.33 (1H, dd, J = 1.8, 7.3 Hz), 7.38 (1H, dt, J = 1.8, 8.2 Hz), 7.70 (1H, dd, J = 1.8, 7.3 Hz), 8.16 (1H, dd, J = 1.8, 5.0 Hz). | ESI-MS m/z: 344 [M + H]$^+$. |
| I-446 | starting material: IV-43 yield: 80% | | $^1$H-NMR (400 MHz, CDCl$_3$) δ 3.92 (3H, s), 6.48 (1H, t, J = 74.2 Hz), 6.98-7.02 (1H, m), 7.08-7.15 (5H, m), 7.66 (1H, dd, J = 1.8, 6.9 Hz), 7.72 (1H, dd, J = 1.8, 7.3 Hz), 8.18 (1H, dd, J = 2.3, 5.0 Hz), 8.21 (1H, dd, J = 1.8, 5.0 Hz). | ESI-MS m/z: 345 [M + H]$^+$. |

TABLE 54-continued

| compound | starting material yield | structural formula | NMR | MS |
|---|---|---|---|---|
| I-447 | starting material: IV-56 yield: 76% | | $^1$H-NMR (400 MHz, CDCl$_3$) δ 1.24 (6H, d, J = 6.9 Hz), 2.90 (1H, d, J = 6.9 Hz), 3.93 (3H, s), 6.95-7.03 (3H, m), 7.06 (1H, dd, J = 5.0, 7.3 Hz), 7.21 (2H, d, J = 8.3 Hz), 7.67 (1H, dd, J = 1.8, 7.3 Hz), 7.71 (1H, dd, J = 1.8, 7.3 Hz), 8.18 (2H, dt, J = 1.8, 5.0 Hz). | ESI-MS m/z: 321 [M + H]$^+$. |

TABLE 55

| compound | starting material yield | structural formula | NMR | MS |
|---|---|---|---|---|
| I-448 | starting material: IV-14 yield: 64% | | $^1$H-NMR (400 MHz, CDCl$_3$) δ 2.49 (3H, d, J = 1.6 Hz), 3.27 (2H, t, J = 8.7 Hz), 4.53 (2H, t, J = 8.7 Hz), 6.95 (1H, t, J = 7.3 Hz), 7.18 (1H, dd, J = 5.0, 7.3 Hz), 7.24-7.26 (2H, m), 7.45 (1H, d, J = 2.3 Hz), 7.88 (1H, dd, J = 1.8, 7.3 Hz), 8.30 (1H, dd, J = 1.8, 5.0 Hz), 8.36 (1H, d, J = 2.3 Hz). | ESI-MS m/z: 373 [M + H]$^+$. |
| I-449 | starting material: IV-30 yield: 94% | | $^1$H-NMR (400 MHz, CDCl$_3$) δ 0.93 (3H, d, J = 7.3 Hz), 1.63 (2H, sext, J = 7.3 Hz), 3.14 (3H, s), 3.29 (2H, t, J = 8.7 Hz), 3.57 (2H, t, J = 7.8 Hz), 4.60 (2H, t, J = 8.7 Hz), 6.96 (1H, t, J = 7.3 Hz), 7.05-7.08 (1H, m), 7.23-7.25 (1H, m), 7.30 (1H, d, J = 6.8 Hz), 7.79 (1H, dd, J = 1.8, 7.3 Hz), 8.09 (1H, dd, J = 1.8, 5.0 Hz), 8.22 (2H, s). | ESI-MS m/z: 363 [M + H]$^+$. |
| I-450 | starting material: IV-35 yield: quantitative | | $^1$H-NMR (400 MHz, CDCl$_3$) δ 3.73 (3H, s), 3.29 (2H, t, J = 8.7 Hz), 3.37 (3H, s), 3.62 (2H, t, J = 5.5 Hz), 3.82 (2H, t, J = 5.5 Hz), 4.60 (2H, t, J = 8.7 Hz), 6.96 (1H, t, J = 7.3 Hz), 7.06 (1H, dd, J = 5.0, 7.3 Hz), 7.24 (1H, dd, J = 1.4, 7.3 Hz), 7.30 (1H, d, J = 7.8 Hz), 7.90 (1H, dd, J = 1.8, 7.3 Hz), 8.08 (1H, dd, J = 1.8, 5.0 Hz), 8.23 (2H, s). | ESI-MS m/z: 379 [M + H]$^+$. |

TABLE 55-continued

| compound | starting material yield | structural formula | NMR | MS |
|---|---|---|---|---|
| I-451 | starting material: IV-24 yield: 60% | | ¹H-NMR (400 MHz, CDCl₃) δ 3.45 (3H, s), 3.87 (3H, s), 4.08 (2H, t, J = 13.3 Hz), 7.19 (1H, dd, J = 5.0, 7.3 Hz), 7.58 (1H, dd, J = 2.3, 8.7 Hz), 7.64 (1H, d, J = 2.7 Hz), 7.72 (1H, d, J = 8.7 Hz), 7.55 (1H, dd, J = 2.3, 7.3 Hz), 8.16 (1H, d, J = 2.7 Hz), 8.19 (1H, dd, J = 1.8, 5.0 Hz), 8.48 (1H, d, J = 2.3 Hz). | ESI-MS m/z: 408, 410 [M + H]⁺. |
| I-452 | starting material: IV-30 yield: 72% | | ¹H-NMR (400 MHz, CDCl₃) δ 0.93 (3H, t, J = 7.5 Hz), 1.60-1.70 (2H, m), 3.15 (3H, s), 3.57 (2H, t, J = 7.3 Hz), 3.95 (3H, s), 7.08 (1H, dd, J = 5.0, 7.3 Hz), 7.64 (1H, d, J = 2.3 Hz), 7.67 (1H, dd, J = 1.8, 7.3 Hz), 8.14 (1H, dd, J = 1.8, 5.0 Hz), 8.16 (1H, d, J = 2.3 Hz), 8.17 (2H, s). | ESI-MS m/z: 386, 388 [M + H]⁺. |
| I-453 | starting material: IV-521 yield: 74% | | ¹H-NMR (400 MHz, CDCl₃) δ 2.21 (3H, s), 3.77 (3H, s), 5.24-5.27 (1H, m), 5.77-5.79 (1H, m), 6.99 (1H, d, J = 8.7 Hz), 7.04-7.09 (1H, m), 7.12 (1H, dd, J = 5.0, 7.3 Hz), 7.32-7.44 (3H, m), 7.50 (1H, d, J = 8.7 Hz), 7.71 (1H, dd, J = 1.8, 7.3 Hz), 8.15 (1H, dd, J = 1.8, 5.0 Hz), 8.40 (1H, d, J = 2.3 Hz). | ESI-MS m/z: 319 [M + H]⁺. |
| I-454 | starting material: IV-15 yield: 17% | | ¹H-NMR (400 MHz, CDCl₃) δ 2.38 (3H, s), 3.74 (3H, s), 6.70 (1H, d, J = 11.0 Hz), 6.76 (1H, t, J = 8.3 Hz), 7.13 (1H, dd, J = 5.0, 7.3 Hz), 7.24-7.28 (1H, m), 7.32 (1H, d, J = 2.3 Hz), 7.68 (1H, d, J = 7.3 Hz), 8.04 (1H, s), 8.14 (1H, d, J = 1.8, 5.0 Hz). | ESI-MS m/z: 389, 391 [M + H]⁺. |
| I-455 | starting material: IV-81 yield: 85% | | ¹H-NMR (400 MHz, CDCl₃) δ 2.41 (3H, s), 3.74 (3H, s), 6.73 (1H, t, J = 55.9 Hz), 6.95-7.01 (3H, m), 7.13 (1H, dd, J = 2.3, 7.3 Hz), 7.49 (1H, d, J = 8.2 Hz), 7.65 (1H, dd, J = 1.8, 7.3 Hz), 7.46 (1H, d, J = 8.2 Hz), 7.72 (1H, dd, J = 1.8, 7.3 Hz), 8.15 (1H, dd, J = 1.8, 5.0 Hz), 8.20 (1H, d, J = 2.7 Hz). | ESI-MS m/z: 342 [M + H]⁺. |

TABLE 56

| compound | starting material yield | structural formula | NMR | MS |
|---|---|---|---|---|
| I-456 | starting material: IV-81 yield: 87% | | ¹H-NMR (400 MHz, CDCl₃) δ 2.41 (3H, s), 3.90 (3H, s), 6.73 (1H, t, J = 55.9 Hz), 6.95-7.01 (3H, m), 7.13 (1H, dd, J = 2.3, 7.3 Hz), 7.49 (1H, d, J = 8.2 Hz), 7.65 (1H, dd, J = 1.8, 7.3 Hz), 7.74 (1H, dd, J = 1.8, 7.3 Hz), 8.19-8.22 (2H, m). | ESI-MS m/z: 343 [M + H]⁺. |
| I-457 | starting material: IV-81 yield: 42% | | ¹H-NMR (400 MHz, CDCl₃) δ 2.43 (3H, s), 3.98 (3H, s), 6.74 (1H, t, J = 55.9 Hz), 6.96-7.02 (2H, m), 7.15 (1H, dd, J = 5.0, 7.3 Hz), 7.51 (1H, d, J = 8.2 Hz), 7.75 (1H, dd, J = 1.8, 7.3 Hz), 8.24 (1H, dd, J = 1.8, 5.0 Hz), 8.53 (1H, s), 8.81 (1H, s). | ESI-MS m/z: 344 [M + H]⁺. |
| I-458 | starting material: IV-24 yield: 83% | | ¹H-NMR (400 MHz, CDCl₃) δ 3.45 (3H, s), 3.83 (3H, s), 4.08 (2H, t, J = 13.3 Hz), 6.89-6.96 (2H, m), 7.08 (1H, t, J = 9.2 Hz), 7.19 (1H, dd, J = 5.0, 7.3 Hz), 7.61 (1H, dd, J = 2.7, 8.7 Hz), 7.71 (1H, d, J = 8.7 Hz), 7.78 (1H, dd, J = 2.7, 8.2 Hz), 8.18 (1H, dd, J = 1.8, 4.6 Hz), 8.50 (1H, d, J = 2.3 Hz). | ESI-MS m/z: 391 [M + H]⁺. |
| I-459 | starting material: IV-53 yield: 95% | | ¹H-NMR (400 MHz, CDCl₃) δ 2.34 (3H, s), 3.94 (3H, s), 6.96 7.00 (3H, m), 7.06 (1H, dd, J = 5.0, 7.3 Hz), 7.15-7.18 (2H, m), 7.68 (1H, dd, J = 1.8, 7.3 Hz), 7.70 (1H, dd, J = 1.8, 7.3 Hz), 8.16 (1H, dd, J = 1.8, 5.0 Hz), 8.20 (1H, dd, J = 1.8, 5.0 Hz). | ESI-MS m/z: 293 [M + H]⁺. |
| I-460 | starting material: IV-24 yield: 20% | | ¹H-NMR (400 MHz, CDCl₃) δ 3.45 (3H, s), 3.86 (3H, s), 3.95 (3H, s), 4.07(2H, t, J = 13.3 Hz), 6.41 (1H, d, J = 7.8 Hz), 7.15 (1H, dd, J = 7.3 Hz), 7.53-7.59 (2H, m), 7.69 (1H, d, J = 8.2 Hz), 7.74 (1H, dd, J = 2.3, 7.3 Hz), 8.13 (1H, dd, J = 1.8, 5.0 Hz), 8.46 (1H, d, J = 2.3 Hz). | ESI-MS m/z: 404 [M + H]⁺. |

TABLE 56-continued

| compound | starting material yield | structural formula | NMR | MS |
|---|---|---|---|---|
| I-461 | starting material: IV-14 yield: 19% | | ¹H-NMR (400 MHz, CDCl₃) δ 2.46 (3H, s), 6.61 (1H, d, J = 2.3 Hz), 6.90 (1H, dd, J = 1.4, 6.9 Hz), 7.22 (1H, dd, J = 6.9, 9.2 Hz), 7.27 (1H, dd, J = 5.0, 7.3 Hz), 7.48 (1H, d, J = 7.3 Hz), 7.64 (1H, dd, J = 1.4, 8.3 Hz), 9.91 (1H, d, J = 2.3 Hz), 8.21 (1H, dd, J = 1.8, 7.3 Hz), 8.30 (1H, dd, J = 2.3, 5.0 Hz), 8.34 (1H, d, J = 2.3 Hz). | ESI-MS m/z: 371 [M + H]⁺. |
| I-462 | starting material: IV-81 yield: 10% | | ¹H-NMR (400 MHz, CDCl₃) δ 2.46 (3H, s), 6.61 (1H, d, J = 55.9 Hz), 6.61 (1H, dd, J = 2.3 Hz), 6.93 (1H, dd, J = 1.4, 6.9 Hz), 6.96-7.02 (2H, m), 7.15 (1H, dd, J = 5.0, 7.3 Hz), 7.18-7.22 (1H, m), 7.51 (1H, d, J = 8.2 Hz), 7.60 (1H, dd, J = 1.4, 8.3 Hz), 7.75 (1H, dd, J = 1.8, 7.3 Hz), 7.96 (1H, d, J = 2.3 Hz), 8.24 (1H, dd, J = 1.8, 5.0 Hz). | ESI-MS m/z: 352 [M + H]⁺. |
| I-463 | starting material: IV-1 yield: 33% | | H-NMR (400 MHz, CDCl₃) δ 3.71 (6H, s), 6.64 (2H, d, J = 8.4 Hz), 7.19 (1H, dd, J = 4.9, 7.4 Hz), 7.33 (1H, t, J = 8.4 Hz), 7.55-7.58 (1H, m), 7.64-7.66 (1H, m), 7.70-7.74 (2H, m), 8.45 (1H, d, J = 2.5 Hz). | ESI-MS m/z: 377 [M + H]⁺. |

TABLE 57

| compound | starting material yield | structural formula | NMR | MS |
|---|---|---|---|---|
| I-464 | starting material: IV-100 yield: 87% | 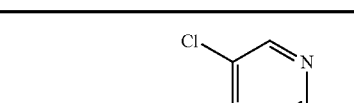 | ¹H-NMR (400 MHz, CDCl₃) δ: 2.05 (3H, t, J = 18.6 Hz), 3.96 (3H, s), 7.61 (1H, dd, J = 2.6, 8.6 Hz), 7.69 (1H, d, J = 2.6 Hz), 7.75 (1H, dd, J = 0.5, 8.6 Hz), 8.22 (1H, d, J = 2.6 Hz), 8.48 (1H, dd, J = 0.5, 2.6 Hz), 8.65 (1H, s), 8.76 (1H, s). | ESI-MS m/z: 379, 381 [M + H]⁺. |

TABLE 57-continued

| compound | starting material yield | structural formula | NMR | MS |
|---|---|---|---|---|
| I-465 | starting material: IV-50 yield: 67% | | ¹H-NMR (400 MHz, CDCl₃) δ: 1.39 (3H, t, J = 7.1 Hz), 4.37 (2H, q, J = 7.1 Hz), 7.15-7.21 (3H, m), 7.39 (1H, ddd, J = 0.8, 4.8, 7.9 Hz), 7.82 (1H, dd, J = 1.9, 7.4 Hz), 7.97-8.00 (1H, m), 8.07-8.10 (2H, m), 8.22 (1H, dd, J = 1.9, 4.9 Hz), 8.63 (1H, dd, J = 1.6, 4.8 Hz), 8.86-8.87 (1H, m). | ESI-MS m/z: 321 [M + H]⁺. |
| I-466 | starting material: IV-14 yield: 8% | | ¹H-NMR (400 MHz, CDCl₃) δ: 2.50 (3H, d, J = 1.8 Hz), 3.81 (3H, s), 6.91 (1H, d, J = 6.0 Hz), 7.22 (1H, dd, J = 5.0, 7.3 Hz), 7.41 (1H, d, J = 2.7 Hz), 7.76 (1H, dd, J = 2.3, 7.3 Hz), 8.21 (1H, dd, J = 2.3, 5.0 Hz), 8.31 (1H, d, J = 2.7 Hz), 8.45 (1H, m), 8.56 (1H, d, J = 4.6 Hz). | ESI-MS m/z: 362 [M + H]⁺. |
| I-467 | starting material: IV-108 yield: 40% | | ¹H-NMR (400 MHz, CDCl₃) δ: 3.90 (3H, s), 6.67 (1H, t, J = 56.5 Hz), 6.95 (1H, d, J = 5.8 Hz), 7.20-7.23 (2H, m), 7.57-7.59 (2H, m), 8.51 (1H, s), 8.59 (1H, d, J = 5.8 Hz), 8.61 (1H, s), 8.77 (1H, s). | ESI-MS m/z: 330 [M + H]⁺. |
| I-468 | starting material: IV-23 yield: 98% | | ¹H-NMR (400 MHz, CDCl₃) δ: 2.16 (2H, quin, J = 7.8 Hz), 2.93 (2H, t, J = 7.8 Hz), 2.98 (2H, t, J = 7.8 Hz), 3.79 (3H, s), 6.99 (1H, d, J = 8.2 Hz), 7.02-7.12 (2H, m), 7.28 (1H, d, J = 2.3 Hz), 7.34 (1H, dd, J = 1.8, 7.3 Hz), 7.38 (1H, dt, J = 1,8, 7.8 Hz), 7.69 (1H, dd, J = 1.8, 7.3 Hz), 8.11-8.27 (2H, m). | ESI-MS m/z: 319 [M + H]⁺. |
| I-469 | starting material: IV-26 yield: 93% | | ¹H-NMR (400 MHz, CDCl₃) δ: 3.28 (2H, t, J = 8.7 Hz), 4.51 (2H, t, J = 8.7 Hz), 6.98 (1H, t, J = 7.3 Hz), 7.21-7.30 (3H, m), 7.89 (1H, dd, J = 1.8, 7.3 Hz), 8.14 (1H, dd, J = 1.8, 4.6 Hz), 8.78 (2H, s). | ESI-MS m/z: 360 [M + H]⁺. |

TABLE 57-continued

| compound | starting material yield | structural formula | NMR | MS |
|---|---|---|---|---|
| I-470 | starting material: IV-26 yield: 84% | | ¹H-NMR (400 MHz, CDCl₃) δ: 3.70 (3H, s), 6.91 (1H, dd, J = 4.6, 9.2 Hz), 7.04-7.15 (2H, m), 7.23-7.29 (1H, m), 7.77 (1H, dd, J = 1.8, 7.3 Hz), 8.18 (1H, dd, J = 1.8, 5.0 Hz), 8.74 (2H, s). | ESI-MS m/z: 366 [M + H]⁺. |
| I-471 | starting material: IV-31 yield: 98% | | ¹H-NMR (400 MHz, CDCl₃) δ: 1.18 (3H, t, J = 6.9 Hz) 3.13 (3H, s), 3.67 (2H, q, J = 7.3 Hz), 3.83 (3H, s), 7.01 (1H, d, J = 7.3 Hz), 7.05-7.09 (2H, m), 7.34 (1H, dd, J = 1.9, 7.4 Hz), 7.40 (1H, t, J = 8.2 Hz), 7.66 (1H, dd, J = 1.8, 7.3 Hz), 8.11 (1H, dd, J = 1.8, 4.5 Hz), 8.18 (2H, s). | ESI-MS m/z: 337 [M + H]⁺. |

TABLE 58

| compound | starting material yield | structural formula | NMR | MS |
|---|---|---|---|---|
| I-472 | starting material: IV-56 yield: 15% | | ¹H-NMR (400 MHz, CDCl₃) δ: 1.24 (6H, d, J = 6.8 Hz), 2.91 (1H, d, J = 6.8 Hz), 4.00 (3H, s), 7.00 (2H, d, J = 8.7 Hz), 7.08 (1H, dd, J = 5.0, 7.3 Hz), 7.22 (2H, d, J = 8.3 Hz), 7.71 (1H, dd, J = 1.8, 7.3 Hz), 8.21 (1H, dd, J = 1.8, 5.0 Hz), 8.55 (1H, s), 8.80 (1H, s). | ESI-MS m/z: 322 [M + H]⁺. |
| I-473 | starting material: IV-14 yield: 79% | | ¹H-NMR (400 MHz, CDCl₃) δ: 2.50 (3H, s), 3.88 (3H, s), 7.02 (1H, dd, J = 5.0, 7.3 Hz), 7.20 (1H, dd, J = 5.0, 7.3 Hz), 7.42 (1H, d, J = 2.3 Hz), 7.65 (1H, dd, J = 1.8, 7.3 Hz), 7.77 (1H, dd, J = 1.8, 7.3 Hz), 8.19 (1H, dd, J = 1.8, 5.0 Hz), 8.23 (1H, dd, J = 2.3, 5.0 Hz), 8.32 (1H, d, J = 2.3 Hz). | ESI-MS m/z: 362 [M + H]⁺. |

TABLE 58-continued

| com-pound | starting material yield | structural formula | NMR | MS |
|---|---|---|---|---|
| I-474 | starting material: IV-14 yield: 68% | | $^1$H-NMR (400 MHz, CDCl$_3$) δ: 2.46-2.53 (6H, m), 3.85 (3H, s), 6.85 (1H, d, J = 7.3 Hz), 7.19 (1H, dd, J = 5.0, 7.3 Hz), 7.41 (1H, d, J = 1.8 Hz), 7.52 (1H, d, J = 7.3 Hz), 7.75 (1H, dd, J = 1.8, 7.3 Hz), 8.17 (1H, dd, J = 1.8, 5.0 Hz), 8.32 (1H, d, J = 2.3 Hz). | ESI-MS m/z: 376 [M + H]$^+$. |
| I-475 | starting material: IV-14 yield: 64% | | $^1$H-NMR (400 MHz, CDCl$_3$) δ: 2.32 (3H, s), 2.50 (3H, d, J = 1.8 Hz), 3.84 (3H, s), 7.19 (1H, dd, J = 5.0, 7.3 Hz), 7.42 (1H, d, J = 2.3 Hz), 7.46 (1H, d, J = 1.8 Hz), 7.75 (1H, dd, J = 1.8, 7.3 Hz), 8.03 (1H, dd, J = 0.9, 2.3 Hz), 8.18 (1H, dd, J = 1.8, 5.0 Hz), 8.32 (1H, d, J = 2.7 Hz). | ESI-MS m/z: 376 [M + H]$^+$. |
| I-476 | starting material: IV-14 yield: 60% | | $^1$H-NMR (400 MHz, CDCl$_3$) δ: 2.51 (3H, d, J = 1.8 Hz), 3.86 (3H, s), 7.20 (1H, dd, J = 5.0, 7.3 Hz), 7.42 (1H, d, J = 1.8), 7.63 (1H, d, J = 2.7 Hz), 7.75 (1H, dd, J = 2.3, 7.8 Hz), 8.17 (1H, d, J = 2.3 Hz), 8.20 (1H, dd, J = 1.8, 5.0 Hz), 8.32 (1H, d, J = 2.3 Hz). | ESI-MS m/z: 396, 398 [M + H]$^+$. |
| I-477 | starting material: IV-30 yield: quantitative | | $^1$H-NMR (400 MHz, CDCl$_3$) δ: 0.93 (3H, t, J = 7.3 Hz), 1.60-1.69 (2H, m), 3.14 (3H, s), 3.57 (2H, t, J = 7.3 Hz), 3.81 (3H, s), 6.71-6.79 (2H, m), 7.04-7.07 (1H, m), 7.28-7.30 (1H, m), 7.62 (1H, dd, J = 1.8, 7.3 Hz), 8.10 (1H, dd, J = 1.8, 5.0 Hz), 8.16 (2H, s). | ESI-MS m/z: 369 [M + H]$^+$. |
| I-478 | starting material: IV-33 yield: 60% | | $^1$H-NMR (400 MHz, CDCl$_3$) δ: 1.06 (3H, t, J = 7.3 Hz), 1.78 (2H, sext, J = 7.3 Hz), 3.13 (2H, t, J = 7.3 Hz), 3.93 (3H, s), 7.02 (1H, dd, J = 5.0, 7.3 Hz), 7.16 (1H, dd, J = 5.0, 7.3 Hz), 7.65 (1H, dd, J = 1.8, 7.3 Hz), 7.73 (1H, dd, J = 1.8, 7.3 Hz), 8.13 (1H, dd, J = 1.8, 4.5 Hz), 8.24 (1H, dd, J = 1.8, 5.0 Hz), 8.41 (2H, s). | ESI-MS m/z: 355 [M + H]$^+$. |

TABLE 58-continued

| compound | starting material yield | structural formula | NMR | MS |
|---|---|---|---|---|
| I-479 | starting material: IV-74 yield: 36% | | $^1$H-NMR (400 MHz, CDCl$_3$) δ: 1.32 (6H, s), 3.31 (3H, s), 3.37 (2H, s), 3.93 (3H, s), 6.97 (1H, dd, J = 5.0, 7.3 Hz), 7.00-7.09 (3H, m), 7.34-7.39 (2H, m), 7.68 (1H, dd, J = 1.8, 7.3 Hz), 7.73 (1H, dd, J = 1.8, 7.3 Hz), 8.17-8.20 (2H, m). | ESI-MS m/z: 365 [M + H]$^+$. |

TABLE 59

| compound | starting material yield | structural formula | NMR | MS |
|---|---|---|---|---|
| I-480 | starting material: IV-24 yield: 51% | | $^1$H-NMR (400 MHz, CDCl$_3$) δ: 3.44 (3H, s), 3.70 (3H, s), 4.07 (2H, t, J = 13.3 Hz), 6.75-6.83 (1H, m), 7.13-7.21 (1H, m), 7.26 (1H, d, J = 5.0 Hz), 7.55 (1H, dd, J = 2.8, 8.7 Hz), 7.66-7.73 (2H, m), 8.17 (1H, dd, J = 2.8, 4.8 Hz), 8.45 (1H, d, J = 2.3 Hz). | ESI-MS m/z: 409 [M + H]$^+$. |
| I-481 | starting material: IV-24 yield: 69% | | $^1$H-NMR (400 MHz, CDCl$_3$) δ: 3.45 (3H, s), 4.08 (2H, t, J = 13.3 Hz), 7.05 (1H, dd, J = 2.8, 9.7 Hz), 7.17-7.21 (1H, m), 7.27 (1H, d, J = 5.0 Hz), 7.60 (1H, dd, J = 2.3, 8.3 Hz), 7.71-7.76 (1H, m), 7.72 (1H, d, J = 8.7 Hz), 8.19 (1H, dd, J = 2.8, 5.1 Hz), 8.45 (1H, d, J = 2.3 Hz). | ESI-MS m/z: 397 [M + H]$^+$. |
| I-482 | starting material: IV-24 yield: 15% | | $^1$H-NMR (400 MHz, CDCl$_3$) δ: 3.45 (3H, s), 3.76 (3H, s), 4.07 (2H, t, J = 13.3 Hz), 6.74-6.86 (2H, m), 7.18 (1H, dd, J = 5.0, 7.3 Hz), 7.30-7.38 (1H, m), 7.56 (1H, dd, J = 2.3, 8.2 Hz), 7.68 (1H, d, J = 8.2 Hz), 7.75 (1H, dd, J = 1.8, 7.3 Hz), 8.19 (1H, dd, J = 1.8, 5.0 Hz), 8.46 (1H, d, J = 2.7 Hz). | ESI-MS m/z: 391 [M + H]$^+$. |

TABLE 59-continued

| compound | starting material yield | structural formula | NMR | MS |
|---|---|---|---|---|
| I-483 | starting material: IV-105 yield: 96% | | ¹H-NMR (400 MHz, CDCl₃) δ: 1.24 (6H, d, J = 6.9 Hz), 2.93 (1H, sep, J = 6.8 Hz), 3.98 (3H, s), 6.99-7.02 (1H, m), 7.05 (2H, d, J = 8.7 Hz), 7.26 (2H, d, J = 8.5 Hz), 7.71 (1H, dd, J = 1.8, 7.3 Hz), 8.24 (1H, dd, J = 1.8, 5.1 Hz), 8.59 (1H, s), 8.74 (1H, s). | ESI-MS m/z: 322 [M + H]⁺. |
| I-484 | starting material: IV-105 yield: 78% | | ¹H-NMR (400 MHz, CDCl₃) δ: 1.26 (6H, d, J = 6.8 Hz), 2.93 (1H, sep, J = 6.8 Hz), 3.90 (3H, s), 6.93 (1H, d, J = 6.0 Hz), 7.03 (2H, d, J = 8.7 Hz), 7.27 (2H, d, J = 8.7 Hz), 8.49 (1H, s), 8.51-8.57 (2H, m), 8.77 (1H, s). | ESI-MS m/z: 322 [M + H]⁺. |
| I-485 | starting material: IV-9 yield: 90% | | ¹H-NMR (400 MHz, CDCl₃) δ: 3.71 (3H, s), 6.65 (1H, t, J = 55.4 Hz), 6.86-6.94 (1H, m), 7.02-7.13 (2H, m), 7.18 (1H, dd, J = 5.0, 7.3 Hz), 7.60 (1H, dd, J = 2.3, 8.2 Hz), 7.66 (1H, d, J = 8.7 Hz), 7.73 (1H, dd, J = 1.8, 7.3 Hz), 8.17 (1H, dd, J = 1.8, 5.0 Hz), 8.45 (1H, d, J = 2.3 Hz). | ESI-MS m/z: 347 [M + H]⁺. |
| I-486 | starting material: IV-9 yield: 82% | | ¹H-NMR (400 MHz, CDCl₃) δ: 2.35 (3H, s), 3.68 (3H, s), 6.64 (1H, t, J = 55.4 Hz), 6.86 (1H, d, J = 8.2 Hz), 7.12 (1H, d, J = 2.3 Hz), 7.14-7.21 (2H, m), 7.59 (1H, dd, J = 2.3, 8.2 Hz), 7.64 (1H, d, J = 8.2 Hz), 7.72 (1H, dd, J = 2.3, 7.3 Hz), 8.15 (1H, dd, J = 1.8, 4.6 Hz), 8.45 (1H, d, J = 1.8 Hz). | ESI-MS m/z: 343 [M + H]⁺. |
| I-487 | starting material: IV-9 yield: 90% | | ¹H-NMR (400 MHz, CDCl₃) δ: 3.27 (2H, t, J = 8.7 Hz), 4.53 (2H, t, J = 8.7 Hz), 6.65 (1H, t, J = 55.4 Hz), 6.95 (1H, t, J = 7.3 Hz) 7.17 (1H, dd, J = 5.0, 7.3 Hz), 7.21-7.30 (2H, m), 7.60-7.69 (2H, m), 7.87 (1H, dd, J = 1.8, 7.3 Hz) 8.13 (1H, dd, J = 1.8, 4.6 Hz) 8.50 (1H, d, J = 1.8 Hz). | ESI-MS m/z: 341 [M + H]⁺. |

TABLE 60

| compound | starting material yield | structural formula | NMR | MS |
|---|---|---|---|---|
| I-488 | starting material: IV-13 yield: 57% | | ¹H-NMR (400 MHz, CDCl₃) δ: 1.99 (3H, t, J = 18.8 Hz), 7.24 (1H, dd, J = 4.5, 7.3 Hz), 7.40 (1H, dd, J = 4.2, 8.3 Hz), 7.60-7.68 (2H, m), 7.79 (1H, dd, J = 1.8, 7.3 Hz), 7.86-7.91 (3H, m), 8.19 (1H, dd, J = 1.8, 8.7 Hz) 8.24 (1H, dd, J = 1.8, 5.0 Hz), 8.43 (1H, br s), 8.83 (1H, dd J = 1.9, 4.6 Hz). | ESI-MS m/z: 364 [M + H]⁺. |
| I-489 | starting material: IV-13 yield: 45% | | ¹H-NMR (400 MHz, CDCl₃) δ: 2.06 (3H, t, J = 18.6 Hz), 2.50 (3H, s), 3.87 (3H, s), 6.84 (1H, d, J = 7.3 Hz), 7.15 (1H, dd, J = 5.0, 7.3 Hz), 7.50-7.57 (2H, m), 7.65 (1H, d, J = 8.6, Hz), 7.74 (1H, dd, J = 1.8, 7.3 Hz), 8.15 (1H, dd, J = 1.8, 5.0 Hz), 8.46 (1H, d, J = 3.2 Hz). | ESI-MS m/z: 358 [M + H]⁺. |
| I-490 | starting material: IV-110 yield: 93% | | ¹H-NMR (400 MHz, CDCl₃) δ: 2.45 (3H, s), 3.97 (3H, s), 6.75 (1H, t, J = 55.4 Hz), 7.00-7.06 (3H, m), 7.56 (1H, d, J = 8.4 Hz), 7.79 (1H, dd, J = 1.9, 7.3 Hz), 8.26 (1H, dd, J = 1.9, 5.0 Hz), 8.63 (1H, s), 8.75 (1H, s). | ESI-MS m/z: 344 [M + H]⁺. |
| I-491 | starting material: IV-110 yield: 95% | | ¹H-NMR (400 MHz, CDCl₃) δ: 2.42 (3H, s), 6.65 (1H, d, J = 55.6 Hz), 6.73 (1H, t, J = 55.4 Hz), 6.95 (1H, dd, J = 1.2, 6.9 Hz), 7.04-7.10 (2H, m), 7.21-7.26 (1H, m), 7.53 (1H, d, J = 8.4 Hz), 7.67 (1H, dd, J = 1.4, 8.9 Hz), 7.97 (1H, d, J = 2.3 Hz), 8.87 (1H, s), 8.87 (1H, s). | ESI-MS m/z: 353 [M + H]⁺. |
| I-492 | starting material: IV-119 yield: 89% | | ¹H-NMR (400 MHz, CDCl₃) δ: 1.94 (3H, t, J = 18.1 Hz), 3.97 (3H, s), 7.02 (1H, dd, J = 5.0, 7.3 Hz), 7.17-7.20 (2H, m), 7.55-7.59 (2H, m), 7.71 (1H, dd, J = 1.9, 7.3 Hz), 8.27 (1H, dd, J = 1.9, 5.0 Hz), 8.63 (1H, s), 8,75 (1H, s). | ESI-MS m/z: 344 [M + H]⁺. |

TABLE 60-continued

| compound | starting material yield | structural formula | NMR | MS |
|---|---|---|---|---|
| I-493 | starting material: IV-113 yield: 69% | | ¹H-NMR (400 MHz, CDCl₃) δ: 2.11 (2H, quint, J = 7.7 Hz), 2.87-2.96 (4H, m), 3.99 (3H, s), 6.84-6.90 (1H, m), 6.95-6.98 (1H, m), 7.02 (1H, dd, J = 5.0, 7.2 Hz), 7.24 (1H, d, J = 8.3 Hz), 7.72 (1H, dd, J = 1.9, 7.2 Hz), 8.25 (1H, dd, J = 1.9, 5.0 Hz), 8.59 (1H, br s), 8.75 (1H, s). | ESI-MS m/z: 320 [M + H]⁺. |
| I-494 | starting material: IV-106 yield: 50% | | ¹H-NMR (400 MHz, CDCl₃) δ: 7.27-7.29 (2H, m), 7.45 (1H, dd, J = 4.2, 8.3 Hz), 7.63-7.65 (2H, m), 7.68 (1H, dd, J = 7.2, 8.2 Hz), 7.85 (1H, dd, J = 1.5, 7.1 Hz), 7.95 (1H, dd, J = 1.4, 8.2 Hz), 8.23 (1H, dd, J = 1.8, 8.3 Hz), 8.77 (1H, s), 8.84 (1H, s), 8.90 (1H, dd, J = 1.8, 4.2 Hz). | ESI-MS m/z: 368 [M + H]⁺. |
| I-495 | starting material: IV-95 yield: 40% | | ¹H-NMR (400 MHz, CDCl₃) δ: 3.81 (3H, s), 6.76 (1H, dd, J = 2.3, 10.6 Hz), 6.82 (1H, dt, J = 2.3, 8.4 Hz), 7.32 (1H, dd, J = 6.5, 8.4 Hz), 7.67-7.70 (1H, m), 7.76 (1H, d, J = 8.4 Hz), 8.56 (1H, d, J = 2.4 Hz), 8.62 (1H, s), 8.74 (1H, s). | ESI-MS m/z: 366 [M + H]⁺. |

TABLE 61

| compound | starting material yield | structural formula | NMR | MS |
|---|---|---|---|---|
| I-496 | starting material: IV-95 yield: 91% | | ¹H-NMR (400 MHz, CDCl₃) δ: 3.80 (3H, s), 6.96 (1H, dd, J = 4.2, 8.9 Hz), 7.07-7.18 (2H, m), 7.68-7.71 (1H, m), 7.77 (1H, d, J = 8.5 Hz), 8.57 (1H, d, J = 2.4 Hz), 8.65 (1H, s), 8.75 (1H, s). | ESI-MS m/z: 366 [M + H]⁺. |

TABLE 61-continued

| compound | starting material yield | structural formula | NMR | MS |
|---|---|---|---|---|
| I-497 | starting material: IV-128 yield: 50% | | ¹H-NMR (400 MHz, CDCl₃) δ: 3.77 (3H, s), 6.72 (1H, dd, J = 2.4, 10.8 Hz), 6.76 (1H, dt, J= 2.4, 8.3 Hz), 6.91 (1H, dd, J = 0.5, 8.8 Hz), 7.11 (1H, dd, J = 4.9, 7.3 Hz), 7.27 (1H, dd, J = 6.6, 8.4 Hz), 7.31 (1H, t, J = 73.5 Hz), 7.51 (1H, dd, J = 2.9, 8.8 Hz), 7.66 (1H, dd, J = 1.9, 7.4 Hz), 7.99 (1H, d, J = 2.9 Hz), 8.12 (1H, dd, J = 1.9, 4.9 Hz). | ESI-MS m/z: 363 [M + H]⁺. |
| I-498 | starting material: IV-39 yield: 48% | | ¹H-NMR (400 MHz, CDCl₃) δ: 7.21 (1H, dd, J = 5.0, 7.4 Hz), 7.23-7.25 (2H, m), 7.45 (1H, dd, J = 5.1, 6.0 Hz), 7.65-7.67 (2H, m), 7.79-7.82 (1H, m), 8.27 (1H, dd, J = 2.0, 5.0 Hz), 8.52 (1H, d, J = 4.5 Hz), 8.57 (1H, d, J = 1.6 Hz). | ESI-MS m/z: 335 [M + H]⁺. |
| I-499 | starting material: IV-112 yield: 54% | | ¹H-NMR (400 MHz, CDCl₃) δ: 2.55 (3H, s), 3.81 (3H, s), 6.71 (1H, t, J = 54.5 Hz), 6.75 (1H, dd, J = 2.4, 10.8 Hz), 6.81 (1H, dt, J = 2.4, 8.2 Hz), 7.31 (1H, dd, J = 6.5, 8.4 Hz), 7.41 (1H, d, J = 2.3 Hz), 8.28 (1H, d, J = 2.3 Hz), 8.59 (1H, s), 8.73 (1H, s). | ESI-MS m/z: 362 [M + H]⁺. |
| I-500 | starting material: IV-112 yield: 40% | | ¹H-NMR (400 MHz, CDCl₃) δ: 2.54 (3H, s), 3.82 (3H, s) 6.71 (1H, t, J = 54.5 Hz), 7.03 (1H, d, J = 8.3 Hz), 6.81 (1H, dt, J = 1.0, 7.5 Hz), 7.36 (1H, dd, J = 1.7, 75 Hz), 7.41 (1H, d, J = 2.3 Hz), 7.43-7.47 (1H, m), 8.29 (1H, d, J = 2.3 Hz), 8.63 (1H, s) 8.74 (1H, s). | ESI-MS m/z: 344 [M + H]⁺. |
| I-501 | starting material: IV-54 yield: 72% | | ¹H-NMR (400 MHz, CDCl₃) δ: 1.25 (3H, t, J = 7.6 Hz), 2.28 (3H, s), 2.40 (3H, s), 2.66 (2H, q, J = 7.6 Hz), 6.98-7.01 (2H, m), 7.07 (1H, dd, J = 5.0, 7.3 Hz), 7.20-7.23 (2H, m), 7.56 (1H, dd, J = 2.0, 7.3 Hz), 8.18 (1H, dd, J = 2.0, 5.0 Hz). | ESI-MS m/z: 295 [M + H]⁺. |

TABLE 61-continued

| compound | starting material yield | structural formula | NMR | MS |
|---|---|---|---|---|
| I-502 | starting material: IV-93 yield: 21% | | ¹H-NMR (400 MHz, CDCl₃) δ: 3.79 (3H, s), 4.62 (2H, td, J = 12.3, 46.6 Hz), 6.89 (1H, d, J = 5.8 Hz), 7.15-7.17 (1H, m), 7.16-7.18 (2H, m), 7.51-7.53 (2H, m), 7.73 (1H, dd, J = 1.9, 7.4 Hz), 8.23 (1H, dd, J = 1.9, 4.9 Hz), 8.45 (1H, s), 8.53 (1H, d, J = 4.8 Hz). | ESI-MS m/z: 361 [M + H]⁺. |
| I-503 | starting material: IV-131 yield: 79% | | ¹H-NMR (400 MHz, CDCl₃) δ: 1.15 (3H, t, J = 6.8 Hz), 1.32 (6H, s), 3.39 (2H, s), 3.44 (2H, q, J = 6.8 Hz), 3.84 (3H, s), 6.88 (1H, d, J = 5.5 Hz), 6.95-7.04 (2H, m), 7.09 (1H, dd, J = 5.0, 7.3 Hz), 7.36-7.40 (2H, m), 7.68 (1H, dd, J = 2.3, 7.3 Hz), 8.20 (1H, dd, J = 2.3, 5.0 Hz), 8.46 (1H, s), 8.51 (1H, d, J = 5.8 Hz). | ESI-MS m/z: 379 [M + H]⁺. |

TABLE 62

| compound | starting material yield | structural formula | NMR | MS |
|---|---|---|---|---|
| I-504 | starting material: IV-131 yield: 35% | | ¹H-NMR (400 MHz, CDCl₃) δ: 1.15 (3H, t, J = 6.8 Hz), 1.33 (6H, s), 3.40 (2H, s), 3.43 (2H, q, J = 6.8 Hz), 4.00 (3H, s), 7.00-7.04 (2H, m), 7.10 (1H, dd, J = 5.0, 7.3 Hz), 7.38-7.42 (2H, m), 7.72 (1H, dd, J = 1.8, 7.3 Hz), 8.22 (1H, dd, J = 1.8, 5.0 Hz), 8.54 (1H, s), 8.80 (1H, s). | ESI-MS m/z: 380 [M + H]⁺. |
| I-505 | starting material: IV-77 yield: 59% | | ¹H-NMR (400 MHz, CDCl₃) δ: 0.82-0.89 (4H, m), 3.30 (3H, s), 3.45 (2H, s), 3.93 (3H, s), 6.97 (1H, dd, J = 5.0, 7.3 Hz), 6.99-7.03 (2H, m), 7.07 (1H, dd, J = 5.0, 7.3 Hz), 7.31-7.34 (2H, m), 7.67 (1H, dd, J = 2.3, 7.3 Hz), 7.72 (1H, dd, J = 1.8, 7.3 Hz), 8.16-8.20 (2H, m). | ESI-MS m/z: 363 [M + H]⁺. |
| I-506 | starting material: IV-81 yield: 31% | | ¹H-NMR (400 MHz, CDCl₃) δ: 2.31 (3H, s), 2.41 (3H, s), 6.72 (1H, t, J = 55.5 Hz), 6.94-6.98 (2H, m), 7.16 (1H, dd, J = 5.0, 7.3 Hz), 7.22 (1H, d, J = 5.0 Hz), 7.49 (1H, d, J = 8.4 Hz), 7.64 (1H, dd, J = 2.0, 7.32 Hz), 8.23 (1H, dd, J = 1.9, 4.9 Hz), 8.46 (1H, s), 8.50 (1H, d, J = 5.0 Hz). | ESI-MS m/z: 327 [M + H]⁺. |

TABLE 62-continued

| compound | starting material yield | structural formula | NMR | MS |
|---|---|---|---|---|
| I-507 | starting material: I-537 yield: 86% | | ¹H-HMR (400 MHz, CDCl₃) δ: 2.31 (3H, s), 3.60 (3H, s), 4.62 (2H, td, J = 12.3, 46.6 Hz), 7.15-7.21 (2H, m), 7.52-7.54 (3H, m), 7.76 (1H, dd, J = 1.9, 7.4 Hz), 8.23 (1H, dd, J = 1.9, 4.9 Hz), 838-8.40 (2H, m). | ESI-MS m/z: 375 [M + H]⁺. |
| I-508 | starting material: VIa-9 yield: 6% | | ¹H-NMR (400 MHz, CDCl₃) δ: 6.60 (1H, t, J = 56.5 Hz), 7.17 (2H, d, J = 8.5 Hz), 7.22 (1H, dd, J = 5.0, 7.3 Hz), 7.46 (2H, d, J = 8.4 Hz), 7.84 (1H, dd, J = 2.0, 7.3 Hz), 7.87 (2H, d, J = 5.0 Hz), 8.18 (1H, t, J = 5.0 H z), 8.25 (1H, dd, J = 1.8, 5.0 Hz), 8.78 (1H, d, J = 1.8 Hz), 8.84 (1H, d, J = 1.8 Hz). | ESI-MS m/z: 350 [M + H]⁺. |
| I-509 | starting material: VIa-10 yield: 38% | | ¹H-NMR (400 MHz, CDCl₃) δ: 3.43 (3H, s), 3.77 (2H, t, J = 13.2 Hz), 7.13-7.16 (2H, m), 7.22 (1H, dd, J = 4.9, 7.3 Hz), 7.45-7.48 (2H, m), 7.84-7.89 (3H, m), 8.16-8.20 (1H, m), 8.28 (1H, dd, J = 1.9, 4.9 Hz), 8.79 (1H, d, J = 1.8 Hz), 8.84 (1H, d, J = 1.8 Hz). | ESI-MS m/z: 394 [M + H]⁺. |
| I-510 | starting material: VIa-6 yield: 17% | | ¹H-NMR (400 MHz, CDCl₃) δ: 1.90 (3H, t, J = 18.1 Hz), 7.13-7.15 (2H, m), 7.24 (1H, dd, J = 5.0, 7.3 Hz), 7.47-7.49 (2H, m), 7.89 (1H, dd, J = 1.9, 7.4 Hz), 8.32 (1H, dd, J = 1.9, 5.0 Hz), 8.95 (1H, s), 8.97-8.99 (2H, m), 9.62 (1H, s). | ESI-MS m/z: 365 [M + H]⁺. |
| I-511 | starting material: VIa-1 yield: 22% | | ¹H-NMR (400 MHz, CDCl₃) δ: 6.58 (1H, t, J = 56.5 Hz), 7.21 (1H, dd, J = 5.0, 7.3 Hz), 7.37 (1H, dd, J = 2.7, 7.3 Hz), 7.53-7.58 (2H, m), 7.62 (1H, dd, J = 2.7, 8.7 Hz), 7.69 (1H, d, J = 8.7 Hz), 7.72 (1H, dd, J = 1.8, 7.3 Hz), 7.77 (1H, dd, J = 2.8, 5.8 Hz), 8.21 (1H, dd, J = 1.8, 5.0 Hz), 8.51 (1H, d, J = 2.6 Hz). | ESI-MS m/z: 367 [M + H]⁺. |

TABLE 63

| compound | starting material yield | structural formula | NMR | MS |
|---|---|---|---|---|
| I-512 | starting material: VIa-10 yield: 24% | | ¹H-NMR (400 MHz, CDCl₃) δ: 3.45 (3H, s), 3.80 (2H, t, J = 13.0 Hz), 4.04 (3H, d, J = 4.5 Hz), 7.13-7.16 (3H, m), 7.53 (2H, d, J = 8.7 Hz), 7.69 (1H, d, J = 1.9, 7.3 Hz), 8.22 (1H, dd, J = 1.8, 5.0 Hz), 8.28 (1H, s), 8.43 (1H, d, J = 4.9 Hz). | ESI-MS m/z: 391 [M + H]⁺. |
| I-513 | starting material: VIa-2 yield: 11% | | ¹H-NMR (400 MHz, CDCl₃) δ: 2.02 (3H, t, J = 18.3 Hz), 3.91 (3H, s), 7.19 (1H, dd, J = 5.0, 7.3 Hz), 7.29 (1H, d, J = 7.3 Hz), 7.60 (1H, dd, J = 2.3, 8.7 Hz), 7.68 (1H, d, J = 8.3 Hz), 7.71 (1H, dd, J = 2.3, 7.3 Hz), 8.13 (1H, d, J = 2.7 Hz), 8.21 (1H, dd, J = 1.8, 5.0 Hz), 8.48 (1H, d, J = 2.7 Hz). | ESI-MS m/z: 378, 380 [M + H]⁺. |
| I-514 | starting material: VIa-8 yield: 40% | | ¹H-NMR (400 MHz, CDCl₃) δ: 7.25-7.27 (2H, m), 7.65-7.67 (2H, m), 7.92 (1H, s), 7.93 (1H, d, J = 1.3 Hz), 8.25 (1H, m), 8.76 (1H, s), 8.83 (1H, d, J = 1.8 Hz), 8.86 (1H, s), 8.90 (1H, d, J = 1.8 Hz). | ESI-MS m/z: 369 [M + H]⁺. |
| I-515 | starting material: VIa-5 yield: 71% | | ¹H-NMR (400 MHz, CDCl₃) δ: 1.24 (3H, t, J = 7.6 Hz), 2.65 (2H, q, J = 7.6 Hz), 3.95 (3H, s), 7.01-7.05 (2H, m), 7.11 (1H, dd, J = 5.0, 7.4 Hz), 7.18-7.22 (2H, m), 7.85 (1H, dd, J = 2.0, 7.4 Hz), 8.13 (1H, d, J = 2.8 Hz), 8.24 (1H, dd, J = 2.0, 5.0 Hz), 8.25 (1H, d, J = 2.8 Hz). | ESI-MS m/z: 308 [M + H]⁺. |
| I-516 | starting material: III-1 Step 1: 42% Step 2: 70% | | ¹H-NMR (400 MHz, CDCl₃) δ: 3.23 (3H, s), 3.24 (3H, s), 3.94 (3H, s), 6.84 (1H, dd, J = 2.3, 7.8 Hz), 6.89 (1H, s), 6.98 (1H, dd, J = 5.0, 7.3 Hz), 7.05 (1H, dd, J = 5.0, 7.3 Hz), 7.12 (1H, d, J = 8.2 Hz), 7.67-7.72 (2H, m), 8.16 (1H, dd, J = 1.8, 4.5 Hz), 8.19 (1H, dd, J = 1.8, 5.0 Hz). | ESI-MS m/z: 307 [M + H]⁺. |
| I-517 | starting material: III-1 Step 1: 90% Step 2: 98% | | ¹H-NMR (400 MHz, CDCl₃) δ: 2.34 (3H, s), 3.93 (3H, s), 6.88 (1H, dd, J = 2.7, 8.7 Hz), 6.93-6.99 (2H, m), 7.08 (1H, dd, J = 5.0, 8.3 Hz), 7.31 (1H, d, J = 8.7 Hz), 7.64 (1H, dd, J = 1.8, 8.7 Hz), 7.71 (1H, dd, J = 1.8, 8.3 Hz), 8.16-8.20 (2H, m). | ESI-MS m/z: 327, 329 [M + H]⁺. |

TABLE 63-continued

| compound | starting material yield | structural formula | NMR | MS |
|---|---|---|---|---|
| I-518 | starting material: III-2 Step 1: 58% Step 2: 30% | 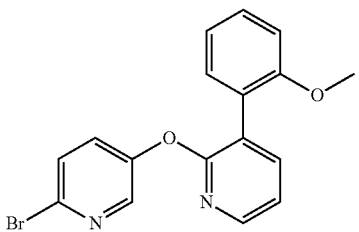 [SMILES: COc1ccccc1-c1cccnc1Oc1ccc(Br)nc1] | ¹H-NMR (400 MHz, CDCl₃) δ: 3.74 (3H, s), 6.98 (1H, d, J = 8.2 Hz), 7.04-7.09 (1H, m), 7.15 (1H, dd, J = 5.0, 7.3 Hz), 7.32 (1H, dd, J = 1.8, 7.3 Hz), 7.35-7.42 (2H, m), 7.46 (1H, d, J = 8.2 Hz), 7.72 (1H, dd, J = 1.8, 7.3 Hz), 8.15 (1H, dd, J = 1.8, 5.0 Hz), 8.20 (1H, d, J = 2.7 Hz). | ESI-MS m/z: 357, 359 [M + H]⁺. |
| I-519 | starting material: III-10 Step 1: 31% Step 2: 77% | 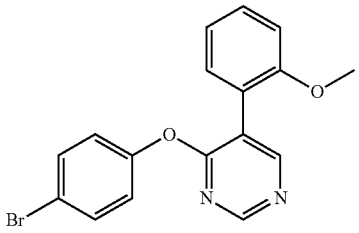 [SMILES: COc1ccccc1-c1cncnc1Oc1ccc(Br)cc1] | ¹H-NMR (400 MHz, CDCl₃) δ: 3.82 (3H, s), 7.00-7.04 (3H, m), 7.08 (1H, dt, J = 1.0, 7.5 Hz), 7.36 (1H, dd, J = 1.7, 7.5 Hz), 7.41-7.46 (1H, m), 7.50-7.54 (2H, m), 8.58 (1H, d, J = 0.4 Hz), 8.72 (1H, d, J = 0.2 Hz). | ESI-MS m/z: 357, 359 [M + H]⁺. |

TABLE 64

| compound | starting material yield | structural formula | NMR | MS |
|---|---|---|---|---|
| I-520 | starting material: III-10 Step 1: 31% Step 2: 55% | 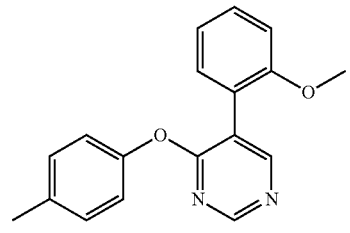 | ¹H-NMR (400 MHz, CDCl₃) δ: 2.36 (3H, s), 3.83 (3H, s), 6.98-7.02 (3H, m), 7.07 (1H, dd, J = 1.0, 7.5 Hz) 7.21 (2H, d, J = 8.3 Hz), 7.37 (1H, dd, J = 1.7, 7.5 Hz), 7.41 (1H, ddd, J = 1.8, 7.5, 8.2 Hz), 8.55 (1H, s), 8.72 (1H, s). | ESI-MS m/z: 293 [M + H]⁺. |
| I-521 | starting material: III-10 Step 1: 31% Step 2: 70% | 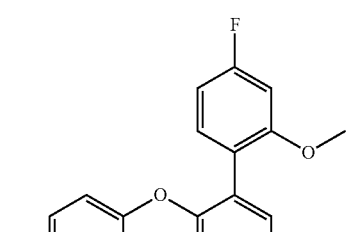 | ¹H-NMR (400 MHz, CDCl₃) δ: 2.36 (3H, s), 3.82 (3H, s), 6.73 (1H, dd, J = 2.3, 10.8 Hz), 6.75 (1H, dt, J = 2.4, 8.2 Hz), 6.98 (2H, d, J = 8.4 Hz), 7.20 (2H, d, J = 8.3 Hz), 7.32 (1H, dd, J = 6.6, 8.4 Hz), 8.51 (1H, s), 8.71 (1H, s). | ESI-MS m/z: 311 [M + H]⁺. |
| I-522 | starting material: III-1 Step 1: 79% Step 2: 89% | 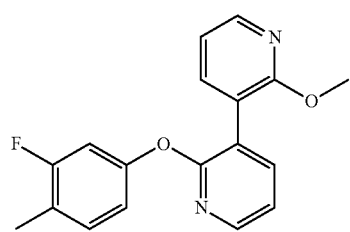 | ¹H-NMR (400 MHz, CDCl₃) δ: 2.24 (3H, d, J = 1.8 Hz), 3.92 (3H, s), 6.78-6.79 (1H, m), 6.80-6.81 (1H, m), 6.99 (1H, dd, J = 5.0, 7.3 Hz), 7.10 (1H, dd, J = 4.9, 7.4 Hz), 7.12-7.17 (1H, m), 7.65 (1H, dd, J = 1.9, 7.3 Hz), 7.71 (1H, dd, J = 1.9, 7.4 Hz), 8.18 (1H, dd, J = 2.0, 4.9 Hz), 8.20 (1H, dd, J = 1.9, 5.0 Hz). | ESI-MS m/z: 311 [M + H]⁺. |

TABLE 64-continued

| compound | starting material yield | structural formula | NMR | MS |
|---|---|---|---|---|
| I-523 | starting material: III-11 Step 1: 58% Step 2: 80% | 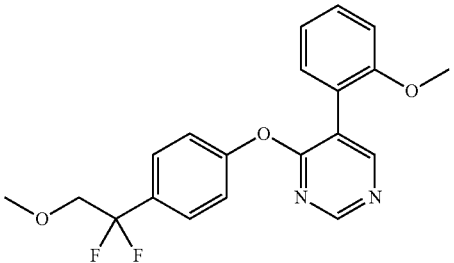 | $^1$H-NMR (400 MHz, CDCl$_3$) δ: 3.45 (3H, s), 3.81 (3H, s), 3.81 (2H, t, J = 13.2 Hz), 7.02 (1H, d, J = 8.3 Hz), 7.07 (1H, dt, J = 1.0, 7.3 Hz), 7.20 (2H, d, J = 8.7 Hz), 7.35 (1H, dd, J = 1.8, 7.3 Hz), 7.42 (1H, ddd, J = 1.8, 7.3, 8.3 Hz), 7.56 (2H, d, J = 8.7 Hz), 8.59 (1H, s), 8.73 (1H, s). | ESI-MS m/z: 373 [M + H]$^+$. |
| I-524 | starting material: III-11 Step 1: 58% Step 2: 85% | 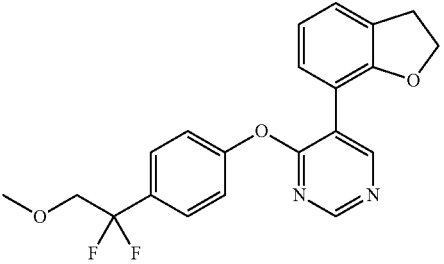 [SMILES: COCC(F)(F)c1ccc(Oc2ncncc2-c2cccc3c2OCC3)cc1] | $^1$H-NMR (400 MHz, CDCl$_3$) δ: 3.29 (2H, t, J = 8.5 Hz), 3.45 (3H, s), 3.82 (2H, t, J = 13.3 Hz), 4.60 (2H, t, J = 8.5 Hz), 6.96 (1H, t, J = 7.6 Hz), 7.19-7.28 (3H, m), 7.32 (1H, d, J = 7.3 Hz), 7.58 (2H, d, J = 8.7 Hz), 8.70 (1H, s), 8.75 (1H, s). | ESI-MS m/z: 385 [M + H]$^+$. |
| I-525 | starting material: III-1 Step 1: 79% Step 2: 81% | 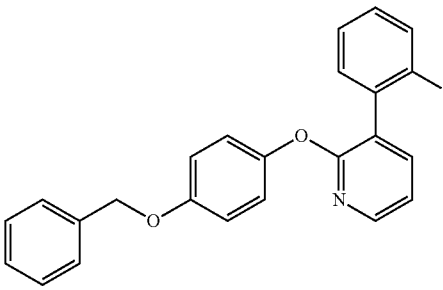 | $^1$H-NMR (400 MHz, CDCl$_3$) δ: 3.79 (3H, s), 5.04 (2H, s), 6.90-7.10 (7H, m), 7.28-7.48 (7H, m), 7.66 (1H, dd, J = 2.3, 7.3 Hz), 8.14 (1H, dd, J = 2.3, 5.0 Hz). | ESI-MS m/z: 384 [M + H]$^+$. |
| I-526 | starting material: III-10 Step 1: 17% Step 2: 64% | 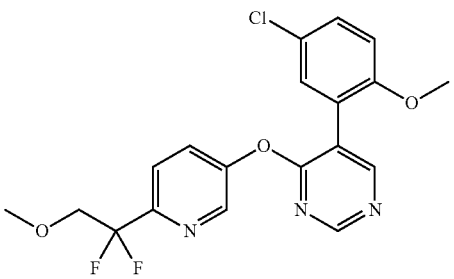 | $^1$H-NMR (400 MHz, CDCl$_3$) δ: 3.45 (3H, s), 3.80 (3H, s), 4.09 (2H, t, J = 13.3 Hz), 6.94 (1H, d, J = 8.7 Hz), 7.34 (1H, d, J = 2.8 Hz), 7.40 (1H, dd, J = 2.7, 8.7 Hz), 7.62 (1H, dd, J = 2.8, 8.7 Hz), 7.76 (1H, d, J = 8.7 Hz), 8.50 (1H, d, J = 2.3 Hz), 8.61 (1H, s), 8.74 (1H, s). | ESI-MS m/z: 408, 410 [M + H]$^+$. |
| I-527 | starting material: III-10 Step 1: 65% Step 2: 94% | 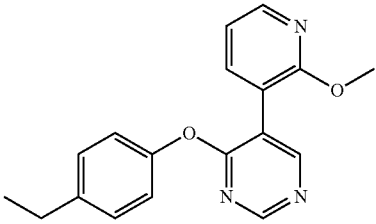 | $^1$H-NMR (400 MHz, CDCl$_3$) δ: 1.26 (3H, t, J = 7.7 Hz), 2.68 (2H, q, J = 7.7 Hz), 3.98 (3H, s), 7.00-7.06 (3H, m), 7.23-7.27 (2H, m), 7.72 (1H, dd, J = 2.0, 7.2 Hz), 8.25 (1H, dd, J = 2.0, 5.1 Hz), 8.59 (1H, s), 8.74 (1H, s). | ESI-MS m/z: 308 [M + H]$^+$. |

TABLE 65

| compound | starting material yield | structural formula | NMR | MS |
|---|---|---|---|---|
| I-528 | starting material: III-1 Step 1: 71% Step 2: 28% | | $^1$H-NMR (400 MHz, CDCl$_3$) δ: 3.84 (3H, s), 5.05 (2H, s), 6.92 (1H, dd, J = 2.7, 8.2 Hz), 6.97-7.00 (2H, m), 7.04-7.10 (3H, m), 7.22-7.25 (2H, m), 7.30-7.44 (6H, m), 7.74 (1H, dd, J = 1.4, 7.3 Hz), 8.12 (1H, dd, J = 1.4, 5.0 Hz). | ESI-MS m/z: 384 [M + H]$^+$. |
| I-529 | starting material: III-11 Step 1: 39% Step 2: 17% | | $^1$H-NMR (400 MHz, CDCl$_3$) δ: 3.96 (3H, s), 7.05 (1H, dd, J = 5.0, 7.3 Hz), 7.29 (1H, dd, J = 2.8, 8.7 Hz), 7.48 (1H, d, J = 2.8 Hz), 7.55 (1H, d, J = 8.7 Hz), 7.69 (1H, dd, J = 1.9, 7.3 Hz), 8.28 (1H, dd, J = 1.9, 5.0 Hz), 8.64 (1H, s), 8.75 (1H, s). | ESI-MS m/z: 382, 384 [M + H]$^+$. |
| I-530 | starting material: III-11 Step 1: 39% Step 2: 26% | | $^1$H-NMR (400 MHz, CDCl$_3$) δ: 3.95 (3H, s), 7.03-7.06 (3H, m), 7.64-7.69 (2H, m), 8.29 (1H, m), 8.67 (1H, m), 8.78 (1H, s). | ESI-MS m/z: 366 [M + H]$^+$. |
| I-531 | starting material: III-8 Step 1: 59% Step 2: 82% | | $^1$H-NMR (400 MHz, CDCl$_3$) δ: 2.31 (3H, s), 7.08-7.12 (2H, m), 7.16 (1H, dd, J = 4.9, 7.3 Hz), 7.20-7.23 (3H, m), 7.64 (1H, dd, J = 1.9, 7.3 Hz), 8.22 (1H, dd J = 1.9, 4.9 Hz), 8.46 (1H, s), 8.50 (1H, d, J = 5.0 Hz). | ESI-MS m/z: 347 [M + H]$^+$. |
| I-532 | starting material: III-9 Step 1: 71% Step 2: 86% | | $^1$H-NMR (400 MHz, CDCl$_3$) δ: 3.82 (3H, s), 5.05 (2H, s), 6.95-7.08 (5H, m), 7.11 (1H, t, J = 7.3 Hz), 7.29-7.47 (6H, m), 7.50 (1H, d, J = 7.3 Hz), 8.06 (1H, d, J = 2.7 Hz), 8.32 (1H, d, J = 2.7 Hz). | ESI-MS m/z: 385 [M + H]$^+$. |

TABLE 65-continued

| compound | starting material yield | structural formula | NMR | MS |
|---|---|---|---|---|
| I-533 | starting material: IV-95 Step 1: 67% Step 2: 9% | 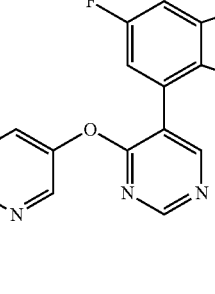 | $^1$H-NMR (400 MHz, CDCl$_3$) δ: 3.31 (2H, t, J = 8.5 Hz), 4.62 (2H, t, J = 8.7 Hz), 7.01-7.06 (2H, m), 7.73 (1H, dd, J = 2.3, 8.6 Hz), 7.78 (1H, d, J = 8.4 Hz), 8.62 (1H, d, J = 2.4 Hz), 8.72 (1H, s), 8.80 (1H, s) | ESI-MS m/z: 378 [M + H]$^+$. |
| I-534 | starting material: IV-93 Step 1: 92% Step 2: 23% | 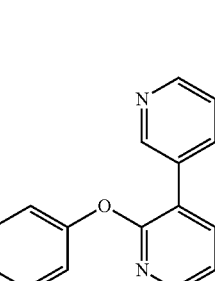 | $^1$H-NMR (400 MHz, CDCl$_3$) δ: 3.74 (3H, s), 4.63 (2H, td, J = 12.2, 46.5 Hz), 7.16-7.21 (3H, m), 7.53-7.56 (2H, m), 7.77 (1H, dd, J = 2.0, 7.4 Hz), 8.25 (1H, dd, J = 2.0, 4.9 Hz), 8.47 (1H, s), 8.70 (1H, s). | ESI-MS m/z: 439, 441 [M + H]$^+$. |
| I-535 | starting material: IV-93 Step 1: 92% Step 2: 23% | 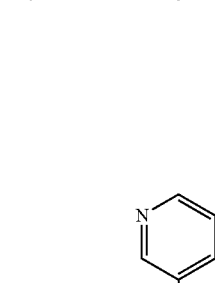 | $^1$H-NMR (400 MHz, CDCl$_3$) δ: 4.04 (3H, d, J = 4.6 Hz), 4.63 (2H, td, J = 12.2, 46.5 Hz), 7.15-7.20 (3H, m), 7.53-7.56 (2H, m), 7.70 (1H, dd, J = 1.9, 7.4 Hz), 8.23 (1H, dd, J = 2.0, 5.0 Hz), 8.28 (1H, s), 8.45 (1H, d, J = 6.3 Hz). | ESI-MS m/z: 379 [M + H]$^+$. |

TABLE 66

| compound | starting material yield | structural formula | NMR | MS |
|---|---|---|---|---|
| I-536 | starting material: IV-110 Step 1: 61% Step 2: 35% |  | $^1$H-NMR (400 MHz, CDCl$_3$) δ: 2.42 (3H, s), 6.73 (1H, t, J = 55.4 Hz), 7.00-7.07 (2H, m), 7.53 (1H, d, J = 8.4 Hz), 7.91 (1H, d, J = 2.0 Hz), 7.93 (1H, s), 8.24 (1H, m), 8.73 (1H, s), 8.84 (1H, d, J = 1.8 Hz), 8.85 (1H, s), 8.90 (1H, d, J = 1.8 Hz). | ESI-MS m/z: 365 [M + H]$^+$. |

TABLE 66-continued

| compound | starting material yield | structural formula | NMR | MS |
|---|---|---|---|---|
| I-537 | starting material: IV-119 Step 1→2: 11% (2 steps) | 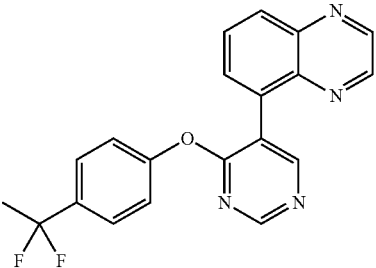 [SMILES: CC(F)(F)c1ccc(Oc2ncncc2-c2cccc3nccnc23)cc1] | $^1$H-NMR (400 MHz, CDCl$_3$) δ: 1.92 (3H, t, J = 18.1 Hz), 7.17-7.20 (2H, m), 7.52-7.55 (2H, m), 7.92 (1H, dd, J = 7.1, 9.8 Hz), 7.93 (1H, s), 8.22-8.26 (1H, m), 8.76 (1H, s), 8.84 (1H, d, J = 1.8 Hz), 8.85 (1H, s), 8.90 (1H, d, J = 1.8 Hz). | ESI-MS m/z: 365 [M + H]$^+$. |
| I-538 | starting material: I-70 Step 1→2: 48% (2 steps) | 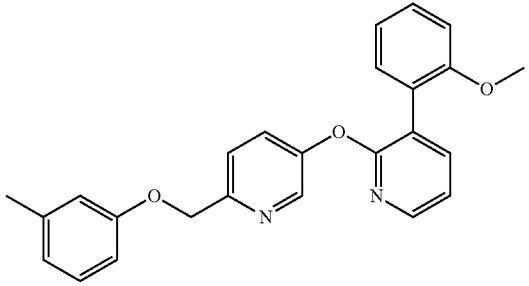 | $^1$H-NMR (400 MHz, CDCl$_3$) δ: 2.33 (3H, s), 3.76 (3H, s), 5.18 (2H, s), 6.78-6.82 (3H, m), 6.98 (1H, d, J = 8.2 Hz), 7.07 (1H, t, J = 7.3 Hz), 7.13 (1H, dd, J = 5.0, 7.3 Hz), 7.17 (1H, t, J = 8.2 Hz), 7.34 (1H, dd, J = 1.8, 7.3 Hz), 7.39 (1H, ddd, J = 1.8, 7.3, 8.2 Hz), 7.48 (1H, dd, J = 2.3, 8.2 Hz), 7.52 (1H, t, J = 8.2 Hz), 7.72 (1H, dd, J = 1.8, 7.3 Hz), 8.15 (1H, dd, J = 1.8, 5.0 Hz), 8.41 (1H, d, J = 2.7 Hz). | ESI-MS m/z: 399 [M + H]$^+$. |
| I-539 | starting material: I-172 yield: 12% | 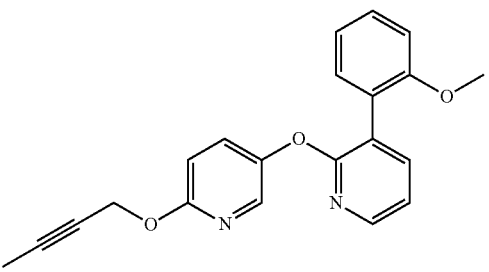 [SMILES: CC#CCOc1ccc(Oc2ncccc2-c2ccccc2OC)cn1] | $^1$H-NMR (400 MHz, CDCl$_3$) δ: 1.88 (3H, t, J = 2.3 Hz), 3.80 (3H, s), 4.91 (2H, q, J = 2.3 Hz), 6.81 (1H, d, J = 9.2 Hz), 6.99 (1H, d, J = 8.2 Hz), 7.04-7.10 (2H, m), 7.33-7.42 (3H, m), 7.68 (1H, dd, J = 1.8, 7.3 Hz), 7.97 (1H, d, J = 2.8 Hz), 8.12 (1H, dd, J = 1.8, 5.0 Hz). | ESI-MS m/z: 347 [M + H]$^+$. |
| I-540 | starting material: I-79 yield: 50% | 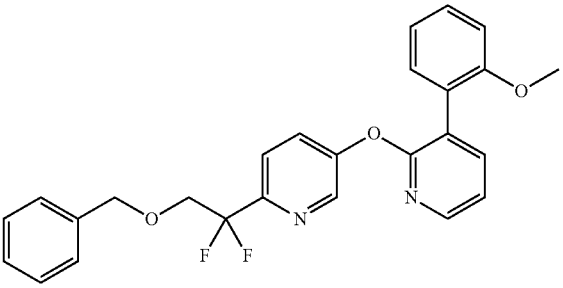 [SMILES: COc1ccccc1-c1cccnc1Oc1ccc(C(F)(F)COCc2ccccc2)nc1] | $^1$H-NMR (400 MHz, CDCl$_3$) δ: 3.73 (3H, s), 4.12 (2H, t, J = 13.2 Hz), 4.62 (2H, s), 6.89 (1H, d, J = 8.3 Hz), 7.06 (1H, t, J = 4.6, 7.3 Hz), 7.17 (1H, dd, J = 4.6, 7.3 Hz), 7.22-7.36 (6H, m), 7.40 (1H, t, J = 7.3 Hz), 7.55 (1H, t, J = 2.7, 8.7 Hz), 7.69 (1H, d, J = 8.7 Hz), 7.73 (1H, t, J = 1.8, 7.3 Hz), 8.16 (1H, dd, J = 1.8, 5.0 Hz), 8.44 (1H, d, J = 2.7 Hz). | ESI-MS m/z: 449 [M + H]$^+$. |
| I-541 | starting material: I-347 yield: 50% | 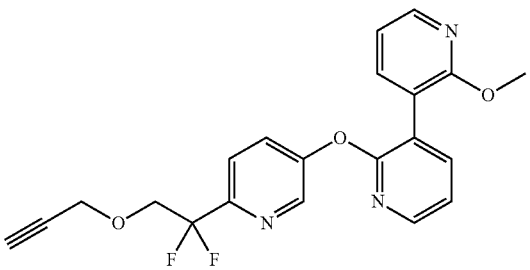 [SMILES: C#CCOCC(F)(F)c1ccc(Oc2ncccc2-c2cccnc2OC)cn1] | $^1$H-NMR (400 MHz, CDCl$_3$) δ: 2.47 (1H, t, J = 2.3 Hz), 3.88 (3H, s), 4.19-4.28 (4H, m), 7.01 (1H, dd, J = 5.0, 7.3 Hz), 7.18 (1H, dd, J = 4.6, 7.3 Hz), 7.57 (1H, dd, J = 2.7, 8.7 Hz), 7.65 (1H, dd, J = 1.9, 7.3 Hz), 7.70 (1H, d, J = 8.3 Hz), 7.76 (1H, dd, J = 2.3, 7.3 Hz), 8.18 (1H, dd, J = 1.8, 5.0 Hz), 8.22 (1H, dd, J = 1.8, 5.1 Hz), 8.47 (1H, d, J = 2.7 Hz). | ESI-MS m/z: 398 [M + H]$^+$. |

TABLE 66-continued

| compound | starting material yield | structural formula | NMR | MS |
|---|---|---|---|---|
| I-542 | starting material: I-434 yield: 39% | | ¹H-NMR (400 MHz, CDCl₃) δ: 3.45 (3H, s), 3.79 (2H, t, J = 13.3 Hz), 3.88 (3H, s), 6.99 (1H, dd, J = 5.0, 7.3 Hz), 7.10-7.20 (3H, m), 7.51 (2H, d, J = 8.7 Hz), 7.64 (1H, dd, J = 1.8, 7.3 Hz), 7.74 (1H, dd, J = 2.3, 5.0 Hz), 8.18-8.21 (2H, m). | ESI-MS m/z: 373 [M + H]⁺. |
| I-543 | starting material: I-434 yield: 48% | | ¹H-NMR (400 MHz, CDCl₃) δ: 2.47 (1H, t, J = 2.3 Hz), 3.87 (3H, s), 3.95 (2H, t, J = 13.3 Hz), 4.25 (2H, d, J = 2.3 Hz), 6.99 (1H, dd, J = 5.0, 7.3 Hz), 7.12-7.19 (3H, m), 7.52 (2H, d, J = 8.7 Hz), 7.65 (1H, dd, J = 1.8, 7.3 Hz), 7.74 (1H, dd, J = 2.3, 7.3 Hz), 8.19-8.21 (2H, m). | ESI-MS m/z: 397 [M + H]⁺. |

TABLE 67

| compound | starting material yield | structural formula | NMR | MS |
|---|---|---|---|---|
| I-544 | starting material: I-434 yield: 39% | | ¹H-NMR (400 MHz, CDCl₃) δ: 3.81 (2H, t, J = 13.3 Hz), 3.95 (3H, s), 4.62 (2H, s), 6.96 (1H, dd, J = 5.0, 7.3 Hz), 7.11-7.15 (3H, m), 7.25-7.34 (5H, m), 7.52 (2H, d, J = 8.7 Hz), 7.65 (1H, dd, J = 1.8, 7.3 Hz), 7.74 (1H, dd, J = 2.3, 7.3 Hz), 8.19 (2H, dt, J = 1.8, 5.0 Hz). | ESI-MS m/z: 449 [M + H]⁺. |
| I-545 | starting material: I-79 yield: 9% | | ¹H-NMR (400 MHz, CDCl₃) δ: 1.42-1.48 (2H, m), 1.85-1.95 (2H, m), 2.13-2.20 (2H, m), 3.71 (3H, s), 3.99-4.05 (3H, m), 6.97 (1H, d, J = 8.2 Hz), 7.06 (1H, t, J = 7.3 Hz), 7.17 (1H, dd, J = 2.3, 5.0 Hz), 7.32 (1H, dd, J = 2.3, 7.3 Hz), 7.37-7.41 (1H, m), 7.55 (1H, dd, J = 2.7, 8.7 Hz), 7.68 (1H, d, J = 8.7 Hz), 7.73 (1H, dd, J = 1.8, 7.3 Hz), 8.17 (1H, dd, J = 1.8, 5.0 Hz), 8.44 (1H, d, J = 2.7 Hz). | ESI-MS m/z: 413 [M + H]⁺. |

TABLE 67-continued

| compound | starting material yield | structural formula | NMR | MS |
|---|---|---|---|---|
| I-546 | starting material: I-154 yield: 81% | | ¹H-NMR (400 MHz, CDCl₃) δ: 1.12 (6H, d, J = 6.0 Hz), 3.68 (1H, sep, J = 6.0 Hz), 3.71 (3H, s), 4.08 (2H, d, J = 13.3 Hz), 6.70 (1H, dd, J = 2.3, 11.0 Hz), 6.77 (1H, dt, J = 2.7, 8.3 Hz), 7.17 (1H, dd, J = 5.0, 7.3 Hz), 7.26 (1H, dd, J = 6.9, 8.3 Hz), 7.54 (1H, dd, J = 2.7, 8.7 Hz), 7.67-7.78 (2H, 2m), 8.16 (1H, dd, J = 2.3, 8.7 Hz), 8.44 (1H, d, J = 2.3 Hz). | ESI-MS m/z: 419 [M + H]⁺. |
| I-547 | starting material: I-154 yield: quantitative | | ¹H-NMR (400 MHz, CDCl₃) δ: 0.84 (3H, t, J = 7.3 Hz), 1.50-1.61 (2H, m), 3.50 (2H, t, J = 6.9 Hz), 3.70 (3H, s), 4.09 (2H, t, J = 13.3 Hz), 6.69 (1H, dd, J = 2.3, 10.6 Hz), 6.76 (1H, dt, J = 2.3, 8.3 Hz), 7.16 (1H, dd, J = 5.0, 7.3 Hz), 7.26 (1H, dd, J = 5.0, 8.2 Hz), 7.54 (1H, dd, J = 2.7, 8.3 Hz), 7.68 (1H, d, J = 8.2 Hz), 7.70 (1H, dd, J = 1.8, 7.3 Hz), 8.16 (1H, dd, J = 1.8, 5.0 Hz), 8.44 (1H, d, J = 2.3 Hz). | ESI-MS m/z: 419 [M + H]⁺. |
| I-548 | starting material: I-80 yield: 65% | | ¹H-NMR (400 MHz, CDCl₃) δ: 0.76 (3H, t, J = 7.3 Hz), 1.35-1.42 (2H, m), 2.34 (3H, s), 2.41 (2H, t, J = 8.7 Hz), 3.21 (2H, t, J = 14.6 Hz), 3.72 (3H, s), 6.97 (1H, d, J = 8.3 Hz), 7.05 (1H, dt, J = 0.9, 7.3 Hz), 7.15 (1H, dd, J = 5.0, 7.3 Hz), 7.32 (1H, dd, J = 1.8, 7.3 Hz), 7.36-7.41 (1H, m), 7.53 (1H, dd, J = 2.7, 8.7 Hz), 7.65 (1H, d, J = 8.7 Hz), 7.73 (1H, dd, J = 1.8, 7.3 Hz), 8.14 (1H, dd, J = 1.8, 5.0 Hz), 8.44 (1H, d, J = 2.7 Hz). | ESI-MS m/z: 414 [M + H]⁺. |
| I-549 | starting material: I-156 yield: 65% | | ¹H-NMR (400 MHz, CDCl₃) δ: 2.04 (3H, s), 3.69 (3H, s), 4.92 (2H, t, J = 13.3 Hz), 6.69 (1H, dd, J = 2.3, 11.0 Hz), 6.77 (1H, dt, J = 2.3, 8.3 Hz), 7.17 (1H, dd, J = 4.6, 7.3 Hz), 7.22 (1H, s), 7.26 (1H, dd, J = 6.4, 8.7 Hz), 7.29 (1H, s), 7.51 (1H, dd, J = 2.3, 8.3 Hz), 7.58 (1H, d, J = 8.7 Hz), 7.71 (1H, dd, J = 1.8, 7.3 Hz), 8.16 (1H, dd, J = 1.8, 5.0 Hz), 8.47 (1H, d, J = 2.3 Hz). | ESI-MS m/z: 441 [M + H]⁺. |
| I-550 | starting material: I-338 yield: quantitative | | ¹H-NMR (400 MHz, CDCl₃) δ: 3.18 (6H, s), 3.83 (3H, s), 7.01 (1H, d, J = 8.2 Hz), 7.05-7.09 (2H, m), 7.34 (1H, dd, J = 1.7, 7.4 Hz), 7.38-7.42 (1H, m), 7.65 (1H, dd, J = 2.0, 7.3 Hz), 8.09 (1H, dd, J = 1.9, 4.9 Hz), 8.19 (2H, s). | ESI-MS m/z: 323 [M + H]⁺. |

TABLE 67-continued

| compound | starting material yield | structural formula | NMR | MS |
|---|---|---|---|---|
| I-551 | starting material: I-338 yield: 22% | | $^1$H-NMR (400 MHz, CDCl$_3$) δ: 2.18 (1H, t, J = 2.3 Hz), 3.22 (3H, s), 3.82 (3H, s), 4.48 (2H, d, J = 2.3 Hz), 7.01 (1H, d, J = 8.2 Hz), 7.05-7.09 (2H, m), 7.34 (1H, dd, J = 1.8, 7.8 Hz), 7.40 (1H, dt, J = 1.8, 9.6 Hz), 7.66 (1H, dd, J = 1.8, 7.3 Hz), 8.10 (1H, dd, J = 1.8, 5.0 Hz), 8.24 (2H, s). | ESI-MS m/z: 347 [M + H]$^+$. |

TABLE 68

| compound | starting material yield | structural formula | NMR | MS |
|---|---|---|---|---|
| I-552 | starting material: I-191 yield: 16% | | $^1$H-NMR (400 MHz, CDCl$_3$) δ: 2.18 (1H, t, J = 2.3 Hz), 3.23 (3H, s), 3.81 (3H, s), 4.48 (2H, d, J = 2.3 Hz), 6.71-6.79 (2H, m), 7.07 (1H, dd, J = 5.0, 7.3 Hz), 7.28 (1H, dd, J = 6.4, 8.3 Hz), 7.63 (1H, dd, J = 1.8, 7.3 Hz), 8.09 (1H, dd, J = 1.8, 5.0 Hz), 8.22 (2H, s). | ESI-MS m/z: 365 [M + H]$^+$. |
| I-553 | starting material: I-191 yield: 93% | | $^1$H-NMR (400 MHz, CDCl$_3$) δ: 3.12 (3H, s), 3.81 (3H, s), 4.26 (2H, td, J = 1.4, 5.5 Hz), 5.14-5.19 (2H, m), 5.83-5.92 (1H, m), 6.71-6.79 (2H, m), 7.05-7.08 (1H, m), 7.28-7.30 (1H, m), 7.62 (1H, dd, J = 2.3, 7.3 Hz), 8.10 (1H, dd, J = 1.8, 5.0 Hz), 8.18 (2H, s). | ESI-MS m/z: 367 [M + H]$^+$. |
| I-554 | starting material: I-353 yield: 86% | | $^1$H-NMR (400 MHz, CDCl$_3$) δ: 0.95 (3H, t, J = 7.3 Hz), 1.30-1.40 (2H, m), 1.56-1.64 (2H, m), 3.14 (3H, s), 3.61 (2H, J = 7.3 Hz), 3.97 (3H, s), 7.01 (1H, dd, J = 5.0, 7.3 Hz), 7.08 (1H, dd, J = 5.0, 7.3 Hz), 7.65-7.70 (2H, m), 8.13 (1H, dd, J = 1.8, 5.0 Hz), 8.18 (2H, s), 8.23 (1H, dd, J = 1.8, 5.0 Hz). | ESI-MS m/z: 366 [M + H]$^+$. |

TABLE 68-continued

| compound | starting material yield | structural formula | NMR | MS |
|---|---|---|---|---|
| I-555 | starting material: IV-29 Step 1: 63% Step 2: 95% | | $^1$H-NMR (400 MHz, CDCl$_3$) δ: 3.77 (8H, s), 3.82 (3H, s), 7.01 (1H, d, J = 9.2 Hz), 7.06-7.10 (2H, m), 7.34 (1H, dd, J = 1.4, 7.4 Hz), 7.40 (1H, dt, J = 1.8, 8.3 Hz), 7.67 (1H, dd, J = 1.8, 6.8 Hz), 8.10 (1H, dd, J = 1.8, 5.0 Hz), 8.21 (2H, s). | ESI-MS m/z: 365 [M + H]$^+$. |
| I-556 | starting material: IV-29 Step 1: 78% Step 2: 81% | | $^1$H-NMR (400 MHz, CDCl$_3$) δ: 1.19 (6H, t, J = 6.8 Hz), 3.60 (4H, q, J = 6.9 Hz), 3.83 (3H, s), 7.00 (1H, d, J = 8.2 Hz), 7.05-7.09 (2H, m), 7.34 (1H, dd, J = 1.8, 7.8 Hz), 7.38-7.42 (1H, m), 7.66 (1H, dd, J = 1.8, 7.3 Hz), 8.11 (1H, dd, J = 1.8, 4.7 Hz), 8.17 (2H, s). | ESI-MS m/z: 351 [M + H]$^+$. |
| I-557 | starting material: IV-29 Step 1: 78% Step 2: 87% | | $^1$H-NMR (400 MHz, CDCl$_3$) δ: 1.19 (6H, t, J = 7.3 Hz), 3.61 (4H, q, J = 7.3 Hz), 3.81 (3H, s), 6.71-6.79 (2H, m), 7.04-7.08 (1H, m), 7.26-7.30 (1H, m), 7.60 (1H, dd, J = 1.8, 7.3 Hz), 8.11 (1H, dd, J = 1.8, 4.6 Hz), 8.16 (2H, s). | ESI-MS m/z: 369 [M + H]$^+$. |
| I-558 | starting material: IV-29 Step 1: 78% Step 2: 80% | | $^1$H-NMR (400 MHz, CDCl$_3$) δ: 1.20 (6H, t, J = 6.9 Hz), 3.29 (2H, t, J = 8.7 Hz), 3.61 (4H, q, J = 7.3 Hz), 4.60 (2H, t, J = 8.7 Hz), 6.95 (1H, t, J = 7.3 Hz), 7.06 (1H, m), 7.23-7.31 (2H, m), 7.79 (1H, dd, J = 2.3, 7.3 Hz), 8.10 (1H, dd, J = 1.8, 5.0 Hz), 8.22 (2H, s). | ESI-MS m/z: 363 [M + H]$^+$. |
| I-559 | starting material: IV-29 Step 1: 83% Step 2: 89% | | $^1$H-NMR (400 MHz, CDCl$_3$) δ: 0.91 (6H, d, J = 6.9 Hz), 2.06-2.13 (1H, m), 3.14 (3H, s), 3.43 (2H, d, J = 7.8 Hz), 3.83 (3H, s), 7.00 (1H, d, J = 8.3 Hz), 7.05-7.08 (2H, m), 7.34 (1H, dd, J = 1.4, 7.3 Hz), 7.40 (1H, dt, J = 1.8, 8.3), 7.66 (1H, dd, J = 1.8, 7.3 Hz), 8.11 (1H, dd, J = 1.8, 5.0 Hz), 8.17 (2H, s). | ESI-MS m/z: 365 [M + H]$^+$. |

TABLE 69

| compound | starting material yield | structural formula | NMR | MS |
|---|---|---|---|---|
| I-560 | starting material: IV-29 Step 1: 83% Step 2: 94% | | ¹H-NMR (400 MHz, CDCl₃) δ: 0.92 (6H, d, J = 6.9 Hz), 2.06-2.13 (1H, m), 3.14 (3H, s), 3.43 (2H, d, J = 7.3 Hz), 3.81 (3H, s), 6.71-6.79 (2H, m), 7.04-7.07 (1H, m), 7.26-7.30 (1H, m), 7.62 (1H, dd, J = 1.8, 6.9 Hz), 8.11 (1H, dd, J = 1.8, 5.0 Hz), 8.16 (2H, s). | ESI-MS m/z: 383 [M + H]⁺. |
| I-561 | starting material: IV-29 Step 1: 83% Step 2: 98% | | ¹H-NMR (400 MHz, CDCl₃) δ: 0.92 (6H, d, J = 6.9 Hz), 2.07-2.14 (1H, m), 3.15 (3H, s), 3.29 (2H, t, J = 8.7 Hz), 3.43 (2H, d, J = 7.8 Hz), 4.60 (2H, d, J = 8.7 Hz), 6.95 (1H, t, J = 7.8 Hz), 7.04-7.08 (1H, m), 7.23-7.31 (2H, m), 7.79 (1H, dd, J = 1.8, 7.3 Hz), 8.09 (1H, dd, J = 1.8, 5.1 Hz), 8.22 (2H, s). | ESI-MS m/z: 377 [M + H]⁺. |
| I-562 | starting material: IV-29 Step 1: 93% Step 2: 94% | | ¹H-NMR (400 MHz, CDCl₃) δ: 0.28 (2H, q, J = 4.6 Hz), 0.48-0.53 (2H, m), 1.06-1.13 (1H, m), 3.21 (3H, s), 3.52 (2H, d, J = 6.9 Hz), 3.97 (3H, s), 7.00-7.03 (1H, m), 7.07-7.10 (1H, m), 7.66-7.70 (2H, m), 8.12 (1H, dd, J = 1.8, 5.0 Hz), 8.19 (2H, s), 8.23 (1H, dd, J = 1.8, 5.0 Hz). | ESI-MS m/z: 364 [M + H]⁺. |
| I-563 | starting material: IV-29 Step 1: 93% Step 2: 94% | | ¹H-NMR (400 MHz, CDCl₃) δ: 0.27 (2H, q, J = 4.6 Hz), 0.48-0.52 (2H, m), 1.08-1.13 (1H, m), 3.21 (3H, s), 3.52 (2H, d, J = 6.9 Hz), 3.83 (3H, s), 7.00 (1H, d, J = 8.7 Hz), 7.05-7.09 (2H, m), 7.34 (1H, dd, J = 1.9, 7.8 Hz), 7.40 (1H, dt, J = 1.4, 8.3 Hz), 7.66 (1H, dd, J = 1.8, 7.3 Hz), 8.10 (1H, dd, J = 1.8, 5.0 Hz), 8.18 (2H, s). | ESI-MS m/z: 363 [M + H]⁺. |
| I-564 | starting material: IV-29 Step 1: 93% Step 2: 92% | | ¹H-NMR (400 MHz, CDCl₃) δ: 0.27 (2H, q, J = 4.6 Hz), 0.48-0.52 (2H, m), 1.06-1.13 (1H, m), 3.21 (3H, s), 3.52 (2H, d, J = 6.4 Hz), 3.81 (3H, s), 6.71-6.80 (2H, m), 7.05-7.08 (1H, m), 7.28-7.30 (1H, m), 7.62 (1H, dd, J = 1.8, 7.3 Hz), 8.10 (1H, dd, J = 1.8, 5.0 Hz), 8.17 (2H, s). | ESI-MS m/z: 381 [M + H]⁺. |

TABLE 69-continued

| compound | starting material yield | structural formula | NMR | MS |
|---|---|---|---|---|
| I-565 | starting material: IV-29 Step 1: 93% Step 2: 95% | | $^1$H-NMR (400 MHz, CDCl$_3$) δ: 0.28 (2H, q, J = 5.0 Hz), 0.48-0.51 (2H, m), 1.07-1.12 (1H, m), 3.21 (3H, s), 3.30 (2H, t, J = 8.7 Hz), 3.53 (2H, d, J = 6.9 Hz), 4.60 (2H, t, J = 8.7 Hz), 6.95 (1H, t, J = 7.3 Hz), 7.05-7.08 (1H, m), 7.24-7.31 (2H, m), 7.80 (1H, dd, J = 1.8, 7.3 Hz), 8.09 (1H, dd, J = 2.3, 5.1 Hz), 8.23 (2H, s). | ESI-MS m/z: 375 [M + H]$^+$. |
| I-566 | starting material: IV-29 Step 1: 72% Step 2: 63% | | $^1$H-NMR (400 MHz, CDCl$_3$) δ: 1.41 (3H, t, J = 7.3 Hz), 3.16 (2H, q, J = 7.3 Hz), 3.77 (3H, s), 6.72 (1H, dd, J = 2.3, 11.0 Hz), 6.78 (1H, dt, J = 2.7, 8.2 Hz), 7.13-7.16 (1H, m), 7.25-7.30 (1H, m), 7.67 (1H, dd, J = 1.8, 7.3 Hz), 8.12 (1H, dd, J = 1.8, 4.5 Hz), 8.40 (2H, s). | ESI-MS m/z: 358 [M + H]$^+$. |
| I-567 | starting material: I-385 yield: 49% | | $^1$H-NMR (400 MHz, CDCl$_3$) δ: 1.23 (6H, d, J = 6.4 Hz), 3.24 (3H, s), 3.80 (3H, s), 4.32 (2H, s), 4.60 (1H, sept, J = 6.4 Hz), 6.71-6.79 (2H, m), 7.06 (1H, dd, J = 5.0, 7.3 Hz), 7.27 (1H, dd, J = 6.8, 8.3 Hz), 7.62 (1H, dd, J = 1.8, 7.3 Hz), 8.08 (1H, dd, J = 1.8, 5.0 Hz), 8.18 (2H, s). | ESI-MS m/z: 427 [M + H]$^+$. |

TABLE 70

| compound | starting material yield | structural formula | NMR | MS |
|---|---|---|---|---|
| I-568 | starting material: I-221 yield: 90% | 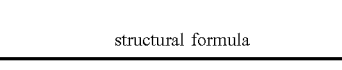 | $^1$H-NMR (400 MHz, CDCl$_3$) δ: 3.86 (3H, s), 7.21-7.24 (3H, m), 7.57 (1H, s), 7.65 (2H, m), 7.78 (1H, dd, J = 1.9, 7.4 Hz), 8.30 (1H, dd, J = 1.9, 4.9 Hz). | ESI-MS m/z: 398, 400 [M + H]$^+$. |

TABLE 70-continued

| compound | starting material yield | structural formula | NMR | MS |
|---|---|---|---|---|
| I-569 | starting material: I-191 Step 1: 79% Step 2: 76% | | ¹H-NMR (400 MHz, CDCl₃) δ: 3.14-3.19 (2H, m), 3.26-3.31 (2H, m), 3.75 (3H, s), 6.72 (1H, dd, J = 2.3, 11.0 Hz), 6.78 (1H, ddd, J = 2.3, 8.3, 8.3 Hz), 7.16 (1H, dd, J = 5.0, 7.3 Hz), 7.18-7.22 (1H, m), 7.25-7.32 (5H, m), 7.69 (1H, dd, J = 1.8, 7.3 Hz), 8.13 (1H, dd, J = 1.8, 5.0 Hz), 8.52 (2H, s). | ESI-MS m/z: 402 [M + H]⁺. |
| I-570 | starting material: I-353 Step 1: 45% Step 2: 78% | | ¹H-NMR (400 MHz, CDCl₃) δ: 3.14-3.19 (2H, m), 3.27-3.32 (2H, m), 3.91 (3H, s), 7.02 (1H, dd, J = 5.0, 7.3 Hz), 7.16-7.22 (2H, m), 7.26-7.32 (4H, m), 7.67 (1H, dd, J = 1.8, 7.3 Hz), 7.75 (1H, dd, J = 1.8, 7.3 Hz), 8.15 (1H, dd, J = 1.8, 5.0 Hz), 8.24 (1H, dd, J = 1.8, 5.0 Hz), 8.46 (2H, s). | ESI-MS m/z: 385 [M + H]⁺. |
| I-571 | starting material: I-390 Step 1: 42% Step 2: 20% | | ¹H-NMR (400 MHz, CDCl₃) δ: 2.72-2.79 (2H, m), 2.82-2.88 (2H, m), 3.84 (3H, s), 3.93 (3H, s), 6.97-7.03 (3H, m), 7.05-7.09 (2H, m), 7.15-7.20 (2H, m), 7.30 (1H, s), 7.66-7.72 (2H, m), 8.17 (1H, dd, J = 1.8, 5.0 Hz), 8.20 (1H, dd, J = 1.8, 5.0 Hz). | ESI-MS m/z: 387 [M + H]⁺. |
| I-572 | starting material: I-390 Step 1: 72% Step 2: 86% (Pd(OH)₂/C used instead of PD/C) | | ¹H-NMR (400 MHz, CDCl₃) δ: 2.94-2.99 (2H, m), 3.15-3.19 (2H, m), 3.92 (3H, s), 6.99 (1H, dd, J = 5.0, 7.3 Hz), 7.02-7.05 (2H, m), 7.08 (1H, dd, J = 5.0, 7.3 Hz), 7.16-7.19 (2H, m), 7.59 (1H, s), 7.67 (1H, dd, J = 1.8, 7.3 Hz), 7.71 (1H, dd, J = 1.8, 7.3 Hz), 8.17 (1H, dd, J = 1.8, 5.0 Hz), 8.20 (1H, dd, J = 1.8, 5.0 Hz), 8.65 (1H, s). | ESI-MS m/z: 390 [M + H]⁺. |
| I-573 | starting material: I-390 Step 1: 74% Step 2: 43% (Pd(OH)₂/C used instead of Pd/C) | | ¹H-NMR (400 MHz, CDCl₃) δ: 3.09-3.15 (2H, m), 3.32-3.36 (2H, m), 3.92 (3H, s), 6.98 (1H, dd, J = 5.0, 7.3 Hz), 7.01-7.05 (2H, m), 7.07 (1H, dd, J = 5.0, 7.3 Hz), 7.18-7.24 (3H, m), 7.68 (1H, dd, J = 1.8, 7.3 Hz), 7.69-7.72 (2H, s), 8.17 (1H, dd, J = 1.8, 5.0 Hz), 8.19 (1H, dd, J = 1.8, 5.0 Hz). | ESI-MS m/z: 390 [M + H]⁺. |

TABLE 70-continued

| compound | starting material yield | structural formula | NMR | MS |
|---|---|---|---|---|
| I-574 | starting material: III-10 Step 1: 65% Step 2: 90% Step 3: 15% | | $^1$H-NMR (400 MHz, CDCl$_3$) δ: 1.23 (3H, t, J = 7.7 Hz), 2.65 (2H, q, J = 7.7 Hz), 6.64 (1H, d, J = 2.2 Hz), 6.96 (1H, dd, J = 1.2, 7.0 Hz), 7.05-7.10 (2H, m), 7.19-7.25 (3H, m), 7.66 (1H, dd, J = 1.9, 9.0 Hz), 7.98 (1H, d, J = 2.2 Hz), 8.84-8.88 (2H, m). | ESI-MS m/z: 317 [M + H]$^+$. |
| I-575 | starting material: 5-Br-2-tBu-pyrimidine Step 1: 98% Step 2: quantitative Step 3: 7% Step 4: 64% | | $^1$H-NMR (400 MHz, CDCl$_3$) δ: 1.42 (9H, s), 3.77 (3H, s), 6.71 (1H, d, J = 10.5 Hz), 6.77 (1H, ddd, J = 1.8, 8.2, 10.5 Hz), 7.15 (1H, ddd, J = 1.8, 5.0, 8.2 Hz), 7.28 (1H, t, J = 7.3 Hz), 7.68 (1H, dd, J = 1.8, 7.3 Hz), 8.13 (1H, dd, J = 1.8, 5.0 Hz), 8.52 (2H, s). | ESI-MS m/z: 354 [M + H]$^+$. |

TABLE 71

| compound | starting material yield | structural formula | NMR | MS |
|---|---|---|---|---|
| I-576 | starting material: IV-42 yield: 70% | | $^1$H-NMR (400 MHz, CDCl$_3$) δ: 3.74 (3H, s), 6.96-6.98 (1H, m), 7.03-7.07 (1H, m), 7.09-7.13 (3H, m), 7.20 (2H, d, J = 8.2 Hz), 7.32 (1H, dd, J = 1.8, 7.3 Hz), 7.36-7.40 (1H, m), 7.71 (1H, dd, J = 2.3, 7.3 Hz), 8.17 (1H, dd, J = 1.8, 7.5 Hz). | ESI-MS m/z: 360 [M + H]$^+$. |
| I-577 | starting material: IV-79 yield: 41% | | $^1$H-NMR (400 MHz, CDCl$_3$) δ: 6.60-6.61 (1H, m), 6.61 (1H, t, J = 56.6 Hz), 6.91 (1H, dd, J = 1.4, 6.9 Hz), 7.19-7.23 (4H, m), 7.47-7.50 (2H, m), 7.62 (1H, dd, J = 1.4, 8.7 Hz), 7.94 (1H, d, J = 2.3 Hz), 8.02 (1H, dd, J = 2.3, 7.3 Hz), 8.30 (1H, dd, J = 2.3, 5.0 Hz). | ESI-MS m/z: 338 [M + H]$^+$. |

TABLE 71-continued

| compound | starting material yield | structural formula | NMR | MS |
|---|---|---|---|---|
| I-578 | starting material: I-338 yield: 22% | | ¹H-NMR (400 MHz, CDCl₃) δ: 3.82 (3H, s), 4.63 (2H, d, J = 6.0 Hz), 5.39 (1H, t, J = 5.5 Hz), 7.00 (1H, d, J = 8.2 Hz), 7.05-7.10 (2H, m), 7.29-7.43 (7H, m), 7.67 (1H, dd, J = 1.8, 7.3 Hz), 8.11 (1H, dd, J = 1.9, 4.6 Hz), 8.19 (2H, s). | ESI-MS m/z: 385 [M + H]⁺. |
| I-579 | starting material: I-191 Step 1: 60% Step 2: 67% | | ¹H-NMR (400 MHz, CDCl₃) δ: 2.39 (3H, s), 3.12-3.18 (2H, m), 3.21-3.26 (2H, m), 3.78 (3H, s), 6.72 (1H, dd, J = 2.3, 11.0 Hz), 6.76-6.81 (1H, m), 7.11-7.23 (5H, m), 7.26-7.31 (1H, m), 7.69 (1H, dd, J = 1.8, 7.3 Hz), 8.13 (1H, dd, J = 1.8, 5.0 Hz), 8.54 (2H, s). | ESI-MS m/z: 416 [M + H]⁺. |
| I-580 | starting material: I-191 Step 1: 71% Step 2: 77% | | ¹H-NMR (400 MHz, CDCl₃) δ: 2.33 (3H, s), 3.10-3.15 (2H, m), 3.25-3.29 (2H, m), 3.75 (3H, s), 6.72 (1H, dd, J = 2.3, 11.0 Hz), 6.76-6.81 (1H, m), 7.00-7.20 (5H, m), 7.26-7.30 (1H, m), 7.69 (1H, dd, J = 1.8, 7.3 Hz), 8.13 (1H, dd, J = 1.8, 5.0 Hz), 8.52 (2H, s). | ESI-MS m/z: 416 [M + H]⁺. |
| I-581 | starting material: I-399 yield: 38% | | ¹H-NMR (400 MHz, CDCl₃) δ: 3.26 (2H, t, J = 7.8 Hz), 3.91 (3H, s), 4.67 (2H, t, J = 7.8 Hz), 6.98 (1H, dd, J = 5.0, 7.3 Hz), 7.01-7.04 (2H, m), 7.08 (1H, dd, J = 5.0, 7.3 Hz), 7.16-7.19 (2H, m), 7.59 (2H, s), 7.66 (1H, dd, J = 1.8, 7.3 Hz), 7.71 (1H, dd, J = 2.3, 7.3 Hz), 8.17 (1H, dd, J = 2.3, 5.0 Hz), 8.20 (1H, dd, J = 1.8, 5.0 Hz). | ESI-MS m/z: 374 [M + H]⁺. |

TABLE 71-continued

| compound | starting material yield | structural formula | NMR | MS |
|---|---|---|---|---|
| I-582 | starting material: I-44 yield: 35% | | $^1$H-NMR (400 MHz, CDCl$_3$) δ: 6.89 (1H, dd, J = 1.4, 6.9 Hz), 7.20 (1H, dd, J = 6.9, 8.7 Hz), 7.28 (1H, dd, J = 5.0, 7.8 Hz), 7.62 (1H, dd, J = 1.4, 8.7 Hz), 7.68-7.69 (2H, m), 7.77 (1H, d, J = 3.7 Hz), 7.99 (1H, dd, J = 1.8, 7.3 Hz), 8.30 (1H, dd, J = 1.8, 5.0 Hz), 8.54 (1H, s). | ESI-MS m/z: 375 [M + H]$^+$. |

Experimental Example 1: Antifungal Activity Evaluation Test

The minimum inhibitory concentration (MIC) for Trichophyton mentagrophytes and Trichophyton rubrum was measured by the following procedure by reference to Clinical and Laboratory standards Institute (CLSI) guidelines M38-A2. Reference document for the measurement method: National Committee for a Clinical Laboratory Standards. Reference method for broth dilution antifungal susceptibility testing of filamentous fungi. Approved standard Second edition M38-A2. Wayne, Pa.: National Committee for a Clinical Laboratory Standards, 2008.

Test compound solution: A test compound was dissolved in dimethyl sulfoxide (DMSO) at a concentration of 2.5 mg/mL to give a stock solution. The stock solution was appropriately diluted with DMSO to prepare a 2-fold dilution series. As control compounds, terbinafine and amorolfine were used.

Test strains: Trichophyton mentagrophytes SM-110 and Trichophyton rubrum KD-1130 were used.

Preparation of fungal culture to be inoculated: The above-mentioned test strain was suspended in 0.05% Tween 80-containing saline, and the fungi of the genus Trichophyton were prepared to a fungal concentration of 1×10$^6$ cells/mL by using a hemocytometer. Then, using MOPS-buffered RPMI 1640 medium (pH 7.0) as a test medium, a fungal culture of the fungi of the genus Trichophyton was diluted 250-fold (4×10$^3$ cells/mL) to give a fungal culture for inoculation.

MIC measurement of genus Trichophyton fungi: MOPS-buffered RPMI 1640 medium (pH 7.0) was dispensed by 100 µL to given wells of a 96 well U-bottom microplate. Then, the test compound solution (2 µL) was added, the mixture was sufficiently stirred by a plate mixer. The fungal culture (100 µL) was inoculated and the mixture was cultured at 35° C. for 4 days (final fungal concentration: 2×10$^3$ cells/mL). After the culture, the minimum drug concentration of a well in which a growth inhibitory action of not less than 80% was visually observed as compared to a growth control was taken as a minimum inhibitory concentration (MIC: µg/mL).

The results are shown in Tables 72-79.

The abbreviations in the Tables mean the following fungi and compounds.

T. menta.: Trichophyton mentagrophytes
T. rubrum: Trichophyton rubrum
TBF: terbinafine
AMF: amorolfine

TABLE 72

| compound | MIC (T. menta.) | MIC (T. rubrum) |
|---|---|---|
| I-1 | A | A |
| I-2 | A | A |
| I-3 | A | A |
| I-4 | A | A |
| I-5 | B | A |
| I-6 | A | A |
| I-7 | A | A |
| I-8 | A | A |
| I-9 | B | A |
| I-10 | A | A |
| I-11 | A | A |
| I-12 | A | A |
| I-13 | A | A |
| I-14 | A | A |
| I-15 | B | B |
| I-16 | A | A |
| I-17 | B | B |
| I-19 | C | C |
| I-20 | C | B |
| I-21 | B | B |
| I-23 | A | A |
| I-24 | C | C |
| I-25 | B | B |
| I-26 | A | A |
| I-27 | B | B |
| I-28 | B | B |
| I-29 | A | A |
| I-30 | A | A |
| I-31 | A | A |
| I-32 | B | A |
| I-33 | C | C |
| I-34 | A | A |
| I-35 | A | A |
| I-36 | A | B |
| I-37 | B | B |
| I-38 | A | A |
| I-39 | A | B |
| I-40 | B | B |
| I-41 | A | A |
| I-42 | B | B |
| I-43 | B | B |
| I-44 | A | A |
| I-45 | C | B |
| I-47 | C | C |
| I-48 | C | B |
| I-49 | C | C |
| I-50 | B | B |
| I-51 | A | A |
| I-52 | B | A |
| I-53 | B | A |
| I-54 | B | B |

TABLE 72-continued

| compound | MIC (T. menta.) | MIC (T. rubrum) |
| --- | --- | --- |
| I-55 | B | B |
| I-56 | B | B |
| I-57 | B | B |
| I-59 | B | B |
| I-60 | B | B |
| I-61 | C | C |
| I-62 | C | B |
| I-63 | B | B |
| I-64 | A | A |
| I-65 | B | A |
| I-66 | C | B |
| I-67 | B | B |
| I-68 | C | C |
| I-69 | C | C |
| I-71 | C | C |
| I-72 | B | B |
| I-73 | A | A |
| I-74 | A | A |
| I-75 | A | A |
| I-76 | A | A |
| I-77 | A | A |
| I-78 | A | A |
| I-79 | B | C |
| I-80 | B | B |
| I-81 | A | A |
| I-82 | A | A |
| I-83 | A | A |
| I-84 | A | A |

TABLE 73

| compound | MIC (T. menta.) | MIC (T. rubrum) |
| --- | --- | --- |
| I-85 | A | A |
| I-86 | B | B |
| I-87 | B | B |
| I-88 | A | A |
| I-89 | B | B |
| I-90 | B | B |
| I-91 | B | B |
| I-92 | B | B |
| I-93 | B | B |
| I-94 | A | A |
| I-95 | B | B |
| I-96 | A | A |
| I-97 | B | B |
| I-98 | B | B |
| I-99 | B | B |
| I-100 | A | A |
| I-101 | B | B |
| I-102 | B | B |
| I-104 | B | B |
| I-105 | C | C |
| I-106 | C | C |
| I-107 | C | C |
| I-108 | A | B |
| I-109 | A | A |
| I-110 | A | B |
| I-111 | B | B |
| I-112 | B | B |
| I-113 | A | B |
| I-114 | B | B |
| I-115 | A | A |
| I-116 | A | A |
| I-117 | A | A |
| I-118 | A | A |
| I-119 | A | A |
| I-120 | A | A |
| I-121 | A | A |
| I-122 | A | A |
| I-123 | A | A |
| I-124 | B | B |
| I-125 | A | B |

TABLE 73-continued

| compound | MIC (T. menta.) | MIC (T. rubrum) |
| --- | --- | --- |
| I-126 | B | B |
| I-127 | C | C |
| I-128 | A | A |
| I-129 | A | A |
| I-130 | B | B |
| I-131 | B | B |
| I-132 | B | C |
| I-133 | C | C |
| I-134 | A | A |
| I-135 | A | A |
| I-136 | A | A |
| I-137 | A | A |
| I-138 | A | A |
| I-139 | C | C |
| I-140 | B | B |
| I-141 | C | C |
| I-142 | A | A |
| I-143 | B | B |
| I-144 | A | A |
| I-145 | A | A |
| I-146 | B | C |
| I-147 | A | B |
| I-148 | B | B |
| I-149 | B | B |
| I-150 | A | A |
| I-151 | B | B |
| I-152 | B | B |
| I-153 | A | A |
| I-154 | B | B |
| I-155 | A | A |
| I-157 | A | A |
| I-158 | A | B |
| I-159 | A | B |
| I-160 | A | A |
| I-161 | A | A |
| I-162 | A | A |
| I-163 | A | A |
| I-165 | A | A |
| I-166 | A | A |
| I-167 | B | B |

TABLE 74

| compound | MIC (T. menta.) | MIC (T. rubrum.) |
| --- | --- | --- |
| I-168 | B | B |
| I-169 | B | B |
| I-170 | B | B |
| I-171 | A | A |
| I-173 | A | A |
| I-174 | A | A |
| I-175 | B | B |
| I-176 | A | A |
| I-177 | A | A |
| I-178 | A | A |
| I-179 | A | A |
| I-180 | A | A |
| I-181 | B | A |
| I-182 | A | A |
| I-183 | A | A |
| I-184 | A | A |
| I-185 | A | A |
| I-186 | A | A |
| I-187 | C | C |
| I-188 | A | A |
| I-189 | B | B |
| I-191 | B | B |
| I-192 | A | A |
| I-193 | A | A |
| I-194 | A | B |
| I-195 | B | B |
| I-196 | B | B |
| I-198 | B | B |

TABLE 74-continued

| compound | MIC (T. menta.) | MIC (T. rubrum.) |
| --- | --- | --- |
| I-199 | A | A |
| I-200 | A | A |
| I-201 | A | A |
| I-202 | A | A |
| I-203 | A | A |
| I-204 | A | A |
| I-205 | A | A |
| I-206 | A | A |
| I-207 | A | A |
| I-208 | A | A |
| I-209 | A | A |
| I-210 | A | A |
| I-211 | A | A |
| I-212 | A | A |
| I-213 | A | A |
| I-216 | A | A |
| I-217 | C | C |
| I-218 | A | A |
| I-219 | A | A |
| I-220 | A | A |
| I-221 | B | B |
| I-222 | A | A |
| I-223 | B | B |
| I-224 | A | A |
| I-225 | A | A |
| I-226 | A | A |
| I-227 | A | A |
| I-228 | A | A |
| I-229 | B | C |
| I-230 | B | B |
| I-231 | C | C |
| I-232 | B | B |
| I-233 | B | B |
| I-234 | A | A |
| I-235 | B | B |
| I-236 | C | C |
| I-237 | A | A |
| I-238 | B | B |
| I-239 | B | B |
| I-240 | A | A |
| I-241 | A | A |
| I-242 | B | C |
| I-243 | B | B |
| I-244 | C | C |
| I-245 | A | A |
| I-246 | C | C |
| I-248 | C | C |
| I-249 | B | B |
| I-251 | C | C |
| I-252 | B | B |
| I-253 | A | A |
| I-254 | A | A |

TABLE 75

| compound | MIC (T. menta.) | MIC (T. rubrum) |
| --- | --- | --- |
| I-255 | A | A |
| I-256 | A | A |
| I-258 | A | A |
| I-259 | B | B |
| I-260 | B | A |
| I-261 | A | A |
| I-262 | B | B |
| I-263 | A | A |
| I-264 | A | A |
| I-265 | B | B |
| I-266 | A | A |
| I-267 | A | A |
| I-268 | A | A |
| I-269 | A | A |
| I-270 | A | A |
| I-271 | A | A |
| I-272 | A | A |
| I-273 | A | A |
| I-274 | B | B |
| I-275 | B | B |
| I-276 | B | B |
| I-277 | A | A |
| I-278 | B | B |
| I-279 | B | B |
| I-280 | A | A |
| I-281 | A | A |
| I-282 | A | A |
| I-283 | A | A |
| I-284 | A | A |
| I-285 | A | A |
| I-286 | A | A |
| I-287 | B | B |
| I-288 | A | A |
| I-289 | A | A |
| I-290 | A | A |
| I-291 | A | A |
| I-292 | A | A |
| I-293 | C | C |
| I-294 | B | B |
| I-295 | A | A |
| I-296 | A | A |
| I-297 | A | A |
| I-298 | A | A |
| I-299 | A | A |
| I-300 | A | A |
| I-301 | A | A |
| I-302 | A | A |
| I-303 | A | A |
| I-304 | A | A |
| I-305 | A | A |
| I-306 | A | A |
| I-307 | A | A |
| I-308 | A | A |
| I-309 | B | A |
| I-310 | A | A |
| I-311 | B | B |
| I-312 | A | A |
| I-313 | A | A |
| I-314 | B | A |
| I-315 | A | A |
| I-316 | A | A |
| I-317 | A | A |
| I-318 | A | A |
| I-319 | A | A |
| I-320 | A | A |
| I-321 | A | A |
| I-322 | A | A |
| I-323 | A | A |
| I-324 | A | A |
| I-325 | A | A |
| I-326 | A | A |
| I-327 | A | A |
| I-328 | A | A |
| I-329 | A | A |
| I-330 | A | A |
| I-331 | A | A |
| I-332 | A | A |
| I-333 | A | A |
| I-334 | A | A |
| I-335 | A | A |

TABLE 76

| compound | MIC (T. menta.) | MIC (T. rubrum) |
| --- | --- | --- |
| I-336 | A | A |
| I-338 | B | B |
| I-339 | A | A |
| I-340 | A | A |

TABLE 76-continued

| compound | MIC (T. menta.) | MIC (T. rubrum) |
| --- | --- | --- |
| I-341 | B | A |
| I-342 | B | B |
| I-343 | B | B |
| I-344 | A | A |
| I-345 | A | A |
| I-346 | C | C |
| I-347 | C | C |
| I-348 | B | B |
| I-349 | C | C |
| I-350 | A | A |
| I-351 | B | B |
| I-353 | C | B |
| I-354 | A | B |
| I-355 | A | A |
| I-356 | A | A |
| I-357 | B | C |
| I-358 | A | A |
| I-359 | A | A |
| I-360 | A | A |
| TBF | A | A |
| AMF | A | A |

MIC
A: ≤0.1 µg/mL
B: 0.2-0.78 µg/mL
C: 1.56-6.25 µg/mL

TABLE 77

| compound | MIC (T. menta.) | MIC (T. rubrum) |
| --- | --- | --- |
| I-361 | B | B |
| I-362 | A | A |
| I-363 | A | A |
| I-365 | A | B |
| I-366 | A | A |
| I-367 | A | A |
| I-368 | A | A |
| I-369 | A | A |
| I-370 | A | A |
| I-371 | A | A |
| I-374 | A | A |
| I-375 | A | A |
| I-377 | A | A |
| I-378 | A | A |
| I-379 | A | A |
| I-380 | A | A |
| I-381 | A | A |
| I-384 | A | A |
| I-386 | A | A |
| I-387 | A | A |
| I-388 | A | A |
| I-390 | A | A |
| I-392 | A | A |
| I-394 | A | A |
| I-396 | A | A |
| I-397 | A | A |
| I-398 | A | A |
| I-400 | A | A |
| I-401 | A | A |
| I-404 | A | A |
| I-407 | A | A |
| I-408 | A | A |
| I-409 | A | A |
| I-411 | A | A |
| I-412 | A | A |
| I-413 | A | A |
| I-414 | A | A |
| I-415 | A | A |
| I-416 | A | A |
| I-418 | A | A |
| I-419 | A | A |
| I-421 | A | A |
| I-422 | B | B |

TABLE 77-continued

| compound | MIC (T. menta.) | MIC (T. rubrum) |
| --- | --- | --- |
| I-423 | A | A |
| I-424 | B | A |
| I-425 | A | A |
| I-426 | A | A |
| I-428 | A | A |
| I-429 | A | A |
| I-430 | A | A |
| I-431 | A | A |
| I-432 | A | A |
| I-433 | A | A |
| I-434 | B | C |
| I-435 | B | B |
| I-436 | A | A |
| I-439 | B | B |
| I-440 | A | A |
| I-441 | A | A |
| I-442 | A | A |
| I-443 | A | A |
| I-444 | A | A |
| I-445 | A | A |
| I-446 | A | A |
| I-447 | A | A |
| I-448 | A | A |
| I-449 | A | A |
| I-450 | A | A |
| I-451 | A | A |
| I-452 | A | A |
| I-453 | A | A |
| I-454 | A | A |
| I-455 | A | A |
| I-456 | A | A |
| I-457 | A | A |
| I-458 | A | A |
| I-459 | A | A |
| I-460 | A | A |
| I-461 | A | A |
| I-462 | A | A |

TABLE 78

| compound | MIC (T. menta.) | MIC (T. rubrum) |
| --- | --- | --- |
| I-463 | A | A |
| I-464 | A | A |
| I-465 | A | A |
| I-466 | B | B |
| I-467 | B | B |
| I-468 | A | A |
| I-469 | A | A |
| I-470 | A | A |
| I-471 | A | A |
| I-472 | A | A |
| I-473 | A | A |
| I-474 | A | A |
| I-475 | A | A |
| I-476 | A | A |
| I-477 | A | A |
| I-478 | A | A |
| I-479 | A | A |
| I-480 | A | A |
| I-481 | A | A |
| I-482 | A | A |
| I-483 | A | A |
| I-484 | A | A |
| I-485 | A | A |
| I-486 | A | A |
| I-487 | A | A |
| I-488 | A | A |
| I-489 | A | A |
| I-490 | A | A |
| I-491 | A | A |
| I-492 | A | A |
| I-493 | A | A |

TABLE 78-continued

| compound | MIC (T. menta.) | MIC (T. rubrum) |
| --- | --- | --- |
| I-494 | A | A |
| I-495 | A | A |
| I-496 | A | A |
| I-497 | A | A |
| I-498 | A | A |
| I-499 | A | A |
| I-500 | A | A |
| I-501 | A | A |
| I-502 | A | A |
| I-503 | A | A |
| I-504 | A | A |
| I-505 | A | A |
| I-506 | A | A |
| I-507 | A | A |
| I-508 | A | A |
| I-509 | A | A |
| I-510 | A | A |
| I-511 | A | A |
| I-512 | A | A |
| I-513 | A | A |
| I-514 | A | A |
| I-515 | A | A |
| I-516 | A | A |
| I-517 | A | A |
| I-518 | A | A |
| I-519 | A | A |
| I-520 | A | A |
| I-521 | A | A |
| I-522 | A | A |
| I-523 | A | A |
| I-524 | A | A |
| I-525 | A | A |
| I-526 | A | A |
| I-527 | A | A |
| I-528 | A | A |
| I-529 | A | A |
| I-530 | A | A |
| I-531 | A | A |
| I-532 | A | A |
| I-533 | A | A |
| I-534 | A | A |
| I-535 | A | A |
| I-536 | A | A |
| I-537 | A | A |
| I-538 | A | A |
| I-539 | A | A |
| I-540 | A | A |
| I-541 | A | A |
| I-542 | A | A |

TABLE 79

| compound | MIC (T. menta.) | MIC (T. rubrum) |
| --- | --- | --- |
| I-543 | A | A |
| I-544 | A | A |
| I-545 | A | A |
| I-546 | A | A |
| I-547 | A | A |
| I-548 | A | A |
| I-549 | A | A |
| I-550 | A | A |
| I-551 | A | A |
| I-552 | A | A |
| I-553 | A | A |
| I-554 | A | A |
| I-555 | B | A |
| I-556 | A | A |
| I-557 | A | A |
| I-558 | A | A |
| I-559 | A | A |
| I-560 | A | A |
| I-561 | A | A |
| I-562 | A | A |
| I-563 | A | A |
| I-564 | A | A |
| I-565 | A | A |
| I-566 | A | A |
| I-567 | A | A |
| I-568 | A | A |
| I-569 | A | A |
| I-570 | A | A |
| I-571 | A | B |
| I-572 | A | A |
| I-573 | A | A |
| I-574 | A | A |
| I-575 | A | A |
| I-576 | A | A |
| I-577 | A | A |
| I-578 | A | A |
| I-579 | A | A |
| I-580 | A | A |
| I-581 | A | A |
| I-582 | A | A |

Experimental Example 2: Nail Permeability Test

Permeability through human nail was measured by the method shown below using Franz cell.

Test Preparation: A test compound was dissolved in a propylene glycol:ethanol (1:4) mixed solution at a concentration of 5% to give a test preparation. As control compounds terbinafine and amorolfine were used.

(1) Human nail (thickness 300-500 μm) was fixed using a nail adapter for Franz cell, and mounted on Franz cell.
(2) The receptor chamber of the Franz cell was filled with phosphate buffer, and placed in a thermostatic chamber at 32° C.
(3) A test preparation was applied to the aforementioned human nail at 61 μL/cm$^2$, after which a receptor solution was collected over days, and the concentration of the test compound in the receptor was measured by a liquid chromatography mass spectrometry method (LC/MS/MS). The cumulative amount of drug permeation (μg/cm$^2$) was calculated from the measured drug concentration in the receptor. A cumulative amount of drug permeation relative to the time after start of the test was plotted and the slope at final 4 time points was taken as Flux (μg/cm$^2$/day).

The results are shown in Table 80.

The abbreviations in the Table mean the following compounds

TBF: terbinafine
AMF: amorolfine

TABLE 80

| compound | nail permeability (μg/cm$^2$/day) |
| --- | --- |
| I-1 | B |
| I-12 | B |
| I-26 | B |
| I-28 | A |
| I-35 | B |
| I-44 | B |
| I-68 | B |
| I-73 | C |
| I-79 | B |
| I-81 | B |

TABLE 80-continued

| compound | nail permeability (μg/cm²/day) |
|---|---|
| I-84 | B |
| I-90 | A |
| I-96 | B |
| I-100 | B |
| I-110 | B |
| I-115 | B |
| I-120 | B |
| I-121 | C |
| I-145 | B |
| I-161 | B |
| I-168 | B |
| I-179 | B |
| I-192 | B |
| I-206 | B |
| I-210 | B |
| I-216 | B |
| I-219 | B |
| I-237 | B |
| I-252 | A |
| I-253 | B |
| I-261 | B |
| I-295 | B |
| I-297 | B |
| I-310 | B |
| I-311 | B |
| I-312 | B |
| I-324 | B |
| I-330 | C |
| I-335 | C |
| I-336 | C |
| I-343 | A |
| I-346 | B |
| I-348 | B |
| I-349 | A |
| I-350 | B |
| I-351 | B |
| I-354 | B |
| I-355 | B |
| I-356 | B |
| I-357 | A |
| I-358 | B |
| I-359 | B |
| I-360 | B |
| TBF | D |
| AMF | D | nail permeability
A: ≥0.1
B: 0.01 - less than 0.1
C: 0.001 - less than 0.01
D: <0.001

INDUSTRIAL APPLICABILITY

The biaryl derivative (I) or a salt thereof of the present invention shows an excellent antifungal activity against the causative microorganism of superficial mycosis, and an antifungal agent containing same as an active ingredient is useful for the treatment of prophylaxis of infections caused by fungi in mammals including human.

This application is based on a patent application No. 2015-185966 filed in Japan (filing date: Sep. 18, 2015), the contents of which are incorporated herein by reference in their entireties.

The invention claimed is:

1. A biaryl derivative represented by the formula (I) or a salt thereof:

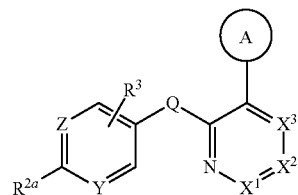

wherein ring A is a ring selected from the group consisting of

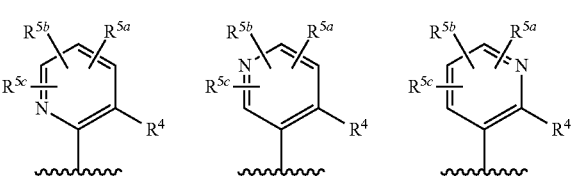

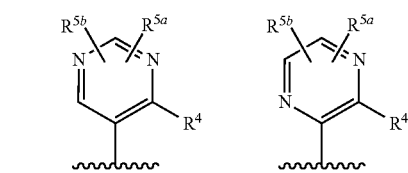

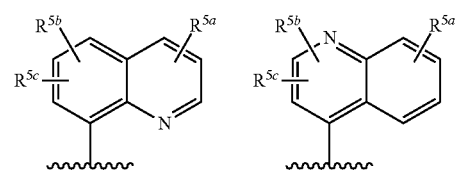

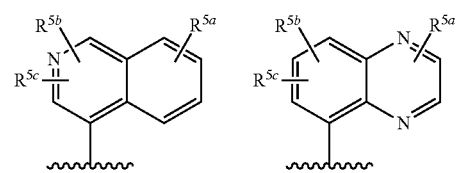

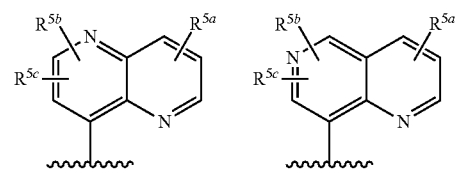

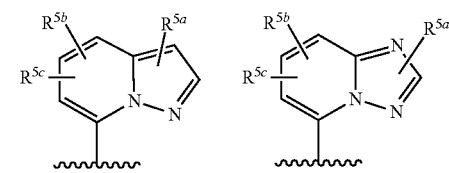

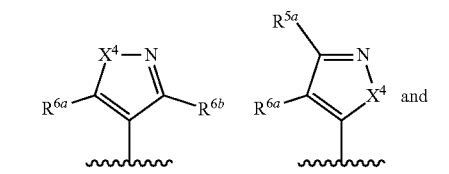

and

-continued

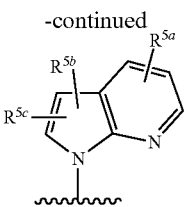

wherein
n is 1 or 2,
$R^4$ is
halogen,
cyano,
hydroxyl,
$C_1-C_6$ haloalkyl,
heterocycloalkyl,
heterocycloalkyloxy,
a 5-membered ring heteroaryl group,
$C_1-C_6$ haloalkoxy,
$C_2-C_6$ alkenyl,
$C_2-C_6$ alkenyl-$C_1-C_6$ alkoxy,
$C_2-C_6$ alkynyl,
$C_2-C_6$ alkynyl-$C_1-C_6$ alkoxy,
$C_1-C_6$ alkylthio,
—$NR^dR^e$, wherein $R^d$ and $R^e$ are each independently hydrogen or $C_1-C_6$ alkyl,
nitro,
formyl,
$C_1-C_6$ alkylcarbonyl,
$C_1-C_6$ alkoxycarbonyl,
$C_1-C_6$ alkylcarbonyloxy group, or
an optionally substituted group selected from the group consisting of $C_1-C_6$ alkyl, $C_3-C_7$ cycloalkyl, and $C_1-C_6$ alkoxy,
$R^{5a}$, $R^{5b}$, and $R^{5c}$ are each independently
hydrogen,
halogen,
cyano,
$C_1-C_6$ alkyl,
$C_1-C_6$ alkoxy,
$C_1-C_6$ haloalkyl,
$C_1-C_6$ haloalkoxy,
$C_3-C_7$ cycloalkyl,
$C_1-C_6$ alkylcarbonyl, or
$C_1-C_6$ alkoxycarbonyl,
$X^4$ is $NR^f$, O, or S, wherein $R^f$ is hydrogen or $C_1-C_6$ alkyl, and
$R^{6a}$ and $R^{6b}$ are each independently
hydrogen,
halogen,
$C_1-C_6$ haloalkyl,
$C_1-C_6$ haloalkoxy, or
an optionally substituted group selected from the group consisting of
$C_1-C_6$ alkyl,
$C_3-C_7$ cycloalkyl,
$C_1-C_6$ alkoxy, and
$C_1-C_6$ alkylthio,
Q is O,
$X^1$, $X^2$ and $X^3$ are each $CR^1$,
Y is CH,
Z is $CR^{2b}$,
each $R^1$ independently is
hydrogen,
halogen,
$C_1-C_6$ alkyl,
$C_1-C_6$ haloalkyl,
$C_1-C_6$ alkoxy or
$C_1-C_6$ haloalkoxy,
$R^{2a}$ and $R^{2b}$ are each independently
hydrogen,
halogen,
hydroxyl,
cyano,
formyl,
a pentafluorosulfanyl group,
—$NR^aR^b$, wherein $R^a$ and $R^b$ are each independently hydrogen or an optionally substituted $C_1-C_6$ alkyl group, provided that $R^a$ and $R^b$ are not both hydrogen,
an optionally substituted group selected from the group consisting of
$C_1-C_6$ alkyl,
$C_1-C_6$ haloalkyl,
$C_1-C_6$ alkoxy,
$C_1-C_6$ haloalkoxy,
$C_1-C_4$ alkoxy-$C_1-C_4$ alkyl,
$C_1-C_4$ alkoxy-$C_1-C_4$ haloalkyl,
$C_1-C_6$ alkylcarbonyl,
$C_1-C_6$ alkoxycarbonyl,
$C_1-C_6$ alkylcarbonyloxy,
$C_3-C_7$ cycloalkyl,
heterocycloalkyl,
heterocycloalkyloxy,
$C_2-C_6$ alkenyl,
$C_2-C_6$ alkenyloxy,
$C_2-C_6$ alkenyl-$C_1-C_6$ alkyl,
$C_2-C_6$ alkenyl-$C_1-C_6$ alkoxy,
$C_2-C_6$ alkenyloxy-$C_1-C_4$ alkyl,
$C_2-C_6$ alkenyloxy-$C_1-C_4$ alkoxy,
$C_2-C_6$ alkenyloxy-$C_1-C_4$ haloalkyl,
$C_2-C_6$ alkenyloxy-$C_1-C_4$ haloalkoxy,
$C_2-C_6$ alkynyl,
$C_2-C_6$ alkynyloxy,
$C_2-C_6$ alkynyl-$C_1-C_6$ alkyl,
$C_2-C_6$ alkynyl-$C_1-C_6$ alkoxy,
$C_2-C_6$ alkynyloxy-$C_1-C_4$ alkyl,
$C_2-C_6$ alkynyloxy-$C_1-C_4$ alkoxy,
$C_2-C_6$ alkynyloxy-$C_1-C_4$ haloalkyl,
$C_2-C_6$ alkynyloxy-$C_1-C_4$ haloalkoxy,
$C_1-C_6$ alkylthio, and
$C_1-C_6$ haloalkylthio,
or
a group of formula (I-A)

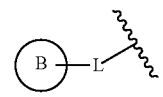

(I-A)

wherein
L is a single bond, —$(CH_2)_p$—, —$O(CH_2)_p$—, —$(CH_2)_pO$—, —$(CH_2)_pO(CH_2)_q$—, —$NR^c(CH_2)_p$—, —$(CH_2)_pNR^c$ or —$(CH_2)_pNR^c(CH_2)_q$—, wherein one or more hydrogen atoms of $(CH_2)_p$ and $(CH_2)_q$ are each optionally substituted by halogen, $C_1-C_4$ alkyl, or $C_3-C_7$ cycloalkyl,
p is 1, 2 or 3,
q is 1, 2 or 3,
$R^c$ is hydrogen or $C_1-C_6$ alkyl, and ring B is an optionally substituted carbocycle, or an optionally substituted heterocycle, or $R^{2a}$ and $R^{2b}$ can be joined to form —$(CH_2)_r$— that is optionally substituted by halogen, hydroxyl, or oxo and r is 3, 4, 5, or 6, and $R^3$ is
hydrogen,
halogen,
$C_1$-$C_6$ haloalkyl,
$C_1$-$C_6$ haloalkoxy, or
an optionally substituted group selected from the group consisting of $C_1$-$C_6$ alkyl, $C_1$-$C_6$ alkoxy, $C_3$-$C_7$ cycloalkyl, $C_2$-$C_6$ alkenyl, $C_2$-$C_6$ alkynyl, and aralkyl.

2. The biaryl derivative according to claim 1 or a salt thereof, wherein $R^{2a}$ and $R^{2b}$ are each independently
hydrogen,
halogen,
cyano,
a pentafluorosulfanyl group,
—$NR^aR^b$, wherein $R^a$ and $R^b$ are each independently
hydrogen,
$C_1$-$C_6$ alkyl,
$C_1$-$C_6$ alkyl substituted by cyano,
$C_1$-$C_6$ alkyl substituted by $C_1$-$C_4$ alkoxy,
$C_1$-$C_6$ alkyl substituted by $C_1$-$C_6$ alkoxycarbonyl,
$C_1$-$C_6$ alkyl substituted by $C_3$-$C_7$ cycloalkyl, or
$C_1$-$C_6$ alkyl substituted by $C_2$-$C_6$ alkenyl; provided that $R^a$ and $R^b$ are not both
hydrogen,
$C_1$-$C_6$ alkyl,
$C_1$-$C_6$ alkyl substituted by —$OR^g$, wherein $R^g$ is
$C_1$-$C_6$ alkyl,
$C_1$-$C_6$ haloalkyl,
$C_1$-$C_4$ alkoxy-$C_1$-$C_4$ alkyl,
$C_2$-$C_6$ alkenyl-$C_1$-$C_6$ alkyl,
$C_2$-$C_6$ alkynyl-$C_1$-$C_6$ alkyl,
cyanomethyl,
$C_3$-$C_7$ cycloalkyl,
$C_1$-$C_6$ alkylcarbonyl, or
—$CONR^jR^k$ wherein $R^j$ and $R^k$ are each independently hydrogen or $C_1$-$C_6$ alkyl, $C_1$-$C_6$ alkyl substituted by $C_1$-$C_6$ alkoxycarbonyl,
$C_1$-$C_6$ alkyl substituted by cyano,
$C_1$-$C_6$ haloalkyl,
$C_1$-$C_6$ haloalkyl substituted by heterocycloalkyl,
$C_1$-$C_6$ haloalkyl substituted by —$NR^hR^i$, wherein $R^h$ is $C_1$-$C_6$ alkyl and $R^i$ is
hydrogen,
$C_1$-$C_6$ alkyl,
$C_1$-$C_6$ alkoxy,
cyanomethyl,
$C_1$-$C_6$ alkylcarbonyl, or
$C_1$-$C_6$ alkoxycarbonyl,
$C_1$-$C_6$ alkoxy,
$C_1$-$C_6$ alkoxy substituted by $C_1$-$C_6$ alkoxycarbonyl,
$C_1$-$C_6$ haloalkoxy,
$C_1$-$C_4$ alkoxy-$C_1$-$C_4$ alkyl,
$C_1$-$C_4$ alkoxy-$C_1$-$C_4$ haloalkyl,
$C_1$-$C_4$ alkoxy-$C_1$-$C_4$ haloalkyl substituted by $C_1$-$C_4$ alkoxy,
$C_1$-$C_6$ alkylcarbonyl,
$C_1$-$C_6$ alkoxycarbonyl,
$C_1$-$C_6$ alkylcarbonyloxy,
$C_3$-$C_7$ cycloalkyl,
$C_3$-$C_7$ cycloalkyl substituted by $C_1$-$C_6$ alkyl,
$C_3$-$C_7$ cycloalkyl substituted by $C_1$-$C_4$ alkoxy-$C_1$-$C_4$ alkyl,
heterocycloalkyl,
heterocycloalkyloxy,
$C_2$-$C_6$ alkenyl,
$C_2$-$C_6$ alkenyloxy,
$C_2$-$C_6$ alkenyl-$C_1$-$C_6$ alkyl,
$C_2$-$C_6$ alkenyl-$C_1$-$C_6$ alkoxy,
$C_2$-$C_6$ alkenyloxy-$C_1$-$C_4$ alkyl,
$C_2$-$C_6$ alkenyloxy-$C_1$-$C_4$ alkoxy,
$C_2$-$C_6$ alkenyloxy-$C_1$-$C_4$ haloalkyl,
$C_2$-$C_6$ alkenyloxy-$C_1$-$C_4$ haloalkoxy,
$C_2$-$C_6$ alkynyl,
$C_2$-$C_6$ alkynyloxy,
$C_2$-$C_6$ alkynyl-$C_1$-$C_6$ alkyl,
$C_2$-$C_6$ alkynyl-$C_1$-$C_6$ alkoxy,
$C_2$-$C_6$ alkynyloxy-$C_1$-$C_4$ alkyl,
$C_2$-$C_6$ alkynyloxy-$C_1$-$C_4$ alkoxy,
$C_2$-$C_6$ alkynyloxy-$C_1$-$C_4$ haloalkyl,
$C_2$-$C_6$ alkynyloxy-$C_1$-$C_4$ haloalkoxy,
$C_1$-$C_6$ alkylthio,
$C_1$-$C_6$ haloalkylthio, or
a group of formula (I-A)

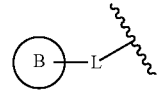

(I-A)

wherein
L is a single bond, —$(CH_2)_p$—, —$O(CH_2)_p$—, —$(CH_2)_pO$—, —$NR^c(CH_2)_p$—, or —$(CH_2)_pNR^c$—, wherein one or more hydrogen atoms of $(CH_2)_p$ are each optionally substituted by halogen,
p is 1 or 2,
$R^c$ is hydrogen or methyl, and
ring B is phenyl, pyrrolyl, furyl, thienyl, imidazolyl, triazolyl, pyrazolyl, oxazolyl, isoxazolyl, thiazolyl, isothiazolyl, thiadiazolyl, oxadiazolyl, pyridyl, pyridazinyl, pyrimidinyl, or pyrazinyl, or $R^{2a}$ and $R^{2b}$ can be joined to form —$(CH_2)_r$— that is optionally substituted by halogen, hydroxyl, or oxo and r is 3, 4, 5, or 6, and $R^3$ is
hydrogen,
halogen,
$C_1$-$C_6$ alkyl,
$C_1$-$C_6$ haloalkyl,
$C_1$-$C_6$ alkoxy,
$C_1$-$C_6$ haloalkoxy,
$C_3$-$C_7$ cycloalkyl,
$C_2$-$C_6$ alkenyl,
$C_2$-$C_6$ alkynyl, or
aralkyl, $R^4$ is
halogen,
cyano,
hydroxyl,
$C_1$-$C_6$ alkyl,
$C_1$-$C_6$ haloalkyl,
$C_3$-$C_7$ cycloalkyl,
heterocycloalkyl,
heterocycloalkyloxy,
a 5-membered ring heteroaryl group,
$C_1$-$C_6$ alkoxy, C$_1$-C$_6$ haloalkoxy,
C$_2$-C$_6$ alkenyl,
C$_2$-C$_6$ alkenyl-C$_1$-C$_6$ alkoxy,
C$_2$-C$_6$ alkynyl,
C$_2$-C$_6$ alkynyl-C$_1$-C$_6$ alkoxy,
C$_1$-C$_6$ alkylthio,
—NR$^d$R$^e$, wherein R$^d$ and R$^e$ are each independently hydrogen or C$_1$-C$_6$ alkyl, nitro,
formyl,
C$_1$-C$_6$ alkylcarbonyl,
C$_1$-C$_6$ alkoxycarbonyl, or
C$_1$-C$_6$ alkylcarbonyloxy group,
R$^{6'}$ and R$^{6b}$ are each independently
hydrogen,
halogen,
C$_1$-C$_6$ alkyl,
C$_1$-C$_6$ haloalkyl,
C$_3$-C$_7$ cycloalkyl,
C$_1$-C$_6$ alkoxy,
C$_1$-C$_6$ haloalkoxy, or
C$_1$-C$_6$ alkylthio.

3. The biaryl derivative according to claim 1 or a salt thereof, wherein X$^1$ is CH.

4. The biaryl derivative according to claim 1 or a salt thereof, wherein X$^1$ and X$^3$ are CH, X$^2$ is CR$^1$, and R$^1$ is hydrogen or halogen.

5. The biaryl derivative according to claim 1 or a salt thereof, wherein X$^1$, X$^2$ and X$^3$ are each CH.

6. The biaryl derivative according to claim 1 or a salt thereof, wherein ring A is a ring selected from the group consisting of

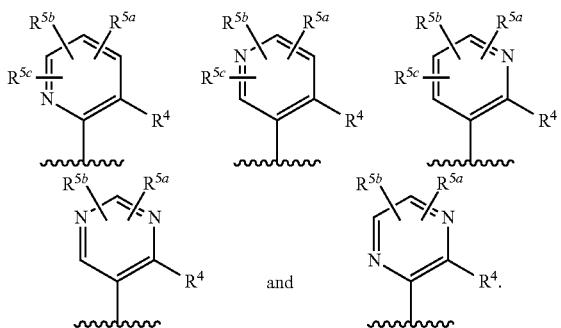

7. The biaryl derivative according to claim 1 or a salt thereof, wherein ring A is a ring selected from the group consisting of:

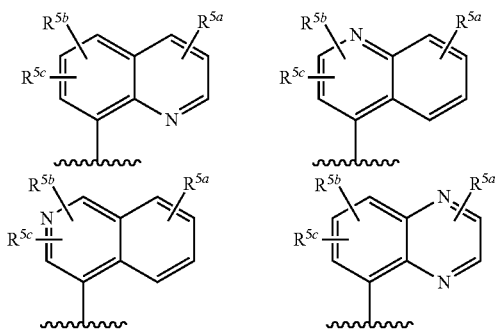

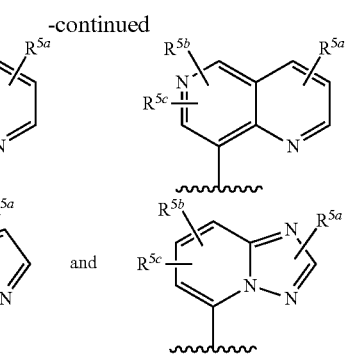

8. The biaryl derivative according to claim 1 or a salt thereof, wherein ring A is a ring selected from the group consisting of:

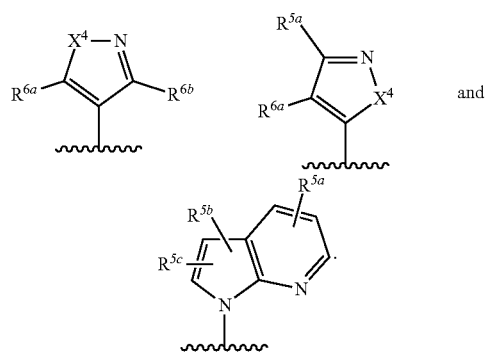

9. The biaryl derivative according to claim 1 or a salt thereof, wherein R$^4$ is halogen, cyano, a C$_1$-C$_6$ alkyl, a C$_1$-C$_6$ haloalkyl, a C$_3$-C$_7$ cycloalkyl, a C$_1$-C$_6$ alkoxy, a C$_1$-C$_6$ haloalkoxy, a vinyl, an ethynyl, or a C$_1$-C$_6$ alkylthio.

10. The biaryl derivative according to claim 1 or a salt thereof, wherein R$^4$ is halogen, C$_1$-C$_4$ alkyl, C$_1$-C$_4$ haloalkyl, cyclopropyl, a C$_1$-C$_4$ alkoxy, or C$_1$-C$_4$ haloalkoxy.

11. The biaryl derivative according to claim 1 or a salt thereof, wherein
R$^{2a}$ is
hydrogen,
halogen,
cyano,
a pentafluorosulfanyl group,
—NR$^a$R$^b$, wherein R$^a$ and R$^b$ are each independently
hydrogen,
C$_1$-C$_6$ alkyl,
C$_1$-C$_6$ alkyl substituted by cyano,
C$_1$-C$_6$ alkyl substituted by C$_1$-C$_4$ alkoxy,
C$_1$-C$_6$ alkyl substituted by C$_1$-C$_6$ alkoxycarbonyl,
C$_1$-C$_6$ alkyl substituted by C$_3$-C$_7$ cycloalkyl, or
C$_1$-C$_6$ alkyl substituted by C$_2$-C$_6$ alkenyl, provided that R$^a$ and R$^b$ are not both hydrogen,
C$_1$-C$_6$ alkyl,
C$_1$-C$_6$ alkyl substituted by —OR$^g$, wherein R$^g$ is
C$_1$-C$_6$ alkyl,
C$_1$-C$_6$ haloalkyl,
C$_1$-C$_4$ alkoxy-C$_1$-C$_4$ alkyl,
C$_2$-C$_6$ alkenyl-C$_1$-C$_6$ alkyl,
C$_2$-C$_6$ alkynyl-C$_1$-C$_6$ alkyl,
cyanomethyl, C₃-C₇ cycloalkyl,
C₁-C₆ alkylcarbonyl, or
—CONR$^j$R$^k$ wherein R$^j$ and R$^k$ are each independently hydrogen or C₁-C₆ alkyl,
C₁-C₆ alkyl substituted by C₁-C₆ alkoxycarbonyl,
C₁-C₆ alkyl substituted by cyano,
C₁-C₆ haloalkyl,
C₁-C₆ haloalkyl substituted by heterocycloalkyl,
C₁-C₆ haloalkyl substituted by —NR$^h$R$^i$, wherein R$^h$ is C₁-C₆ alkyl and R$^i$ is hydrogen, C₁-C₆ alkyl, or C₁-C₆ alkylcarbonyl,
C₁-C₆ alkoxy,
C₁-C₆ alkoxy substituted by C₁-C₆ alkoxycarbonyl,
C₁-C₆ haloalkoxy,
C₁-C₄ alkoxy-C₁-C₄ alkyl,
C₁-C₄ alkoxy-C₁-C₄ haloalkyl,
C₁-C₄ alkoxy-C₁-C₄ haloalkyl substituted by C₁-C₄ alkoxy,
C₁-C₆ alkylcarbonyl,
C₁-C₆ alkoxycarbonyl,
C₁-C₆ alkylcarbonyloxy,
C₃-C₇ cycloalkyl,
C₃-C₇ cycloalkyl substituted by C₁-C₆ alkyl,
C₃-C₇ cycloalkyl substituted by C₁-C₄ alkoxy-C₁-C₄ alkyl,
heterocycloalkyl,
heterocycloalkyloxy,
C₂-C₆ alkenyl,
C₂-C₆ alkenyloxy,
C₂-C₆ alkynyl,
C₂-C₆ alkynyloxy,
C₂-C₆ alkynyloxy-C₁-C₄ alkyl,
C₁-C₆ alkylthio,
C₁-C₆ haloalkylthio, or
a group of formula (I-A)

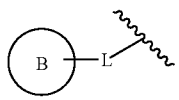

(I-A)

wherein
L is a single bond, —(CH₂)$_p$—, —O(CH₂)$_p$—, —(CH₂)$_p$O—, —NR$^c$(CH₂)$_p$— or —(CH₂)$_p$NR$^c$—, wherein one or more hydrogen atoms of (CH₂)$_p$ are optionally substituted by halogen,
p is 1 or 2,
R$^c$ is hydrogen or methyl, and
ring B is phenyl, imidazolyl, pyrazolyl, oxazolyl, thiazolyl, or oxadiazolyl, and
R$^{2b}$ is
hydrogen,
halogen,
cyano,
C₁-C₆ alkyl,
C₁-C₆ haloalkyl,
C₁-C₆ alkoxy,
C₁-C₆ haloalkoxy, or
C₃-C₇ cycloalkyl, or
R$^{2a}$ and R$^{2b}$ can be joined to form —(CH₂)$_r$— that is optionally substituted by halogen, hydroxyl, or oxo and r is 3, 4, 5, or 6.

12. The biaryl derivative according to claim 1 or a salt thereof, wherein
R$^{2a}$ is
hydrogen,
halogen,
cyano,
—NR$^a$R$^b$, wherein R$^a$ and R$^b$ are each independently hydrogen,
C₁-C₆ alkyl,
C₁-C₆ alkyl substituted by C₁-C₄ alkoxy, or
C₁-C₆ alkyl substituted by C₁-C₆ alkoxycarbonyl, provided that R$^a$ and R$^b$ are not both hydrogen,
C₁-C₆ alkyl,
C₁-C₆ haloalkyl,
C₁-C₆ alkoxy,
C₁-C₆ haloalkoxy,
C₁-C₄ alkoxy-C₁-C₄ alkyl,
C₁-C₄ alkoxy-C₁-C₄ haloalkyl,
C₁-C₆ alkylcarbonyl,
C₁-C₆ alkoxycarbonyl,
C₃-C₇ cycloalkyl, or
a group of formula (I-A)

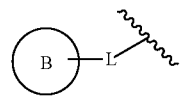

(I-A)

wherein
L is a single bond, —(CH₂)$_p$—, —O(CH₂)$_p$—, or —(CH₂)$_p$O—, wherein one or more hydrogen atoms of (CH₂)$_p$ are optionally substituted by halogen,
p is 1 or 2, and
ring B is phenyl or pyrazolyl, and
R$^{2b}$ is
hydrogen,
halogen, or
methyl, or
R$^{2a}$ and R$^{2b}$ can be joined to form —(CH₂)$_r$— and r is 3 or 4.

13. The biaryl derivative according to claim 1 or a salt thereof, wherein R$^{2a}$ and R$^{2b}$ are each independently hydrogen, C₁-C₄ alkyl, C₁-C₄ haloalkyl, C₁-C₄ alkoxy, C₁-C₄ haloalkoxy, C₁-C₄ alkoxy-C₁-C₄ alkyl, C₁-C₄ alkoxy-C₁-C₄ haloalkyl or C₃-C₇ cycloalkyl, provided that R$^{2a}$ and R$^{2b}$ are not both hydrogen.

14. The biaryl derivative according to claim 1 or a salt thereof, wherein R$^{2b}$ is hydrogen or C₁-C₄ alkyl.

15. A biaryl derivative, or a salt thereof, selected from the group consisting of:

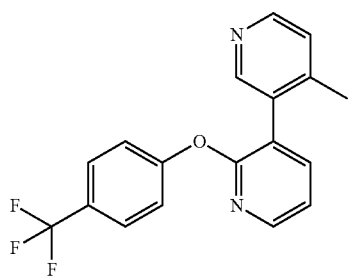

(I-206)

(I-210)
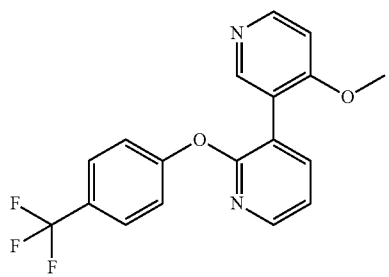
(I-212)
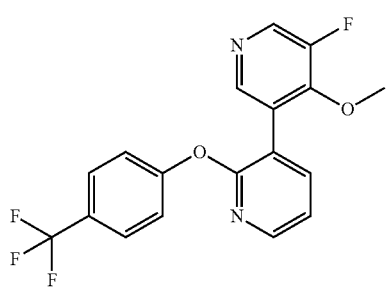
(I-216)
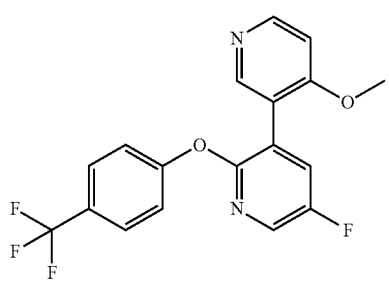
(I-218)
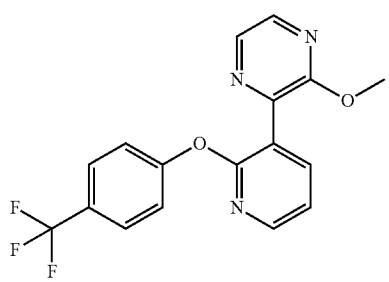
(I-219)
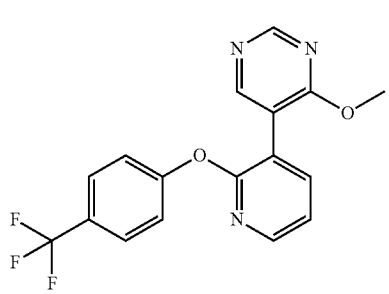
(I-226)
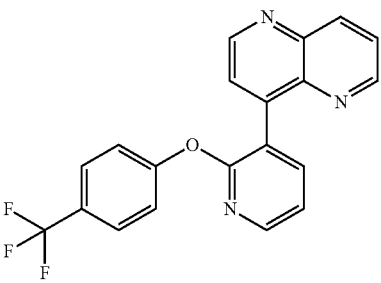
(I-227)
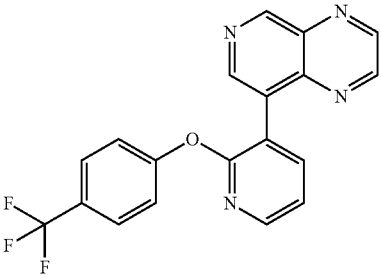
(I-228)
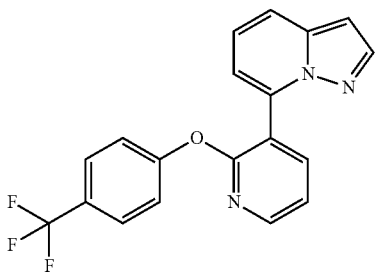
(I-235)
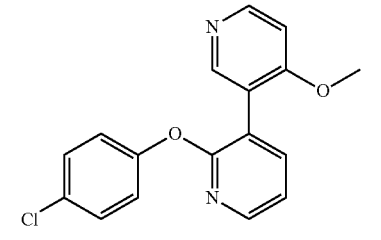
(I-237)
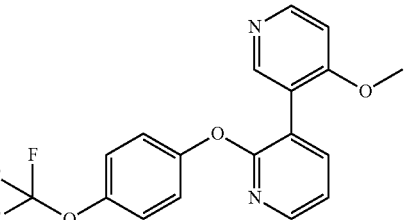
(I-245)
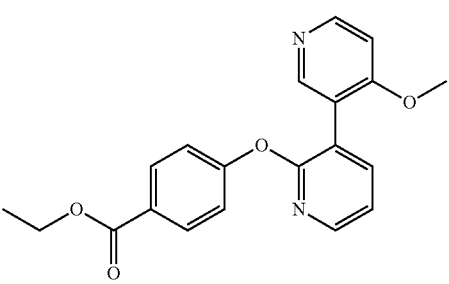

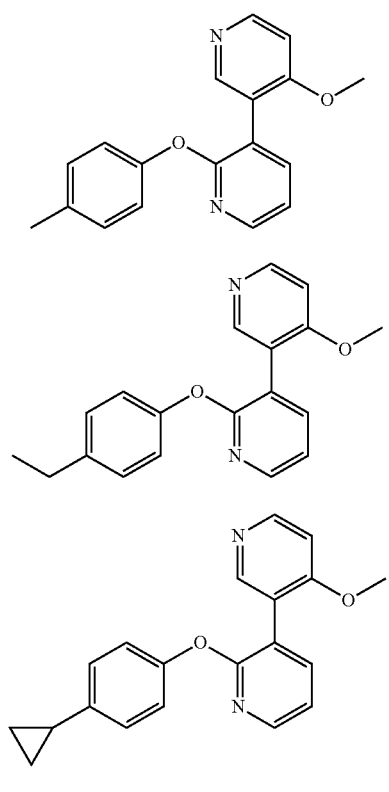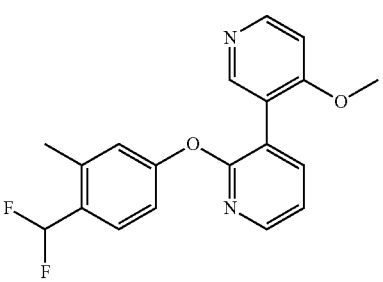

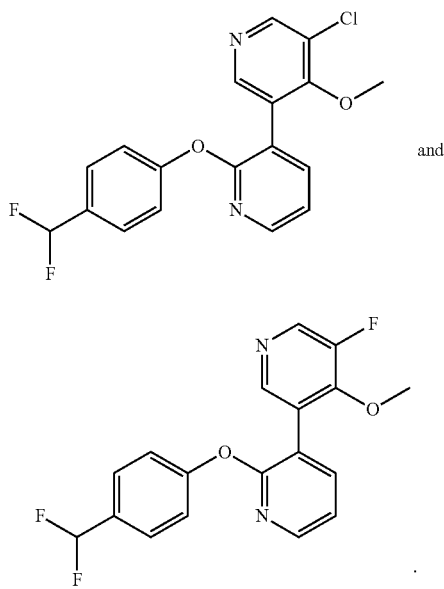

(I-355) and (I-356)

16. A medicament comprising the biaryl derivative according to claim 1 or a salt thereof.

17. A method for treating fungal infections in a mammal, comprising administering an effective amount of the biaryl derivative according to claim 1 or a salt thereof to the mammal.

18. A method for treating superficial mycosis in a mammal, comprising administering an effective amount of the biaryl derivative according to claim 1 or a salt thereof to the mammal.

19. A method for treating tinea unguium in a mammal, comprising administering an effective amount of the biaryl derivative according to claim 1 or a salt thereof to the mammal.

20. A method for treating fungal infections in a mammal, comprising administering an effective amount of the biaryl derivative according to claim 15 or a salt thereof to the mammal.

21. A method for treating superficial mycosis in a mammal, comprising administering an effective amount of the biaryl derivative according to claim 15 or a salt thereof to the mammal.

22. A method for treating tinea unguium in a mammal, comprising administering an effective amount of the biaryl derivative according to claim 15 or a salt thereof to the mammal.

* * * * *